US012479842B2

(12) United States Patent
Beaulieu et al.

(10) Patent No.: US 12,479,842 B2
(45) **Date of Patent: *Nov. 25, 2025**

(54) PYRIDO[3,2-D]PYRIMIDINE COMPOUNDS USES THEREOF FOR TREATING A PROLIFERATIVE DISEASE

(71) Applicant: Universite de Montreal, Montréal (CA)

(72) Inventors: Pierre Louis Beaulieu, Rosemère (CA); Eric Beaulieu, Mercier (CA); Joanne Tan, San Mateo, CA (US); Yannick Rose, Montréal (CA); Michael Dore, Saint-Bruno-de-Montarville (CA); Doris Schuetz, Montréal (CA); Mukund Ghavre, Saint-Laurent (CA); Jacques Banville, Saint-Hubert (CA)

(73) Assignee: Universite de Montreal, Montreal (CA)

( * ) Notice: Subject to any disclaimer, the term of this patent is extended or adjusted under 35 U.S.C. 154(b) by 0 days.

This patent is subject to a terminal disclaimer.

(21) Appl. No.: 18/287,610

(22) PCT Filed: Apr. 19, 2022

(86) PCT No.: PCT/CA2022/050592

§ 371 (c)(1),
(2) Date: Oct. 19, 2023

(87) PCT Pub. No.: WO2022/221939

PCT Pub. Date: Oct. 27, 2022

(65) Prior Publication Data

US 2024/0217971 A1 Jul. 4, 2024

Related U.S. Application Data

(60) Provisional application No. 63/201,219, filed on Apr. 19, 2021.

(51) Int. Cl.

| | |
|---|---|
| ***C07D 471/04*** | (2006.01) |
| ***A61K 31/519*** | (2006.01) |
| ***A61K 31/5377*** | (2006.01) |
| ***A61K 31/541*** | (2006.01) |
| ***A61K 31/675*** | (2006.01) |
| ***A61P 35/00*** | (2006.01) |
| ***C07D 519/00*** | (2006.01) |
| ***C07F 9/6561*** | (2006.01) |

(52) U.S. Cl.
CPC .......... *C07D 471/04* (2013.01); *A61K 31/519* (2013.01); *A61K 31/5377* (2013.01); *A61K 31/541* (2013.01); *A61K 31/675* (2013.01); *A61P 35/00* (2018.01); *C07D 519/00* (2013.01); *C07F 9/6561* (2013.01)

(58) Field of Classification Search
CPC .................................................... C07D 471/04
USPC ........................................................... 514/81
See application file for complete search history.

(56) References Cited

U.S. PATENT DOCUMENTS

| | | | | |
|---|---|---|---|---|
| 5,654,307 | A | 8/1997 | Bridges et al. | |
| 12,060,353 | B2 * | 8/2024 | Beaulieu ................. | A61P 35/00 |
| 12,139,488 | B2 * | 11/2024 | Beaulieu .............. | A61K 31/541 |
| 2013/0023531 | A1 | 1/2013 | Mantoulidis et al. | |
| 2015/0158854 | A1 | 6/2015 | Kuo et al. | |
| 2024/0140945 | A1 | 5/2024 | Beaulieu et al. | |

FOREIGN PATENT DOCUMENTS

| | | | |
|---|---|---|---|
| CN | 110437253 | A | 11/2019 |
| CN | 110903286 | A | 3/2020 |
| WO | WO-2010/026262 | A1 | 3/2010 |
| WO | WO-2010/094695 | A1 | 8/2010 |
| WO | WO-2012/101238 | A1 | 8/2012 |
| WO | WO-2015/162516 | A1 | 10/2015 |
| WO | WO-2020/033413 | A2 | 2/2020 |
| WO | WO-2022/221940 | A1 | 10/2022 |

OTHER PUBLICATIONS

International Search Report for International Application No. PCT/CA2022/050592, mailed Jun. 29, 2022 (3 pages).
International Search Report for International Application No. PCT/CA2022/050593, mailed Jun. 30, 2022 (3 pages).
Written Opinion for International Application No. PCT/CA2022/050592, mailed Jun. 29, 2022 (5 pages).
Written Opinion for International Application No. PCT/CA2022/050593, mailed Jun. 30, 2022 (7 pages).

* cited by examiner

*Primary Examiner* — Niloofar Rahmani
(74) *Attorney, Agent, or Firm* — Clark & Elbing LLP

(57) ABSTRACT

Compounds, compositions and their use in the treatment of a proliferative disease or condition such as a said proliferative disease or disorder is associated with a RAF gene mutation and/or a RAS gene mutation. The compounds disclosed are of Formula I or a pharmaceutically acceptable salt or solvate thereof, wherein $R^1$, $R^2$, $R^3$, $X^1$, $X^2$, $X^3$ and $X^4$ are as defined herein.

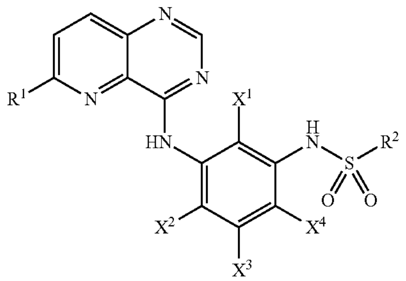

22 Claims, 5 Drawing Sheets

PYRIDO[3,2-D]PYRIMIDINE COMPOUNDS USES THEREOF FOR TREATING A PROLIFERATIVE DISEASE

RELATED APPLICATION

The present application claims priority under applicable law to U.S. provisional application No. 63/201,219 filed on Apr. 19, 2021, the content of which is incorporated herein by reference in its entirety for all purposes.

TECHNICAL FIELD

This disclosure generally relates to pyrido[3,2-d]pyrimidine compounds, pharmaceutical compositions comprising the same and their use in the treatment and prevention of diseases characterized by dysregulation of the RAS-ERK pathway (e.g. cancer, RASopathies).

BACKGROUND

The RAS-RAF-MEK-ERK (RAS: rat sarcoma; RAF: rapidly accelerated fibrosarcoma; MEK: mitogen-activated protein kinase; ERK: extracellular signal-regulated kinase) signaling pathway (hereafter referred to as the RAS-ERK pathway) plays a critical role in transmitting proliferation signals generated by growth factor receptors from the plasma membrane to the nucleus. The pathway is dysregulated in a large proportion of cancers by activation of receptor tyrosine kinases (RTKs) (e.g. ERB1, ERBB2, FLT3, RET, KIT), activation or inactivation of RAS regulators (SOS1 and NF1) as well as constitutively activating mutations in RAS genes (H-, K- and NRAS; overall 30% of cancers) and in the BRAF gene (8% of cancers). The prevalence of KRAS mutations is especially high in pancreatic (>90%), colorectal (50%), and lung (30%) cancers. For their part, BRAF mutations are found with notably high frequencies in malignant melanoma (70%), thyroid cancer (40%) and colorectal cancer (10%) (mutation frequencies based on COSMIC (Catalogue Of Somatic Mutations In Cancer; Wellcome Trust Sanger Institute) release v95, Nov. 24, 2021).

RAS proteins are small GTPases that convey extracellular growth signals to intracellular effectors to control vital processes like cell differentiation, proliferation and survival (*Nat. Rev. Cancer* 2003, 3, 459). Physiological activation of RAS occurs at the plasma membrane after stimulation of RTKs, which leads to GTP loading of the GTPase and thus its activation. Activated RAS interacts and activates a battery of effector molecules, with the RAF kinases being the most critical RAS interactors in the context of cancer development (*Nature Rev. Drug Discov.* 2014, 13, 828).

Oncogenic mutations at Glycine 12, Glycine 13 or Glutamine 61 in RAS isoforms lead to aberrant and constitutive signaling in human cancer (*Nat. Rev. Cancer* 2003, 3, 459) (COSMIC release v95, November 24 2021).

Downstream of RAS, mammalian cells express three RAF paralogs (ARAF, BRAF and CRAF) that share a conserved C-terminal kinase domain (KD) (*Nat. Rev. Mol. Cell Biol.* 2015, 16, 281) and an N-terminal regulatory region (NTR) comprising a RAS-binding domain (RBD). In unstimulated cells, RAF proteins are sequestered in the cytoplasm as monomers. Binding of GTP-bound activated RAS to the RBD induces membrane anchoring of RAF kinases (*Nat. Rev. Mol. Cell Biol.* 2015, 16, 281). Concomitantly, RAF proteins undergo kinase domain side-to-side dimerization and catalytic activation (*Nature* 2009, 461, 542). Activated RAF proteins convey signals through a phosphorylation cascade from RAF to MEK and then MEK to ERK, leading to phosphorylation by ERK of an array of substrates eliciting cell-specific responses (*Nat. Rev. Mol. Cell Biol.* 2020, October; 21(10), 607).

Activating mutations in RAF isoforms have so far been mostly restricted to the BRAF gene, although rare variants were observed in ARAF and CRAF, underlining the functional importance of this isoform (COSMIC release v95, Nov. 24, 2021). The most common cancer mutation in BRAF, a valine to glutamic acid substitution at position 600 (referred to as $BRAF^{V600E}$), enhances BRAF activity by stabilizing its active form (Cell 2004, 116, 855). Apart from the V600E allele, a diverse set of mutations occur at other residues (e.g. G466V, D594G, etc.) that lead to increased RAF signaling through a variety of mechanisms (*Nat. Rev. Mol. Cell Biol.* 2015, 16, 281). These have been grouped in three main classes (1 to 3) depending on their level of dependence to RAS activity and to RAF dimerization (*Nature* 2017 Aug. 10; 548(7666):234-238). The key role of wild-type BRAF and CRAF in mediating RAS-driven oncogenesis by stimulating ERK signaling is extensively validated (*Cancer Cell* 2011, 19, 652; *Cancer Discov.* 2012, 2, 685; *Nat. Commun.* 2017, 8, 15262). Tumor cells thus rely on elevated and continued signaling of the RAS-ERK pathway through RAS and RAF activation, providing strong support for the concept of targeting RAF family kinases in cancers.

To address existing medical needs, the past decade has seen the development of a broad set of ATP-competitive RAF inhibitors (*Nat. Rev. Cancer* 2017, 17, 676). Efforts have focused mainly on the most common RAS-independent BRAF mutation ($BRAF^{V600E}$), leading to the development and FDA approval of sulfonamide derivatives such as vemurafenib and dabrafenib. Some of these RAF inhibitors have shown impressive efficacy against metastatic melanomas harboring the recurrent $BRAF^{V600E}$ allele and have been approved for treating this patient population (*N. Engl. J. Med.* 2011, 364, 2507; *Lancet* 2012, 380, 358). The clinical responses against $BRAF^{V600E}$ dependent melanomas result from potent ATP-competitive inhibition of the monomeric form of this specific dimerization-independent BRAF mutant protein (*Cancer Cell* 2015, 28, 370). Unfortunately, acquired resistance to these agents invariably develops, which is mostly caused by re-activation of the RAS-ERK pathway in part through mechanisms that stimulate RAF dimerization. These include upregulation of RTK signaling, RAS mutations, and $BRAF^{V600E}$ amplification or truncation (*Sci. Signal.* 2010, 3, ra84; *Nature* 2010, 468, 973; *Nature* 2011, 480, 387; *Nature Commun.* 2012, 3, 724).

Concurrently, tumors exhibiting RAS activity—owing to activating RAS mutations or elevated RTK signaling, but which are otherwise wild-type for BRAF—show primary resistance to $BRAF^{V600E}$ inhibitors (*Nature* 2010, 464, 431). RAF inhibitors were oppositely found to induce ERK signaling in conditions where RAS activity is elevated and therefore enhances tumor cell proliferation (*Nature* 2010, 464, 431). This counterintuitive phenomenon, known as the paradoxical effect, was also observed in normal tissues relying on physiological RAS activity and is the basis for some of the adverse effects seen with RAF inhibitors in melanoma patients such as the development of new secondary tumors (e.g. squamous cell carcinomas and keratoacanthomas) (*Nat. Rev. Cancer* 2014, 14, 455). As a consequence, $BRAF^{V600E}$ inhibitors are ineffective and even contraindicated against RAS-driven cancers. The underlying mechanism results from the compounds' ability to promote RAF kinase domain dimerization in the presence of active RAS (*Nature* 2010, 464, 431). This event is not restricted to BRAF, but also involves other RAF family members and is dictated by the compound binding mode and affinity (*Nat. Chem. Biol.* 2013, 9, 428).

Two strategies have recently been pursued to circumvent the limitation of first-generation RAF inhibitors in RAS-mutated cancers. The first one relies on the observation that paradoxical ERK activation is a dose-dependent phenomenon, i.e. induction occurs at sub-saturating inhibitor concentrations but the pathway is suppressed at saturating concentrations when the compound occupies both protomers of RAF dimers. This first strategy therefore focused on developing molecules with higher binding affinities to all RAF paralogs in order to saturate RAF proteins at lower drug concentration thereby reducing paradoxical pathway induction (*Bioorg. Med. Chem. Lett.* 2012, 22, 6237; *Cancer Res.* 2013, 73, 7043; *J. Med. Chem.* 2015, 58, 4165; *Cancer Cell* 2017, 31, 466; *J Med Chem.* 2020, 63, 2013; *Clin Cancer Res.* 2021, 27, 2061; *Nature* 2021, 594, 418). These compounds however retain strong RAF dimer induction capabilities and thus paradoxically stimulate RAS-ERK signaling, although with a lower amplitude than previous generations of RAF inhibitors. Although this class of compounds show improved properties, they were recently showed to mostly spare the ARAF isoform, which leads to paradoxical pathway activation and primary resistance as well as to the emergence of acquired resistance in vitro and in clinical settings (Clin Cancer Res. 2021, 27, 2061; Nature 2021, 594, 418). The second strategy consisted in designing compounds that conformationally bias the BRAF kinase domain in the inactive state and thus do not paradoxically induce ERK signaling. This has given rise to the “Paradox Breaker” (PB) molecule PLX8394, a derivative of PLX4032/vemurafenib (*Nature* 2015, 526, 583). These molecules retained high potency against $BRAF^{V600E}$ and therefore should prove useful for treating $BRAF^{V600E}$-dependent melanomas. However, while PLX8394 does not induce ERK signaling in RAS-mutant cell lines that have been tested, it remains ineffective and is not useful against RAS-mutant tumors.

There remains a need for inhibitors that potently and consistently block RAS-ERK signaling and cellular proliferation in human tumor cells bearing a variety of RAS and RAF genotypes. The development of such inhibitors importantly being also devoid of paradoxical pathway induction in a variety of RAS-mutant tumor cell lines is highly desirable.

SUMMARY

According to one aspect, the present technology relates to a compound of Formula I:

Formula I

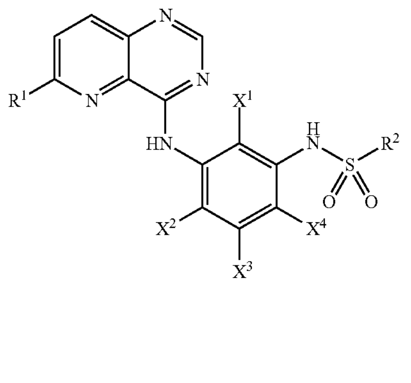

wherein:

$R^1$ is selected from substituted or unsubstituted $OR^3$, $SR^3$, $NH_2$, $NHR^3$, $N(R^3)_2$, $C_{3-8}$cycloalkyl, $C_{4-8}$heterocycloalkyl, $C_{6-10}$aryl and $C_{5-10}$heteroaryl, for example, selected from substituted or unsubstituted $C_{6-10}$aryl and $C_{5-10}$heteroaryl; $R^2$ is selected from substituted $C_6$aryl or $C_{5-10}$heteroaryl, substituted or unsubstituted $C_{4-8}$heterocycloalkyl, and $N(R^3)_2$;

$R^3$ is independently in each occurrence selected from substituted or unsubstituted $C_{1-8}$-alkyl, $C_{3-8}$cycloalkyl, $C_{4-8}$heterocycloalkyl, $C_{6-10}$aryl and $C_{5-10}$heteroaryl;

$X^1$ is halo or an electron-withdrawing group;

$X^2$ is selected from H, halo, and an electron-withdrawing group;

$X^3$ and $X^4$ are each selected from H, halo, an electron-withdrawing group, $C_{1-3}$alkyl, $C_{3-4}$cycloalkyl, and $OC_{1-3}$alkyl;

or a pharmaceutically acceptable salt or solvate thereof.

The compounds of Formula I are also defined according to any of the embodiments, alone or in combination, and examples described throughout the present document.

According to another aspect, the present technology relates to a pharmaceutical composition for a use as defined in any one of the aforementioned embodiments, the composition comprising a compound as herein defined together with a pharmaceutically acceptable carrier, diluent or excipient.

In a further aspect, the present technology relates to the use of a compound as herein defined for the treatment of a disease or disorder selected from a proliferative disease or disorder, a developmental anomaly caused by dysregulation of the RAS-ERK signaling cascade (RASopathies), or an inflammatory disease or an immune system disorder.

The present technology also further relates to a method for the treatment of a disease or disorder selected from a proliferative disease or disorder, a developmental anomaly caused by dysregulation of the RAS-ERK signaling cascade (RASopathies), or an inflammatory disease or an immune system disorder, comprising administering a compound as herein defined to a subject in need thereof. A method for inhibiting abnormal proliferation of cells, comprising contacting the cells with a compound as defined herein is also contemplated.

In one embodiment of the above uses and methods, the disease or disorder is selected from a neoplasm and a developmental anomaly, for instance, a disease or disorder associated with a RAF gene mutation (e.g. ARAF, BRAF, or CRAF), a disease or disorder associated with a RAS gene mutation (e.g. KRAS), or a disease or disorder associated with both a RAF gene mutation and a RAS gene mutation. In one embodiment, the disease or disorder is associated with a receptor tyrosine kinase mutation or amplification (e.g. EGFR, HER2) or a mutation in a regulator of RAS downstream of the receptor (e.g. SOS1 gain of function, NF1 loss of function).

For instance, the disease or disorder is a neoplasm, such as those selected from melanoma, thyroid carcinoma (e.g. papillary thyroid carcinoma), colorectal, ovarian, breast cancer, endometrial cancer, liver cancer, sarcoma, stomach cancer, pancreatic carcinoma, Barret’s adenocarcinoma, glioma (e.g. ependymoma), lung cancer (e.g. non-small cell lung cancer), head and neck cancer, acute lymphoblastic leukemia, acute myelogenous leukemia, non-Hodgkin’s lymphoma, and hairy-cell leukemia. For instance, the neoplasm is selected from colon or colorectal cancer, lung cancer, pancreatic cancer, thyroid cancer, breast cancer and melanoma. For instance, any of the present uses and methods comprises inhibiting the RAS-ERK signaling pathway without substantial induction of a paradoxical pathway.

Additional objects and features of the present compound, compositions, methods and uses will become more apparent upon reading of the following non-restrictive description of exemplary embodiments and examples section, which should not be interpreted as limiting the scope of the invention.

DETAILED DESCRIPTION

Figure 1:
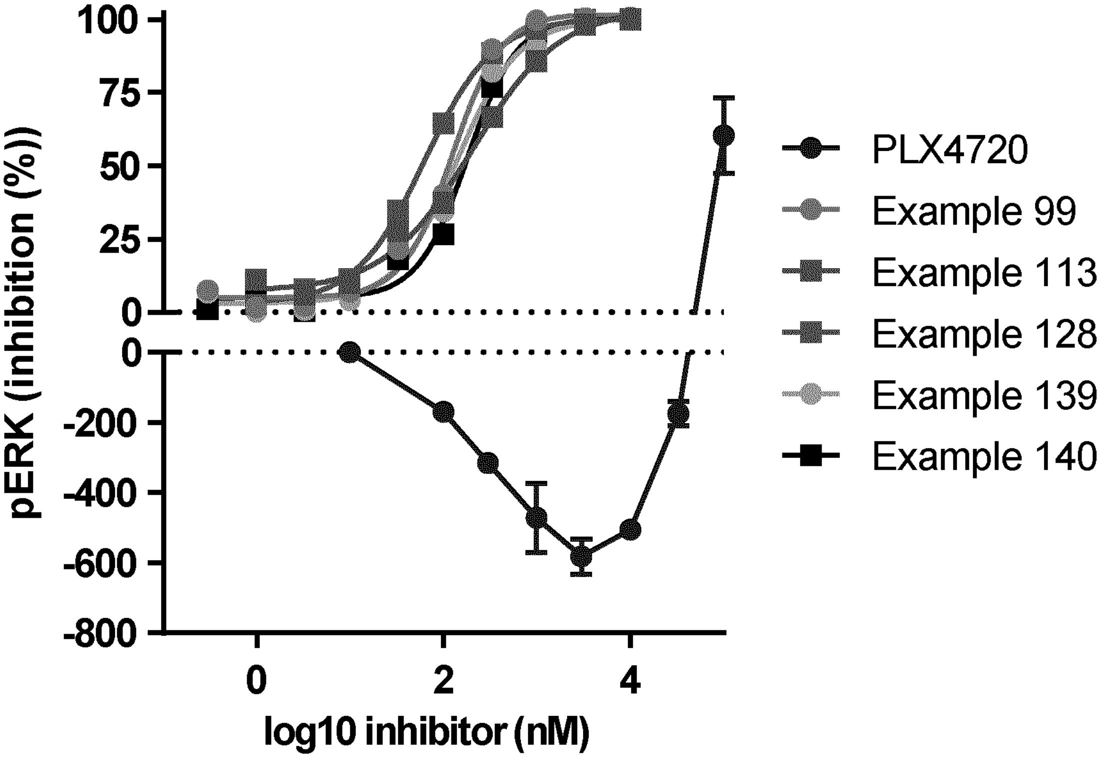
FIG. 1 shows representative $IC_{50}$ inhibition dose response curves for compounds as described herein that do not induce paradoxical induction of pERK signaling ($Y_{MIN}$>−20%) in RAS-mutant HCT116 cells (Examples 99, 113, 128, 139, 140) and a compound (PLX4720; CAS #918505-84-7) that causes strong induction of the pathway in the same cell line ($Y_{MIN}$~−600%).

All technical and scientific terms and expressions used herein have the same definitions as those commonly understood by a person skilled in the art to which the present technology pertains. The definition of some terms and expressions used is nevertheless provided below. To the extent the definitions of terms in the publications, patents, and patent applications incorporated herein by reference are contrary to the definitions set forth in this specification, the definitions in this specification will control. The section headings used herein are for organizational purposes only and are not to be construed as limiting the subject matter disclosed.

i. Definitions

Chemical structures described herein are drawn according to conventional standards. Also, when an atom, such as a carbon atom, as drawn seems to include an incomplete valency, then the valency is assumed to be satisfied by one or more hydrogen atoms even though these are not necessarily explicitly drawn. Hydrogen atoms should be inferred to be part of the compound.

The terminology used herein is for the purpose of describing particular embodiments only and is not intended to be limiting. It should be noted that, the singular forms "a", "an", and "the" include plural forms as well, unless the content clearly dictates otherwise. Thus, for example, reference to a composition containing "a compound" also contemplates a mixture of two or more compounds. It should also be noted that the term "or" is generally employed in its sense including "and/or" unless the context clearly dictates otherwise. Furthermore, to the extent that the terms "including", "includes", "having", "has", "with", or variants thereof are used in either the detailed description and/or the claims, such terms are intended to be inclusive in a manner similar to the term "comprising".

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

As used herein, the terms "compounds", "compounds herein described", "compounds of the present application", "pyrido[3,2-d]pyrimidine compounds", "pyridopyrimidine compounds" and equivalent expressions refer to compounds described in the present application, e.g. those encompassed by structural Formula I, optionally with reference to any of the applicable embodiments, and also includes exemplary compounds, such as the compounds of Examples 1 to 691, as well as their pharmaceutically acceptable salts, solvates, esters, and prodrugs when applicable. When a zwitterionic form is possible, the compound may be drawn as its neutral form for practical purposes, but the compound is understood to also include its zwitterionic form. Embodiments herein may also exclude one or more of the compounds. Compounds may be identified either by their chemical structure or their chemical name. In a case where the chemical structure and chemical name would conflict, the chemical structure will prevail.

Unless otherwise stated, structures depicted herein are also meant to include all isomeric (e.g., enantiomeric, diastereomeric, and geometric (or conformational)) forms of the structure when applicable; for example, the R and S configurations for each asymmetric center. Therefore, single stereochemical isomers as well as enantiomeric, diastereomeric, and geometric (or conformational) mixtures of the present compounds are within the scope of the present description. The therapeutic compound unless otherwise noted, also encompasses all possible tautomeric forms of the illustrated compound, if any. The term also includes isotopically labeled compounds where one or more atoms have an atomic mass different from the atomic mass most abundantly found in nature. Examples of isotopes that may be incorporated into the present compounds include, but are not limited to, $^{2}H$ (D), $^{3}H$ (T), $^{11}C$, $^{13}C$, $^{14}C$ $^{15}N$, $^{18}O$, $^{17}O$, any one of the isotopes of sulfur, etc. The compound may also exist in unsolvated forms as well as solvated forms, including hydrated forms. The compound may exist in multiple crystalline or amorphous forms. In general, all physical forms are equivalent for the uses contemplated herein and are intended to be within the scope of the present invention.

Where a particular enantiomer is preferred, it may, in some embodiments be provided substantially free of the corresponding enantiomer and may also be enantiomerically enriched. "Enantiomerically enriched" means that the compound is made up of a significantly greater proportion of one enantiomer. In certain embodiments the compound is made up of at least about 90% by weight of a preferred enantiomer. In other embodiments the compound is made up of at least about 95%, 98%, or 99% by weight of a preferred enantiomer. Preferred enantiomers may be isolated from racemic mixtures by any method known to those skilled in the art, including high-pressure liquid chromatography (HPLC) on chiral support and the formation and crystallization of chiral salts or be prepared by asymmetric syntheses.

The expression "pharmaceutically acceptable salt" refers to those salts of the compounds of the present description which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). The salts can be prepared in situ during the final isolation and purification of the compounds of the present description, or separately by reacting a free base function of the compound with a suitable organic or inorganic acid (acid addition salts) or by reacting an acidic function of the compound with a suitable organic or inorganic base (base-addition salts).

The term "solvate" refers to a physical association of one of the present compound with one or more solvent molecules, including water and non-aqueous solvent molecules. This physical association may include hydrogen bonding. In certain instances, the solvate will be capable of isolation, for example when one or more solvent molecules are incorporated in the crystal lattice of a crystalline solid. The term "solvate" encompasses both solution-phase and isolable solvates.

Exemplary solvates include, without limitation, hydrates, hemihydrates, ethanolates, hemiethanolates, n-propanolates, iso-propanolates, 1-butanolates, 2-butanolate, and solvates of other physiologically acceptable solvents, such as the Class 3 solvents described in the *International Conference on Harmonization* (*ICH*), *Guide for Industry, Q3C Impurities: Residual Solvents* (1997). Accordingly, the compound as herein described also includes each of its solvates and mixtures thereof.

As used herein, the expression "pharmaceutically acceptable ester" refers to esters of the compounds formed by the process of the present description which may hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates of hydroxyl groups, and alkyl esters of an acidic group. Other ester groups include sulfonate or sulfate esters.

The expression "pharmaceutically acceptable prodrugs" as used herein refers to those prodrugs of the compounds formed by the process of the present description which are, within the scope of sound medical judgment, suitable for use in contact with the tissues of humans and lower animals with undue toxicity, irritation, allergic response, and the like, commensurate with a reasonable benefit/risk ratio, and effective for their intended use. "Prodrug", as used herein means a compound which is convertible in vivo by metabolic means (e.g. by hydrolysis) to afford any compound delineated by the formulae of the instant description.

Abbreviations may also be used throughout the application, unless otherwise noted, such abbreviations are intended to have the meaning generally understood by the field. Examples of such abbreviations include Me (methyl), Et (ethyl), Pr (propyl), i-Pr (isopropyl), Bu (butyl), t-Bu (tert-butyl), i-Bu (iso-butyl), s-Bu (sec-butyl), c-Bu (cyclobutyl), Ph (phenyl), Bn (benzyl), Bz (benzoyl), CBz or Cbz or Z (carbobenzyloxy), Boc or BOC (tert-butoxycarbonyl), and Su or Suc (succinimide). For more certainty, additional definitions of specific abbreviations are also included in the introduction of the Examples section.

The number of carbon atoms in a hydrocarbyl substituent can be indicated by the prefix "$C_x$-$C_y$" or "$C_{x-y}$" where x is the minimum and y is the maximum number of carbon atoms in the substituent.

However, when the prefix "$C_x$-$C_y$" or "$C_{x-y}$" is associated with a group incorporating one or more heteroatom(s) by definition (e.g. heterocycloalkyl, heteroaryl, etc), then x and y define respectively the minimum and maximum number of atoms in the cycle, including carbon atoms as well as heteroatom(s).

The term "alkyl" as used herein, refers to a saturated, straight- or branched-chain hydrocarbon radical typically containing from 1 to 20 carbon atoms. For example, "$C_1$-$C_8$ alkyl" contains from one to eight carbon atoms. Examples of alkyl radicals include, but are not limited to, methyl, ethyl, propyl, isopropyl, n-butyl, tert-butyl, neopentyl, n-hexyl, heptyl, octyl radicals and the like.

The term "alkenyl" as used herein, denotes a straight- or branched-chain hydrocarbon radical containing one or more double bonds and typically from 2 to 20 carbon atoms. For example, "$C_{2-8}$ alkenyl" contains from two to eight carbon atoms. Alkenyl groups include, but are not limited to, for example, ethenyl, propenyl, butenyl, 1-methyl-2-buten-1-yl, heptenyl, octenyl and the like.

The term "alkynyl" as used herein, denotes a straight- or branched-chain hydrocarbon radical containing one or more triple bonds and typically from 2 to 20 carbon atoms. For example, "$C_{2-8}$ alkynyl" contains from two to eight carbon atoms. Representative alkynyl groups include, but are not limited to, for example, ethynyl, 1-propynyl, 1-butynyl, heptynyl, octynyl and the like.

The terms "cycloalkyl", "alicyclic", "carbocycle", "carbocyclic" and equivalent expressions refer to a group comprising a saturated or partially unsaturated (non aromatic) carbocyclic ring in a monocyclic or polycyclic ring system, including spiro (sharing one atom), fused (sharing at least one bond) or bridged (sharing two or more bonds) carbocyclic ring systems, having from three to fifteen ring members. Examples of cycloalkyl groups include, without limitation, cyclopropyl, cyclobutyl, cyclopentyl, cyclopenten-1-yl, cyclopenten-2-yl, cyclopenten-3-yl, cyclohexyl, cyclohexen-1-yl, cyclohexen-2-yl, cyclohexen-3-yl, cycloheptyl, bicyclo[4,3,0]nonanyl, norbornyl, and the like. The term cycloalkyl includes both unsubstituted cycloalkyl groups and substituted cycloalkyl groups. The term "$C_3$-$C_n$cycloalkyl" refers to a cycloalkyl group having from 3 to the indicated "n" number of carbon atoms in the ring structure. Unless the number of carbons is otherwise specified, "lower cycloalkyl" groups as herein used, have at least 3 and equal or less than 8 carbon atoms in their ring structure.

As used herein, the terms "heterocycle", "heterocycloalkyl", "heterocyclyl", "heterocyclic radical", and "heterocyclic ring" are used interchangeably and refer to a chemically stable 3- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 1-3 heteroatoms selected from oxygen, sulfur or nitrogen, the nitrogen may be N (as in 3,4-dihydro-2H-pyrrolyl), NH (as in pyrrolidinyl), or NR (as in N-substituted pyrrolidinyl). A heterocyclic ring can be attached to its pendant group at any heteroatom or carbon atom that results in a chemically stable structure and any of the ring atoms can be optionally substituted.

Examples of heterocycloalkyl groups include, but are not limited to, 1,3-dioxolanyl, pyrrolidinyl, pyrrolidonyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, tetrahydrofuranyl, tetrahydropyranyl, tetrahydrothiopyranyl, tetrahydrodithienyl, tetrahydrothienyl, thiomorpholino, thioxanyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, 2H-pyranyl, 4H-pyranyl, dioxanyl, dithianyl, dithiolanyl, dihydropyranyl, dihydrothienyl, dihydrofuranyl, 3-azabicyclo[3,1,0]hexanyl, 3-azabicyclo[4,1,0]heptanyl, quinolizinyl, quinuclidinyl, tetrahydroquinolinyl, tetrahydroisoquinolinyl, decahydroquinolinyl, and the like. Heterocyclic groups also include groups in which a heterocyclic ring is fused to one or more aryl, heteroaryl, or cycloaliphatic rings, such as indolinyl, 3H-indolyl, chromanyl, chromenyl, phenanthridinyl, 2-azabicyclo[2.2.1]heptanyl, octahydroindolyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted. The term "$C_{3-n}$heterocycloalkyl" refers to a heterocycloalkyl group having from 3 to the indicated "n" number of atoms in the ring structure, including carbon atoms and heteroatoms.

As used herein, the term "partially unsaturated" refers to a ring moiety that includes at least one double or triple bond between ring atoms but is not aromatic. The term "partially unsaturated" is intended to encompass rings having multiple sites of unsaturation but is not intended to include aryl or heteroaryl moieties, as herein defined.

The term "aryl" used alone or as part of a larger moiety as in "aralkyl", "aralkoxy", "aryloxy", or "aryloxyalkyl", refers to aromatic groups having 4n+2 conjugated π(pi) electrons, wherein n is an integer from 1 to 3, in a monocyclic moiety or a bicyclic or tricyclic fused ring system having a total of six to 15 ring members, wherein at least one ring in the system is aromatic and wherein each ring in the system contains three to seven ring members. The term "aryl" may be used interchangeably with the term "aryl ring". In certain embodiments of the present description, "aryl" refers to an aromatic ring system which includes, but not limited to, phenyl, biphenyl, naphthyl, azulenyl, anthracyl and the like, which may bear one or more substituents. The term "aralkyl" or "arylalkyl" refers to an alkyl residue attached to an aryl ring. Examples of aralkyl include, but are not limited to, benzyl, phenethyl, and the like. Also included within the scope of the term "aryl", as it is used herein, is a group in which an aromatic ring is fused to one or more non-aromatic rings, such as indanyl, indenyl, phthalimidyl, naphthimidyl, fluorenyl, phenanthridinyl, or tetrahydronaphthyl, and the like. The term "$C_{6-n}$aryl" refers to a aryl group having from 6 to the indicated "n" number of atoms in the ring structure.

The term "heteroaryl", used alone or as part of a larger moiety, e.g., "heteroaralkyl", or "heteroaralkoxy", refers to aromatic groups having 4n+2 conjugated π(pi) electrons, wherein n is an integer from 1 to 3 (e.g. having 5 to 18 ring atoms, preferably 5, 6, or 9 ring atoms; having 6, 10, or 14 π electrons shared in a cyclic array); and having, in addition to carbon atoms, from one to five heteroatoms. The term "heteroatom" includes but is not limited to nitrogen, oxygen, or sulfur, and includes any oxidized form of nitrogen or sulfur, and any quaternized form of a basic nitrogen. A heteroaryl may be a single ring, or two or more fused rings. The term "heteroaryl", as used herein, also includes groups in which a heteroaromatic ring is fused to one or more aryl, cycloaliphatic, or heterocyclic rings, where the radical or point of attachment is on the heteroaromatic ring. Nonlimiting examples of heteroaryl groups include thienyl, furanyl (furyl), pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, triazinyl, indolyl, 3H-indolyl, isoindolyl, indolizinyl, benzothienyl (benzothiophenyl), benzofuranyl, dibenzofuranyl, indazolyl, benzimidazolyl, benzoxazolyl, benzothiazolyl, benzotriazolyl, pyrrolopyridinyl (e.g. pyrrolo[3,2-b]pyridinyl or pyrrolo[3,2-c]pyridinyl), pyrazolopyridinyl (e.g. pyrazolo[1,5-a]pyridinyl), furopyridinyl, purinyl, imidazopyrazinyl (e.g. imidazo[4,5-b]pyrazinyl), quinolyl (quinolinyl), isoquinolyl (isoquinolinyl), quinolonyl, isoquinolonyl, cinnolinyl, phthalazinyl, quinazolinyl, quinoxalinyl, 4H-quinolizinyl, naphthyridinyl, and pteridinyl carbazolyl, acridinyl, phenanthridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. Heteroaryl groups include rings that are optionally substituted. The term "heteroaralkyl" refers to an alkyl group substituted by a heteroaryl, wherein the alkyl and heteroaryl portions independently are optionally substituted. Examples include, but are not limited to, pyridinylmethyl, pyrimidinylethyl and the like. For instance, the term "$C_{5-n}$heteroaryl" refers to a heteroaryl group having from 5 to the indicated "n" number of atoms in the ring structure, including carbon atoms and heteroatoms.

As described herein, compounds of the present description may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at each position. Combinations of substituents envisioned under the present description are preferably those that result in the formation of chemically stable or chemically feasible compounds. The term "chemically stable", as used herein, refers to compounds that are not substantially altered when subjected to conditions to allow for their production, detection, and, in certain embodiments, their recovery, purification, and use for one or more of the purposes disclosed herein.

The term "halo" designates a halogen atom, i.e. a fluorine, chlorine, bromine or iodine atom, preferably fluorine or chlorine.

The term "optionally substituted" refers to groups that are substituted or unsubstituted by independent replacement of one, two, or three or more of the hydrogen atoms thereon with substituents including, but not limited to F, Cl, Br, I, OH, $CO_2H$, alkoxy, oxo, thiooxo, $NO_2$, CN, $CF_3$, $NH_2$, NHalkyl, NHalkenyl, NHalkynyl, NHcycloalkyl, NHaryl, NHheteroaryl, NHheterocyclic, dialkylamino, diarylamino, diheteroarylamino, O-alkyl, O-alkenyl, O-alkynyl, O-cycloalkyl, O-aryl, O-heteroaryl, O-haloalkyl, O-heterocyclic, C(O)alkyl, C(O)alkenyl, C(O)alkynyl, C(O)cycloalkyl, C(O)aryl, C(O)heteroaryl, C(O)heterocycloalkyl, $CO_2$alkyl, $CO_2$alkenyl, $CO_2$alkynyl, $CO_2$cycloalkyl, $CO_2$aryl, $CO_2$heteroaryl, $CO_2$heterocycloalkyl, OC(O)alkyl, OC(O)alkenyl, OC(O)alkynyl, OC(O)cycloalkyl, OC(O)aryl, OC(O)heteroaryl, OC(O)heterocycloalkyl, C(O)$NH_2$, C(O)NHalkyl, C(O)NHalkenyl, C(O)NHalkynyl, C(O)NHcycloalkyl, C(O)NHaryl, C(O)NHheteroaryl, C(O)NHheterocycloalkyl, $OCO_2$alkyl, $OCO_2$alkenyl, $OCO_2$alkynyl, $OCO_2$cycloalkyl, $OCO_2$aryl, $OCO_2$heteroaryl, $OCO_2$heterocycloalkyl, OC(O)$NH_2$, OC(O)NHalkyl, OC(O)NHalkenyl, OC(O)NHalkynyl, OC(O)NHcycloalkyl, OC(O)NHaryl, OC(O)NHheteroaryl, OC(O)NHheterocycloalkyl, NHC(O)alkyl, NHC(O)alkenyl, NHC(O)alkynyl, NHC(O)cycloalkyl, NHC(O)aryl, NHC(O)heteroaryl, NHC(O)heterocycloalkyl, $NHCO_2$alkyl, $NHCO_2$alkenyl, $NHCO_2$alkynyl, $NHCO_2$cycloalkyl, $NHCO_2$aryl, $NHCO_2$heteroaryl, $NHCO_2$heterocycloalkyl, NHC(O)$NH_2$, NHC(O)NHalkyl, NHC(O)NHalkenyl, NHC(O)NHalkenyl, NHC(O)NHcycloalkyl, NHC(O)NHaryl, NHC(O)NHheteroaryl, NHC(O)NHheterocycloalkyl, NHC(S)$NH_2$, NHC(S)NHalkyl, NHC(S)NHalkenyl, NHC(S)NHalkynyl, NHC(S)NHcycloalkyl, NHC(S)NHaryl, NHC(S)NHheteroaryl, NHC(S)NHheterocycloalkyl, NHC(NH)$NH_2$, NHC(NH)NHalkyl, NHC(NH)NHalkenyl, NHC(NH)NHalkenyl, NHC(NH)NHcycloalkyl, NHC(NH)NHaryl, NHC(NH)NHheteroaryl, NHC(NH)NHheterocycloalkyl, NHC(NH)alkyl, NHC(NH)alkenyl, NHC(NH)alkenyl, NHC(NH)cycloalkyl, NHC(NH)aryl, NHC(NH)heteroaryl, NHC(NH)heterocycloalkyl, C(NH)NHalkyl, C(NH)NHalkenyl, C(NH)NHalkynyl, C(NH)NHcycloalkyl, C(NH)NHaryl, C(NH)NHheteroaryl, C(NH)NHheterocycloalkyl, P(O)$(alkyl)_2$, P(O)$(alkenyl)_2$, P(O)$(alkynyl)_2$, P(O)$(cycloalkyl)_2$, P(O)$(aryl)_2$, P(O)$(heteroaryl)_2$, P(O)$(heterocycloalkyl)_2$, P(O)$(Oalkyl)_2$, P(O)$(OH)_2$, P(O)$(Oalkenyl)_2$, P(O)$(Oalkynyl)_2$, P(O)$(Ocycloalkyl)_2$, P(O)$(Oaryl)_2$, P(O)$(Oheteroaryl)_2$, P(O)$(Oheterocycloalkyl)_2$, S(O)alkyl, S(O)alkenyl, S(O)alkynyl, S(O)cycloalkyl, S(O)aryl, $S(O)_2$alkyl, $S(O)_2$alkenyl, $S(O)_2$alkynyl, $S(O)_2$cycloalkyl, $S(O)_2$aryl, S(O)heteroaryl, S(O)heterocycloalkyl, $SO_2NH_2$, $SO_2$NHalkyl, $SO_2$NHalkenyl, $SO_2$NHalkynyl, $SO_2$NHcycloalkyl, $SO_2$NHaryl, $SO_2$NHheteroaryl, $SO_2$NHheterocycloalkyl, $NHSO_2$alkyl, $NHSO_2$alkenyl, $NHSO_2$alkynyl, $NHSO_2$cycloalkyl, $NHSO_2$aryl, $NHSO_2$heteroaryl, $NHSO_2$heterocycloalkyl, $CH_2NH_2$, $CH_2SO_2CH_3$, alkyl, alkenyl, alkynyl, aryl, arylalkyl, heteroaryl, heteroarylalkyl, heterocycloalkyl, cycloalkyl, carbocyclic, heterocyclic, polyalkoxyalkyl, polyalkoxy, methoxymethoxy, methoxyethoxy, SH, S-alkyl, S-alkenyl, S-alkynyl, S-cycloalkyl, S-aryl, S-heteroaryl, S-heterocycloalkyl, or methylthiomethyl.

ii. Compounds

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof. The recitation of an embodiment herein includes that embodiment as any single embodiment or in combination with any other embodiments or portions thereof. As such, the following embodiments are present alone or in combination if applicable.

The present compounds present a pyrido[3,2-d]pyrimidine core structure to which is attached defined substituents to achieve the product's beneficial activity. Examples of pyridopyrimidine compounds as defined herein are illustrated by general Formula I:

Formula I

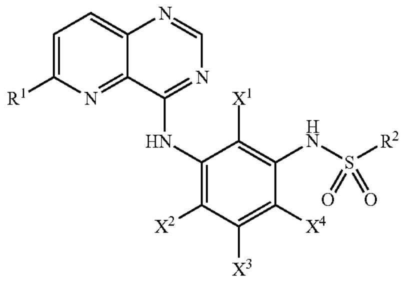

wherein:

$R^1$ is selected from substituted or unsubstituted $OR^3$, $SR^3$, $NH_2$, $NHR^3$, $N(R^3)_2$, $C_{3-8}$cycloalkyl, $C_{4-8}$heterocycloalkyl, $C_{6-10}$aryl and $C_{5-10}$heteroaryl, for example, selected from substituted or unsubstituted $C_{6-10}$aryl and $C_{5-10}$heteroaryl;

$R^2$ is selected from substituted $C_6$aryl or $C_{5-10}$heteroaryl, substituted or unsubstituted $C_{4-8}$heterocycloalkyl, and $N(R^3)_2$;

$R^3$ is independently in each occurrence selected from substituted or unsubstituted $C_{1-8}$alkyl, $C_{3-8}$cycloalkyl, $C_{4-8}$heterocycloalkyl, $C_{6-10}$aryl and $C_{5-10}$heteroaryl, preferably $R^3$ is a substituted or unsubstituted $C_{1-8}$alkyl (e.g. $C_{1-3}$alkyl);

$X^1$ is halo or an electron-withdrawing group;

$X^2$ is selected from H, halo, and an electron-withdrawing group;

$X^3$ and $X^4$ are each selected from H, halo, an electron-withdrawing group, $C_{1-3}$alkyl, $C_{3-4}$cycloalkyl, and $OC_{1-3}$alkyl;

or a pharmaceutically acceptable salt or solvate thereof.

For example, the electron-withdrawing group is selected from perhaloalkyl (e.g. $CF_3$ or $CCl_3$), CN, $NO_2$, sulfonate, alkylsulfonyl (e.g. $SO_2Me$ or $SO_2CF_3$), alkylcarbonyl (e.g. C(O)Me), carboxylate, alkoxycarbonyl (e.g. C(O)OMe), and aminocarbonyl (e.g. C(O)$NH_2$). In one embodiment, $X^1$ is Cl and $X^2$ is F, or $X^1$ is F and $X^2$ is H, or $X^1$ and $X^2$ are both F. In another embodiment, $X^3$ and $X^4$ are each H. In yet another embodiment, $X^3$ is F and $X^4$ is H.

For instance, the aminoarylsulfonamide moiety in Formula I may be designated L and preferably be selected from:

L1

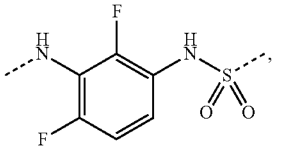

L2

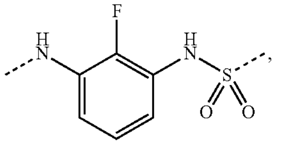

L3

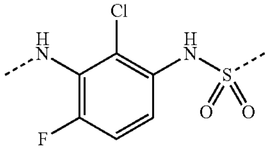

or

L4

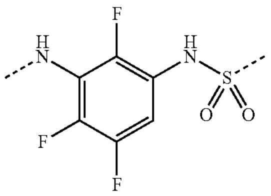

where the dashed line (---) represents a bond.

In one example, $R^2$ is a substituted $C_6$aryl or $C_{5-10}$heteroaryl, e.g. $R^2$ is a $C_6$aryl substituted with at least one group selected from F, Cl, Br, CN, $NO_2$, and a substituted or unsubstituted $C_{1-3}$alkyl, $C_{3-4}$cycloalkyl or $OC_{1-3}$alkyl group. For instance, $R^2$ is a group of the formula:

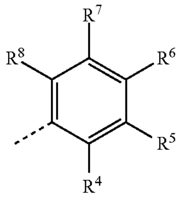

wherein:

$R^4$ is selected from H, F, Cl, Br, CN, and a substituted or unsubstituted $C_{1-3}$alkyl, $C_{3-4}$cycloalkyl or $OC_{1-3}$alkyl, e.g. $R^4$ is selected from H, F, Cl, Br, Me, Et, CN, $CHF_2$, and $CF_3$;

$R^5$ is selected from H, F, Cl, CN, and a substituted or unsubstituted $C_{1-3}$alkyl, $C_{3-4}$cycloalkyl, or $OC_{1-3}$alkyl, e.g. $R^5$ is selected from H, F, Me, $CF_3$, CN, and Cl;

$R^6$ is selected from H, F, Cl, Br, $NO_2$, $NH_2$, and a substituted or unsubstituted $C_{1-3}$alkyl, $C_{3-4}$cycloalkyl or $OC_{1-3}$alkyl, e.g. $R^6$ is selected from H, F, Cl, Br, and a substituted or unsubstituted $C_{1-3}$alkyl, $C_{3-4}$cycloalkyl or $OC_{1-3}$alkyl, or $R^6$ is selected from H, F, Cl, Me, Et, and OMe;

$R^7$ is selected from H, F, Cl, and a substituted or unsubstituted $C_{1-3}$alkyl, e.g. $R^7$ is selected from H, Me, F, and Cl;

$R^8$ is selected from H, F, and a substituted or unsubstituted $C_{1-3}$alkyl, e.g. $R^7$ is selected from H, Me and F;

or $R^4$ and $R^5$ or $R^5$ and $R^6$ are taken together with their adjacent carbon atoms to form a substituted or unsubstituted carbocycle or heterocycle provided that the heterocycle ($R^2$) is not a benzoxazolinone; and (---) represents a bond;

wherein when $R^4$ is H or F, then at least one of $R^5$, $R^6$, $R^7$ or $R^3$ is other than H or F; and wherein when $R^5$ is CN, then at least one of $R^4$, $R^6$, $R^7$ or $R^3$ is other than H.

In one embodiment, $R^3$ is H. In another embodiment, $R^4$ is selected from F, Cl, Et and Me, $R^5$, $R^7$, and $R^3$ are each H, and $R^6$ is selected from H, C, Me and OMe. In a further embodiment, $R^4$ is selected from F, Cl, and Me, $R^5$ is selected from F and Cl, and $R^6$, $R^7$ and $R^3$ are each H.

In another embodiment, $R^4$ is selected from C, Br and Me, $R^5$ is selected from H, F, Cl or methyl, $R^6$ is selected from H, F, Cl, Me and OMe, and $R^7$ and $R^3$ are each H.

In a further embodiment, $R^4$ is selected from C and a substituted or unsubstituted $C_{1-3}$alkyl (e.g. Me), preferably $R^4$ is Cl or Me; $R^5$ is selected from H, F, Cl, and a substituted or unsubstituted $C_{1-3}$alkyl (e.g., Me), preferably $R^5$ is F, Cl or Me; $R^6$ is selected from H, F, Cl, a substituted or unsubstituted $C_{1-3}$alkyl (e.g., Me), and a substituted or unsubstituted $OC_{1-3}$alkyl (e.g. $OCH_3$), preferably $R^6$ is H or F, or $R^6$ is Cl or a substituted or unsubstituted $C_{1-3}$alkyl or substituted or unsubstituted $OC_{1-3}$alkyl, or $CH_3$ or $OCH_3$; and $R^7$ and $R^3$ are each H. In yet another embodiment, $R^6$ is a substituted $C_{1-3}$alkyl.

In another example, $R^2$ is a substituted $C_{5-10}$heteroaryl, such as a group of the formula:

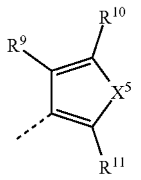

wherein:

$X^5$ is selected from NH, $NC_{1-3}$alkyl, $NC_{3-4}$cycloalkyl, O and S;

$R^9$, $R^{10}$, $R^{11}$ are each independently selected from H, F, Cl, CN, and a substituted or unsubstituted $C_{1-3}$alkyl, $C_{3-4}$cycloalkyl, $C(O)OC_{1-3}$alkyl or $OC_{1-3}$alkyl, provided that one of $R^9$ and $R^{11}$ is H and the other is not H; and (---) represents a bond.

Alternatively, $R^2$ is a group of the formula:

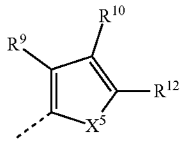

wherein:

$X^5$ is selected from NH, $NC_{1-3}$alkyl, $NC_{3-4}$cycloalkyl, O and S;

$R^9$ is selected from F, Cl, CN, and a substituted or unsubstituted $C_{1-3}$alkyl, $C_{3-4}$cycloalkyl, $C(O)OC_{1-3}$alkyl or $OC_{1-3}$alkyl;

$R^{10}$ and $R^{12}$ are each independently selected from H, F, Cl, CN, and a substituted or unsubstituted $C_{1-3}$alkyl, $C_{3-4}$cycloalkyl, $C(O)OC_{1-3}$alkyl or $OC_{1-3}$alkyl; and (---) represents a bond.

In a preferred embodiment, $R^9$ and $R^{10}$ are each independently selected from F, Cl, CN, and a substituted or unsubstituted $C_{1-3}$alkyl, $C_{3-4}$cycloalkyl, $C(O)OC_{1-3}$alkyl or $OC_{1-3}$ alkyl, preferably Cl and a substituted or unsubstituted $C_{1-3}$alkyl, more preferably $R^9$ and $R^{10}$ are both Cl. In another embodiment, $X^5$ is O or S, preferably S.

In another embodiment, $R^2$ is a substituted $C_{5-10}$heteroaryl, such as a group of the formula:

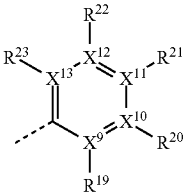

wherein:

$X^9$, $X^{10}$, $X^{11}$, $X^{12}$, and $X^{13}$ are independently selected from N and C, wherein at least one and at most two of $X^9$, $X^{10}$, $X^{11}$, $X^{12}$, and $X^{13}$ are N; and $R^{19}$, $R^{20}$, $R^{21}$, $R^{22}$ and $R^{23}$ are selected from H, F, Cl, Br, CN, $NO_2$, $NH_2$, and a substituted or unsubstituted $C_{1-3}$alkyl, $C_{3-4}$cycloalkyl or $OC_{1-3}$alkyl, or are absent when their attached $X^9$, $X^{10}$, $X^{11}$, $X^{12}$, or $X^{13}$ is N;

wherein at least one of $X^9$ and $X^{13}$ is not N; and wherein when one of $X^9$ and $X^{13}$ is N, then the other is not N or CH.

In another example, $R^2$ is a $C_{57}$heterocycloalkyl. For instance, $R^2$ is a group of the formula:

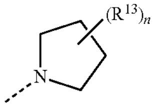

wherein:

$R^{13}$ is independently in each occurrence selected from F, Cl, and a substituted or unsubstituted $C_{1-3}$alkyl, $C_{3-4}$cycloalkyl, or $C_{1-3}$alkoxy;

n is an integer selected from 0 to 8; or n is between 2 and 8 and two $R^{13}$ are taken together with their adjacent carbon atoms to form a $C_{3-4}$cycloalkyl ; and (---) represents a bond.

In one embodiment, $R^{13}$ is in the 3-position. In another embodiment, n is 1 or 2, and $R^{13}$ is selected from F, Me, OMe, and $CH_2OMe$. For instance, $R^{13}$ is a methoxy group and n is 1.

In a further embodiment, $R^2$ is $N(R^3)_2$, for instance, wherein $R^3$ is selected from substituted or unsubstituted $C_{1-8}$alkyl or $C_{3-8}$cycloalkyl.

Non-limiting examples of $R^2$ are as follow:

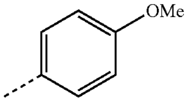
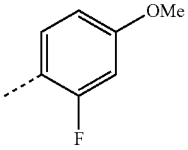

-continued

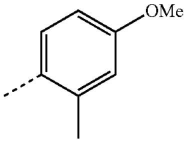
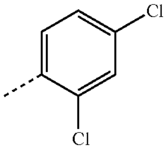
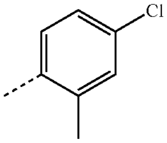
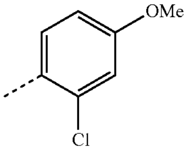
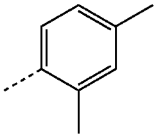
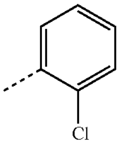
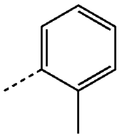
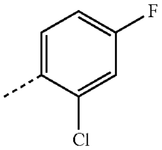
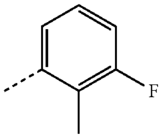
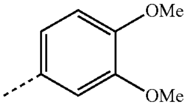
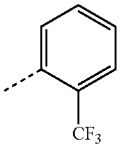
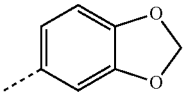
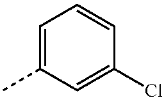
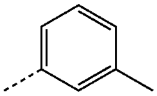
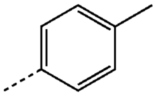
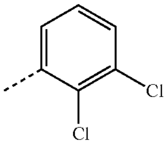
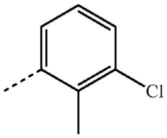
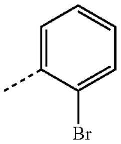
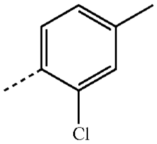
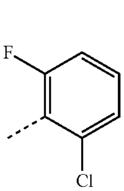
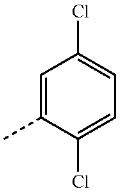
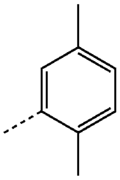
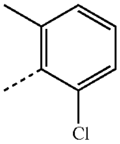
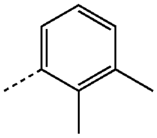
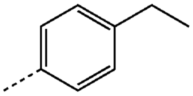
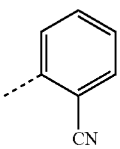
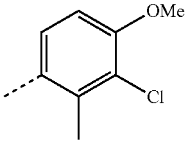
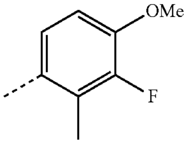
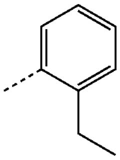
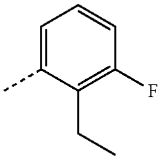
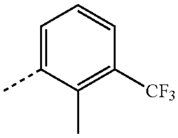

-continued
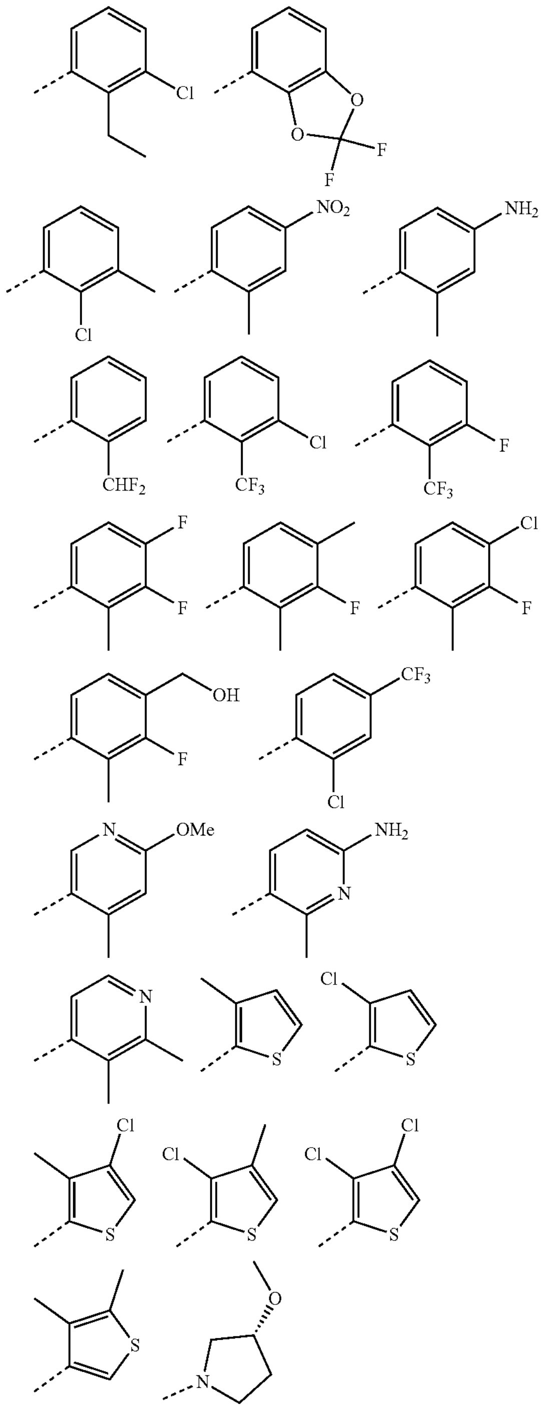
wherein (----) represents a bond.
In one embodiment, $R^2$ is a group selected from:
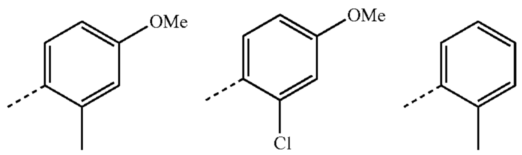
-continued
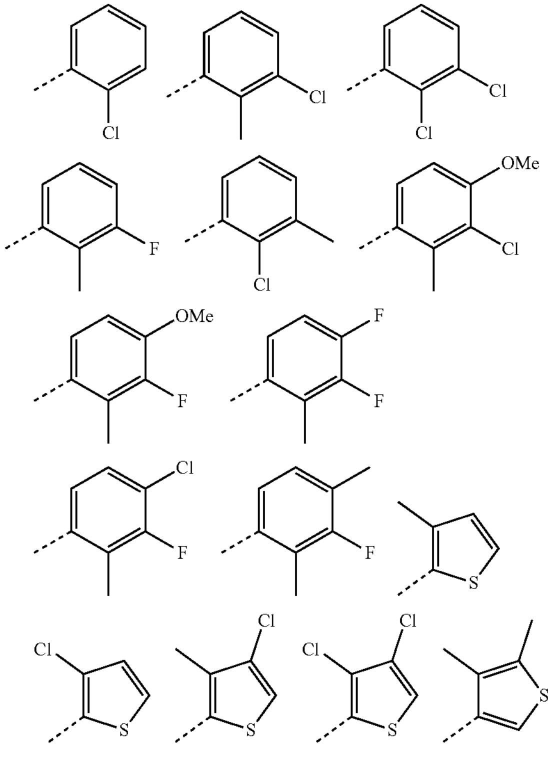
wherein (----) represents a bond.
In another embodiment, $R^2$ is a group selected from:
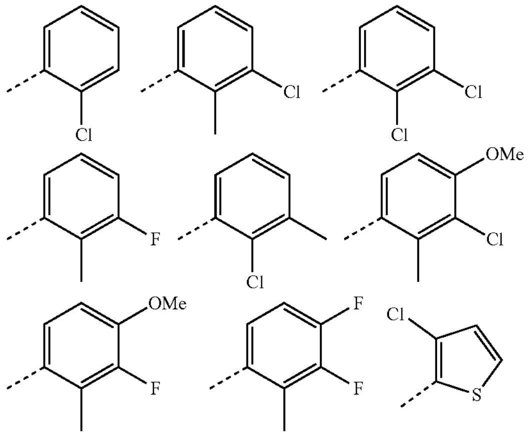
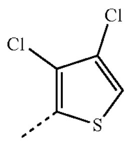
wherein (----) represents a bond.
In a further embodiment, the compound of Formula I is a compound of Formula II, or a pharmaceutically acceptable salt or solvate thereof:

Formula II

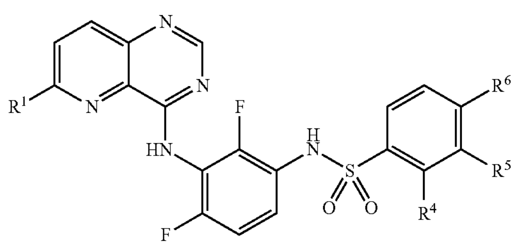

wherein $R^1$, $R^4$, $R^5$, and $R^6$ are each independently as defined herein, preferably, $R^4$ is selected from Cl, Br and Me, $R^5$ is selected from H, F, Cl or methyl, and $R^6$ is selected from H, F, Cl, Me and OMe.

In yet another embodiment, the compound of Formula I is a compound of Formula III, or a pharmaceutically acceptable salt or solvate thereof:

Formula III

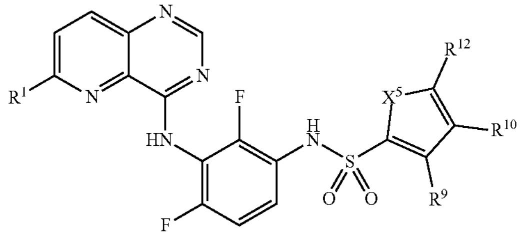

wherein $R^1$, $R^9$, $R^{10}$, $R^{12}$, and $X^5$ are each independently as defined herein.

In one embodiment of the compound of Formula I or II, $R^1$ is a substituted or unsubstituted $C_{5-6}$ heteroaryl group, or a substituted or unsubstituted $C_9$heteroaryl group. In another embodiment, $R^1$ is a substituted or unsubstituted group selected from thienyl, imidazolyl, pyrazolyl, triazolyl, thiazolyl, pyridyl, pyrimidinyl, indolyl, indazolyl, benzimidazolyl, benzotriazolyl, pyrrolopyridinyl (e.g. pyrrolo[3,2-b]pyridinyl or pyrrolo[3,2-c]pyridinyl), pyrazolopyridinyl (e.g. pyrazolo[1,5-a]pyridinyl), purinyl, imidazopyrazinyl (e.g. imidazo[4,5-b]pyrazinyl), and quinolyl (quinolinyl).

Examples of $R^1$ include a substituted or unsubstituted group selected from:

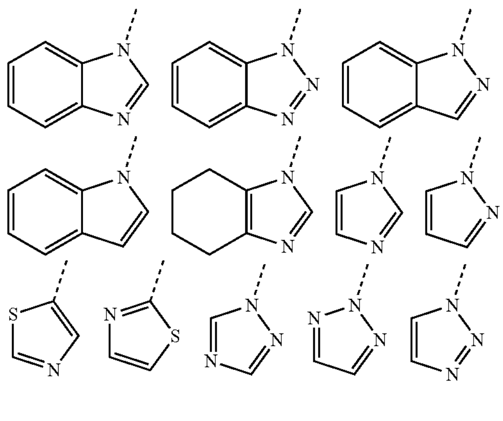

-continued

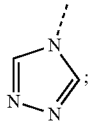

wherein ( --- ) represents a bond.

For instance, $R^1$ is a substituted or unsubstituted group selected from:

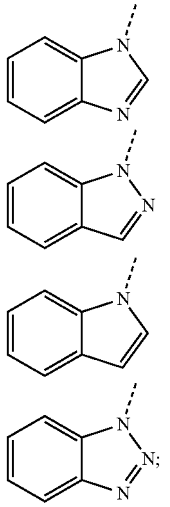

wherein ( --- ) represents a bond.

In one embodiment, $R^1$ is one of the above groups further substituted with at least one substituent selected from OH, halo, CN, $NO_2$, $C_{1-6}$alkyl, $C_{2-6}$alkenyl, $C_{2-6}$alkynyl, $OC_{1-6}$ alkyl, $C_{5-10}$heteroaryl, $C_{3-10}$cycloalkyl, $C_{4-10}$heterocycloalkyl, $C(O)R^{15}$, $C(O)N(R^{14})_2$, $SO_2R^{15}$, $SO_2N(R^{14})_2$, $N(R^{16})C(O)R^{15}$, $N(R^{16})SO_2R^{15}$, $N(R^{16})C(O)N(R^{14})_2$, $N(R^{16})SO_2N(R^{14})_2$, $N(R^{14})_2$, $P(O)(R^{15})_2$, $CH_2C(O)R^{15}$, $CH_2C(O)N(R^{14})_2$, $CH_2SO_2R^{15}$, $CH_2SO_2N(R^{14})_2$, $CH_2N(R^{16})C(O)R^{15}$, $CH_2N(R^{16})SO_2R^{15}$, $CH_2N(R^{16})C(O)N(R^{14})_2$, $CH_2N(R^{16})SO_2N(R^{14})_2$, and $CH_2N(R^{14})_2$;

wherein:

$R^{14}$ is independently in each occurrence selected from H, $C_{1-6}$alkyl, $C_{2-6}$alkenyl, $C_{2-6}$alkynyl, $C_{3-10}$cycloalkyl, $C_{4-10}$heterocycloalkyl, $C_6$aryl, and $C_{5-10}$heteroaryl, or two $R^{14}$ are taken together with their adjacent nitrogen atom to form a $C_{4-10}$heterocycloalkyl group;

$R^{15}$ is independently in each occurrence selected from $C_{1-6}$alkyl, $C_{2-6}$alkenyl, $C_{2-6}$alkynyl, $C_{3-7}$cycloalkyl, $C_6$aryl, and $C_{5-6}$heteroaryl; and $R^{16}$ is independently in each occurrence selected from H, $C_{1-6}$alkyl, $C_{2-6}$alkenyl, $C_{2-6}$alkynyl, $C_{3-7}$cycloalkyl, $C_6$aryl, and $C_{5-6}$heteroaryl;

wherein said alkyl, alkenyl, alkynyl, cycloalkyl, heterocycloalkyl, aryl or heteroaryl group, included in $R^1$ (including in the definitions of $R^{14}$, $R^{15}$, and $R^{16}$), is optionally further substituted.

In another embodiment, $R^1$ is a group of the formula:

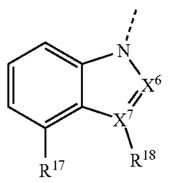

wherein:

$R^{17}$ is selected from H, OH, halo, CN, $NO_2$, $C_{1-6}$alkyl, $C_{2-6}$alkenyl, $C_{2-6}$alkynyl, $OC_{1-6}$alkyl, $C_{5-10}$heteroaryl, $C_{3-10}$cycloalkyl, $C_{4-10}$heterocycloalkyl, $C(O)R^{15}$, $C(O)N(R^{14})_2$, $SO_2R^{15}$, $SO_2N(R^{14})_2$, $N(R^{16})C(O)R^{15}$, $N(R^{16})SO_2R^{15}$, $N(R^{16})C(O)N(R^{14})_2$, $N(R^{16})SO_2N(R^{14})_2$, $N(R^{14})_2$, $P(O)(R^{15})_2$, $CH_2C(O)R^{15}$, $CH_2C(O)N(R^{14})_2$, $CH_2SO_2R^{15}$, $CH_2SO_2N(R^{14})_2$, $CH_2N(R^{16})C(O)R^{15}$, $CH_2N(R^{16})SO_2R^{15}$, $CH_2N(R^{16})C(O)N(R^{14})_2$, $CH_2N(R^{16})SO_2N(R^{14})_2$, and $CH_2N(R^{14})_2$;

$X^6$ is N or CH; and $X^7$ is N and $R^{18}$ is absent; or $X^7$ is C and $R^{18}$ is selected from $C_{1-6}$alkyl, $C_{2-6}$alkenyl, $C_{2-6}$alkynyl, $OC_{1-6}$alkyl, $C_{5-10}$heteroaryl, $C_{3-10}$cycloalkyl, $C_{4-10}$heterocycloalkyl, $C(O)R^{15}$, $C(O)N(R^{14})_2$, $SO_2R^{15}$, $SO_2N(R^{14})_2$, $N(R^{16})C(O)R^{15}$, $N(R^{16})SO_2R^{15}$, $N(R^{16})C(O)N(R^{14})_2$, $N(R^{16})SO_2N(R^{14})_2$, $N(R^{14})_2$, $P(O)(R^{15})_2$, $CH_2C(O)R^{15}$, $CH_2C(O)N(R^{14})_2$, $CH_2SO_2R^{15}$, $CH_2SO_2N(R^{14})_2$, $CH_2N(R^{16})C(O)R^{15}$, $CH_2N(R^{16})SO_2R^{15}$, $CH_2N(R^{16})C(O)N(R^{14})_2$, $CH_2N(R^{16})SO_2N(R^{14})_2$, and $CH_2N(R^{14})_2$;

wherein $R^{14}$, $R^{15}$, and $R^{16}$ are as defined above;

wherein said alkyl, alkenyl, alkynyl, cycloalkyl, heterocycloalkyl, or heteroaryl, included in $R^1$ (including in the definitions of $R^1$, $R^{15}$, $R^{16}$, $R^{17}$ and $R^{18}$), is optionally further substituted; and wherein (---) represents a bond.

In another embodiment, $R^1$ is a group of the formula:

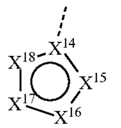

wherein:

$X^{14}$ is selected from C and N;

$X^{15}$, $X^{16}$, $X^{17}$, and $X^{18}$ are independently selected from O, N, S, and $CR^{17}$, wherein $R^{17}$ is as herein defined;

wherein at least one and at most three of $X^{14}$, $X^{15}$, $X^{16}$, $X^{17}$, and $X^{18}$ are O, N, or S, and two double bonds and present in the cycle in order for aromaticity to be maintained.

In a further embodiment, the compound of Formula I is a compound of Formula IV or V, or a pharmaceutically acceptable salt or solvate thereof:

Formula IV

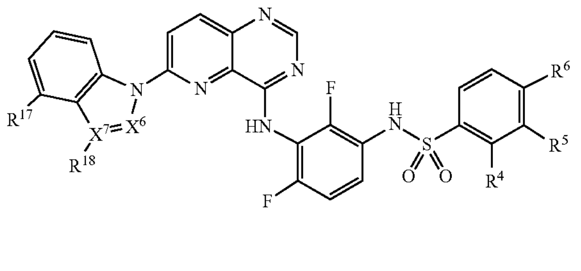

-continued

Formula V

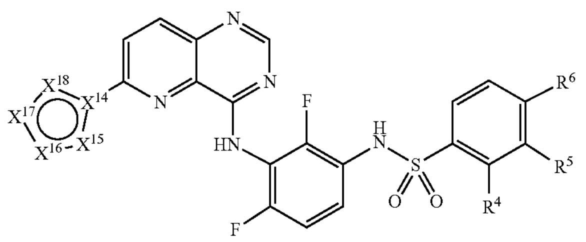

wherein $R^4$, $R^5$, $R^6$, $R^{17}$, $R^{18}$, $X^6$, $X^7$, $X^{14}$, $X^{15}$, $X^{16}$, $X^{17}$, and $X^{18}$ are each independently as defined herein, preferably $R^4$ is selected from Cl, Br and Me, $R^5$ is selected from H, F, Cl or methyl, and $R^6$ is selected from H, F, Cl, Me and OMe.

In a further embodiment, the compound of Formula I is a compound of Formula VI or VII, or a pharmaceutically acceptable salt or solvate thereof:

Formula VI

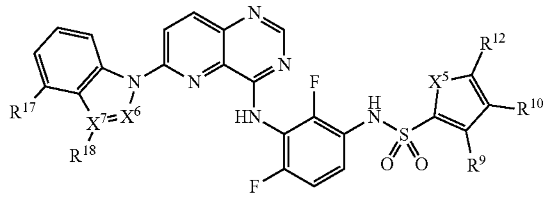

Formula VII

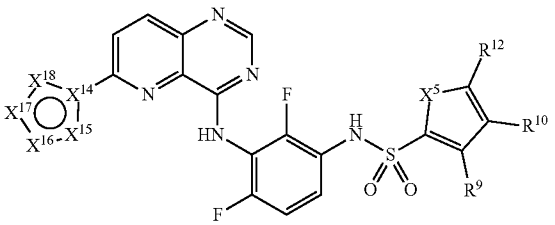

wherein $R^9$, $R^{10}$, $R^{12}$, $R^{17}$, $R^{18}$, $X^5$, $X^6$, $X^7$, $X^{14}$, $X^{15}$, $X^{16}$, $X^{17}$ and $X^{18}$ are each independently as defined herein.

In one embodiment of the above formulae, $X^6$ is N. In another embodiment, $X^6$ is CH.

In another embodiment, $X^7$ is N, $R^{17}$ is selected from H, OH, CN, $C_{1-6}$alkyl, $C_{2-6}$alkenyl, $C_{2-6}$alkynyl, $OC_{1-6}$alkyl, $C_{5-10}$heteroaryl, $C_{3-10}$cycloalkyl, $C_{4-10}$heterocycloalkyl, $C(O)R^{15}$, $C(O)N(R^{14})_2$, $SO_2R^{15}$, $SO_2N(R^{14})_2$, $N(R^{16})C(O)R^{15}$, $N(R^{16})SO_2R^{15}$, $N(R^{16})C(O)N(R^{14})_2$, $N(R^{16})SO_2N(R^{14})_2$, $N(R^{14})_2$, $P(O)(R^{15})_2$, $CH_2C(O)R^{15}$, $CH_2C(O)N(R^{14})_2$, $CH_2SO_2R^{15}$, $CH_2SO_2N(R^{14})_2$, $CH_2N(R^{16})C(O)R^{15}$, $CH_2N(R^{16})SO_2R^{15}$, $CH_2N(R^{16})C(O)N(R^{14})_2$, $CH_2N(R^{16})SO_2N(R^{14})_2$, and $CH_2N(R^{14})_2$, and $R^{18}$ is absent, wherein said alkyl, alkenyl, alkynyl, cycloalkyl, heterocycloalkyl, or heteroaryl, in $R^{14}$, $R^{15}$, $R^{16}$, or $R^{17}$, is optionally further substituted, preferably $R^{17}$ is selected from $C_{1-6}$alkyl, $C_{5-10}$heteroaryl, $C_{4-10}$heterocycloalkyl, $N(R^{14})_2$, $N(R^{16})C(O)R^{15}$, $N(R^{16})SO_2R^{15}$, $C(O)N(R^{14})_2$, and $SO_2N(R^{14})_2$, wherein said alkyl, alkenyl, alkynyl, cycloalkyl, heterocycloalkyl, or heteroaryl, in $R^{14}$, $R^{15}$, $R^{16}$, or $R^{17}$, is optionally further substituted. For instance, $R^{17}$ is selected from $R^{17}$ is H, $NH_2$, and an optionally substituted $C_{5-10}$heteroaryl or $C_{4-10}$heterocycloalkyl, preferably $R^{17}$ is an optionally substituted $C_{5-10}$heteroaryl or $C_{4-10}$heterocycloalkyl.

In a further embodiment, $R^{17}$ is an optionally substituted $C_{4-10}$heterocycloalkyl, wherein said heterocycloalkyl may be mono or bicyclic and include from 1 to 3 heteroatoms, preferably wherein $X^7$ is N. In a preferred embodiment, the heterocycloalkyl is substituted, for instance, with at least one group selected from F, OH, oxo, CN, $C_{1-4}$alkyl and $OC_{1-4}$alkyl, wherein said $C_{1-4}$alkyl is optionally further substituted (e.g. with F, OH, $OC_{1-3}$alkyl, etc.). For instance, the heterocycloalkyl may be selected from optionally substituted piperidine, piperazine, thiomorpholine and morpholine groups, or a bicyclic structure (bridged or spiro) containing a piperidine, piperazine, thiomorpholine or morpholine ring.

In a further embodiment, $X^7$ is C, for instance, $X^7$ is C and $R^{18}$ is selected from $C_{1-6}$alkyl, $C_{5-10}$heteroaryl, $C_{3-10}$cycloalkyl, $C_{4-10}$heterocycloalkyl, $C(O)R^{15}$, $C(O)N(R^{14})_2$, $SO_2R^{15}$, $SO_2N(R^{14})_2$, $N(R^{16})C(O)R^{15}$, $N(R^{16})SO_2R^{15}$, $N(R^{16})C(O)N(R^{14})_2$, $N(R^{16})SO_2N(R^{14})_2$, $N(R^{14})_2$, $P(O)(R^{15})_2$, $CH_2C(O)R^{15}$, $CH_2C(O)N(R^{14})_2$, $CH_2SO_2R^{15}$, $CH_2SO_2N(R^{14})_2$, $CH_2N(R^{16})C(O)R^{15}$, $CH_2N(R^{16})SO_2R^{15}$, $CH_2N(R^{16})C(O)N(R^{14})_2$, $CH_2N(R^{16})SO_2N(R^{14})_2$, and $CH_2N(R^{14})_2$, wherein said alkyl, alkenyl, alkynyl, cycloalkyl, heterocycloalkyl, or heteroaryl, in $R^{14}$, $R^{15}$, $R^{16}$, or $R^{18}$, is optionally further substituted, preferably $R^{18}$ is selected from $C(O)N(R^{14})_2$, $SO_2R^{15}$, and $SO_2N(R^{14})_2$. In a subclass of these embodiments, $R^{17}$ is selected from H, OH, $C_{1-6}$alkyl, $N(R^{14})_2$, and an optionally substituted $C_{5-10}$heteroaryl. For instance, $R^{17}$ is selected from H, $NH_2$, and an optionally substituted $C_{5-10}$heteroaryl, preferably H or $NH_2$.

In yet another embodiment, $R^{14}$ is independently in each occurrence selected from H, optionally substituted $C_{1-6}$alkyl, optionally substituted $C_{3-10}$cycloalkyl, optionally substituted $C_{4-10}$heterocycloalkyl, and optionally substituted $C_{5-6}$heteroaryl, or two $R^{14}$ are taken together with their adjacent nitrogen atom to form a $C_{4-10}$heterocycloalkyl group.

In another embodiment, $R^{17}$ is $N(R^{14})_2$ wherein said $R^{14}$ are taken together with their adjacent nitrogen atom to form a $C_{4-10}$heterocycloalkyl group, wherein said heterocycloalkyl may be mono or bicyclic and include from 1 to 3 heteroatoms, preferably wherein $X^7$ is N. In a preferred embodiment, the heterocycloalkyl is substituted, for instance, with at least one group selected from F, OH, oxo, CN, $C_{1-4}$alkyl and $OC_{1-4}$alkyl, wherein said $C_{1-4}$alkyl is optionally further substituted (e.g. with F, OH, $OC_{1-3}$alkyl, etc.). For instance, the heterocycloalkyl may be selected from optionally substituted piperidine, piperazine, thiomorpholine and morpholine groups, or a bicyclic structure (bridged or spiro) containing a piperidine, piperazine, thiomorpholine or morpholine ring.

In another example, $R^1$ is selected from:

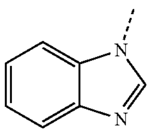 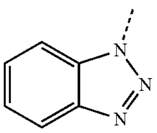 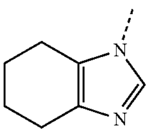

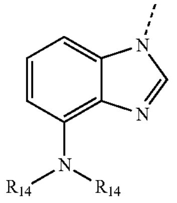 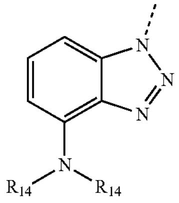

-continued

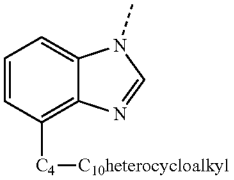 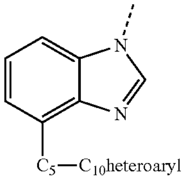

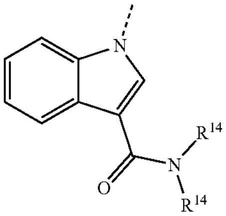 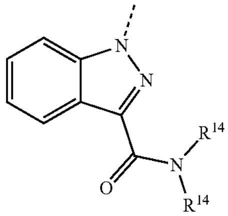

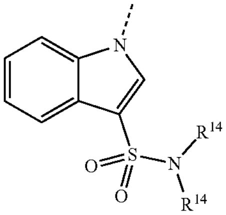 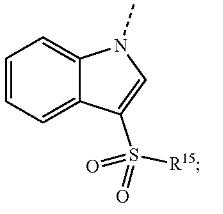

wherein $R^{14}$ is as defined herein and (---) represents a bond.

In a further example, $R^1$ is selected from:

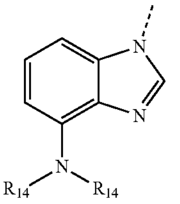 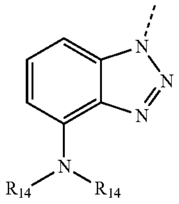

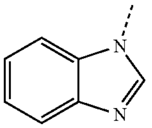 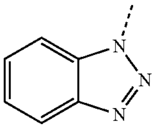

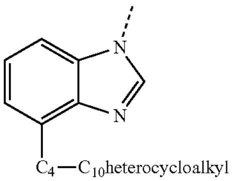 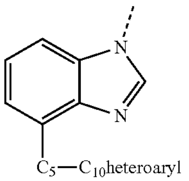

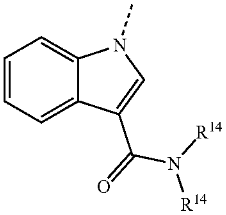 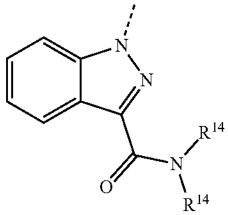

-continued

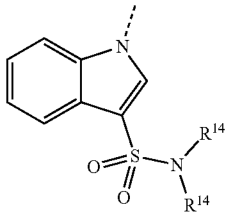

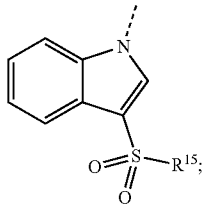

wherein $R^{14}$ is as defined herein and (----) represents a bond.

In a further embodiment, $R^1$ is a substituted or unsubstituted $C_4$.-heterocycloalkyl group. In another example, $R^1$ is a $C_{4-5}$heterocycloalkyl optionally substituted with one or two groups selected from halo, OH, $C_{1-6}$alkyl, and $OC_{1-6}$alkyl. For instance, $R^1$ is a N-pyrrolidinyl group substituted with one or two groups selected from F and OH.

Further subgeneric embodiments are also presented in the examples section, including for each $R^1$ (A group), $R^2$ (B group) and L groups. Examples of combinations are also set forth further below and in Tables 3, 4 and 5. Representative preferred compounds of Examples 1 to 691 are also described herein.

More specifically, preferred examples of $R^1$ are selected from groups A1 to A514 defined as follows:

A1

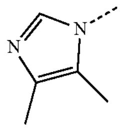

A2

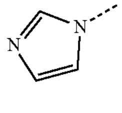

A3

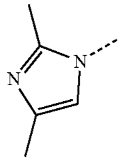

A4

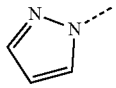

A5

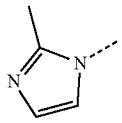

A6

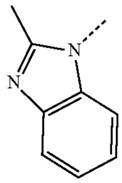

-continued

A7

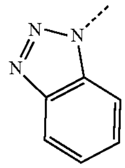

A8

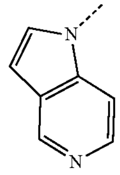

A9

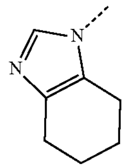

A10

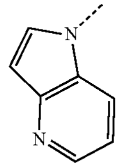

A11

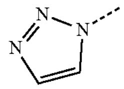

A12

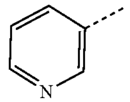

A13

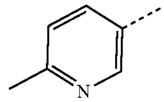

A14

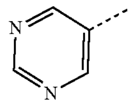

A15

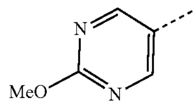

A16

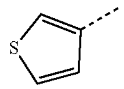

A17

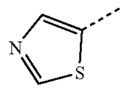

-continued
A18
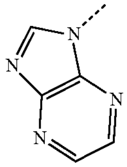
A19
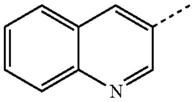
A20
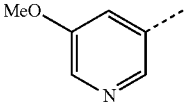
A21
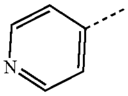
A22
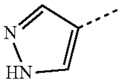
A23
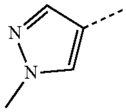
A24
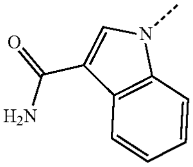
A25
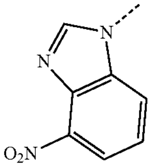
A26
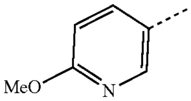
A27
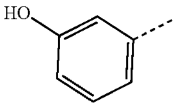
A28
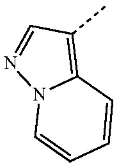
A29
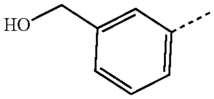
-continued
A30
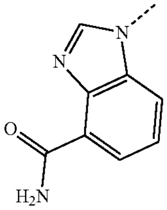
A31
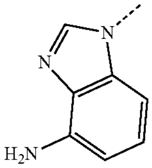
A32
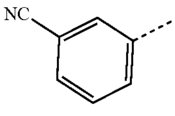
A33
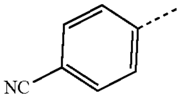
A34
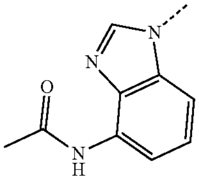
A35
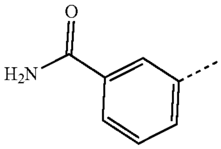
A36
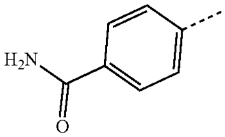
A37
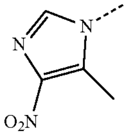
A38
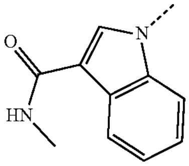
A39
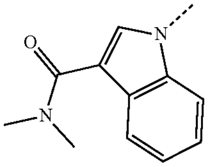

-continued
A40
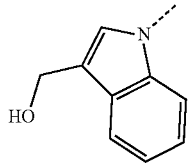
A41
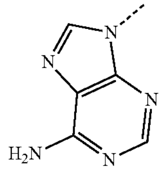
A42
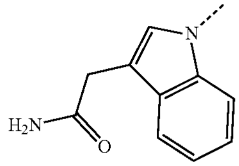
A43
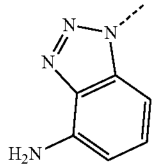
A44
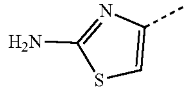
A45
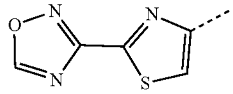
A46
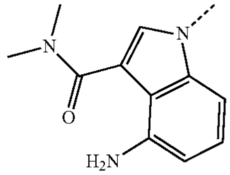
A47
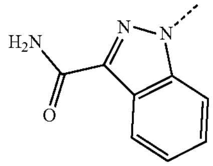
A48
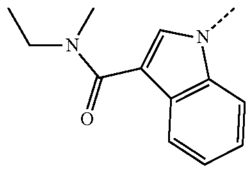
-continued
A49
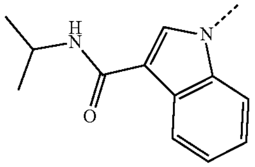
A50
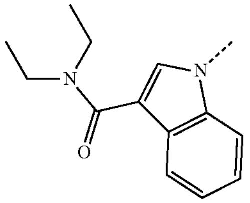
A51
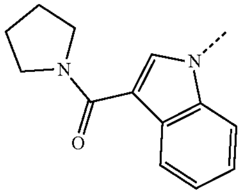
A52
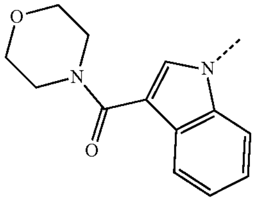
A53
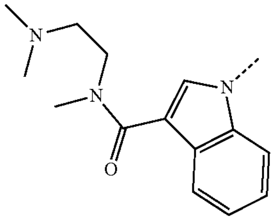
A54
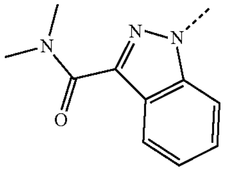
A55
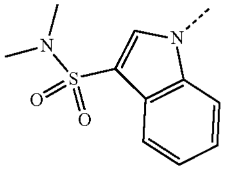
A56
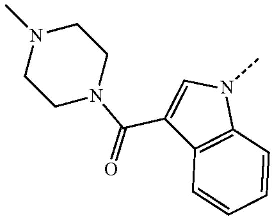

-continued
A57
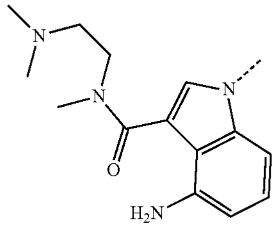
A58
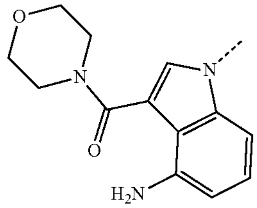
A59
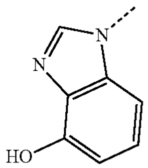
A60
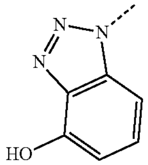
A61
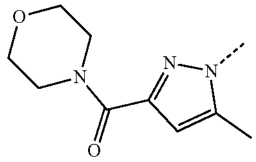
A62
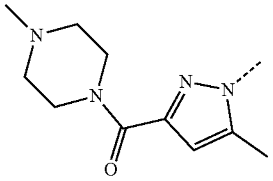
A63
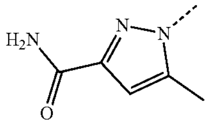
A64
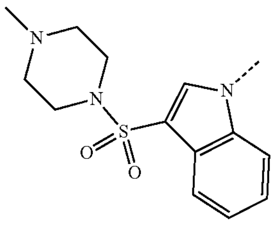
-continued
A65
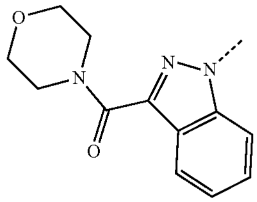
A66
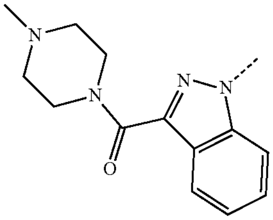
A67
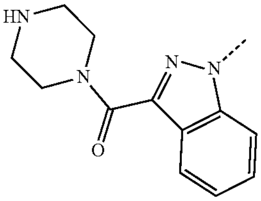
A68
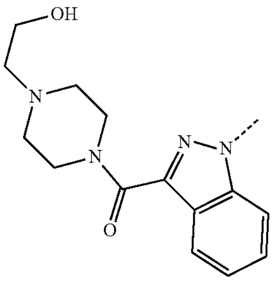
A69
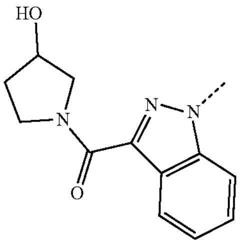
A70
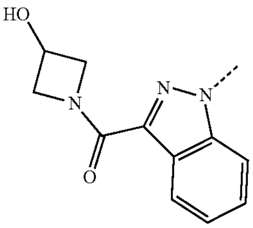

-continued
A71
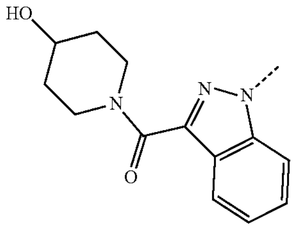
A72
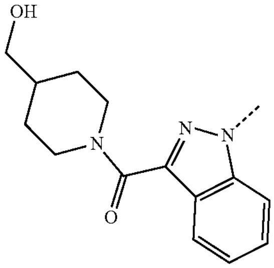
A73
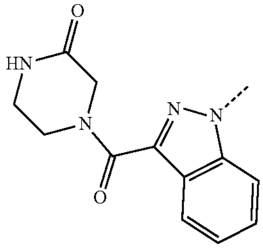
A74
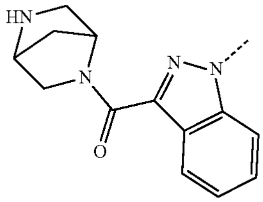
A75
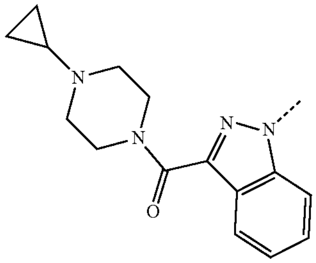
A76
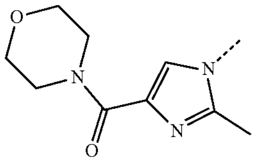
A77
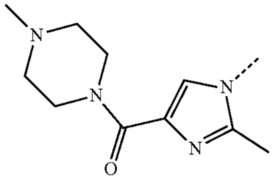
-continued
A78
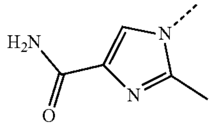
A79
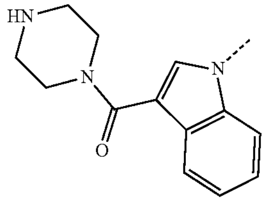
A80
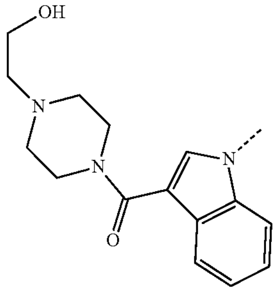
A81
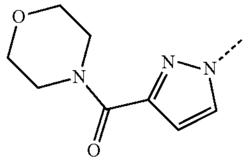
A82
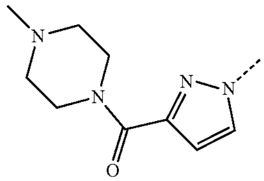
A83
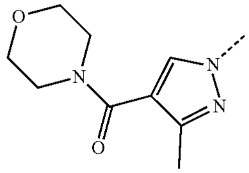
A84
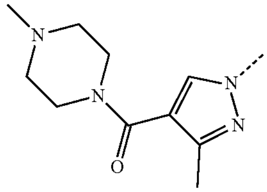
A85
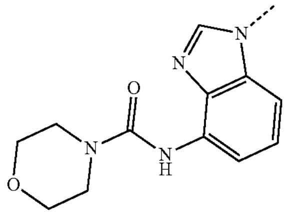

-continued
A86
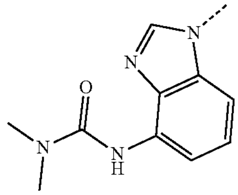
A87
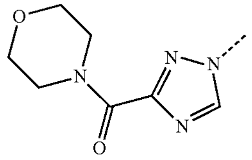
A88
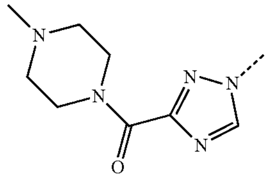
A89
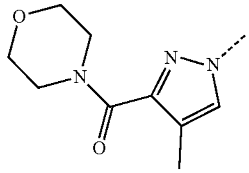
A90
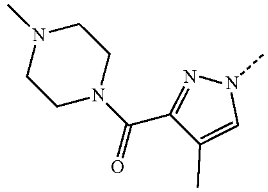
A91
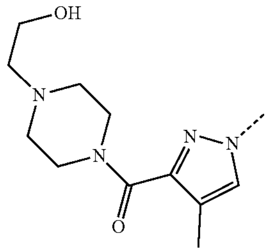
A92
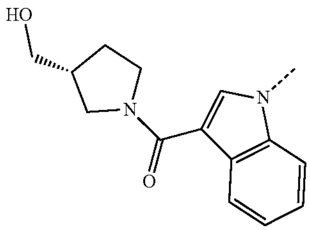
-continued
A93
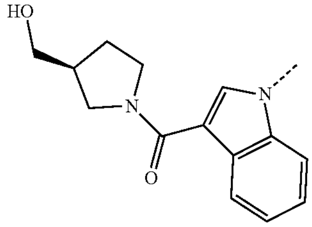
A94
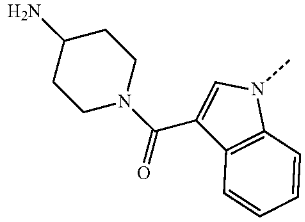
A95
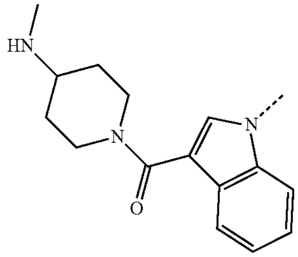
A96
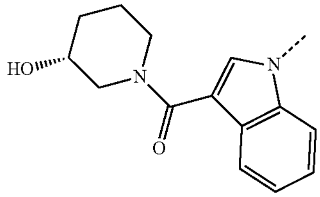
A97
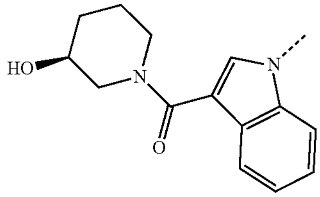
A98
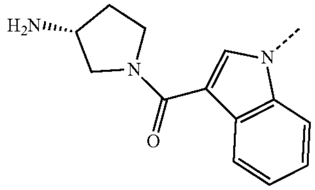
A99
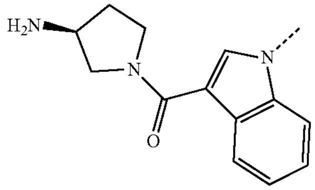

-continued
A100
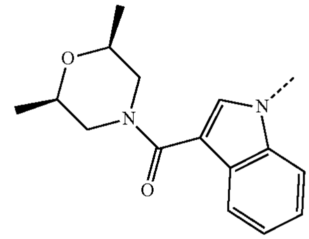
A101
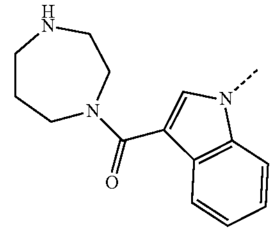
A102
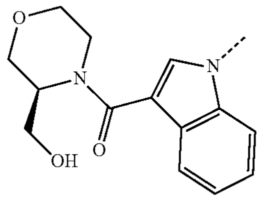
A103
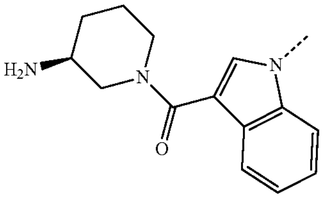
A104
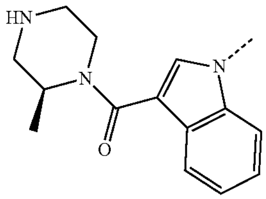
A105
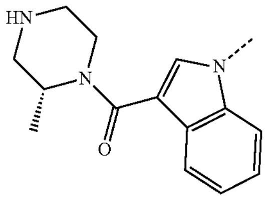
A106
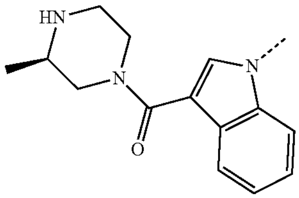
-continued
A107
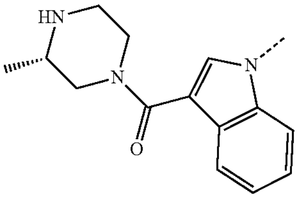
A108
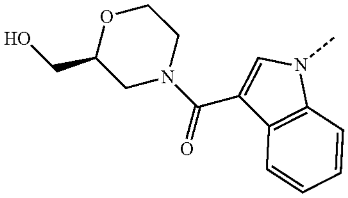
A109
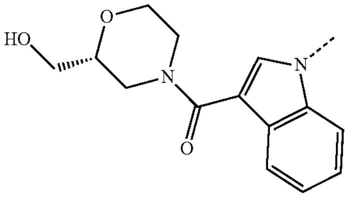
A110
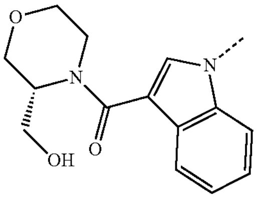
A111
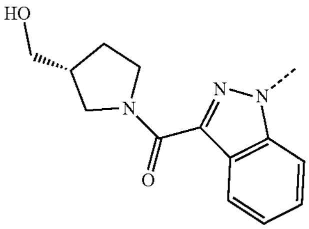
A112
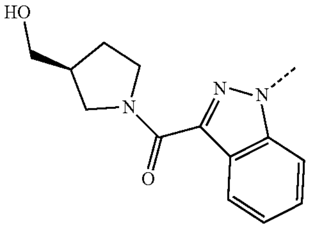
A113
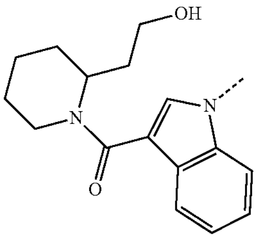

-continued
A114
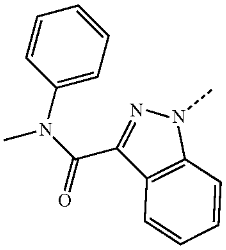
A115
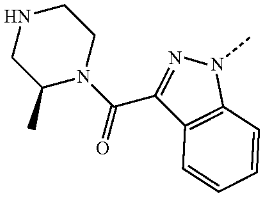
A116
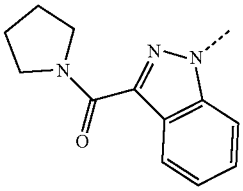
A117
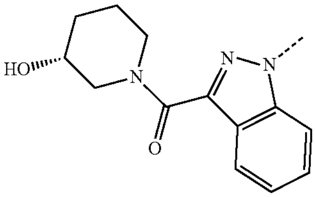
A118
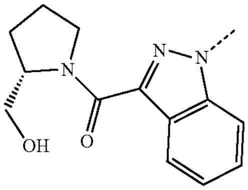
A119
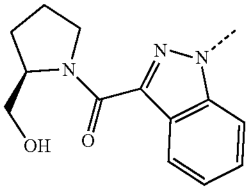
A120
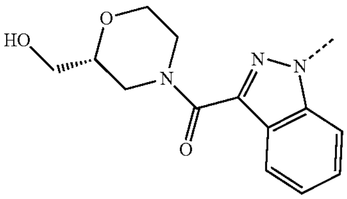
-continued
A121
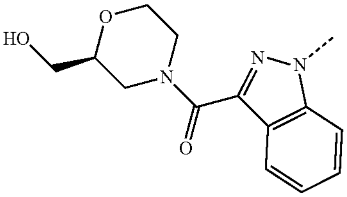
A122
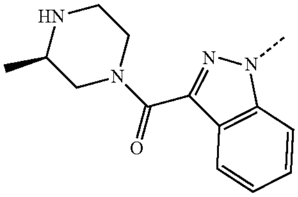
A123
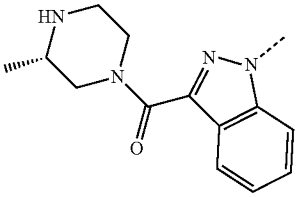
A124
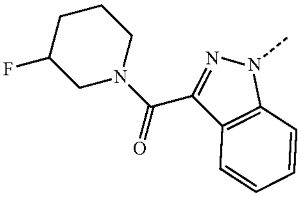
A125
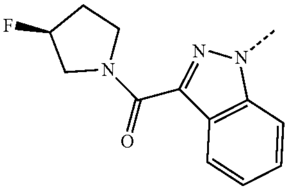
A126
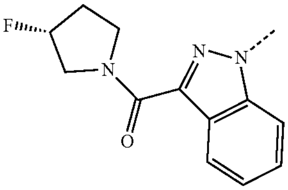
A127
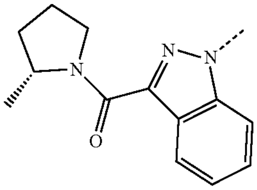
A128
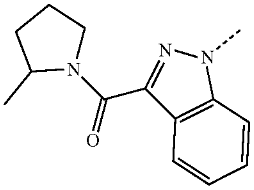

-continued
A129
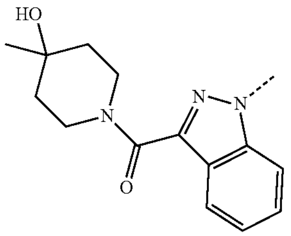
A130
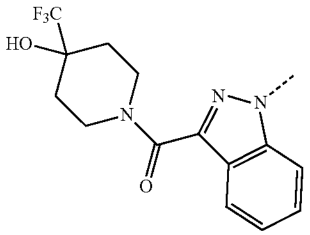
A131
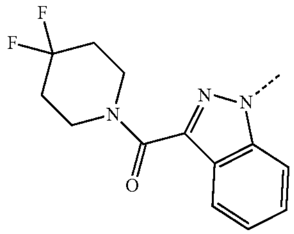
A132
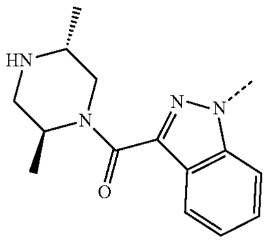
A133
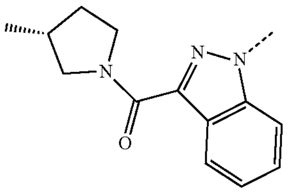
A134
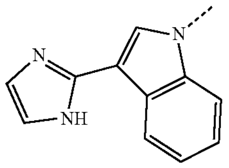
A135
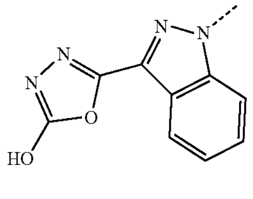
-continued
A136
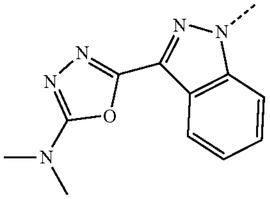
A137
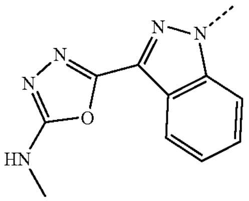
A138
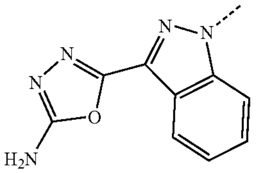
A139
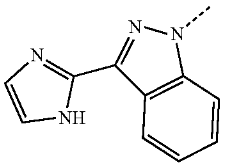
A140
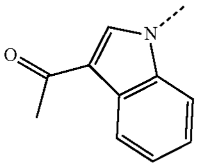
A141
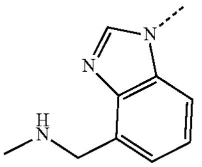
A142
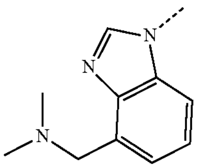
A143
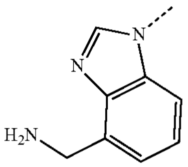

-continued
A144
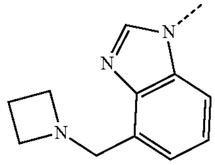
A145
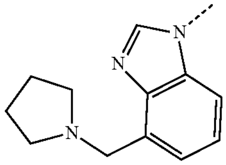
A146
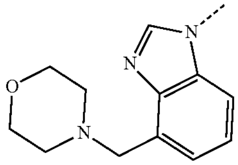
A147
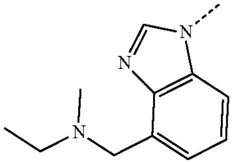
A148
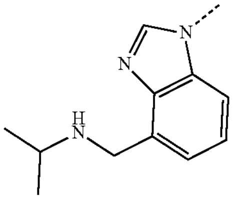
A149
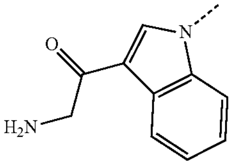
A150
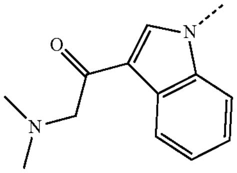
A151
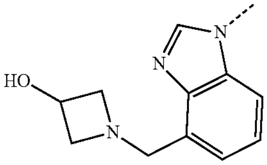
A152
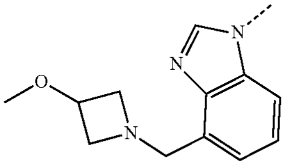
-continued
A153
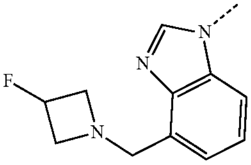
A154
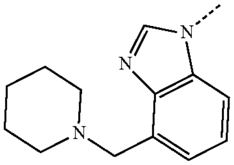
A155
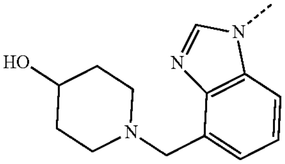
A156
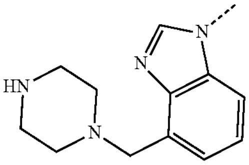
A157
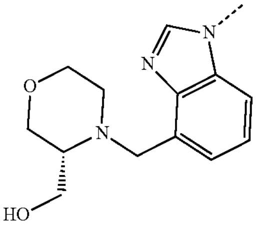
A158
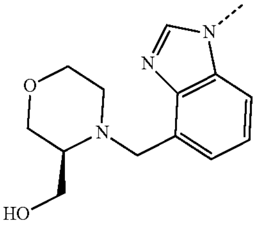
A159
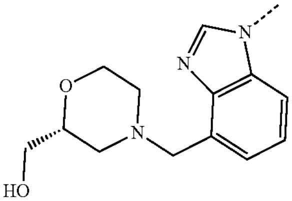
A160
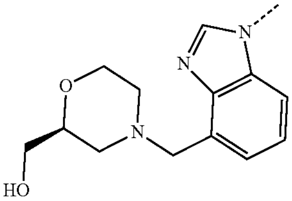

-continued
A161
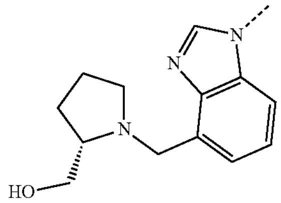
A162
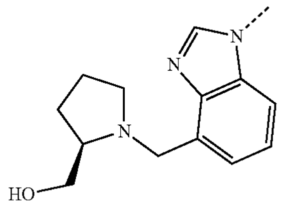
A163
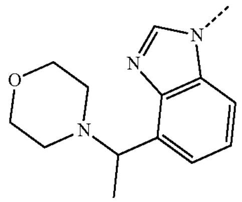
A164
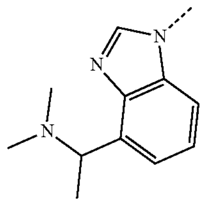
A165
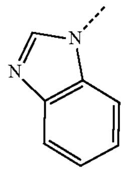
A166
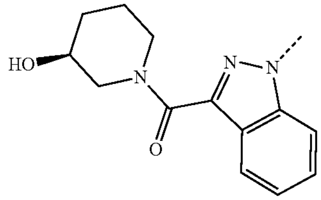
A167
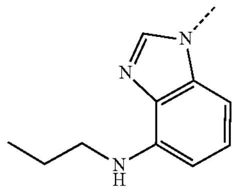
A168
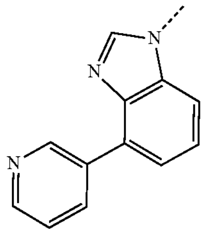
A169
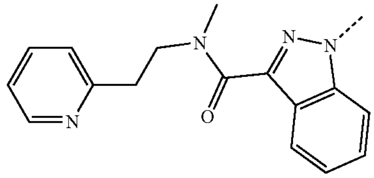
A170
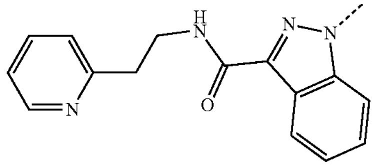
A171
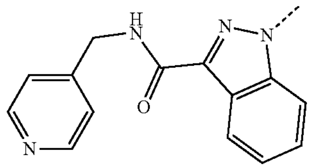
A172
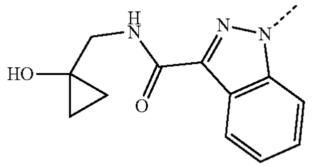
A173
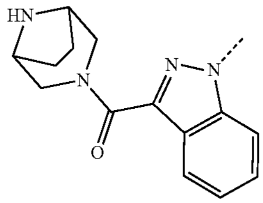
A174
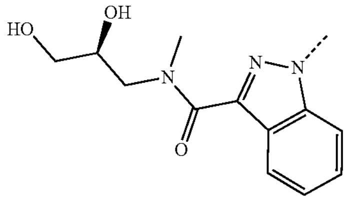
A175
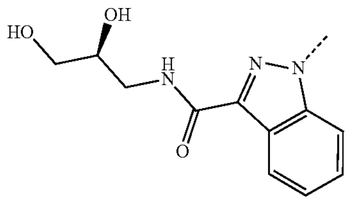

-continued
A176
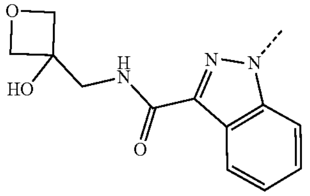
A177
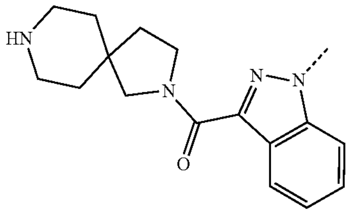
A178
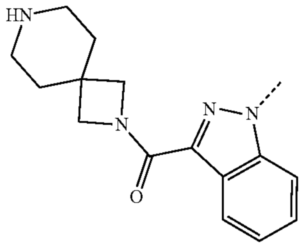
A179
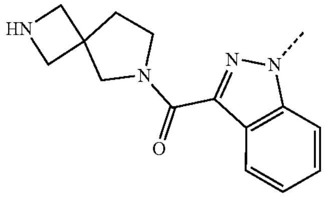
A180
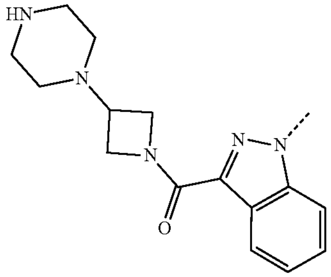
A181
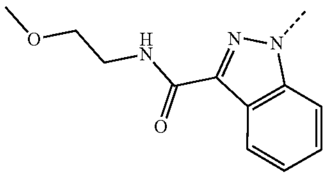
A182
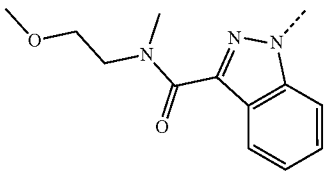
-continued
A183
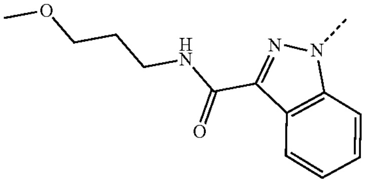
A184
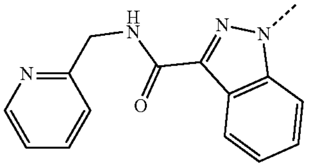
A185
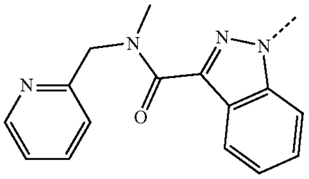
A186
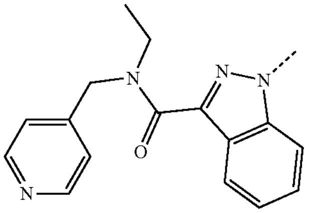
A187
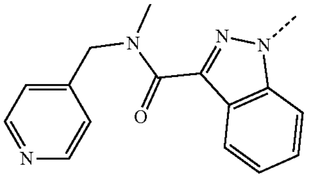
A188
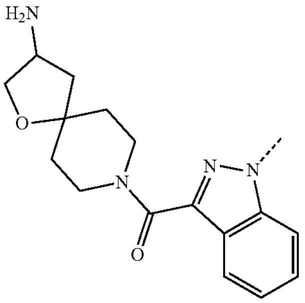
A189
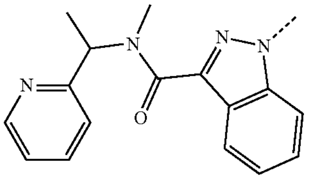

-continued
A190
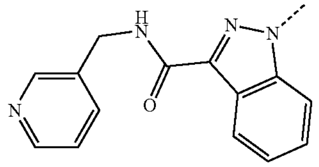
A191
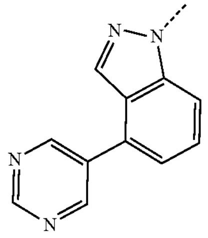
A192
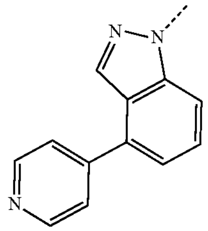
A193
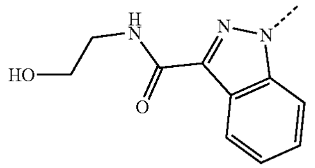
A194
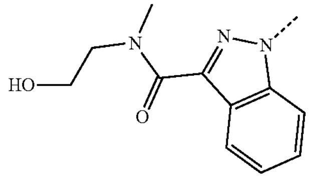
A195
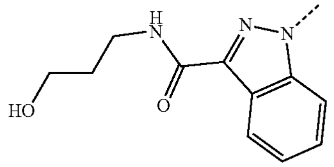
A196
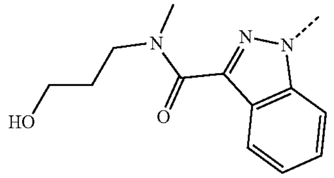
A197
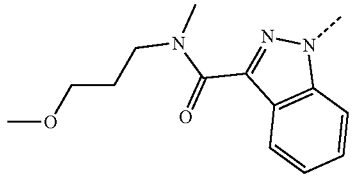
-continued
A198
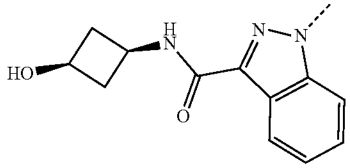
A199
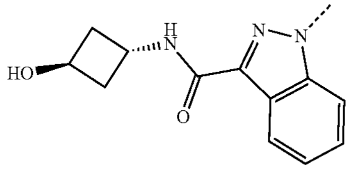
A200
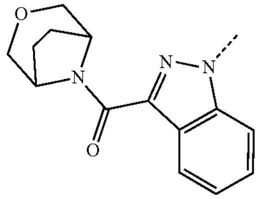
A201
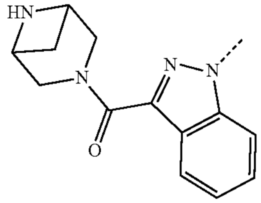
A202
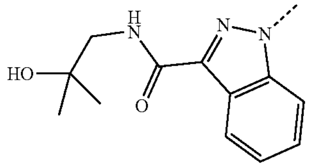
A203
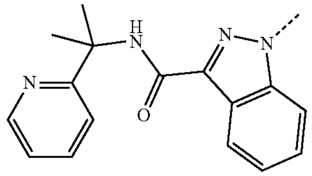
A204
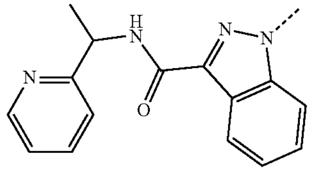
A205
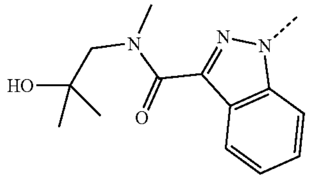

-continued
A206
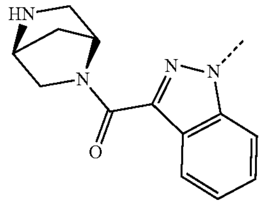
A207
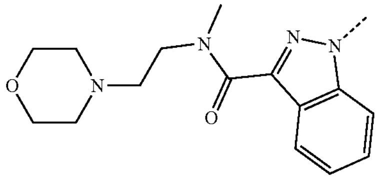
A208
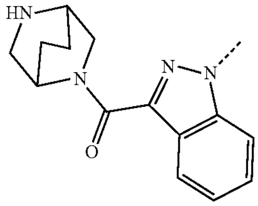
A209
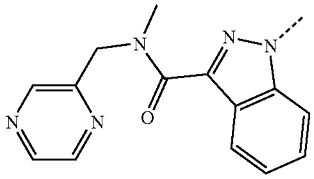
A210
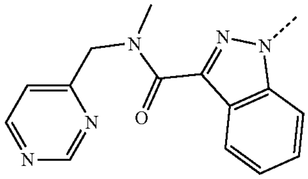
A211
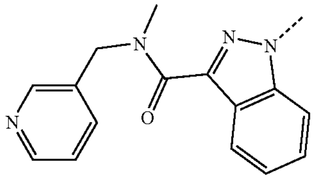
A212
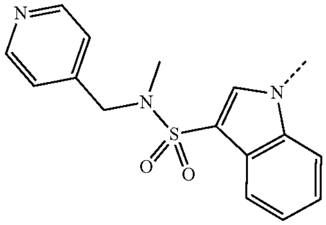
A213
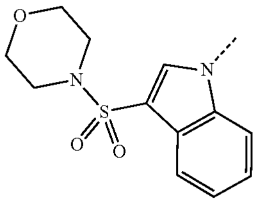
-continued
A214
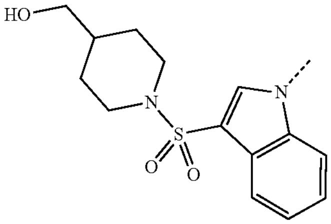
A215
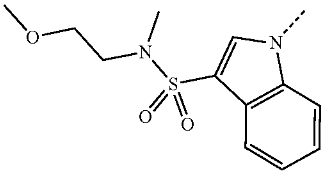
A216
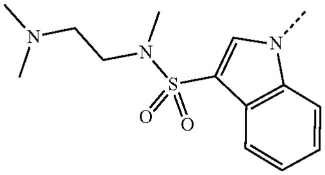
A217
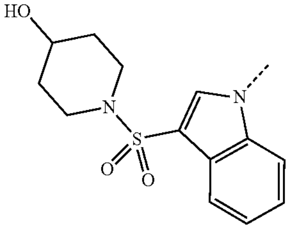
A218
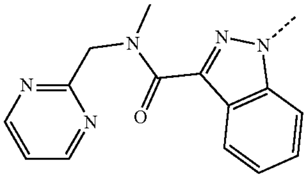
A219
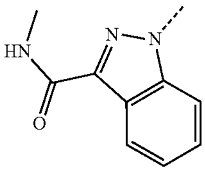
A220
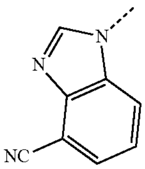
A221
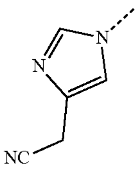

-continued
A222
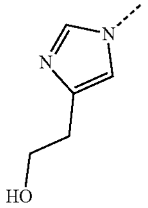
A223
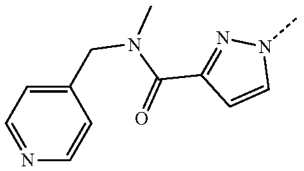
A224
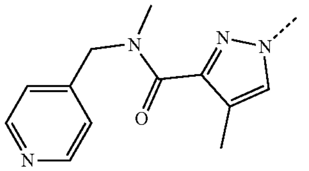
A225
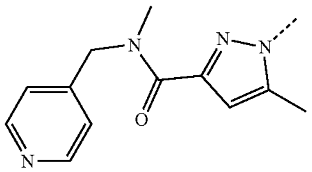
A226
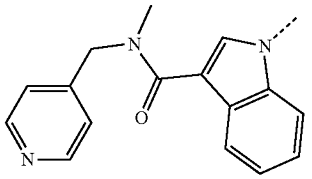
A227
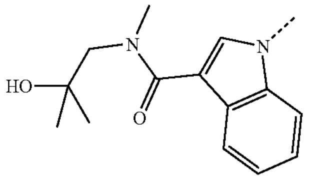
A228
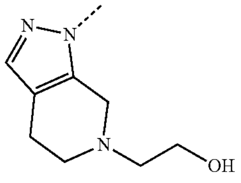
A229
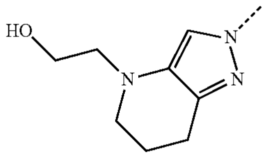
-continued
A230
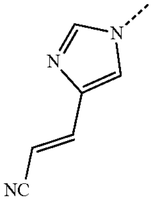
A231
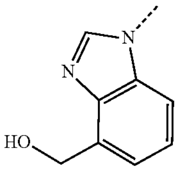
A232
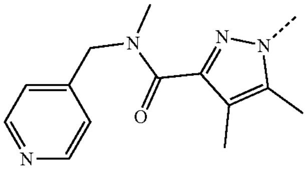
A233
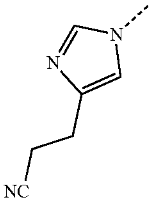
A234
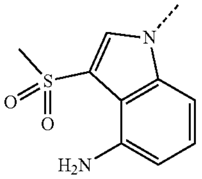
A235
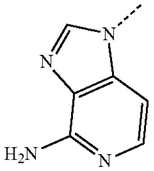
A236
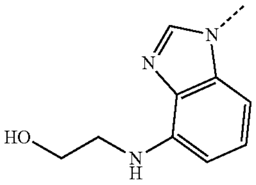
A237
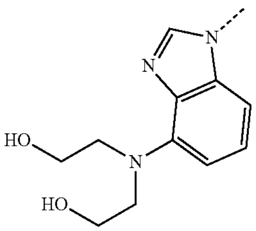

-continued
A238
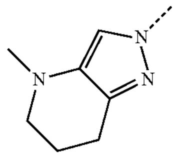
A239
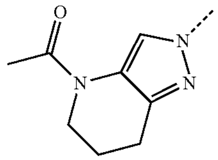
A240
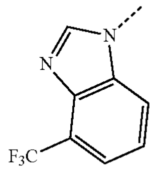
A241
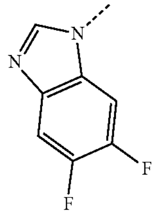
A242
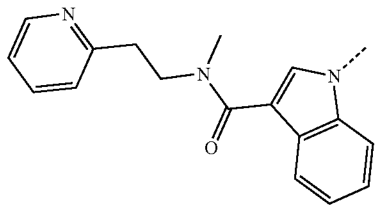
A243
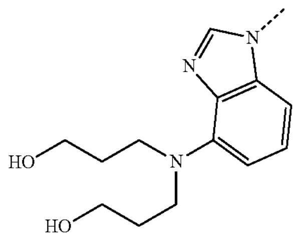
A244
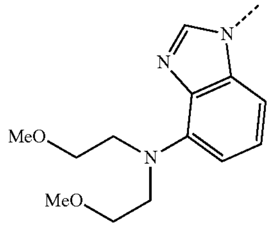
-continued
A245
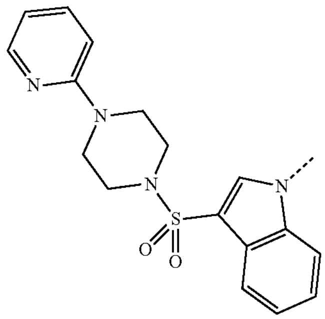
A246
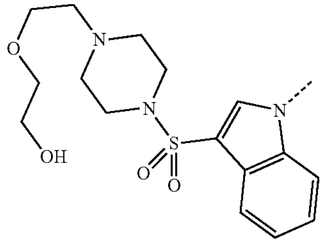
A247
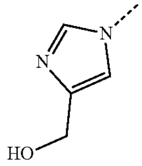
A248
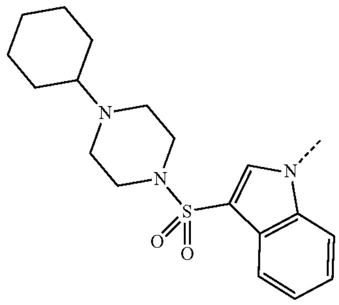
A249
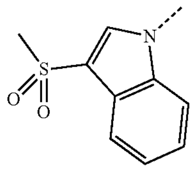
A250
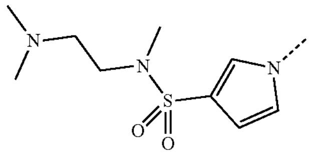
A251
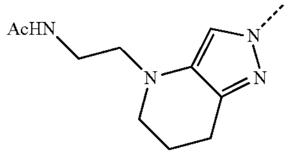

-continued
A252
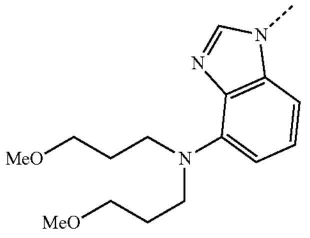
A253
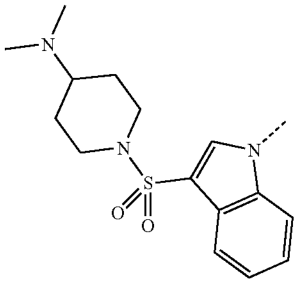
254
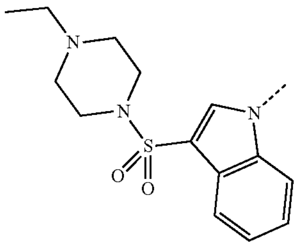
A255
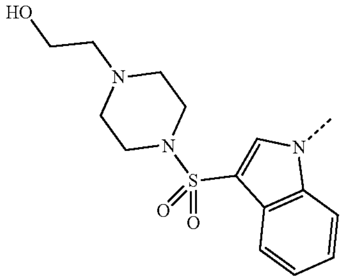
A256
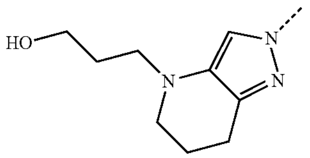
A257
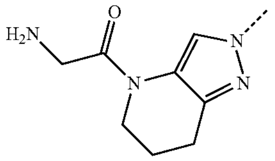
A258
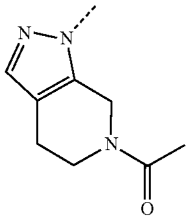
-continued
A259
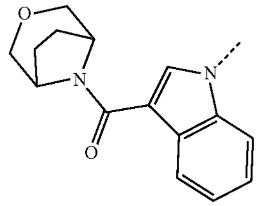
A260
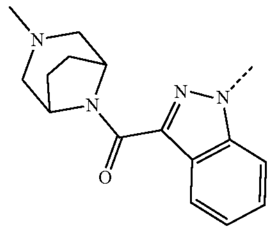
A261
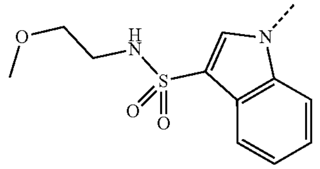
A262
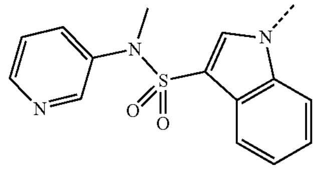
A263
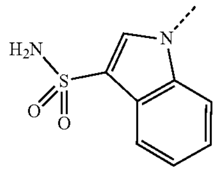
A264
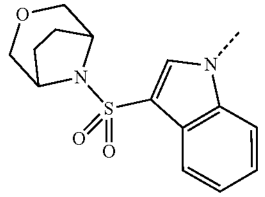
A265
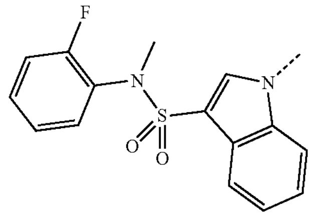
A266
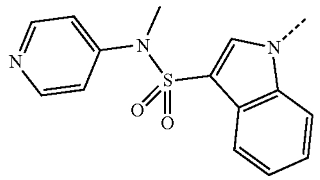

-continued
A267
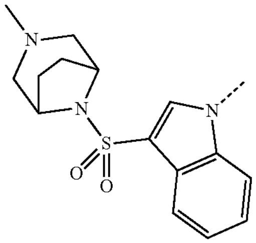
A268
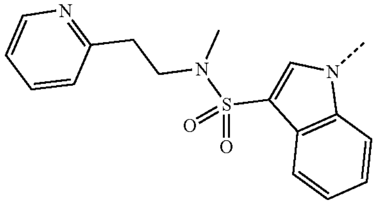
A269
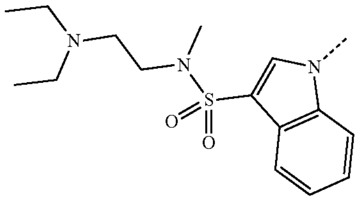
A270
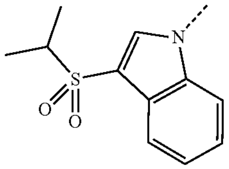
A271
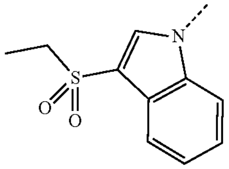
A272
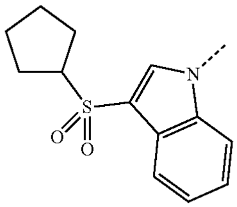
A273
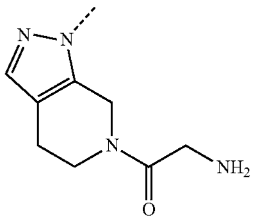
-continued
A274
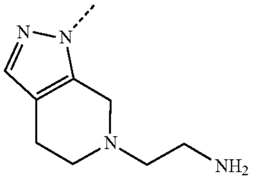
A275
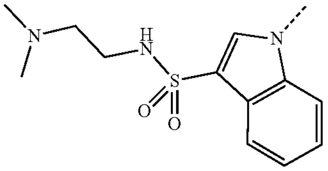
A276
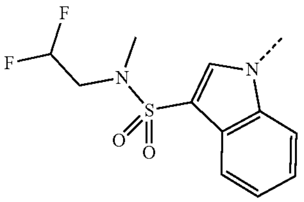
A277
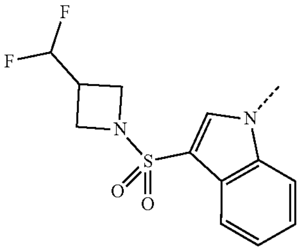
A278
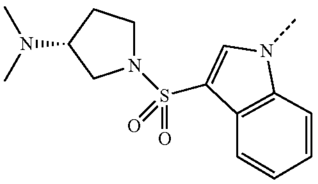
A279
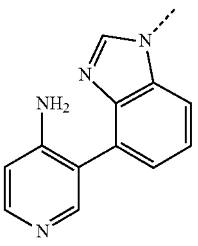
A280
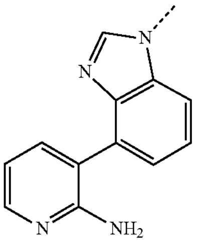

-continued
A281
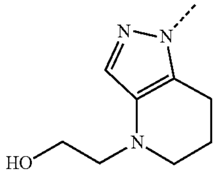
A282
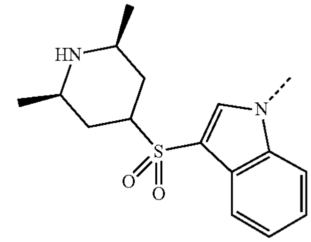
A283
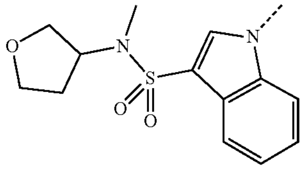
A284
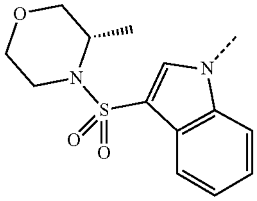
A285
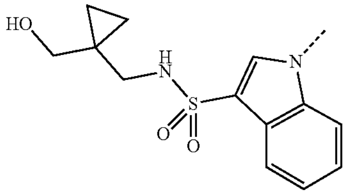
A286
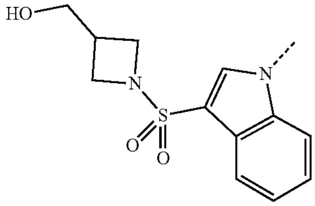
A287
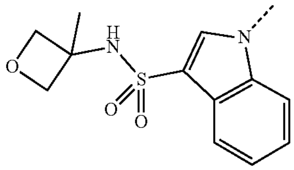
A288
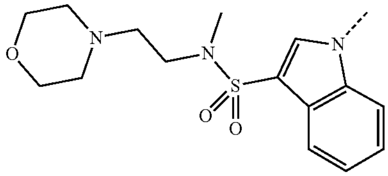
-continued
A289
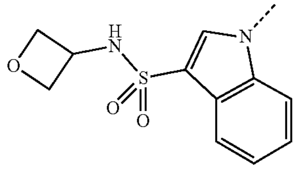
A290
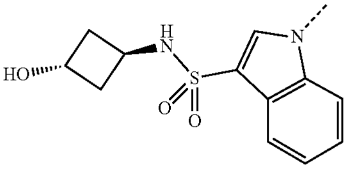
A291
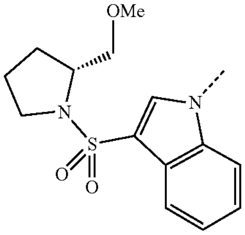
A292
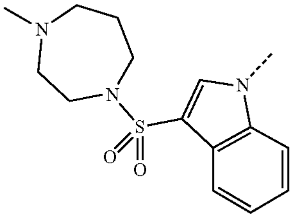
A293
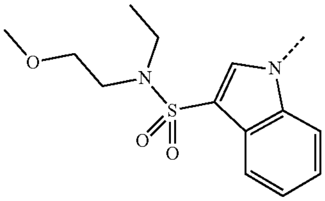
A294
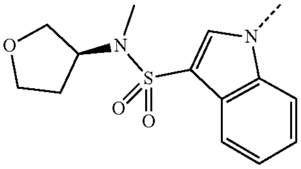
A295
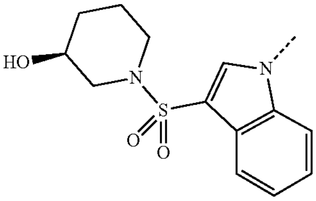
A296
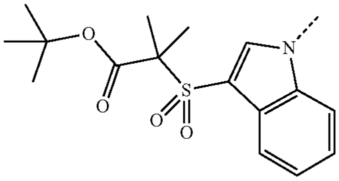

-continued
A297
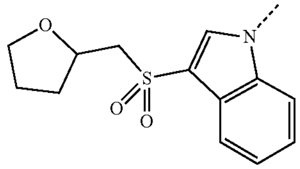
A298
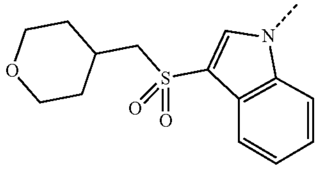
A299
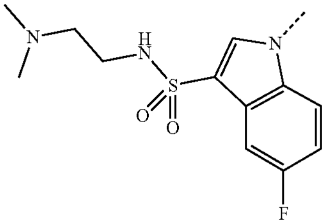
A300
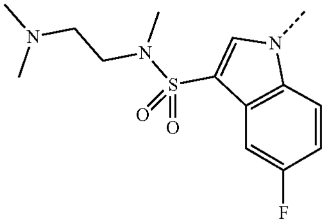
A301
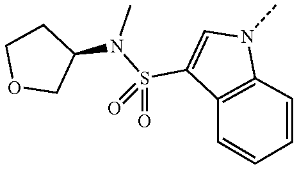
A302
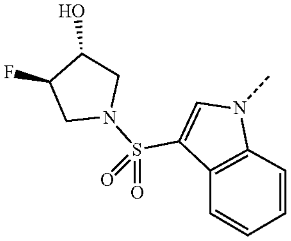
A303
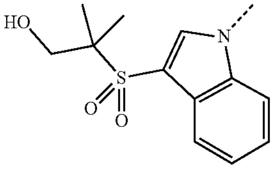
A304
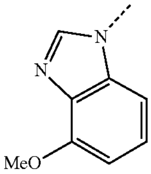
-continued
A305
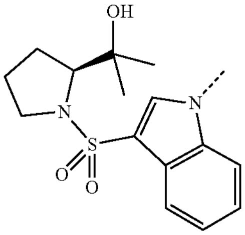
A306
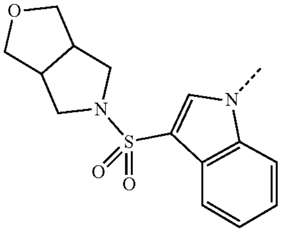
A307
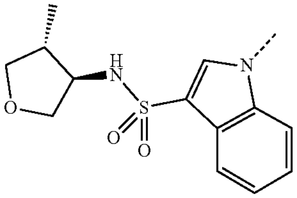
A308
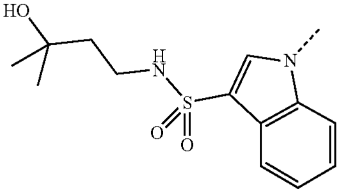
A309
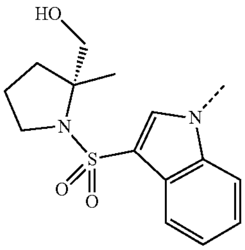
A310
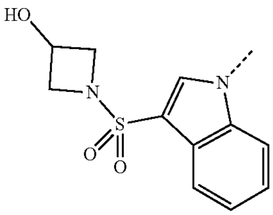
A311
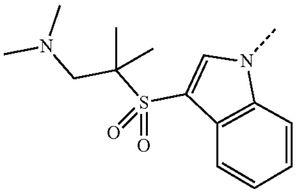

-continued
A312
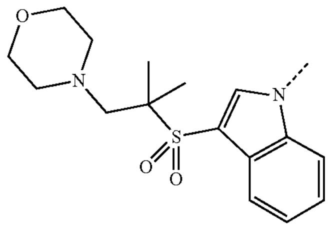
A313
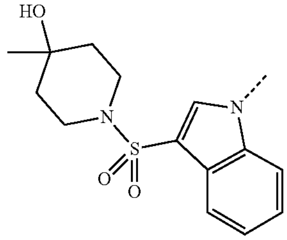
A314
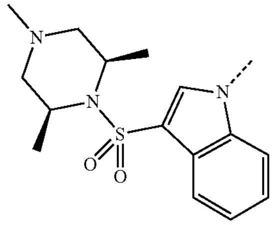
A315
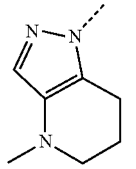
A316
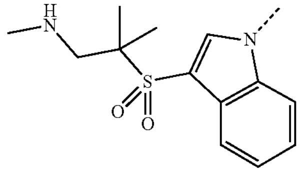
A317
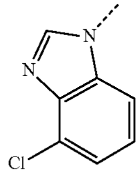
A318
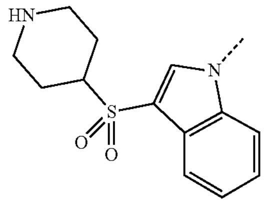
-continued
A319
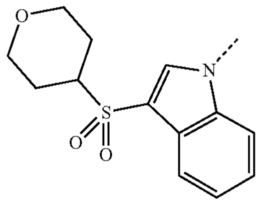
A320
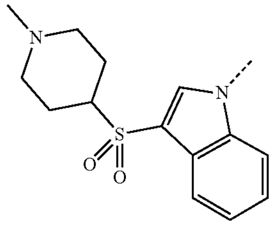
A321
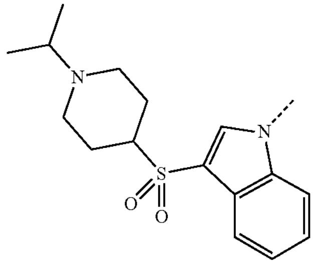
A322
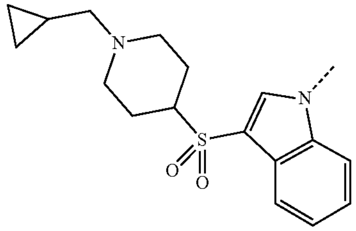
A323
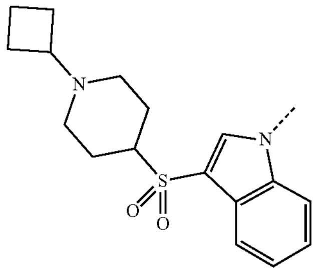
A324
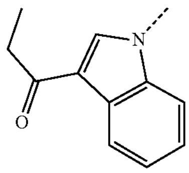
A325
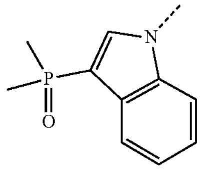

-continued
A326
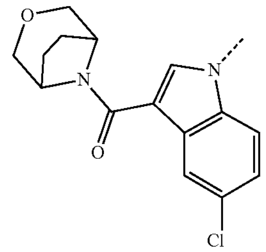
A327
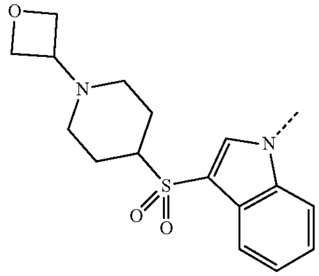
A328
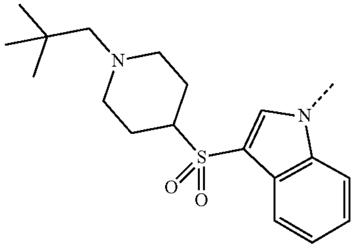
A329
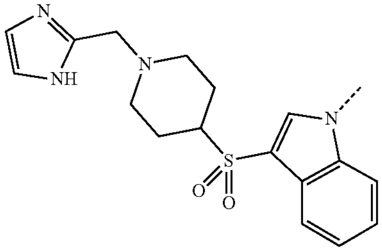
A330
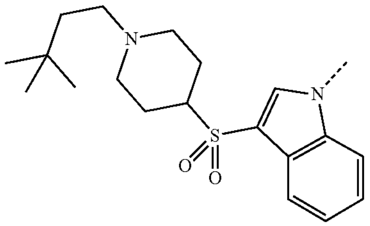
A331
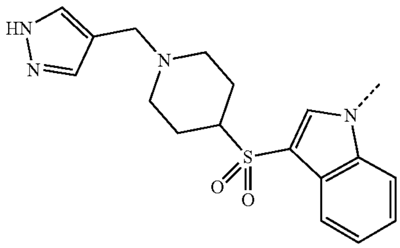
-continued
A332
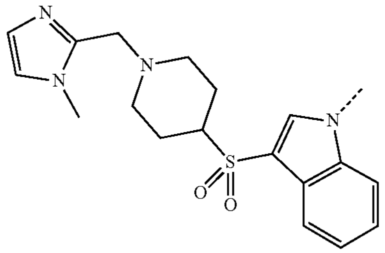
A333
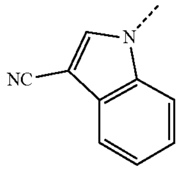
A334
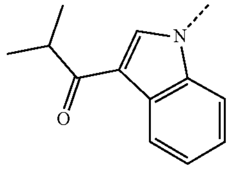
A335
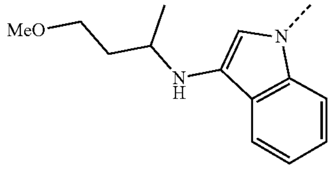
A336
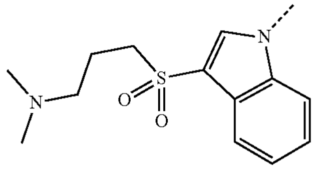
A337
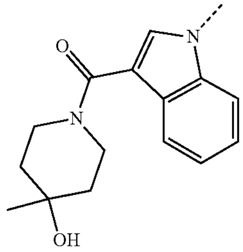
A338
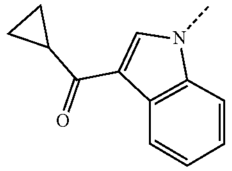

-continued
A339
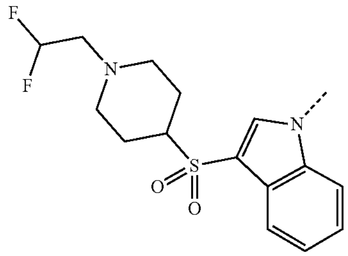
A340
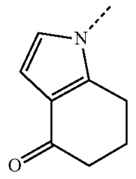
A341
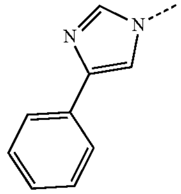
A342
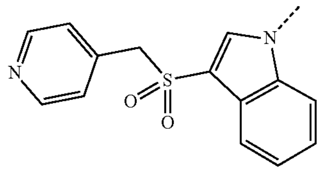
A343
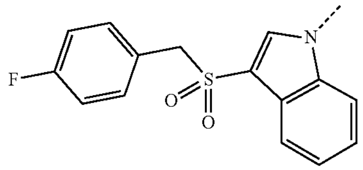
A344
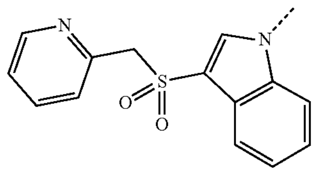
A345
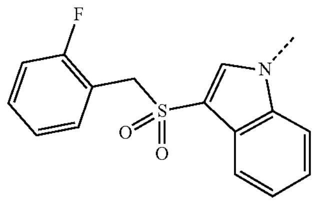
A346
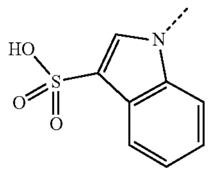
-continued
A347
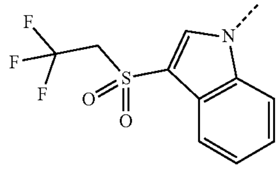
A348
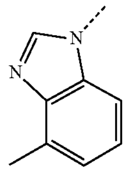
A349
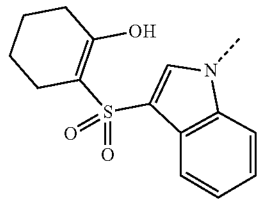
A350
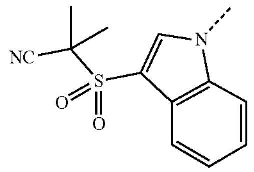
A351
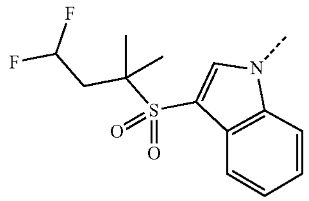
A352
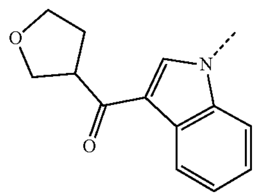
A353
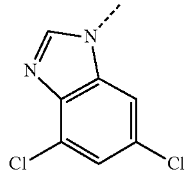
A354
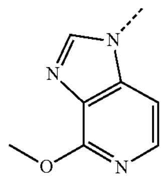

-continued
A355
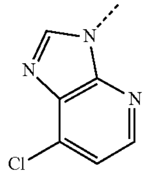
A356
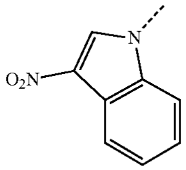
A357
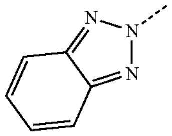
A358
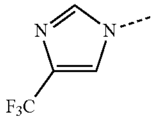
A359
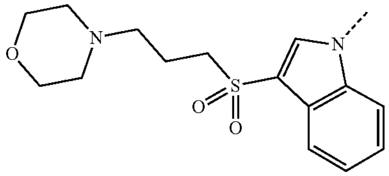
A360
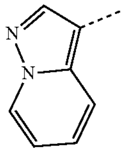
A361
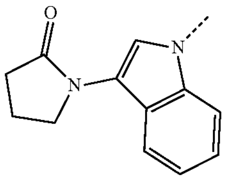
A362
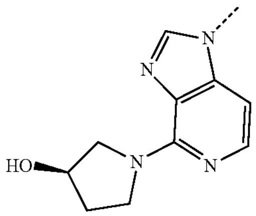
-continued
A363
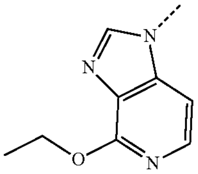
A364
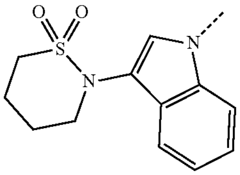
A365
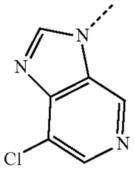
A366
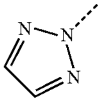
A367
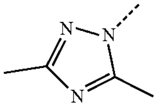
A368
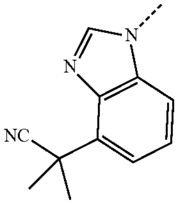
A369
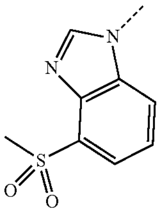
A370
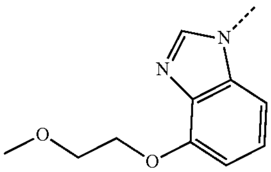
A371
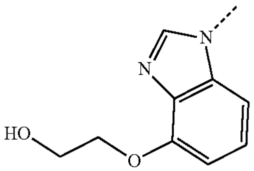

-continued
A372
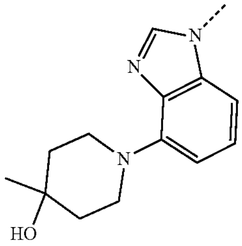
A373
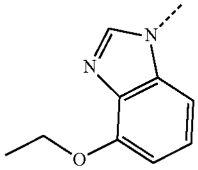
A374
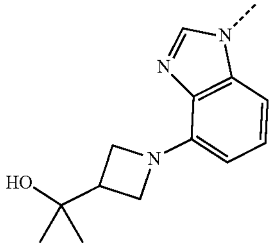
A375
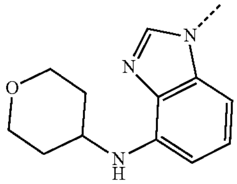
A376
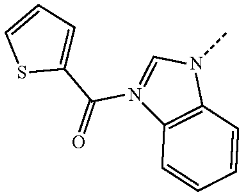
A377
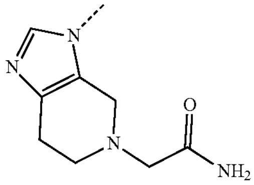
A378
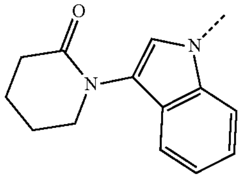
A379
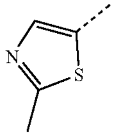
-continued
A380
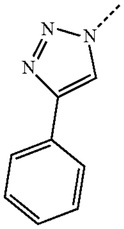
A381
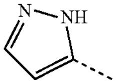
A382
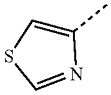
A383
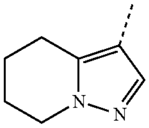
A384
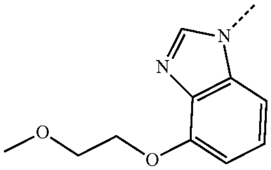
A385
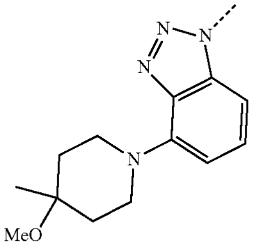
A386
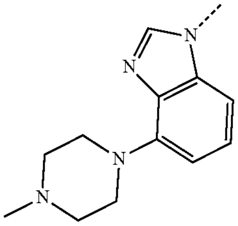
A387
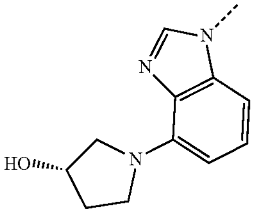

-continued
A388
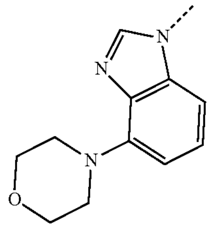
A389
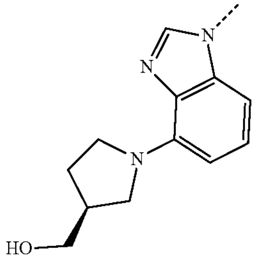
A390
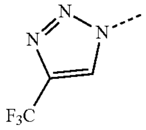
A391
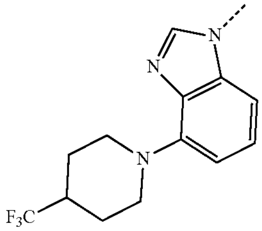
A392
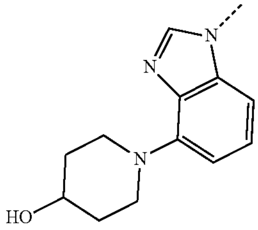
A393
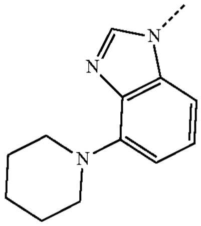
A394
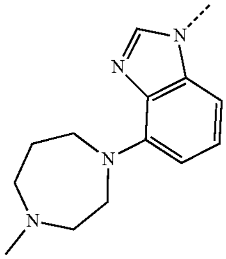
-continued
A395
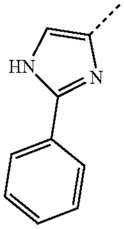
A396
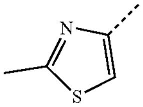
A397
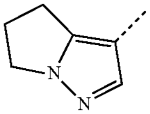
A398
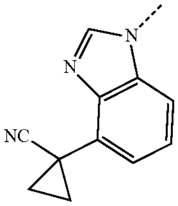
A399
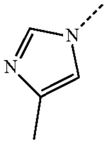
A400
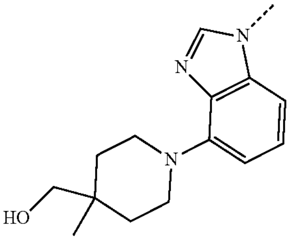
A401
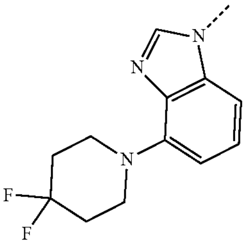
A402
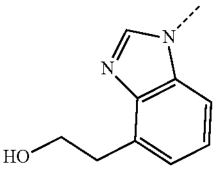

-continued
A403
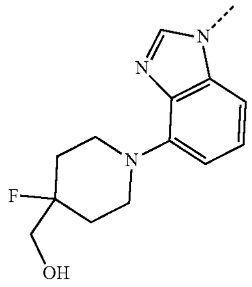
A404
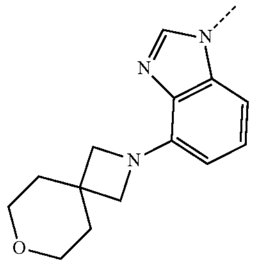
A405
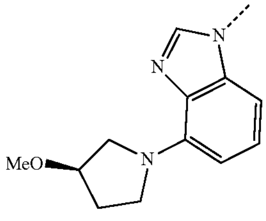
A406
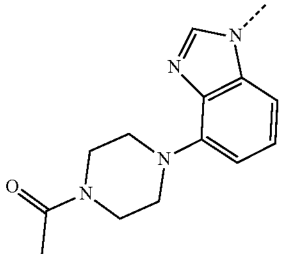
A407
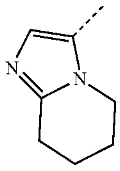
A408
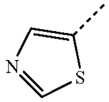
A409
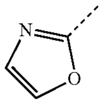
A410
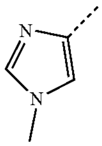
-continued
A411
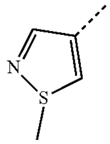
A412
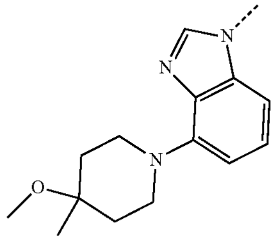
A413
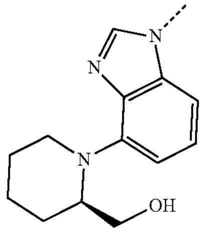
A414
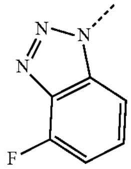
A415
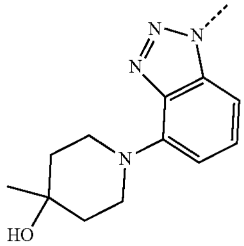
A416
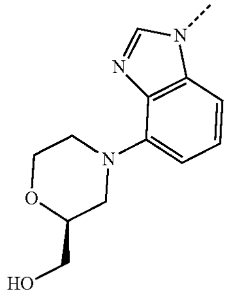
A417
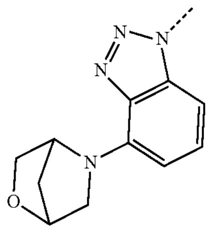

-continued
A418
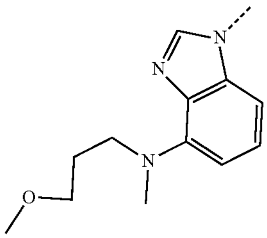
A419
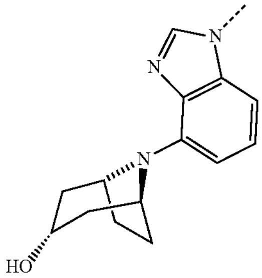
A420
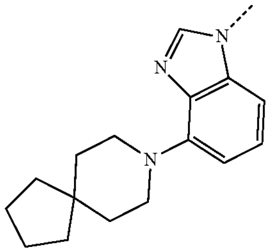
A421
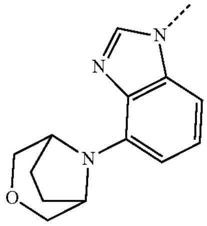
A422
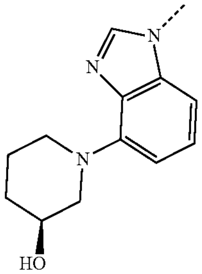
A423
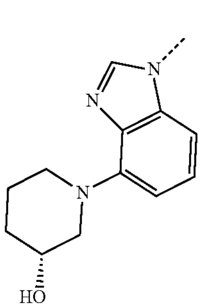
-continued
A424
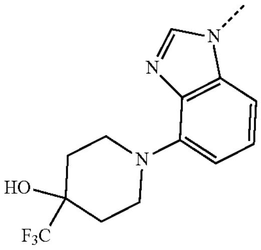
A425
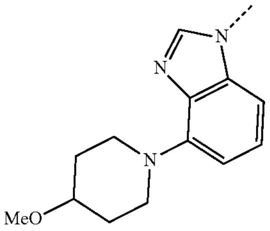
A426
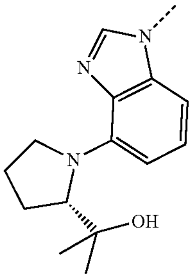
A427
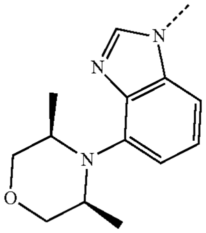
A428
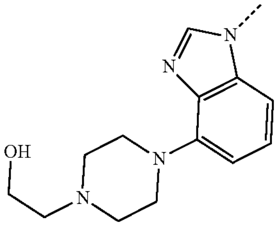
A429
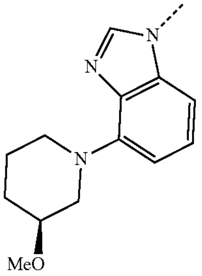

-continued
A430
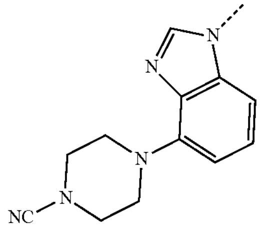
A431
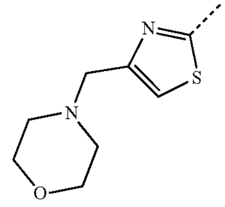
A432
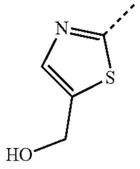
A433
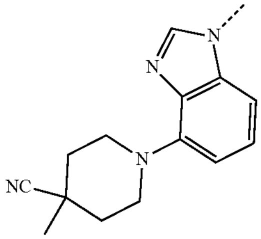
A434
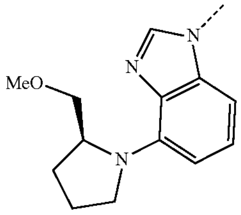
A435
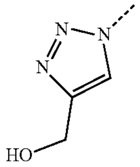
A436
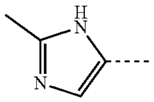
-continued
A437
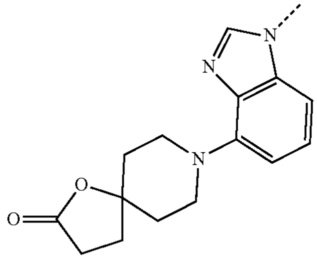
A438
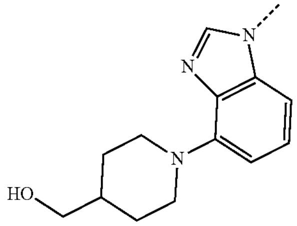
A439
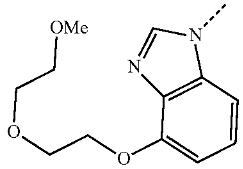
A440
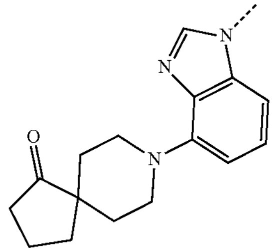
A441
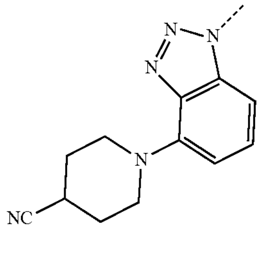
A442
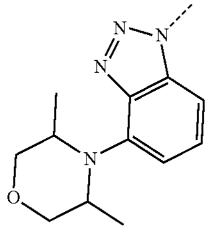

-continued
A443
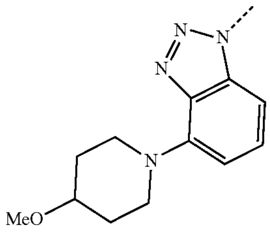
A444
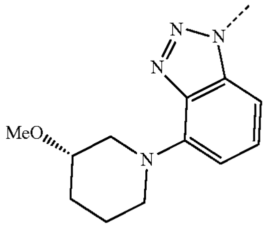
A445
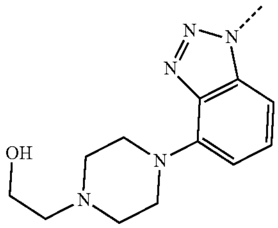
A446
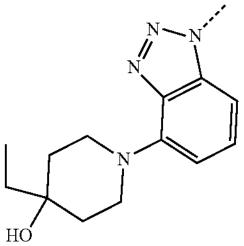
A447
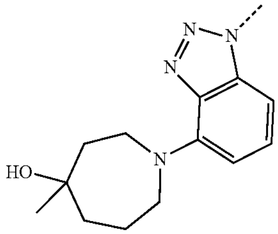
A448
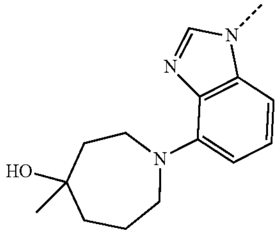
-continued
A449
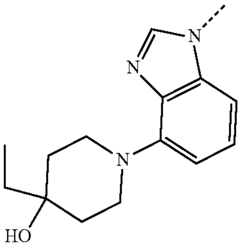
A450
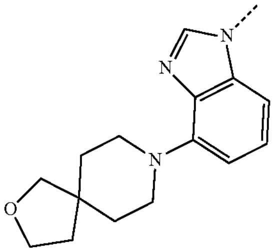
A451
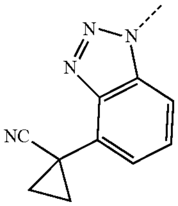
A452
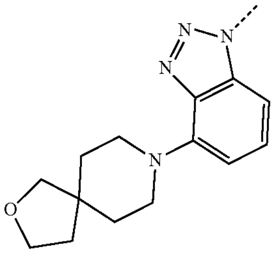
A453
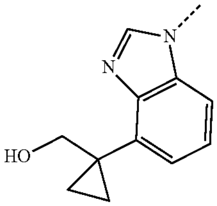
A454
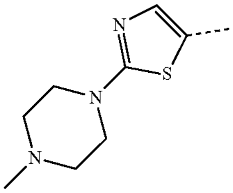
A455
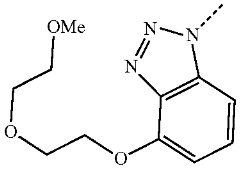

-continued
A456
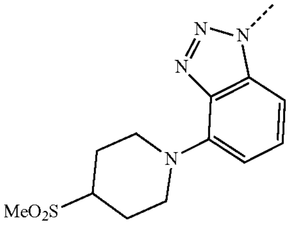
A457
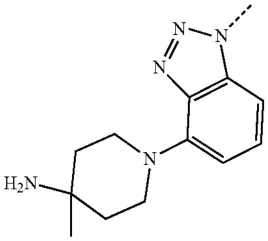
A458
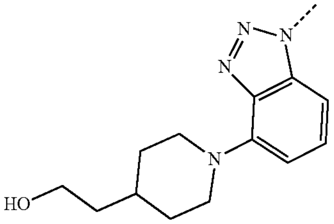
A459
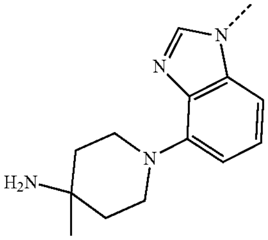
A460
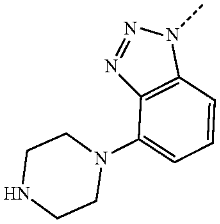
A461
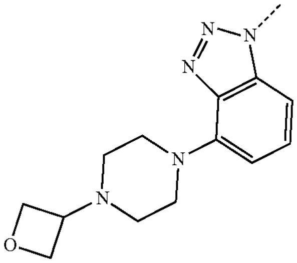
-continued
A462
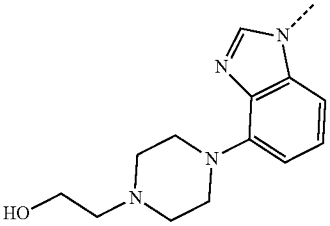
A463
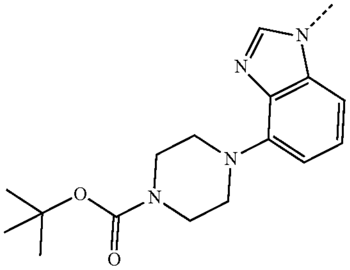
A464
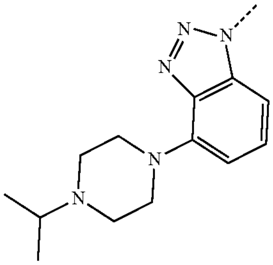
A465
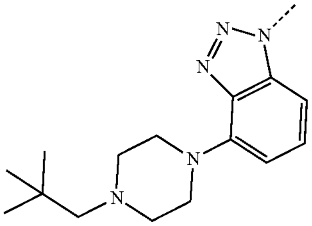
A466
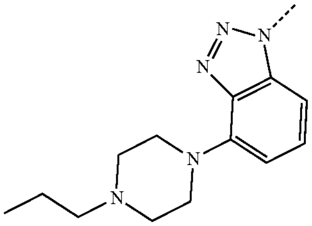
A467
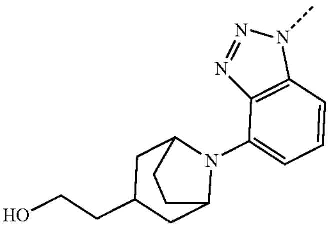

-continued
A468
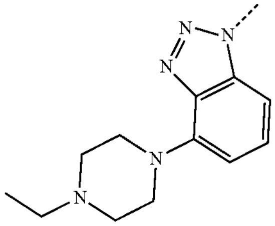
A469
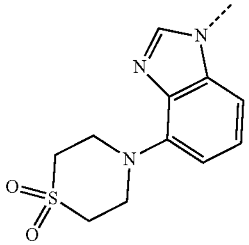
A470
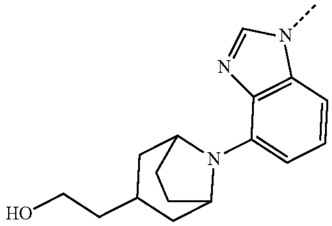
A471
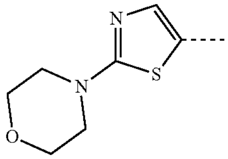
A472
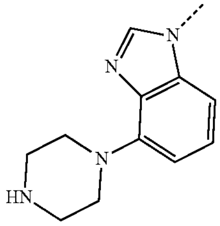
A473
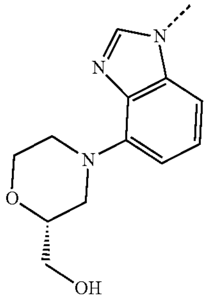
A474
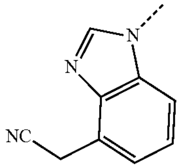
-continued
A475
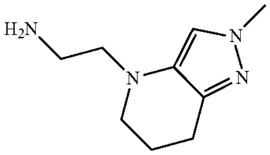
A476
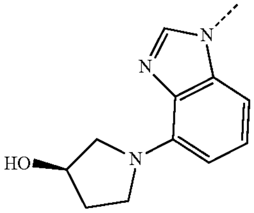
A477
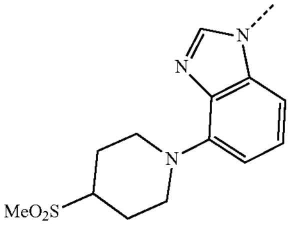
A478
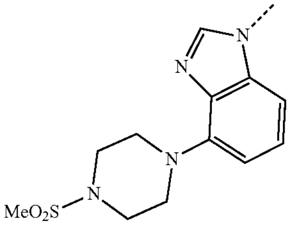
A479
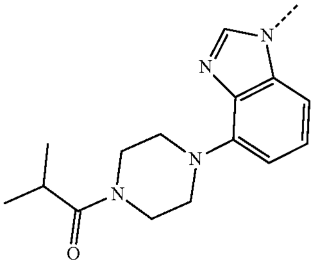
A480
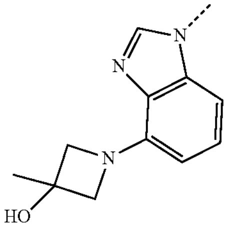
A481
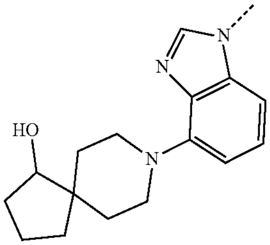

-continued
A482
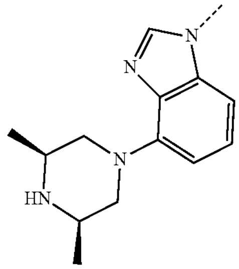
A483
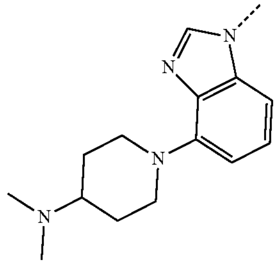
A484
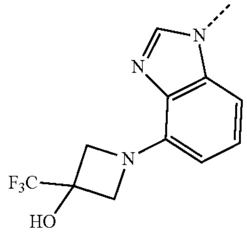
A485
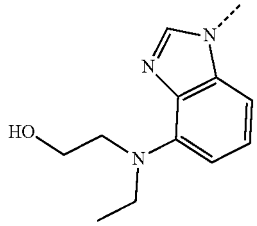
A486
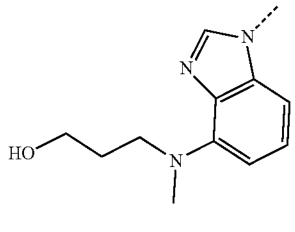
A487
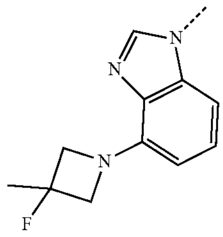
-continued
A488
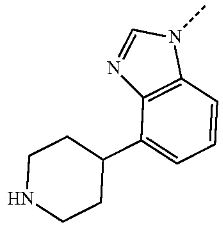
A489
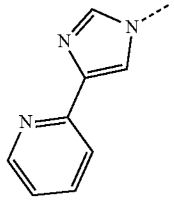
A490
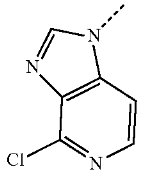
A491
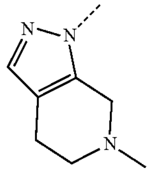
A492
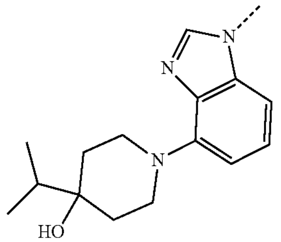
A493
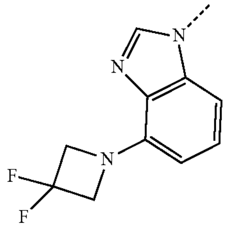
A494
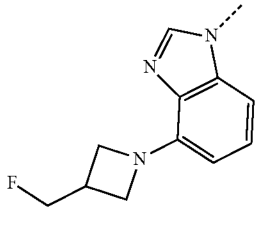

-continued
A495
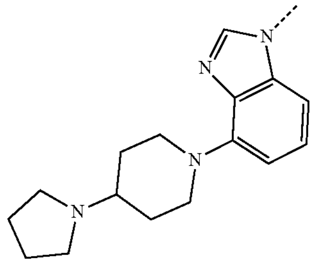
A496
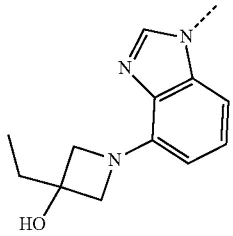
A497
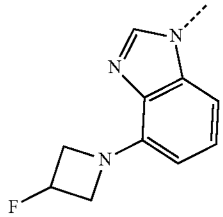
A498
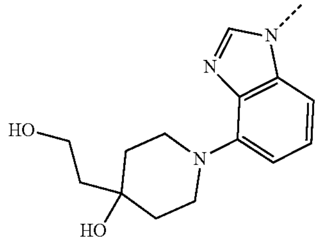
A499
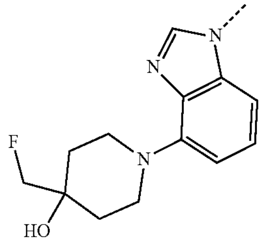
A500
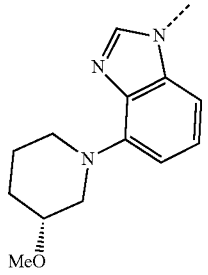
-continued
A501
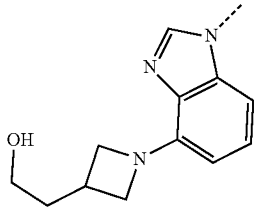
A502
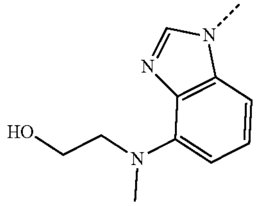
A503
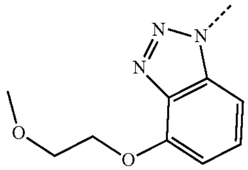
A504
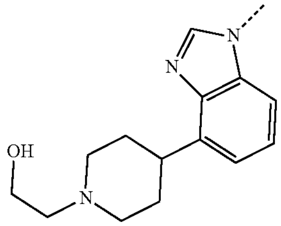
A505
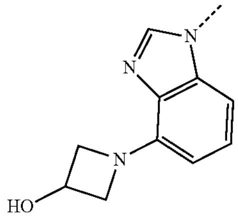
A506
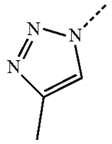
A507
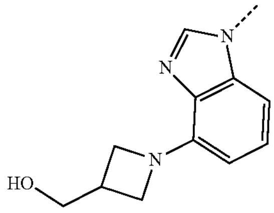

-continued
A508
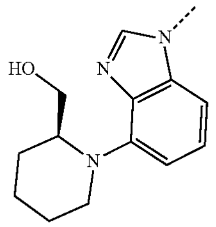
A509
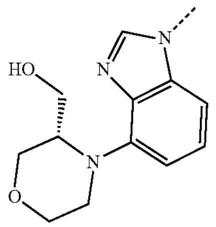
A510
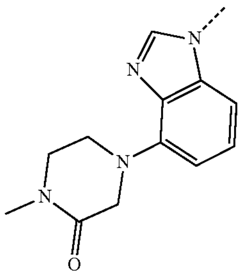
A511
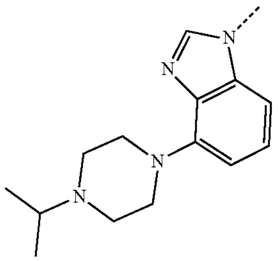
A512
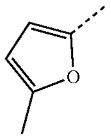
A513
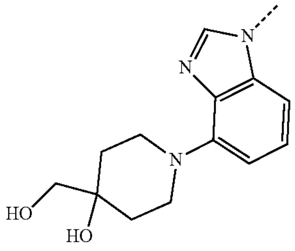
-continued
A514
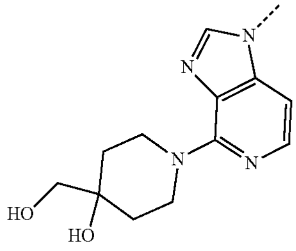
wherein (---) represents a bond serving as a point of attachment between $R^1$ and the rest of the molecule.
Preferred examples of $R^2$ are selected from groups 1 to B56 defined as follows:
B1
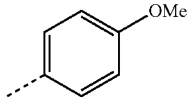
B2
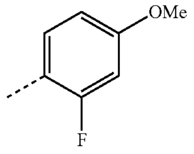
B3
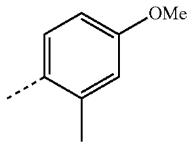
B4
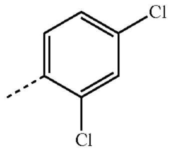
B5
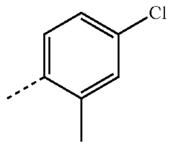
B6
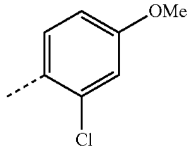
B7
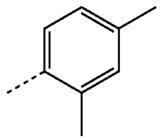

-continued
B8
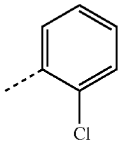
B9
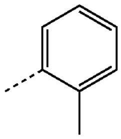
B10
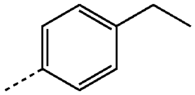
B11
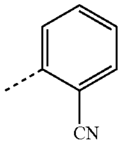
B12
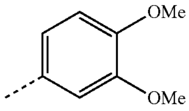
B13
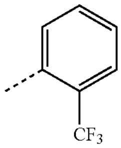
B14
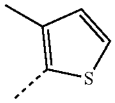
B15
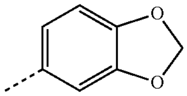
B16
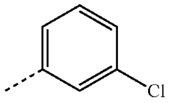
B17
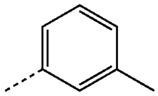
B18
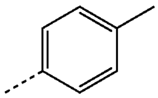
B19
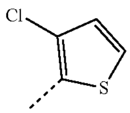
-continued
B20
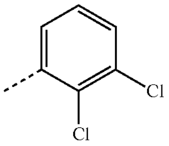
B21
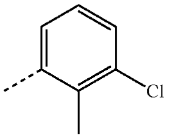
B22
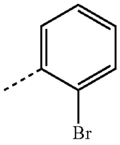
B23
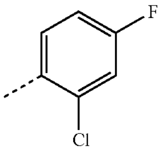
B24
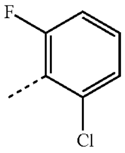
B25
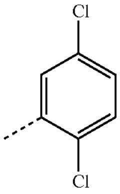
B26
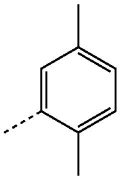
B27
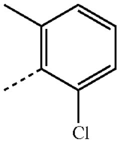
B28
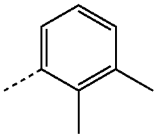

-continued
B29
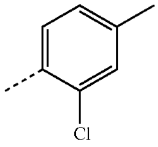
B30
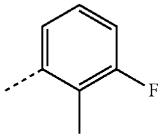
B31
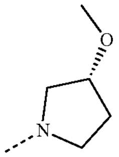
B32
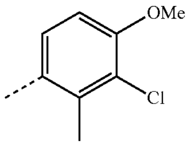
B33
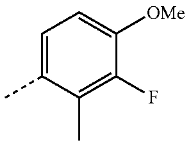
B34
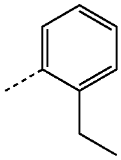
B35
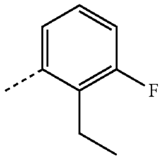
B36
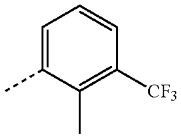
B37
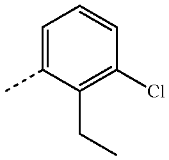
-continued
B38
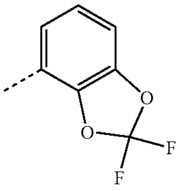
B39
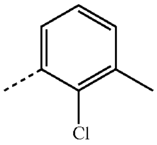
B40
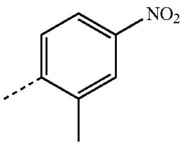
B41
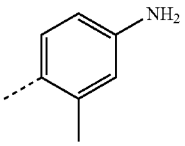
B42
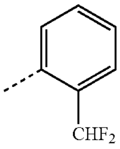
B43
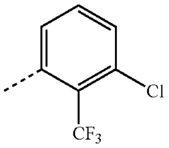
B44
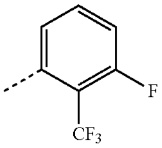
B45
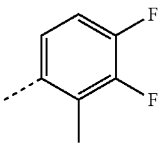
B46
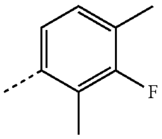
B47
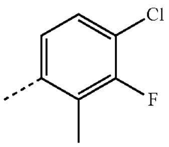

-continued

B48

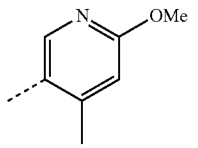

B49

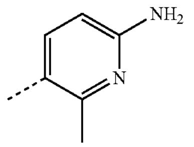

B50

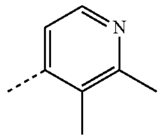

B51

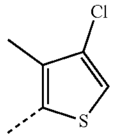

B52

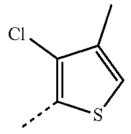

B53

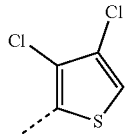

B54

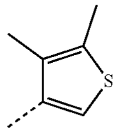

B55

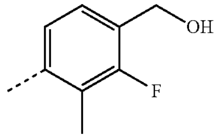

B56

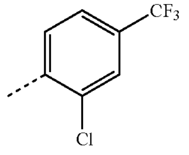

wherein (----) represents a bond serving as a point of attachment between $R^2$ and the rest of the molecule.

The following embodiments depict combinations of $R^1$ (A1 to A514), $R^2$ (1 to B56) and L (L1 to L3) groups that can be combined to produce compounds of Formula I.

A1-L-B1; A1-L-B2; A1-L-B3; A1-L-B4 to B54; A1-L-B55; A1-L-B56;

A2-L-B1; A2-L-B2; A2-L-B3; A2-L-B4 to B54; A2-L-B55; A2-L-B56;

A3-L-B1; A3-L-B2; A3-L-B3; A3-L-B4 to B54; A3-L-B55; A3-L-B56;

A4 to A512-L-B1; A4 to A512-L-B2; A4 to A512-L-B3; A4 to A512-L-B4 to B54; A4 to A512-L-B55; A4 to A512-L-B56;

A513-L-B1; A513-L-B2; A513-L-B3; A513-L-B4 to B54; A513-L-B55; A513-L-B56;

A514-L-B1; A514-L-B2; A514-L-B3; A514-L-B4 to B54; A514-L-B55; A514-L-B56;

Exemplary compounds as defined herein include each single compound covered in Tables 3, 4, and 5 under Examples 1 to 691.

Examples of preferred compounds are, namely, Examples 3, 6, 8, 19, 20-22, 30, 31, 43, 46, 48, 68, 76, 83, 84, 91-93, 99-102, 111, 113-115, 123, 124-128, 131, 139-141, 168, 171, 176, 177, 180, 188-190, 198, 202-206, 240, 244, 247, 248, 250-253, 261, 262, 264-275,277-280,282, 284-286, 290, 292, 294-299, 304, 305, 307-310, 312-315, 317-319, 321-323, 325, 328, 331, 333-337, 342, 346, 347, 350, 351, 354, 355, 356, 359, 361, 364-367, 370, 372, 377, 378, 381, 385-389, 395-398, 400, 401, 403, 408-412, 416-419, 421-423, 426-429, 431-433, 435-439, 441-445, 447-453, 454, 456, 458, 461, 462, 464, 466-469, 484, 486, 488, 490, 497, 502, 509, 511, 514, 517, 520, 524, 529, 530, 533, 538-543, 546, 548, 552-554, 556, 557, 560, 561, 562, 568, 569, 571, 572, 574, 575, 578, 580-583, 585, 586, 588-590, 592, 596-600, 602, 604, 605, 608-612, 614-617, 619-621, 623, 625-630, 632, 636, 638, 640, 641, 643-652, 654-660, 665 and 667-691 from Tables 3, 4 and 5, or a salt and/or solvate thereof.

Examples of more preferred compounds include Examples 3, 6, 20-22, 43, 46, 48, 68, 76, 84, 91-93, 99-102, 123, 125, 168, 171, 177, 188, 202, 205, 206, 251, 266, 272, 296-299, 304, 305, 307-310, 312, 318, 321, 331, 342, 354, 355, 359, 364, 366, 377, 378, 381, 385-387, 389, 395, 397, 400, 401, 403, 411, 412, 416-419, 421-423, 426-429, 431-433, 435-438, 441, 443-445, 451-454, 456, 458, 462, 466-469, 486, 497, 502, 509, 517, 520, 524, 527, 529, 530, 538-540, 546, 552, 554, 556, 558, 560, 562, 571, 572, 578, 580-583, 585, 586, 588, 589, 592, 597, 599, 600, 604, 605, 608-610, 615, 617, 619-621, 623, 625-628, 630, 632-638, 640, 641, 643, 645-649, 665, 671-680, 682, 683, 685 and 688-690 from Tables 3, 4 and 5, or a salt and/or solvate thereof.

More specifically, the compound may be selected from Examples 20, 84, 99-102, 123, 205, 251, 266, 296-299, 308, 312, 318, 321, 342, 355, 385, 387, 412, 421, 432 462, 509, 517, 520, 524, 529, 530, 538, 539, 546, 554, 556, 560, 562, 568, 571, 572, 578, 580-583, 586, 588, 592, 597, 600, 605, 608, 609, 615, 617,621, 628, 630, 632, 633, 636, 637, 641, 643, 648, 649, 665, 672-675, 679, 682 and 688 from Tables 3, 4 and 5, or a salt and/or solvate thereof.

It is understood that any of the above compounds may be in any amorphous, crystalline or polymorphic form, including any salt or solvate form, or a mixture thereof. The compounds of the present description may be further modified by appending various functionalities via any synthetic means delineated herein to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

These compounds may be prepared by conventional chemical synthesis, such as those exemplified in the Schemes and Examples of the present disclosure. As can be appreciated by the skilled artisan, further methods of synthesizing the compounds of the formulae herein will be evident to those of ordinary skill in the art. Additionally, the various synthetic steps may be performed in an alternate sequence or order to give the desired compounds.

iii. Methods, Uses, Formulations and Administration

As used herein, the term “effective amount” means that amount of a drug or pharmaceutical agent that will elicit the biological or medical response of a tissue, system, animal or human that is being sought, for instance, by a researcher or clinician. Furthermore, the term “therapeutically effective amount” means any amount which, as compared to a corresponding subject who has not received such amount, results in treatment, healing, prevention, or amelioration of a disease, disorder, or symptom thereof, or a decrease in the rate of advancement of a disease or disorder. The term also includes within its scope amounts effective to enhance normal physiological function.

As used herein, the terms “treatment,” “treat,” and “treating” refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

In one embodiment, the disease or condition to be treated is a proliferative disease or disorder or a kinase-mediated disease or disorder. More specifically, the disease or disorder to be treated include a proliferative disease or disorder, a developmental anomaly caused by dysregulation of the RAS-ERK signaling cascade (RASopathies), an inflammatory disease or an immune system disorder.

According to some examples, the proliferative disease or disorder to be treated is a neoplasm, an inflammatory disease or condition or a developmental anomaly, involving a constitutively activating mutation in RAS and/or RAF genes (e.g. KRAS and/or ARAF, BRAF, or CRAF mutations). The disease or disorder may also be further associated with a receptor tyrosine kinase mutation or amplification (e.g. EGFR, HER2) or a mutation in a regulator of RAS downstream of the receptor (e.g. SOS1 gain of function, NF1 loss of function). For instance, the compounds as defined herein are inhibitors of signal enzymes (ex. B- and CRAF) which are involved in controlling cell proliferation not only in tumors harboring RAF mutations (e.g. $BRAF^{V600E}$) but importantly also in the context of mutated RAS-driven cancers. Thus, the present compounds may be used for example for the treatment of diseases connected with the activity of these signal enzymes and characterized by excessive or abnormal cell proliferation.

According to one embodiment, the disease or disorder is characterized by uncontrolled cell proliferation, i.e. a “proliferative disorder” or “proliferative disease”. More specifically, these diseases and disorders relate to cells having the capacity for autonomous growth, i.e. an abnormal state of condition characterized by rapidly proliferating cell growth which generally forms a distinct mass that show partial or total lack of structural organization and functional coordination with normal tissue.

For instance, the proliferative disorder or disease is defined as a “neoplasm”, “neoplastic disorder”, “neoplasia” “cancer,” and “tumor” which terms are collectively meant to encompass hematopoietic neoplasms (e.g. lymphomas or leukemias) as well as solid neoplasms (e.g. sarcomas or carcinomas), including all types of pre-cancerous and cancerous growths, or oncogenic processes, metastatic tissues or malignantly transformed cells, tissues, or organs, irrespective of histopathologic type or stage of invasiveness. Hematopoietic neoplasms are malignant tumors affecting hematopoietic structures (structures pertaining to the formation of blood cells) and components of the immune system, including leukemias (related to leukocytes (white blood cells) and their precursors in the blood and bone marrow) arising from myeloid, lymphoid or erythroid lineages, and lymphomas (related to lymphocytes). Solid neoplasms include sarcomas, which are malignant neoplasms that originate from connective tissues such as muscle, cartilage, blood vessels, fibrous tissue, fat or bone. Solid neoplasms also include carcinomas, which are malignant neoplasms arising from epithelial structures, including external epithelia (e.g., skin and linings of the gastrointestinal tract, lungs, and cervix), and internal epithelia that line various glands (e.g., breast, pancreas, thyroid). Examples of neoplasms include leukemia, and hepatocellular cancers, sarcoma, vascular endothelial cancers, breast cancers, central nervous system cancers (e.g. astrocytoma, gliosarcoma, neuroblastoma, oligodendroglioma and glioblastoma), prostate cancers, lung and bronchus cancers, larynx cancers, esophagus cancers, colon cancers, colorectal cancers, gastro-intestinal cancers, melanomas, ovarian and endometrial cancer, renal and bladder cancer, liver cancer, endocrine cancer (e.g. thyroid), and pancreatic cancer. For instance, the disease or disorder is selected from colon cancer, lung cancer, pancreatic cancer, thyroid cancer, breast cancer and skin cancer. Examples of neoplasm include melanoma, papillary thyroid carcinoma, colorectal, ovarian, breast cancer, endometrial cancer, liver cancer, sarcoma, stomach cancer, Barret’s adenocarcinoma, glioma (including ependymoma), lung cancer (including non-small cell lung cancer), head and neck cancer, acute lymphoblastic leukemia, acute myelogenous leukemia, non-Hodgkin’s lymphoma, and hairy-cell leukemia.

In an embodiment, patients presenting one of the above-mentioned hematopoietic or solid neoplasms have previously received treatment with a RAS-ERK pathway-targeted inhibitor (including RTK, RAF, MEK or ERK inhibitor) but have developed resistance to the said inhibitor. The inhibitor includes standard of care treatments such as vemurafenib, dabrafenib, cobimetinib, trametinib, YERVOY, OPDIVO or any combination of these pharmaceutical agents.

In an embodiment, the disease to be treated is defined by developmental anomalies caused by dysregulation of the RAS-ERK signaling cascade (RASopathies: e.g. Noonan syndrome, Costello syndrome, LEOPARD syndrome, cardiofaciocutaneous syndrome and hypertrophic cardiomyopathy).

In an embodiment, the disease to be treated is defined as an inflammatory disease or immune system disorder. Examples of such inflammatory diseases or immune system disorders including inflammatory bowel disease, Crohn’s disease, ulcerative colitis, systemic lupus erythematosis (SLE), rheumatoid arthritis, multiple sclerosis, thyroiditis, type 1 diabetes, sarcoidosis, psoriasis, allergic rhinitis, asthma, COPD (chronic obstructive pulmonary disease).

In one embodiment, the compounds as herein defined are inhibitors of RAS-ERK signaling and cellular proliferation in tumor cells bearing at least one mutated RAS or RAF genotype, without or substantially without inducing the paradoxical pathway.

The term "patient or subject" as used herein refers to an animal such as a mammal. A subject may therefore refer to, for example, mice, rats, dogs, cats, horses, cows, pigs, guinea pigs, primates including humans and the like. Preferably the subject is a human.

The present description therefore further relates to a method of treating a subject, such as a human subject, suffering from a proliferative disease or disorder, e.g. a RAF-mutated and/or mutated RAS-driven cancer. The method comprises administering a therapeutically effective amount of a compound as defined herein, to a subject in need of such treatment.

In certain embodiments, the present description provides a method of treating a disorder (as described herein) in a subject, comprising administering to the subject identified as in need thereof, a compound of the present description. The identification of those patients who are in need of treatment for the disorders described above is well within the ability and knowledge of one skilled in the art. Certain of the methods for identification of patients which are at risk of developing the above disorders which can be treated by the subject method are appreciated in the medical arts, such as family history, and the presence of risk factors associated with the development of that disease state in the subject patient. A clinician skilled in the art can readily identify such candidate patients, by the use of, for example, clinical tests, physical examination, medical/family history, and genetic determination.

A method of assessing the efficacy of a treatment in a subject includes determining the pre-treatment symptoms of a disorder by methods well known in the art and then administering a therapeutically effective amount of a compound of the present description, to the subject. After an appropriate period of time following the administration of the compound (e.g., 1 week, 2 weeks, one month, six months), the symptoms of the disorder are determined again. The modulation (e.g., decrease) of symptoms and/or of a biomarker (e.g. pERK or pMEK) of the disorder indicates efficacy of the treatment. The symptoms and/or biomarker of the disorder may be determined periodically throughout treatment. For example, the symptoms and/or biomarker of the disorder may be checked every few days, weeks or months to assess the further efficacy of the treatment. A decrease in symptoms and/or biomarker of the disorder indicates that the treatment is efficacious.

In some embodiments, the therapeutically effective amount of a compound as defined herein can be administered to a patient alone or in a composition, admixed with a pharmaceutically acceptable carrier, adjuvant, or vehicle.

The expression "pharmaceutically acceptable carrier, adjuvant, or vehicle" and equivalent expressions, refer to a non-toxic carrier, adjuvant, or vehicle that does not destroy the pharmacological activity of the compound with which it is formulated. Pharmaceutically acceptable carriers, adjuvants or vehicles that may be used in the compositions of this disclosure include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Compositions described herein may be administered orally, parenterally, by inhalation spray, topically, rectally, nasally, buccally, or via an implanted reservoir. The term "parenteral" as used herein includes subcutaneous, intravenous, intramuscular, intraarticular, intrasynovial, intrasternal, intrathecal, intrahepatic, intralesional and intracranial injection or infusion techniques. Other modes of administration also include intradermal or transdermal administration.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, surfactants, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a provided compound, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled.

Examples of other biodegradable polymers include poly (orthoesters) and poly(anhydrides). Depot injectable formulations are also prepared by entrapping the compound in liposomes or microemulsions that are compatible with body tissues.

Compositions for rectal administration are preferably suppositories which can be prepared by mixing the compounds of the present description with suitable non-irritating excipients or carriers such as cocoa butter, polyethylene glycol or a suppository wax which are solid at ambient temperature but liquid at body temperature and therefore melt in the rectum and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone (PVP), sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The composition can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of the present description include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of the present description. Additionally, the description contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Pharmaceutically acceptable compositions provided herein may also be administered by nasal aerosol or inhalation. Such compositions are prepared according to techniques well-known in the art of pharmaceutical formulation and may be prepared as solutions in saline, employing benzyl alcohol or other suitable preservatives, absorption promotors to enhance bioavailability, fluorocarbons, and/or other conventional solubilizing or dispersing agents.

Pharmaceutically acceptable compositions provided herein may be formulated for oral administration. Such formulations may be administered with or without food. In some embodiments, pharmaceutically acceptable compositions of this disclosure are administered without food. In other embodiments, pharmaceutically acceptable compositions of this disclosure are administered with food.

The amount of compound that may be combined with carrier materials to produce a composition in a single dosage form will vary depending upon the patient to be treated and the particular mode of administration. Provided compositions may be formulated such that a dosage of between 0.01-100 mg/kg body weight/day of the inhibitor can be administered to a patient receiving these compositions.

It should also be understood that a specific dosage and treatment regimen for any particular patient will depend upon a variety of factors, including age, body weight, general health, sex, diet, time of administration, rate of excretion, drug combination, the judgment of the treating physician, and the severity of the symptoms associated with the proliferative disease or disorder. The amount of a provided compound in the composition will also depend upon the particular compound in the composition.

Compounds or compositions described herein may be administered using any amount and any route of administration effective for treating or lessening the severity of the symptoms as contemplated herein. The exact amount required will vary from subject to subject, depending on the species, age, and general condition of the subject, the severity of the infection, the particular agent, its mode of administration, and the like. Provided compounds are preferably formulated in unit dosage form for ease of administration and uniformity of dosage. The expression "unit dosage form" as used herein refers to a physically discrete unit of agent appropriate for the patient to be treated. It will be understood, however, that the total daily usage of the compounds and compositions of the present disclosure will be decided by the attending physician within the scope of sound medical judgment.

Pharmaceutically acceptable compositions of this disclosure can be administered to humans and other animals orally, rectally, parenterally, intracisternally, intraperitoneally, topically (as by powders, ointments, or drops), buccally, as an oral or nasal spray, or the like, depending on the severity of the infection being treated. In certain embodiments, provided compounds may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

It will be understood, that the total daily usage of the compounds and compositions of the present description will be decided by the attending physician within the scope of sound medical judgment. The total daily inhibiting dose of the compound of the present description administered to a subject in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In one embodiment, treatment regimens according to the present description comprise administration to a patient in need of such treatment from about 10 mg to about 1000 mg of the compound(s) of the present description per day in single or multiple doses.

Depending upon the disease or disorder to be treated, additional therapeutic agents may also be present in the compositions of this disclosure or administered separately as part of a dosage regimen, e.g. an additional chemotherapeutic agent. Non-limiting examples of additional therapeutic agents which could be used in combination with the present compounds include antiproliferative compounds such as aromatase inhibitors; anti-estrogens; anti-androgens; gonadorelin agonists; topoisomerase I inhibitors; topoisomerase II inhibitors; microtubule active agents; alkylating agents; retinoids, carotenoids, tocopherol; cyclooxygenase inhibitors; MMP inhibitors; antimetabolites; platin compounds; methionine aminopeptidase inhibitors; bisphosphonates; antiproliferative antibodies; heparanase inhibitors; inhibitor of Ras oncogenic isoforms; telomerase inhibitors; proteasome inhibitors; compounds used in the treatment of hematologic malignancies; kinesin spindle protein inhibitors; Hsp90 inhibitors; mTOR inhibitors; PI3K inhibitors; Flt-3 inhibitors; CDK4/6 inhibitors; HER2 inhbiitors (Herceptin, Trastuzumab); EGFR inhibitors (Iressa, Tarceva, Nerlynx, Tykerb, Erbitux); RAS inhibitors; MEK inhibitors (Trametinib, Binimetinib, Cobimetinib); ERK inhibitors (Ulixertinib); anti-PD-1 antibodies (Opdivo, Keytruda); anti-CTLA4 antibodies (Yervoy); antitumor antibiotics; nitrosoureas; compounds targeting/decreasing protein or lipid kinase activity, compounds targeting/decreasing protein or lipid phosphatase activity, or any further anti-angiogenic compounds.

The treatment may also be complemented with other treatments or interventions such as surgery, radiotherapy (e.g., gamma-radiation, neutron beam radiotherapy, electron beam radiotherapy, proton therapy, brachytherapy, and systemic radioactive isotopes), a biologic response modifier (e.g., an interferon, an interleukin, tumor necrosis factor (TNF), and agents used to attenuate an adverse effect.

The recitation of an embodiment for a variable herein includes that embodiment as any single embodiment or in combination with any other embodiments or portions thereof. The recitation of an embodiment herein includes that embodiment as any single embodiment or in combination with any other embodiments or portions thereof.

EXAMPLES

List of Abbreviations

Ac: acetyl
AcOEt or EtOAc: ethyl acetate
AcOH: acetic acid
Ar: aryl
ATCC: American Type Culture Collection
ATP: adenosine triphosphate
BINOL: [1,1'-binaphthalene]-2,2'-diol
Boc: tert-butyloxycarbonyl
BOP: (benzotriazol-1-yloxy)tris(dimethylamino)phosphonium hexafluorophosphate
br: broad
BSA: bovine serum albumin
CCL: cancer cell lines
$CDCl_3$: deuterated chloroform
DCE: 1,2-dichloroethane
DCM: dichloromethane
DIEA (or DIPEA): N,N-diisopropylethylamine (Huenig's base)
DME: 1,2-dimethoxyethane
DMF: N,N-dimethylformamide
DMSO: dimethylsulfoxide
DMSO-$d_6$: deuterated dimethylsulfoxide
DTT: dithiothreitol
EA: ethyl acetate
$EC_{50}$: half-maximal effective concentration
ECL: enhanced chemiluminescence
EDTA: ethylenediamine tetraacetic acid
$Et_2O$: diethyl ether
EtOH: ethanol
Eu: Europium
FBS: fetal bovine serum
GST: glutathion S-transferase
HATU: O-(7-azabenzotriazol-1-yl)-N,N,N',N',-tetramethyluronium hexafluorophosphate
HEPES: 4-(2-hydroxyethyl)-1-piperazineethanesulfonic acid
Het: heterocycle
Hex: hexanes
HRMS: high resolution mass spectrometry
HPLC: high performance liquid chromatography
HRP: horseradish peroxidase
$IC_{50}$: half-maximal inhibitory concentration
IPA: isopropanol
iPrOH: isopropanol
LCMS: liquid chromatography mass spectrometry
MeCN: acetonitrile
MS: mass spectrometry
NMP: N-methylpyrrolidone
NMR: nuclear magnetic resonance
ON: overnight
PBS: phosphate buffered saline
pERK: phosphorylated extracellular signal-regulated kinase
PMB: para-methoxybenzyl
PMSF: phenylmethylsulfonyl-fluoride
Rf: retention factor
RPMI-1640: Roswell Park Memorial Institute medium
RT: room temperature
SDS: sodium dodecylsulfate
SDS-PAGE: sodium dodecyl-sulfate-polyacrylamide gel electrophoresis
SEM: trimethylsilylethoxymethyl
SNAr: Nucleophilic aromatic substitution TBST: Tris buffered saline with 0.2% Tween-20

TBTU: 0-(benzotriazol-1-yl)-N,N,N',N'-tetramethyluronium tetrafluoroborate

TEV: tobacco etch virus protease

TFA: trifluoroacetic acid

THF: tetrahydrofuran

TLC: silica gel thin layer chromatography

Ts: para-Toluenesulfonate $Y_{MIN}$: minimal data point of a dosage-activity curve The following non-limiting examples are illustrative embodiments and should not be construed as further limiting the scope of the present invention. These examples will be better understood with reference to the accompanying figures.

The Examples set forth herein below provide syntheses and experimental results obtained for certain exemplary compounds. As it is well known to a person skilled in the art, reactions are performed in an inert atmosphere (nitrogen or argon) where necessary to protect reaction components from air and moisture. Temperatures are given in degrees Celsius (° C.). Solution percentages and ratios express a volume to volume relationship, unless otherwise stated. The reactants used in the examples below may be obtained either as described herein, or if not described herein, are themselves either commercially available or may be prepared from commercially available materials by methods known in the art. Flash chromatography is carried out on silica ($SiO_2$) using a Teledyne Isco Rf Combiflash instrument at 254 nm using commercial normal phase silica. Mass spectra analyses are recorded using electrospray mass spectrometry. NMR are recorded on a 400 MHz Varian instrument.

Preparative HPLC was performed using an Agilent instrument using a Phenomenex-Kinetex C18, (21×100 mm, 5 µm) column at a flow rate of 20 mL/min (RT) and UV detection at 220 and 254 nm.

The mobile phase consisted of Solvent A (5% MeOH, 95% water+0.1% formic acid) and Solvent B (95% MeOH, 5% water+0.1% formic acid) unless stated otherwise. As specified in the text, 0.05% TFA or 0.1% AcOH or other additives were occasionally used as additives instead of 0.1% formic acid in both solvents. MeCN was also used instead of MeOH in both mobile phases for more challenging separations as specified in the text. Specific gradient conditions are provided in the examples but the following is representative: T(0)→T(3 min) isocratic using between 10 to 50% solvent B depending on compound polarity, followed by a 12 minutes gradient to 100% solvent B. Last 5 minutes 100% solvent B.

LCMS analyses were performed on an Agilent instrument. Liquid chromatography was performed on a Phenomenex Kinetex C18 column (2.6 µm; 100 Å; 3×30 mm) at a flow rate of 1.5 mL/min (RT) with UV detection at 220 and 254 nm. The mobile phase consisted of solvent A (95% $H_2O$/5% MeOH/0.1% AcOH) and solvent B (95% MeOH/5% $H_2O$/0.1% AcOH) using the following gradient: T(0) 100% A→T(0.5 min) 100% B→isocratic 100% B to T(2 min). MS detection was performed in parallel using APCI detection in both positive and negative modes.

Unless otherwise indicated, all numbers expressing quantities of ingredients, reaction conditions, concentrations, properties, stabilities, and so forth used in the specification and claims are to be understood as being modified in all instances by the term “about.” At the very least, each numerical parameter should at least be construed in light of the number of reported significant digits and by applying ordinary rounding techniques. Accordingly, unless indicated to the contrary, the numerical parameters set forth in the present specification and attached claims are approximations that may vary depending upon the properties sought to be obtained. Notwithstanding that the numerical ranges and parameters setting forth the broad scope of the embodiments are approximations, the numerical values set forth in the specific examples are reported as precisely as possible. Any numerical value, however, inherently contain certain errors resulting from variations in experiments, testing measurements, statistical analyses and such.

Synthesis, Biological Activity and Characterization of Examples:

All compounds as herein defined were prepared according to methods as indicated in Tables 3 to 5. Characterization data by mass spectrometry and NMR are provided for each of the Examples. The compounds are tested in the assays described in the biological Experimental section. The convention used for reporting biological data is provided as a footnote in the respective Tables.

Synthetic Method A:

Commercially available 2,6-difluoro-3-nitrobenzoic acid A-1 (Synthetic Method A) can be converted to carbamate A-2 via a Curtius reaction following the procedure described in *J. Med. Chem.* 2003, 46, 1905. Catalytic hydrogenolysis of nitroarene A-2 using hydrogen gas and a catalyst such as palladium metal on carbon or palladium hydroxide on carbon (Pearlman’s catalyst) yields aniline A-3. Reaction of aniline A-3 with sulfonylating agents such as sulfonyl chlorides in the presence of an organic base such as pyridine that can be used as solvent, with or without a catalyst such as 4-dimethylaminopyridine, and in the presence or not of an additional solvent such as dichloromethane or tetrahydrofuran yields sulfonamide intermediate A-4 that can be deprotected to aniline salts such as A-5 using strong acid (e.g. solutions of anhydrous hydrochloric acid in dioxane). Alternatively, 2,6-difluoroaniline A-6 can be converted to its acetanilide A-7 using an acetylating agent such as acetic anhydride and converted to mono-protected dianiline A-8 as described in WO 2012/101238A1. Sulfonylation to sulfonamide A-9 is achieved under similar conditions used for the conversion of carbamate A-3 to sulfonamide A-4 using a sulfonylating reagent in the presence of an organic base such as pyridine, with or without a catalyst such as 4-dimethylaminopyridine and solvents such as dichloromethane or tetrahydrofuran. Treatment of acetanilide A-9 with aqueous hydrochloric acid in the presence of a co-solvent such as an alcohol provides aniline salt A-5.

Synthetic Method A
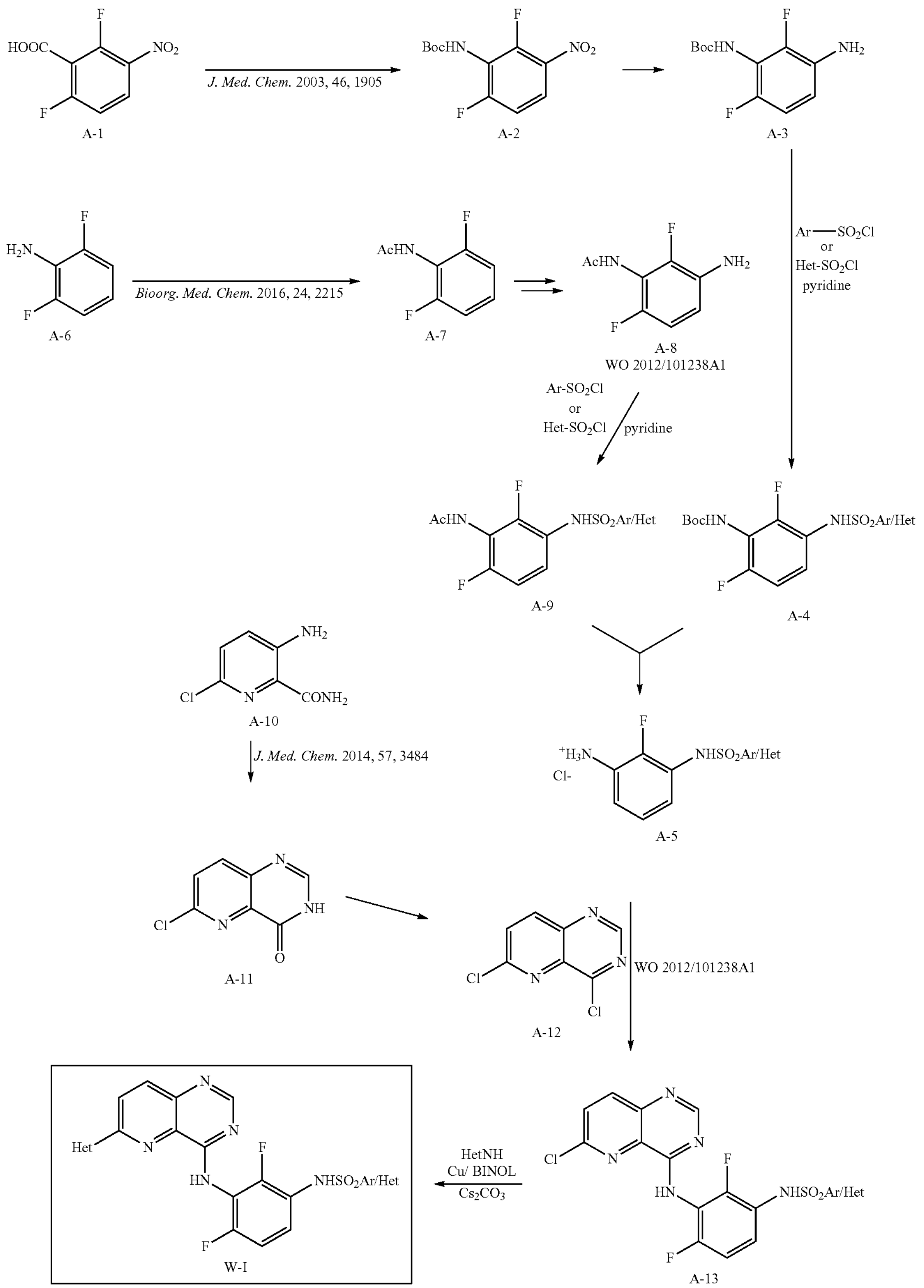

Commercially available 3-amino-6-chloro-2-pyridinecarboxamide A-10 can be transformed into pyridopyrimidinone A-11 by adapting a procedure described in *J. Med. Chem.* 2014, 57, 3484 and converted to dichloro derivative A-12 using chlorinating agents such as thionyl chloride or phosphoryl chloride in the presence of a catalytic amount of DMF following a procedure also described in *J. Med. Chem.* 2014, 57, 3484.

Following a similar procedure to that described in WO 2012/101238A1, intermediate A-13 can be obtained by heating dichloropyridine A-12 with aniline salts A-5 in an organic acid such as acetic acid. Final inhibitors of the general structure W-I that contain a N-linked heterocycle are then obtained by heating chloropyridine A-13 intermediates with heterocycles containing a free NH group such as imidazoles, triazoles, pyrrazoles, benzimidazoles, benzotriazoles, indoles, indazoles and the likes, in the presence of a catalytic amount of copper powder, a ligand (e.g. BINOL) and an inorganic base such as cesium carbonate, in solvents such as DMSO or N-methylpyrrolidone (NMP). In some cases, the presence of copper powder and the ligand is not necessary and the coupling are performed by heating at temperatures ranging from 80° to 140° C. under typical SNAr conditions in the presence of bases and solvents identical to those described above.

Synthetic Method B:

An alternative method to construct inhibitors of general structure W-I is provided by Method B. Using the same intermediate A-2 described in Method A as a starting material, 3-nitroaniline salt B-1 can be obtained by cleavage of the carbamate protecting group under acidic conditions (e.g. using solutions of anhydrous hydrogen chloride in dioxane or trifluoroacetic acid). Using similar conditions as described in WO 2012/101238A1, aniline salt B-1 react with dichloro-pyridopyrimidine A-12 to provide intermediate B-2. Reduction of the nitro group to the corresponding aniline B-3 is performed using metal salts such a tin(II) chloride in alcoholic solvents. Heating chloropyridine B-3 intermediates with heterocycles containing a free NH group such as imidazoles, triazoles, pyrrazoles, benzimidazoles, benzotriazoles, indoles, indazoles and the likes, in the presence of a catalytic amount of copper powder, a ligand (e.g. BINOL) and an inorganic base such as cesium carbonate, in solvents such as DMSO or N-methylpyrrolidone then provides anilines B-4 that contain a N-linked heterocycle on the pyridine ring. Finally, anilines B-4 can be converted to inhibitors of general formula W-I that contain a N-linked heterocycle using sulfonylating agents such as sulfonyl chlorides in the presence of an organic base such as pyridine, with or without a catalyst such as 4-dimethylaminopyridine and solvents such as dichloromethane or tetrahydrofuran.

Synthetic Method B

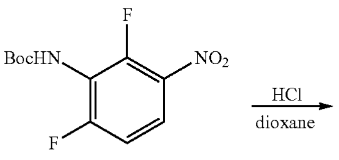

A-2

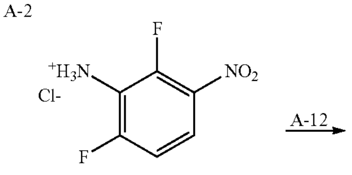

B-1

-continued

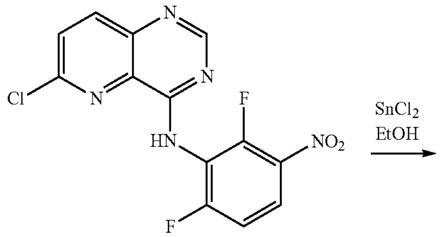

B-2

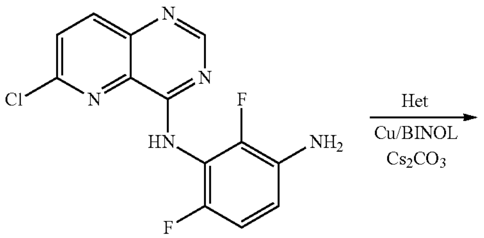

B-3

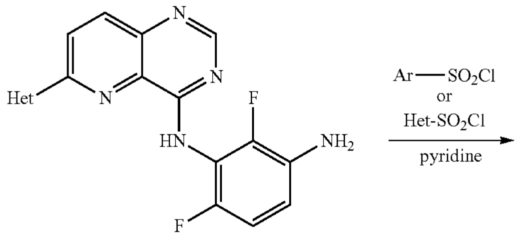

B-4

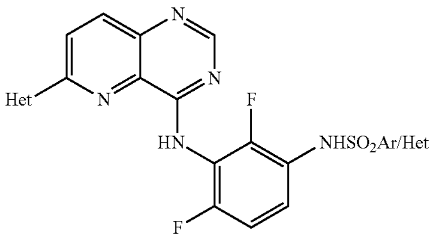

W-I

Synthetic Method C:

Inhibitors of type W-II that contain a C-linked aryl or heterocycle at the 2-position of the pyridine ring can be obtained by metal-catalyzed cross-coupling of chloropyridine A-13 with aryl or heteroaryl boronic acids and derivatives including boronate esters following typical Suzuki-Miyaura protocols. Inorganic aqueous bases such as sodium or potassium carbonate or potassium phosphate can be used as bases, in solvents such as 1,4-dioxane or 1,2-dimethoxyethane (DME) at temperatures in the range of 70-110° C. under ordinary thermal conditions or under microwave irradiation. Alternatively, organotin species can be used under similar conditions following typical Stille coupling protocols in the presence of an organic base such as triethylamine.

Synthetic Method C

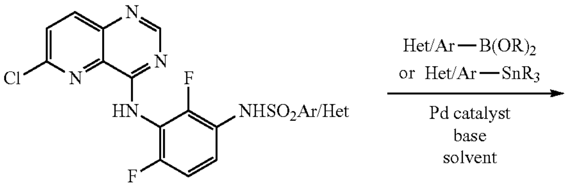

A-13

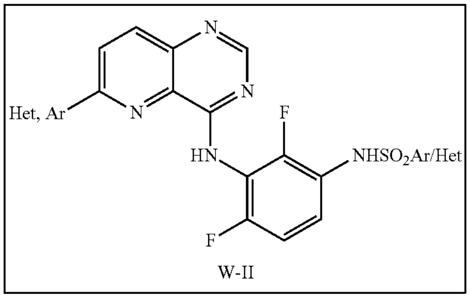

W-II

-continued

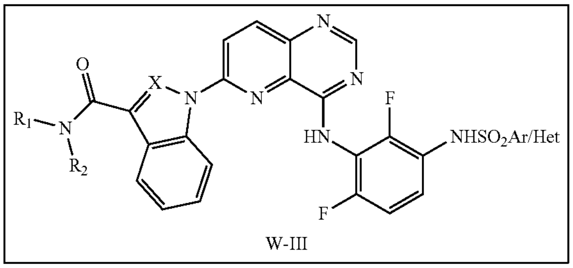

W-III

Synthetic Method D:

Using the protocol described in Synthetic Method A, chloropyridine A-13 was coupled to the methyl esters of 3-indole or 3-indazolecarboxylic acid to provide intermediates D-1 or D-2 respectively, after saponification using an aqueous solution of an inorganic hydroxide such as sodium, potassium or lithium hydroxide. Carboxylic acids D-1 and D-2 were then reacted with primary and secondary amines using typical procedures for the construction of amide bonds (e.g. BOP, HATU or TBTU and the like in the presence of an organic base such as DIEA or triethylamine in solvents such as NMP, DMF, THF or DMSO at ambient temperature). In cases were functionalities on the amine reagents are reactive under conditions of amide bond formation (e.g. an additional amine function), that reactive substituent can be protected (e.g. as a tert-butylcarbamate) and the protecting group removed as a last step to reveal the desired inhibitor of formula W-III.

Synthetic Method D

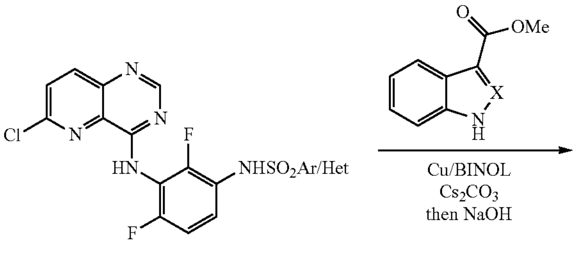

A-13

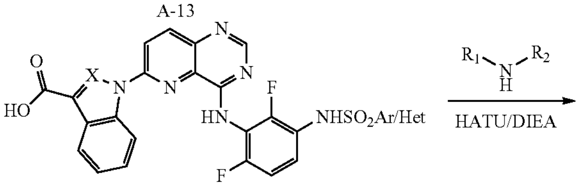

D-1: X = CH
D-2: X = N

Synthetic Method E:

Bromobenzimidazole E-2 can be obtained by reacting 3-bromo-1,2-phenylenediamine E-1 with formic acid and formylated using a strong bases such as a combination of an inorganic hydride and an alkyllithium (e.g. tert-butylliyhium) and a formylating agent such DMF in aprotic solvents such as THF at low temperatures as described in WO 2004/076411 to provide the formylbenzimidazole E-3. Coupling of benzimidazole E-3 with chloropyridine A-13 can be performed under the general protocol of Method A to provide aldehyde intermediate E-4. Reaction of E-4 with amines under standard reductive amination conditions (e.g. using reducing agents such as inorganic borohydrides or cyanoborohydrides in the presence of weak organic acids such as AcOH) provides inhibitors of general formula W-IV as shown in general synthetic method E.

Synthetic Method E

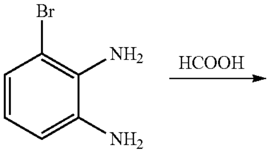

E-1

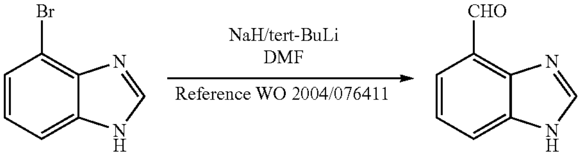

E-2

E-3

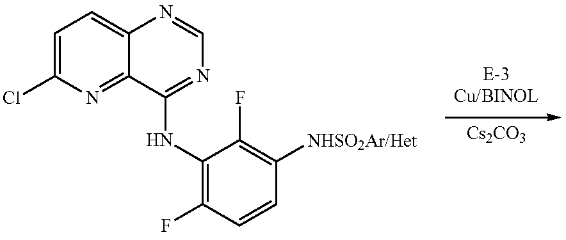

A-13

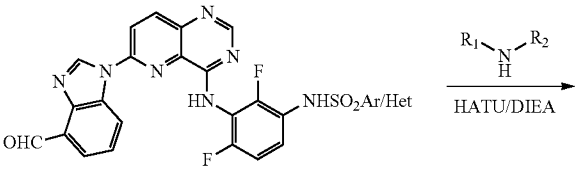

E-4

-continued

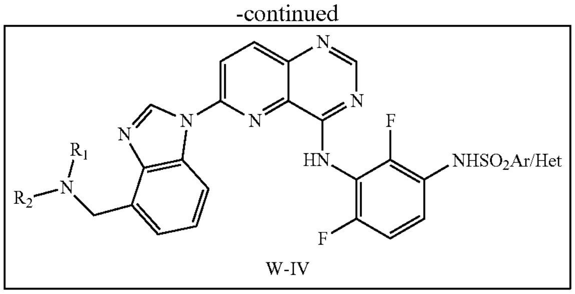

W-IV

Synthetic Method F:

Bromobenzimidazole E-2 is commercially available or can be prepared as described under General Method E (Step 1). Cross-coupling to heteroaryl boronic acids or boronate esters can be performed under palladium-catalyzed Suzuki-Miyaura cross-coupling conditions in the presence of a base such as sodium or potassium carbonate in a solvent such as dioxane or dimethoxyethane and water, to provide intermediates F-1. Coupling of substituted benzimidazole derivative F-1 with chloropyridine A-13 can then be performed under the general protocol of Method A to provide inhibitors of general structure W-V.

Synthetic Method F

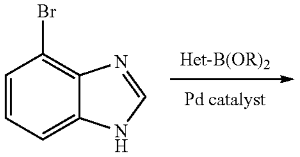

E-2

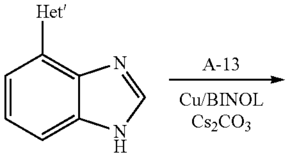

F-1

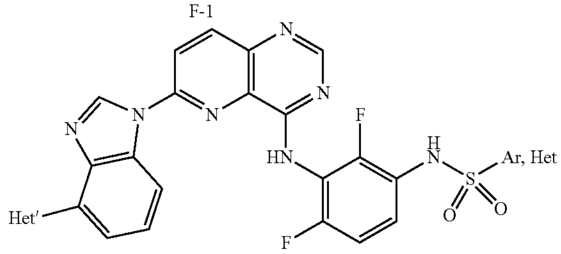

W-V

Synthetic Method G:

N-Tosyl protected indole-3-sulfonyl chloride G-1 (prepared by the procedure described in *Chemical and Pharmaceutical Bulletin* 2009, 57, 591) is reacted with primary or secondary amines in a solvent such as THF and in the presence of a tertiary base such as DIEA or triethylamine to provide intermediate sulfonamides G-2 after removal of the tosyl protecting group upon treatment with an aqueous inorganic base such as KOH. Final inhibitors of the general structure W-VI are then obtained by heating sulfonamides G-2 with chloropyridine A-13 intermediates under the usual conditions as described previously.

Synthetic Method G

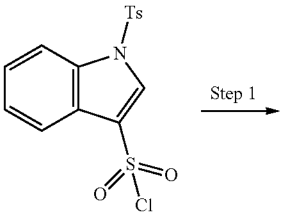

G-1

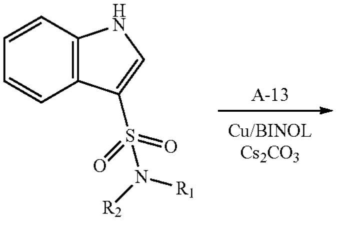

G-2

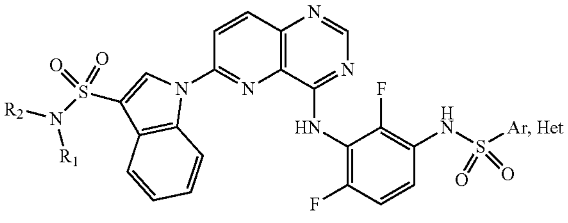

W-VI

Synthetic Method H:

3-Indolethiocyanate H-1 (prepared following the procedure described in *Phosphorus, Sulfur and Silicon and the Related Elements* 2014, 189, 1378) is reduced to the corresponding sulfide salt using a reducing agent such as sodium sulfide nonahydrate and directly alkylated without isolation with an alkyl halide to provide sulfide intermediates H-2. Sulfide intermediates H-2 are then converted to sulfone intermediates H-3 using an oxidizing agent such as 3-chloroperoxybenzoic acid. Final inhibitors of the general structure W-VII are then obtained by heating indolesulfones H-3 with chloropyridine A-13 intermediates under usual conditions as described previously.

Synthetic Method H

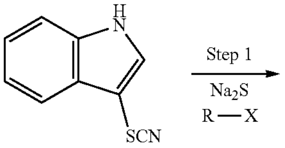

H-1

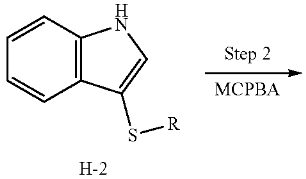

H-2

-continued

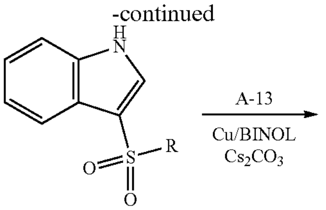

H-3

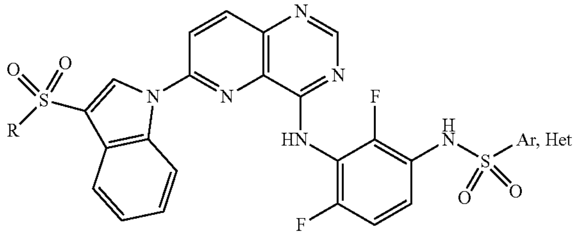

W-VII

Synthetic Method I:

A bright red solution of commercially available 3-fluoro-2-nitroaniline 1-1 reacts with primary or secondary amines in solvents such as MeCN, DMSO or NMP and in the presence of an inorganic base such as potassium carbonate or an organic base such as DIEA to provide intermediates I-2 upon heating at temperature ranging from 40° C. to 120° C. under thermal or microwave conditions. Reduction of the nitro group of intermediate 1-2 can be achieved using metals such as Fe or Zn in the presence of ammonium chloride at temperatures ranging from 40° C. to 80° C. in an alcoholic solvent such as isopropanol. 1,2-phenylenediamine intermediates (see J-1) are then converted directly to the desired benzimidazole intermediates 1-3 upon heating with formic acid at temperatures ranging from 40° C. to 80° C. Final inhibitors of the general structure W-VIII are then obtained by heating benzimidazoles 1-3 with chloropyridine A-13 intermediates under usual conditions as described previously.

Synthetic Method I

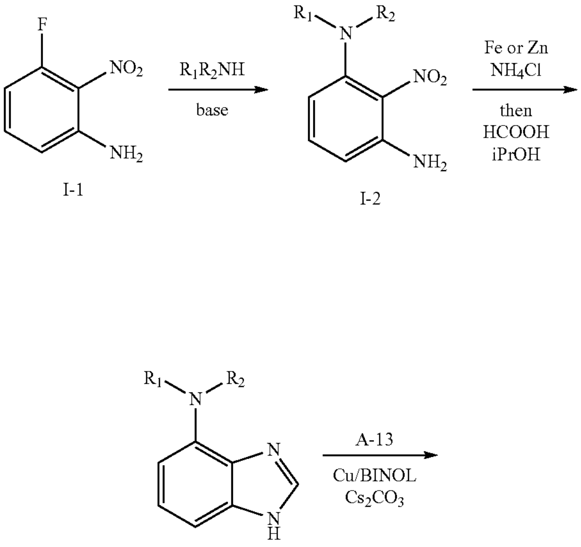

I-1 I-2 I-3

-continued

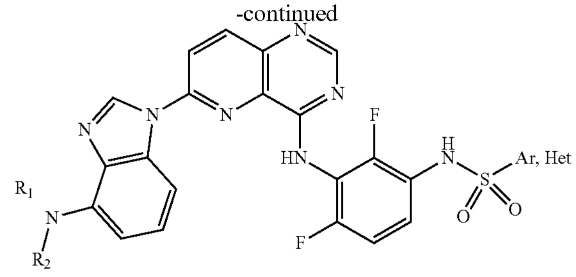

W-VIII

Synthetic Method J:

Nitroanilines 1-2 obtained as described under synthetic method I are reduced to 1,2-phenylenediamines J-1 using metals such as Fe or Zn in the presence of ammonium chloride at temperature ranging from 40° C. to 80° C. in an alcoholic solvent such as isopropanol. 1,2-phenylenediamine intermediates (see J-1) are then converted to the desired benzotriazole intermediates J-2 upon treatment with an inorganic nitrite such as sodium nitrite under acidic conditions (for example AcOH). Final inhibitors of the general structure W-IX are then obtained by heating intermediates 1-3 with chloropyridine A-13 intermediates under usual conditions as described previously.

Synthetic Method J

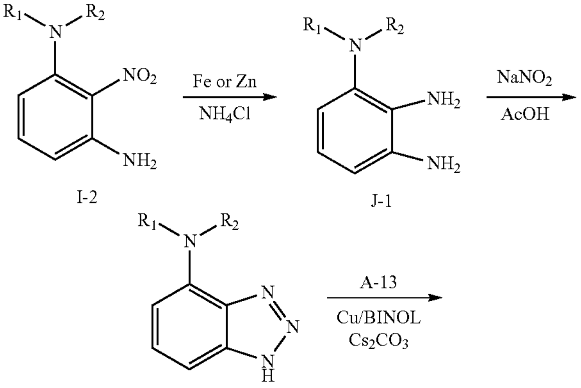

I-2 J-1 J-2

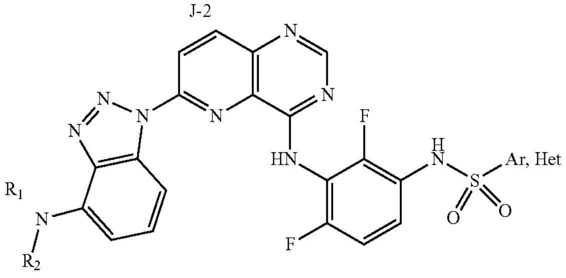

W-IX

The procedures to prepare inhibitors that do not or only partially fall under the above general synthetic procedures are described specifically in the following.

Sulfonyl Chlorides:

The following sulfonyl chlorides were obtained from commercial sources and used as received: 4-methoxybenzenesulfonyl chloride, 2,4-dichlorobenzenesulfonyl chloride, 2,4-dimethylbenzenesulfonyl chloride, 2-chlorobenzenesulfonyl chloride, 2-methylbenzenesulfonyl chloride, 4-ethylbenzenesulfonyl chloride, 2-cyanobenzenesulfonyl chloride, 2,4-dimethoxybenzenesulfonyl chloride, 2-trifluoromethylbenzenesulfonyl chloride, 3-chlorobenzenesulfonyl chloride, 3-methylbenzenesulfonyl chloride, 2,3-dichlorobenzenesulfonyl chloride, 3-chloro-2-methylbenzenesulfonyl chloride, 2-bromobenzenesulfonyl chloride, 2-chloro-4-fluorobenzenesulfonyl chloride, 2-chloro-6-fluorobenzenesulfonyl chloride, 2,5-dichlorobenzenesulfonyl chloride, 2,5-dimethylbenzenesulfonyl chloride, 2-chloro-6-methylbenzenesulfonyl chloride, 3-fluoro-2-methylbenzenesulfonyl chloride, 2-chloro-4-methylbenzenesulfonyl chloride, 1,3-benzodioxole-5-sulfonyl chloride, 2-chloro-4-(trifluoromethyl)-benzenesulfonyl chloride, 2-methyl-4-nitrobenzenesulfonyl chloride, 2-(difluoromethyl)benzenesulfonyl chloride.

Other sulfonyl chlorides were prepared by using or adapting literature procedures as described below.

2-Fluoro-4-methoxybenzenesulfonyl chloride

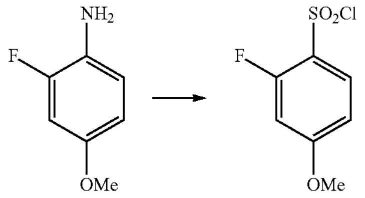 [SMILES: COc1ccc(N)c(F)c1 ; COc1ccc(S(=O)(=O)Cl)c(F)c1]

Following a procedure described in EP2752410A1, 2-fluoro-4-mehoxyaniline (1.00 g, 7.1 mmol) was dissolved in acetonitrile (25 mL) and conc. HCl (10 mL) was added. The mixture was cooled to 0° C. in an ice-salt bath. A solution of $NaNO_2$ (0.59 g, 8.5 mmol) in water (1 mL) was then added in portions and the mixture stirred for 1.5 h at 0° C. (light brown solution with a small amount of white solids in suspension). To the resulting mixture, AcOH (12 mL) was added and after stirring for 10 minutes at 0° C., $NaHSO_3$ (7.37 g, 10 equiv., 71 mmol) was added. After stirring for 5 min, Cu(II) chloride (0.96 g, 1 equiv.) and CuCl (70 mg, 0.1 equiv.) were added and the green suspension was stirred in the ice bath, allowing the temperature to rise to RT over 1 h after which it was stirred for an additional 18 h at RT (TLC $R_f$: 0.45 in 2:1 hexane/EtOAc). The reaction mixture was then poured into water (100 mL) and extracted with EtOAc. The extract was washed with water, dried over $MgSO_4$ and filtered through a pad of silica gel (15 mL) using 1:1 hex/EA as eluent. Removal of volatiles under reduced pressure gave 1.22 g of a clear light brown oil (TLC shows the presence of more polar unidentified impurities following aqueous work-up). $^1H$ NMR ($CDCl_3$) δ: 7.88 (t, J=8.6 Hz, 1H), 6.76-6.93 (m, 2H), 3.93 (s, 3H). Homogeneity ~70% by $^1H$ NMR.

4-Chloro-2-methylbenzenesulfonyl chloride

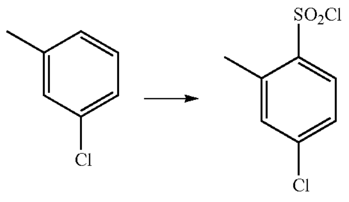

Prepared by chlorosulfonylation of meta-chlorotoluene following the procedure described in Acta Crystallographica Section E 2009, 65 (4), o800. meta-Chlorotoluene (1 mL) was dissolved in $CHCl_3$ (4 mL) and the solution cooled in an ice bath. Chlorosulfonic acid (2.5 mL) was added dropwise over 15 min as HCl gas was slowly evolved. After completion, the reaction mixture was allowed to warm up to RT. TLC shows no more starting material (Rf=0.8 in 8:2 hex/EA) and a new spot (Rf=0.7 in 8:2 hex/EA) that trails somewhat is formed. The reaction mixture was poured over ice (50 mL), DCM (15 mL) was added and the product organic phase was separated, washed with cold water, dried ($MgSO_4$) and concentrated to a colorless oil (0.87 g) that was used without further purification: $^1H$ NMR ($CDCl_3$) δ: 8.01 (d, J=8.6 Hz, 1H), 7.43 (s, 1H), 7.40 (dd, J=8.6, 2.0 Hz, 1H), 2.78 (s, 3H).

The following sulfonyl chlorides were prepared using a similar procedure with some modifications as described below:

4-Methoxy-2-methylbenzenesulfonyl chloride

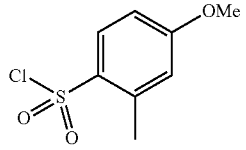

3-Methoxytoluene (6.00 g) was dissolved in $CHCl_3$ (30 mL) and the solution cooled to −35° C. (bath temperature). Chlorosulfonic acid (15 mL) was added dropwise over 20 min (no $HCl/SO_2$ gas evolution is noticeable). The clear solution was then stirred for 15 min at −30 to −25° C. (no gas evolution was noticed). The reaction mixture was poured carefully over ice (50 mL), DCM (50 mL) was added and the slightly milky product organic phase was separated, washed with cold water, dried ($MgSO_4$) and concentrated to a colorless oil that was dried under vacuum (8.28 g, 76% yield). NMR shows the presence of a single isomer: $^1H$ NMR ($CDCl_3$) δ: 8.01 (d, J=8.6 Hz, 1H), 6.72-6.95 (m, 2H), 3.90 (s, 3H), 2.75 (s, 3H).

2-Chloro-4-methoxybenzenesulfonyl chloride

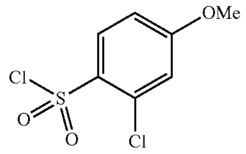 [SMILES: COc1ccc(S(=O)(=O)Cl)c(Cl)c1]

3-Chloroanisole (1.00 g) was dissolved in $CHCl_3$ (4 mL) and the solution cooled to about −35° C. Chlorosulfonic acid (2.5 mL) in $CHCl_3$ (2 mL) was added dropwise over 15 min. After completion, there is only baseline material by TLC (SM Rf=0.8 in 8:2 hex/EA). Upon warming the reaction mixture to RT gas evolution was noticed and isomeric products appeared by TLC (Rf=0.30 and 0.25 in 8:2 hex/EA). After stirring at RT for 30 min, a white precipitate began forming. The reaction mixture was poured over ice (50 mL), DCM (15 mL) was added and the organic product phase was separated, washed with cold water, dried ($MgSO_4$) and concentrated to a colorless oil that crystallized as white needles on standing (0.89 g). $^1$H NMR shows a mixture of 2 isomers in a 60:40 ratio that were separated by flash chromatography on silica gel using 8:2 hexane/EtOAc as eluent. Desired isomer (more polar): $^1$H NMR ($CDCl_3$) δ: 7.90 (d, J=8.6 Hz, 1H), 7.04-7.19 (m, 2H), 4.08 (s, 3H).

2,3-Dimethylbenzenesulfonyl chloride

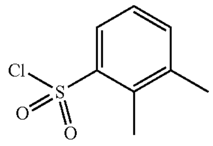

Isolated as the minor isomer after chlorosulfonylation of o-xylene as described in WO2003/055478. $^1$H NMR ($CDCl_3$) δ: 7.96 (d, J=7.8 Hz, 1H), 7.52 (d, J=7.4 Hz, 1H), 7.30 (t, J=7.8 Hz, 1H), 2.71 (s, 3H), 2.41 (s, 3H).

3-Fluoro-2-methyl-4-methoxybenzenesulfonyl chloride

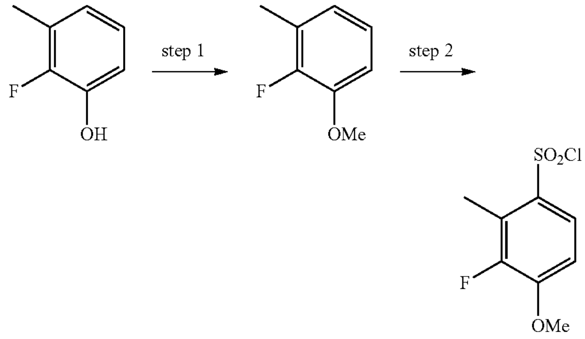

Step 1: To a solution of 2-fluoro-3-methylphenol (4.32 mL, 39.7 mmol) in acetone (50 mL) was added potassium carbonate (6.58 g, 47.6 mmol) followed by iodomethane (2.75 mL, 43.7 mmol). The reaction mixture was then refluxed overnight at 60° C. The reaction mixture was then cooled to RT, filtered (2×10 mL acetone for rinses) and concentrated under reduced pressure. The crude product was extracted from water (30 mL) and EtOAc (2×50 mL). The organic layer was then separated, dried with $Na_2SO_4$, filtered and concentrated under reduced pressure. The residue was purified by flash chromatography on silica gel using 0 to 5% EtOAc/hexanes to afford 2-fluoro-3-methylanisole as a clear colorless liquid (5.30 g, 95% yield): $^1$H NMR ($CDCl_3$) δ: 6.95 (td, J=8.0, 1.4 Hz, 1H), 6.85-6.71 (m, 2H), 3.87 (s, 3H), 2.28 (d, J=2.3 Hz, 3H).

Step 2: To a solution of 2-fluoro-3-methylanisole from step 1 (1.00 g, 7.13 mmol) in DCM (5.6 mL) was added a solution of chlorosulfonic acid (1.13 mL, 16.5 mmol) in DCM (5.6 mL) over a 5 minute period. The pale brown reaction mixture containing a viscous liquid layer was stirred at RT for 10 min and then quenched by pouring into a mixture of water (10 mL) and ice (5 g). The aqueous phase was extracted with DCM (2×10 mL), dried on $Na_2SO_4$, filtered and concentrated under reduced pressure to give the desired sulfonyl chloride as a colorless liquid (1.70 g, 100% yield). The material was used without further purification: $^1$H NMR ($CDCl_3$) δ: 7.87 (dd, J=9.0, 1.8 Hz, 1H), 6.97-6.86 (m, 1H), 3.97 (s, 3H), 2.66 (d, J=2.8 Hz, 3H).

3-Chloro-2-methyl-4-methoxybenzenesulfonyl chloride

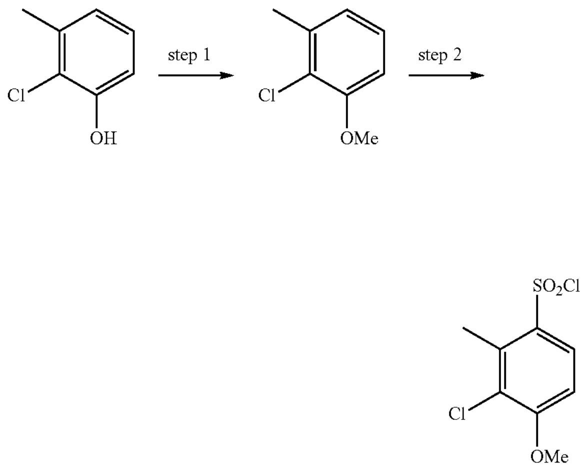

Following a similar procedure (Step 1) as for 3-fluoro-2-methyl-4-methoxybenzenesulfonyl chloride and starting from 2-chloro-3-methylphenol, 2-chloro-3-methylanisole was obtained in quantitative yield as a colorless liquid: $^1$H NMR ($CDCl_3$) δ: 7.12 (t, J=7.9 Hz, 1H), 6.87-6.83 (m, 1H), 6.79 (d, J=8.2 Hz, 1H), 3.89 (s, 3H), 2.38 (s, 3H).

Treatment with chlorosulfonic acid as described for 3-fluoro-2-methyl-4-methoxybenzenesulfonyl chloride (Step 2) provided the desired 3-chloro-2-methyl-4-methoxybenzenesulfonyl chloride as a colorless liquid in 96% yield: $^1$H NMR ($CDCl_3$) δ: 8.02 (d, J=9.1 Hz, 1H), 6.90 (d, J=9.1 Hz, 1H), 4.00 (s, 3H), 2.83 (s, 3H).

2-Ethylbenzenesulfonyl chloride

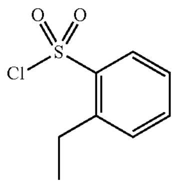

2-Ethylbenzenethiol (1.46 mL, 10.3 mmol) and KCl (776 mg, 10.3 mmol) were dissolved in water (38 mL) and Oxone® (15.8 g, 25.8 mmol) was added in small portions. After stirring for 1 h at RT, the reaction was considered complete by LCMS analysis and the reaction mixture was extracted with EtOAc (4×5 mL). The extract was dried ($Na_2SO_4$) and concentrated under reduced pressure to give a white crystalline solid (1.43 g, 68% yield) that was used as such: $^1$H NMR ($CDCl_3$) δ: 8.07 (dd, J=8.1, 1.3 Hz, 1H), 7.66 (td, J=7.6, 1.3 Hz, 1H), 7.49 (d, J=7.7 Hz, 1H), 7.45-7.38 (m, 1H), 3.20 (q, J=7.5 Hz), 1.36 (t, J=7.5 Hz).

3-Fluoro-2-ethylbenzenesulfonyl chloride

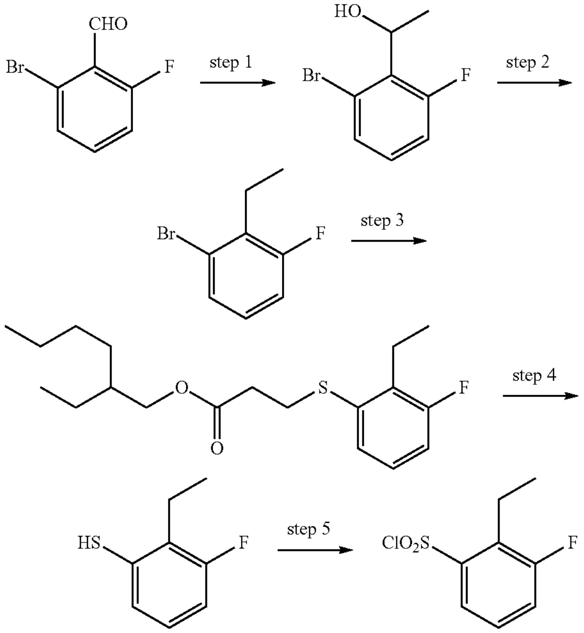

Step 1: 2-Bromo-6-fluorobenzaldehyde (6.00 g, 29.5 mmol) was dissolved in dry THF (60 mL) and the solution cooled to −78° C. under an argon atmosphere. Methylmagnesium bromide (3.0 M solution in diethylether, 13.4 mL, 40.3 mmol) was added dropwise and the mixture was stirred at −78° C. for 30 min. The reaction was then quenched with 10% hydrochloric acid (50 mL) and the product was extracted into ether (2×50 mL). The extract was dried ($MgSO_4$) and concentrated and the residue was purified by Combiflash® on silica gel using 10-30% EtOAc in hexanes as eluent to give the desired alcohol derivative as a colorless oil (6.20 g, 96% yield): $^1$H NMR ($CDCl_3$) δ: 7.35 (ddd, J=7.9, 3.1, 2.0 Hz, 1H), 7.16-6.99 (m, 2H), 5.35 (q, J=6.7 Hz, 1H), 1.61 (dd, J=6.8, 1.1 Hz, 3H).

Step 2: Indium (III) chloride (412 mg, 1.83 mmol) was suspended in DCM (40 mL) and chlorodiisopropylsilane (8.42 mL, 49.3 mmol) was added. The alcohol from step 1 (4.00 g, 18.3 mmol) in DCM (8 mL) was added and the mixture was stirred for 3 h at RT to give a clear solution. The reaction mixture was quenched with water (50 mL), extracted with diethylether (3×20 mL), washed with brine and dried ($MgSO_4$). Concentration and purification by flash chromatography using hexanes as eluent provided the silylated ether of the starting alcohol.

The material was dissolved in DCE (41 mL) and chlorodiisopropylsilane (0.78 mL, 4.6 mmol) and indium (III) chloride (103 mg, 4.6 mmol) were added. The mixture was stirred for 3 h at 80° C. After cooling to ambient temperature, the reaction mixture was diluted with hexane (100 mL) washed with water (100 mL) and the aqueous phase was back-extracted with hexane (2×50 mL). The combined organic phases were dried ($Na_2SO_4$) and concentrated to give a colorless oil that was purified by flash chromatography on silica gel using hexanes as eluent to afford the 2-bromo-6-fluoro-ethylbenzene (3.71 g, 100%) as a colorless oil: 1H-NMR ($CDCl_3$) δ: 7.32 (d, J=7.8 Hz, 1H), 7.11-6.91 (m, 2H), 2.82 (dq, J=7.5, 2.2 Hz, 2H), 1.20-1.15 (m, 3H).

Step 3: the arylbromide from step 2 (3.71 g, 18.3 mmol) was dissolved in toluene (60 mL) and N,N-Diisopropylethylamine (6.40 mL, 36.5 mmol) was added. The solution was then degassed through 3 cycles of evacuation and back-filling with nitrogen. Tris(dibenzylideneacetone) dipalladium(0) (836 mg, 0.9 mmol), 4,4-bis(diphenylphosphino)-9,9-dimethylxanthene (1.08 g, 1.83 mmol) and 2-ethylhexyl-3-mercaptopropionate (4.59 mL, 19.2 mmol) were added and the mixture was degassed twice more before refluxing overnight under a nitrogen atmosphere. The reaction mixture was then cooled to RT, quenched with water (50 mL) and extracted with EtOAc (2×50 mL). The combined organic phases were washed with 10% aqueous HCl (75 mL) and dried ($Na_2SO_4$). Concentration under reduced pressure and purification of the residue by flash chromatography using 0-15% EtOAc in hexanes as eluent gave the desired sulfide intermediate (4.00 g) as an orange oil contaminated with some unreacted starting thiol. This material was used as such in the next step.

Step 4: the crude sulfide derivative from step 3 (4.00 g, assume 11.7 mmol) was dissolved in THF (41 mL) and potassion tert-butoxide (1.0 M in THF, 14.1 mL, 14.1 mmol) was added dropwise. The resulting solution was stirred at RT for 1 h. The reaction was then quenched by addition of a saturated aqueous $NH_4Cl$ solution (40 mL) and extracted with EtOAc (2×30 mL). The combined organic phases were concentrated and the dark orange residue was passed through a small pad of silica gel using hexanes for washings to afford a mixture of thiol and disulfide (1.50 g) that was used as such in the next step (caution: stench).

Step 5: the crude mixture of thiophenol and disulfide from Step 4 (1.50 g, assume 9.6 mmol) and KCl (723 mg (9.6 mmol) were suspended in water (40 mL) and Oxone® (14.8 g, 24 mmol) was added in portions. After stirring for 1 h at RT, the reaction mixture was extracted with EtOAc (2×20 mL) and the extract was dried ($Na_2SO_4$) and concentrated under reduced pressure to give the crude sulfonyl chloride that was used as such for preparing the corresponding fragment A-5 and aniline A-8 (see Table 1).

3-Chloro-2-ethylbenzenesulfonyl chloride

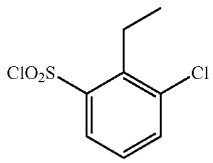

The sulfonyl chloride was prepared following the same procedure as for 3-fluoro-2-ethylbenzenesulfonyl chloride but starting from 2-bromo-6-chlorobenzaldehyde:

Step 1 (98% yield as a white solid): $^1$H NMR ($CDCl_3$) δ: 7.49 (dd, J=8.0, 1.2 Hz, 1H), 7.33 (dd, J=8.0, 1.2 Hz, 1H), 7.05 (t, J=8.0 Hz, 1H), 5.58 (q, J=6.9 Hz, 1H), 1.64 (d, J=6.9 Hz, 3H).

Step 2 (100% yield as a colorless oil): $^1$H-NMR ($CDCl_3$) δ: 7.43 (dd, J=8.0, 1.2 Hz, 1H), 7.29 (dd, J=8.0, 1.2 Hz, 1H), 6.96 (t, J=8.0 Hz, 1H), 2.97 (q, J=7.5 Hz, 2H), 1.17 (t, J=7.5 Hz, 3H).

Step 3 (81% yield as an orange oil): $^1$H-NMR ($CDCl_3$) δ: 7.24-7.18 (m, 2H), 7.08 (t, J=7.9 Hz, 1H), 4.07-3.96 (m, 2H), 3.17 (t, J=7.4 Hz, 2H), 2.96 (q, J=7.5 Hz, 2H), 2.64 (t, J=7.4 Hz, 2H), 1.56 (dd, J=11.9, 5.8 Hz, 2H), 1.40-1.21 (m, 9H), 1.16 (t, J=7.5 Hz, 3H), 0.89 (t, J=7.4 Hz, 6H).

Step 4 (99% yield as a colorless liquid): $^1$H-NMR ($CDCl_3$) δ: 7.15 (d, J=7.9 Hz, 2H), 6.97-6.92 (m, 1H), 3.41 (s, 1H), 2.87 (q, J=7.5 Hz, 2H), 1.18 (t, J=7.5 Hz, 3H).

Step 5 (crude material used without purification): $^1$H-NMR ($CDCl_3$) δ: 8.03 (dd, J=8.2, 1.3 Hz, 1H), 7.73 (dd, J=8.0. 1.3 Hz, 1H), 7.37 (t, J=8.1 Hz, 1H), 3.30 (q, J=7.4 Hz, 2H), 1.33 (t, J=7.4 Hz, 3H).

2-Methyl-3-(trifluoromethyl)benzenesulfonyl chloride

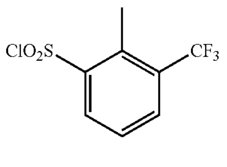

The sulfonyl chloride was prepared following the same procedure as for 3-fluoro-2-ethylbenzenesulfonyl chloride but starting from commercially available 2-methyl-3-(trifluoromethyl)bromobenzene:

Step 3 (100% yield as an orange oil): $^1$H-NMR ($CDCl_3$) δ: 7.49 (d, J=7.9 Hz, 2H), 7.26-7.19 (m, 1H), 4.06-4.00 (m, 2H), 3.18 (dd, J=9.1, 5.6 Hz, 2H), 2.65 (dd, J=9.2, 5.6 Hz, 2H), 2.50 (d, J=1.3 Hz, 3H), 1.33-1.23 (m, 11H), 0.88 (td, J=7.4, 2.3 Hz, 6H).

Step 4 (quantitative yield as a colorless oil): $^1$H-NMR ($CDCl_3$) δ: 7.43 (dd, J=7.9, 2.2 Hz, 2H), 7.12 (t, J=7.8 Hz, 1H), 3.42 (s, 1H), 2.43 (s, 3H).

Step 5 (quantitative yield as a white solid): $^1$H-NMR ($CDCl_3$) δ: 8.31 (d, J=8.1 Hz, 1H), 8.00 (t, J=7.7 Hz, 1H), 7.55 (dd, J=15.6, 7.6 Hz, 1H), 2.93 (s, 3H).

General Procedure for the Preparation of Sulfonyl Chlorides from Aryl Bromides:

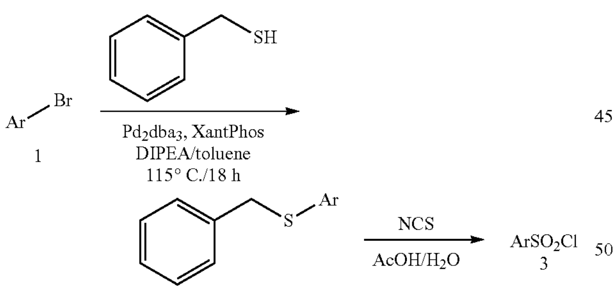

2

Step 1: Aryl bromide 1 (1.00 mmol) was diluted in toluene (1.70 mL). The mixture was degassed with nitrogen bubbling through the solution for 5 min. Tris(dibenzylideneacetone)-dipalladium(0) (0.02 mmol), 4,4-Bis(diphenylphosphino)-9,9-dimethylxanthene (0.04 mmol) and N,N-diisopropylethylamine (2.0 mmol) were added and then the mixture was degassed again for 5 min. Benzyl mercaptan (1 mmol) was then added and the resulting mixture was heated at reflux overnight (oil bath T°=115° C.). After completion, the reaction was cooled down to room temperature, diluted with EtOAc (20 mL) and quenched with $H_2O$ (20 mL). The aqueous layer was extracted with EtOAc (2×20 mL). The combined organic layers were washed with brine (50.0 mL), dried ($Na_2SO_4$), filtered and concentrated under reduced pressure. The crude was further purified by flash chromatography (0-10% EtOAc in Hexanes, 35 mL/min, product eluted at 100% hexane). Fractions of interest were collected and concentrated under reduced pressure to afford the title compound 2.

Step 2: Compound 2 (1.00 mmol) was dissolved in acetic acid (1.90 mL) and $H_2O$ (0.65 mL) was added to afford a heterogeneous solution. N-Chlorosuccinimide (4.00 mmol) was added portion-wise. The reaction was stirred and monitored by LCMS (samples were quenched with N-methyl piperazine). After completion of the reaction, the mixture was concentrated under reduced pressure. The resulting mixture was slowly poured into a saturated aqueous $NaHCO_3$ solution which generates a gas release. The mixture was extracted with EtOAc (2×75 mL). The combined organic layers were washed with brine, dried ($Na_2SO_4$), filtered and concentrated under reduced pressure. The crude compound was further purified by normal phase chromatography (0-40% EtOAc in Hexanes, 60 mL/min, product came out at 100% Hexane). Fractions of interest were collected and concentrated under reduced pressure to afford the title compound 3.

2-Chloro-3-methylbenzenesulfonyl chloride

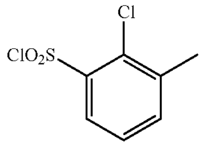

The sulfonyl chloride was prepared following the general procedure starting from commercially available 1-bromo-2-chloro-3-methylbenzene:

Benzyl(2-chloro-3-methylphenyl)sulfide: Yellow solid, 51% yield, 95% purity (at 220 nm). ($ES^-$) M−H=247.2; $^1$H NMR (400 MHz, $CDCl_3$) δ 7.39-7.35 (m, 2H), 7.33-7.28 (m, 2H), 7.28-7.23 (m, 1H+$CDCl_3$), 7.11-7.03 (m, 3H), 4.15 (s, 2H), 2.38 (s, 3H).

2-Chloro-3-methylbenzenesulfonyl chloride: Pale yellow oil, 70% yield, 60% purity (at 254 nm). LCMS: LCMS sample was quenched with N-methylpiperazine (resulting sulfonamide MW=288.8), (ES+) M+H=289.2. Used as crude.

3-Fluoro-2-(trifluoromethyl)benzenesulfonyl chloride

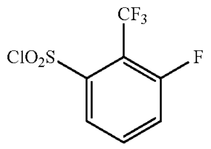 [SMILES: O=S(=O)(Cl)c1cccc(F)c1C(F)(F)F]

The sulfonyl chloride was prepared following the general procedure starting from commercially available 1-bromo-3-fluoro-2-(trifluoromethyl)benzene:

Benzyl(3-fluoro-2-(trifluoromethyl)phenyl)sulfide: yellow oil, 66% yield, 98% purity (at 254 nm). ($ES^-$) M−H=285.2.

3-Fluoro-2-(trifluoromethyl)benzenesulfonyl chloride: pale yellow oil, 93% yield, 98% purity (at 254 nm) LCMS: LCMS sample was quenched with N-methylpiperazine (resulting sulfonamide MW=326.1), (ES+) M+H=327.1

3-Chloro-2-(trifluoromethyl)benzenesulfonyl chloride

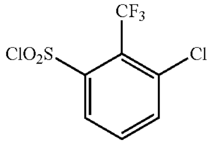 [SMILES: O=S(=O)(Cl)c1cccc(Cl)c1C(F)(F)F]

The sulfonyl chloride was prepared following the general procedure starting from commercially available 1-bromo-3-chloro-2-(trifluoromethyl)benzene:

Benzyl(3-chloro-2-(trifluoromethyl)phenyl)sulfide: white solid, 59% yield, 90% purity (at 220 nm). ($ES^-$) M−H=301.2; $^1H$ NMR (400 MHz, $CDCl_3$) δ 7.46-7.14 (m, 8H+$CDCl_3$), 4.16 (s, 2H).

3-Chloro-2-(trifluoromethyl)benzenesulfonyl chloride

Colorless oil, 66% yield. LCMS: LCMS sample was quenched with N-methylpiperazine (resulting sulfonamide MW=343.5), ($ES^+$) M+H=343.2. Used as crude.

3,4-Difluoro-2-methylbenzenesulfonyl chloride

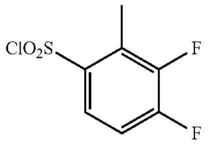

The sulfonyl chloride was prepared following the general procedure starting from commercially available 1-bromo-3-chloro-2-(trifluoromethyl)benzene:

Benzyl(3,4-difluoro-2-methylphenyl)sulfide: orange oil, 96% yield, 96% purity (at 254 nm). ($ES^-$) M−H=249.2; $^1H$ NMR (400 MHz, DMSO-$d_6$) δ 7.32-7.17 (m, 7H), 4.16 (s, 2H), 2.18 (d, J=2.7 Hz, 3H).

3,4-Difluoro-2-methylbenzenesulfonyl chloride: pale yellow oil, 49% yield. LCMS: LCMS sample was quenched with N-methylpiperazine (resulting sulfonamide MW=290.3), ($ES^+$) M+H=291.2; $^1H$ NMR (400 MHz, DMSO-$d_6$) δ 7.56 (ddd, J=8.4, 5.5, 1.8 Hz, 1H), 7.15 (dd, J=18.4, 8.4 Hz, 1H), 2.46 (d, J=2.8 Hz, 3H).

2,4-Dimethyl-3-fluorobenzenesulfonyl chloride

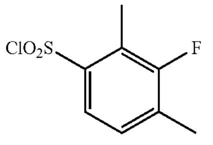

The sulfonyl chloride was prepared following the general procedure starting from commercially available 1-bromo-2,4-dimethyl-3-fluorobenzene:

benzyl(3-fluoro-2,4-dimethylphenyl)sulfide: Orange oil, 95% yield of crude, 80% purity (at 254 nm). Used as crude.

3-fluoro-2,4-dimethylbenzene-1-sulfonyl chloride: Orange oil, 89% yield of crude, 74% purity (at 254 nm). LCMS: LCMS sample was quenched with N-methylpiperazine (resulting sulfonamide MW=286.4), ($ES^+$) M+H=287.1. Used as crude.

2-Methylpyridine-3-sulfonyl chloride

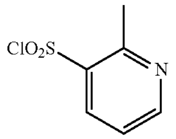

The sulfonyl chloride was prepared following the general procedure starting from commercially available 3-bromo-2-methylpyriine:

3-(Benzylthio)-2-methylpyridine: orange liquid, 88% yield, 94% purity (at 220 nm)., ($ES^+$) M+H=215.8, ($ES^-$) M−H=214.1. $^1H$ NMR (400 MHz, DMSO-$d_6$) δ 8.30 (dd, J=4.9, 1.5 Hz, 1H), 7.57-7.45 (m, 1H), 7.31-7.27 (m, 5H), 7.07 (dd, J=7.6, 5.1 Hz, 1H), 4.09 (s, 2H), 2.58 (s, 3H).

2-Methylpyridine-3-sulfonyl chloride: pale yellow oil, 100% yield, 95% purity (at 254 nm)., LCMS sample was diluted with $H_2O$ (resulting sulfonic acid MW=173.1) ($ES^-$) M−H=171.9; $^1H$ NMR (400 MHz, $CDCl_3$) δ 8.80 (dd, J=4.8, 1.6 Hz, 1H), 8.33 (dd, J=8.1, 1.7 Hz, 1H), 7.43-7.36 (m, 1H), 3.02 (s, 3H).

6-Methoxy-4-methylpyridine-3-sulfonyl chloride

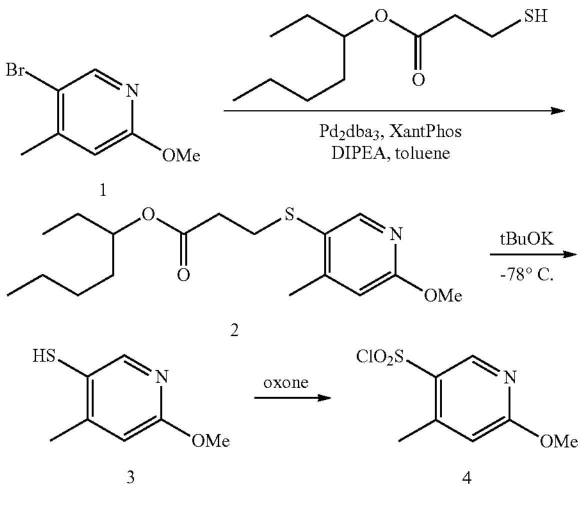

Preparation of 2-ethylhexyl 3-((6-methoxy-4-methylpyridin-3-yl)thio)propanoate (2): 5-bromo-2-methoxy-4-methylpyridine (6.00 g, 29.7 mmol) was dissolved in toluene (100 mL) and N,N-diisopropylethylamine (10.4 mL, 59.4 mmol) was added. The mixture was degassed with nitrogen bubbling through the solution for 5 min. Tris(dibenzylideneacetone)dipalladium(0) (1.36 g, 1.49 mmol), 4,4-bis(diphenylphosphino)-9,9-dimethylxanthene (1.75 g, 2.97 mmol) and 2-ethylhexyl-3-mercaptopropionate (7.47 mL, 31.2 mmol) were added. The mixture was degassed again for 5 min. The mixture was heated at reflux overnight (oil bath T=117° C.). The reaction was cooled down to room temperature, diluted with EtOAc (100 mL) and quenched with $H_2O$ (100 mL). The organic and aqueous layers were separated and the aqueous layer was extracted with EtOAc (2×50.0 mL). The combined organic layers were washed with HCl (10% in $H_2O$, 50.0 mL), dried ($Na_2SO_4$), filtered and concentrated under reduced pressure. The crude was purified by flash chromatography (330 g silica gel column, EtOAc-Hexanes, 0-20%) to afford the title compound as an orange oil (10.0 g, 99% yield). ($ES^+$) M+H=340.2; $^1H$ NMR (400 MHz, $CDCl_3$) δ 8.19 (s, 1H), 6.64 (s, 1H), 3.99 (dd, J=5.9, 2.4 Hz, 2H), 3.93 (s, 3H), 2.96 (t, J=7.3 Hz, 2H), 2.55 (t, J=7.3 Hz, 2H), 2.42 (d, J=0.5 Hz, 3H), 1.56 (dt, J=12.1, 6.0 Hz, 1H), 1.39-1.22 (m, 8H), 0.88 (m, 6H).

Preparation of 6-methoxy-4-methylpyridine-3-thiol (3): to a −78° C. solution of 2 (10.0 g, 29.5 mmol) in THF (105 mL) was added potassium t-butoxide (1.00 M in THF, 35.3 mL, 35.3 mmol) dropwise and a precipitate was formed. The resulting suspension was stirred at −78° C. for 30 minutes. The reaction was quenched by the addition of $NH_4Cl$ (50.0 mL) and the mixture was extracted with $CH_2Cl_2$ (2×50.0 mL). The combined organic layers were dried ($Na_2SO_4$), filtered and concentrated under reduced pressure to afford a dark orange liquid. The crude was purified by flash chromatography (100% Hexanes) to afford a mixture of the title compound and its disulfide (4.56 g) which was used in the next step without further purification. Thiol 3: ($ES^+$) M+H=156.9 and disulfide: Rt=1.92 min, ($ES^+$) M+H=309.0.

Preparation of 6-methoxy-4-methylpyridine-3-sulfonyl chloride (4): to a mixture of the thiol 3 (4.56 g, 29.4 mmol) in $H_2O$ (123 mL) was added potassium chloride (2.21 g, 29.3 mmol) followed by a portion-wise addition of OXONE (45.2 g, 73.5 mmol). After completion of the reaction (1 h), the mixture was extracted with EtOAc (2×20.0 mL) and the combined organic layers were dried ($Na_2SO_4$) and concentrated under reduced pressure. The crude product obtained was used without any further purification.

3-Methylpyridine-4-sulfonyl chloride

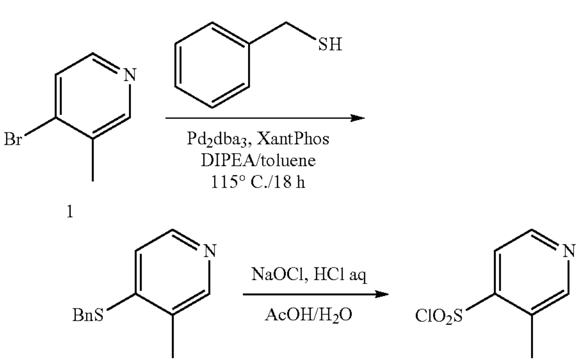

1 2 3

Step 1: 4-Bromopyridine (1.00 mmol) was dissolved in toluene (1.70 mL) and N,N-diisopropylethylamine (2.00 mmol) was added. The mixture was degassed with nitrogen bubbling through the solution for 5 min. Tris(dibenzylideneacetone)-dipalladium(0) (0.02 mmol), 4,4-Bis(diphenylphosphino)-9,9-dimethylxanthene (0.04 mmol) and the phenylmethanethiol/benzyl mercaptan (1.00 mmol) were added. The mixture was degassed again for 5 min. The mixture was heated at reflux for 18 h (oil bath T=115° C.). The reaction was cooled down to room temperature, diluted with EtOAc (10.0 mL) and quenched with $H_2O$ (10.0 mL). The aqueous and organic layers were separated and the aqueous layer was extracted with EtOAc (2×10.0 mL) and the combined organic phases were washed with HCl (10% in $H_2O$, 10.0 mL), dried ($Na_2SO_4$), filtered and concentrated under reduced pressure. The crude was purified by flash chromatography (EtOAc-Hexanes, 10% to 35%) to afford sulfide 2: (90% yield). ($ES^+$) M+H=216.1; $^1H$ NMR (400 MHz, $CDCl_3$) δ 8.28 (d, J=4.6, 1H), 8.24 (s, 1H), 7.43-7.27 (m, 5H), 7.20 (t, J=5.4 Hz, 1H), 4.25 (s, 2H), 2.28 (s, 3H).

Step 2: Compound 2 (1.00 mmol) was dissolved $CH_2Cl_2$ (11.5 mL) and cooled to −10° C. HCl (1.00 M in $H_2O$, 5.70 mL) was added and stirred at −10° C. for 5 min. Sodium hypochlorite (10% solution in $H_2O$, 3.00 mmol) was added over 10 min maintaining temp below 0° C. The mixture was stirred at 0° C. for 10 min. The organic and aqueous layer were separated. Organic layer was dried ($Na_2SO_4$). The crude sulfonyl chloride was used in the next step without further purification or evaporation: LCMS sample was quenched with N-methylpiperazine (resulting sulfonamide MW=255.3); ($ES^+$) M+H+=256.2.

2,3-Dimethylpyridine-4-sulfonyl chloride

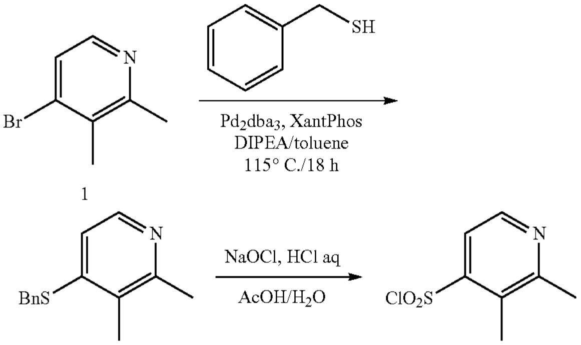

1 2 3

The same procedure as for 3-methylpyridine-4-sulfonyl chloride was used starting from 2,3-dimethyl-4-bromopyridine:

Step 1: 4-(Benzylthio)-2,3-dimethylpyridine (2): (92% yield). ($ES^+$) M+H=230.2; $^1H$ NMR (400 MHz, $CDCl_3$) δ: 8.17 (d, J=5.5 Hz, 1H), 7.42-7.28 (m, 5H), 6.99 (d, J=5.5 Hz, 1H), 4.18 (s, 2H), 2.53 (s, 3H), 2.24 (s, 3H).

Step 2: 2,3-Dimethylpyridine-4-sulfonyl chloride (3): LCMS sample was quenched with N-methylpiperazine (resulting sulfonamide MW=269.3); ($ES^+$) $M+H^+$=270.2.

Sulfonyl Chloride of Group B49:

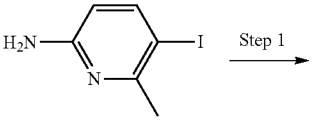

-continued

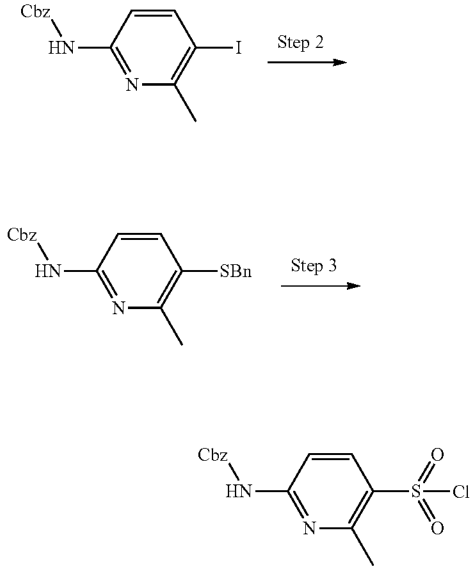

B49

Step 1: to a solution of the commercially available aminopyridine (1.00 g, 4.27 mmol) and N-benzylcarbamoyl chloride (0.9421 g, 5.5546 mmol) in EtOAc (20 mL) was added 20 mL of a saturated solution of aq. $NaHCO_3$. The solution was stirred 16 h at RT. Upon completion, EtOAc was added to the reaction mixture, and the organic layer was separated, washed with brine, dried over $MgSO_4$ then filtered and concentrated. The residu was adsorbed on $SiO_2$ then purified on $SiO_2$ with EtOAc in hexanes to afford the desired protected aminopyridine (1000 mg, 2.72 mmol, 64%). $^1$H NMR (400 MHz, DMSO-$d_6$) δ: 10.35 (s, 1H), 8.09 (d, J=8.61 Hz, 1H), 7.47 (d, J=9.00 Hz, 1H), 7.23-7.44 (m, 4H), 5.16 (s, 2H), 2.53 (s, 3H) MS m/z 369.2 (MH+).

Step 2: A degassed solution of the iodopyridine from step 1 (0.61 g, 1.66 mmol), tris(dibenzylideneacetone)-dipalladium(0) chloroform adduct (86 mg, 0.0828 mmol), 9,9-dimethyl-9 h-xanthene-4,5-diyl)bis(diphenylphosphine (96 mg, 0.166 mmol), dipea (0.576 mL, 3.31 mmol) and benzyl mercaptan (0.233 mL, 1.99 mmol) in toluene (15 mL) was stirred under $N_2$ at 115° C. for 3 h. Upon completion, $SiO_2$ added to the reaction mixture and concentrated under vacuum. The residu was purified on $SiO_2$ column with EtOAc in hexanes to provide the expected sulfide (560 mg, 93%). $^1$H NMR (400 MHz, $CDCl_3$) δ: 7.71 (d, J=8.61 Hz, 1H), 7.54 (d, J=8.61 Hz, 1H), 7.46 (br. s., 1H), 7.31-7.43 (m, 5H), 7.19-7.26 (m, 2H), 7.12-7.19 (m, 2H), 5.22 (s, 2H), 3.96 (s, 2H), 2.41 (s, 3H). MS m/z 365.2 (MH+).

Step 3: To a solution of the sulfide from step 2 (300 mg, 0.823 mmol) in 90% AcOH in water (16 mL) was added N-chlorosuccinimide (330 mg, 2.47 mmol). The reaction mixture was stirred at room temperature for 3 hours. The reaction mixture was evaporated to dryness then diluted in EtOAc and washed with water followed by brine. The organic layer was dried over $MgSO_4$, filtered and concentrated under vacuum to afford the desired sulfonyl chloride B49 that was used as is (282 mg, 99%): $^1$H NMR (400 MHz, $CDCl_3$) δ: 8.28 (d, J=9.00 Hz, 1H), 8.02 (d, J=9.00 Hz, 1H), 7.72 (br. s., H), 7.34-7.60 (m, 5H), 5.27 (s, 2H), 2.86 (s, 3H). MS m/z 341.2 (MH+).

2,2-Difluorobenzo[d][1,3]dioxole-4-sulfonyl chloride

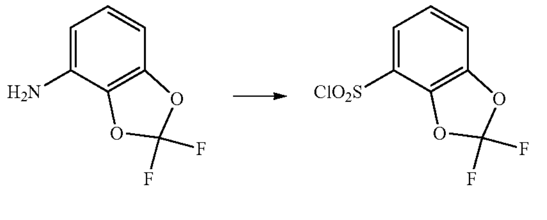 [SMILES: Nc1cccc2c1OC(F)(F)O2 ; O=S(=O)(Cl)c1cccc2c1OC(F)(F)O2]

Thionyl chloride (5.96 mL) was added dropwise over 20 min to water (30 mL) and the mixture stirred for 48 h at RT to produce as sulfur dioxide containing solution. In a separate vessel, 2,2,-difluorobenzo[d][1,3]dioxol-4-amine (1.00 g, 5.78 mmol) was added dropwise to ice-cooled conc. HCl (7 mL) to produce a white precipitate. A solution of sodium nitrite (523 mg, 7.5 mmol) in water (2 mL) was added dropwise over 5 min to the aniline hydrochloride to produce an orange reaction mixture. The orange suspension was then added gradually at 5° C. to the sulfur dioxide solution from above to which 10 mg of cuprous chloride had previously been added. The mixture was stirred for an additional 2 h in an ice bath (gas evolution is observed and an orange liquid is deposited at the bottow of the flask). After completion as determined by LCMS analysis, the reaction mixture was extracted with DCM (2×20 mL), dried ($Na_2SO_4$), filtered and concentrated to give the desired sulfonyl chloride as an orange oil that was used without further purification (100% crude yield): 1H-NMR (400 MHz, $CDCl_3$) δ 7.65 (dd, J=8.4, 1.1 Hz, 1H), 7.44 (dd, J=8.1, 1.1 Hz, 1H), 7.32 (t, J=8.2 Hz, 1H).

4-Chloro-3-fluoro-2-methylbenzenesulfonyl chloride

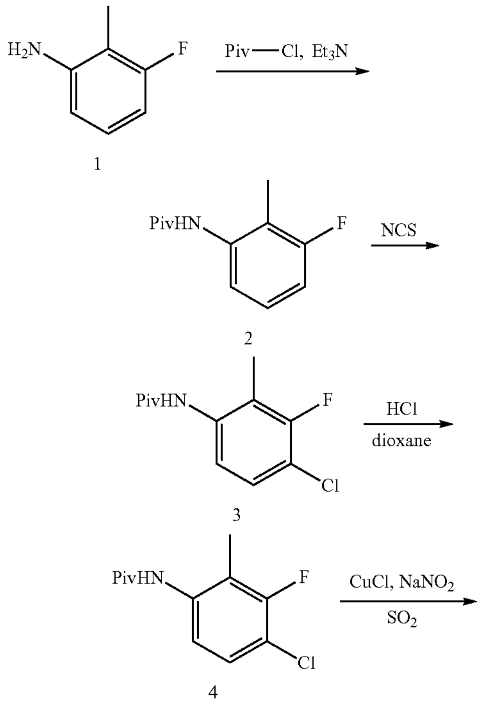

-continued

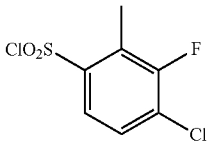

5

Preparation of N-(3-fluoro-2-methylphenyl)pivalamide (2): to a THF (240 mL) solution of 3-fluoro-2-methylaniline (10.9 mL, 93.0 mmol) at 0° C. was added triethylamine (14.9 mL, 106 mmol) followed by pivaloyl chloride (13.1 mL, 105 mmol) over 10 min. The mixture was warmed up to room temperature and stirred for 2 h. Volatiles were evaporated under reduced pressure and the residue was partitioned between $H_2O$ (250 mL) and EtOAc (150 mL). Organic and aqueous layers were separated. Aqueous layer was extracted with EtOAc (4×60 mL). Combined organic layers were washed with brine (60 mL), dried ($Na_2SO_4$) and concentrated under reduced pressure to give the title compound (18.5 g, 95% yield) as a solid. ($ES^+$) M+H=210.2.

Preparation of N-(4-chloro-3-fluoro-2-methylphenyl) pivalamide (3): to a DMF (50.0 mL) solution of compound 2 (4.20 g, 20.1 mmol) at room temperature was added N-chlorosuccinimide (2.76 g, 20.1 mmol) over 10 min (in 3 portions). The mixture was heated at 80° C. for for 90 min. Additional N-chlorosuccinimide (541 mg, 4.01 mmol) was added and this was stirred for 45 min at 80° C. The mixture was cooled to room temperature and was diluted with EtOAc (30 mL) and water (60 mL). Organic and aqueous layers were separated. Aqueous layer was extracted with EtOAc (3×20 mL). Combined organic layers were washed with $H_2O$ (3×30 mL), brine (20.0 mL), dried ($Na_2SO_4$) and concentrated under reduced pressure to give crude compound (5.20 g). The crude was dissolved in cyclohexane (30 mL) and heated at 45-50° C. until all solid dissolved. The solution was cooled to room temperature. White solid precipitated was filtered and washed with cyclohexane (3×5 mL) to give the title compound as a solid (1.95 g, 40% yield). ($ES^+$) M+H=244.1.

Preparation of 4-chloro-3-fluoro-2-methylaniline (4): to a dioxane (18 mL) solution of compound 3 (1.60 g, 6.57 mmol) at room temperature was added HCl (6.00 M in water, 23 mL, 138 mmol) over 5 min. The mixture was heated at 100° C. for 20 h. The mixture was cooled to room temperature. Solid $K_2CO_3$ (exothermic) was added portion-wise until pH=8-9 was obtained. The mixture was extracted with EtOAc (4×20 mL). Combined organic layers were washed with brine (20 mL), dried ($Na_2SO_4$) and concentrated under reduced pressure to give 1.6 g of crude which was dried under vacuum for 24 h to give the title compound as an oil (850 mg, 81% yield). This was used in the next reaction without further purification. $^1H$ NMR (400 MHz, $CDCl_3$) δ 6.99 (t, J=8.3 Hz, 1H), 6.40 (d, J=8.6 Hz, 1H), 2.22-2.06 (m, 3H).

Preparation of 4-chloro-3-fluoro-2-methylbenzene-1-sulfonyl chloride (5): under ice-cooling, thionyl chloride (29.1 mL, 395 mmol) was added dropwise to $H_2O$ (92.1 mL) over 20 min. This solution containing sulfur dioxide was stirred at 0° C. for 2 h and at room temperature for 18 h. Separately, HCl (conc.) (23 mL) was added portion-wise to compound 4 (3.00 g, 18.8 mmol) at 0° C. to afford a beige precipitate. This was stirred at 0° C. for 5 min. A solution of sodium nitrite (1.70 g, 24.4 mmol) in $H_2O$ (2 mL) was added dropwise over approximately 10 min. The above-mentioned sulfur dioxide solution containing copper (I) chloride (38.4 mg, 376 umol) was added to the reaction mixture gradually at 5° C., over 40 min. Under ice-cooling, the mixture was further stirred for 2 h and then at room temperature for 4 days. The mixture was diluted with $CH_2Cl_2$ (20 mL). Aqueous and organic layers were separated. Aqueous layer was extracted with $CH_2Cl_2$ (3×20 mL). Combined organic layers were dried ($Na_2SO_4$), filtered and concentrated to afford crude compound 5 (1.95 g, 30% yield, 70% purity) as an oil. Crude was used in the next step without further purification. LCMS: LCMS sample was quenched with N-methylpiperazine (resulting sulfonamide MW=306.784); ($ES^+$) M+H=307.1; $^1H$ NMR (400 MHz, $CDCl_3$) δ 7.81 (d, J=8.4 Hz, 1H), 7.46 (t, J=7.5 Hz, 1H), 2.69 (s, 3H).

3-Methyl-2-thiophenylsulfonyl chloride

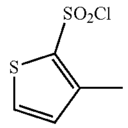

Prepared by chlorosulfonylation of 3-methylthiophene as described in U.S. Pat. No. 3,991,081. $^1H$ NMR ($CDCl_3$) δ: 7.67 (d, J=5.1 Hz, 1H), 7.03 (d, J=5.1 Hz, 1H), 2.63 (s, 3H).

3-Chloro-2-thiophenylsulfonyl chloride

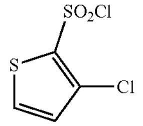

3-Chlorothiophene (1.00 g) was dissolved in $CHCl_3$ (10 mL) and the solution cooled to −30° C. Chlorosulfonic acid (2.4 mL) was added dropwise over 5 min (no gas evolution is noticeable). The orange-brown solution was then stirred for 30 min allowing temperature to rise to −10° C. then to RT over another 30 min. The reaction mixture was then stirred at RT for 2 h (no gas evolution was noticed and TLC shows formation of the product (Rf=0.4 in 8:2 hex/EA)). The reaction mixture was poured over ice (50 mL), DCM (25 mL) was added and the milky product organic phase was separated, washed with cold water, dried ($MgSO_4$) and concentrated to a yellow oil that was dried under vacuum and used without further purification (0.55 g). $^1H$ NMR ($CDCl_3$) δ: 7.76 (d, J=5.7 Hz, 1H), 7.16 (d, J=5.7 Hz, 1H).

4-Chloro-3-methylthiophene-2-sulfonyl chloride

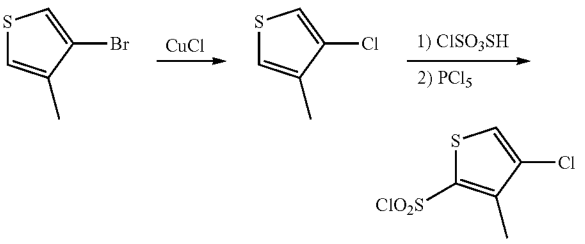

Preparation of 3-chloro-4-methylthiophene: In a 100 mL flask, copper (1) chloride (5.76 g, 56.5 mmol) was added to 3-bromo-4-methylthiophene (3.16 mL, 28.2 mmol) in DMF (20.1 mL) at room temperature. This was heated at 160° C. in an oil bath for 24 h. Crude was poured onto $H_2O$ (50 mL). The resulting mixture was stirred for 10 min at room temperature. Brown-green solid formed was filtered, washed with water (3×10.0 mL) and $Et_2O$ (4×10.0 mL). Filtrate was extracted with $Et_2O$ (3×25.0 mL). Combined organic layers were washed with $H_2O$ (2×20.0 mL), brine (20.0 mL), dried ($Na_2SO_4$) and concentrated under reduced pressure to give orange oil (0.890 g, 59% yield of crude). $^1H$ NMR (400 MHz, $CDCl_3$) δ 7.09 (d, J=3.5 Hz, 1H), 6.99-6.95 (m, 1H), 2.22-2.21 (m, 3H).

Preparation of 4-chloro-3-methylthiophene-2-sulfonyl chloride: 3-Chloro-4-methylthiophene (1.00 g, 7.54 mmol) was dissolved in $CHCl_3$ (4.43 mL) and a solution of chlorosulfonic acid (1.19 mL, 17.3 mmol) in $CHCl_3$ (1.48 mL) was added over 5 min at room temperature. The mixture was stirred for 10 min. Phosphorus pentachloride (4.13 g, 18.9 mmol) was added to the reaction mixture followed by $CHCl_3$ (7.50 mL). This was heated at 50° C. for 1 h. Reaction mixture was slowly added to the aqueous $NaHCO_3$ solution+ice (30 mL). This was stirred for 10 min. Extracted with $CH_2Cl_2$ (4×10 mL). Combined organic layers were dried ($Na_2SO_4$), concentrated under reduced pressure to give the title compound as an oil (1.30 g, 30% yield, 40% purity). This was used in the next reaction without further purification. LCMS: LCMS sample was quenched with N-methyl piperazine; ($ES^+$) M+H=295.1; $^1H$ NMR (400 MHz, $CDCl_3$) δ 7.57 (s, 1H), 2.57 (s, 3H).

3,4-Dichlorothiophene-2-sulfonyl chloride

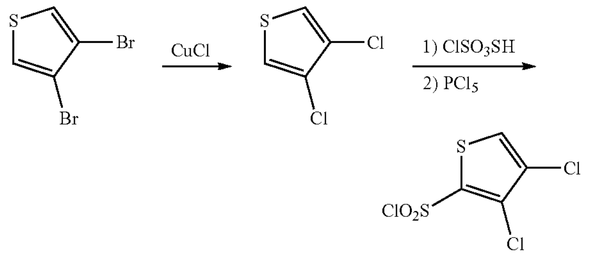

Preparation of 3,4-dichlorothiophene: in a 100 mL flask, copper (1) chloride (13.9 g, 137 mmol) was added to 3,4-dibromothiophene (5.03 mL, 45.5 mmol) in DMF (32 mL) at room temperature. This was heated at 160° C. in an oil bath for 24 h. Crude was poured onto $H_2O$ (100 mL) and diluted with $Et_2O$ (60 mL). The mixture was stirred for 10 min at room temperature. The brown-green solid formed was filtered, washed with $H_2O$ (3×20 mL) then $Et_2O$ (4×20 mL). Filtrate was extracted with $Et_2O$ (4×30 mL). Combined organic layers were washed with $H_2O$ (2×30 mL), brine (30 mL), dried ($MgSO_4$) and concentrated under reduced pressure to give the title compound 2 (5.50 g, 79% yield) as a red oil. $^1H$ NMR (400 MHz, $CDCl_3$) δ 7.21 (s, 2H).

Preparation of 3,4-dichlorothiophene-2-sulfonyl chloride: to a $CHCl_3$ (5.98 mL) solution of compound 2 (1.61 g, 10.5 mmol) was added a solution of chlorosulfonic acid (757 μL, 11.0 mmol) in $CHCl_3$ (1.99 mL) over 5 min. The mixture was stirred for 20 min at room temperature. Phosphorus pentachloride (5.77 g, 26.3 mmol) was added to the mixture in 4 portions. The mixture was heated at 50° C. for 18 h.

Volatiles were removed under reduced pressure and the residue was dissolved in $CH_2Cl_2$ (25 mL), washed with aqueous saturated $NaHCO_3$ (3×15 mL), $H_2O$ (3×10 mL) and brine (10 mL). Organic layer was dried ($Na_2SO_4$) and concentrated under reduced pressure to give the title compound 3 (2.32 g, 88% yield). LCMS: LCMS sample was quenched with N-methylpiperazine (resulting sulfonamide MW=315.240); ($ES^+$) M+H=315.1.

(3R)-3-Methoxy 1-pyrrolidinesulfonyl chloride

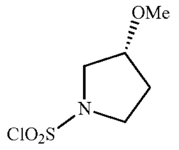

(R)-3-methoxypyrrolidine hydrochloride salt (0.30 g, 2.1 mmol) was suspended in a mixture of 4 mL of toluene and 2 mL of DCM. Triethylamine (0.64 mL, 4.6 mmol) was added and the mixture was sonicated for 4-5 min. affording a fine white suspension. In a separate flask, 4 mL of toluene was cooled to −40° C. in an acetonitrile/dry ice bath. Sulfuryl chloride (0.71 mL, 8.7 mmol) was added and the solution was stirred for 5 min. The pyrrolidine suspension was then added dropwise to the cold (−40° C.) sulfuryl chloride solution over 10 min. The resulting suspension was allowed to stir at the same temperature for 1 hour and was then allowed to warm to room temperature. The solids were filtered out and rinsed with toluene. The filtrate was concentrated to afford the desired product as a pale brown oil that was used without further purification (0.40 g). $^1H$ NMR ($CDCl_3$) δ: 4.07 (tt, J=4.6, 2.1 Hz, 1H), 3.48-3.69 (m, 4H), 3.36 (s, 3H), 2.12-2.23 (m, 1H), 1.98-2.12 (m, 1H).

General Synthetic Method A: Preparation of Difluoroaniline Hydrochloride Intermediate A-5 (Ar=4-methoxyphenyl) from tert-butylcarbamate A-2.

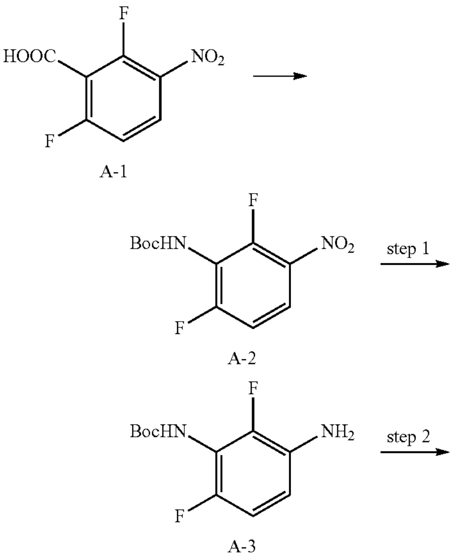

-continued

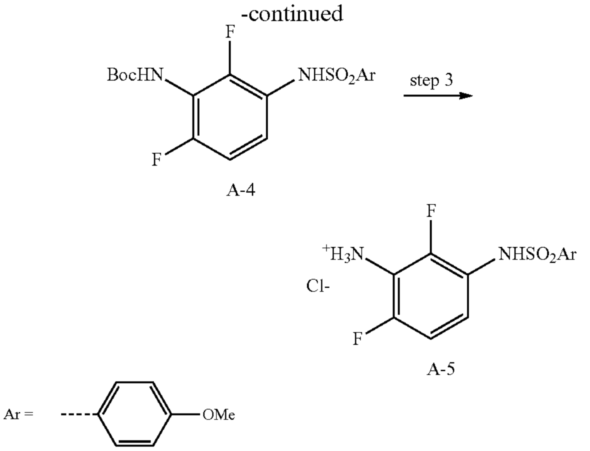

A-4

A-5

Step 1—Preparation of aniline intermediate A-3: Nitroarene A-2 (5.00 g, 18 mmol, prepared following the procedure described in *J. Med. Chem.* 2003, 46, 1905) and 20% $Pd(OH)_2$ on C (130 mg) were suspended in MeOH (50 mL) and the mixture stirred under a hydrogen-containing balloon for 18 h when reduction was shown to be complete by TLC analysis (Rf=0.45 in 2:1 hexane/EtOAc). The suspension was filtered through a pad of Celite® to remove the catalyst using MeOH for washings and the solvent evaporated under reduced pressure. Upon exposure to air, the originally colorless solution quickly became a very dark greenish blue. The crude intermediate aniline A-3 was obtained as a dark greenish purple foam that was used immediately in the next step without further purification: $^1H$ NMR (DMSO-$d_6$) δ: 8.58 (s, 1H), 6.77 (td, J=9.4, 2.0 Hz, 1H), 6.60 (td, J=9.4, 5.5 Hz, 1H), 4.97 (s, 2H), 1.43 (s, 9H).

Step 2—Preparation of sulfonamide A-4 (Ar=4-methoxyphenyl): Crude aniline A-3 from step 1 (assume 18 mmol) was dissolved in THF (30 mL) and excess 4-methoxyphenylsulfonyl chloride (7.53 g, 36 mmol) was added followed by pyridine (6 mL). The mixture was stirred at 50° C. for 18 h. THF was removed under reduced pressure and the residue partitioned between EtOAc and water. The extract was washed with saturated aqueous $NaHCO_3$ and brine and dried over $MgSO_4$. The drying agent slurry was passed through a 75 mL pad of silica gel using EtOAc for washings to remove drying agent and baseline material. Removal of solvent gave a brown oil that was purified by flash chromatography on silica (~250 mL) using 20-50% EtOAc in hexane as eluent. After drying under vacuum, the product A-4 was obtained as a brownish foam (8.16 g) contaminated with unreacted sulfonyl chloride in a 2:1 ratio by $^1H$ NMR. The material was used directly as such in the next step: $^1H$ NMR ($CDCl_3$) δ: 7.68 (d, J=9.0 Hz, 2H), 7.41 (td, J=8.8, 5.5 Hz, 1H), 6.85-6.98 (m, 3H), 6.57 (br. s, 1H), 5.85 (br. s, 1H), 3.85 (s, 3H), 1.46 (s, 9H). MS m/z 413.0 (M−H), m/z 313.0 (M−H-Boc), Step 3—Preparation of aniline hydrochloride A-5 (Ar=4-methoxyphenyl): The crude carbamate A-4 from step 3 (8.16 g) was stirred at RT in 4N HCl in dioxane (25 mL) for 1.5 h during which time a beige solid progressively precipitated After 1.5 h, another 10 mL of 4N HCl in dioxane was added and stirring continued for an additional 1 h. The reaction mixture was then diluted with 50 mL of diethyl ether and the beige precipitate was collected by filtration, washed with ether and dried under vacuum. Aniline salt A-5 (4.38 g) was obtained in pure form in 68% overall yield from nitroareneA-2: $^1H$ NMR (DMSO-$d_6$) δ: 9.73 (s, 1H), 7.62 (d, J=8.6 Hz, 2H), 7.06 (d, J=9.0 Hz, 2H), 6.69-6.88 (m, 1H), 6.30 (td, J=8.6, 5.5 Hz, 1H), 3.81 (s, 3H). MS m/z 313.0 (M−H).

General Synthetic Method A: Preparation of Difluoroaniline Hydrochloride Intermediate A-5 (Ar=2,3-dichlorophenyl) from Acetanilide A-8.

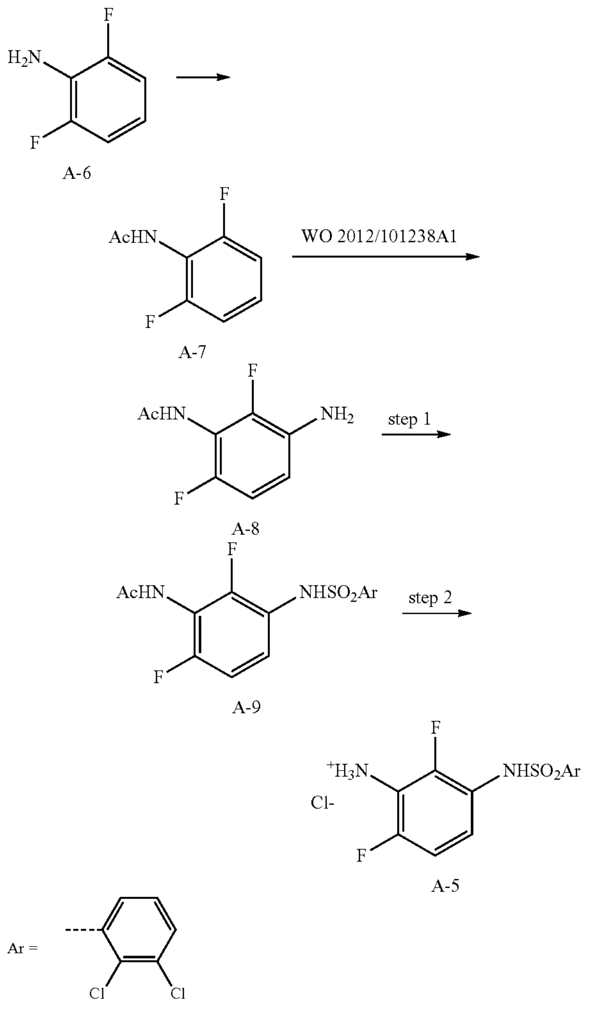

A-6

A-7

A-8

A-9

A-5

Preparation of acetanilide A-8: Acetanilide A-7 can be prepared by acetylation of 2,6-difluoroaniline A-6 with acetic anhydride following the literature procedure described in *Bioorg. Med. Chem.* 2016, 24, 2215. Intermediate A-7 was converted to acetanilide A-8 by sequential nitration followed by reduction of the nitro group to the aniline as described in WO 2012/101238A1.

Step 1—Preparation of sulfonamide A-9 (Ar=2,3-dichlorophenyl): Aniline A-8 (8.50 g, 45.5 mmol) was dissolved in THF (145 mL) and pyridine (4 eq., 14.7 mL) was added to the brown solution followed by 2,3-dichlorobenzenesulfonyl chloride (1.2 eq., 13.45 g). The resulting reaction mixture was stirred at 45° C. for 3.5 hours after which conversion was judged to be complete as monitored by LCMS. The reaction mixture was allowed to cool to room temperature then partitioned between EtOAc and 2-Me-THF (1:1) and water. A 1N HCl solution was added until a slightly acid pH was obtained. A significant amount of off-white solids were present in the biphasic mixture and were filtered out (first crop). The layers of the filtrate were separated, and the aqueous layer was extracted two more times with EtOAc.

The combined organic extracts were washed once with water then with brine, dried over MgSO4, filtered and concentrated down to ~20 mL. The resulting suspension was sonicated, and the solids were collected by filtration and washed with EtOH (crop 2). Both crops were combined and dried under reduced pressure. A-9 (15.3 g, 85% yield) was obtained as a beige solid that was used without further purification: $^1H$ NMR (DMSO-$d_6$) δ: 10.61 (s, 1H), 9.67 (s, 1H), 7.95 (dd, J=8.0, 1.4 Hz, 1H), 7.85 (dd, J=8.0, 1.4 Hz, 1H), 7.51 (t, J=8.0 Hz, 1H), 7.05-7.18 (m, 2H), 2.00 (s, 3H). MS m/z 395.0 ($MH^+$).

Step 2—Preparation of aniline hydrochloride A-5 (Ar=2, 3-dichlorophenyl): In a 500 mL round-bottomed flask, acetanilide A-9 (7.00 g, 17.7 mmol) was suspended in ethanol (65 mL) and a 1:1 mixture of concentrated HCl and water (65 mL) was added. The flask was equipped with a stoppered reflux condenser and heated at 80° C. with stirring. After 24 hours, conversion was ~70% as judged by LCMS monitoring. Additional EtOH (65 mL) and 6N HCl (65 mL) were added to the suspension and stirring at 80° C. resumed for 7 more hours after which LCMS indicated complete conversion to the desired aniline. The reaction mixture was diluted with 50 mL of water while still warm and filtered through a plug of cotton to remove a small amount of insoluble materials. It was then concentrated to dryness under reduced pressure. The residue was azeotropically dried by evaporation of toluene 3× under reduced pressure then dried under vacuum, affording 7.2 g of the desired product A-5 as its HCl salt in the form of a yellow solid: $^1H$ NMR (DMSO-$d_6$) δ: 10.30 (s, 1H), 7.93 (dd, J=8.2, 1.2 Hz, 1H), 7.83 (dd, J=8.0, 1.4 Hz, 1H), 7.49 (t, J=8.0 Hz, 6H), 6.68-6.96 (m, 1H), 6.31 (td, J=8.6, 5.5 Hz, 1H). MS m/z 350.9 (M−H).

The following A-5 intermediates were prepared using the relevant sulfonyl chlorides and similar sequences proceeding through either carbamate A-2 or acetanilide A-8 as described in Table 1:

TABLE 1

| A-5 | SM | MS m/z (M—H) | $^1H$ NMR (400 MHz) |
|---|---|---|---|
| 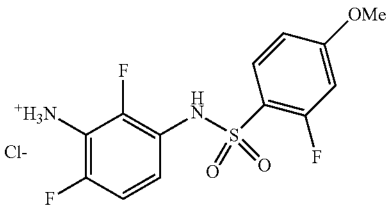 [SMILES: [Cl-] ; COc1ccc(S(=O)(=O)Nc2ccc(F)c([NH3+])c2F)c(F)c1] | A-2 | 331.0 | Not determined |
| 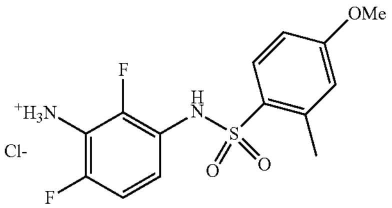 | A-2 | 327.0 | $^1H$ NMR (DMSO-$d_6$) δ: 9.77 (s, 1H), 7.60 (d, J = 9.0 Hz, 1H), 6.93 (d, J = 2.3 Hz, 1H), 6.81 (dd, J = 8.8, 2.5 Hz, 1H), 6.72-6.79 (m, 1H), 6.32 (td, J = 8.6, 5.5 Hz, 1H), 3.78 (s, 3H), 2.56 (s, 3H). |
| 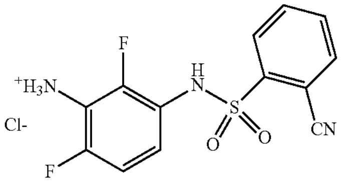 | A-2 | 308.0 | $^1H$ NMR (DMSO-$d_6$) δ: 10.34 (s, 1H), 8.07 (dd, J = 7.4, 1.2 Hz, 1H), 7.77-7.95 (m, 3H), 6.67-6.90 (m, 1H), 6.30 (td, J = 8.4, 5.5 Hz, 1H). |
| 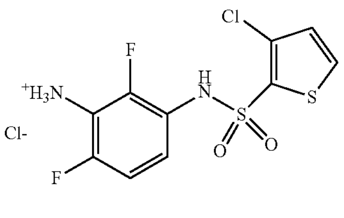 [SMILES: [Cl-] ; [NH3+]c1c(F)ccc(NS(=O)(=O)c2sccc2Cl)c1F] | A-2 | 322.9 | Not determined |
| 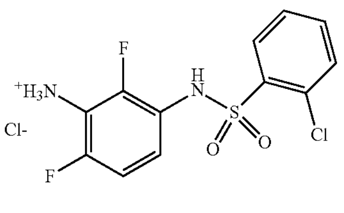 [SMILES: [Cl-] ; [NH3+]c1c(F)ccc(NS(=O)(=O)c2ccccc2Cl)c1F] | A-8 | 317.0 | $^1H$ NMR (DMSO-$d_6$) δ: 10.12 (s, 1H), 7.85 (dd, J = 7.8, 1.6 Hz, 1H), 7.59-7.71 (m, 2H), 7.46 (td, J = 7.5, 1.4 Hz, 1H), 6.74-6.82 (m, 1H), 6.31 (td, J = 8.6, 5.5 Hz, 1H) |

TABLE 1-continued

| A-5 | SM | MS m/z (M—H) | $^1$H NMR (400 MHz) |
|---|---|---|---|
| 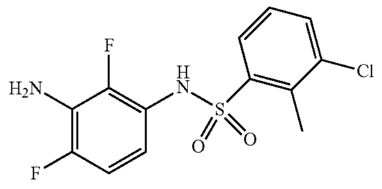 [SMILES: Cc1c(Cl)cccc1S(=O)(=O)Nc1ccc(F)c(N)c1F] | A-8 | 331.0 | $^1$H NMR ($CDCl_3$) δ: 7.84 (d, J = 7.8 Hz, 1H), 7.58 (d, J = 7.8 Hz, 1H), 7.21 (t, J = 8.0 Hz, 1H), 6.68-6.74 (m, 2H), 6.63 (br. s., 1H), 2.75 (s, 3H) |
| 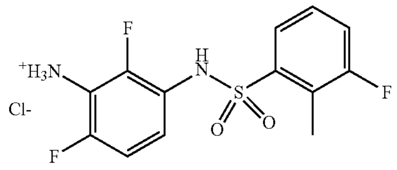 [SMILES: [Cl-] ; Cc1c(F)cccc1S(=O)(=O)Nc1ccc(F)c([NH3+])c1F] | A-2 | 315.0 | $^1$H NMR (DMSO-$d_6$) δ: 10.10 (s, 1H), 7.54 (d, J = 7.8 Hz, 1H), 7.46 (td, J = 9.0, 1.2 Hz, 1H), 7.35 (td, J = 8.2, 5.5 Hz, 1H), 6.79 (ddd, J = 10.9, 9.1, 2.0 Hz, 1H), 6.32 (td, J = 8.6, 5.5 Hz, 1H), 2.49 (d, J = 2.0 Hz, 3H) |
| 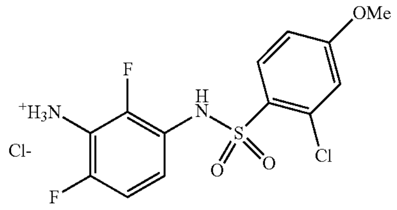 [SMILES: [Cl-] ; COc1ccc(S(=O)(=O)Nc2ccc(F)c([NH3+])c2F)c(Cl)c1] | A-2 | 346.9 | $^1$H NMR ($CDCl_3$) δ: 7.84 (d, J = 8.2 Hz, 1H), 7.74 (br. s., 1H), 6.95 (s, 1H), 6.89 (br. s., 1H), 6.76 (br. d, J = 7.8 Hz, 1H), 6.53-6.72 (m, 1H), 5.52 (br. s., 3H), 3.78 (s, 3H) |
| 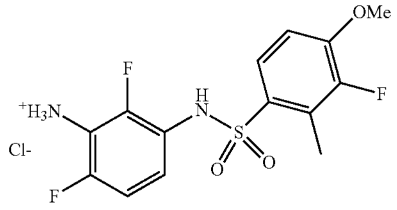 [SMILES: [Cl-] ; COc1ccc(S(=O)(=O)Nc2ccc(F)c([NH3+])c2F)c(C)c1F] | A-8 | 347.1 | $^1$H NMR (DMSO-$d_6$) δ: 9.94 (s, 1H), 7.48 (dd, J = 8.9, 1.5 Hz, 1H), 7.07 (t, J = 8.6 Hz, 1H), 6.78 (ddd, J = 10.8, 9.0, 1.9 Hz, 1H), 6.33 (td, J = 8.6, 5,5 Hz, 1H), 3.86 (s, 3H), 2.48 (d, J = 2.7 Hz, 3H) |
| 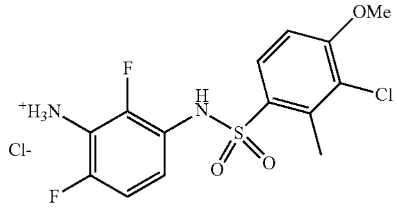 [SMILES: [Cl-] ; COc1ccc(S(=O)(=O)Nc2ccc(F)c([NH3+])c2F)c(C)c1Cl] | A-8 | 363.2 | $^1$H NMR (DMSO-$d_6$) δ: 10.00 (s, 1H), 7.67 (d, J = 8.9 Hz, 1H), 7.07 (d, J = 9.0 Hz, 1H), 6.78 (ddd, J = 9.0, 6.5, 1.9 Hz, 1H), 6.33 (td (J = 8.7, 5.5 Hz, 1H), 3.89 (s, 3H), 2.65 (s, 3H) |
| 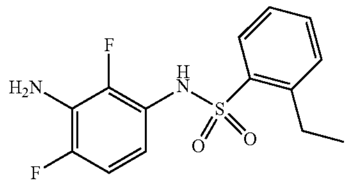 [SMILES: CCc1ccccc1S(=O)(=O)Nc1ccc(F)c(N)c1F] | A-8 | 313.0 | $^1$H NMR ($CDCl_3$) δ: 7.86 (dd, J = 8.0, 1.3 Hz, 1H), 7.49 (td, J = 7.6, 1.3 Hz, 1H), 7.38-7.29 (m, J = 7.7 Hz, 1H), 7.24-7.19 (m, 1H), 6.72-6.62 (m, 2H), 6.54 (brs, 1H), 3.04 (q, J = 7.5 Hz, 2H), 1.30 (t, J = 7.5 Hz, 3H) |
| 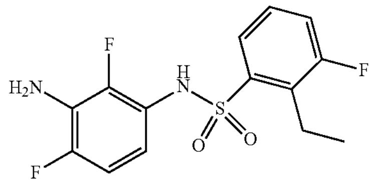 [SMILES: CCc1c(F)cccc1S(=O)(=O)Nc1ccc(F)c(N)c1F] | A-8 | 331.0 | $^1$H NMR ($CDCl_3$) δ: 7.70-7.64 (m, 1H), 7.24-7.19 (m, 2H), 6.73-6.65 (m, 2H), 6.63 (s, 1H), 3.01 (qd, J = 7.4, 2.1 Hz, 2H), 1.25 (t, J = 7.4 Hz, 3H) |

TABLE 1-continued

| A-5 | SM | MS m/z (M—H) | $^1H$ NMR (400 MHz) |
|---|---|---|---|
| 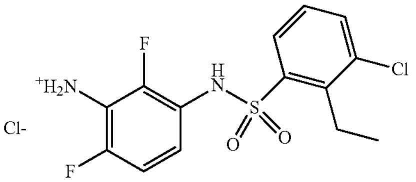 [SMILES: [Cl-] ; CCc1c(Cl)cccc1S(=O)(=O)Nc1ccc(F)c([NH3+])c1F] | A-8 | 346.8 | $^1H$ NMR (DMSO-$d_6$) δ: 10.21 (s, 1H), 7.71 (ddd, J = 8.0, 4.9, 1.2 Hz, 1H), 7.35 (t, J = 8.0 Hz, 1H), 7.02-6.92 (m, 1H), 6.87-6.75 (m, 1H), 6.60 (bs, 1H), 6.28 (td, J = 8.6, 5.6 Hz, 1H), 3.12 (q, J = 7.2 Hz, 2H), 1.18 (t, J = 7.3 Hz, 3H) |
| 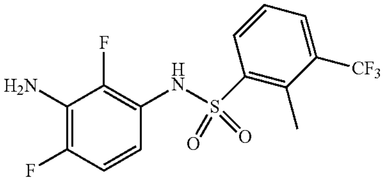 [SMILES: Cc1c(C(F)(F)F)cccc1S(=O)(=O)Nc1ccc(F)c(N)c1F] | A-8 | 366.3 | $^1H$ NMR ($CDCl_3$) δ: 8.12 (d, J = 8.1 Hz, 1H), 7.84 (d, J = 8.0 Hz, 1H), 7.37 (t, J = 8.0 Hz, 1H), 6.74-6.64 (m, 2H), 6.61 (s, 1H), 3.88-3.62 (bs), 2.83 (s, 3H) |
| 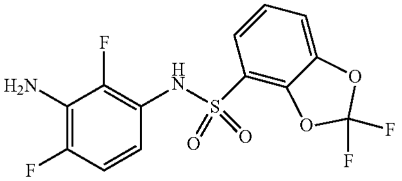 [SMILES: Nc1c(F)ccc(NS(=O)(=O)c2cccc3c2OC(F)(F)O3)c1F] | A-8 | 364.3 | $^1H$-NMR (DMSO-$d_6$) δ 10.38 (s, 1H), 7.70 (dd, J = 7.6, 1.6 Hz, 1H), 7.44-7.26 (m, 2H), 6.82 (ddd, J = 10.7, 9.0, 1.9 Hz, 1H), 6.32 (td, J = 8.6, 5.5 Hz, 1H), 5.27 (s, 2H). |
| 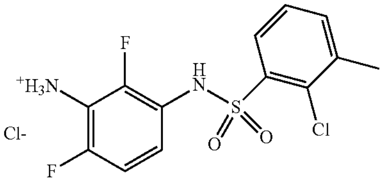 [SMILES: [Cl-] ; Cc1cccc(S(=O)(=O)Nc2ccc(F)c([NH3+])c2F)c1Cl] | A-8 | 333.1 | $^1H$ NMR (400 MHz, DMSO-$d_6$) δ 10.06 (s, 1H), 7.72 (dd, J = 7.9, 1.1 Hz, 1H), 7.65-7.61 (m, 1H), 7.36 (t, J = 7.7 Hz, 1H), 6.76 (ddd, J = 10.7, 9.0, 1.9 Hz, 1H), 6.28 (td, J = 8.6, 5.4 Hz, 1H), 2.42 (s, 3H) |
| 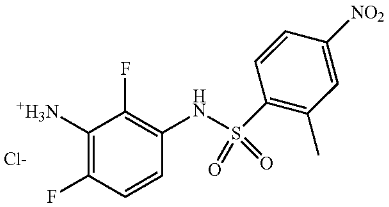 [SMILES: [Cl-] ; Cc1cc([N+](=O)[O-])ccc1S(=O)(=O)Nc1ccc(F)c([NH3+])c1F] | A-8 | 344.2 | $^1H$ NMR (DMSO-$d_6$) δ: 10.33 (s, 1H), 8.29 (d, J = 2.35 Hz, 1 H), 8.13 (dd, J = 8.61, 2.35 Hz, 1H), 7.91 (d, J = 8.61 Hz, 1 H), 2.72 (s, 2H), 6.88-7.01 (m, 1H), 6.70-6.86 (m, 1H), 6.60 (td, J = 8.41, 5.09 Hz, 1H), 6.32 (td, J = 8.51, 5.67 Hz, 1 H) |
| 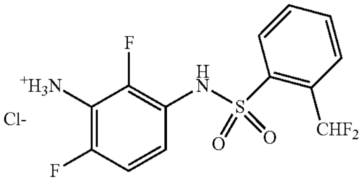 [SMILES: [Cl-] ; [NH3+]c1c(F)ccc(NS(=O)(=O)c2ccccc2C(F)F)c1F] | A-8 | 338.2 | $^1H$ NMR (DMSO-$d_6$) δ: 10.38 (s, 1H), 8.59 (s, 1H), 7.92-8.39 (m, 4H), 7.45-7.66 (m, 1H) |
| 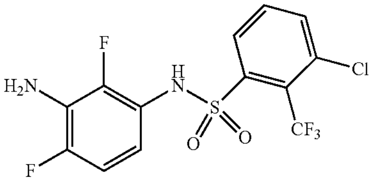 [SMILES: Nc1c(F)ccc(NS(=O)(=O)c2cccc(Cl)c2C(F)(F)F)c1F] | A-8 | 385.2 | $^1H$ NMR (400 MHz, DMSO-$d_6$) δ 10.27 (s, 1H), 8.00 (dd, J = 8.0, 4.5 Hz, 2H), 7.81 (t, J = 8.1 Hz, 1H), 6.83 (ddd, J = 10.7, 9.1, 1.8 Hz, 1H), 6.35 (td, J = 8.6, 5.5 Hz, 1H), 5.31 (s, 2H) |
| 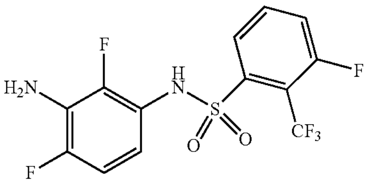 [SMILES: Nc1c(F)ccc(NS(=O)(=O)c2cccc(F)c2C(F)(F)F)c1F] | A-8 | 388.2 | $^1H$ NMR (400 MHz, DMSO-$d_6$) δ 10.25 (s, 1H), 7.96-7.70 (m, 3H), 6.83 (m, 1H), 6.37 (m, 1H), 5.30 (s, 2H) |

TABLE 1-continued

| A-5 | SM | MS m/z (M—H) | $^1H$ NMR (400 MHz) |
|---|---|---|---|
| 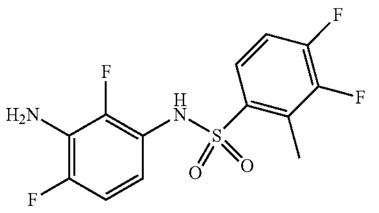 [SMILES: Cc1c(S(=O)(=O)Nc2ccc(F)c(N)c2F)ccc(F)c1F] | A-8 | 335.2 | $^1H$ NMR (400 MHz, DMSO-$d_6$) δ 10.15 (s, 1H), 7.54 (ddd, J = 8.8, 5.0, 1.3 Hz, 1H), 7.40 (dd, J = 17.3, 9.1 Hz, 1H), 6.80 (ddd, J = 10.7, 9.1, 1.8 Hz, 1H), 6.32 (td, J = 8.6, 5.5 Hz, 1H), 5.28 (s, 2H), 2.54 (d, J = 2.5 Hz, 3H) |
| 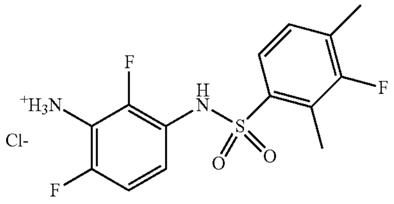 [SMILES: [Cl-] ; Cc1ccc(S(=O)(=O)Nc2ccc(F)c([NH3+])c2F)c(C)c1F] | A-8 | 329.1 | $^1H$ NMR (400 MHz, DMSO-$d_6$) δ 10.03 (s, 1H), 7.43 (d, J = 8.1 Hz, 1H), 7.22 (t, J = 7.8 Hz, 1H), 6.78 (ddd, J = 10.8, 9.0, 1.9 Hz, 1H), 6.33 (td, J = 8.6, 5.5 Hz, 1H), 2.48 (d, J = 2.4 Hz, 3H), 2.26 (d, J = 1.9 Hz, 3H) |
| 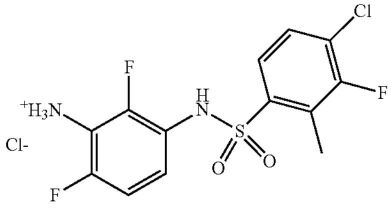 [SMILES: [Cl-] ; Cc1c(S(=O)(=O)Nc2ccc(F)c([NH3+])c2F)ccc(Cl)c1F] | A-8 | 349.1 | $^1H$ NMR (400 MHz, DMSO-$d_6$) δ 10.21 (s, 1H), 7.60-7.55 (m, 1H), 7.55-7.50 (m, 1H), 6.81 (ddd, J = 10.7, 9.0, 1.8 Hz, 1H), 6.32 (td, J = 8.6, 5.5 Hz, 1H), 2.53 (d, J = 2.6 Hz, 3H) |
| 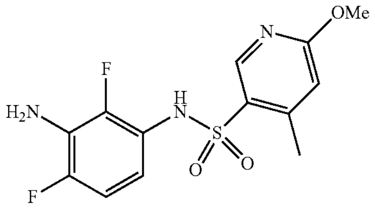 [SMILES: COc1cc(C)c(S(=O)(=O)Nc2ccc(F)c(N)c2F)cn1] | A-8 | 330.0 | Not determined |
| 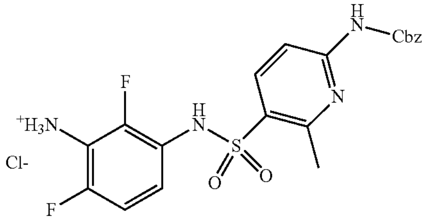 [SMILES: [Cl-] ; Cc1nc(NC(=O)OCc2ccccc2)ccc1S(=O)(=O)Nc1ccc(F)c([NH3+])c1F] | A-8 | 449.2 | $^1H$ NMR (DMSO-$d_6$) δ: 10.71 (s, 1H), 10.02 (s, 1H), 7.91-8.07 (m, 1H), 7.74 (d, J = 8.61 Hz, 1H), 7.28-7.47 (m, 4H), 6.80 (t, J = 8.80Hz, 1H), 6.33 (dt, J = 5.48, 8.61 Hz, 1H), 5.76 (s, 1H), 5.24 (s, 1H), 5.18 (s, 2H), 2.63-2.66 (m, 3H) |
| 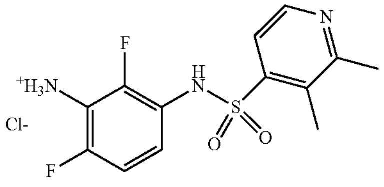 [SMILES: [Cl-] ; Cc1nccc(S(=O)(=O)Nc2ccc(F)c([NH3+])c2F)c1C] | A-8 | 314.2 | $^1H$ NMR (400 MHz, DMSO-$d_6$) δ 10.59 (s, 1H), 8.57 (d, J = 5.6 Hz, 1H), 7.72 (d, J = 5.6 Hz, 1H), 6.97 (br s, 3H), 6.80 (ddd, J = 10.7, 9.1, 1.8 Hz, 1H), 6.30 (td, J = 8.6, 5.4 Hz, 1H), 2.69 (s, 3H), 2.58 (s, 3H) |
| 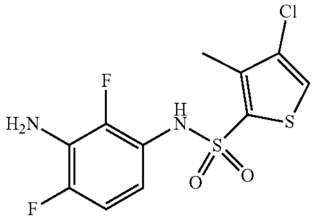 [SMILES: Cc1c(Cl)csc1S(=O)(=O)Nc1ccc(F)c(N)c1F] | A-8 | 337.2 | $^1H$ NMR (400 MHz, DMSO-$d_6$) δ 10.27 (s, 1H), 7.92 (s, 1H), 6.93-6.75 (m, 1H), 6.35 (td, J = 8.5, 5.5 Hz, 1H), 5.32 (s, 2H), 2.22 (s, 3H) |

TABLE 1-continued
| A-5 | SM | MS m/z (M—H) | $^1$H NMR (400 MHz) |
|---|---|---|---|
| 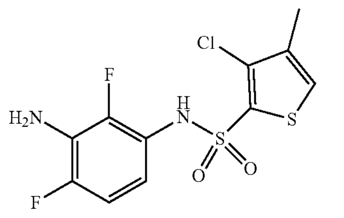 [SMILES: Cc1csc(S(=O)(=O)Nc2ccc(F)c(N)c2F)c1Cl] | A-8 | 337.2 | $^1$H NMR (400 MHz, $CDCl_3$) δ 7.20 (m, 1H), 7.03 (br s, 1H), 6.87 (td, J = 8.8, 5.4 Hz, 1H), 6.73 (td, J = 9.8, 2.0 Hz, 1H), 2.21 (s, 3H) |
| 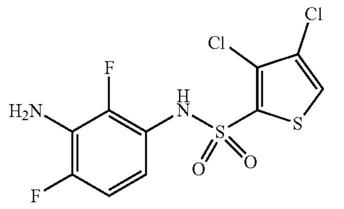 [SMILES: Nc1c(F)ccc(NS(=O)(=O)c2scc(Cl)c2Cl)c1F] | A-8 | 357.2 | $^1$H NMR (400 MHz, DMSO-$d_6$) δ 10.59 (s, 1H), 8.15 (s, 1H), 6.98-6.71 (m, 1H), 6.35 (td, J = 8.5, 5.5 Hz, 1H), 5.34 (s, 2H) |
| 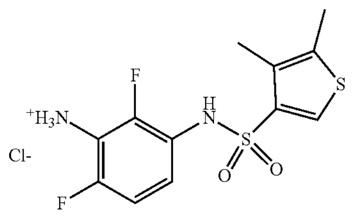 [SMILES: [Cl-] ; Cc1scc(S(=O)(=O)Nc2ccc(F)c([NH3+])c2F)c1C] | A-8 | 319.1 | Not determined |
| 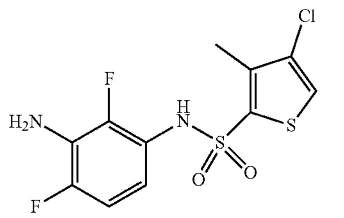 [SMILES: Cc1c(Cl)csc1S(=O)(=O)Nc1ccc(F)c(N)c1F] | A-8 | 337.2 | $^1$H NMR (400 MHz, DMSO-$d_6$) δ 10.27 (s, 1H), 7.92 (s, 1H), 6.93-6.75 (m, 1H), 6.35 (td, J = 8.5, 5.5 Hz, 1H), 5.32 (s, 2H), 2.22 (s, 3H). |
| 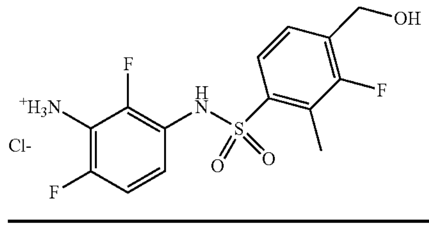 | A-8 | | Not determined |

General Synthetic Method A—Preparation of Inhibitors W-I from Intermediates A-5:

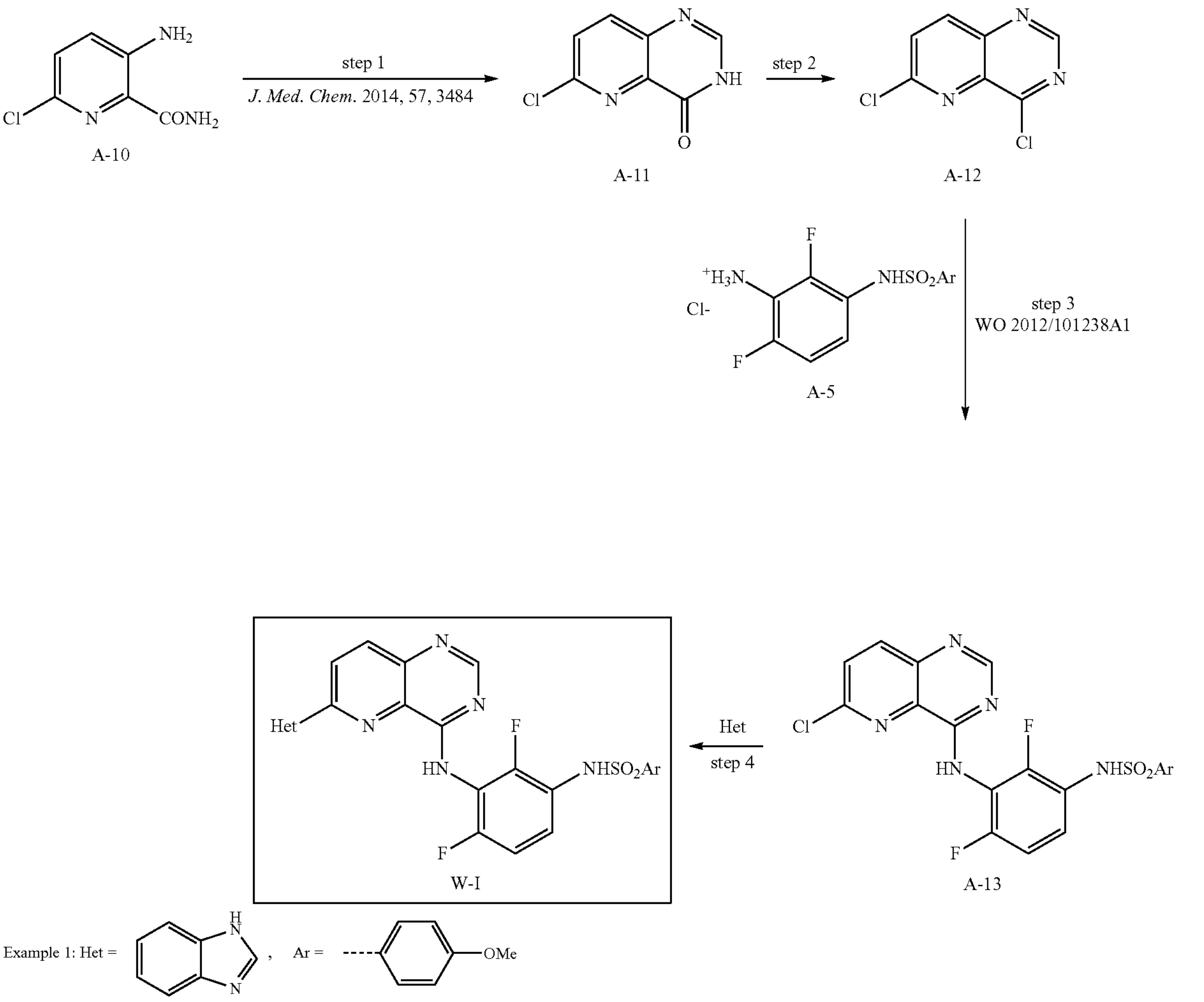

A-10 A-11 A-12 A-5 A-13 W-I

Example 1: Het = , Ar =

Step 1—Preparation of pyridopyrimidone A-11: Adapting a procedure described in J. Med. Chem. 2014, 57, 3484 commercially available 3-amino-6-chloropicolinamide A-10 (9.00 g, 52.5 mmol) was suspended in 116 mL of triethylorthoformate in a 250 mL round bottom flask and to the brown suspension was added 4-methylbenzenesulfonic acid hydrate (0.027 g, 0.14 mmol). The mixture was stirred with the unstoppered flask open to air, in an oil bath set at 140° C. After 52 hours, LCMS showed complete consumption of starting material. The beige suspension was allowed to cool to room temperature then concentrated to a slurry of ~15-20 mL under reduced pressure. It was then diluted with 20 mL of a 1:1 EtOAc/$Et_2O$ mixture and sonicated. The solids were then collected by filtration, washed with 10-15 mL of the EtOAc/$Et_2O$ mixture and dried under vacuum to give A-11 (6.73 g, 70% yield): $^1H$ NMR (DMSO-$d_6$) δ: 12.74 (br. s., 1H), 8.20 (s, 1H), 8.15 (d, J=8.6 Hz, 1H), 7.88 (d, J=8.6 Hz, 1H). MS m/z 182.0 ($MH^+$).

Step 2—Preparation of dichloropyridopyrimidine A-12: Following the procedure described in *J. Med. Chem.* 2014, 57, 3484, pyrimidone A-11 (8.61 g, 47 mmol) was suspended in thionyl chloride (60 mL) and to the mixture was added 2 drops of DMF. The flask was equipped with a reflux condenser and heated in an oil bath at 80° C. for 6 hours by which time the thick pasty slurry had become a dark brown solution for about 30 minutes. LCMS analysis revealed the starting material was essentially completely consumed. After cooling to room temperature, the mixture was concentrated then dried under reduced pressure. A-12, obtained as a beige solid was used as such, without further purification (9.51 g): $^1H$ NMR ($CDCl_3$) δ: 9.14 (s, 1H), 8.35 (d, J=9.0 Hz, 1H), 7.87 (d, J=9.0 Hz, 1H).

Step 3—Preparation of chloropyridine intermediate A-13 (Ar=4-methoxyphenyl): Following similar protocols described in WO 2012/101238A1, crude dichloropyridopyrimidine A-12 (0.44 g, 2.2 mmol, 1.2 equiv.) and aniline hydrochloride A-5 (Ar=4-methoxyphenyl: 0.65 g, 1.8 mmol) were dissolved in acetic acid (5 mL) and the mixture stirred at 50° C. for 1 h (LCMS shows complete conversion). The reaction mixture was diluted with 3× the volume of water and the resulting beige suspension was stirred vigorously for 30 min and then the product was collected by filtration, washed with water and dried under vacuum. Chloropyridine A-13 (Ar=4-methoxyphenyl) was obtained as a beige solid (0.88 g): $^1H$ NMR (DMSO-$d_6$) δ: 10.10 (br. s, 2H), 8.50 (s, 1H), 8.28 (d, J=9.0 Hz, 1H), 7.99 (d, J=9.0 Hz, 1H), 7.67 (d, J=8.9 Hz, 2H), 7.13-7.30 (m, 2H), 7.09 (d, J=9.0 Hz, 2H), 3.81 (s, 3H). MS m/z 478.0 ($MH^+$).

The following A-13 chloropyridine intermediates were prepared in a similar fashion and are described in Table 2:

TABLE 2

| A-13 | MS m/z (MH+) | $^1$H NMR (400 MHz) |
|---|---|---|
| 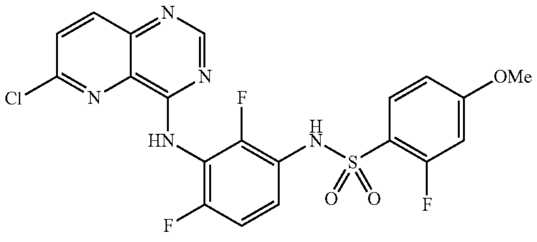 [SMILES: COc1ccc(S(=O)(=O)Nc2ccc(F)c(Nc3ncnc4ccc(Cl)nc34)c2F)c(F)c1] | 496.0 | $^1$H NMR (DMSO-$d_6$) δ: 10.36 (s, 1H), 10.11 (s, 1H), 8.47 (s, 1H), 8.28 (d, J = 8.6 Hz, 1H), 7.99 (d, J = 9.0 Hz, 1H), 7.61 (t, J = 8.6 Hz, 1H), 7.22-7.32 (m, 1H), 7.18 (t, J = 9.0 Hz, 1H), 7.05 (dd, J = 12.1, 2.3 Hz, 1H), 6.89 (dd, J = 9.0, 2.3 Hz, 1H), 3.81 (s, 3H) |
| 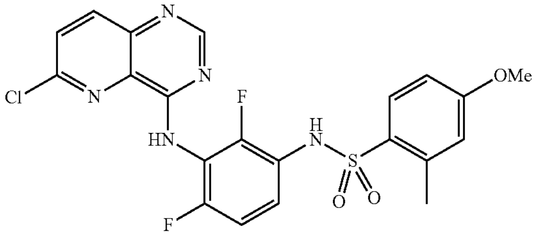 [SMILES: COc1ccc(S(=O)(=O)Nc2ccc(F)c(Nc3ncnc4ccc(Cl)nc34)c2F)c(C)c1] | 492.0 | $^1$H NMR (DMSO-$d_6$) δ: 10.11 (d, J = 2.7 Hz, 2H), 8.49 (s, 1H), 8.28 (d, J = 9.0 Hz, 1H), 7.99 (d, J = 9.0 Hz, 1H), 7.67 (d, J = 8.6 Hz, 1H), 7.23 (td, J = 8.5, 5.7 Hz, 1H), 7.15 (t, J = 9.2 Hz, 1H), 6.94 (d, J = 2.3 Hz, 1H), 6.86 (dd, J = 8.8, 2.5 Hz, 1H), 3.79 (s, 3H), 2.56 (s, 3H) |
| 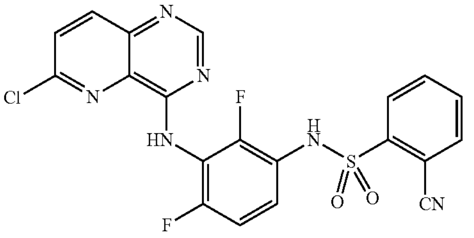 [SMILES: N#Cc1ccccc1S(=O)(=O)Nc1ccc(F)c(Nc2ncnc3ccc(Cl)nc23)c1F] | 473.0 | $^1$H NMR (DMSO-$d_6$) δ: 10.74 (s, 1H), 10.13 (br. s., 1H), 8.50 (s, 1H), 8.27 (d, J = 8.6 Hz, 1H), 8.10 (d, J = 7.4 Hz, 1H), 7.78-8.02 (m, 4H), 7.28-7.37 (m, 1H), 7.23 (t, J = 9.0 Hz, 1H) |
| 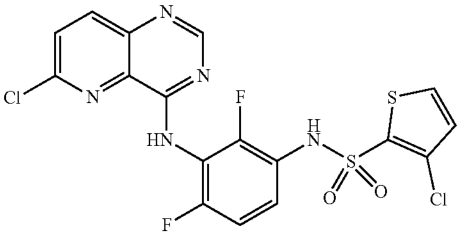 [SMILES: O=S(=O)(Nc1ccc(F)c(Nc2ncnc3ccc(Cl)nc23)c1F)c1sccc1Cl] | 487.9 | $^1$H NMR (DMSO-$d_6$) δ: 10.70 (s, 1H), 10.24 (br. s., 1H), 8.55 (s, 1H), 8.28 (d, J = 8.6 Hz, 1H), 8.01 (d, J = 4.3 Hz, 1H), 7.99 (s, 1H), 7.15-7.35 (m, 3H) |
| 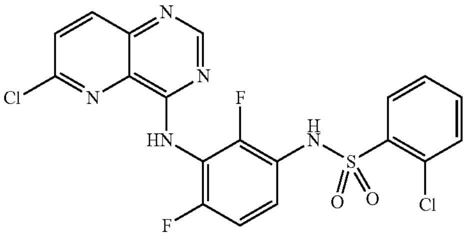 [SMILES: O=S(=O)(Nc1ccc(F)c(Nc2ncnc3ccc(Cl)nc23)c1F)c1ccccc1Cl] | 484.0 | $^1$H NMR (DMSO-$d_6$) δ: 10.48 (s, 1H), 10.16 (br. s., 1H), 8.49 (s, 1H), 8.28 (d, J = 8.6 Hz, 1H), 7.99 (d, J = 8.6 Hz, 1H), 7.91 (dd, J = 7.8, 1.6 Hz, 1H), 7.62-7.71 (m, 2H), 7.47-7.54 (m, 1H), 7.25 (td, J = 8.6, 5.9 Hz, 1H), 7.17 (td, J = 9.2, 1.2 Hz, 1H) |
| 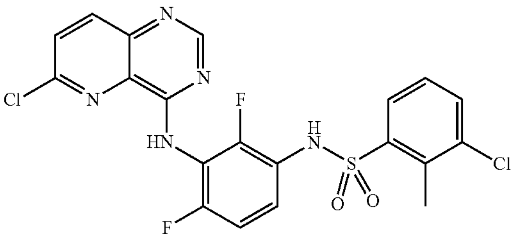 [SMILES: Cc1c(Cl)cccc1S(=O)(=O)Nc1ccc(F)c(Nc2ncnc3ccc(Cl)nc23)c1F] | 496.0 | $^1$H NMR (DMSO-$d_6$) δ: 10.51 (s, 1H), 10.11 (s, 1H), 8.49 (s, 1H), 8.28 (d, J = 9.0 Hz, 1H), 7.98 (d, J = 9.0 Hz, 1H), 7.71-7.80 (m, 2H), 7.38 (t, J = 8.0 Hz, 1H), 7.27 (td, J = 8.6, 5.9 Hz, 1H), 7.19 (td, J = 9.0, 1.0 Hz, 1H), 2.64 (s, 3H) |

TABLE 2-continued

| A-13 | MS m/z (MH+) | $^{1}$H NMR (400 MHz) |
|---|---|---|
| 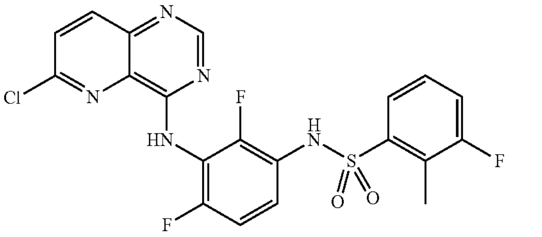 [SMILES: Cc1c(F)cccc1S(=O)(=O)Nc1ccc(F)c(Nc2ncnc3ccc(Cl)nc23)c1F] | 480.0 | $^{1}$H NMR (DMSO-$d_6$) δ: 10.46 (s, 1H), 10.11 (s, 1H), 8.48 (s, 1H), 8.28 (d, J = 9.0 Hz, 1H), 7.99 (d, J = 8.6 Hz, 1H), 7.61 (d, J = 7.8 Hz, 1H), 7.45-7.52 (m, 1H), 7.36-7.43 (m, 1H), 7.27 (td, J = 8.6, 5.9 Hz, 1H), 7.19 (t, J = 9.4 Hz, 1H), 2.48 (d, J = 2.0 Hz, 3H) |
| 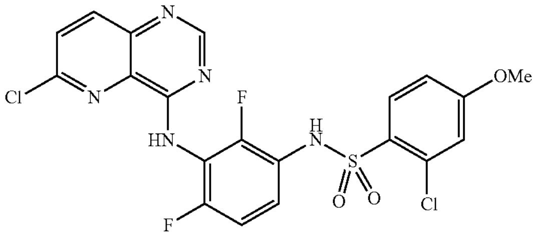 [SMILES: COc1ccc(S(=O)(=O)Nc2ccc(F)c(Nc3ncnc4ccc(Cl)nc34)c2F)c(Cl)c1] | 513.9 | $^{1}$H NMR ($CDCl_3$) δ: 8.75 (s, 1H), 8.45 (br. s., 1H), 8.36 (d, J = 9.0 Hz, 1H), 8.17 (br. s., 1H), 7.91 (d, J = 9.0 Hz, 1H), 7.74 (d, J = 9.0 Hz, 1H), 7.56 (td, J = 8.8, 5.5 Hz, 1H), 6.93-7.05 (m, 2H), 6.81 (dd, J = 9.0, 2.3 Hz, 1H), 3.85 (s, 3H) |
| 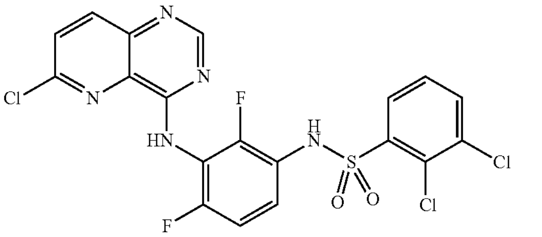 [SMILES: O=S(=O)(Nc1ccc(F)c(Nc2ncnc3ccc(Cl)nc23)c1F)c1cccc(Cl)c1Cl] | 515.9 | $^{1}$H NMR (DMSO-$d_6$) δ: 10.67 (s, 1H), 10.10 (s, 1H), 8.48 (s, 1H), 8.27 (d, J = 9.0 Hz, 1H), 7.98 (d, J = 8.6 Hz, 1H), 7.93 (dd, J = 8.2, 1.2 Hz, 1H), 7.89 (dd, J = 7.8, 1.6 Hz, 1H), 7.52 (t, J = 8.0 Hz, 1H), 7.26 (td, J = 8.7, 5.7 Hz, 1H), 7.16 (t, J = 9.0 Hz, 1H) |
| 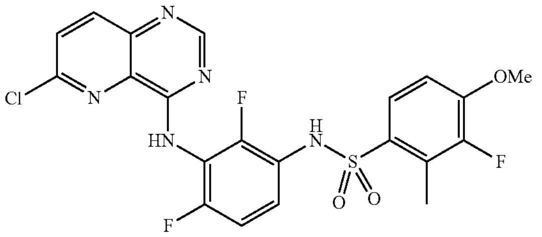 | 510.3 | $^{1}$H NMR (DMSO-$d_6$) δ: 10.38 (broad s, 1H), 10.30 (s, 1H), 8.55 (s, 1H), 8.31 (d, J = 8.8 Hz, 1H), 8.03 (d, J = 8.8 Hz, 1H), 7.57 (dd, J = 8.9, 1.3 Hz, 1H), 7.28 (td, J = 8.8, 5.7 Hz, 1H), 7.19 (td, J = 9.2, 1.3 Hz, 1H), 7.13 (t, J = 8.6 Hz, 1H), 3.88 (s, 3H), 2.46 (d, J = 2.6 Hz, 3H) |
| 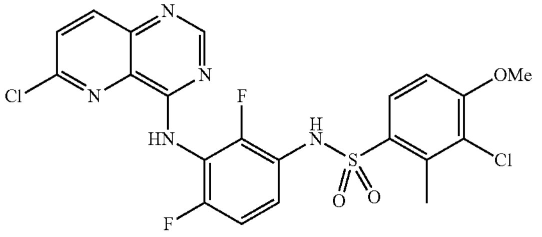 [SMILES: COc1ccc(S(=O)(=O)Nc2ccc(F)c(Nc3ncnc4ccc(Cl)nc34)c2F)c(C)c1F] | 526.3 | $^{1}$H NMR (DMSO-$d_6$) δ: 10.48 (broad s, 1H), 10.37 (d, J = 4.2 Hz, 1H), 8.56 (d, J = 13.9 Hz, 1H), 8.31 (t, J = 7.9 Hz, 1H), 8.03 (dd, J = 8.7, 6.3 Hz, 1H), 7.76 (d, J = 9.0 Hz, 1H), 7.28 (dd, J = 14.5, 8.7 Hz, 1H), 7.19 (t, J = 9.1 Hz, 1H), 7.13 (d, J = 9.0 Hz, 1H), 3.91 (s, 3H), 2.64 (s, 3H) |
| 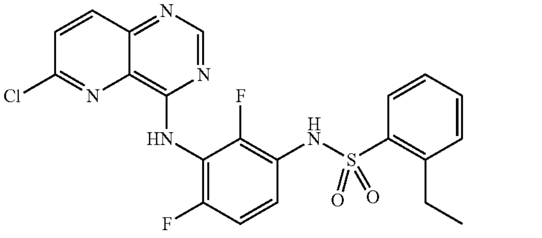 [SMILES: CCc1ccccc1S(=O)(=O)Nc1ccc(F)c(Nc2ncnc3ccc(Cl)nc23)c1F] | 476.3 | $^{1}$H NMR (DMSO-$d_6$) δ: 10.34 (s, 1H), 8.31 (d, J = 9.0 Hz, 1 H) 8.61 (s, 1H), 8.03 (d, J = 9.0 Hz, 1H), 7.53-7.61 (m, 1 H) 7.75 (dd, J = 8.02, 1.4 Hz, 1H), 7.46 (d, J = 1.2 Hz, 1H), 7.30-7.38 (m, 1H), 7.11-7.25 (m, 2H), 2.99 (q, J = 7.4 Hz, 2H), 1.18 (t, J = 7.4 Hz, 3 H). |

TABLE 2-continued

| A-13 | MS m/z ($MH^+$) | $^{1}$H NMR (400 MHz) |
|---|---|---|
| 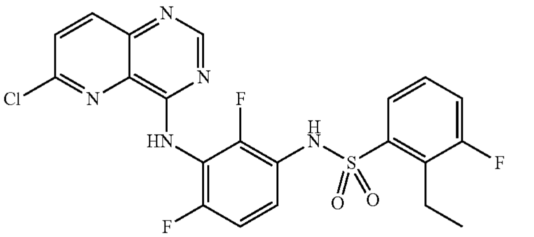 [SMILES: CCc1c(F)cccc1S(=O)(=O)Nc1ccc(F)c(Nc2ncnc3ccc(Cl)nc23)c1F] | 494.2 | $^{1}$H NMR (DMSO-$d_6$) δ: 10.51 (s, 1 H) 8.55 (s, 1 H) 8.29 (d, J = 9.0 Hz, 1 H) 8.01 (d, J = 8.6 Hz, 1 H) 7.61 (d, J = 7.8 Hz, 1 H) 7.45-7.52 (m, 1 H) 7.37-7.44 (m, 1 H) 7.15-7.28 (m, 2 H) 2.95 (q, J = 7.4 Hz, 2 H) 1.14 (t, J = 7.2 Hz, 3 H) |
| 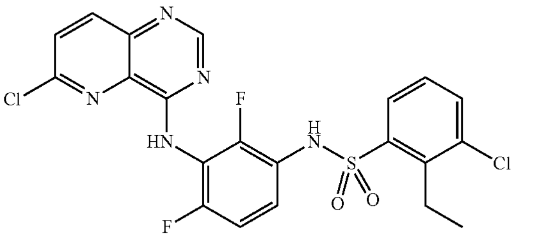 [SMILES: CCc1c(Cl)cccc1S(=O)(=O)Nc1ccc(F)c(Nc2ncnc3ccc(Cl)nc23)c1F] | 510.2 | $^{1}$H NMR (DMSO-$d_6$) δ: 10.56 (s, 1H), 10.12 (s, 1H), 8.50 (s, 1H), 8.28 (d, J = 9.00 Hz, 1H), 7.99 (d, J = 9.00 Hz, 1H), 7.75 (dd, J = 0.78, 7.04 Hz, 1H), 7.74 (dd, J = 0.78, 8.22 Hz, 1H), 7.40 (t, J = 8.02 Hz, 1H), 7.22 (dd, J = 2.30, 10.20 Hz, 1H), 7.17 (q, J = 9.40 Hz, 1H), 3.12 (q, J = 7.30 Hz, 2H), 1.19 (t, J = 7.24 Hz, 3H) |
| 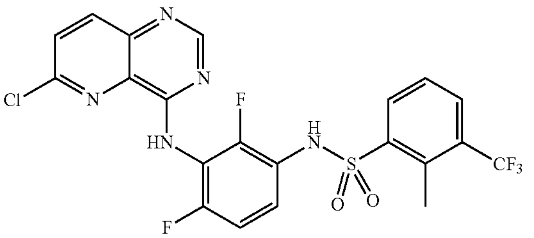 [SMILES: Cc1c(C(F)(F)F)cccc1S(=O)(=O)Nc1ccc(F)c(Nc2ncnc3ccc(Cl)nc23)c1F] | 530.2 | $^{1}$H NMR (DMSO-$d_6$) δ: 8.48 (s, 1H), 8-34-8.23 (m, 3H), 8.16 (d, J = 7.8 Hz, 1H), 7.96 (d, J = 8.8 Hz, 1H), 7.70 (d, J = 7.6 Hz, 1H), 7.41 (t, J = 7.9 Hz, 1H), 7.03 (td, J = 9.4, 6.0 Hz, 1H), 6.72 (t, J = 9.3 Hz, 1H), 2.76 (s, 3H) |
| 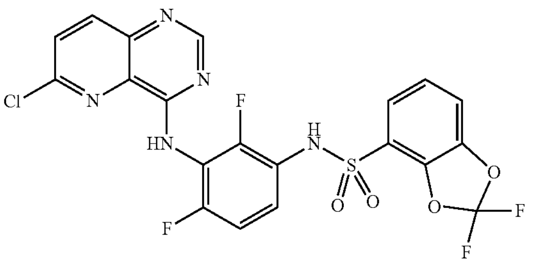 [SMILES: O=S(=O)(Nc1ccc(F)c(Nc2ncnc3ccc(Cl)nc23)c1F)c1cccc2c1OC(F)(F)O2] | 528.2 | $^{1}$H NMR (DMSO-$d_6$) δ 10.77 (s, 1H), 10.11 (s, 1H), 8.46 (s, 1H), 8.28 (d, J = 8.61 Hz, 1H), 7.99 (d, J = 9.00 Hz, 1H), 7.74 (d, J = 7.43 Hz, 1H), 7.27-7.45 (m, 2H), 7.17-7.27 (bs, 1H), 6.96 (bs, 1H) |
| 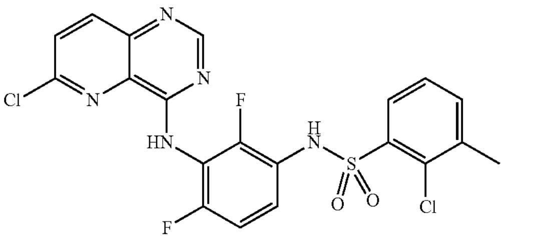 [SMILES: Cc1cccc(S(=O)(=O)Nc2ccc(F)c(Nc3ncnc4ccc(Cl)nc34)c2F)c1Cl] | 496.2 | $^{1}$H NMR (400 MHz, DMSO-$d_6$) δ 10.46 (s, 1H), 10.19 (br , 1Hs), 8.51 (s, 1H), 8.28 (d, J = 8.8 Hz, 1H), 8.00 (d, J = 8.8 Hz, 1H), 7.78 (dd, J = 7.9, 1.1 Hz, 1H), 7.65 (dd, J = 7.6, 0.9 Hz, 1H), 7.40 (t, J = 7.8 Hz, 1H), 7.27-7.12 (m, 2H), 2.40 (s, 3H). |
| 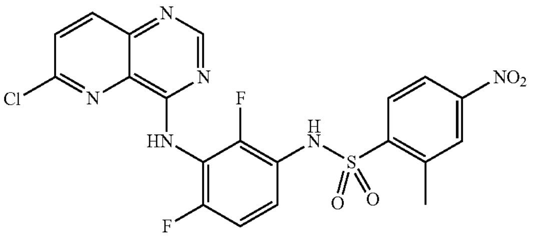 [SMILES: Cc1cc([N+](=O)[O-])ccc1S(=O)(=O)Nc1ccc(F)c(Nc2ncnc3ccc(Cl)nc23)c1F] | 507.2 | $^{1}$H NMR (400 MHz, $CDCl_3$) δ: 8.70 (s, 1H), 8.26 (d, J = 9.00 Hz, 1H), 8.00-8.19 (m, 4H), 7.54 (d, J = 4.70 Hz, 1H), 6.91-7.13 (m, 1H), 2.80 (s, 3H) |

TABLE 2-continued

| A-13 | MS m/z (MH+) | $^1$H NMR (400 MHz) |
|---|---|---|
| 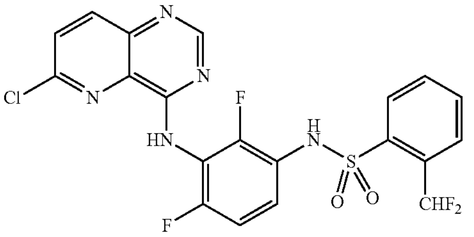 | 498.2 | $^1$H NMR (400 MHz, DMSO-$d_6$) δ: 10.60 (s, 1 H) 10.09 (s, 1 H) 8.42-8.64 (m, 1 H) 8.21-8.33 (m, 1 H) 7.95-8.06 (m, 1 H) 7.67-7.93 (m, 3 H) 7.42-7.67 (m, 1 H) 7.06-7.40 (m, 3 H) |
| 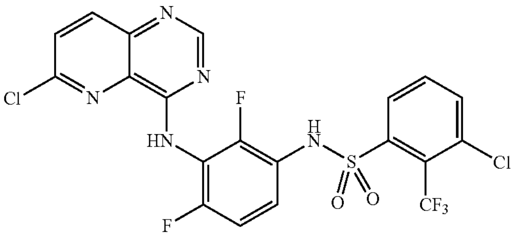 [SMILES: O=S(=O)(Nc1ccc(F)c(Nc2ncnc3ccc(Cl)nc23)c1F)c1cccc(Cl)c1C(F)(F)F] | 550.2 | $^1$H NMR (400 MHz, DMSO-$d_6$) δ 10.69 (s, 1H), 10.21 (brs, 1H), 8.51 (d, J = 2.0 Hz, 1H), 8.29 (d, J = 8.8 Hz, 1H), 8.09-8.02 (m, 2H), 8.00 (dd, J = 8.8, 0.9 Hz, 1H), 7.86 (t, J = 8.2 Hz, 1H), 7.34-7.26 (m, 1H), 7.22 (t, J = 9.3 Hz, 1H). |
| 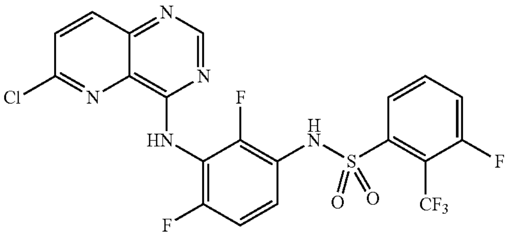 [SMILES: O=S(=O)(Nc1ccc(F)c(Nc2ncnc3ccc(Cl)nc23)c1F)c1cccc(F)c1C(F)(F)F] | 534.1 | $^1$H NMR (400 MHz, DMSO-$d_6$) δ 10.65 (s, 1H), 10.17 (s, 1H), 8.49 (s, 1H), 8.28 (d, J = 8.8 Hz, 1H), 8.00 (d, J = 8.8 Hz, 1H), 7.97-7.89 (m, 2H), 7.85 (dd, J = 11.4, 9.2 Hz, 1H), 7.31 (td, J = 8.9, 5.8 Hz, 1H), 7.22 (td, J = 8.9, 1.0 Hz, 1H) |
| 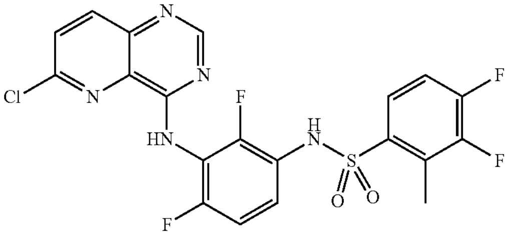 [SMILES: Cc1c(S(=O)(=O)Nc2ccc(F)c(Nc3ncnc4ccc(Cl)nc34)c2F)ccc(F)c1F] | 498.2 | $^1$H NMR (400 MHz, DMSO-$d_6$) δ 10.54 (s, 1H), 10.42 (s, 1H), 8.56 (s, 1H), 8.32 (d, J = 8.8 Hz, 1H), 8.04 (d, J = 8.8 Hz, 1H), 7.61 (ddd, J = 8.8, 5.0, 1.1 Hz, 1H), 7.46 (dd, J = 17.2, 9.1 Hz, 1H), 7.30 (td, J = 8.7, 5.7 Hz, 1H), 7.21 (td, J = 9.1, 1.1 Hz, 1H), 2.52 (d, J = 2.5 Hz, 3H) |
| 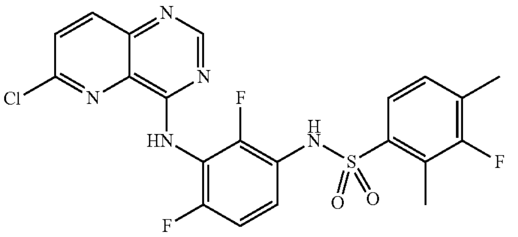 [SMILES: Cc1ccc(S(=O)(=O)Nc2ccc(F)c(Nc3ncnc4ccc(Cl)nc34)c2F)c(C)c1F] | 494.1 | $^1$H NMR (400 MHz, DMSO-$d_6$) δ 10.39 (s, 1H), 10.11 (s, 1H), 8.48 (s, 1H), 8.28 (d, J = 8.8 Hz, 1H), 7.99 (d, J = 8.8 Hz, 1H), 7.50 (d, J = 8.2 Hz, 1H), 7.30-7.23 (m, 2H), 7.18 (td, J = 9.2, 1.3 Hz, 1H), 2.46 (d, J = 2.4 Hz, 3H), 2.26 (d, J = 1.8 Hz, 3H) |
| 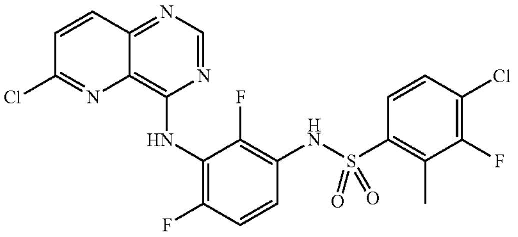 [SMILES: Cc1c(S(=O)(=O)Nc2ccc(F)c(Nc3ncnc4ccc(Cl)nc34)c2F)ccc(Cl)c1F] | 514.0 | $^1$H NMR (400 MHz, DMSO-$d_6$) δ 10.60 (s, 1H), 10.37 (s, 1H), 8.59-8.47 (m, 1H), 8.31 (d, J = 8.8 Hz, 1H), 8.03 (d, J = 8.8 Hz, 1H), 7.66-7.56 (m, 2H), 7.31 (td, J = 8.7, 5.9 Hz, 1H), 7.22 (t, J = 9.1 Hz, 1H), 2.52 (d, J = 2.5 Hz, 3H) |

TABLE 2-continued

| A-13 | MS m/z ($MH^+$) | $^1H$ NMR (400 MHz) |
|---|---|---|
| 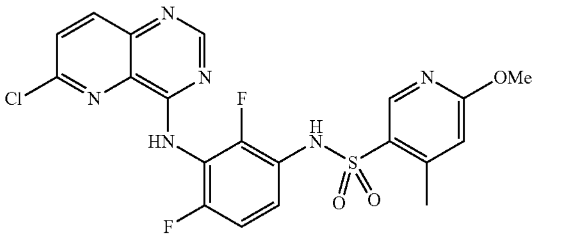 [SMILES: COc1cc(C)c(S(=O)(=O)Nc2ccc(F)c(Nc3ncnc4ccc(Cl)nc34)c2F)cn1] | 493.2 | $^1H$ NMR (400 MHz, DMSO-$d_6$) δ: 10.36 (s, 1H), 10.10 (s, 1H), 8.46 (s, 1H), 8.39 (s, 1H), 8.28 (d, J = 9.00 Hz, 1H), 7.99 (d, J = 8.61 Hz, 1H), 7.32(dt, J = 5.67, 8.71 Hz, 1H), 7.12-7.29 (m, 1H), 6.87 (s, 1H), 3.88 (s, 3H), 2.54 (s, 3H) |
| 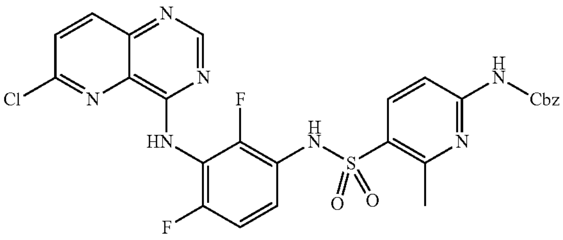 [SMILES: Cc1nc(NC(=O)OCc2ccccc2)ccc1S(=O)(=O)Nc1ccc(F)c(Nc2ncnc3ccc(Cl)nc23)c1F] | 612.4 | $^1H$ NMR (400 MHz, DMSO-$d_6$) δ: 12.73 (br. s., 1H), 11.95 (br. s., 1H), 10.74 (s, 1H), 10.38 (s, 1H), 8.27 (d, J = 9.00 Hz, 1H), 8.20 (d, J = 3.52 Hz, 1H), 8.15 (d, J = 8.61 Hz, 1H), 7.96-8.01 (m, 1H), 7.88 (d, J = 8.61 Hz, 1H), 7.78 (d, J = 9.00 Hz, 1H), 7.24-7.48 (m, 4H), 7.13-7.24 (m, 1H), 5.12-5.22 (m, 2H), 2.65 (s, 3H) |
| 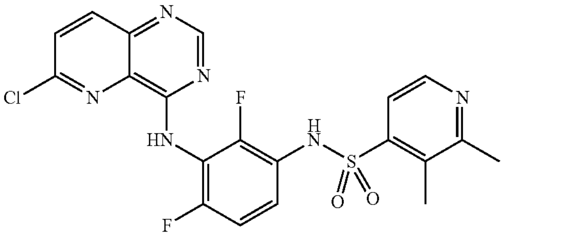 [SMILES: Cc1nccc(S(=O)(=O)Nc2ccc(F)c(Nc3ncnc4ccc(Cl)nc34)c2F)c1C] | 477.3 | $^1H$ NMR (400 MHz, DMSO-$d_6$) δ: 10.62 (s, 1H), 10.10 (s, 1H), 8.34-8.60 (m, 2H), 8.28 (d, J = 9.00 Hz, 1H), 7.99 (d, J = 9.00 Hz, 1H), 7.49 (d, J = 5.09 Hz, 1H), 7.09-7.33 (m, 2H), 2.53 (s, 6H) |
| 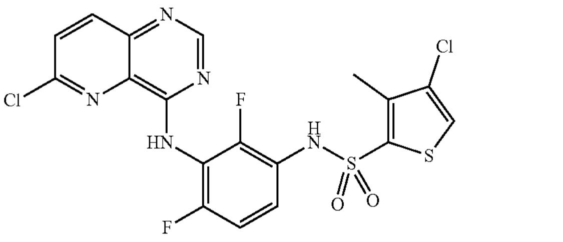 [SMILES: Cc1c(Cl)csc1S(=O)(=O)Nc1ccc(F)c(Nc2ncnc3ccc(Cl)nc23)c1F] | 502.2 | $^1H$ NMR (400 MHz, DMSO-$d_6$) δ: 10.61 (s, 1 H) 10.32 (br. s., 1H), 8.51-8.59 (m, 1H), 8.21-8.34 (m, 1H), 7.98-8.03 (m, 1H), 7.96 (s, 1H), 7.32 (td, J = 8.6, 5.9 Hz, 1H), 7.21-7.27 (m, 1 H) 2.20 (s, 3 H) |
| 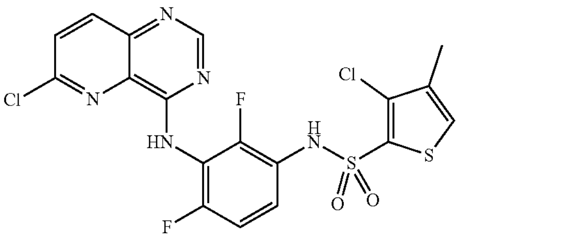 [SMILES: Cc1csc(S(=O)(=O)Nc2ccc(F)c(Nc3ncnc4ccc(Cl)nc34)c2F)c1Cl] | 502.1 | Not determined |
| 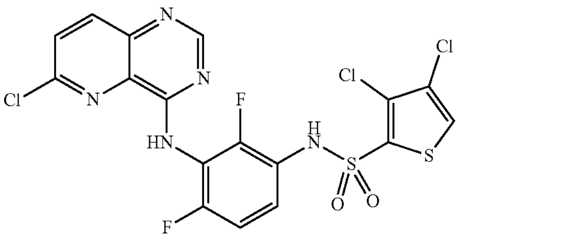 [SMILES: O=S(=O)(Nc1ccc(F)c(Nc2ncnc3ccc(Cl)nc23)c1F)c1scc(Cl)c1Cl] | 522.2 | $^1H$ NMR (400 MHz, DMSO-$d_6$) δ 10.96 (s, 1H), 10.19 (d, J = 11.4 Hz, 1H), 8.52 (d, J = 3.6 Hz, 1H), 8.28 (d, J = 8.9 Hz, 1H), 8.22 (d, J = 1.8 Hz, 1H), 8.00 (dd, J = 8.8, 2.4 Hz, 1H), 7.32 (dd, J = 14.7, 7.7 Hz, 1H), 7.24 (t, J = 9.0 Hz, 1H). |

TABLE 2-continued

| A-13 | MS m/z $(MH^+)$ | $^1H$ NMR (400 MHz) |
|---|---|---|
| 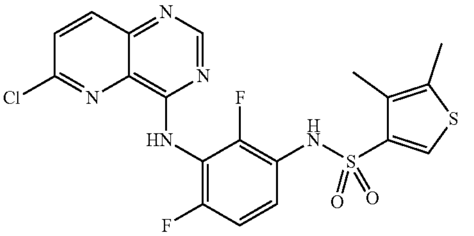 [SMILES: Cc1scc(S(=O)(=O)Nc2ccc(F)c(Nc3ncnc4ccc(Cl)nc34)c2F)c1C] | 482.3 | $^1H$ NMR (400 MHz, DMSO-$d_6$) δ 10.19 (s, 1H), 10.13 (s, 1H), 8.55-8.51 (m, 1H), 8.32-8.24 (m, 1H), 8.05-7.96 (m, 1H), 7.90-7.86 (m, 1H), 7.31-7.23 (m, 1H), 7.20-7.12 (m, 1H), 2.30 (s, 3H), 2.21 (s, 3H). |
| 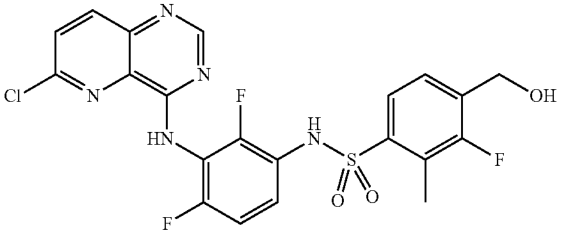 [SMILES: Cc1c(S(=O)(=O)Nc2ccc(F)c(Nc3ncnc4ccc(Cl)nc34)c2F)ccc(CO)c1F] | | Not determined |

Step 4—Preparation of Example 1 (W-I: Ar=4-methoxyphenyl, Het=1-benzimidazolyl): Chloropyridine A-13 (Ar=4-methoxyphenyl; 25 mg, 0.05 mmol), benzimidazole (11 mg, 0.09 mmol, 1.8 equiv.), Cu powder (0.3 mg), racemic-BINOL (0.5 mg) and cesium carbonate (2.3 equiv., 39 mg, 0.12 mmol) were weighed in a 4 mL vial and DMSO (0.7 mL) was added. The vial was capped and the mixture was stirred at 125° C. for 2 h (a dark orange-brown solution is produced). LCMS shows complete conversion to the desired product. The reaction mixture was acidified with AcOH (200 μL) and injected on a preparative reversed-phase HPLC using a 30-100% MeOH 0.05% TFA gradient. Inhibitor 1-TFA salt was obtained as a beige powder after lyophilization (17 mg).

Other examples of inhibitors prepared in a similar fashion are described in Tables 3 and 4 (Method A).

Synthesis of Inhibitors W-I Using Synthetic Method B (Example 8):

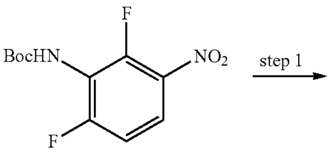

A-2

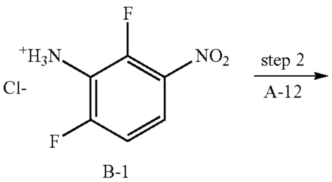

B-1

-continued

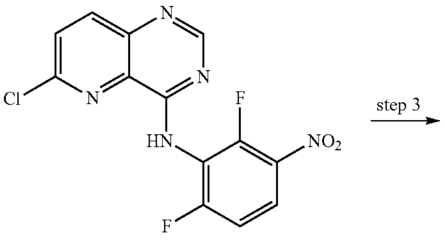

B-2

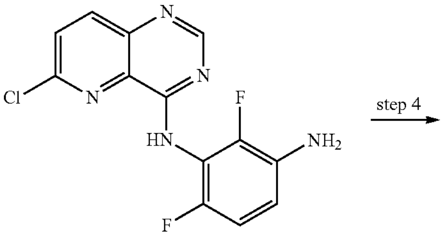

B-3

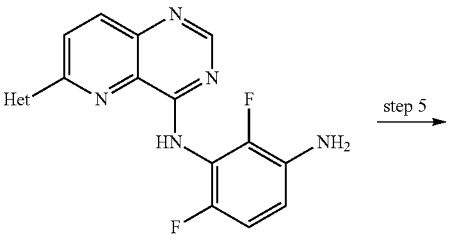

B-4

-continued

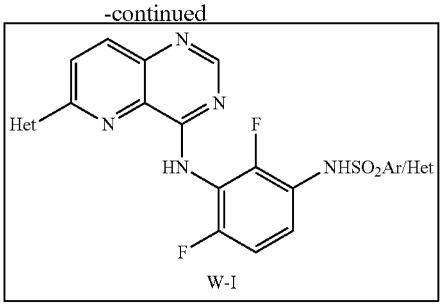

W-I

Example 8:

Het = 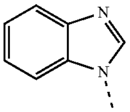

Ar = 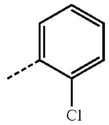

Step 1: Carbamate A-2 (1.50 g) was dissolved in 8.2 mL of a 4M HCl solution in dioxane. After 5 minutes at room temperature, the pale brown solution became a pale yellow suspension. It was allowed to stir for 16 h (LCMS showed complete conversion to the desired product). The reaction mixture was concentrated to dryness under reduced pressure and the solid residue was co-evaporated with toluene 2× and dried under vacuum. The resulting pale green solid (1.11 g, 97% yield) was used as such without further purification: $^1$H NMR (DMSO-$d_6$) δ: 7.31 (ddd, J=9.2, 8.0, 5.5 Hz, 1H), 7.10-7.18 (m, 1H).

Step 2: Aniline hydrochoride salt B-1 from step 1 (600 mg, 2.85 mmol) and dichloropyridopyrimidine A-12 (1.1 equiv., 627 mg, 3.13 mmol) were suspended in AcOH (8 mL) and stirred at 50° C. for 1.5 h at which point the reaction was found to be complete by LCMS. The dark brown solution was allowed to cool to room temperature then slowly poured into 30 mL of ice/water. Once the ice had melted, the suspension was sonicated and the solids were collected by filtration and washed with water. After drying under vacuum, chloropyridine B-2 (878 mg, 91% yield) was obtained as a beige solid which was used as such without further purification: $^1$H NMR (DMSO-$d_6$) δ: 10.39 (s, 1H), 8.61 (s, 1H), 8.33 (d, J=9.0 Hz, 1H), 8.29 (td, J=9.2, 5.9 Hz, 1H), 8.04 (d, J=9.0 Hz, 1H), 7.56 (td, J=9.0, 1.0 Hz, 1H). MS m/z 338.0 (MH$^+$).

Step 3: Nitroarene B-2 (875 mg, 2.6 mmol) and tin(II) dichloride dihydrate (5 equiv., 2.92 g, 13 mmol) were suspended in 20 mL of ethanol. The mixture was heated to 60° C., affording a dark orange solution, and stirred at that temperature for 2 h at which point the reaction was analyzed by LCMS and found to be complete. The mixture was allowed to cool to room temperature then concentrated under reduced pressure to remove most of the ethanol. The concentrate was taken up into EtOAc (150 mL) and a 1N solution of NaOH was added until two, almost clear phases were obtained. The layers were separated and the aqueous layer was extracted 3 more times with 50 mL of EtOAc. The combined organic layers were washed with water then brine, dried over $MgSO_4$, filtered, concentrated and dried under vacuum. Aniline B-3 (792 mg, 99% yield) was obtained as a pale brown-yellow solid that was used as such without further purification: $^1$H NMR (DMSO-$d_6$) δ: 9.99 (s, 1H), 8.53 (s, 1H), 8.27 (d, J=8.6 Hz, 1H), 7.98 (d, J=8.6 Hz, 1H), 6.89 (td, J=9.2, 1.6 Hz, 1H), 6.74 (td, J=9.4, 5.5 Hz, 1H), 5.07 (s, 2H). MS m/z 308.0 (MH$^+$).

Step 4—Preparation of aniline B-4 (Het=1-benzimidazolyl): Chloropyridopyrimidine B-3 (495 mg, 1.6 mmol) was charged in a 50 mL flask and dissolved in 6 mL of DMSO. Benzimidazole (1.15 equiv., 220 mg, 1.85 mmol), cesium carbonate (2.3 equiv., 1.21 g, 3.7 mmol), copper powder (0.01 equiv., 1 mg) and BINOL (0.01 equiv., 4.5 mg) were then added. The resulting dark mixture was stirred at 100° C. for 2 h. LCMS analysis at that point revealed ~40% conversion. The temperature was increased to 120° C. and the mixture was allowed to stir for another 2 hours at which point only a trace of the starting aniline was present. The mixture was allowed to cool to room temperature then neutralized (pH 7) with 1N HCl. It was then partitioned between water (75 mL) and DCM (100 mL). After stirring, ~ 5 g of Celite® was added to the brown emulsion which was filtered through a pad of Celite®, washing with DCM. The filtrate (two clear layers) was transferred into a separatory funnel and the layers were separated. The aqueous phase was extracted two more times with DCM and the combined organic layers were washed twice with water and once with brine. The organic portion was then dried over $MgSO_4$, filtered and concentrated. The residue was purified by flash chromatography (combiflash) on a 24 g column using a 100% DCM to 40% i-PrOH in DCM gradient. The appropriate fractions (Rf=0.25 in 1:9 i-PrOH/DCM) were combined and concentrated to affords 124 mg of B-4 (Het=1-benzimidazolyl) as a dark yellow solid which is a 1:1 molar mixture of the desired product and unreacted benzimidazole. The crude material was used with no further purification for the sulfonylation step (Step 5): $^1$H NMR (DMSO-$d_6$) δ: 9.79 (s, 1H), 9.39 (s, 1H), 8.56 (s, 1H), 8.52 (d, J=9.4 Hz, 1H), 8.47 (d, J=9.0 Hz, 1H), 8.39 (d, J=7.8 Hz, 1H), 7.83 (d, J=7.4 Hz, 1H), 7.37-7.49 (m, 2H), 6.95 (td, J=9.2, 1.6 Hz, 1H), 6.78 (td, J=9.4, 5.5 Hz, 1H), 5.13 (s, 2H). MS m/z 390.1 (MH$^+$).

Step 5 (Example 8): 2-chlorobenzenesulfonyl chloride (2 equiv., 26 mg, 0.12 mmol) was weighed in a 4 mL vial and dissolved in 0.5 mL of THF. Crude aniline B-4 was then added (24 mg, 0.06 mmol) followed by pyridine (6 equiv., 30 μL, 0.37 mmol). The resulting mixture was stirred at 50° C. for 18 h at which point the reaction was found to be complete by LCMS (also present in the mixture was a side product corresponding to the addition of the sulfonyl chloride onto residual benzimidazole that contaminated the starting material (MS m/z 293.0: MH$^+$). The reaction mixture was allowed to cool to room temperature then quenched by the addition of 0.2 mL of acetic acid and diluted to 2 mL with methanol. The product was isolated by prep-HPLC (MeOH/$H_2O$/0.1% formic acid conditions, 50%→100% methanol gradient). The fractions containing the major peak were pooled and partially concentrated to remove methanol. The resulting suspension was dissolved by the addition of a few milliliters of acetonitrile then the solution was frozen and lyophilized. Obtained 9.8 mg of the desired product (Example 8) as a beige solid.

Other examples of inhibitors prepared in a similar fashion are described in Tables 3 and 4 (Method B).

Synthesis of Inhibitors W-II Using Synthetic Method C and Organoboron Reagents Through Suzuki-Miyaura Cross-Coupling (Examples 71 and 510):

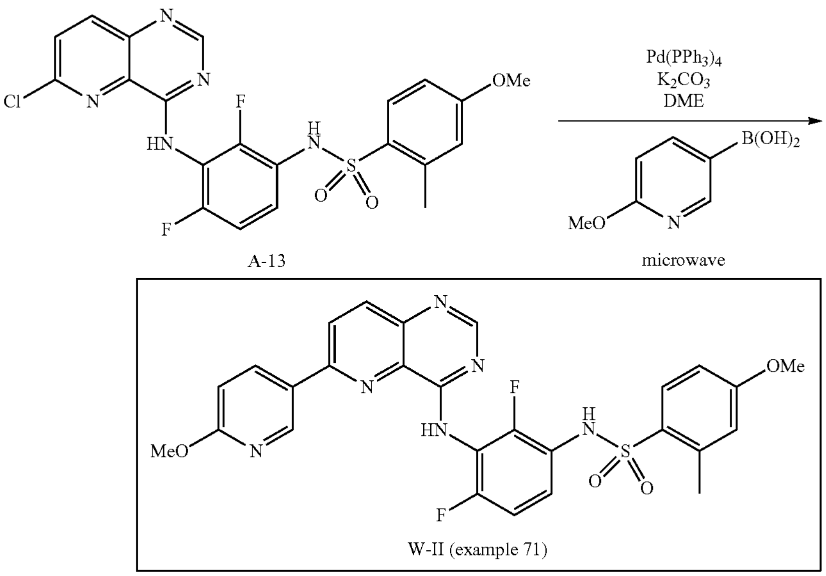

A-13

W-II (example 71)

A 2 mL microwave vial was charged with 30 mg (1 equiv.) of chloropyridopyrimidine A-13, 2 equiv. of 6-methoxy-pyridyl-3-boronic acid (19 mg) and 4 equiv. of anhydrous potassium carbonate (34 mg). DME (1.5 mL) and water (0.5 mL) were then added and nitrogen gas was bubbled through the mixture for 2 minutes. Tetrakis(triphenylphosphine)palladium(0) (0.05 equiv., 3.5 mg) was added, nitrogen gas was bubbled through the mixture for another 2 minutes and the vial was sealed. The reaction mixture was then irradiated in a microwave for 1 h at 90° C. LCMS analysis at that point revealed the reaction was complete. The reaction mixture was treated with 0.6 mL of acetic acid and concentrated to ~0.5 mL under reduced pressure. It was then diluted to 2 mL with methanol and DMSO, filtered and purified by prep HPLC ($MeOH/H_2O$/0.1% formic acid conditions, 50%→100% methanol gradient). The appropriate fractions were combined and partially concentrated to remove methanol. The resulting suspension was dissolved by the addition of a few milliliters of acetonitrile then the solution was frozen and lyophilized. The inhibitor of Example 71 was obtained as a beige solid (15 mg).

Other examples of inhibitors prepared in a similar fashion using the appropriate chloropyridine fragment A-13 (Table 2) and commercially available boronic acids or boronate esters are listed under method C in Table 4. The analog of Example 510 was prepared in a similar fashion using the commercially available boronate ester, cesium carbonate as base, trans-dichlorobis(triphenylphosphine)-palladium(II) as catalyst and dioxane as solvent.

Synthesis of Inhibitors W-II Using Synthetic Method C and Organotin Reagents Through Stille Cross-Coupling (Example 561):

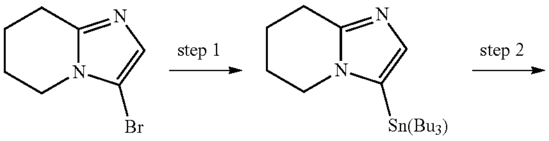

-continued

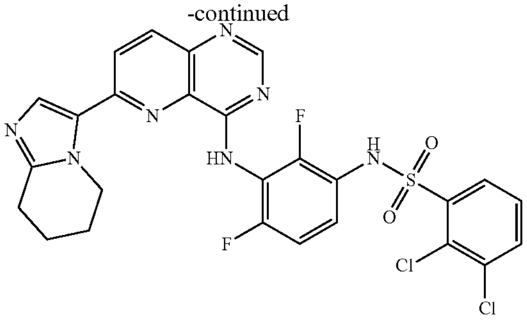

Example 561

Step 1: To a solution of the commercially available bromide (100 mg, 0.497 mmol) in THF (5 mL) at −78° C. under $N_2$ was added a solution of 2.5M nBuLi in hexanes (0.24 mL, 0.597 mmol) and stirred at this temperature for 30 min. After this time, tri-n-butyltin chloride (0.13 mL, 0.497 mmol) was added and the resulting solution was stirred for 30 min. After completion, EtOAc was added and the organic layer was washed with brine then dried over $MgSO_4$, filtered and concentrated under vacuum to provide the organotin intermediate (154 mg, 75%). MS m/z 413.2 ($MH^+$).

Step 2: A vial charged with the organotin reagent from step 1 (40 mg, 0.0968 mmol), 2,3-dichloro-N-[3-[(6-chloropyrido[3,2-d]pyrimidin-4-yl)amino]-2,4-difluoro-phenyl]benzenesulfonamide (50 mg, 0.0968 mmol), copper(I) iodide (1.2 mg, 0.0290 mmol), (R)-(+)-2,2"-bis(diphenylphosphino)-1,1"-binaphthyl (12 mg, 0.0194 mmol) and 1,1'-bis(diphenylphosphino)ferrocene-palladium(ii)dichloride dichloromethane complex (7.1 mg, 0.00968 mmol) in PhMe-DMF 1:1 (0.5 mL) was degassed and purged 3 times with $N_2$. The mixture was stirred at 90° C. for 16 h hours under a $N_2$ atmosphere. Upon completion, the reaction mixture was diluted with EtOAc, then washed 3 times with aq. 10% KF solution, followed by brine. The organic layer was dried over $MgSO_4$, filtered and concentrated under vacuum. The residue was purified on reverse phase HPLC with ACN in 0.1% aq. HCOOH to afford upon lyophilisation Example 561 (2.7 mg, 5%). $^1$H NMR (400 MHz, DMSO-$d_6$) δ: 10.73 (br. s., 1H), 9.44 (s, 1H), 8.76 (d, J=9.00 Hz, 1H), 8.39-8.62 (m, 2H), 8.23 (d, J=8.22 Hz, 1H), 7.91 (dd, J=1.17, 7.83 Hz, 2H), 7.51 (t, J=8.02 Hz, 2H), 7.27 (br. s., 1H), 7.17 (br. s., 1H), 6.83 (d, J=8.22 Hz, 1H), 4.41 (s, 1H), 3.98-4.15 (m, 2H), 3.51-3.60 (m, 2H), 1.54-1.79 (m, 4H), 1.17-1.38 (m, 3H). MS m/z 712.3 (MH$^+$).

Other examples of inhibitors prepared in a similar fashion using the appropriate chloropyridine fragment A-13 (Table 2) and either commercially available organotin compounds or bromides that wer converted to the corresponding organotin species as described above for step 1, are listed under method C in Table 4 (Examples 562-565, 590 and 591).

General Method for the Synthesis of Inhibitors of Formula W-III (Method D, X═CH)—Synthesis of Example 109:

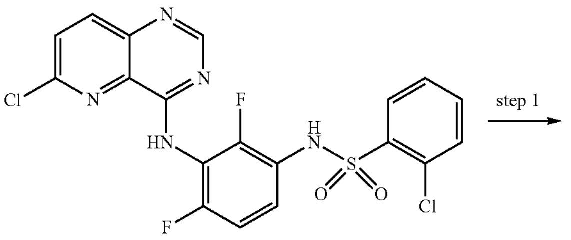

A-13

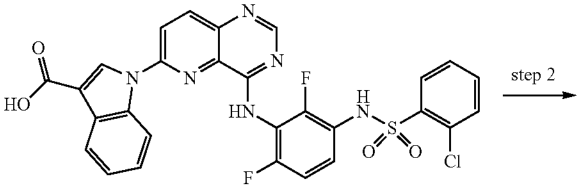

D-1

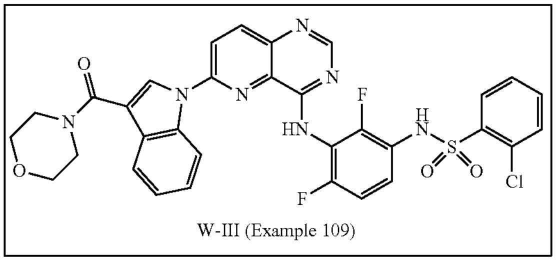

W-III (Example 109)

Step 1—Preparation of carboxylic acid D-1: Chloropyridopyrimidine A-13 (Ar=2-chlorophenyl) (150 mg, 0.3 mmol, 1 equiv.) was charged in a 4 mL vial followed by methyl indole-3-carboxylate (71 mg, 0.4 mmol, 1.3 equiv.), copper (0) (0.6 mg, 0.03 equiv.), BINOL (2.7 mg, 0.03 equiv.), cesium carbonate (150 mg, 0.47 mmol, 1.5 equiv.) and DMSO (1.5 mL). The resulting mixture was stirred at 100° C. for 1.75 h affording a dark brown solution (LCMS analysis shows complete conversion). The reaction was allowed to cool to room temperature then 6 equivalents (0.5 mL) of 4N sodium hydroxide was added to the mixture. It was stirred at 50° C. for 1 h (LCMS shows complete conversion to the carboxylic acid). The mixture was diluted with water (2 mL) and filtered through a Celite® plug to remove insoluble particles. It was then acidified to~pH 1 with 1 N HCl and diluted with 10 mL of water affording a gel-like suspension (not filterable). The mixture was extracted 3× with EtOAc and the combined organic layers were washed twice with water and once with brine then dried over $MgSO_4$, filtered and concentrated to afford 220 mg of the crude carboxylic acid as a yellow solid: $^1$H NMR (DMSO-$d_6$) δ: 12.56 (br. s., 1H), 10.53 (s, 1H), 9.99 (s, 1H), 8.97 (s, 1H), 8.50 (s, 1H), 8.47 (d, J=9.0 Hz, 1H), 8.43 (d, J=9.4 Hz, 1H), 8.23-8.29 (m, 1H), 8.16-8.22 (m, 1H), 7.91 (dd, J=8.0, 1.4 Hz, 1H), 7.62-7.71 (m, 2H), 7.48-7.55 (m, 1H), 7.35-7.44 (m, 2H), 7.24-7.33 (m, 1H), 7.21-7.24 (m, 1H), 7.16-7.21 (m, 1H). MS m/z 607.0 (MH$^+$).

Step 2—Preparation of inhibitor W-III (Example 109): To the crude carboxylic acid from Step 1 (30 mg, 1 equiv.) in NMP (1 mL) was added DIEA (40 μL, 6 equiv.) and HATU (30 mg, 2 equiv.). The solution was allowed to stir for 2-3 min. affording a dark yellow solution. Morpholine (7 mg, 2 equiv.) was added and the reaction mixture was stirred at room temperature for 3 h at which point the reaction was found to be complete by LCMS. The reaction was quenched by the addition of 0.2 mL of acetic acid then diluted to 2 mL with methanol, filtered and purified by prep-HPLC (MeOH/$H_2O$/0.1% formic acid conditions, 50%→100% methanol gradient). The appropriate fractions were combined and partially concentrated to remove methanol. The resulting suspension was dissolved by the addition of a few milliliters of acetonitrile then the solution was frozen and lyophilized. Amide Example 109 (14.5 mg) was obtained as an off-white solid.

Other examples of inhibitors prepared in a similar fashion are listed under method D in Table 4.

General Method for the Synthesis of Inhibitors of Formula W-III (Method D, X═N)—Synthesis of Example 127:

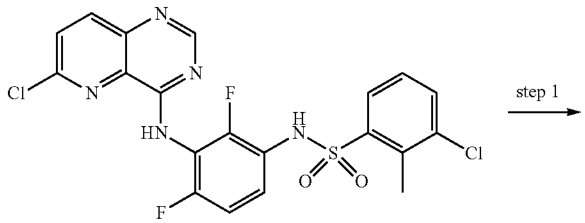

A-13

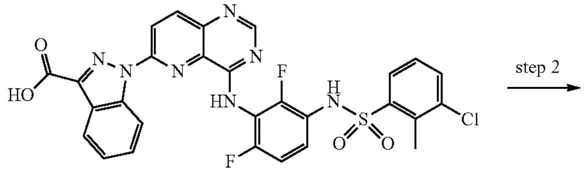

D-2

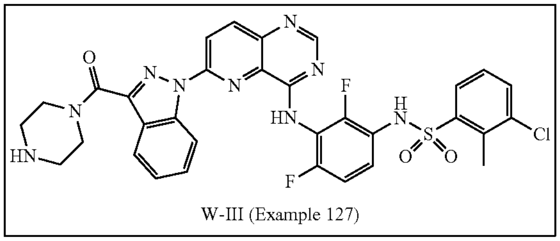

W-III (Example 127)

Step 1—Preparation of carboxylic acid D-2: Chloropyridopyrimidine A-13 (Ar=3-chloro-2-methylphenyl) (300 mg, 0.6 mmol, 1 equiv.) was charged in a 4 mL vial followed by 3-indazolecarboxylic acid methyl ester (140 mg, 0.79 mmol, 1.3 equiv.), copper (0) (1 mg, 0.03 equiv.), BINOL (5 mg, 0.03 equiv.), cesium carbonate (295 mg, 0.91 mmol, 1.5 equiv.) and DMSO (2 mL). The vial was stoppered and the mixture was stirred at 100° C. for 1.5 h affording a dark brown solution. LCMS analysis revealed the reaction was essentially complete. The reaction was allowed to cool to room temperature then 6 equivalents (0.9 mL) of a 4N solution of sodium hydroxide was added. The mixture was stirred at 50° C. for 1.5 h (LCMS shows complete saponification of the methyl ester). The mixture was diluted with water (3 mL) and filtered through a Celite® plug while still hot, to remove insoluble particles. It was then acidified to pH ~1 with 1N HCl and diluted with 10 mL of water affording a fine suspension after sonication. The solids were collected by filtration and dried under vacuum. The crude carboxylic acid D-2 (Ar=3-methyl-2-chlorophenyl) was obtained as a beige solid (398 mg): $^1$H NMR (DMSO-$d_6$) δ: 13.70 (br. s, 1H), 10.58 (s, 1H), 9.48 (s, 1H), 9.03 (d, J=8.6 Hz, 1H), 8.65 (d, J=9.0 Hz, 1H), 8.54 (br. s., 1H), 8.48 (d, J=9.0 Hz, 1H), 8.26 (d, J=7.8 Hz, 1H), 7.79 (d, J=7.8 Hz, 1H), 7.75 (d, J=7.8 Hz, 1H), 7.68 (t, J=7.6 Hz, 1H), 7.54 (t, J=7.6 Hz, 1H), 7.40 (t, J=8.0 Hz, 1H), 7.28-7.36 (m, 1H), 7.25 (t, J=9.0 Hz, 1H), 2.66 (s, 3H). MS m/z 622.0 ($MH^+$).

Step 2—Preparation of inhibitor W-III (Example 127): The crude carboxylic acid from Step 1 (30 mg, 1 equiv.) was dissolved in NMP (1 mL) and DIEA (50 μL, 6 equiv.) and HATU (37 mg, 2 equiv.) were added. The solution was stirred at room temperature for 2-3 min. affording a dark yellow solution. N-Boc-piperazine (18 mg, 2 equiv.) was then added and the reaction mixture was stirred at room temperature for 2 h at which point the reaction was found to be complete by LCMS. The reaction was quenched by the addition of 1 mL of a saturated solution of ammonium chloride then diluted to 4 mL with water. The resulting suspension was then sonicated, and the solids were collected by filtration. They were then washed with water and dried under vacuum. The solids were then taken up in DCM (1 mL) and MeOH (0.5 mL) and treated with 1 mL of a 4 N solution of HCl in dioxane. After 2 hours of stirring at room temperature, LCMS analysis showed complete cleavage of the Boc protecting group. The mixture was concentrated to dryness, the residue dissolved in MeOH and purified by prep-HPLC (MeOH/$H_2O$/0.1% formic acid conditions, 30%→100% methanol gradient). The appropriate fractions were combined and partially concentrated to remove methanol. The resulting suspension was dissolved by the addition of a few milliliters of acetonitrile then the solution was frozen and lyophilized. The amide of Example 127 (14 mg) was obtained as a pale yellow solid.

Other examples of inhibitors prepared in a similar fashion are listed under method D in Table 4.

General Method for the Synthesis of Inhibitors of Formula W-IV (Method E)—Synthesis of Example 227:

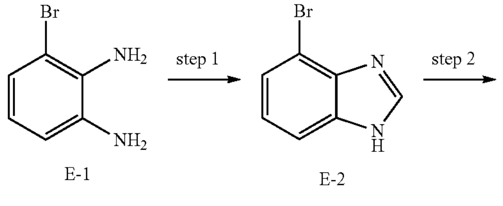

E-1 E-2

-continued

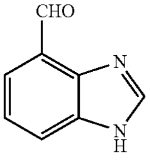

E-3

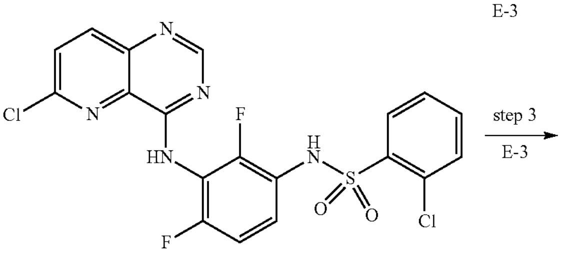

A-13

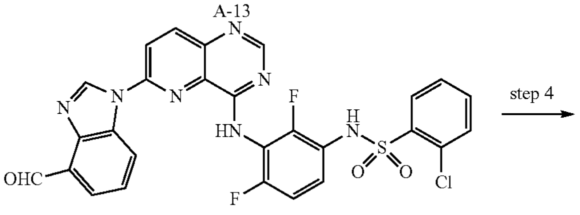

E-4

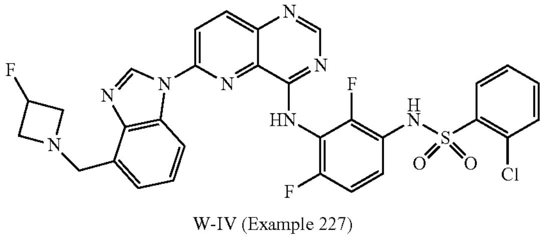

W-IV (Example 227)

Step 1—Preparation of intermediate E-2: 3-Bromo-1,2-phenylenediamine (2.00 g, 10.7 mmol) was charged in a 50 mL flask along with 15 mL of formic acid. The mixture was brought to reflux in a 120° C. oil bath and stirred for 4 h. The mixture was concentrated under reduced pressure to a dark oily residue, diluted with water and cooled in an ice bath. Neutralization of the mixture was started with 1 N NaOH and finished with a saturated $NaHCO_3$ solution. The dark brown solids were collected by filtration in a Buchner funnel and washed with water. The solids were then dried under vacuum, affording 1.91 g of the desired bromobenzimidazole E-2 as a dark brown solid that was used as such: $^1$H NMR (DMSO-$d_6$) δ: 12.81 (br. s., 1H), 8.30 (s, 1H), 7.58 (d, J=8.2 Hz, 1H), 7.41 (d, J=7.8 Hz, 1H), 7.14 (t, J=8.0 Hz, 1H). MS m/z 197.0 ($MH^+$).

Step 2—Preparation of intermediate E-3: Adapting a procedure described in WO 2004/076411A2, bromobenzimidazole E-2 (350 mg, 1.776 mmol) was dissolved in 8 mL of anhydrous THF. 60% Sodium hydride dispersion in mineral oil (78 mg, 1.95 mmol) was added at room temperature. After 10 minutes, the reaction was cooled to −78° C. and 1.4 molar tert-butyllithium (2.66 ml, 3.73 mmol) in pentane was added dropwise. The reaction mixture became very thick and stirring was difficult. After 30 minutes, the mixture was quenched by the addition of DMF (0.55 ml, 7.1 mmol). It was allowed to warm to room temperature then partitioned between EtOAc and a 1:1 mixture of water and a saturated solution of $NaHCO_3$. The layers were separated and the aqueous layer was further extracted 3× with EtOAc.

The combined organic layers were washed once with brine then dried over $Na_2SO_4$. The organic layer was then filtered and concentrated down to a residue. The resulting dark brown gummy solid was triturated twice with 2 mL of hexanes to remove the mineral oil from the NaH. The solid was then taken up in 6 mL of EtOAc and sonicated. The solids were collected by filtration and dried under suction to give E-3 (117 mg) as a dark brown solid: $^1H$ NMR (DMSO-$d_6$) δ: 13.01 (br. s., 1H), 10.17 (s, 1H), 8.31 (s, 1H), 8.04 (d, J=7.8 Hz, 1H), 7.88 (d, J=7.4 Hz, 1H), 7.43 (t, J=7.8 Hz, 1H). A second crop of product (148 mg of ~80% homogeneity) was recovered from mother liquors.

Step 3—Preparation of intermediate E-4: Chloropyridopyrimidine A-13 (Ar=2-chlorophenyl: 75 mg, 1 equiv.) was charged in a 4 mL vial along with crude benzimidazole E-3 from step 2 (26 mg, 1.15 equiv.), copper (0) (0.3 mg, 0.03 equiv.), BINOL (1.3 mg, 0.03 equiv.), cesium carbonate (76 mg, 1.5 equiv.) and DMSO (1 mL). The resulting mixture was stirred at 100° C. for 1 h at which point LCMS showed complete reaction. The mixture was allowed to cool to room temperature then quenched by the addition of 0.1 mL of acetic acid. The mixture was diluted to 10 mL with water then sonicated. The precipitate was collected by filtration and washed with water. The brown solids were then dried under vacuum. Crude intermediate E-4 (98 mg) was obtained as a brown solid and used as such in step 4: $^1H$ NMR (DMSO-$d_6$) δ: 10.85 (br. s., 1H), 10.53 (br. s., 1H), 9.84 (s, 1H), 9.54 (br. s., 1H), 8.76 (d, J=7.4 Hz, 1H), 8.45-8.63 (m, 2H), 7.92 (d, J=7.4 Hz, 1H), 7.88 (d, J=7.4 Hz, 1H), 7.55-7.73 (m, 3H), 7.51 (t, J=7.2 Hz, 1H), 7.12-7.34 (m, 2H). MS m/z 592.1 ($MH^+$).

Step 4—Preparation of inhibitor W-IV (Example 227): 3-Fluoroazetidine hydrochloride (17 mg, 0.15 mmol) was charged in a 4 mL vial along with 1 mL of methanol and a 4N solution of sodium hydroxide (0.038 ml, 0.15 mmol). The crude aldehyde E-4 from step 3 (30 mg, 0.051 mmol) was then added and the mixture was heated at 50° C. for 10 minutes. Sodium cyanoborohydride (9.55 mg, 0.15 mmol) was finally added. The reaction mixture was allowed to stir at 50° C. for another 2 h at which time the conversion was complete by LCMS. It was quenched by the addition of an acetic acid solution (0.2 mL) in 0.5 mL of DMSO, the solution was filtered and the product isolated by prep-HPLC (30%→100% MeOH in $H_2O$ gradient, 0.1% formic acid). The appropriate fractions were pooled and concentrated to remove methanol then frozen and lyophilized. The compound of Example 227 (12.7 mg) was isolated as an off-white solid.

General Method for the Synthesis of Inhibitors of Formula W-V (Method F)—Synthesis of Example 243:

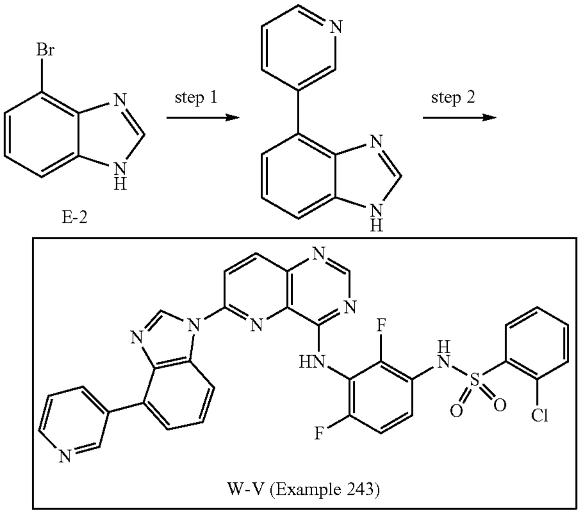

E-2

W-V (Example 243)

Step 1: Bromobenzimidazole E-2 (70 mg, 0.355 mmol), potassium carbonate (196 mg, 1.42 mmol) and 3-pyridylboronic acid (57 mg, 0.46 mmol) were charged in a 4 mL vial and dioxane (2 mL) and water (0.7 mL) were added. Argon gas was bubbled through the mixture for 1 minute and then tetrakis(triphenylphosphine)palladium (0) (16.4 mg, 0.014 mmol) was added. Argon gas was again bubbled through the solution for 3 min, the vial was sealed and heated at 100° C. for 2 hours (conversion to desired product is complete as judged by LCMS analysis). The reaction mixture was allowed to cool to RT, diluted with EtOAc and washed with brine. After drying on $MgSO_4$, the extract was concentrated under reduced pressure and the residue purified by flash chromatography using $Et_3N$ pre-treated silica and a DCM—20% iPrOH/DCM gradient to provide the desired benzimidazole intermediate (58 mg, 84% yield): $^1H$ NMR (DMSO-$d_6$) δ: 12.71 (broad s, 1H), 9.24 (s. 1H), 8.57 (dd, J=5.1, 1.6 Hz, 1H), 8.43 (broad d, J=5.5 Hz, 1H), 8.31 (s, 1H), 7.61 (d, J=7.8 Hz, 1H), 7.52 (ddd, J=7.8, 4.7, 0.8 Hz, 1H), 7.47 (d, J=7.4 Hz, 1H), 7.34 (t, J=7.8 Hz, 1H). MS m/z 196.1 ($MH^+$).

Step 2 (Example 243): the crude benzimidazole from Step 1 was coupled to the chloropyridine A-13 (Ar=2-chlorophenyl) using copper/BINOL catalysis as described for Example 1 (step 4) in general method A.

Other compounds (e.g. Examples 251, 272, 273 and 342) were prepared in a similar fashion using the appropriate commercially available boronic acid in step 1 and chloropyridine intermediate A-13 (Ar=3-fluoro-2-methylphenyl or 2,3-dichlorophenyl).

General Method for the Synthesis of Inhibitors of Formula W-VI (Method G)—Synthesis of Example 437:

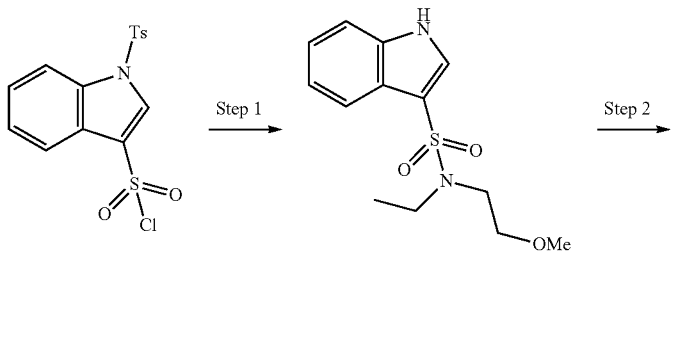

-continued

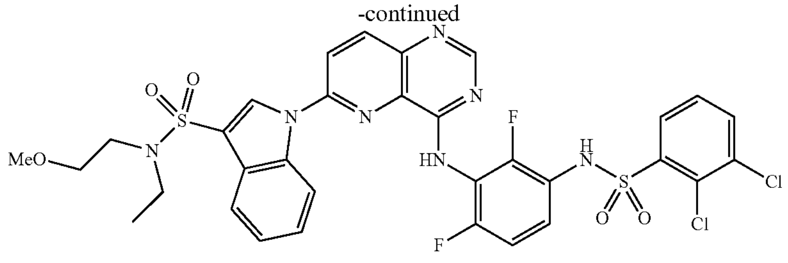

Example 437

Step 1: To a vial with a stirring bar was added the 1-(p-tolylsulfonyl)indole-3-sulfonyl chloride (117 mg, 0.316 mmol) (*Chemical and Pharmaceutical Bulletin* 2009, 57, 591) in anhydrous THF (1.5 mL). The solution was cooled to 0° C. and DIEA (0.11 mL, 0.633 mmol) was added dropwise. N-(2-methoxyethyl)ethylamine (0.039 mL, 0.316 mmol) was then added dropwise and the reaction mixture was gently warmed to room temperature. The reaction was stirred at room temperature for 1 h. After completion, 10% aqueous KOH was added dropwise (same volume as solvent). The reaction was heated at 60° C. overnight. After completion, the reaction mixture was diluted with EtOAc and aq. NH4Cl was added. The layers were separated. The organic layer was washed with brine then dried over $MgSO_4$, filtered and concentrated to dryness to afford the expected sulfonamide derivative (86 mg, 96%) as a light orange oil. MS m/z 283.2 ($MH^+$).

Step 2 (Example 437): indolesulfonamide from Step 1 was coupled to the chloropyridine A-13 (Ar=2,3-dichlorophenyl) using copper/BINOL catalysis as described for Example 1 (step 4) in general method A.

Other examples of inhibitors prepared in a similar fashion using the appropriate amine in step 1 are listed under method G in Table 4.

General Method for the Synthesis of Inhibitors of Formula W-VII (Method H)—Synthesis of Example 466:

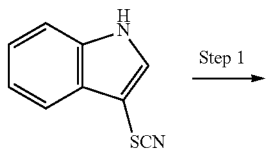

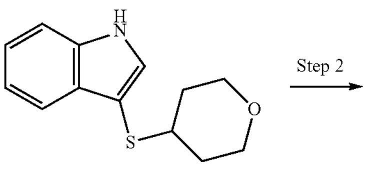

-continued

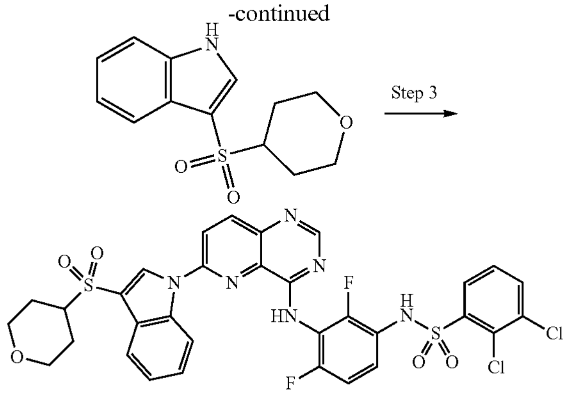

W-VII (Example 466)

Step 1: To a solution of 1H-indol-3-yl-thiocyanate (*Phosphorus, Sulfur and Silicon and the Related Elements* 2014, 189, 1378) (100 mg, 0.574 mmol) in iPrOH (5 mL) was added sodium sulfide nonahydrate (414 mg, 1.72 mmol) dissolved in water 0.5 mL, then the resulting mixture was stirred at 50° C. for 2 hrs. After this time, 4-chlorotetrahydropyran (0.19 mL, 1.72 mmol) was added and stirred at 50° C. overnight. The reaction mixture was diluted with EtOAc (30 mL) and separated. The organic layer was washed with water (15 mL) followed by brine (15 mL), dried over $MgSO_4$ and then concentrated under vacuum to give the crude sulfide, which was used in the next step directly without further purification.

Step 2: The sulfide from step 1 was dissolved in DCM and 3-chloroperoxybenzoic acid (297 mg, 1.72 mmol) was added and stirred at room temperature for 2 h. After completion, the reaction was quenched by adding 10 ml of a 1:1 solution sat·aq. $NaHCO_3$ and 10% aq. Na2SO3. The resulting suspension was stirred at room temperature for 15 min. EtOAc was added and the organic layer was separated. The organic layer was washed with water (15 mL) then saturated brine solution (15 mL). The organic layer was separated, dried ($MgSO_4$) and filtered before concentration to dryness to provide the expected sulfone (154 mg, 98%) which was dissolved in DMSO and use directly in the next step without further purification. MS m/z 266.2 ($MH^+$).

Step 3 (Example 466): indole from Step 2 was coupled to the chloropyridine A-13 (Ar=2,3-dichlorophenyl) using copper/BINOL catalysis as described for Example 1 (step 4) in general method A.

Other examples of inhibitors prepared in a similar fashion using the appropriate alkylating agent in step 1 are listed under method H in Table 4.

General Method for the Synthesis of Inhibitors of Formula W-VIII (Method I)—Synthesis of Examples 524 and 665:

Example 524 (Iron Metal as Reducing Agent for Step 2)

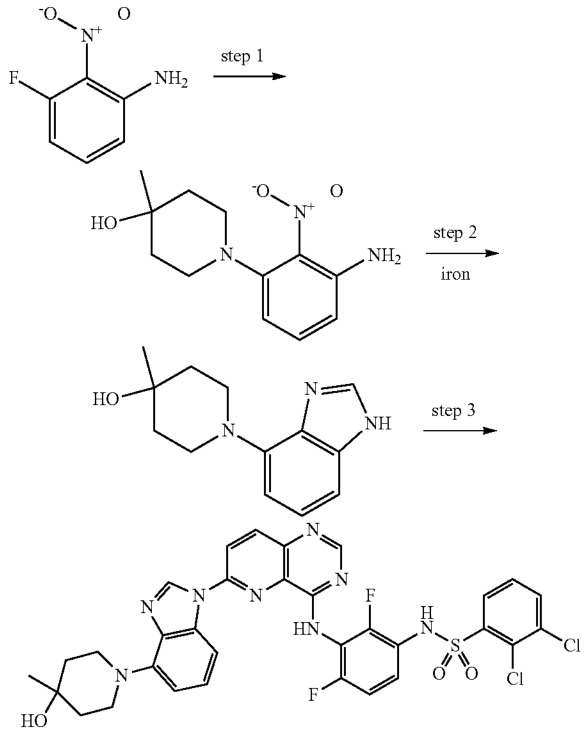

W-VIII (Example 524)

Step 1: 4-Methylpiperidin-4-ol (0.24 g, 1.84 mmol) and potassium carboniate (0.49 g, 3.52 mmol) were added to a solution of 3-fluoro-2-nitro-aniline (0.25 g, 1.60 mmol) in MeCN (2.6 mL). The resulting mixture was stirred at 85° C. for 10 h. MeCN was removed under reduce pressure and EtOAc was added. The suspension was centrifuged and poured into a flask. The solution was concentrated and the crude 1-(3-amino-2-nitro-phenyl)-4-methyl-piperidin-4-ol (0.40 g, 94% yield) was without further purification for the next step. MS m/z 252.2 ($MH^+$).

Step 2 (using iron as reducing agent): Iron (0.37 g, 6.70 mmol) and ammonium chloride (0.36 g, 6.70 mmol) were added to a mixture of 1-(3-amino-2-nitro-phenyl)-4-methyl-piperidin-4-ol 0.34 g, 1.34 mmol) in iPrOH (6.5 mL) and formic aicd (1.9 mL, 49.6 mmol). The result mixture was heated to 90° C. and stirred for 10 h. The reaction mixture was cooled down to room temperature and filtered through Celite®. The solution was concentrated and the crude was purified by column chromatography (silica gel, 0-15% MeOH in DCM) to afford 1-(1H-benzimidazol-4-yl)-4-methyl-piperidin-4-ol (0.17 g, 55% yield) as a reddish foamy solid. MS m/z 232.2 ($MH^+$). $^1$H NMR (400 MHz, DMSO-$d_6$) δ: 12.21 (br. s, 1H), 8.02 (s, 1H), 6.85-7.20 (m, 2H), 6.33-6.67 (m, 1H), 4.24 (s, 1H), 3.15-3.26 (m, 2H), 2.48 (td, J=1.66, 3.72 Hz, 2H), 1.41-1.74 (m, 4H), 1.16 (s, 3H).

Step 3 (Example 524): the benzimidazole from Step 2 was coupled to the chloropyridine A-13 (Ar=2,3-dichlorophenyl) using copper/BINOL catalysis as described for Example 1 (step 4) in general method A.

Example 665 (Zinc Metal as Reducing Agent for Step 2)

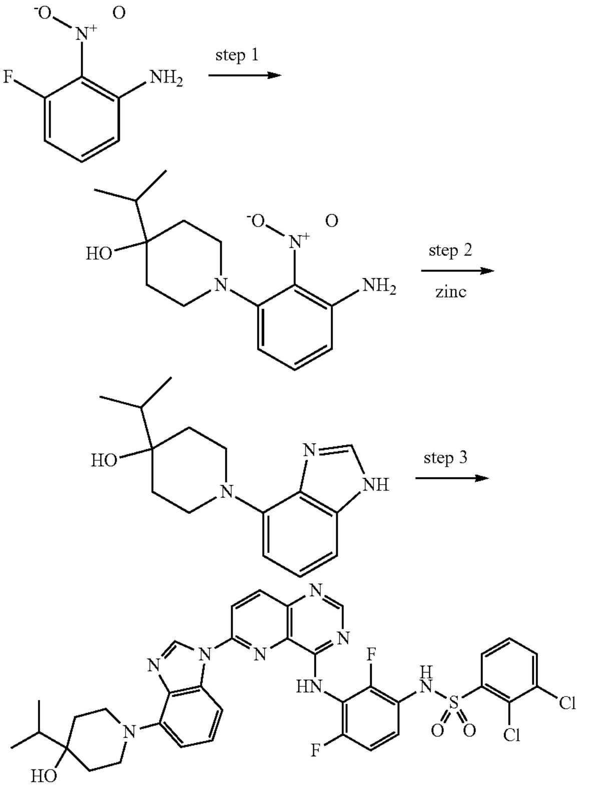

W-VIII (Example 665)

Step 1: Potassium carbonate (1.01 g, 7.33 mmol) and 4-isopropylpiperidin-4-ol (262 mg, 1.83 mmol) (WO2014/139144, 2014, A1) were added to a bright red solution of 3-fluoro-2-nitro-aniline (0.25 g, 1.60 mmol) in ACN (3 mL). The resulting mixture was stirred at 80° C. for 16 h. EtOAc was added and the suspension was centrifuged. The supernatant was separated and concentrated under vacuum to afford the desired nitroaniline (400 mg, 78% yield). MS m/z 280.2 ($MH^+$).

Step 2 (using zinc as reducing agent): To a solution of the nitroaniline from step 1 (280 mg, 1.25 mmol) in isopropyl alcohol (8 mL) was added zinc (820 mg, 12.5 mmol) and ammonium chloride (671 mg, 12.5 mmol). The suspension was stirred at 60° C. for 10 min then formic acid (1.9 mL, 50.2 mmol) was added. The result mixture was heated at 60° C. and stirred for 2 h. After completion, EtOAc was added and the suspension was centrifuged. The supernatant was separated and concentrated under vacuum. The residu was purified on silica gel with MeOH in DCM to afford the expected benzimidazole derivative (284 mg, 76% yield). $^1$H NMR (400 MHz, DMSO-$d_6$) δ: 9.16 (br. s., 1H), 7.22-7.45 (m, 2H), 7.05 (br. s., 1H), 3.76-4.35 (m, 2H), 3.01-3.30 (m, 2H), 1.83 (dt, J=3.94, 12.66 Hz, 2H), 1.46-1.71 (m, 3H), 0.92 (d, J=6.88 Hz, 6H). MS m/z 360.2 ($MH^+$). MS m/z 360.2 ($MH^+$).

Step 3 (Example 665, Table 4): the benzimidazole from Step 2 was coupled to the chloropyridine A-13 (Ar=2,3-dichlorophenyl) using copper/BINOL catalysis as described for Example 1 (step 4) in general method A.

Other examples of inhibitors prepared in a similar fashion using the appropriate amine in step 1 and either Fe or Zn as reducing agent in step 2 are listed under method I in Table 4.

General Method for the Synthesis of Inhibitors of Formula W-IX (Method J)—Synthesis of Example 600:

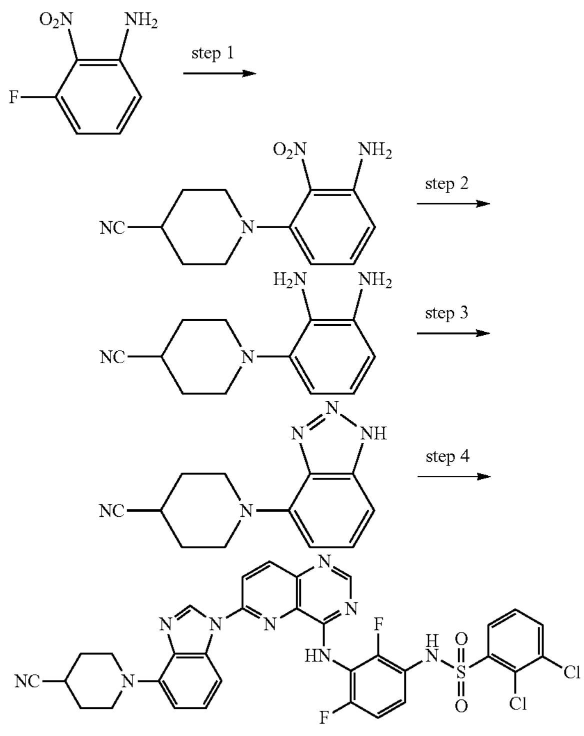

W-IX (Example 600)

Step 1: Piperidine-4-carbonitrile hydrochloride (0.103 g, 0.705 mmol) and potassium carbonate (177 mg, 1.28 mmol) were added to a bright red solution of 3-fluoro-2-nitro-aniline (100 mg, 0.641 mmol) in ACN (5 mL). The resulting mixture was stirred at 90° C. for 16 h. The reaction mixture was diluted with EtOAc (5 mL) and centrifuged. The supernatant containing the desired nitroaniline was separated and used as is in the next step. MS m/z 247.2 ($MH^+$).

Step 2: To the solution of nitroaniline from step 1 was added ammonium chloride (685 mg, 12.8 mmol) and zinc (419 mg, 6.41 mmol). The resulting suspension was stirred at 40° C. for 1 h. The reaction mixture was diluted with EtOAc (30 mL) then centrifuged. The supernatant was separated and concentrated under vacuum. The resulting 1,2-phenylenediamine (101 mg, 73%) was used as is in the next step. MS m/z 217.2 ($MH^+$).

Step 3: The product from step 2 was dissolved in AcOH (3 mL) then sodium nitrite (32 mg, 0.647 mmol) was added and stirred at room temperature for 1 h. The reaction mixture was diluted with EtOAc (60 mL), washed with water (2×20 mL) followed by sat. aq. $NaHCO_3$ (2×20 mL) then brine (20 mL). The separated organic layer was dried over $MgSO_4$, filtered and concentrated under vacuum to afford the desired benzotriazole (75 mg, 0.330 mmol, 51%). $^1H$ NMR (400 MHz, DMSO-$d_6$) δ: 7.30 (t, J=7.88 Hz, 1H), 7.20 (d, J=8.00 Hz, 1H), 6.63 (d, J=7.50 Hz, 1H), 3.85 (br. s., 2H), 3.45 (t, J=9.38 Hz, 2H), 3.15 (td, J=4.24, 8.41 Hz, 1H), 2.00-2.22 (m, 2H), 1.85-2.00 (m, 2H). MS m/z 228.2 ($MH^+$).

Step 4: A solution of the benzotriazole from step 3 (17 mg, 0.076 mmol), 2,3-dichloro-N-[3-[(6-chloropyrido[3,2-d]pyrimidin-4-yl)amino]-2,4-difluoro-phenyl]benzenesulfonamide (30 mg, 0.058 mmol), copper(II)sulfate pentahydrate (1.9 mg, 0.0077 mmol), trans-2-phenyl-1-cyclopropanecarboxylic acid (1.3 mg, 0.0077 mmol) and potassium carbonate (21 mg, 0.155 mmol) in DMSO (1.5 mL) were stirred at 100° C. for 3 h. Upon completion, the mixture was cooled down to room temperature, diluted with DMSO and purified by HPLC (MeOH+0.1% formic acid in water+0.1% formic acid) to afford example 600 (11 mg, 25%). $^1H$ NMR (400 MHz, DMSO-d6) δ: 9.45 (br. s., 1H), 8.76 (d, J=9.01 Hz, 1H), 8.45-8.63 (m, 2H), 8.31 (d, J=8.00 Hz, 1H), 7.73-8.02 (m, 2H), 7.41-7.70 (m, 2H), 7.25 (br. s., 1H), 7.13 (br. s., 1H), 6.87 (d, J=8.00 Hz, 1H), 4.01 (d, J=12.38 Hz, 2H), 3.60 (t, J=10.38 Hz, 2H), 3.20 (br. s., 2H), 2.11 (br. s., 2H), 1.96 (d, J=10.01 Hz, 2H). MS m/z 707.2 ($MH^+$).

Other examples of inhibitors prepared in a similar fashion using the appropriate amine in step 1 are listed under method J in Table 4.

General Method for the Synthesis of Inhibitors of Formula W-X (Method K)—Synthesis of Example 112:

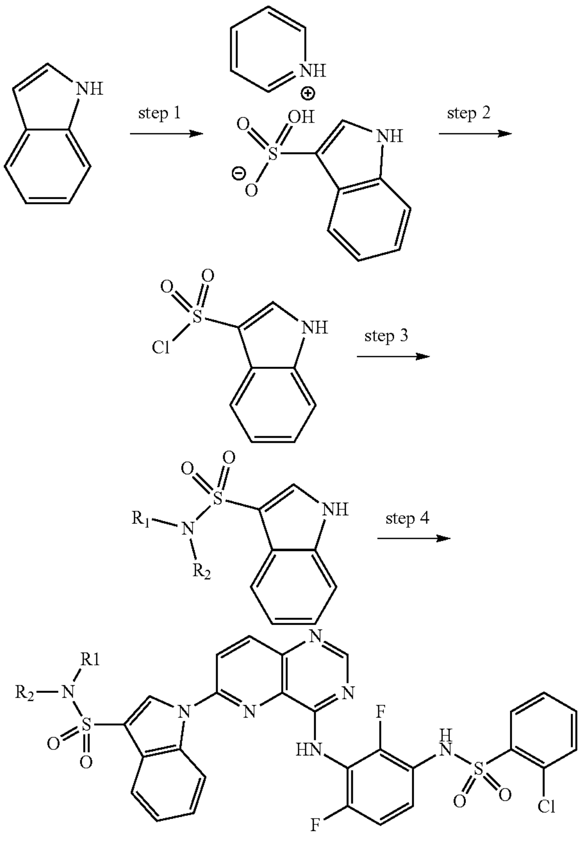

W-X ($R_1$ = $R_2$ = Me: Example 112)

Step 1: 3-indolesulfonyl chloride was prepared as described in Org. Lett. 2011, 13, 3588. A solution of indole (3 g, 25.6 mmol) and sulfur trioxide-pyridine (4.08 g, 25.6 mmol) in pyridine (15 mL) was heated to reflux (115° C.) under stirring for 2 h. After 2 h, the reaction was cooled down to room temperature and was diluted with water (20 mL). The aqueous layer was washed with diethyl ether (20 mL) twice. The aqueous layer was evaporated to dryness to give crude pyridinium 1H-indole-3-sulfonate (5.30 g, 75% yield) as a white solid. The crude material was used as such in the next step.

Step 2: The crude pyridinium 1H-indole-3-sulfonate from step 1 (4.60 g, 16.7 mmol) from the previous step was dissolved in a 1:1 mixture of sulfolane:acetonitrile (50 mL). The white suspension was cooled to 0° C., and $POCl_3$ (3.42 mL, 36.7 mmol) was added dropwise under stirring resulting a light brown solution. The reaction was heated to 70° C. for 1 h. After 1 h, the orange solution was cooled to 0° C. The cold orange solution was added dropwise to a 250 mL of iced water. During the addition, a white precipitate was formed. The solid was filtered, washed with water and dried under vacuum to afford 1H-indole-3-sulfonyl chloride (740 mg, 21% yield) as a grey solid.

Step 3 (general procedure): A solution of 1H-indole-3-sulfonyl chloride from step 2 (100 mg, 0.463 mmol) in anhydrous THF (3 mL) was cooled to 0° C. and amine (2 equiv.) was added dropwise. DIPEA (0.24 mL, 1.39 mmol) was then added and the reaction mixture was warmed to room temperature. The progression of the reaction was monitored by LCMS. When the reaction was completed, it was quenched with $NH_4Cl$ sat. to pH=7. The aqueous layer was extracted with EtOAc (3 times). The combined organic layers were washed with water, brine, dried over $MgSO_4$, filtered and concentrated to give desired sulfonamide.

Step 3 ($R_1$=$R_2$=Me, Example 112): the sulfonyl chloride (200 mg, 0.9 mmol) was charged into a 25 mL flask to which was added THF (4 mL) followed dimethylamine hydrochloride (2 equiv., 150 mg, 1.9 mmol) and DIEA (4 equiv., 0.65 mL, 3.7 mmol). The solution quickly became pale yellow and a yellow gummy oil deposited in the bottom. After 20 minutes of stirring at RT (LCMS showed complete consumption of the sulfonyl chloride). The mixture was partitioned between EtOAc and a saturated solution of $NH_4Cl$. The aqueous layer was extracted with EtOAc and the combined organic layers were washed once more with the saturated $NH_4Cl$ solution then with brine. It was then dried over $MgSO_4$, filtered and concentrated to dryness affording 65 mg of a beige crystallizing solid that was used as such without further purification: $^1H$ NMR (DMSO-$d_6$) δ: 12.17 (br. s., 1H), 7.96 (d, J=3.1 Hz, 1H), 7.81 (d, J=7.8 Hz, 1H), 7.49-7.57 (m, 1H), 7.22-7.28 (m, 1H), 7.16-7.22 (m, 1H), 2.58 (s, 6H). MS m/z 225.1 ($MH^+$).

Step 4 (Example 112, Table 4): prepared from indole sulfonamide from Step 3 and chloropyridine A-13 (Ar=2-chlorophenyl) using general method A.

Other examples of inhibitors prepared in a similar fashion using the appropriate amine in step 1 are listed under method K in Table 4.

Preparation of Example 69

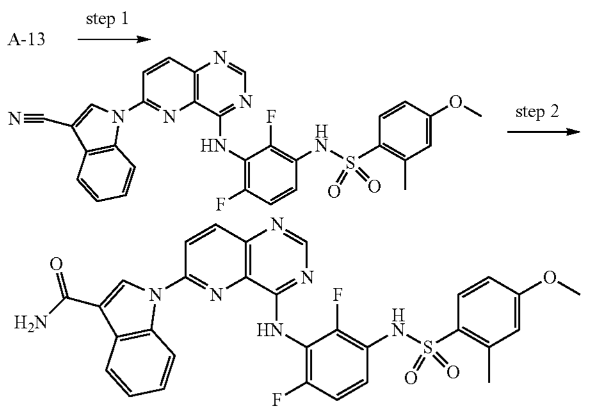

Example 69

Step 1: Following general Synthetic Method A, chloropyridine A-13 (Ar=4-methoxy-2-methylphenyl, was coupled to 3-cyanoindole in the presence of copper powder, BINOL and cesium carbonate at 100° C. in DMSO to provide the crude expected 3-cyanoindole derivative after an acidic aqueous workup and extraction into EtOAc. The material was used directly ion step 2 but an aliquot of the cyano derivative was purified by reversed-phase HPLC for characterization: $^1H$ NMR (DMSO-$d_6$) δ: 10.17 (br. s., 1H), 9.93 (s, 1H), 9.29 (s, 1H), 8.52 (s, 1H), 8.45-8.51 (m, 2H), 8.36 (d, J=8.2 Hz, 1H), 7.76-7.87 (m, 1H), 7.68 (d, J=9.0 Hz, 1H), 7.39-7.59 (m, 2H), 7.15-7.32 (m, 2H), 6.95 (d, J=2.7 Hz, 1H), 6.87 (dd, J=8.8, 2.5 Hz, 1H), 3.79 (s, 3H), 2.58 (s, 3H). MS m/z 598.1 ($MH^+$).

Step 2: the crude nitrile from Step 1 (35 mg, 1.0 equiv.) and ethanol (0.5 mL) were charged into a 4 mL vial followed by 102 μL of 4N NaOH (7 equiv.) affording a dark yellow solution. To this solution at room temperature was added ~30 μL (4 equiv.) of a 30% solution of hydrogen peroxide in water (some bubbling was observed). After 10 minutes of stirring at room temperature, LCMS showed complete consumption of the starting material and the formation of a new peak with the desired mass for the amide product. The reaction was quenched by the addition of a few crystals of sodium thiosulfate and 0.5 mL of acetic acid. It was then diluted to 2 mL with methanol, filtered and purified by prep-HPLC (MeOH/$H_2O$/0.1% formic acid conditions, 50%→100% methanol gradient). The appropriate fractions were combined and partially concentrated to remove methanol. The resulting suspension was dissolved by the addition of a few milliliters of acetonitrile then the solution was frozen and lyophilized. Obtained 7.4 mg of inhibitor of example 69 as a yellow solid.

Example 104 was prepared in a similar fashion using A-13 (Ar=2-chlorophenyl).

Preparation of Examples 70, 83 and 85

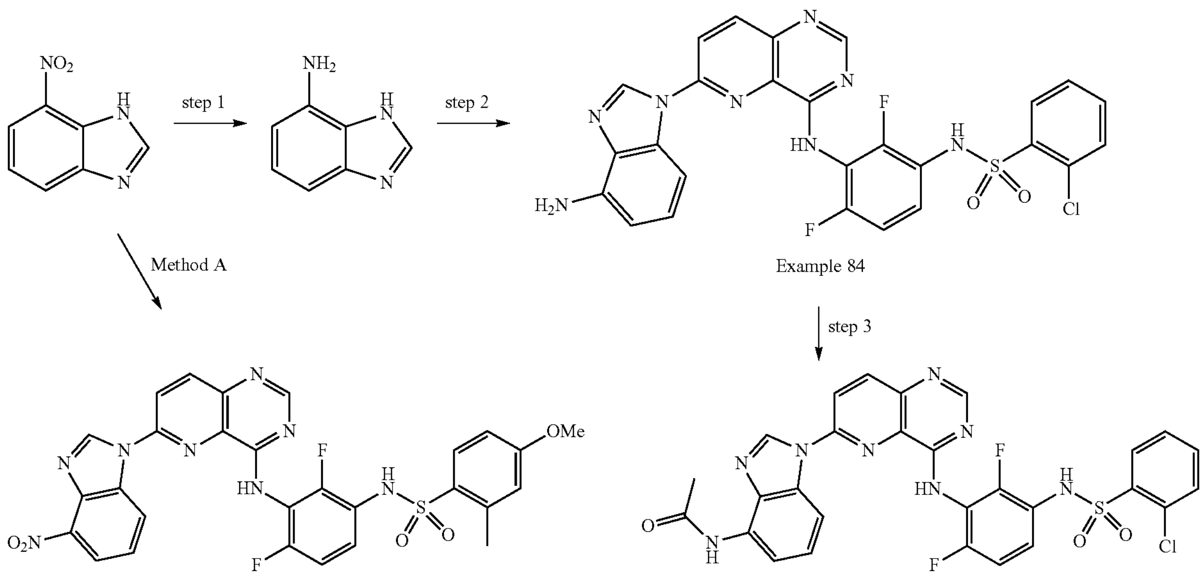

Example 84

Example 70

Example 85

Example 70: 7-Nitrobenzimidazole was prepared from 3-nitrophenylene-1,2-diamine as described in J. Chem. Phys. 2011, 115, 11403 and coupled to A-13 (Ar=4-methoxy-2-methylphenyl) using general Method A.

Step 1 (Example 83): 7-Nitrobenzimidazole (see Example 70, 250 mg) and 20% $Pd(OH)_2/C$ (Pearlman's catalyst, 10 mg, 0.01 equiv.) were suspended in MeOH (3 mL) and stirred under a balloon atmosphere of $H_2$ gas for 4 h (the SM slowly goes into solution as reduction proceeds).

After complete conversion as shown by LCMS, the suspension was filtered through a membrane using MeOH for washings and volatiles removed under reduced pressure. The material was used without further purification: $^1$H NMR (DMSO-$d_6$) δ: 7.99 (s, 1H), 6.87 (t, J=7.8 Hz, 1H), 6.73 (d, J=7.8 Hz, 1H), 6.35 (d, J=7.8 Hz, 1H).

Step 2 (Example 83): Using the aminobenzimidazole from Step 1, chloropyridine A-13 (Ar=2-chlorophenyl) and general Method A, the inhibitor of Example 83 was isolated after two successive reversed-HPLC purifications using 30→100% MeOH-0.1% formic acid followed by 10→100% MeCN-0.1% AcOH as gradients: $^1$H NMR (DMSO-$d_6$) δ: 10.53 (br. s., 1H), 9.87 (s, 1H), 9.17 (s, 1H), 8.49 (s, 1H), 8.44 (s, 2H), 7.92 (dd, J=8.0, 1.4 Hz, 1H), 7.61-7.72 (m, 2H), 7.47-7.56 (m, 1H), 7.41 (d, J=7.8 Hz, 1H), 7.28 (td, J=9.0, 5.5 Hz, 1H), 7.22 (t, J=9.0 Hz, 1H), 7.11 (t, J=8.0 Hz, 1H), 6.57 (d, J=7.4 Hz, 1H), 5.51 (br. s., 2H). MS m/z 579.1.

Other Examples prepared in a similar fashion using the aminobenzimidazole from Step 1 (Fragment A31) and the corresponding A-13 chloropyridines are listed in Tables 4 under Method A.

Step 3 (Example 85): The aminobenzimidazole from Step 2 (23 mg) was dissolved in acetic acid (1 mL) and acetic anhydride (13 mg, 3 equiv.) was added. Stir at RT for 3 h (LCMS shows complete conversion to desired mass). The material was diluted to 1.8 mL with DMSO and purified by prep-HPLC using a 30→100% MeOH-0.1% formic acid gradient.

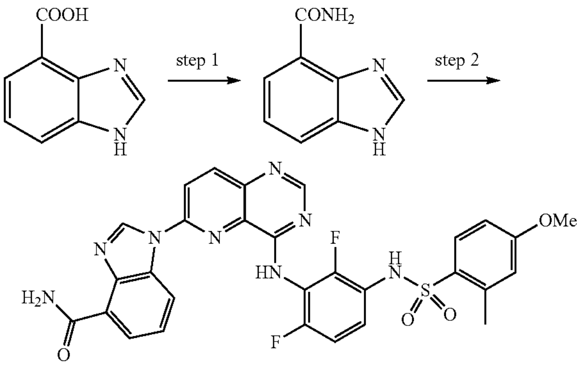

Example 75

Step 1: 7-Benzimidazolecarboxylic acid (500 mg, 3.1 mmol) was suspended in DCM (5 mL) and a drop of DMF was added followed by oxalyl chloride (0.5 mL, 5.9 mmol). The beige slurry was stirred 1 h at RT. Volatiles were then removed under reduced pressure, the residue was re-suspended in THF and volatiles removed once more. The residue was then suspended in THF (5 mL) and conc. aqueous ammonia (1 mL) was added and the mixture stirred for 30 min at RT (the beige suspension progressively turned into a brick-colored suspension. LCMS indicated a 1:1 mixture of starting acid and desired amide. The solids were removed by filtration and the filtrate evaporated to dryness under reduced pressure. The residue was used directly in the next step.

Step 2 (Example 75): the crude benzimidazole from Step 1 was coupled to the chloropyridine A-13 (Ar=4-methoxy-2-methylphenyl) using copper/BINOL catalysis as described for Example 1 (step 4) in general method A.

Preparation of Examples 80 and 81

The nitrile group of compound of Example 77 was hydrolyzed to the corresponding amide using the procedure described for Example 69. Example 81 was prepared in a similar fashion from Example 78.

Preparation of Example 94 and 95

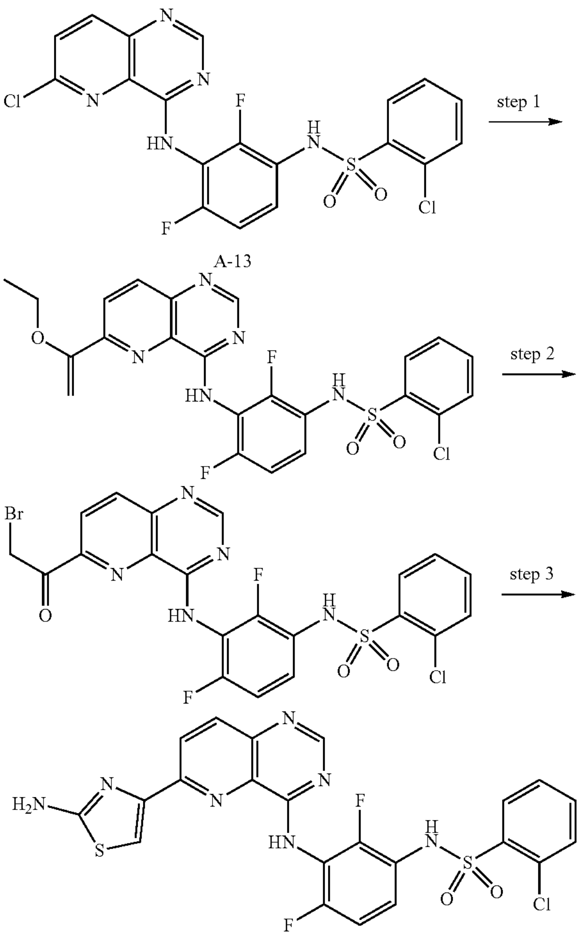

A-13

Example 94

Step 1: To a suspension of the starting chloropyridopyrimidine A-13 (Ar=2-chlorophenyl, 50 mg, 0.1 mmol) in acetonitrile (2 mL) in a 5 mL vial was added 1.1 equiv. of 1-ethoxyvinyl-tributyltin (42 mg, 0.11 mmol). Nitrogen was bubbled through the mixture for 5-7 minutes then bis (triphenylphosphine)palladium dichloride (0.1 equiv., 7 mg) was added. Nitrogen was bubbled through the suspension for another 4-5 minutes then the vial was sealed and the mixture was heated at 80° C. affording a pale yellow solution. It was stirred at that temperature for 18 h (LCMS indicated the conversion was complete). The mixture was allowed to cool to room temperature, filtered through a plug of Celite® to remove insoluble black particles using EtOAc for rinsing. The filtrate was concentrated to dryness under reduced pressure and the resulting pale yellow foam was used as such without further purification (108 mg): MS m/z 518.0 ($MH^+$).

Step 2: The crude enol ether from Step 1 (53 mg, 0.10 mmol) was dissolved in THF (1 mL) and water (0.1 mL) was added followed by 1.1 equiv. of N-bromosuccinimide (20 mg, 0.11 mmol) at room temperature. The resulting mixture was stirred for 1 h (LCMS shows complete conversion). The mixture was diluted with 3-4 mL of toluene and concentrated to an oily residue. It was then taken into 4-5 mL of DCM and dried over $Na_2SO_4$, filtered and concentrated. The residue was purified by flash chromatography through a 3 g silica gel cartridge using a 10% EtOAc in hexanes to 60% EtOAc in hexanes gradient. The appropriate fractions were combined and concentrated to afford the desired product as a pale yellow solid that was used as such in the next Step ($^1H$ NMR and LCMS show some contamination with succinimide): $^1H$ NMR (DMSO-$d_6$) δ: 10.38 (s, 1H), 8.58 (s, 1H), 8.35-8.42 (m, 2H), 7.91 (dd, J=7.8, 1.2 Hz, 1H), 7.59-7.73 (m, 4H), 7.47-7.59 (m, 2H), 7.20-7.35 (m, 2H), 5.43 (s, 1H). MS m/z 568 ($MH^+$).

Step 3: To a suspension the crude bromomethylketone from Step 2 (25 mg, 0.04 mmol) in ethanol (1 mL) was added thiourea (5 mg, 0.07 mmol, 1.5 equiv.). The resulting mixture was brought to 80° C. and stirred at that temperature for 2 h (LCMS shows complete conversion). The mixture was diluted to 2 mL with DMSO, filtered and purified by prep HPLC (MeOH/$H_2O$/0.1% formic acid conditions, 50%→100% methanol gradient). The appropriate fractions were combined and partially concentrated to remove methanol. The resulting suspension was dissolved by the addition of a few milliliters of acetonitrile then the solution was frozen and lyophilized. Obtained 5.5 mg of the desired product (Example 94) as a yellow solid.

Example 95 was prepared in a similar fashion, replacing thiourea in Step 3 by 3-carboxythioamide of 1,2,4-oxadiazole.

Preparation of Example 96 and 115

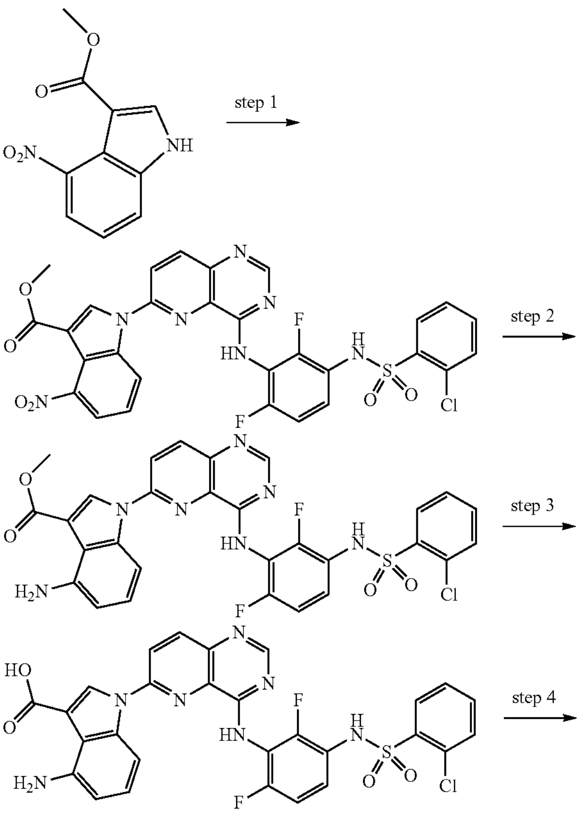

-continued

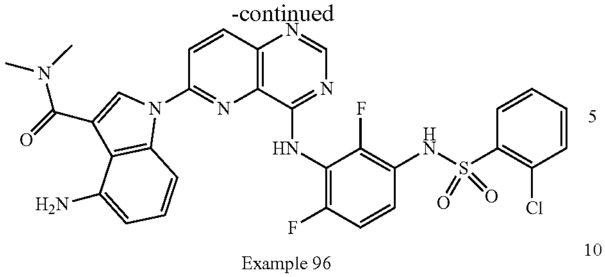

Example 96

Step 1: The methyl ester of 4-nitro-3-indole carboxylic acid was prepared by nitration of methyl 3-indolecarboxylate as described in WO 2008/113760 and *Bioorg. Med. Chem. Lett.* 2011, 21, 1782. The indole derivative was reacted with chloropyridine A-13 (Ar=2 chlorophenyl) under the standard conditions of general Method A.

Step 2: the crude methyl ester from Step 1 (33 mg, 0.05 mmol) was suspended in MeOH (1 mL) and 4N NaOH (75 μL, 6 equiv.) and LiOH (2 mg, 0.05 mmol) were added. The mixture was stirred at RT for 18 h and then at 50° C. for 2 h to complete conversion (LCMS). The reaction mixture was then acidified with 1N HCl and the precipitated product was collected by filtration, washed with water and dried under vacuum to give the desired carboxylic acid (30 mg): MS m/z 650.0 (M−H).

Step 3: the crude nitroindolecarboxylic acid from Step 2 (30 mg, 0.046 mmol) was dissolved in NMP (0.8 mL). To the yellow solution was added 8 equiv. of DIEA (64 μL) followed by 2 equiv. of HATU (35 mg). The mixture was stirred for 2-3 min. then dimethylamine hydrochloride (7.4 mg, 2 equiv.) was added. The resulting dark yellow solution was stirred for 3 h at room temperature at which point the reaction was found to be complete by LCMS. The reaction was quenched by the addition of a 1 N solution of HCl until an acidic pH was obtained. The mixture was diluted with 8 mL of water, sonicated and the resulting solids were collected by filtration through a small fritted glass funnel. They were then dried under reduced pressure overnight and the product was used as such for the subsequent nitro reduction (27 mg): MS m/z 679 ($MH^+$).

Step 4: To a suspension of the crude acid from Step 3 (27 mg, 0.040 mmol) in ethanol (1 mL) and EtOAc (0.5 mL) was added 4 equiv. of $SnCl_2$-$2H_2O$ (36 mg). The resulting mixture was brought to 60° C. and stirred for 2 h (complete by LCMS). The mixture was concentrated to remove EtOH then diluted with EtOAc (4 mL) and water (0.5 mL). ~1 mL of a 1N NaOH solution was added to the thick emulsion/suspension but did not clear up the mixture. The mixture was concentrated down to almost dryness then~0.5 g of sodium sulfate decahydrate was added to the flask along with some fresh EtOAc. The suspension was sonicated, decanted and the EtOAc extract filtered. This was repeated once more with EtOAc then once with DCM then once with a 1:1 mixture of both. The combined extracts were then dried over $Na_2SO_4$, filtered once more and concentrated. The residue was taken up in DMSO (1.5 mL) and purified by prep HPLC ($MeOH/H_2O$/0.1% formic acid conditions, 50%→100% methanol gradient). The appropriate fractions were combined and partially concentrated to remove methanol. The resulting suspension was dissolved by the addition of a few milliliters of acetonitrile then the solution was frozen and lyophilized (6.6 mg of Example 96 as a yellow solid).

Example 115 was prepared in a similar fashion by replacing dimethylamine hydrochloride in Step 4 by morpholine.

Preparation of Example 100

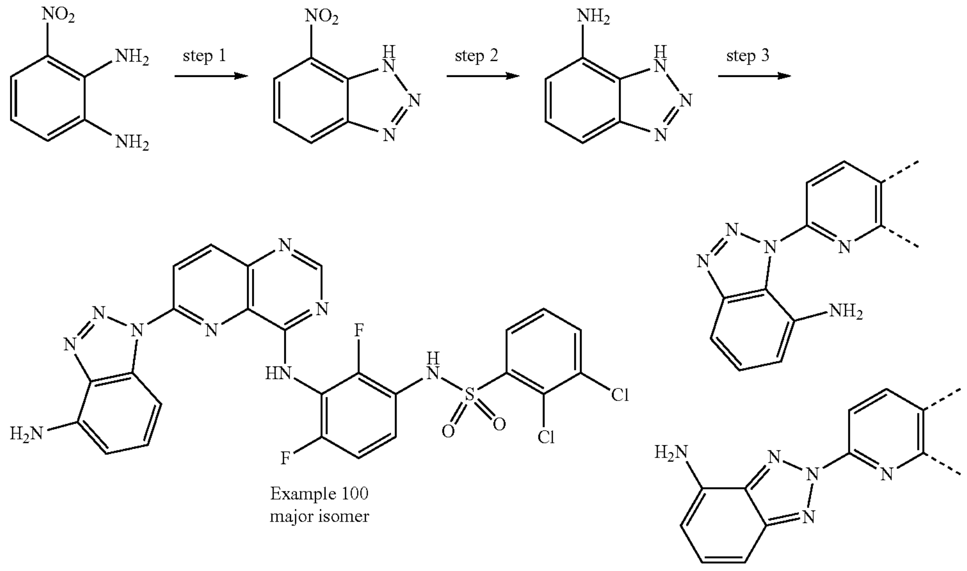

Example 100
major isomer minor isomers

Step 1: 7-Nitrobenzotriazole was prepared as an orange-pink solid from 3-nitro-1,2-phenylenediamine using the procedure described in WO 2010/069833: $^1H$ NMR (DMSO-$d_6$) δ: 8.58 (d, J=8.2 Hz, 1H), 8.46 (d, J=7.8 Hz, 1H), 7.63 (t, J=8.0 Hz, 1H).

Step 2: The nitrobenzotriazole from Step 1 was hydrogenolyzed over 20% $Pd(OH)_2$ on charcoal using a balloon atmosphere of hydrogen gas to provide the desired aminobenzotriazole as an orange solid that was used without purification: $^1$H NMR (DMSO-$d_6$) δ: 7.11 (t, J=7.8 Hz, 1H), 6.81 (d, J=8.2 Hz, 1H), 6.38 (d, J=7.8 Hz, 1H), 5.86 (br. s., 2H).

Step 3: Using the aminobenzotriazole from Step 2, chloropyridine A-13 (Ar=2,3-dichlorophenyl) and general Method A, the inhibitor of Example 100 was formed as a mixture of isomers that were separated by reversed-phase HPLC under the usual conditions. Example 100 was present as the most abundant isomer.

Other Examples prepared in a similar fashion and using the corresponding A-13 chloropyridines include Examples 91-93 and 206.

Preparation of Example 103

This compound was prepared following the procedure described for Example 69 using the corresponding 3-cyanoindazole instead of 3-cyanoindole and A-13 (Ar=2-chlorophenyl).

Preparation of Example 116

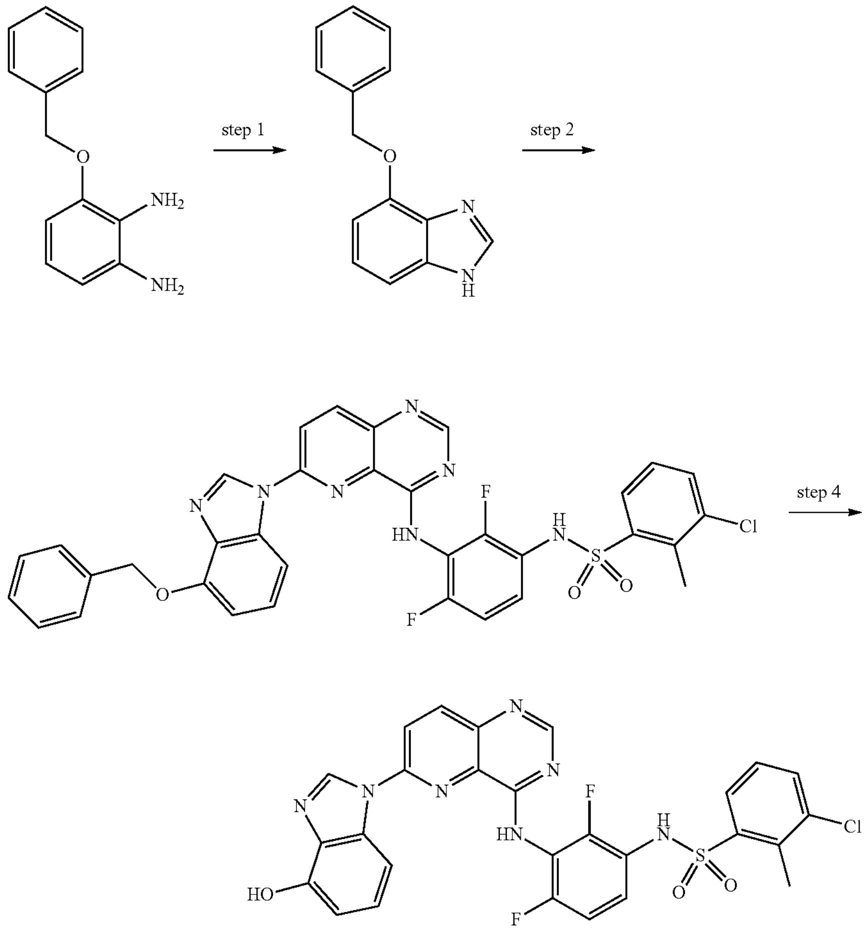

Example 116

Step 1: 3-Benzyloxy-1,2-phenylenediamine was prepared following the procedure described in WO1992/021663A1. The diamine (1.00 g, 4.67 mmol) was suspended in formic acid (10 mL) and the mixture stirred at 100° C. for 4 h (LCMS indicated complete conversion). The reaction mixture was cooled to RT and most of the formic acid removed under reduced pressure. The residue was added slowly to excess sat. aq. $NaHCO_3$ (caution: frothing). The free base initially came out as a dark beige gum but turned into a light beige precipitate after stirring. The product was collected by filtration, washed with water and dried under vacuum (0.96 g, 1:1 mixture of tautomers by $^1$H NMR): $^1$H NMR (DMSO-$d_6$) δ: 12.72 (br. s., 0.5H), 12.44 (br. s., 0.5H), 8.10 (s, 1H), 7.56 (d, J=7.0 Hz, 1H), 7.50 (d, J=7.4 Hz, 1H), 7.29-7.45 (m, 3H), 7.25 (d, J=7.8 Hz, 0.5H), 7.02-7.18 (m, 1.5H), 6.87 (d, J=7.8 Hz, 0.5H), 6.75 (d, J=7.0 Hz, 0.5H), 5.36 (s, 1H), 5.28 (s, 1H). MS m/z 225.1 (M $H^+$).

Step 2: The benzimidazole from Step 1 was coupled to chloropyridine A-13 (Ar=3-chloro-2-methyl) using the general procedure of Method A. After 1 h at 95° C., the reaction mixture was poured into water, acidified with AcOH and a small amount of 1 N HCl and extracted with EtOAc. The extract was washed with water and brine, dried ($MgSO_4$) and concentrated under reduced pressure. The residue and catalytic 20% $Pd(OH)_2$ on charcoal (5 mg) were suspended in THF (3 mL)+AcOH (1 mL) and stirred under a balloon of $H_2$ gas for 18 h (LCMS shows product, some remaining starting material and impurities). The reaction mixture was filtered to remove catalyst, concentrated and the residue dissolved in 1.8 mL DMSO and purified by prep-HPLC using 50-100% MeOH-0.1% HCOOH gradient. Example 116 (90% homogeneous) was obtained.

Preparation of Example 117

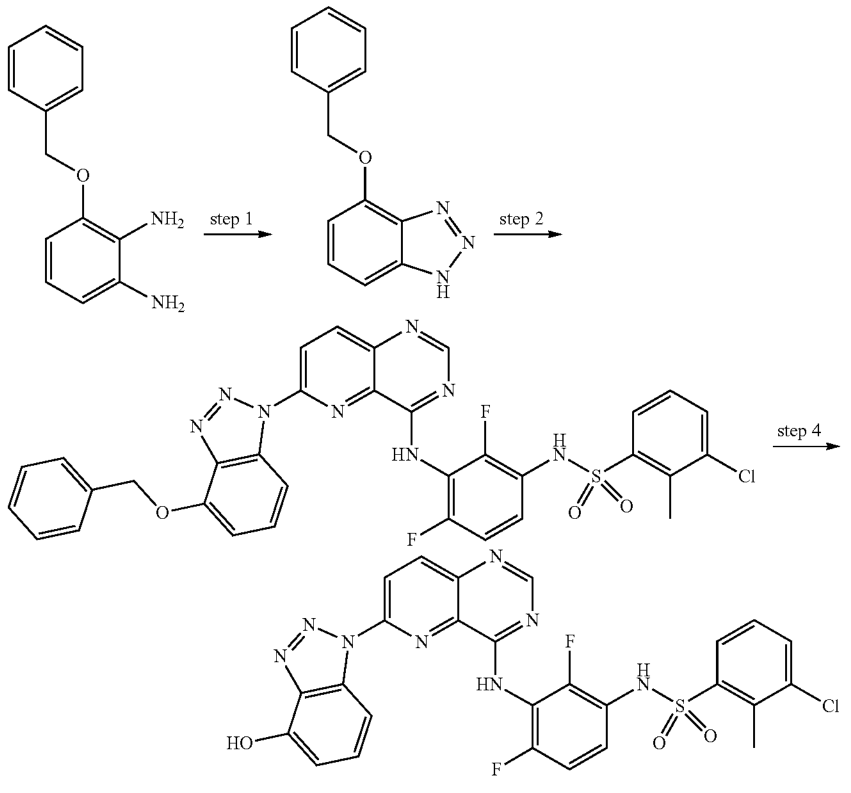

Example 117

Step 1: 3-Benzyloxy-1,2-phenylenediamine was prepared following the procedure described in WO1992/021663A1. The diamine (1.00 g, 4.67 mmol) was dissolved in AcOH (8 mL) and sodium nitrite (0.335 g, 4.9 mmol) was added in portions. A mildly exothermic reaction takes place with slight gas evolution. The mixture was stirred at RT for 15 min and then at 60° C. for 3.5 h (LCMS shows complete conversion). The reaction mixture was cooled to RT, diluted with an equal volume of water and stirred at RT for 1 h before collecting the beige precipitate. The product was wash with water and dried under vacuum (1.01 g): $^1H$ NMR ($CDCl_3$) δ: 7.43-7.57 (m, 3H), 7.28-7.43 (m, 4H), 6.84 (d, J=7.8 Hz, 1H), 5.36 (s, 2H). MS m/z 226.1 ($MH^+$).

Step 2: Following an identical procedure as described for Example 116, the benzotriazole from Step 1 (30 mg) was coupled to chloropyridine A-13 (Ar=3-chloro-2-methyl) using the general procedure of Method A and the product hydrogenolyzed to remove the benzyl ether protecting group to give Example 117 (15 mg).

Preparation of Example 120-122

The General Method D described for Example 127 was used, replacing methyl indazole-3-carboxylate by methyl 5-methyl-pyrazole-3-carboxylate in Step 1.

Preparation of Example 136-138

The General Method D described for Example 127 was used, replacing methyl indazole-3-carboxylate by ethyl 2-methyl-imidazole-4-carboxylate in Step 1.

Preparation of Example 145 and 146

The General Method D described for Example 127 was used, replacing methyl indazole-3-carboxylate by methyl pyrazole-3-carboxylate in Step 1.

Preparation of Example 147 and 148

The General Method D described for Example 127 was used, replacing methyl indazole-3-carboxylate by ethyl 3-methyl-pyrazole-4-carboxylate in Step 1. An 85:15 mixture of isomers was carried through to Step 2. Examples 147 and 148 were isolated as the major components.

Preparation of Example 149 and 150

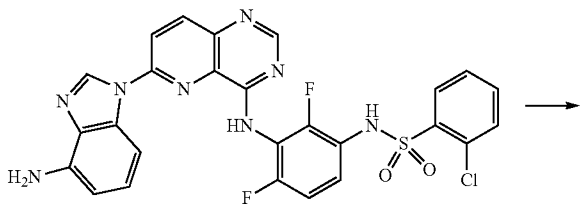

Example 83

-continued

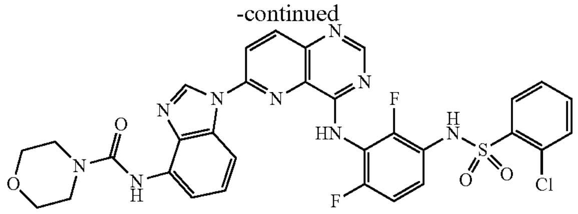

Example 149

The aminobenzimidazole (Example 83, 30 mg) was dissolved in pyridine (0.5 mL) and morpholinecarbamoyl chloride (31 mg, 4 equiv.) was added. The mixture was stirred at 60° C. for 2 h (complete conversion to desired mass by LCMS). The burgundy solution was concentrated under reduced pressure, the residue dissolved in 3:1 DMSO-AcOH (1.8 mL) and the material purified by prep-HPLC using 50→100% MeOH-0.1% HCOOH gradient.

Example 150 was prepared in a similar fashion but using N—N-dimethylcarbamoyl chloride instead of morpholinecarbamoyl chloride. The reaction was heated to 75° C. for 18 h to complete.

Preparation of Example 151 and 152

The General Method D described for Example 127 was used, replacing methyl indazole-3-carboxylate by methyl 1,2,4-triazole-3-carboxylate in Step 1.

Preparation of Example 153-155

The General Method D described for Example 127 was used, replacing methyl indazole-3-carboxylate by ethyl 4-methyl-pyrazole-3-carboxylate in Step 1.

Preparation of Example 207

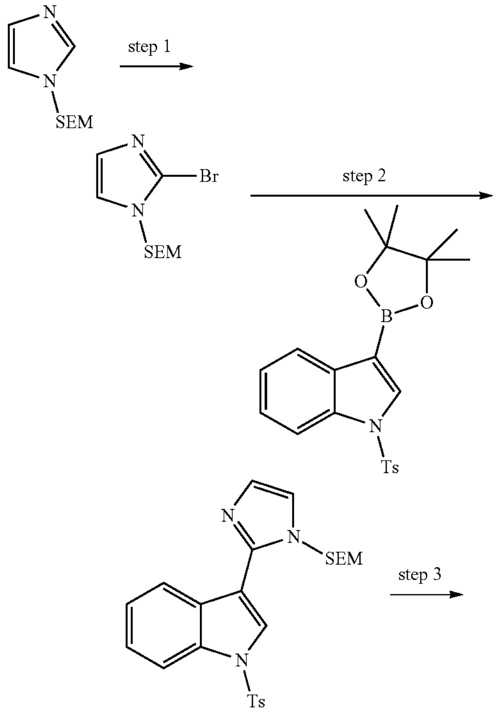

-continued

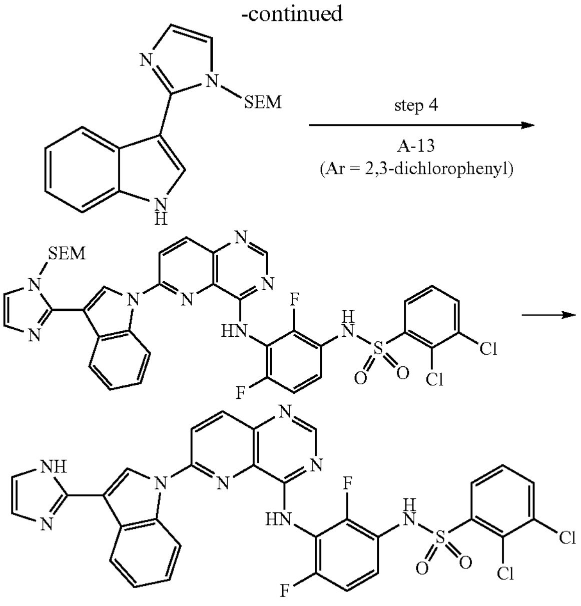

Example 207

Step 1: To a solution of 1-((2-(trimethylsilyl)ethoxy)methyl)-1H-imidazole, prepared following the procedure described in WO 2013/041457 (1.80 g, 9.1 mmol) in anhydrous THF (16 mL) at −78° C. was slowly added n-butyllithium (6.24 ml, 9.98 mmol of a 1.6M in hexanes). Once the addition was complete, the pale yellow solution was allowed to stir for 5 minutes before a solution of carbon tetrabromide (3.31 g, 9.98 mmol) in 8 mL of THF was added slowly at −78° C. The solution went darker yellow then very dark brown at the end of the addition. It was allowed to stir at the same temperature for 15 minutes then quenched with a saturated solution of ammonium chloride. After warming to room temperature, EtOAc was added and the dark brown to black biphasic mixture was treated with Celite® and filtered to facilitate the phase separation. The layers were separated and the aqueous layer was extracted twice more with EtOAc. The combined organic layers were washed once with brine then dried over $MgSO_4$ and filtered. After concentration, the residue was purified by flash column chromatography (combiflash, 40 g column, 0%→40% EtOAc in hexanes; product is slightly UV visible by TLC, used $KMnO_4$ stain to check fractions). Affords 1.944 g of the desired product as a pale yellow-brown oil: $^1$H NMR ($CDCl_3$) δ: 7.11 (d, J=1.2 Hz, 1H), 7.06 (d, J=1.2 Hz, 1H), 5.28 (s, 2H), 3.54 (t, J=7.8 Hz, 2H), 0.92 (t, J=8.2 Hz, 2H), 0.00 (s, 9H).

Step 2: The N-tosyl-3-indoleboronic ester (132 mg, 0.33 mmol), the SEM-protected bromo imidazole from Step 1 (111 mg, 0.4 mmol), potassium carbonate (184 mg, 1.33 mmol), DMF (3 mL) and water (1 mL) were charged in a microwave vial. Nitrogen was bubbled through the suspension for 3-4 min. Tetrakis(triphenylphosphine)palladium(0) (19 mg, 0.017 mmol) was added and nitrogen was bubbled through the mixture for another 3-4 min with sonication. The vial was then capped and irradiated in the microwave at 80° C. for 1 h. LCMS analysis at that point revealed the boronic ester had been consumed. The reaction mixture was allowed to cool to room temperature then diluted with water and extracted 3× with a 2:1 EtOAc/hexanes mixture. The combined organic layers were washed twice with water and once with brine. They were then dried over $MgSO_4$, filtered and concentrated. The residue was purified by flash chromatography (isco combiflash, 12 g silica gel column, 0%→35% EtOAc in hexanes gradient). After pooling and concentrating the appropriate fractions, 33 mg of the desired product were obtained (8 mg of a homocoupled bis-indole side-product were also obtained): $^1$H NMR ($CDCl_3$) δ: 8.20 (d, J=7.8 Hz, 1H), 8.09 (s, 1H), 8.03 (d, J=8.2 Hz, 1H), 7.79 (d, J=8.6 Hz, 2H), 7.38 (t, J=7.4 Hz, 1H), 7.32 (t, J=7.8 Hz, 1H), 7.20-7.26 (m, 3H), 7.14 (s, 1H), 5.32 (s, 2H), 3.64 (t, J=8.2 Hz, 2H), 2.35 (s, 3H), 1.01 (t, J=8.6 Hz, 2H), 0.04 (s, 9H). MS m/z 468.0 ($MH^+$).

Step 3: The product from Step 2 (32 mg) was dissolved in methanol (3 mL) and crushed potassium hydroxide (115 mg, 30 equiv.) was added. The resulting solution was refluxed for 4 h (LCMS showed complete consumption of the starting material). The reaction was quenched by the addition of a saturated ammonium chloride solution then water and EtOAc were added. The layers were separated and the aqueous layer was extracted once more with EtOAc. The combined organic extracts were washed once with water then once with brine, dried over $MgSO_4$, filtered and concentrated. After drying under reduced pressure the desired indole derivative was obtained as a beige solid (23 mg) that was used as such in the next step: MS m/z 324.0 ($MH^+$).

Step 4: Following general method A, chloropyridine A-13 (Ar=2,3-dichlorophenyl, 38 mg, 0.07 mmol) and the indole from Step 3 (23 mg, 0.07 mmol) were coupled by heating for 1.5 h at 100° C. under copper catalysis to provide the expected crude product (65 mg) that was used directly in the next step: $^1$H NMR (DMSO-$d_6$) δ: 10.72 (s, 1H), 9.81 (s, 1H), 8.89 (br. s., 1H), 8.49-8.62 (m, 2H), 8.37-8.49 (m, 2H), 7.98-8.07 (m, 1H), 7.95 (d, J=7.8 Hz, 1H), 7.90 (d, J=7.8 Hz, 1H), 7.79-7.88 (m, 1H), 7.54 (t, J=8.2 Hz, 1H), 7.50 (t, J=8.2 Hz, 1H), 7.44 (t, J=7.0 Hz, 1H), 7.27-7.34 (m, 1H), 7.23 (t, J=8.8 Hz, 1H), 5.68 (s, 2H), 3.55 (t, J=8.0 Hz, 2H), 0.83 (t, J=8.6 Hz, 2H), −0.15 (s, 9H). MS m/z 793.1 ($MH^+$).

Step 5: The crude SEM-protected material from Step 4 was suspended in 2 mL of ethanol then 1 mL of 6N HCl was added. The resulting suspension was brought to 80° C. at which temperature it was stirred for 4.5 h. The reaction was then concentrated down to a residue which was re-dissolved in 1.5 mL of DMSO, filtered and the filtrate was purified by prep-HPLC (MeOH/$H_2O$/0.1% formic acid conditions, 30%→100% methanol gradient). The fractions containing the desired product were all contaminated by a co-eluting impurity. The fractions were combined, concentrated and lyophilized. The powder was re-dissolved in DMSO/MeOH and purified a second time by prep-HPLC (MeOH/$H_2O$/0.05% TFA conditions, 30%→100% methanol gradient). The appropriate fractions were concentrated, frozen and lyophilized affording 16.3 mg of the desired product 207 as a TFA salt (yellow powder).

Preparation of Example 208

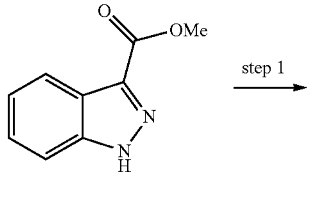

-continued

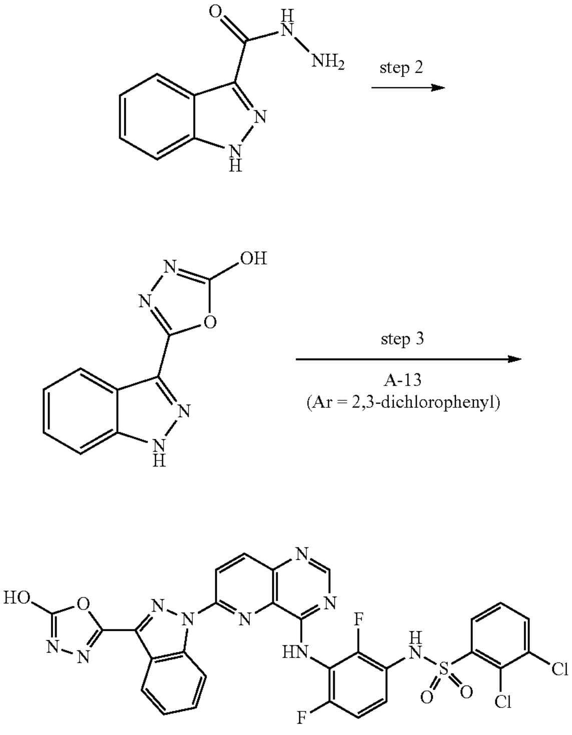

Example 208

Step 1: Methyl 1H-indazole-3-carboxylate (350 mg, 1.98 mmol) was charged in a pressure tube along with 5 mL of EtOH (anhydrous) and hydrazine hydrate (0.244 ml, 4.97 mmol). The tube was sealed and heated at 100° C. in an oil bath. After 4 h the reaction was complete by LCMS. The colorless solution was cooled in an ice water bath with stirring affording a significant amount of crystalline material. The white solids were collected by filtration and washed with a small amount of $Et_2O$. After drying, 255 mg of the hydrazide were obtained: $^1$H NMR (DMSO-$d_6$) δ: 12.98 (br. s., 1H), 9.55 (br. s., 1H), 8.14 (d, J=8.2 Hz, 1H), 7.60 (d, J=8.6 Hz, 1H), 7.40 (t, J=7.6 Hz, 1H), 7.23 (t, J=7.4 Hz, 1H), 4.46 (br. s., 2H). MS m/z 175.1 (M−H).

Step 2: To a solution of 1H-indazole-3-carbohydrazide from Step 1 (250 mg, 1.42 mmol) in 3 mL of DMF was added triethylamine (0.59 ml, 4.26 mmol). The colorless solution was cooled to 0° C. in an ice water bath then di(1H-imidazol-1-yl)methanone (345 mg, 2.13 mmol) was added in one portion. The solution immediately became yellow. It was removed from the ice bath and allowed to stir at room temperature overnight. By then, LCMS analysis of an aliquot revealed the reaction was complete. It was diluted with water then acidified with 1N HCl and allowed to stir for 10 minutes to destroy any remaining CDI. The white solids were then collected by filtration, dried under reduced pressure and use as such in the next step (300 mg): MS m/z 203.0 ($MH^+$). Step 3: Following general method A, chloropyridine A-13 (Ar=2,3-dichlorophenyl, 35 mg, 0.068 mmol) and the indole from Step 3 (25 mg, 0.075 mmol) were coupled by heating for 1.5 hours at 100° C. under copper catalysis to provide after reversed-phase HPLC purification (MeCN/$H_2O$, 0.1% acetic acid, 60%→100% MeCN gradient) inhibitor 208 as a beige powder (25 mg).

Preparation of Example 209

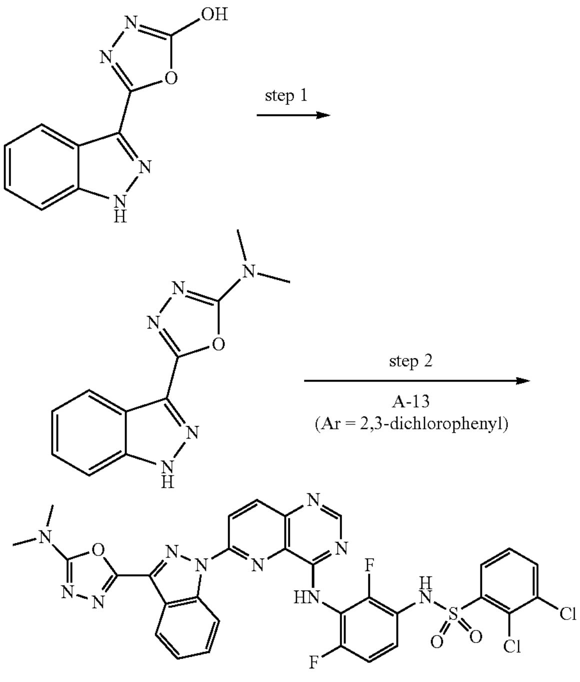

Example 209

Step 1: The crude product from Step 2 from the synthesis of Example 208 (80 mg, 0.4 mmol) was charged in a 4 mL vial followed by dimethylamine hydrochloride (64.5 mg, 0.79 mmol), DMF (2 mL) and DIEA (0.21 ml, 1.18 mmol). The yellow solution was stirred for 2 minutes then BOP reagent was added in one portion (193 mg, 0.44 mmol). The reaction was allowed to stir at room temperature for 60 h. It was then diluted with water and a saturated solution of ammonium chloride. The resulting suspension was sonicated and the solids were collected by filtration, washed with water and dried under reduced pressure to give 45 mg of the desired product as an off-white solid: $^1$H NMR (DMSO-$d_6$) δ: 13.75 (br. s., 1H), 8.12 (d, J=8.2 Hz, 1H), 7.66 (d, J=8.2 Hz, 1H), 7.48 (t, J=7.6 Hz, 1H), 7.31 (t, J=7.6 Hz, 1H), 3.12 (s, 6H). MS m/z 230.1 ($MH^+$).

Step 2: Following general method A, chloropyridine A-13 (Ar=2,3-dichlorophenyl, 35 mg, 0.068 mmol) and the indole from Step 3 (17 mg, 0.075 mmol) were coupled by heating for 1.5 hours at 100° C. under copper catalysis. The mixture was then allowed to cool to room temperature then quenched by the addition of 0.2 mL of acetic acid. Methanol (2 mL) was then added and the suspension was sonicated. The solids were collected and washed with a small amount of methanol then dried under reduced pressure. Example 209 was obtained as a beige powder (32 mg).

Example 210 was prepared in a similar fashion by substituting dimethylamine hydrochloride for methylamine hydrochloride in Step 1. Example 211 was prepared by substituting dimethylamine hydrochloride in Step 1 by 4-methoxybenzylamine. Following coupling to chloropyridine A-13 (Ar=2,3-dichlorophenyl), the PMB protecting group was removed by heating at 60-70° C. in DCM for 6 h.

Preparation of Example 212

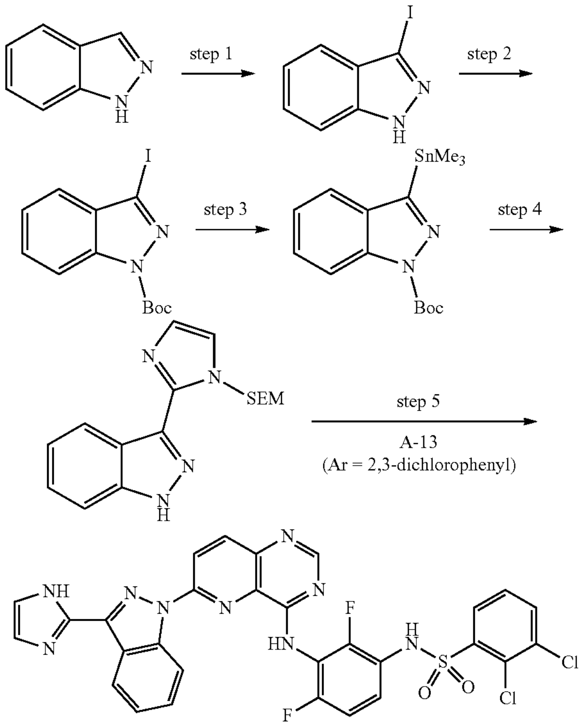

Example 212

Step 1: 3-Iodoindazole was prepared by iodination of indazole following the procedure described in WO 2011/138265.

Step 2/3: 3-Iodoindazole was protected as the N-Boc derivative and stannylated to the 3-trimethylstannane derivative following the procedure described in WO 2016/058544.

Step 4: the stannane derivative from Step 3 (270 mg, 0.71 mmol) was charged in a 4 mL vial followed by 2-bromo-1-((2-(trimethylsilyl)ethoxy)methyl)-1H-imidazole prepared in Step 1 of Example 207 (197 mg, 0.71 mmol), tetrakis triphenylphosphine palladium (0) (41 mg, 0.035 mmol) and 2 mL of toluene. The vial was degased with argon for 2 minutes then sealed and heated at 110° C. for 20 h. The black reaction mixture was poured into water, extracted with EtOAc, washed with brine and dried ($MgSO_4$). Concentration gave a mixture of N-Boc (42 mg) and NH-indazole (54 mg) products that were separable by flash chromatography. N-Boc product: $^1$H NMR ($CDCl_3$) δ: 8.64 (d, J=7.8 Hz, 1H), 8.17 (d, J=8.6 Hz, 1H), 7.58 (t, J=7.8 Hz, 1H), 7.42 (t, J=7.4 Hz, 1H), 7.31 (d, J=9.0 Hz, 2H), 6.07 (s, 2H), 3.63 (t, J=8.6 Hz, 2H), 1.75 (s, 9H), 0.93 (t, J=7.8 Hz, 2H), −0.09 (s, 9H). MS m/z 415.2 ($MH^+$). The N-Boc material was suspended in DCM and TFA (150 μL) was added. After stirring for 2 hours, the conversion to the deprotected indazole was judged to be complete by LCMS. Toluene (2 mL) was added and volatiles removed under reduced pressure to give the desired indazole that was used without further purification in the next step: MS m/z 315.2 ($MH^+$).

Step 5: The starting chloro-pyridopyrimidine A-13 (Ar=2, 3-dichlorophenyl, 58 mg, 1 equiv.) was coupled to the indazole from Step 4 (41 mg, 1.15 equiv.) using general Method A. After stirring at 100° C. for 3 h the reaction was complete by LCMS. The mixture was allowed to cool to room temperature then quenched by the addition of 0.15 mL of acetic acid. Water (5 mL) was then added and the suspension was sonicated. The solids were collected on a fritted glass filter and washed with water and hexanes (54 mg). The crude material was dissolved in TFA (0.5 mL) and stirred at room temperature for 3 hours at which point LCMS showed complete deprotection of the SEM group. The mixture was concentrated to a residue then taken up in 1 mL of DMSO and 0.5 mL of MeOH. It was filtered and the filtrate was purified by prep-HPLC (MeOH/$H_2O$, 0.05% TFA, 60%→100% MeOH gradient). The appropriate fractions were combined and concentrated to remove methanol. Some acetonitrile was added and the solution was frozen and lyophilized. Example 212 (21.5 mg) was obtained as a yellow solid.

Example 213 was prepared in a similar fashion using the corresponding A-13 (Ar=2-chlorophenyl).

Preparation of Example 223

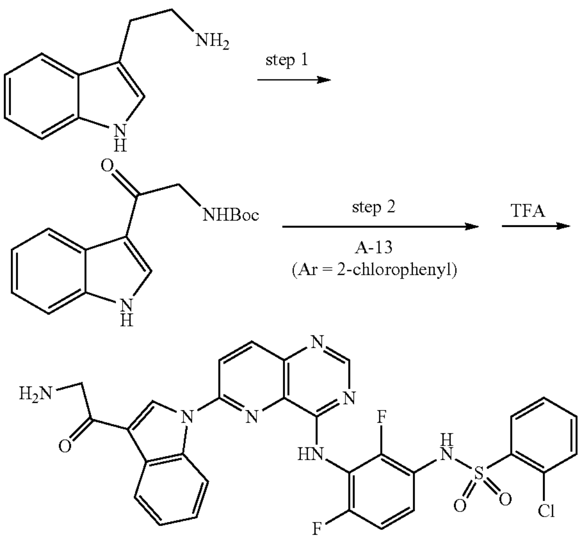

Example 223

Step 1: Tryptamine was protected as the Boc-carbamate and oxidized to the protected aminomethyl ketone as described in J. Am. Chem. Soc. 2004, 126, 12888.

Step 2: using general Method A the indole derivative from Step 1 was coupled to A-13 (Ar=2-chlorophenyl). The crude product was deprotected by stirring 30 minutes in 2:1 DCM-TFA. Example 223 (yellow solid) was isolated as a TFA salt after reversed phase HPLC purification (30%→100% MeOH-0.05% TFA).

Preparation of Example 224

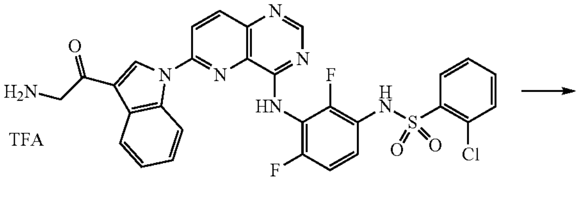

-continued

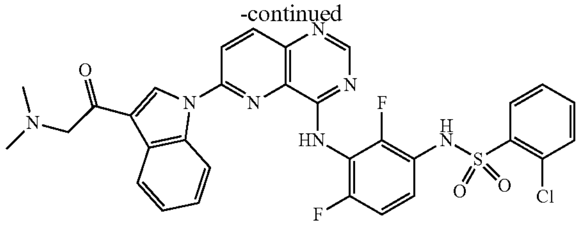

Example 224

To a suspension of crude aminomethyl ketone 223-TFA salt (50 mg, 0.068 mmol) in methanol (0.6 mL) at room temperature was added a 1N solution of sodium hydroxide (0.082 ml, 0.082 mmol). The suspension became a dark solution. A 37% wt solution of formaldehyde (55 mg, 0.681 mmol) was then added and the mixture was stirred at 40° C. for 5 minutes. Sodium cyanoborohydride (13 mg, 0.20 mmol) was added and the solution was stirred at 50° C. for 2 h (LCMS showed complete consumption of starting material and the formation of the desired product). The reaction was quenched by the addition of 0.2 mL of acetic acid and diluted to 2 mL with DMSO. The mixture was filtered through a syringe filter and purified by prep-HPLC (30%→100% MeOH-0.1% formic acid). The appropriate fractions were pooled and concentrated to remove methanol then frozen and lyophilized. Example 224 (3.3 mg) was obtained as a pale yellow solid.

Preparation of Example 237

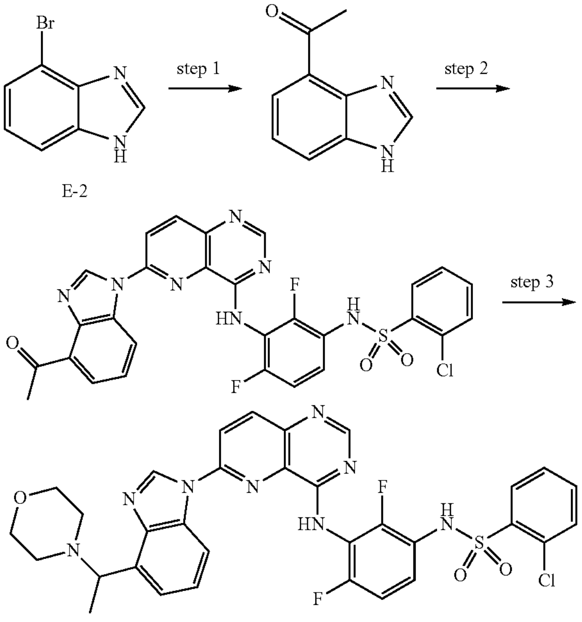

Example 237

Step 1: Bromobenzimidazole E-2 prepared as described under General Method E (Step 1) was converted to the acetyl derivative following a similar procedure as that described in Method E for the preparation of E-3 (Step 2), but replacing DMF by N,N-dimethylacetamide for the carbonylation step. The product was obtained as a brown solid (131 mg) that was used directly in the next step.

Step 2: The benzimidazole derivative from Step 1 (50 mg) was coupled at 100° C. for 3 hours to A-13 (Ar=2-chlorophenyl, 130 mg) using the General Method A. The expected crude intermediate was obtained as a brown solid (168 mg) that was used directly in the next step: $^{1}$H NMR (DMSO-$d_6$) δ: 10.53 (br. s., 1H), 9.84 (s, 1H), 9.45 (br. s., 1H), 8.66 (d, J=8.2 Hz, 1H), 8.47-8.59 (m, 3H), 7.92 (dd, J=7.8, 1.2 Hz, 1H), 7.86 (d, J=7.0 Hz, 1H), 7.61-7.71 (m, 2H), 7.55 (t, J=7.8 Hz, 1H), 7.47-7.53 (m, 1H), 7.28 (td, J=8.7, 5.7 Hz, 1H), 7.22 (t, J=9.2 Hz, 1H), 3.01 (s, 3H). MS m/z 605.8 ($MH^+$).

Step 3: morpholine (17 mg, 0.20 mmol) was charged in a 1 dram vial along with 1 mL of methanol. The crude acetylbenzimidazole from Step 2 (40 mg, 0.066 mmol) was then charged and the mixture was heated at 50° C. for 10 minutes. Sodium cyanoborohydride (12.5 mg, 0.2 mmol) was added and the reaction mixture was stirred at 50° C. for 20 h (LCMS shows ~ 50% conversion). Another portion of morpholine (17 mg, 0.2 mmol) and sodium cyanoborohydride (12.5 mg, 0.2 mmol) were added and the mixture was allowed to stir at 70° C. for another 7 h. After ~70% conversion (LCMS) the reaction was quenched by the addition of an acetic acid solution (0.2 mL) in 0.5 mL of DMSO. The solution was filtered and purified by prep-HPLC (30%→100% MeOH-0.1% formic acid). The appropriate fractions were pooled and concentrated to remove methanol then frozen and lyophilized. Example 237 (10 mg) was obtained as a pale yellow solid.

Example 238 was obtained in a similar fashion replacing morpholine by dimethylamine hydrochloride and adding an equivalent amount of 4N NaOH to neutralize the hydrochloride salt.

Preparation of Examples 239 and 652 (Table 5)

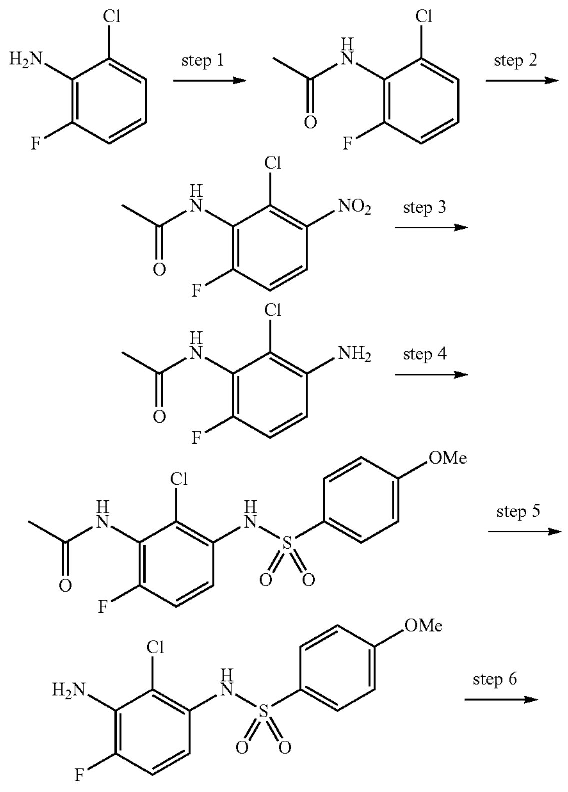

-continued

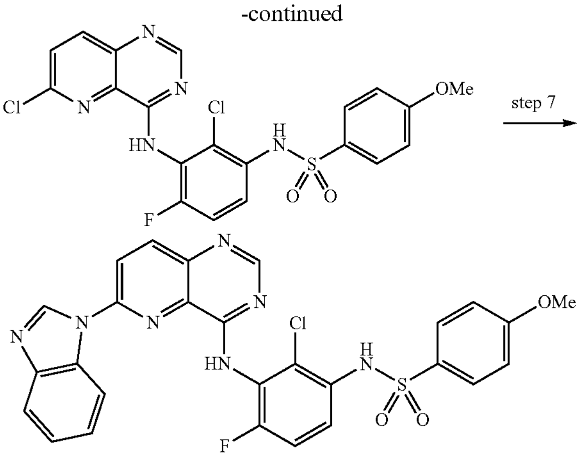

Example 239

Step 1: 2-chloro-6-fluoroaniline (10 g) were charged in a 250 mL flask and dissolved in 40 mL of glacial acetic acid. Acetic anhydride (7.47 mL) were added at room temperature and the resulting mixture was stirred at 90° C. for 1 h at which point LCMS analysis revealed the reaction was complete. Volatiles were removed under reduced pressure, the residue was dissolved in DCM and slowly neutralized with a saturated solution of $NaHCO_3$. The layers were separated and the aqueous layer was extracted 3× with DCM. The combined organic layers were washed once with water then dried over $MgSO_4$, filtered and concentrated. After vacuum drying, the desired product was obtained as white to pale pink crystals (12.79 g): $^{1}$H NMR ($CDCl_3$) δ: 7.16-7.26 (m, 2H), 7.03-7.13 (m, 1H), 6.93 (br. s., 1H), 2.23 (br. s., 3H). MS m/z 188.1 ($MH^+$).

Step 2: The acetanilide from step 1 (12.75 g) was taken up in 25 mL of conc. sulfuric acid and cooled to 0° C. in an ice bath. Nitric acid (90%, 3.31 mL) was slowly added. After 5-10 minutes the mixture became a solid mass. It was allowed to warm to room temperature which produced a thick burgundy sludge. After a total of 4 h, the reaction was monitored by LCMS which revealed some remaining starting material. Another 5 mL of sulfuric acid was added to improve fluidity followed by 0.3 mL of 90% nitric acid. The mixture was allowed to stir at room temperature for another 18 hours. The mixture was then cooled to 0° C. and poured on crushed ice (~150 mL). Once the ice had melted, the suspension was sonicated and the yellow solids were collected by filtration, washed with water and dried (15.1 g of crude product). The crude solid was taken into 50 mL of acetonitrile and brought to reflux affording a clear dark red solution. The heating was stopped and the mixture was allowed to cool to room temperature over 1 hour then stirred at room temperature for 2 h. By that time the mixture had become a solid mass which was broken up with a spatula and sonicated. The solids were then collected by filtration and washed with a small amount of cold acetonitrile. The desired off-white nitro compound (6.63 g) was obtained as a single regioisomer as shown by NMR (mother liquors yielded a second crop of 2.16 g that contained 7% of 6-chloro-2-fluoro-3-nitroacetanilide): $^{1}$H NMR ($CDCl_3$) δ: 7.90 (dd, J=9.2, 4.9 Hz, 1H), 7.24 (dd, J=9.2, 8.4 Hz, 1H), 6.98 (br. s., 1H), 2.28 (s, 3H). MS m/z 233.0 ($MH^+$).

Step 3: To a solution of the nitroacetanilide from Step 2 (500 mg, 2.15 mmol) in 15 mL of ethanol was added a solution $NH_4Cl$ (60 mg, 1.12 mmol) in 1.35 mL of water.

The mixture was warmed to 70° C. then iron powder (600 mg, 10.75 mmol) was added in three portions, 10 minutes apart. The resulting dark red to burgundy mixture was stirred at 70° C. for 20 h. LCMS of a filtered aliquot of the reaction mixture at that point revealed the reaction was complete. The mixture was filtered through a pad of Celite®. The dark brown filtrate was concentrated to dryness then taken into EtOAc to which was added $MgSO_4$. The suspension was stirred then filtered affording a clear pale yellow solution. The solution was concentrated to dryness to afford the desired product (440 mg) as a pale yellow solid that was used as such without further purification: $^1H$ NMR ($CDCl_3$) δ: 6.92 (t, J=9.0 Hz, 1H), 6.76 (br. s., 1H), 6.68 (dd, J=8.6, 4.7 Hz, 1H), 3.98 (br. s., 2H), 2.24 (br. s., 3H). MS m/z 203.1 ($MH^+$).

Step 4: The aniline from Step 3 was sulfonylated using 4-methoxybenzenesulfonyl chloride in the usual manner as described for A-9 in General Method A: $^1H$ NMR (DMSO-$d_6$) δ: 9.89 (s, 1H), 9.67 (s, 1H), 7.57-7.74 (m, 2H), 7.23 (t, J=9.2 Hz, 1H), 7.13 (dd, J=8.8, 5.3 Hz, 1H), 7.02-7.10 (m, 2H), 3.82 (s, 3H), 2.00 (s, 3H). MS m/z 373.0 ($MH^+$).

Step 5: the acetanilide from Step 4 (200 mg, 0.54 mmol) was taken into 1.5 mL of ethanol then a 1:1 mixture of concentrated HCl and water (2 mL) was added slowly. The yellow slurry was then brought to 80° C. and stirred for 1 hour. At that point, 1 mL of ethanol was added to improve the solubility. The mixture was allowed to stir at the same temperature for another 5 h (the mixture had become a clear yellow solution by then). LCMS analysis at that point showed <3% of remaining starting material. The mixture was concentrated to remove the majority of the ethanol then cooled on ice. It was basified with 4N NaOH to pH 5-6. The resulting suspension was sonicated and the solids were collected by filtration and washed with water. After drying under reduced pressure, 156 mg of the desired product were obtained as a beige solid: $^1H$ NMR (DMSO-$d_6$) δ: 9.53 (s, 1H), 7.53-7.72 (m, 2H), 7.00-7.14 (m, 2H), 6.95 (dd, J=10.8, 8.8 Hz, 1H), 6.36 (dd, J=8.6, 5.1 Hz, 1H), 5.39 (s, 2H), 3.81 (s, 3H). MS m/z 329.0 (M−H).

Step 6: The aniline from Step 5 (75 mg, 0.23 mmol) was coupled to dichloropyridopyrimidine A-12 (125 mg, 0.63 mmol) in AcOH at 50° C. as described for the preparation of A-13 in General Method A. The expected product (125 mg) was obtained as a beige solid: $^1H$ NMR (DMSO-$d_6$) δ: 10.18 (s, 1H), 9.95 (s, 1H), 8.50 (s, 1H), 8.27 (d, J=8.6 Hz, 1H), 7.99 (d, J=9.0 Hz, 1H), 7.65-7.69 (m, 2H), 7.33 (t, J=9.0 Hz, 1H), 7.26 (dd, J=9.0, 5.5 Hz, 1H), 7.04-7.12 (m, 2H), 3.81 (s, 3H). MS m/z 496.0 ($MH^+$).

Step 7 (Example 239 Table 5): benzimidazole was coupled to the chloropyridine from Step 6 using copper/BINOL catalysis as described for Example 1 (step 4) in general method A.

Example 652 (Table 5) was prepared in an analogous fashion using 2,3-dichlorophenylsulfonyl chloride in step 4 and fragment A31 for step 7.

Preparation of Examples 240, 646 and 647 (Table 5)

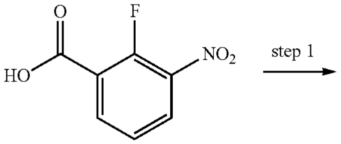

-continued

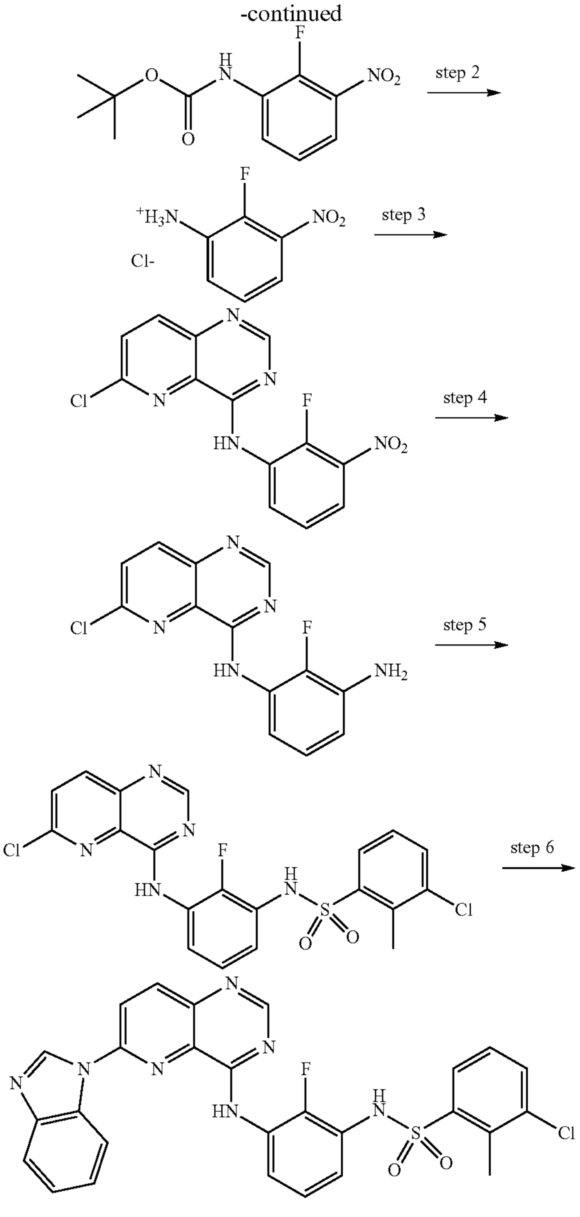

Example 240

Step 1: 2-Fluoro-3-nitrobenzoic acid (1.50 g, 8.1 mmol) was dissolved in DCM (7 mL) and 2 drops of DMF was added followed by portion-wise addition of oxalyl chloride (1.23 mL). The mixture was stirred ON at RT after which volatiles were removed under reduced pressure and the acid chloride residue dried under vacuum for ½ h. The white solid was dissolved in DCM (5 mL) and DMF (3 mL) was added followed by $NaN_3$ (0.58 g, 1.1 equiv.). Stir at RT for 35 min. tert-BuOH (0.86 mL) was then added and the mixture immersed in an oil bath preheated to 65° C. The mixture was refluxed for 4 h ($N_2$ evolution). Cool back to RT, remove DCM under reduced pressure, pour into water (100 mL) and extract product into EtOAc. Wash extract with $NaHCO_3$, water and brine and dry ($MgSO_4$). Concentration under reduced pressure gave a light yellow crystalline solid that was dried under vacuum: $^1H$ NMR ($CDCl_3$) δ: 8.46 (t, J=7.2 Hz, 1H), 7.59-7.73 (m, 1H), 7.24 (td, J=8.6, 1.0 Hz, 1H), 6.87 (br. s., 1H), 1.55 (s, 9H). MS m/z 155.1 (M−H-Boc).

Step 2: The nitroarene from Step 1 (0.74 g) and 4N HCl in dioxane (5 mL) were stirred at RT for 18 h (a precipitate gradually formed over the first 30 min). LCMS shows complete conversion.

Dilute with diethyl ether (30 mL), collect precipitate, wash with ether and dry the white solid in air (0.45 g): $^1$H NMR (DMSO-$d_6$) δ: 7.14-7.20 (m, 1H), 7.04-7.14 (m, 2H).

Step 3: the aniline hydrochloride from Step 2 (143 mg, 0.74 mmol) and dichloropyridopyrimidine A-12 (178 mg, 0.89 mmol) were suspended in AcOH (3 mL) and the mixture stirred at 55° C. until complete consumption of the aniline by LCMS (additional portions of A-13 were added as needed to complete the conversion). The reaction mixture was filtered to remove insoluble hydroxypyrimidine contaminant (use AcOH for washings) and the orange filtrate was diluted with water to precipitate the product as a light orange solid. The material was collected by filtration, washed with water and dried (198 mg): $^1$H NMR (DMSO-$d_6$) δ: 10.35 (s, 1H), 8.65 (s, 1H), 8.32 (d, J=8.6 Hz, 1H), 8.14 (t, J=6.8 Hz, 1H), 8.06 (t, J=7.8 Hz, 1H), 8.02 (d, J=8.6 Hz, 1H), 7.51 (t, J=8.2 Hz, 1H). MS m/z 320.0 ($MH^+$).

Step 4: The nitroarene from Step 3 (198 mg, 0.62 mmol) and tin(II)chloride dehydrate (630 mg, 2.8 mmol) were suspended in EtOH (7 mL) and the mixture stirred at 65° C. for 2 h (LCMS shows completion). The reaction mixture was poured into 1 N NaOH and extracted with EtOAc. The extract was washed with water, dried ($MgSO_4$) and concentrated to give the aniline as an orange solid (176 mg): $^1$H NMR (DMSO-$d_6$) δ: 9.74 (s, 1H), 8.60 (s, 1H), 8.27 (d, J=8.6 Hz, 1H), 7.98 (d, J=9.0 Hz, 1H), 6.99-7.12 (m, 1H), 6.90 (t, J=8.0 Hz, 1H), 6.66 (td, J=8.2, 1.6 Hz, 1H), 5.22 (s, 21H). MS m/z 290.1 ($MH^+$).

Step 5: The aniline from Step 4 (176 mg, 0.6 mmol) was dissolved in THF (4 mL) and pyridine (0.2 mL, 2.4 mmol) was added followed by 3-chloro-2-methylbenzenesulfonyl chloride (150 mg, 0.67 mmol). The mixture was stirred at RT for 18 h (LCMS shows aniline remaining). Add another 25 mg of the sulfonyl chloride and continue stirring at 55° C. for another 7 h (LCMS shows completion). The beige slurry was cooled to RT, made acidic with AcOH (0.25 mL), diluted with 1:1 EtOAc-ether and the solid collected by filtration, washed with ether and dried (210 mg): $^1$H NMR (DMSO-$d_6$) δ: 10.61 (br. s., 1H), 8.86 (d, J=4.7 Hz, 1H), 8.58 (s, 1H), 8.29 (d, J=9.0 Hz, 1H), 8.21 (d, J=6.3 Hz, 1H), 8.00 (d, J=8.6 Hz, 1H), 7.93 (t, J=6.5 Hz, 1H), 7.81 (d, J=7.8 Hz, 1H), 7.74 (d, J=7.8 Hz, 1H), 7.52 (br. s., 1H), 7.38 (t, J=8.2 Hz, 1H), 7.17 (d, J=5.1 Hz, 2H), 6.98 (d, J=6.7 Hz, 1H), 2.66 (s, 3H). MS m/z 480.0 ($MH^+$).

Step 6 (Example 240, Table 5): benzimidazole was coupled to the chloropyridine from Step 5 using copper/BINOL catalysis as described for Example 1 (step 4) in general method A.

Example 646 (Table 5) was prepared in an analogous fashion using 2,3-dichlorophenylsulfonyl chloride in step 5.

Example 647 (Table 5) was prepared in an analogous fashion using 2,3-dichlorophenylsulfonyl chloride in step 4 and fragment A31 for step 6.

Preparation of Example 241 (Table 5)

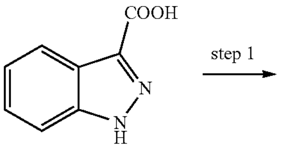

-continued

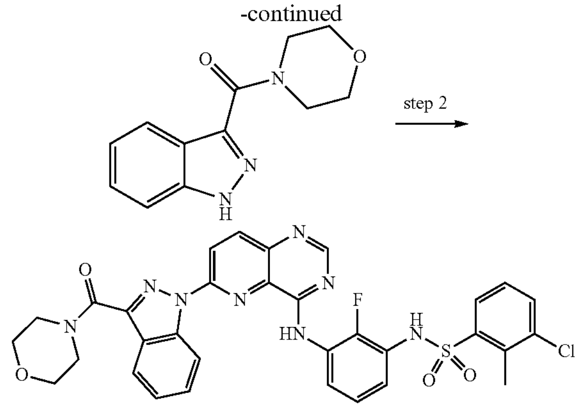

Example 241

Step 1: 3-indazolecarboxylic acid (250 mg, 1.5 mmol) was suspended in DCM (3 mL) and oxalyl chloride (0.26 mL, 3 mmol) was added followed by 2 drops of DMF. The mixture was stirred at RT for 18 h (milky suspension obtained). Volatiles were removed under reduced pressure. The residue was suspended in THF (3 mL) and morpholine (0.3 mL, 3.4 mmol) was added. An exothermic reaction takes place as a white precipitate forms. After 1 h, the reaction mixture was diluted with 1 N HCl and extracted with EtOAc. The extract was washed with brine, dried ($MgSO_4$) and concentrated to give a white foam that was used without further purification in Step 2: $^1$H NMR ($CDCl_3$) δ: 8.40 (d, J=8.2 Hz, 1H), 8.10 (d, J=8.2 Hz, 1H), 7.65-7.71 (m, 1H), 7.52 (t, J=7.4 Hz, 1H), 3.67-3.97 (m, 8H). MS m/z 230.1 (M–H).

Step 2 (Example 241): The indazole from Step 1 was coupled to the chloropyridine from Step 5 of Example 240 using copper/BINOL catalysis as described for Example 1 (step 4) in general method A.

Preparation of Example 242 (Table 4)

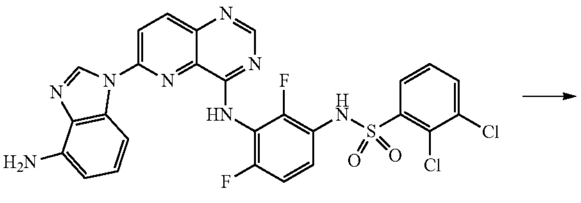

Example 99

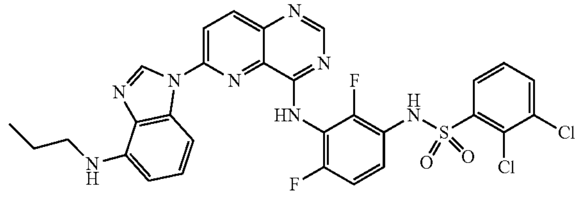

Example 242

The aminobenzimidazole of Example 99 (50 mg, 0.082 mmol) was dissolved in THF (1 mL) and propionaldehyde (14.2 mg, 0.245 mmol, 3 equivalents) was added. After stirring for 2 minutes at RT, sodium cyanoborohydride (10.2 mg, 0.163 mmol) was added and the mixture stirred overnight at RT to provide a mixture of starting material and product. Addition of second portions of propionaldehyde and sodium borohydride did not provide further conversion so the reaction mixture was quenched with 10% formic acid in MeOH (1 mL), filtered and the product isolated by prep-HPLC using a 60%→100% MeOH-0.1% formic acid gradient. The crude product was purified a second time using prep-HPLC using a 30-100% MeOH-0.1% TFA gradient to provide the product of Example 242.

Preparation of Example 316 (Table 3)

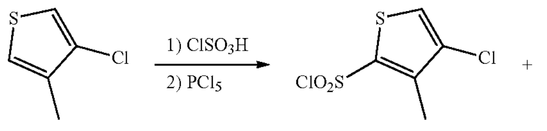

1

2

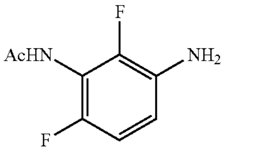

4

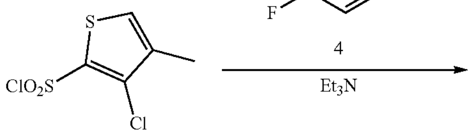

3

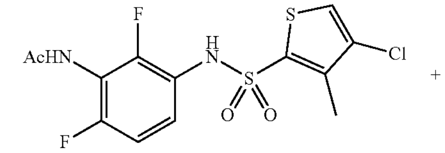

5

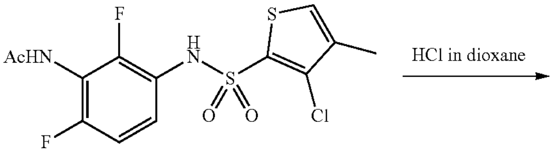

6

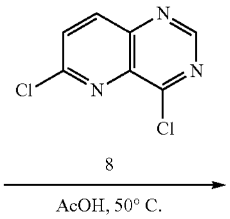

8

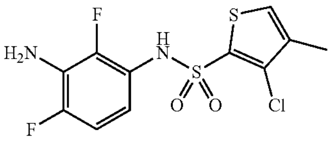

7

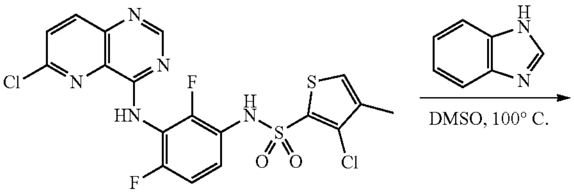

9

-continued

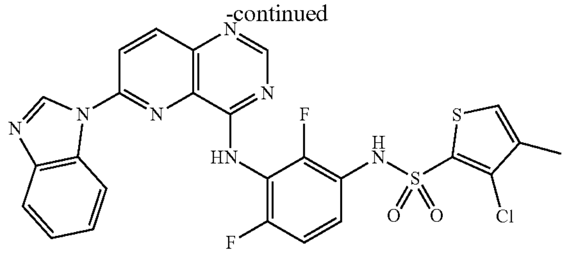

10 Example 316

Preparation of 4-chloro-3-methylthiophene-2-sulfonyl chloride (2 and 3): 3-Chloro-4-methylthiophene 1 (1.00 g, 7.54 mmol) was dissolved in $CHCl_3$ (4.43 mL) and a solution of chlorosulfonic acid (1.19 mL, 17.3 mmol) in $CHCl_3$ (1.48 mL) was added over 5 min at room temperature. The mixture was stirred for 10 min. Phosphorus pentachloride (4.13 g, 18.9 mmol) was added to the reaction mixture followed by $CHCl_3$ (7.50 mL). This was heated at 50° C. for 1 h. Reaction mixture was slowly added to the aqueous $NaHCO_3$ solution+ice (30.0 mL). This was stirred for 10 min. Extracted with $CH_2Cl_2$ (4×10 mL). Combined organic layers were dried ($Na_2SO_4$), filtered and concentrated under reduced pressure to give the mixture of major isomer compound 2 and compound 3 as an oil (1.30 g). This was used in the next reaction without further purification. LCMS: LCMS sample was quenched with N-methylpiperazine; ($ES^+$) M+H=295.1 Preparation of N-(3-(4-chloro-3-methylthiophene-2-sulfonamido)-2,6-difluorophenyl) acetamide (5 and 6): To a $CH_2Cl_2$ solution of a mixture of compound 2 and 3 (1.30 g, 2.37 mmol) was added aniline 4 (400 mg, 2.15 mmol) followed by triethylamine (904 μL, 6.45 mmol). This was stirred at room temperature for 18 h. Reaction mixture was slowly added to ice-water (20 mL) and stirred at room temperature for 10 min. The precipitated solid was filtered, washed with MTBE (3×5 mL) and dried under vacuum to give a mixture of compound 5 and 6 (900 mg) as a solid. LCMS: ($ES^+$) M+H=381.1.

Preparation of N-(3-amino-2,4-difluorophenyl)-4-chloro-3-methylthiophene-2-sulfonamide (7): The mixture of compound 5 and 6 (900 mg, 2.36 mmol) was dissolved in EtOH (5.49 mL) and HCl (6.00 N in $H_2O$, 0.6 mL) was added at room temperature. This was heated at 80° C. for 18 h in an oil bath. The volatiles were then removed under reduced pressure. Residue was dissolved in EtOAc (30 mL) and $H_2O$ (10 mL). Saturated aqueous $NaHCO_3$ was added until pH=8 was obtained. Aqueous and organic layers were separated. Aqueous layer was washed with EtOAc (3×10 mL). Combined organic layers were dried ($Na_2SO_4$), filtered and concentrated under reduced pressure. Purification by flash chromatography (50 g silica gel column, EtOAc/Hexanes, 0-70% over 10 CV) gave the title compound (35 mg) which was re-purified (12 g silica gel column, EtOAc/Hexanes, 20-60%) to afford the title compound 7 (17 mg, 1.76%, 84% purity) as an oil. ($ES^-$) M+H=337.1; $^1H$ NMR (400 MHz, $CDCl_3$) δ 7.20 (m, 1H), 7.03 (br s, 1H), 6.87 (td, J=8.8, 5.4 Hz, 1H), 6.73 (td, J=9.8, 2.0 Hz, 1H), 2.21 (s, 3H).

Preparation of 3-chloro-N-(3-((6-chloropyrido[3,2-d]pyrimidin-4-yl)amino)-2,4-difluoro phenyl)-4-methylthiophene-2-sulfonamide (9): Compound 7 (15.3 mg, 45.2 umol) was added to compound 8 (9.04 mg, 45.2 umol) in acetic acid (200 μL). This mixture was heated at 50° C. for 2 h. The mixture was cooled to room temperature. Volatiles were removed under reduced pressure to give the title compound 9 as a pale-yellow oil (22 mg, crude). This was used in the next reaction without further purification. ($ES^+$) M+H=502.1 and ($ES^-$) M−H=500.2.

Preparation of N-(3-((6-(1H-benzo[d]imidazol-1-yl)pyrido[3,2-d]pyrimidin-4-yl)amino)-2,4-difluorophenyl)-3-chloro-4-methylthiophene-2-sulfonamide 10 (Example 316, Table 3): benzimidazole (4.32 mg, 35.8 umol), compound 9 (15.0 mg, 29.9 umol), and cesium carbonate (11.8 mg, 35.8 umol) were mixed in DMSO (200 μL) under nitrogen. Reaction was stirred at 80° C. for 21 h. The mixture was cooled to room temperature and the residue was purified with reverse phase chromatography (12 g, acetonitrile/water containing 0.1% AmF, 20-70% over 15 CV) to give the title compound 10 (Example 316, Table 3) (5.30 mg, 30% yield, 93% purity). ($ES^+$) M+H=584.3 and ($ES^-$) M−H=582.3; $^1H$ NMR (400 MHz, DMSO-$d_6$) δ 10.64 (s, 1H), 9.76 (s, 1H), 9.29 (s, 1H), 8.44-8.43 (m, 1H), 8.43-8.36 (m, 2H), 8.28 (d, J=8.1 Hz, 1H), 7.73 (d, J=7.7 Hz, 1H), 7.60 (br m, 1H), 7.38-7.27 (m, 2H), 7.16 (dd, J=14.3, 8.3 Hz, 1H), 7.02 (br m, 1H), 2.07-1.99 (m, 3H).

Preparation of Example 320 (Table 3)

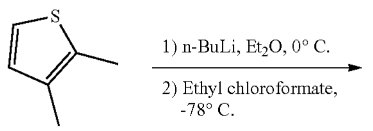

1

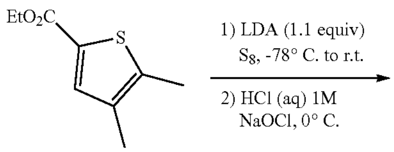

2

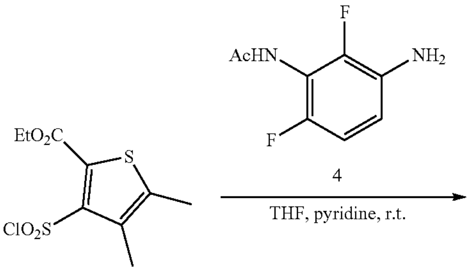

3

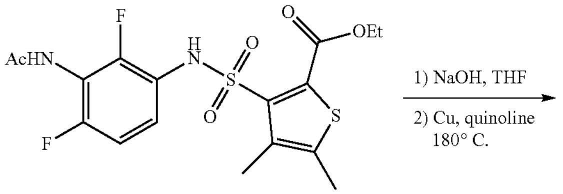

5

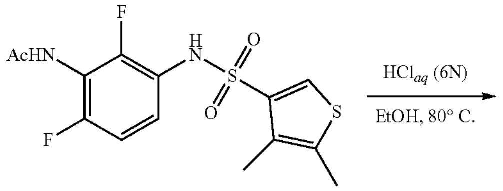

6

-continued

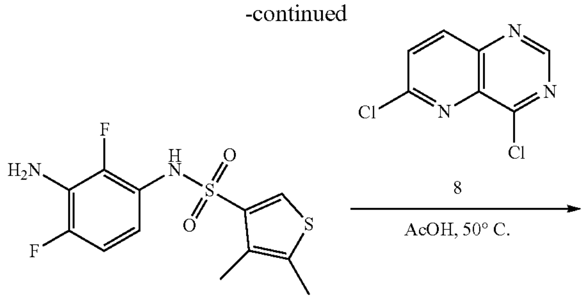

7

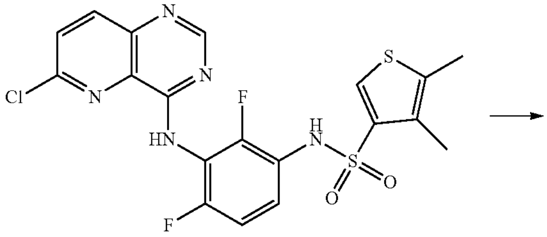

9

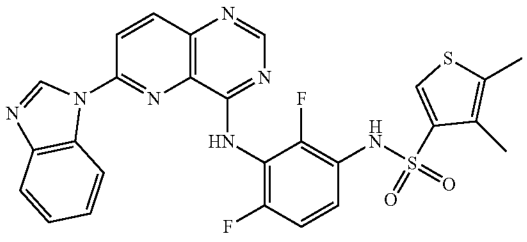

Example 320

Preparation of methyl 3-chloro-4-(chlorosulfonyl)thiophene-2-carboxylate (2): To an $Et_2O$ solution (8.00 mL) of 2,3-dimethylthiophene 1 (499 μL, 4.46 mmol) was added butyllithium (2.50 M in hexanes, 1.96 mL, 4.90 mmol) at 0° C. This was stirred at 0° C. for 1 h. Mixture was cooled to −78° C. Ethyl chloroformate (476 μL, 4.90 mmol) was added drop-wise. This was stirred at −78° C. for 1 h. The reaction mixture was diluted with 1.00 M $NH_4Cl$ (10 mL) and $Et_2O$ (20.0 mL). The mixture was warmed up to room temperature and stirred for 30 min. Aqueous and organic layers were separated. Aqueous layer was extracted with $Et_2O$ (3×15.0 mL). Combined organic layers were dried ($MgSO_4$), filtered and concentrated under reduced pressure. Purification by flash chromatography (25 g silica gel column, EtOAc/Hexanes, 0-30% over 15 CV) gave the title compound 2 (554 mg, 49% yield, 73% purity) as dark green oil. $^1H$ NMR (400 MHz, $CDCl_3$) δ 7.49 (s, 1H), 4.30 (q, J=7.1 Hz, 2H), 2.36 (s, 3H), 2.13 (s, 3H), 1.35 (t, J=7.1 Hz, 3H).

Preparation of ethyl 3-(chlorosulfonyl)-4,5-dimethylthiophene-2-carboxylate (3): To a THF (2.99 mL) solution of ethyl 4,5-dimethylthiophene-2-carboxylate 2 (1.00 g, 5.43 mmol) was added sulfur powder (1.67 g, 6.52 mmol). This was cooled to −78° C. Freshly prepared lithium diisopropylamide solution (1.00 M in THF, 6.79 mL, 6.79 mmol) was added to the mixture drop-wise. The mixture was stirred at −78° C. for 30 min and then slowly warmed up to room temperature over 4 h. The mixture was cooled down to 0° C. $CH_2Cl_2$ (5.00 mL) was added to the mixture followed by HCl (1.00 M in $H_2O$, 5.50 mL). This was stirred at 0° C. for 10 min and sodium hypochlorite (10% solution in $H_2O$, 11.8 mL, 16.3 mmol) was added drop-wise. This was stirred at 0°

C. for 20 min and then at room temperature for 2 h. Additional HCl (1.00 M in $H_2O$, 5.50 mL) was added followed by sodium hypochlorite (10% solution in $H_2O$, 5.91 mL, 8.15 mmol). This was stirred at room temperature for 20 h. The reaction mixture was diluted with $NH_4Cl$ (1.00 M in $H_2O$, 20.0 mL) and $Et_2O$ (30.0 mL). This was stirred at room temperature for 30 min. Aqueous and organic layers were separated. Aqueous layer was extracted with $Et_2O$ (3×25.0 mL). Combined organic layers were dried ($MgSO_4$), filtered and concentrated to give the crude title compound (1.58 g, 40% yield, 40% purity). LCMS sample was quenched with N-methylpiperazine (resulting sulfonamide MW=346.4); ($ES^+$) M+H=347.3.

Preparation of ethyl 3-(N-(3-acetamido-2,4-difluorophenyl)sulfamoyl)-4,5-dimethylthiophene-2-carboxylate (5): Crude sulfonyl chloride 3 (1.58 g, 40% purity, 2.15 mmol) was dissolved in THF (11.3 mL). To this solution was added aniline 4 (400 mg, 2.15 mmol) at room temperature followed by pyridine (209 μL, 2.58 mmol). The resulting mixture was stirred at room temperature for 18 h.

Mixture was diluted with EtOAc (30.0 mL) and water (15.0 mL). Aqueous and organic layers were separated. Aqueous layer was extracted with EtOAc (3×15.0 mL). Combined organic layers were washed with brine (15.0 mL), dried ($Na_2SO_4$), filtered and concentrated under reduced pressure to give crude compound as an oil. Purification by flash chromatography (40 g silica gel column, EtOAc/Hexanes, 0-60% over 15 CV) gave the title compound as an oil (370 mg, 40%). ($ES^+$) M+H=433.3 and ($ES^-$) M−H=431.3.

Preparation of N-(3-(4-chlorothiophene-3-sulfonamido)-2,6-difluorophenyl)acetamide (6): Compound 5 (350 mg, 809 umol) was taken up in THF (4.17 mL) and MeOH (1.04 mL). NaOH (5.00 M in $H_2O$, 600 μL) was added to the mixture. The mixture was stirred 10 min before acidifying using HCl (10% in $H_2O$, 10.0 mL). Volatiles were removed. Residue was azeotroped with toluene (3×10.0 mL) and dried under vacuum over the weekend to get 330 mg of crude carboxylic acid. A microwave vial (5 mL size) was charged with crude carboxylic acid (330 mg), copper (II) acetate (75.6 mg, 408 umol) and 1,10-phenanthroline (149 mg, 816 umol) and the mixture was suspended in NMP (2.79 mL)/quinoline (697 μL). The vial was flushed with nitrogen before subjecting to microwave irradiation at 180° C. for 10 min using high absorbance. The crude was diluted with EtOAc (10.0 mL), washed with $H_2O$ (15.0 ml), HCl (10% in $H_2O$, 2×10.0 mL) and brine (15.0 mL). Organic layer was dried ($Na_2SO_4$), filtered and concentrated under reduced pressure to give the crude title compound 6 (310 mg) which was used in the next step without any further purification. ($ES^+$) M+H=361.2 and ($ES^-$) M−H=359.2.

Prepration of N-(3-amino-2,4-difluorophenyl)-4,5-dimethylthiophene-3-sulfonamide (7): Compound 6 (290 mg, 805 umol) was suspended in EtOH (3.34 mL) and HCl (6.00 N in $H_2O$, 1.00 mL) was added. The reaction mixture was stirred at 80° C. overnight. The solution was cooled to room temperature and volatiles were evaporated under reduced pressure. The residue was azeotroped with MeOH (3×10.0 mL). Residue was purified by reverse phase chromatography (25 g column, $CH_3CN$/water containing 0.1% AmF, 5-50%) to give the title compound which was used in the next reaction without further purification (139 mg, 54% yield). ($ES^+$) M+H=319.1 and ($ES^-$) M−H=317.2.

Prepration of N-(3-((6-chloropyrido[3,2-d]pyrimidin-4-yl)amino)-2,4-difluorophenyl)-4,5-dimethylthiophene-3-sulfonamide (9): Aniline 7 (130 mg, 408 umol) was added to compound 8 (98.0 mg, 490 umol) in acetic acid (1.05 mL). This mixture was heated at 50° C. for 4 h. The mixture was cooled to room temperature and poured onto ice-water mixture (50.0 mL). The mixture was stirred for 20 min. Solid formed was filtered, washed with $H_2O$ (8×10.0 mL) and dried overnight under vacuum to give beige solid (182 mg, 85% purity). This was triturated with $CH_3CN$/MTBE (1:25, 5×5.00 mL) and dried overnight to give the title compound 9 as solid (165 mg, 80% yield, 94% purity). ($ES^+$) M+H=482.3 and ($ES^-$) M−H=480.4; $^1$H NMR (400 MHz, DMSO-$d_6$) δ: 10.19 (s, 1H), 10.13 (s, 1H), 8.55-8.51 (m, 1H), 8.32-8.24 (m, 1H), 8.05-7.96 (m, 1H), 7.90-7.86 (m, 1H), 7.31-7.23 (m, 1H), 7.20-7.12 (m, 1H), 2.30 (s, 3H), 2.21 (s, 3H).

Preparation of example 320 (Table 3): benzimidazole was coupled to chloropyridine 9 described above using copper/BINOL catalysis as described for Example 1 (step 4) in general method A.

Preparation of Example 329 (Table 4)

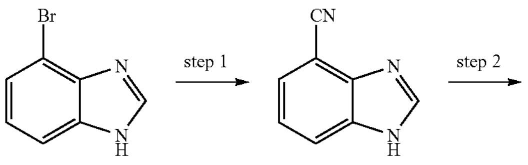

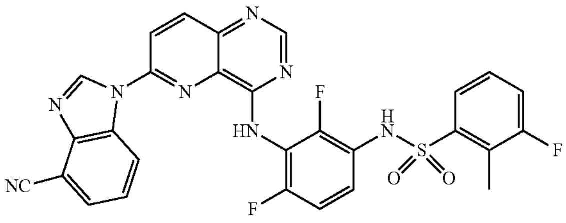

Example 329

Step 1: To a nitrogen-purged (×3) 10 mL microwave vial equipped with a magnetic stir bar, was added 4-bromo-1H-benzo[d]imidazole (99 mg, 0.502 mmol), dicyanozinc (70.8 mg, 0.603 mmol), palladium tetrakistriphenylphosphine (116 mg, 0.100 mmol) in DMF (4 mL). The reaction was heated to 90° C. and allowed to stir for 16 h. The reaction was cooled to room temperature and then extracted with EtOAc. The organic layers were washed with $NaHCO_3$, brine, dried with Na2SO4 and then loaded on Celite. The crude material was purified by SiO2 using MeOH in DCM to afford 1H-benzo[d]imidazole-4-carbonitrile (31 mg, 43.1% yield) as a light pink solid. $^1$H NMR (400 MHz, DMSO-$d_6$) δ: 13.04 (br. s., 1H), 8.45 (s, 1H), 7.90 (d, J=7.83 Hz, 1H), 7.68 (d, J=7.83 Hz, 1H), 7.20-7.44 (m, 1H). MS m/z 142.2 ($MH^+$).

Step 2 (Example 329, Table 4): the benzimidazole fragment from step 1 was coupled to the chloropyridine A-13 (Ar=3-fluoro-2-methylphenyl) using copper/BINOL catalysis as described for Example 1 (step 4) in general method A.

Preparation of Examples 334, 335, 336 and 346 (Table 4)

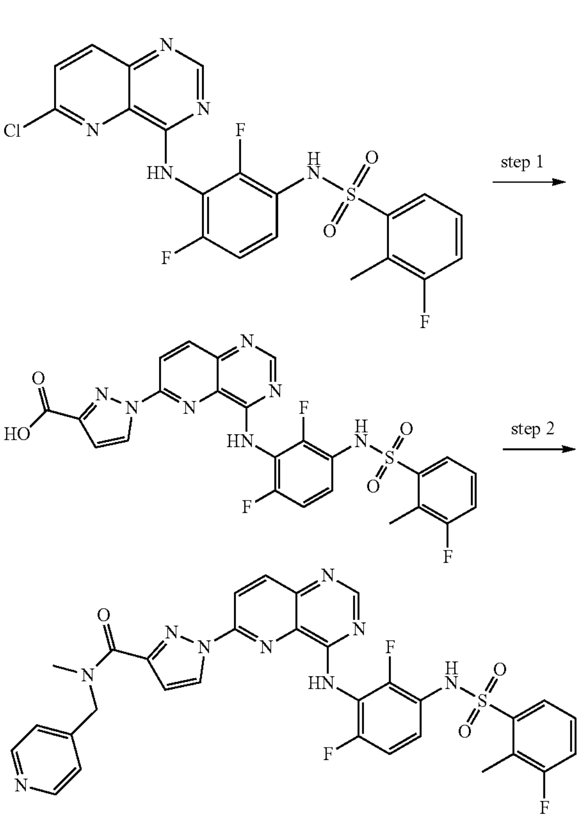

Example 334

Step 1: chloropyridine fragment A-13 (Ar=3-fluoro-2-methylphenyl) (40 mg, 0.083 mmol), methyl 1H-pyrazole-3-carboxylate (13.67 mg, 0.108 mmol), [1,1'-binaphthalene]-2,2'-diol (5.97 mg, 0.021 mmol), copper (1.32 mg, 0.021 mmol) and cesium carbonate (40.7 mg, 0.125 mmol) were charged in a 4 mL vial followed by DMSO (700 μL). The orange/brown solution was allowed to stirr at 100° C. for 16 h. Upon completion, the reaction was allowed to cool down to room temperature and sodium hydroxide (125 μL, 0.50 mmol) 4N aqueous solution was added to the reaction mixture which was then stirred at 50° C. for one more hour. The reaction mixture was allowed to cool down to room temperature and was transferred in 1.5 mL of HCl 1N aqueous solution and the formation of a precipitate was observed. The formed 152recipitate was filtrated, washed with water and dried under high vacuum to obtain the desired product 1-(4-((2,6-difluoro-3-(3-fluoro-2-methylphenylsulfonamido)phenyl)amino)-pyrido[3,2-d]pyrimidin-6-yl)-1H-pyrazole-3-carboxylic acid (43.3 mg, 0.078 mmol, 94% yield) as a yellow solid. MS m/z 556.2 ($MH^+$).

Step 2: The activated ester was prepared by dissolving the acid from step 1 (30 mg, 0.054 mmol) and HATU (41.1 mg, 0.108 mmol) in NMP (1 mL) followed by DIEA (56.4 μL, 0.324 mmol). The solution was stirred 2-3 mintues at room temperature and then N-methyl-1-(pyridin-4-yl)methanamine (13.4 μL, 0.108 mmol) was added. The reaction mixture was stirred at room temperature for 16 h. Upon completion, the reaction was quenched by the addition of 0.5 mL of formic acid, diluted with DMSO and purified by HPLC (ACN/H2O/0.1% formic acid) to afford the product of Example 334 in Table 4 (5.7 mg, 8.64 μmol, 16% yield) as a beige solid. $^1H$ NMR (400 MHz, DMSO-d6) 5:10.52 (br. s., 1H), 10.13 (s, 0.5H), 10.09 (s, 0.5H), 9.39 (br. s., 0.5H), 9.33 (br. s., 0.5H), 8.58 (br. s., 2H), 8.38-8.53 (m, 2H), 8.32 (d, J=9.00 Hz, 0.5H), 8.02 (d, J=9.00 Hz, 0.5H), 7.61 (dd, J=4.30, 7.43 Hz, 1H), 7.47 (d, J=8.22 Hz, 1H), 7.14-7.43 (m, 5H), 7.08 (d, J=2.74 Hz, 0.5H), 7.01 (d, J=2.74 Hz, 0.5H), 5.11 (s, 1), 4.77 (s, 1H), 3.39 (s, 1.5H), 3.03 (s, 1.5H), 2.51 (s, 3H). MS m/z 660.2 ($MH^+$).

Examples 335, 336 and 346 (Table 4) were prepared in an analogous fashion using the appropriate commercially available pyrrazole esters.

Preparation of Examples 339 and 340 (Table 4)

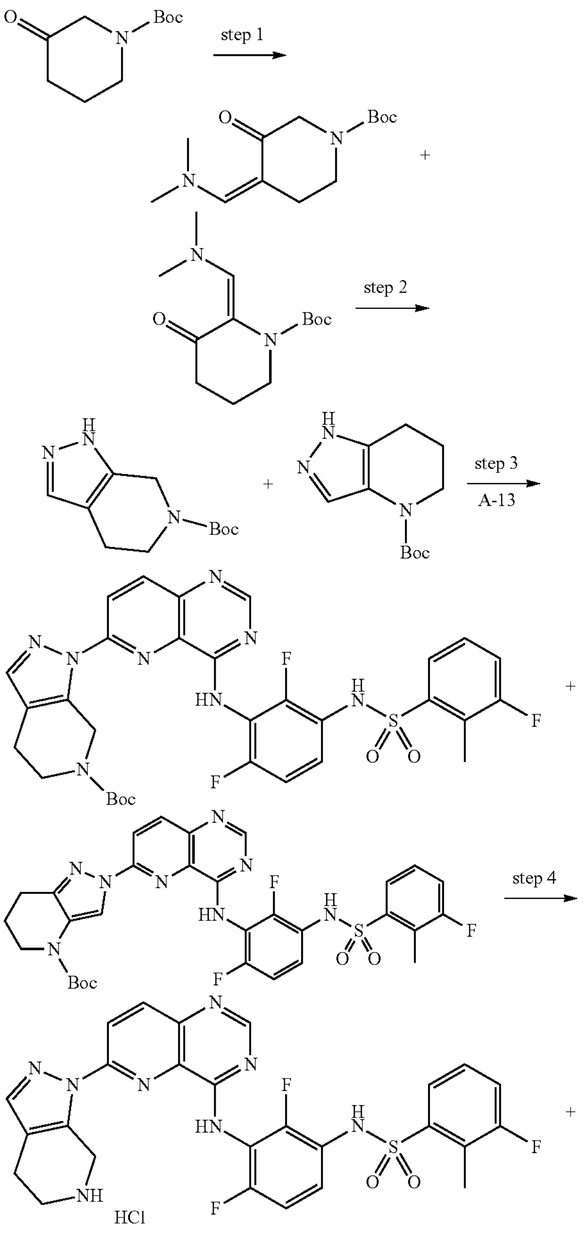

isomer a

-continued

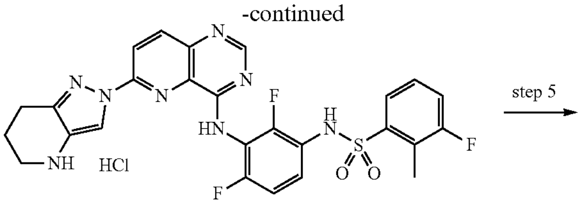

isomer b

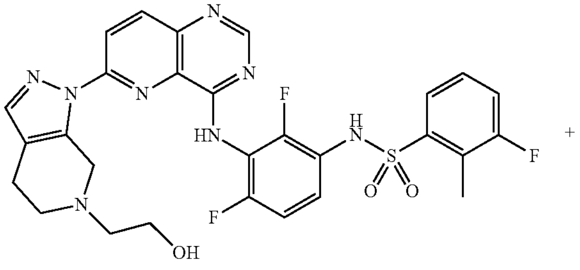

Example 339

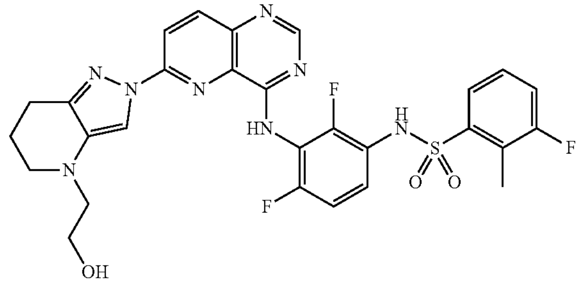

Example 340

Step 1: A stirring solution of 1-boc-3-piperidone (5.00 g, 25.1 mmol) in DMF-DMA (20.8 mL) was heated at 100° C. for 1 h. After completion, the reaction mixture was cooled to room temperature and volatiles were evaporated under reduced pressure to obtain a yellow gummy material. This was co-evaporated with EtOH (5.00 mL×3) to a mixture of regioisomeric products. The material was used in the next step as a crude: ($ES^+$) M+H=225.1.

Step 2: the mixtures of compounds from step 1 and hydrazine hydrate solution (3.19 mL, 50.2 mmol) were mixed in EtOH (33.5 mL. The mixture was heated at 80° C. for 1 h. When LCMS showed full consumption of starting materials, it was cooled to room temperature. Volatiles were evaporated under reduced pressure and the residue was purified by silica gel chromatography with 20-60% ethyl acetate in hexanes. The desired product came out at 60%. The mixture of isomeric pyrrazole derivatives was obtained as a gummy solid (4.04 g, 72% yield): ($ES^+$) M+H=224.1.

Step 3: the mixture of products from step 2 (335 mg, 1.50 mmol), A-13 (Ar=3-fluoro-2-methylphenyl, 480 mg, 1.00 mmol), copper metal (6.36 mg, 100 umol), 1,1'-bi-2-naphthol (58.5 mg, 200 μmol) and cesium carbonate (757 mg, 2.30 mmol) were mixed in DMSO (4.00 mL). The reaction was heated to 125° C. for 3 h. After cooling down to room temperature, the reaction was diluted with water (30.0 mL) and ethyl acetate (30.0 mL) and filtered through Celite. Filtrate was extracted with ethyl acetate (30.0 mL×2). Combined organic layers were washed with brine, dried, and concentrated. Residue was purified by silica gel chromatography 80 g, with 50-70% ethyl acetate in hexanes. The desired product came out at 70% ethyl acetate in hexanes as a yellow solid mixture of regioisomers (567 mg, 85% yield): ($ES^+$) M+H=667.2.

Step 4: the mixture of regioisomeric carbamates from step 4 (567 mg, 850 μmol) was dissolved in dioxane (4.25 mL). To the solution was added HCl (4.0 M in dioxane, 2.13 mL, 8.50 mmol) at room temperature. The reaction was stirred at room temperature for 2 days. Reaction was filtered and washed with dioxane. The mixture of regioisomeric hydrochloride salts was obtained as a yellow solid (542 mg, quantity yield): ($ES^+$) M−HCl+H=567.2.

Separation of regioisomeric pyrrazoles from Step 4: a mixture of regioisomers carbamates from step 3 (1.0 g, 1.5 mmol) was dissolved in dioxane (7.5 mL). To the solution was added HCl (4 M in dioxane, 3.75 mL, 15 mmol) at room temperature. The reaction was stirred at room temperature for 2 days. Reaction was filtered and washed with dioxane. The mixture of regioisomeric hydrochloride salts (850 mg, quantitative yield) was obtained as a yellow solid. The solid was purified by a reverse phase column with 0-20-40% ACN in 10 mM ammonium formate, first isomer (isomer a) came out at 15% ACN in 10 mM ammonium formate, and second isomer (isomer b) came out at 40% ACN in 10 mM ammonium formate. Both compounds were concentrated and the residue was treated with 4 M HCl in dioxane 0.5 mL, the resulting suspension was sonicated, and then filtered, yielding hydrochlorides of isomers a (130 mg, 15% yield) and isomer b (230 mg, 27% yield) as white solids: ($ES^+$) M−HCl+H=567.2.

Step 5 (Examples 339 and 340, Table 4): the mixture of isomers from step 4 (85.0 mg, 150 μmol) was dissolved in MeOH (1.50 mL). To the solution was added glycolaldehyde dimer (56.9 mg, 450 umol). After 5 min, sodium triacetoxyborohydride (163 mg, 750 umol) was added. Reaction was stirred at room temperature overnight. Reaction was quenched with water (10.0 mL) and extracted with ethyl acetate (10 mL×2). Organic layers were combined and washed with brine, dried and concentrated. The residue was purified on reverse phase column with 0-40-60% ACN in 10 mM ammonium formate. The compound of example 339 came out at 20% ACN in 10 mM ammonium formate and the compound of example 340 came out at 40% ACN in 10 mM ammonium formate. After lyophilisation, Example 339 (10 mg, 11% yield) was obtained as white solid. Example 340 (10 mg, 11% yield) was obtained as white solid.

Preparation of Example 343 (Table 4)

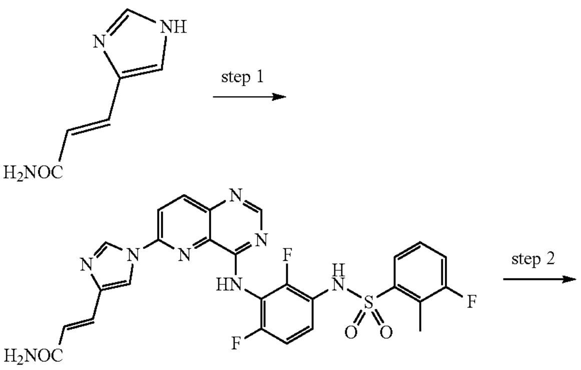

-continued

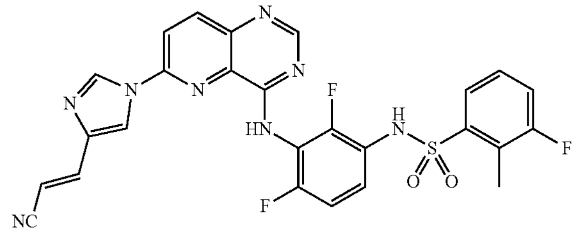

Example 343

Step 1: the commercially available imidazole starting material (which can also be prepared following the procedure described in Tet. Lett. 2002, 43 (1), 61) was coupled to the chloropyridine A-13 (Ar=3-fluoro-2-methylphenyl) using copper/BINOL catalysis as described for Example 1 (step 4) in general method A.

Step 2 (Example 343, Table 4): To a 20 mL scintillation vial equipped with a magnetic stir bar, was added the product from step 1 (91 mg, 0.157 mmol) and 2,4,6-tripropyl-1,3,5,2,4,6-trioxatriphosphinane 2,4,6-trioxide (997 mg, 1.57 mmol). The reaction was heated to 65° C. over the 48 h. Upon completion, the reaction was cooled to room temperature. Water was added to the reaction which cause the product to precipitate. The product was filtered, washed with water, collected and then dried under vacuum overnight to afford (E)-N-(3-((6-(4-(2-cyanovinyl)-1H-imidazol-1-yl)pyrido[3,2-d]pyrimidin-4-yl)amino)-2,4-difluorophenyl)-3-fluoro-2-methylbenzenesulfonamide (63 mg, 69% yield) as a beige solid. $^1$H NMR (400 MHz, DMSO-d6) δ: 10.53 (s, 1H), 10.16 (s, 1H), 9.13 (s, 1H), 8.74 (s, 1H), 8.50 (s, 1H), 8.38-8.48 (m, 2H), 7.61 (d, J=7.83 Hz, 1H), 7.57 (d, J=16.04 Hz, 1H), 7.49 (t, J=8.41 Hz, 1H), 7.40 (dt, J=5.48, 8.02 Hz, 1H), 7.28-7.36 (m, 1H), 7.22-7.28 (m, 1H), 6.24 (d, J=16.04 Hz, 1H), 2.51 (s, 3H). MS m/z 563.2 ($MH^+$).

Preparation of Examples 345 and 361 (Table 4)

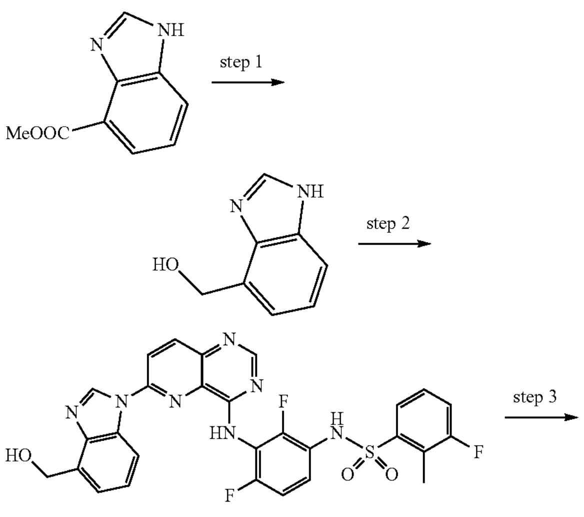

Example 345

-continued

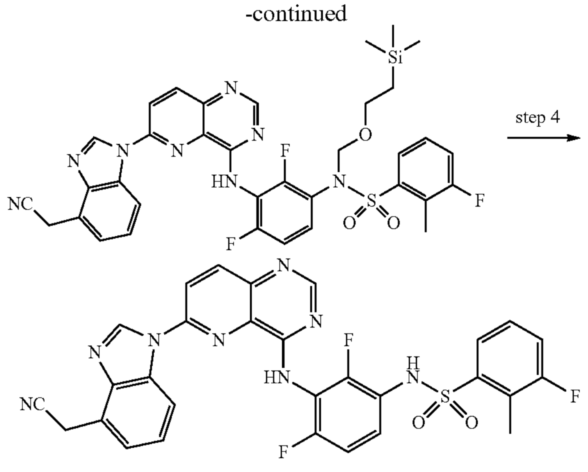

Example 361

Step 1: To a 5 mL vial equipped with a magnetic stir bar under a $N_2$ atmosphere, was added methyl 4-benzimidazole carboxylate (100 mg, 0.568 mmol) in anhydrous THF (2 mL). The reaction was cooled to 0° C. A solution of 1M Lithium aluminum hydride in THF (0.44 mL, 0.437 mmol) was added slowly at over 5 min. The reaction was allowed to warm to room temperature and allowed to stir for 4 hours. An other portion of of 1M Lithium aluminum hydride in THF (0.250 mL) to push the reaction to completion. The reaction was allowed to stir for another 1 hour. The reaction was quenched with MeOH. The reaction was loaded onto Celite and then purified on $SiO_2$ using MeOH in DCM to give the desired benzylic alcohol derivative (58 mg, 0.391 mmol, 90% yield) as a yellow solid. MS m/z 149.2 ($MH^+$).

Step 2 (Example 345): the benzylic alcohol from step 1 was coupled to the chloropyridine A-13 (Ar=3-fluoro-2-methylphenyl) using copper/BINOL catalysis as described for Example 1 (step 4) in general method A.

Step 3: To a 20 mL scintillation vial, was added N-[2,4-difluoro-3-[[6-[4-(hydroxymethyl)benzimidazol-1-yl]pyrido[3,2-d]pyrimidin-4-yl]amino]phenyl]-3-fluoro-2-methyl-benzenesulfonamide (1.00 eq, 138 mg, 0.233 mmol) and DIEA (2.00 eq, 81 μL, 0.467 mmol) in DMF (3.1259 mL). Next, 2-(trimethylsilyl)ethoxymethyl chloride, stabilized, tech. (1.10 eq, 46 μL, 0.257 mmol) was added to the suspension. The reaction was heated to 40° C. and left to stir for 24 h. The reaction was quenched with sat. $NH_4Cl$ and then extracted with brine and EtOAc (×3). The organics were collected, dried by $MgSO_4$, filtered and then concentrated under reduced pressure. The crude material liquid was purified by normal-phase, flash column chromatography using MeOH in DCM. The desired fractions were collected and concentrated under reduced pressure to give the desired protected sulfonamide (153 mg, 91%) as a yellow solid. $^1$H NMR (400 MHz, DMSO-$d_6$) δ: 9.88 (br. s., 1H), 9.30 (s, 1H), 8.49 (br. s., 3H), 8.25 (d, J=8.2 Hz, 1H), 7.66 (d, J=7.8 Hz, 1H), 7.54 (t, J=8.2 Hz, 1H), 7.39-7.48 (m, 2H), 7.29-7.39 (m, 2H), 5.26 (br. s., 1H), 5.07 (s, 2H), 5.00 (s, 2H), 3.60-3.68 (m, 2H), 2.39 (d, J=2.3 Hz, 3H), 0.82-0.90 (m, 2H),—0.03 (s, 9H). MS m/z 722.2 ($MH^+$).

Step 4 (Example 361): a 20 mL vial was charged with the product from step 3 (1.00 eq, 150 mg, 0.208 mmol) and N,N-diisopropylethylamine (2.00 eq, 72 μL, 0.416 mmol) in DMF (2 mL). Next, methanesulfonyl chloride (1.50 eq, 24 μL, 0.312 mmol) was added. The reaction was allowed to stir at room temperature overnight. The reaction was quenched with sat. $NaHCO_3$ and then extracted with EtOAc (×3). The organics were collected, dried by $MgSO_4$, filtered and then concentrated under reduced pressure. The crude was dissolved in MeCN (2 mL) and then potassium cyanide (2.00 eq, 27 mg, 0.416 mmol) was added. The reaction was allowed to stir at room temperature for 36 h. The reaction was quenched with 10% LiCl and then extracted with EtOAc (×3). The organics were collected, dried by $MgSO_4$, filtered and then concentrated under reduced pressure. The crude material was dissolved in 1 mL of DCM and 1 mL of TFA and left to stir at room temperature for 48 h. The DCM was removed under reduced pressure. The crude material was dissolved in DMSO and then purified by prep HPLC using Water:MeCN+0.1% formic acid to afford the analog of Example 361 (36 mg, 0.0593 mmol, 29%) as a light yellow solid after lyophilization. $^1H$ NMR (400 MHz, DMSO-$d_6$) δ: 10.51 (br. s., 1H), 9.82 (s, 1H), 9.38 (s, 1H), 8.46-8.55 (m, 3H), 8.36 (d, J=7.8 Hz, 1H), 7.63 (d, J=7.8 Hz, 1H), 7.41-7.50 (m, 3H), 7.35-7.41 (m, 1H), 7.29 (td, J=9.0, 6.3 Hz, 1H), 7.19 (t, J=9.4 Hz, 1H), 4.38 (s, 2H), 2.50 (br. s., 3H). MS m/z 601.2 ($MH^+$).

Preparation of Example 347 (Table 4)

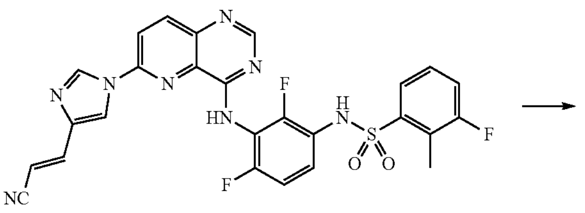

Example 343

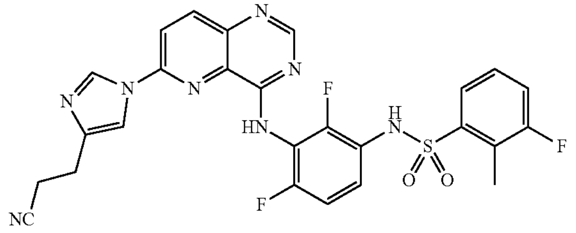

Example 347

To a 20 ml scintillation vial, was added the compound of Example 343 (50 mg, 0.089 mmol) and 5% Pd/C (10 mg, 5.2 μmol) in MeOH (2 ml). The reaction was allowed to stir at room temperature for 16 h under 1 atm of $H_2$. The reaction was filtered through a pad of Celite and then concentrated under reduced pressure. The crude material was purifed by HPLC using Water:MeOH+1% formic acid) to afford the compound of Example 347 in Table 4 (17 mg, 34% yield). $^1H$ NMR (400 MHz, DMSO-$d_6$) δ:10.51 (br. s., 1H), 10.00 (s, 1H), 8.96 (s, 1H), 8.43-8.49 (m, 1H), 8.32-8.43 (m, 2H), 8.30 (s, 1H), 7.62 (d, J=7.83 Hz, 1H), 7.41-7.49 (m, 1H), 7.33-7.41 (m, 1H), 7.23-7.33 (m, 1H), 7.18 (br. s., 1H), 2.87 (s, 4H), 2.50 (s, 3H). MS m/z 565.4 ($MH^+$).

Preparation of Examples 348 and 349 (Table 4)

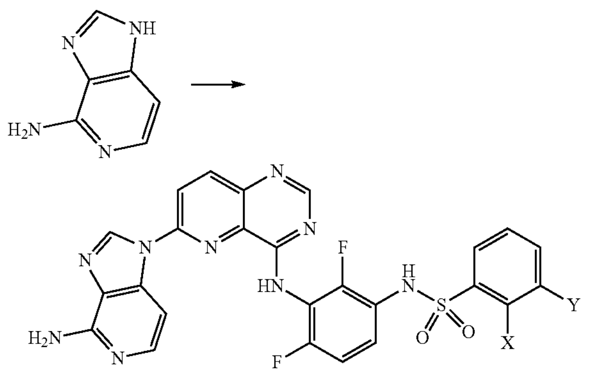

Example 348 (X, Y = Cl)
Example 349 (X = Me, Y = F)

Commercially available 3H-Imidazo[4,5-c]pyridin-4-amine (CAS #6811-77-4) was coupled to the chloropyridine A-13 using copper/BINOL catalysis as described for Example 1 (step 4) in general method A, except that 1.2 equivalents of Cu metal was used.

Preparation of Example 353 (Table 4)

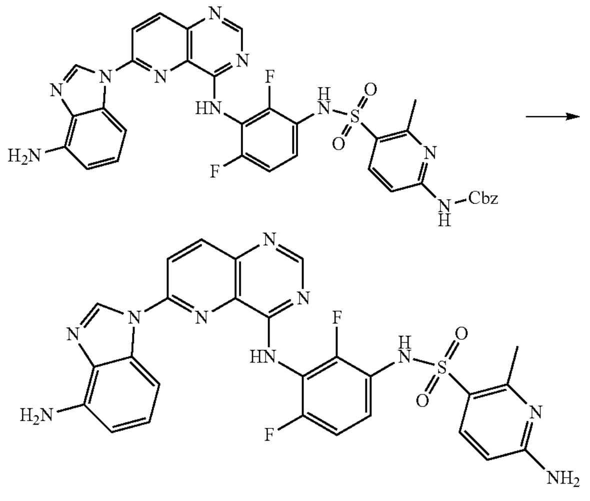

Example 353

The starting Cbz-protected aminopyridine derivative was obtained in the usual fashion by coupling the chloropyridine fragment containing fragment B49 (Table 2) with 4-amino-benzimidazole using copper/BINOL catalysis as described for Example 1 (step 4) in general method A. To a solution of this intermediate (12 mg, 0.0168 mmol) in MeOH (1 mL) was added 5% palladium hydroxide on carbon (23 mg, 0.0084 mmol) and stirred under 1 atm of $H_2$ for 1 h. Upon completion, the suspension was filtered and concentrated under vacuum. The residu was diluted with DMSO and purified by HPLC with MeCN in 0.1% aq. formic acid to 353 (Table 4) (2.0 mg, 20%). $^1H$ NMR (400 MHz, acetic_acid d4) δ: 9.15 (s, 1H), 8.56-8.84 (m, 2H), 8.42 (d, J=9.00 Hz, 1H), 8.08 (s, 1H), 7.98 (d, J=9.39 Hz, 1H), 7.54 (s, 1H), 7.29 (s, 1H), 7.18 (s, 1H), 6.85 (d, J=7.83 Hz, 1H), 6.75 (d, J=9.39 Hz, 1H), 2.65 (s, 3H). MS m/z 575.2 ($MH^+$).

Preparation of Examples 356 and 664

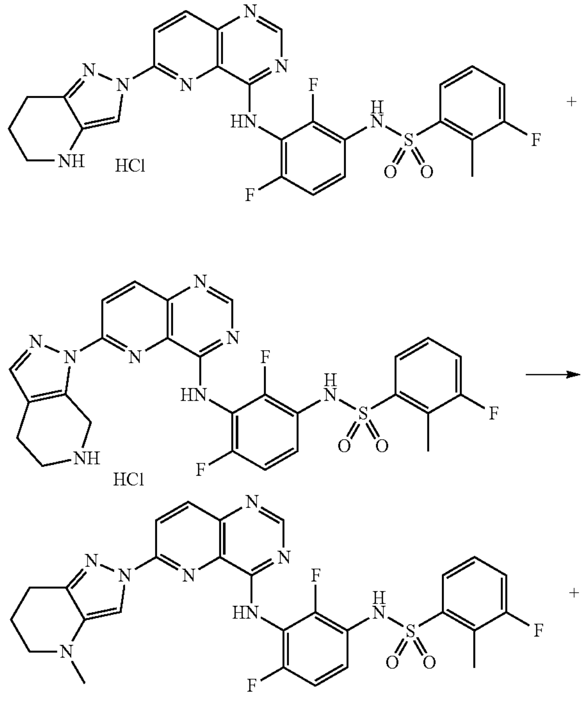

Example 356

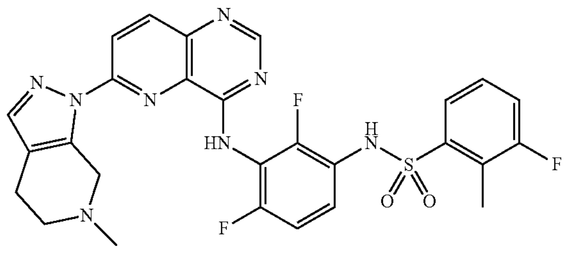

Example 664

A mixture of regioisomeric pyrrazoles from step 4 of Examples 339/340 (100.0 mg, 177 μmol) was dissolved in MeOH (1.77 mL). To the solution was added formaldehyde (65.7 uL, 883 μmol) followed by AcOH (1 drop). After 5 min, sodium triacetoxyborohydride (192 mg, 883 μmol) was added. Reaction was stirred at room temperature overnight. Reaction was concentrated to remove MeOH and then it was diluted with water and ethyl acetate. The aqueous and organic layers were separated and the aqueous layer was extracted with ethyl acetate (10 mL×3). Combined organic layers were dried and concentrated under reduced pressure. The residue was purified on reverse column 30 g, with 0-30-60% ACN in 10 mM ammonium formate. The compound of Example 664 came out at 30% ACN in 10 mM ammonium formate and the compound of Example 356 came out at 50% ACN in 10 mM ammonium formate. After lyophilisation, 664 (20 mg, 20% yield) and 356 (13 mg, 13% yield) were both obtained as white solids.

Preparation of Examples 357 and 393 (Table 4)

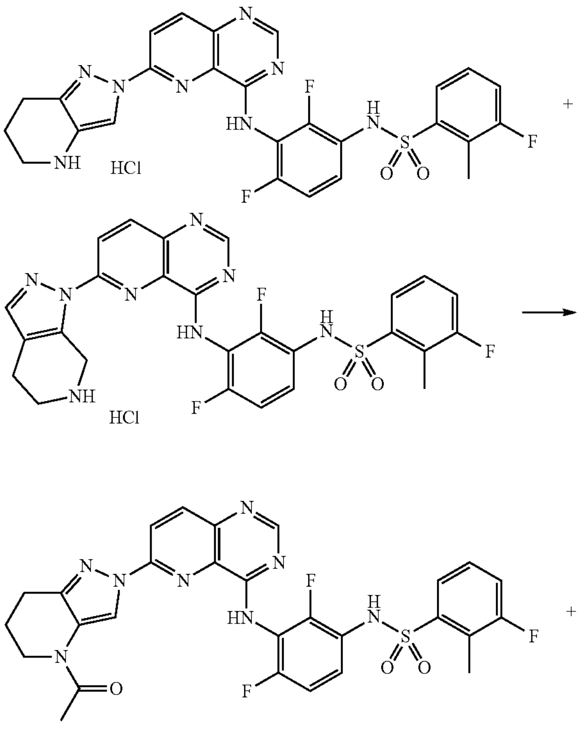

Example 357

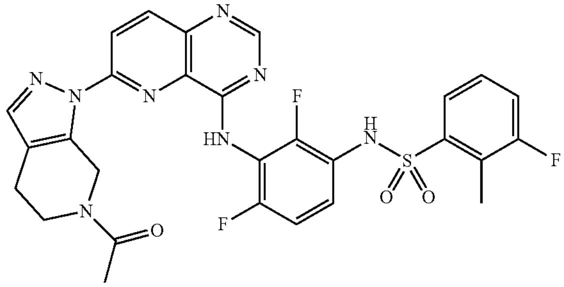

Example 393

A mixture of regioisomeric pyrrazoles from step 4 of Examples 339/340 (50.0 mg, 88.2 μmol) was dissolved in $CH_2Cl_2$ (1.00 mL). To the solution was added acetic anhydride (4.63 μL, 48.5 μmol), followed by N,N-diisopropylethylamine (11.6 μL, 66.2 μmol). Reaction was stirred at room temperature overnight. $Ac_2O$ (10.0 uL) was added to the reaction, and stirred for another day.

Volatiles were removed under reduced pressure and the residue was purified directly on a reverse phase column (30 g), using 0-30-60% ACN in 10 mM ammonium bicarbonate. The compound of Example 393 came out at 30% ACN in 10 mM ammonium bicarbonate and the compound of Example 357 came out at 40% ACN in 10 mM ammonium bicarbonate. After lyophilisation, 393 (10 mg, 19% yield) and 357 (20 mg, 37% yield) were both obtained as a white solid.

Preparation of Examples 362 and 383 (Table 4)

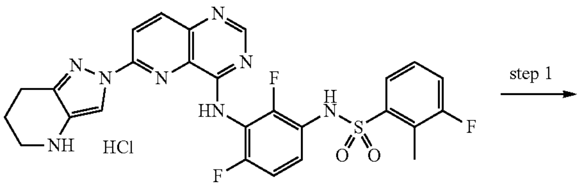

isomer b

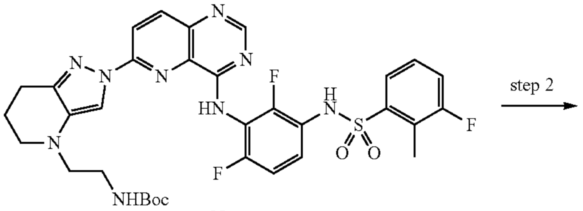

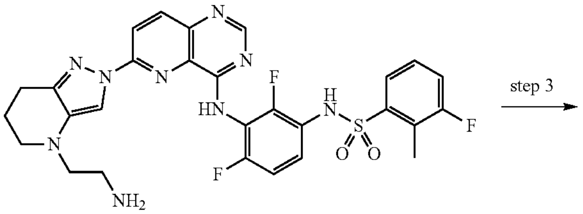

Example 362

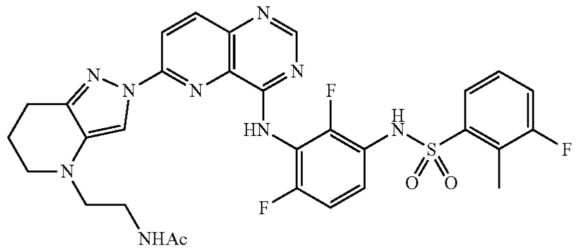

Example 383

Step 1: isomer b from step 4 of Examples 339/340 (30.0 mg, 53.0 μmol) and N-boc-2-aminoacetaldehyde (26.6 mg, 159 μmol) were dissolved in MeOH (530 μL). After 5 min, sodium triacetoxyborohydride (57.6 mg, 265 μmol) was added to the solution. Reaction was stirred at room temperature overnight. Reaction was purified directly on a reverse phase column, using 0-40-70% ACN in 10 mM ammonium formate. The desired carbamate analog came out at 55% ACN in 10 mM ammonium formate and appropriate fractions lyophilized to a yellow solid (7.5 mg, 20% yield): ($ES^+$) M+H=710.0.

Step 2 (Example 362, Table 4): To the carbamate from step 1 (30.0 mg, 53 μmol) in dioxane (500 μL) was added hydrochloric acid (4.00 M in dioxane, 26.4 μL, 106 μmol). Reaction was stirred at room temperature overnight. Volatiles were removed under reduced pressure and the residue was purified directly on a reverse phase column, using 0-20-40% ACN in 10 mM ammonium formate. The compound of Example 362 came out at 30% ACN in 10 mM ammonium formate as a yellow solid after lyophilisation (5.10 mg, 79% yield).

Step 3 (Example 383, Table 4): to a $CH_2Cl_2$ (0.5 mL) and AcOH (0.05 mL) solution of compound 362 (21.5 mg, 35.3 μmol) was added acetic anhydride (3.7 μL, 38.8 umol), followed by N,N-diisopropylethylamine (9.3 μL, 52.9 umol). Reaction was stirred at room temperature overnight. Volatiles were removed under reduced pressure and the residue was purified directly on a reverse phase column, using 0-40-60% ACN in 10 mM ammonium formate. The compound of Example 383 came out at 60% ACN in 10 mM ammonium formate and was obtained as a yellow solid after lyophilisation (10.8 mg, 47% yield).

Preparation of Example 369 (Table 4)

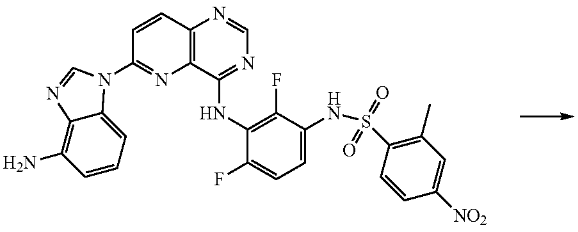

Example 368

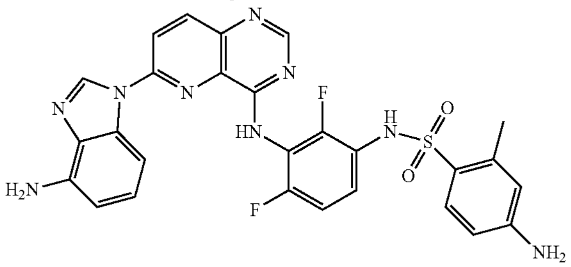

Example 369

To a solution of the nitroarene of Example 368 (26 mg, 0.043 mmol) in MeOH/DCM 1:1 (1 mL) was added 5% palladium hydroxide on carbon (23 mg, 0.0084 mmol) and stirred under 1 atm of $H_2$ for 16 h. Upon completion, the suspension was filtered and concentrated under vacuum. The residu was diluted with DMSO and purified by HPLC with MeCN in 0.1% aq. formic acid to give the compound of Example 369 (2.0 mg, 20%). $^1H$ NMR (400 MHz, acetic_acid-d4) δ: 9.18 (br. s., 1H), 8.57-8.84 (m, 2H), 8.42 (d, J=9.00 Hz, 1H), 8.08 (s, 1H), 7.51-7.69 (m, 2H), 7.29 (td, J=3.96, 8.12 Hz, 1H), 6.98-7.18 (m, 1H), 6.84 (d, J=7.83 Hz, 1H), 6.57 (s, 1H), 6.52 (d, J=8.61 Hz, 1H), 2.53 (s, 3H) MS m/z 574.2 ($MH^+$).

Preparation of Examples 375, 350 and 351 (Table 4)

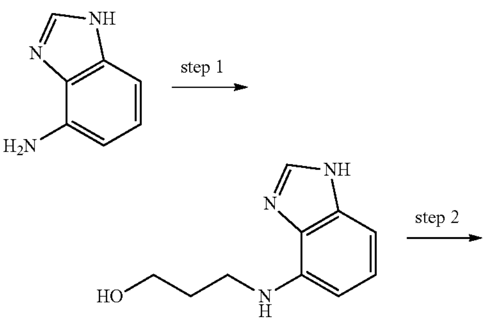

-continued

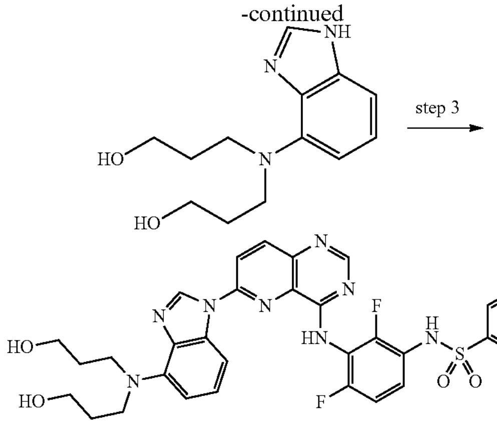

Example 375

Example 350

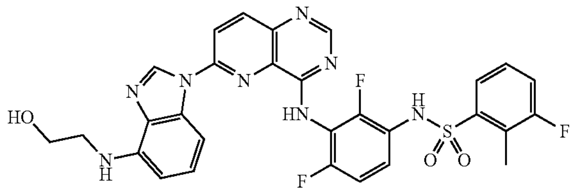

Example 351

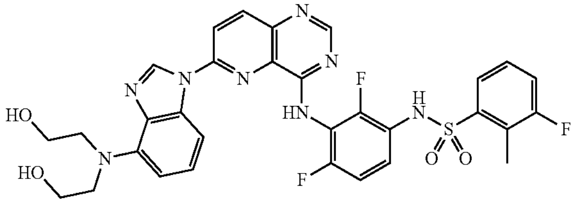

Step 1: 3-[tert-)Butyl(dimethyl)silyl]oxypropanal (0.38 mL, 1.80 mmol was added to a solution of 1H-benzimidazol-4-amine (80 mg, 0.601 mmol) in MeOH (7.5 mL). The reaction was heated to 50° C. for 20 min and then cooled to room temperature. Sodium cyanoborohydride (0.151 g, 2.40 mmol) was added and the reaction was stirred at 50° C. for 16 h. The solvent was removed under reduced pressure and then DCM (3 mL) was added followed by TFA (3 mL). The reaction was allowed to stir at room temperature for 30 min. The solvent was removed under reduced pressure and the crude was dissolved in MeOH. IRA-67 resin was added and the solution was filtered through a cotton plug and then concentrated under reduced pressure to afford 3-(1H-benzimidazol-4-ylamino)propan-1-ol (60 mg, 53% yield). MS m/z 192.2 ($MH^+$).

Step 2: 3-[tert-Butyl(dimethyl)silyl]oxypropanal (98 μL, 0.471 mmol) was added to a solution of 3-(1H-benzimidazol-4-ylamino)propan-1-ol (60 mg, 0.314 mmol) in MeOH (3.1 mL). The reaction was heated to 50° C. for 15 min and was cooled to room temperature. Sodium cyanoborohydride (59 mg, 0.941 mmol) was added and then the reaction was heated to 50° C. and stirred for 10 h. LCMS analysis showed there was still a significant amount of starting material. The solvent was removed under reduced pressure and then DCM (3 mL) was added followed by TFA (3 mL). The reaction was allowed to stir at room temperature for 30 min and was concentrated. The crude was diluted with MeOH and IRA-67 resin was added. The mixture was filtered through a plug of cotton. Sodium cyanoborohydride (3.00 eq, 59 mg, 0.941 mmol) was added. The reaction was heated to 50° C. and left to stir over the weekend. Upon completion, TFA (1 mL) and IRA-67 were added. The resulting mixture was filtered and the solution was concentrated. The crude material was left under vacuum for 2 days to afford 3-[1H-benzimidazol-4-yl(3-hydroxypropyl)amino]propan-1-ol (32 mg, 41% yield). MS m/z 250.2 ($MH^+$).

Step 3 (Example 375, Table 4): the benzimidazole fragment from step 2 was coupled to the chloropyridine A-13 (Ar=3-fluoro-2-methylphenyl) using copper/BINOL catalysis as described for Example 1 (step 4) in general method A.

Example 350 (Table 4) was prepared in a similar fashion using 2-[tert-butyl(dimethyl)silyl]oxyacetaldehyde for step 1. The monoalkylated 4-aminobenzimidazole obtained in step 1 was then converted to the compound of Example 350 using the procedure described above for step 3.

Example 351 (Table 4) was prepared in the same fashion as Example 375 using 3-[tert-butyl(dimethyl)silyl]oxyacetaldehyde for both steps 1 and 2.

Preparation of Examples 376 and 384 (Table 4)

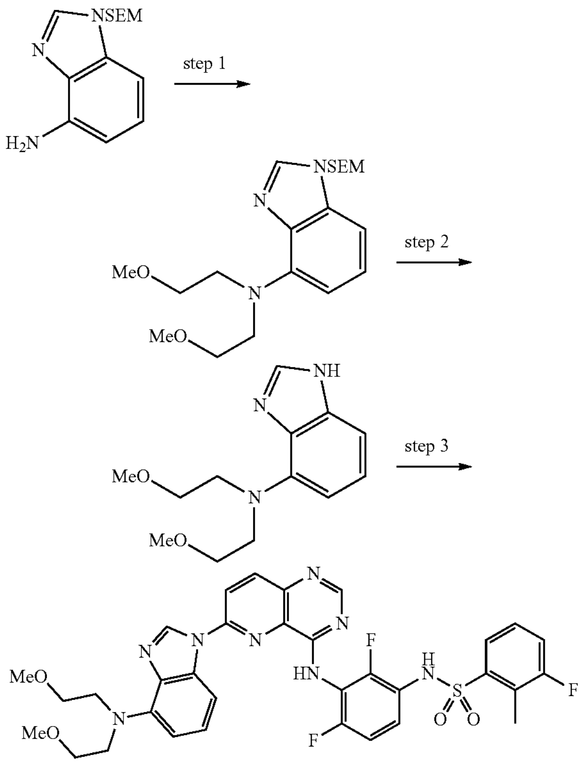

Example 376

Example 384

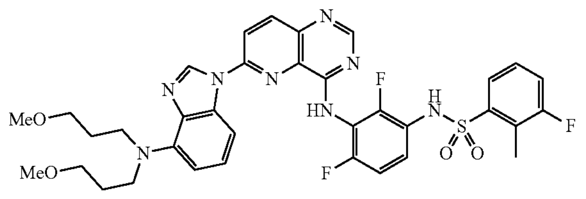

Step 1: A solution of LiHMDS (1 M in THF, 0.76 mL, 0.759 mmol) was added to a solution of 1-(2-trimethylsilylethoxymethyl)benzimidazol-4-amine (described in WO 202105591) (50 mg, 0.190 mmol) in DMF (1.9 mL). The resulting mixture was stirred for 20 min at rt and 1-bromo-2-methoxyethane (6.00 eq, 107 μL, 1.14 mmol) was added. The reaction was stirred at RT for 45 min. Next, an additional 6 eq. of 1-bromo-2-methoxyethane (107 μL) and the resulting mixture was stirred for 2 days. Upon completion, a solution of $NH_4Cl$ (saturated in water) was added and the aqueous mixture was extracted with EtOAc. The organics were combined, dried by $MgSO_4$, filtered and concentrated. The crude was purified by column chromatography (silica gel, 0-80% EtOAc in hexanes) to afford N,N-bis(2-methoxyethyl)-1-(2-trimethylsilylethoxymethyl)benzimidazol-4-amine (40 mg, 56% yield) as a light yellow oil. MS m/z 380.4 ($MH^+$).

Step 2: N,N-bis(2-Methoxyethyl)-1-(2-trimethylsilylethoxymethyl)benzimidazol-4-amine (40 mg, 0.105 mmol) in a mixture of TFA (1 mL) and DCM (1 mL). The reaction was allowed to stir at room temperature for 1 h and and was heated to 40° C. for 1.5 h. The reaction was cooled to room temperature. The reaction was concentrated under reduced pressure and then re-dissolved in MeOH. IRA-67 resin was added and the mixture was filtered through a plug of cotton. The solution was concentrated under reduced pressure to afford N,N-bis(2-methoxyethyl)-1H-benzimidazol-4-amine (26 mg, 100% yield) as a yellow-brown oil. MS m/z 250.2 ($MH^+$).

Step 3 (Example 376, Table 4): the benzimidazole fragment from step 2 was coupled to the chloropyridine A-13 (Ar=3-fluoro-2-methylphenyl) using copper/BINOL catalysis as described for Example 1 (step 4) in general method A.

The compound of Example 384 (Table 4) was prepared in a similar fashion using 1-bromo-3-methoxypropane in step 1: MS m/z 278.4 ($MH^+$).

Preparation of Example 382 (Table 4)

Step 1: A solution of 1-(p-toluenesulfonyl)pyrrole (5 g, 22.6 mmol) prepared as described in WO2021/97057 page 2021 in dry $CH_3CN$ (100 mL) was cooled in an ice-bath and treated drop wise with chlorosulfonic acid (9.0 mL, 136 mmol). The reaction mixture was allowed to warm to room temperature and stirred for 72 h. Upon completion, the mixture was thereafter poured on ice/water and a precipitation occured. The solid was filtered to provide 1-(p-tolylsulfonyl)pyrrole-3-sulfonyl chloride (2.53 g, 35% yield). MS m/z ($MH^+$).

Step 2: To a vial with a stirring bar was added the 1-(p-tolylsulfonyl)pyrrole-3-sulfonyl chloride (86 mg, 0.27 mmol) from step 1 in anhydrous THF (2 mL). To this solution, DIEA (0.094 mL, 0.541 mmol) and N,N,N"-trimethylethylenediamine (0.042 mL, 0.325 mmol) were added. The resulting solution was stirred at room temperature for 1 h. After completion, 10% aqueous KOH (2 mL) was added dropwise. The reaction was heated at 60° C. overnight. After completion, the reaction mixture was diluted with EtOAc and aq. $NH_4Cl$ was added. The layers were separated. The organic layer was washed with brine then dried over $MgSO_4$, filtered and concentrated to dryness to afford N-[2-(dimethylamino)ethyl]-N-methyl-1H-pyrrole-3-sulfonamide (48 mg, 77% yield) as a light orange oil. $^1$H NMR (400 MHz, $CDCl_3$) δ: ppm 2.35-2.48 (m, 6H) 2.61-2.85 (m, 6H) 3.01-3.24 (m, 2H) 6.46 (br. s., 1H) 6.85 (br. s., 1H). MS m/z 232.2 ($MH^+$).

Step 3 (Example 382, Table 4): the pyrrole fragment from step 2 was coupled to the chloropyridine A-13 (Ar=3-fluoro-2-methylphenyl) using copper/BINOL catalysis as described for Example 1 (step 4) in general method A.

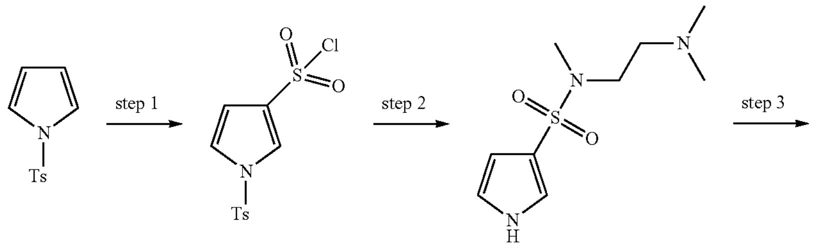

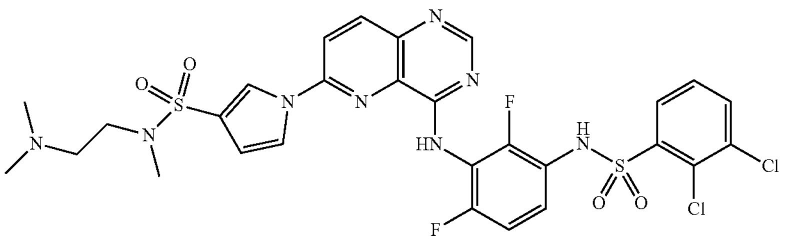

Example 382

Preparation of Example 391 (Table 4)

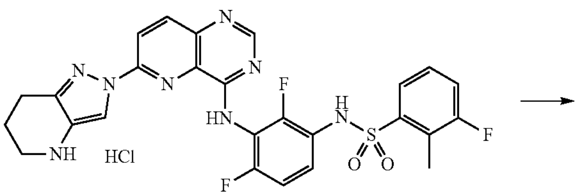

isomer b

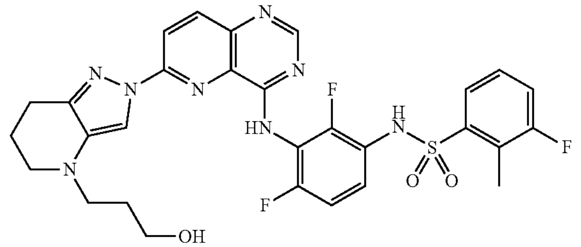

Example 391

Isomer b from step 4 of Examples 339/340 (28.3 mg, 49.9 umol) was added to 3-hydroxypropanal (22.2 mg, 300 μmol), then DCE (1.0 mL) was added, followed by one drop of AcOH and sodium triacetoxyborohydride (65.1 mg, 300 μmol). Reaction was stirred at room temperature overnight. Reaction was purified on prep-HPLC, and the compound of Example 391 (6.3 mg, 20% yield) was obtained as a white solid.

Preparation of Example 392 (Table 4)

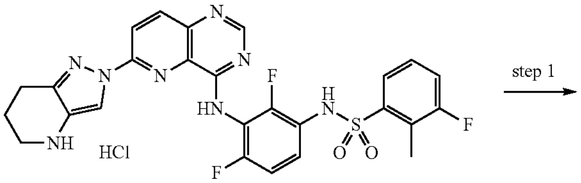

isomer b

-continued

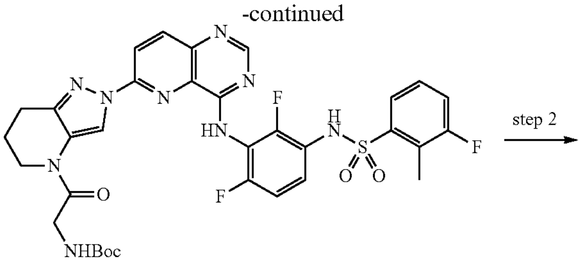

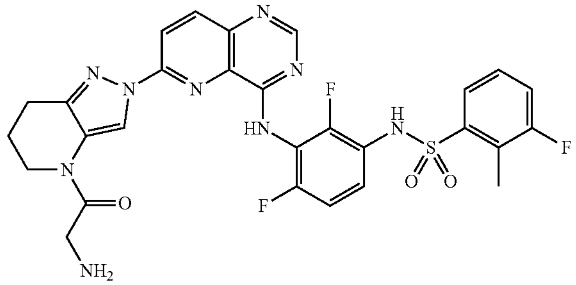

Example 392

Step 1: isomer b from step 4 of Examples 339/340 (30.0 mg, 53.0 μmol), N,N-diisopropylethylamine (23.2 μL, 132 μmol) and Boc-Gly-OH (11.4 mg, 63.5 μmol) were dissolved in DMF (600 μL). To the solution was added HATU (30.8 mg, 79.4 μmol). Reaction was stirred at room temperature overnight. Water (5.00 mL) was added to the reaction and the precipitated product was filtered to yield the desired carbamate (38.0 mg, 99% yield) as a beige solid: ($ES^+$) M+H=724.3.

Step 2 (Example 392, Table 4): to a dioxane (1.00 mL) solution of the product from step 1 (38.0 mg, 52.5 μmol), was added HCl (4 M in dioxane (131 μL, 525 μmol). Reaction was stirred at room temperature over the weekend. Volatiles were removed under reduced pressure and the residue was purified by reverse phase column with 0-20-40% ACN in 10 mM ammonium formate. The compound of Example 392 came out at 25% ACN in 10 mM ammonium formate and was obtained as a white solid after lyophilisation (27.6 mg, 84% yield).

Preparation of Example 414 (Table 4)

The compound of Example 414 was prepared in an analogous fashion as the compound of Example 392 except isomer b from step 4 of Examples 339/340 was used.

Preparation of Example 415 (Table 4)

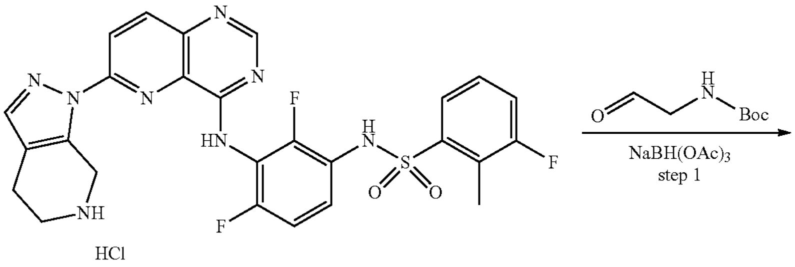

isomer b

-continued

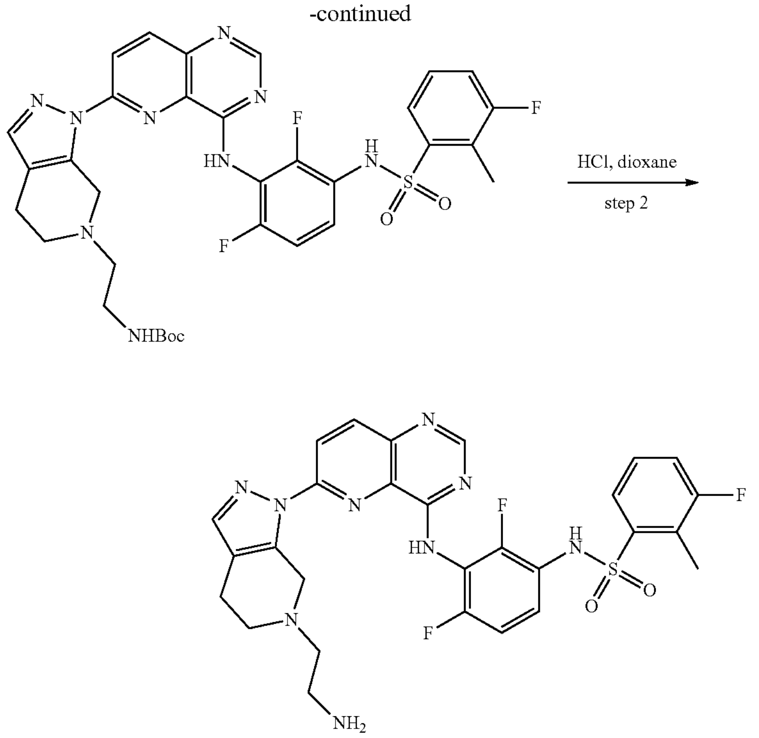

Example 415

Step 1: isomer b from step 4 of Examples 339/340 (15.0 mg, 26.5 μmol) and N-boc-2-aminoacetaldehyde (13.3 mg, 79.4 μmol) were dissolved in DCE (375 μL). After 5 min sodium triacetoxyborohydride (17.3 mg, 79.4 μmol) was added to the solution. Reaction was stirred at room temperature overnight. Reaction was quenched with water (5.00 mL) and extracted by DCM (5 mL×3). Combined organic layers were concentrated under reduced pressure and the resulting crude residue 7a (18.8 mg, 100% yield) was used directly in the next step: ($ES^+$) M+H=710.3.

Step 2: the crude product from step 1 (18.8 mg, 26.5 μmol) was dissolved in dioxane (250 μL), then HCl (4 M in dioxane, 66.3 μL, 265 μmol) was added. Reaction was stirred at room temperature overnight. Volatiles were removed under reduced pressure and the residue was purified by reverse phase column with 0-20-40% ACN in 10 mM ammonium formate. The compound of Example 415 came out at 25% ACN in 10 mM ammonium formate and was obtained as a white solid (formic acid salt form) after lyophilisation (8.20 mg, 51% yield).

Preparation of Example 420 (Table 4)

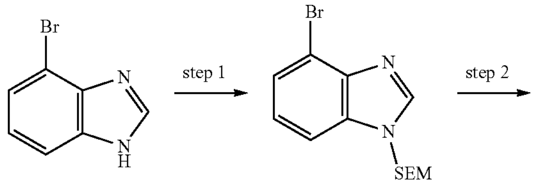

-continued

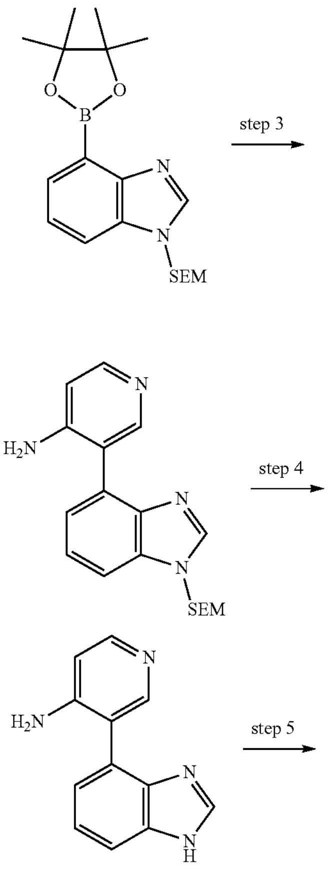

-continued

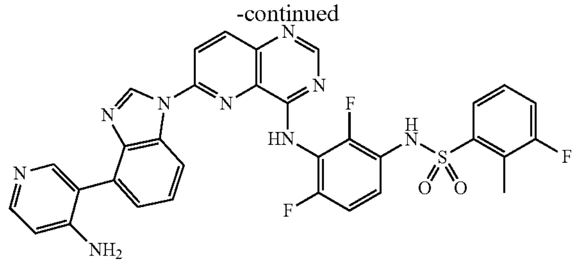

Example 420

Step 1: To a 100 mL round-bottom flask, was added 4-bromo-1H-benzimidazole (1.00 g, 5.08 mmol), 2-(trimethylsilyl)ethoxymethyl chloride (1.1 mL, 6.09 mmol) and 60% NaH (244 mg, 6.09 mmol) in anhydrous DMF (10 mL). The reaction was allowed to stir at room temperature for 1 h. Upon completion, the reaction was quenched with sat. $NH_4Cl$ and then extracted EtOAc (×3). The organics were collected washed with brine, separated then dried by $MgSO_4$, filtered and then concentrated under reduced pressure. The crude material was loaded onto Celite and then purified on $SiO_2$ with EtOAc in hexanes to afford 2-[(4-bromobenzimidazol-1-yl)methoxy]ethyl-trimethyl-silane (1.18 g, 71% yield) as a brown oil. MS m/z 327.2 ($MH^+$).

Step 2: To a flame-dried 5 mL microwave vial, was added 2-[(4-bromobenzimidazol-1-yl)methoxy]ethyl-trimethyl-silane (500 mg, 1.53 mmol) and bis(pinacolato)diboron (776 mg, 3.06 mmol) in DMF (0.30 mL) under a $N_2$ atmosphere. Next, 1,1'-bis(diphenylphosphino)ferrocene-palladium(ii) dichloride dichloromethane complex (279 mg, 0.382 mmol) and potassium acetate (450 mg, 4.58 mmol) were added to the solution. The reaction was sparged with a balloon of argon for a few minutes, sealed and then heated to 100° C. and left to stir for 16 h. The reaction was cooled to room temperature. The crude reaction was used as a crude mixture in the next step.

Step 3: To the crude reaction, were added 4-amino-3-bromopyridine (34 mg, 0.20 mmol), tetrakis(triphenylphosphine)palladium(0) (35 mg, 0.0305 mmol) and sodium carbonate (97 mg, 0.914 mmol). The reaction was sparged with a balloon of Argon for ~5-10 min, sealed and then heated to 100° C. for 24 h. Upon completion, the reaction was cooled to room temperature. The reaction was diluted with brine and extracted with EtOAc (×3). The organics were collected, dried by $MgSO_4$, filtered and then concentrated under reduced pressure. The crude material was loaded onto Celite and then purified on $SiO_2$ with MeOH in DCM to afford 3-[1-(2-trimethylsilylethoxymethyl)benzimidazol-4-yl]pyridin-4-amine (72 mg, 69% yield) as a brown film. MS m/z 341.2 ($MH^+$).

Step 4: To a 20 mL scintillation vial, was added 3-[1-(2-trimethylsilylethoxymethyl)-benzimidazol-4-yl]pyridin-4-amine (72 mg, 0.210 mmol) in DCM (2 mL) and TFA (2 mL). The reaction was left to stir at room temperature for 16 h. Upon completion, the solvent was removed under reduced pressure and then dried under vacuum to afford 3-(1H-benzimidazol-4-yl)pyridin-4-amine TFA salt (68 mg, 100% yield) as a brown oil. MS m/z 211.2 ($MH^+$).

Step 5 (Example 420, Table 4): the benzimidazole fragment from step 4 was coupled to the chloropyridine A-13 (Ar=3-fluoro-2-methylphenyl) using copper/BINOL catalysis as described for Example 1 (step 4) in general method A.

Preparation of Example 424 (Table 4)

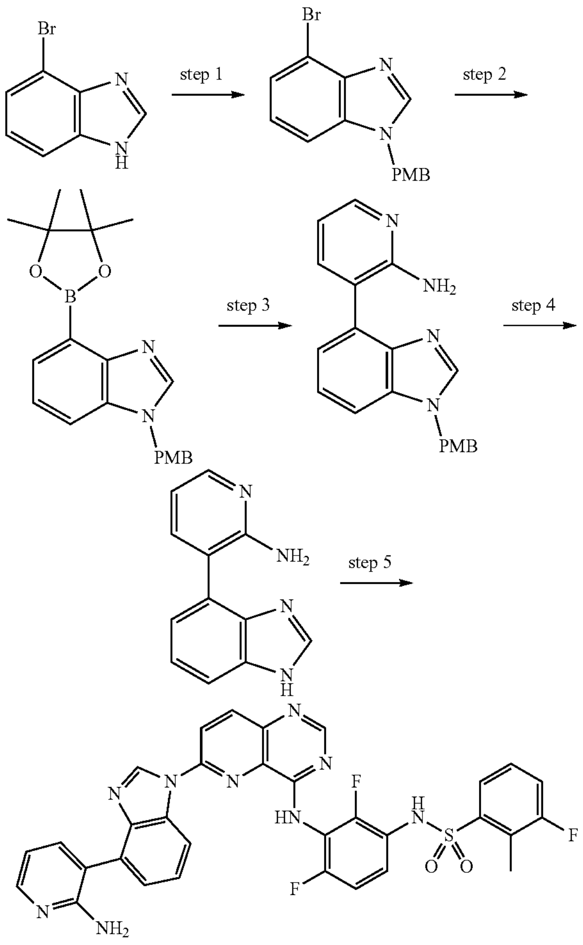

Example 424

Step 1: To a 20 mL scintillation vial, was added 4-bromo-1H-benzimidazole (500 mg, 2.54 mmol), 60% NaH (122 mg, 3.05 mmol) and 4-methoxybenzyl chloride (413 μL, 3.05 mmol) in DMF (5 mL). The reaction was allowed to stir at room temperature for 2 h. The reaction was quenched with sat. $NH_4Cl$ and then extracted with EtOAc (×3). The organics were collected, dried by $MgSO_4$, filtered and then concentrated under reduced pressure. The crude material was loaded onto Celite and then purified on $SiO_2$ with EtOAc in hexanes to afford 4-bromo-1-[(4-methoxyphenyl)methyl]benzimidazole (735 mg, 91% yield) as a brown oil. $^1H$ NMR (400 MHz, DMSO-d6) δ: 8.50 (s, 1H), 7.57 (dd, J=8.2, 0.8 Hz, 1H), 7.29 (ddd, J=8.6, 3.1, 2.0 Hz, 2H), 7.14 (t, J=7.8 Hz, 2H), 6.86-6.89 (m, 2H), 5.43 (s, 2H), 3.70 (s, 3H). Minor isomer: 8.46 (s, 1H), 7.70 (dd, J=8.0, 1.0 Hz, 1H), 7.42 (d, J=7.8 Hz, 2H), 7.04 (d, J=9.0 Hz, 2H), 6.90 (m, J=3.5 Hz, 2H), 5.72 (s, 2H), 3.70 (s, 3H). MS m/z 317.2 ($MH^+$).

Step 2: To a flame-dried 5 mL microwave vial, was added the protected benzimidazole from step 1 (200 mg, 0.631 mmol) and bis(pinacolato)diboron (320 mg, 1.26 mmol) in DMF (0.3000 mL) under a $N_2$ atmosphere. Next, 1,1'-bis(diphenylphosphino)ferrocene-palladium(ii)dichloride dichloromethane complex (231 mg, 0.315 mmol) and then potassium acetate (186 mg, 1.89 mmol) was added to the solution. The reaction was sparged with a balloon of argon for a few minutes, sealed and then heated to 100° C. and left to stir for 24 h. The reaction was cooled to room temperature. The reaction was extracted diluted with brine and extracted with EtOAc (x3). The organics were collected, dried by $MgSO_4$, filtered through a plug of celite and then concentrated under reduced pressure. The crude material was loaded onto Celite and then purified on $SiO_2$ with EtOac in hexanes. The desired fractions were collected and concentrated under reduced pressure to afford 1-[(4-methoxyphenyl)methyl]-4-(4,4,5,5-tetramethyl-1,3,2-dioxaborolan-2-yl)benzimidazole (82 mg, 36% yield) as a brown oil. MS m/z 365.4 ($MH^+$).

Step 3: To a flame-dried 5 mL microwave vial, was added 1-[(4-methoxyphenyl)methyl]-4-(4,4,5,5-tetramethyl-1,3,2-dioxaborolan-2-yl)benzimidazole (56 mg, 0.154 mmol) and 2-amino-3-bromopyridine (35 mg, 0.200 mmol) under a $N_2$ atmosphere. Next, sodium carbonate (49 mg, 0.461 mmol) and then tetrakis(triphenylphosphine)palladium(0) (18 mg, 0.0154 mmol) were added to the solution. The reaction was sparged with a balloon of argon for ~5-10 min, sealed and then heated to 80° C. and left to stir 16 h. The reaction was cooled to room temperature. The reaction was diluted with brine and extracted with EtOAc (x3). The organics were collected, dried by MgSO4, filtered and then concentrated under reduced pressure. The crude material was loaded onto Celite and then purified on $SiO_2$ with MeOH in DCM. The desired fractions were collected and concentrated under reduced pressure to afford 3-[1-[(4-methoxyphenyl)methyl]benzimidazol-4-yl]pyridin-2-amine (15 mg, 0.0445 mmol, 29% yield) as a white solid. MS m/z 331.2 ($MH^+$).

Step 4: To a 20 mL scintillation vial, was added 3-[1-[(4-methoxyphenyl)methyl]-benzimidazol-4-yl]pyridin-2-amine (15 mg, 0.0445 mmol) in TFA (2 mL). The reaction was heated to 80° C. and stirred for 96 h. The solvent was removed under reduced pressure and then the product was co-evaporated with Toluene (x3) to afford 3-(1H-benzimidazol-4-yl)pyridin-2-amine TFA salt (14 mg, 100%). MS m/z 211.2 ($MH^+$).

Step 5 (Example 424, Table 4): the benzimidazole fragment from step 4 was coupled to the chloropyridine A-13 (Ar=3-fluoro-2-methylphenyl) using copper/BINOL catalysis as described for Example 1 (step 4) in general method A.

Preparation of Examples 425 and 460 (Table 4)

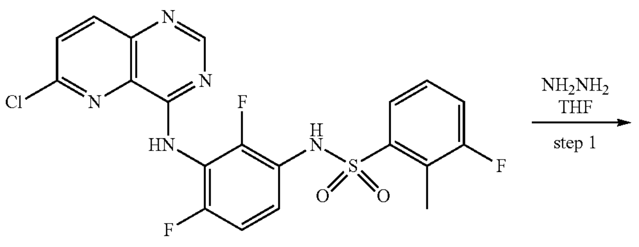

A-13

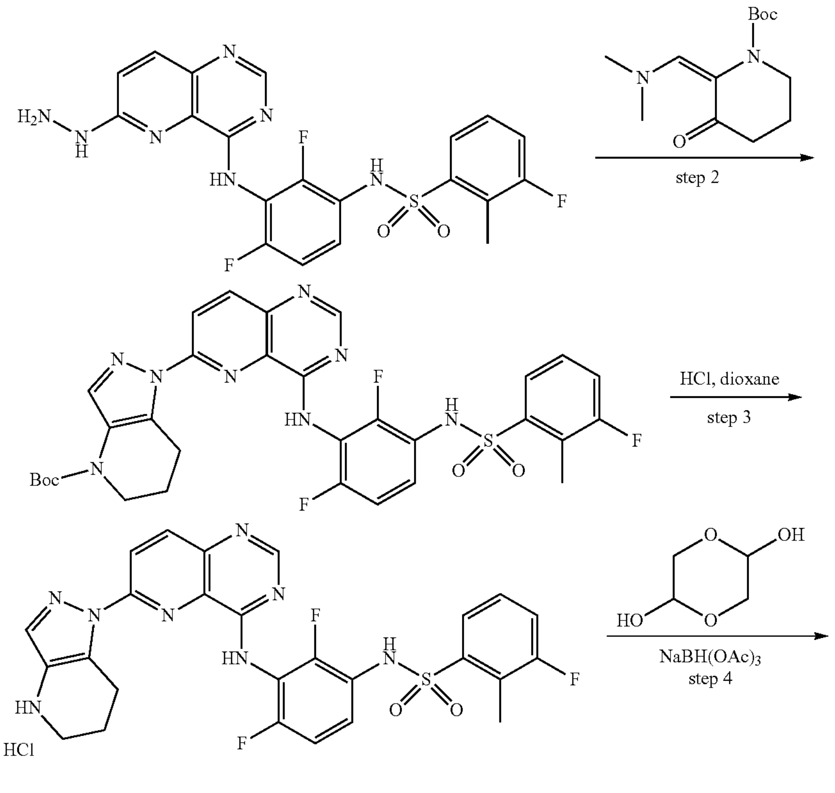

-continued

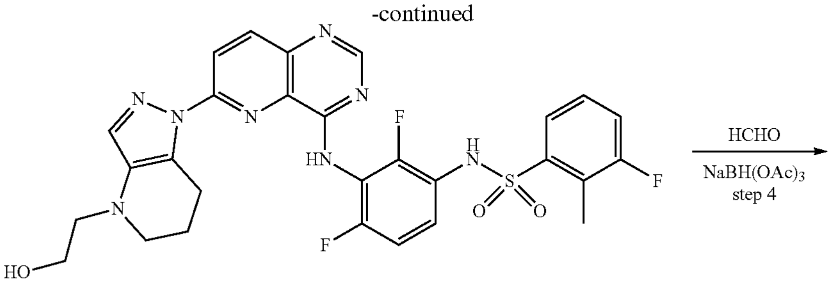

Example 425

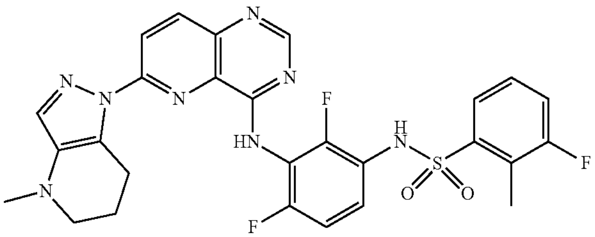

Example 460

Step 1: Compound A-13 (800 mg, 1.67 mmol) and hydrazine (1.00 M solution in THF, 3.33 mL, 3.33 mmol) were mixed in THF (6.67 mL). Reaction was stirred at 80° C. overnight. Reaction was cooled to room temperature and hexanes (50 mL) were added. The solid formed was filtered and washed with hexanes (5 mL×2). It was dried under air circulation, yielding 819 mg of beige solid. The crude solid product was further purified by 0-10% MeOH in $CH_2Cl_2$. Desired product came out at 10% MeOH in DCM, yielding the expected hydrazine derivative (550 mg, 69% yield) as a beige solid: ($ES^+$) M+H=476.1.

Step 2: the product from step 1 (350 mg, 736 μmol) and the crude vinylogous amide obtained in step 1 of Examples 339/340 (206 mg, 810 μmol) were mixed in EtOH (3.68 mL), the reaction was stirred at room temperature overnight. Reaction was concentrated to remove EtOH, and AcOH (5.25 mL) was added. Reaction was stirred at 80° C. for 1 h. Volatiles were removed under reduced pressure and the residue was purified by reverse phase column with 0-50-100% ACN in 10 mM ammonium formate. The desired pyrrazole derivative (85 mg, 17% yield) came out at 90% ACN in 10 mM ammonium formate as a white solid after lyophilisation: ($ES^+$) M+H=667.2.

Step 3: to a dioxane (637 μL) solution of the product from step 2 (85.0 mg, 127 μmol), was added HCl (4 M in dioxane, 319 μL, 1.27 mmol). The reaction was stirred at room temperature overnight. HCl (4 M in dioxane, 0.5 mL, 1.98 mmol) was added and it was then heated to 50° C. for another day. The reaction was filtered and washed with dioxane (2.0 mL). The desired hydrochloride salt (70.0 mg, 97% yield) was obtained as a beige solid: ($ES^+$) M+H=567.3.

Step 4 (Example 425, Table 4): the hydrochloride salt from step 3 (20.0 mg, 35.3 μmol) and glycolaldehyde dimer (17.9 mg, 141 μmol) were dissolved in DCE (500 μL). After 5 min sodium triacetoxyborohydride (38.4 mg, 177 umol) was added to the solution. Reaction was stirred at room temperature for 2 h. Volatiles were removed under reduced pressure and the solid residue was purified by reverse phase with 0-20-50% ACN in 10 mM ammonium bicarbonate. The title compound 425 was obtained as a yellow solid after lyophilisation (8.00 mg, 37% yield).

Step 4 (Example 460, Table 4): the hydrochloride salt from step 3 (15.0 mg, 26.5 μmol) and aqueous formaldehyde (9.86 μL, 132 umol) were dissolved in DCE (265 μL). To the solution was added sodium triacetoxyborohydride (28.8 mg, 132 μmol) followed by AcOH (1 drop). Reaction was stirred at room temperature overnight. Volatiles were removed under reduced pressure. To the solid residue was added MeOH (1.00 mL) and water (10 mL). Mixture was filtered to obtain solid A, which was kept aside. The resulting filtrate was extracted with ethyl acetate (5 mL×5). Organic layers were combined and concentrated to yield solid B. Solids A and B were combined and MeOH (2 mL) was added. The slurry was heated to 80° C. until solid dissolved. It was then cooled to room temperature, and was filtered to obtain the compound of example 460 (11.3 mg, 74% yield) as a yellow solid.

Examples 443 and 444 (Table 4)

These two analogs were prepared following general method G using 5-fluoroindole as starting material and the appropriate amines. The indole sulfonamides were coupled to the chloropyridine A-13 (Ar=2,3-dichlorophenyl) using copper/BINOL catalysis as described for Example 1 (step 4) in general method A.

Preparation of Examples 447, 456, 457 and 461 (Table 4)

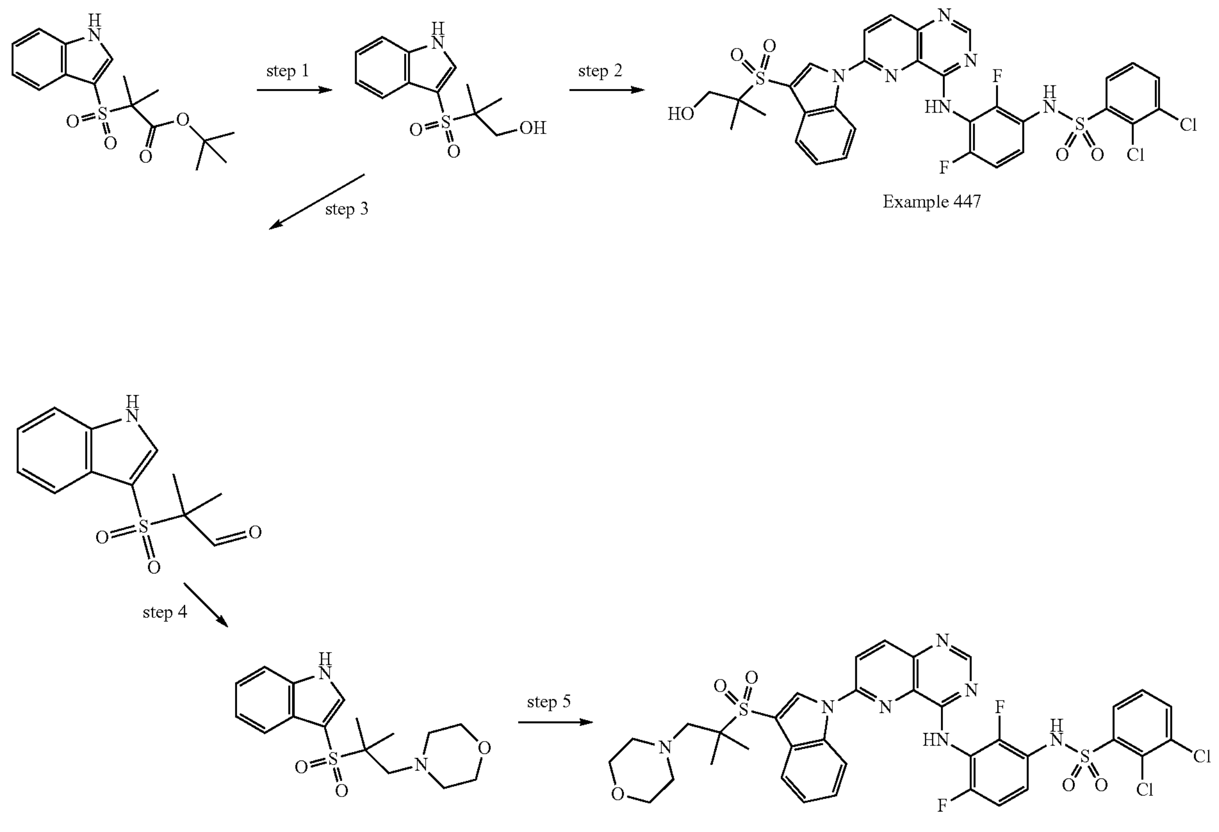

Example 447

Example 457

Step 1: the 3-indolesulfone ester was prepared from 1H-indol-3-yl-thiocyanate (*Phosphorus, Sulfur and Silicon and the Related Elements* 2014, 189, 1378) as described under general method H. To a solution of this material (100 mg, 0.309 mmol) in DCM (3 mL) at −78° C. was added a 1M solution of diisobutylaluminum hydride (2.5 mL, 3.72 mmol) in two portions. The reaction mixture was warmed to room temperature and stirred 2 h. The reaction mixture was diluted with diethyl ether (30 mL) and cool to 0° C. The reaction was quenched by a slow addition of 0.15 mL water followed by 0.15 mL of 15% aqueous sodium hydroxide and 0.37 mL water. The solution was warmed to room temperature and stirred 15 min. Anhydrous magnesium sulfate was added to the stirred solution. After 15 min, the suspension was filtered to remove salts. Evaporation to dryness gave the corresponding alcohol (68 mg, 87%) as a solid. $^1$H NMR (400 MHz, $CDCl_3$) δ: 8.91 (br. S., 1H), 7.87-8.08 (m, 1H), 7.81 (d, J=3.13 Hz, 1H), 7.43-7.61 (m, 1H), 7.32-7.43 (m, 2H), 3.81 (d, J=6.65 Hz, 2H), 1.39 (s, 6H). MS m/z 254.2 ($MH^+$).

Step 2 (Example 447, Table 4): indole sulfone from step 1 was coupled to the chloropyridine A-13 (Ar=2,3-dichlorophenyl) using copper/BINOL catalysis as described for Example 1 (step 4) in general method A.

Step 3: A stirred solution of the alcohol from step 1 (350 mg, 1.38 mmol) in DCM (4 mL) was treated with 1,1,1-tris (acetyloxy)-1,1-dihydro-1,2-benzodioxol-3-(1 h)-one (1289 mg, 3.04 mmol. After 2 h at RT, a saturated aq. $Na_2SO_3$ (1.0 mL) and a saturated aq. $NaHCO_3$ (1.0 mL) were added, and then the biphasic mixture was stirred for 30 min. The mixture was diluted with DCM (3 mL), the layers were separated, and then the aqueous layer was extracted with $CH_2Cl_2$ (2×4 mL). The combined organic extracts were dried with $MgSO_4$, filtered, and concentrated to afford the desired aldehyde intermediate (350 mg, 96%). 1H NMR (400 MHz, $CDCl_3$) δ: 9.86 (s, 1H), 8.88 (br. s., 1H), 7.87-7.98 (m, 1H), 7.73 (d, J=3.13 Hz, 1H), 7.44-7.52 (m, 1H), 7.29-7.40 (m, 2H), 1.55 (s, 6H). MS m/z 250.2 (MH−).

Step 4: The aldehyde from step 3 (30 mg, 0.119 mmol) and morpholine (0.021 mL, 0.239 mmol) were mixed in ACN (1 mL) with one drop of Acetic acid and stirred 16 h at 70° C. Then DCE was added followed by sodium triacetoxyborohydride (127 mg, 0.597 mmol) and the resulting suspension was stirred at room temperature for 16 h. The reaction was quenched by adding a saturated aq. $NaHCO_3$ (5 mL) and stirred for 15 min. The solution was extracted with EtOAc (3×10 mL). The organic phase was washed with brine (10 mL), separated, dried over $MgSO_4$, filtered an concentrated under vacuum to afford the desired aminosulfone (29 mg, 75%). MS m/z 286.2 (MH−).

Step 5 (Example 457, Table 4): indole sulfone from step 4 was coupled to the chloropyridine A-13 (Ar=2,3-dichlorophenyl) using copper/BINOL catalysis as described for Example 1 (step 4) in general method A to provide the compound of Example 457.

Other analogs in Table 4 (456 and 461) were prepared in this fashion using the appropriate amine in step 4.

Preparation of Example 465 (Table 4)

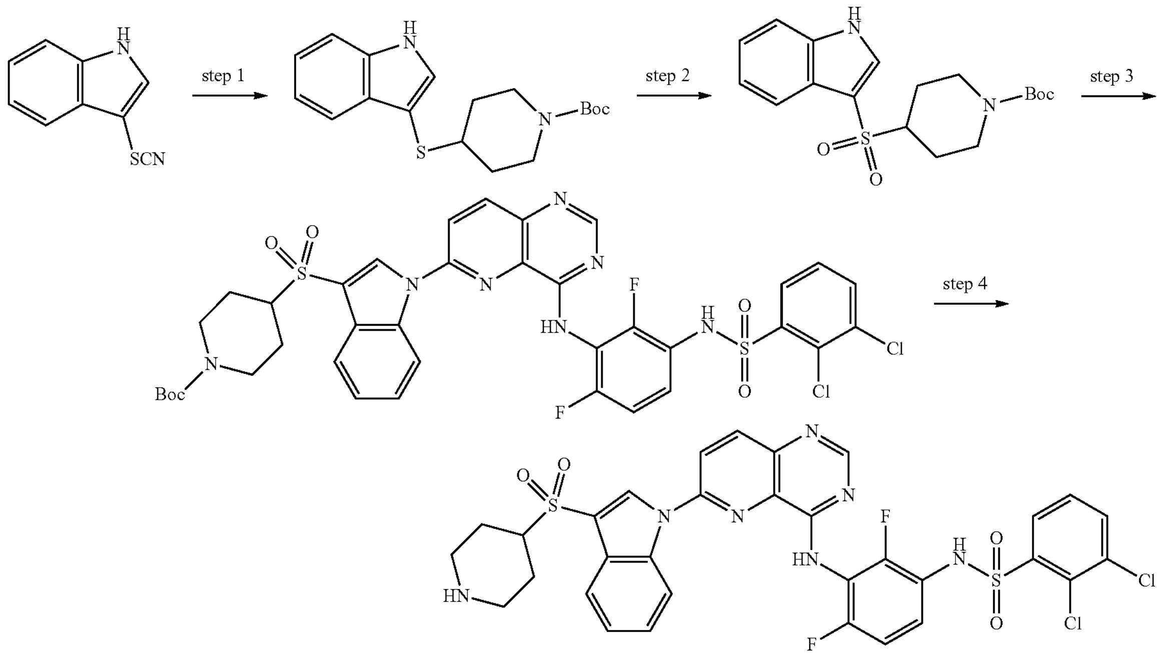

Example 465

Step 1: To a solution of 1H-indol-3-yl-thiocyanate (*Phosphorus, Sulfur and Silicon and the Related Elements* 2014, 189, 1378) (500 mg, 2.87 mmol) in iPrOH (15 mL) was added sodium sulfide nonahydrate (2068 mg, 8.61 mmol) dissolved in water 1 mL, then the resulting mixture was stirred at 50° C. for 2 h. After this time, 1-piperidinecarboxylic acid, 4-bromo-, 1,1-dimethylethyl ester (1.1 mL, 5.74 mmol) was added and stirred at 50° C. overnight. The reaction mixture was diluted with EtOAc (30 mL) and separated. The organic layer was washed with water (15 mL) followed by brine (15 mL), dried over $MgSO_4$ and then concentrated under vacuum to give the crude sulfide, which was used in the next step directly without further purification.

Step 2: The sulfide from step 1 was dissolved in DCM and 3-chloroperoxybenzoic acid (1486 mg, 8.61 mmol) was added and stirred at room temperature for 2 h. After completion, the reaction was quenched by adding 10 mL of a 1:1 solution sat. aq. $NaHCO_3$ and 10% aq. Na2SO3. The resulting suspension was stirred at room temperature for 15 min. EtOAc was added and the organic layer was separated. The organic layer was washed with water (15 mL) then saturated brine solution (15 mL). The organic layer was separated, dried ($MgSO_4$) and filtered before concentration to dryness. The residue was purified on silica gel with EtOAc in hexanes to provide the desired sulfone (985 mg, 94% yield). $^1H$ NMR (400 MHz, DMSO-$d_6$) δ:12.29 (br. s., 1H), 8.00 (d, J=3.13 Hz, 1H), 7.77 (d, J=7.43 Hz, 1H), 7.54 (d, J=7.83 Hz, 1H), 7.14-7.30 (m, 2H), 3.80-4.08 (m, 3H), 2.72 (br. s., 2H), 1.99 (s, 1H), 1.91 (d, J=10.96 Hz, 2H), 1.24-1.35 (m, 9H). MS m/z 365.2 ($MH^+$).

Step 3: indole sulfone from step 2 was coupled to the chloropyridine A-13 (Ar=2,3-dichlorophenyl) using copper/BINOL catalysis as described for Example 1 (step 4) in general method A.

Step 4 (Example 465, Table 4): the N-Boc-protected piperidone from step 3 (170 mg, 0.201 mmol) was stirred in TFA (1.0 mL, 13.1 mmol) for 30 minutes then concentrated under vacuum. The residue was co-evaporated with ACN to provide Example 465 (170 mg, 93%). $^1H$ NMR (400 MHz, DMSO-$d_6$) δ: 9.84 (s, 1H), 9.05 (s, 1H), 8.54 (s, 1H), 8.43-8.52 (m, 2H), 8.34 (d, J=8.61 Hz, 1H), 8.16 (s, 1H), 7.88-7.99 (m, 2H), 7.65 (dd, J=1.17, 7.83 Hz, 1H), 7.43-7.59 (m, 2H), 7.36 (t, J=8.02 Hz, 1H), 6.96-7.13 (m, 1H), 6.72-6.89 (m, 1H), 3.47-3.60 (m, 1H), 3.24 (br. s., 2H), 2.78 (t, J=11.93 Hz, 2H), 2.14 (d, J=12.13 Hz, 2H), 1.72 (d, J=9.39 Hz, 2H). MS m/z 744.3 ($MH^+$).

Preparation of Example 467 (Table 4)

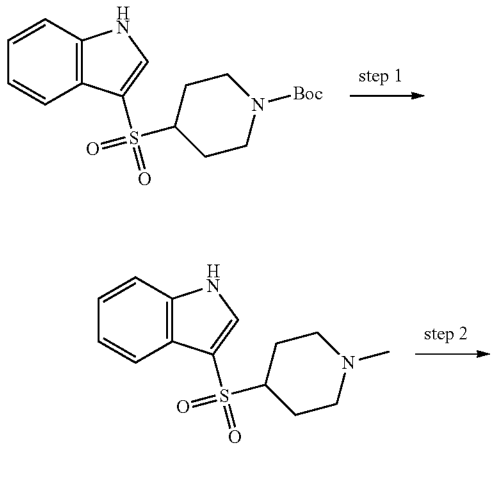

-continued

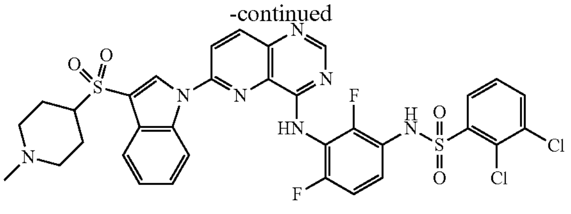

Example 467

Step 1: Lithium aluminum hydride (26 mg, 0.686 mmol) was added to a cold (0° C.) stirring solution of tert-butyl 4-(1H-indol-3-ylsulfonyl)piperidine-1-carboxylate (Example 465, step 2: 50 mg, 0.137 mmol) in $Et_2O$ 25 mL. After stirring 16 h at room temperature the reaction mixture was diluted with $Et_2O$ and cool at 0° C. The reaction was quenched by a slow addition of 0.150 mL water followed by 0.150 mL of 15% aqueous sodium hydroxide and 0.370 mL water. The solution was warmed to room temperature and stirred 15 min. Anhydrous magnesium sulfate was added to the stirred solution. After 15 min, the suspension was filtered to remove salts. Evaporation to dryness gave the desired N-Methylpiperidine sulfone (68 mg, 87%) as a solid. MS m/z 279.2 ($MH^+$).

Step 2: indole sulfone from step 1 was coupled to the chloropyridine A-13 (Ar=2,3-dichlorophenyl) using copper/BINOL catalysis as described for Example 1 (step 4) in general method A to provide the product of Example 467 after reverse phase HPLC with ACN in aq. 0.1% HCOOH.

Preparation of Examples 468-470 and 474-479 (Table 4)

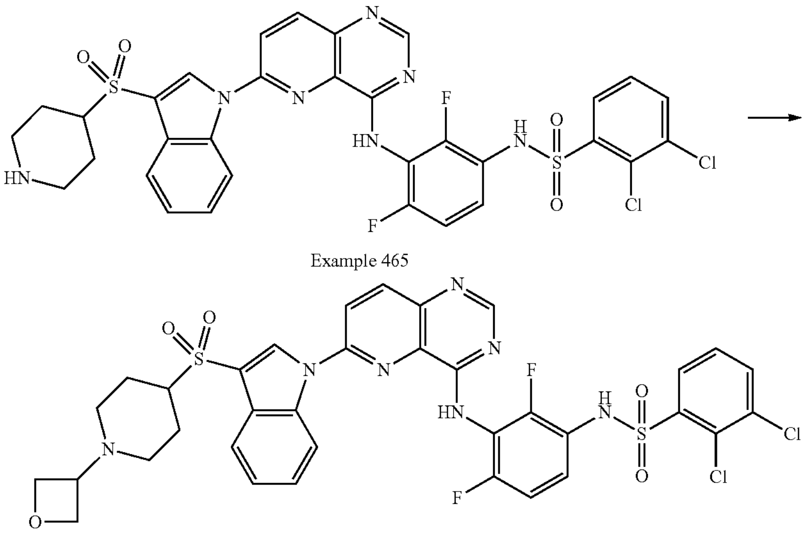

Example 465

Example 474

Example 465 (25 mg, 0.0291 mmol), 3-oxetanone (0.0055 mL, 0.0873 mmol) and DIEA (1 eq, 0.0051 mL, 0.0291 mmol) were suspended in DCE (1 mL) and stirred at 60° C. for 30 min. Then sodium triacetoxyborohydride (19 mg, 0.0873 mmol) was added and the suspension was stirred 16 h at 60° C. Upon completion, the solvent was removed under vaccum and the residu was purified on reverse phase HPLC with ACN in aq. 0.1% HCOOH to afford Example 474 (12 mg, 49%). $^1$H NMR (400 MHz, DMSO-$d_6$) δ: 9.97 (s, 1H), 8.92 (s, 1H), 8.36-8.64 (m, 4H), 8.28 (d, J=8.61 Hz, 1H), 7.83-8.03 (m, 3H), 7.44-7.50 (m, 3H), 7.42 (s, 1H), 4.38-4.51 (m, 2H), 4.31 (t, J=6.06 Hz, 3H), 2.72 (br. s., 2H), 2.31 (s, 1H), 1.99 (br. s., 2H), 1.75 (m, 2H), 1.63 (m, 2H). MS m/z 800.3 ($MH^+$).

Other examples were prepared in a similar fashion using the appropriate aldehyde or ketone and can be found in Table 4 (e.g. Examples 468-470 and 475-479).

Preparation of Example 472 (Table 4)

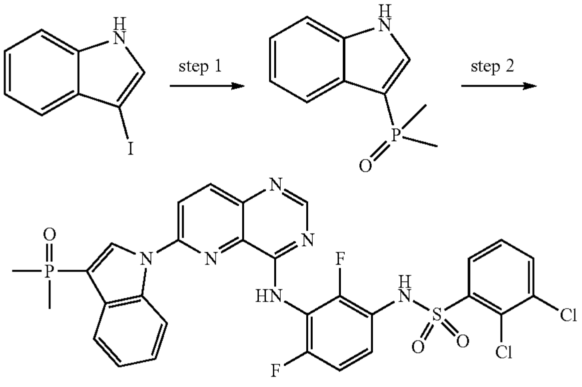

Example 472

Step 1: To a stirred suspension of 3-iodoindole (600 mg, 2.47 mmol) in dry dioxane (10 mL) at room temperature were added methylphosphonoylmethane (212 mg, 2.72 mmol), (9,9-dimethyl-9 h-xanthene-4,5-diyl)bis(diphenylphosphine) (143 mg, 0.247 mmol) and cesium carbonate (1207 mg, 3.70 mmol). The reaction mixture was degassed and back-filled with argon three times. tris(dibenzylideneacetone)dipalladium (113 mg, 0.123 mmol) was added to the reaction mixture and the reaction vial was sealed. The reaction mixture was heated to 90° C. and stirred 16 h. The reaction mixture was cooled to room temperature and concentrated under reduced pressure. The crude material was purified by flash column chromatography $SiO_2$ with EtOac in hexanes to afford the desired 3-indolephosphine oxide (220 mg, 46%, 50% homogeneity). MS m/z 194.2 ($MH^+$).

Step 2 (Example 472, Table 4): the indole from step 2 was coupled to the chloropyridine intermediate A-13 using copper/BINOL catalysis as described for Example 1 (step 4) in general method A.

Preparation of Example 483 (Table 4)

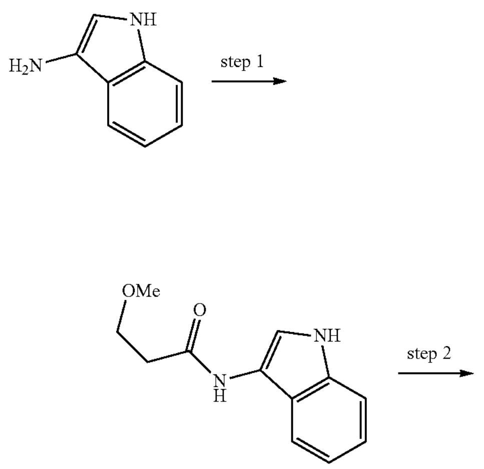

-continued

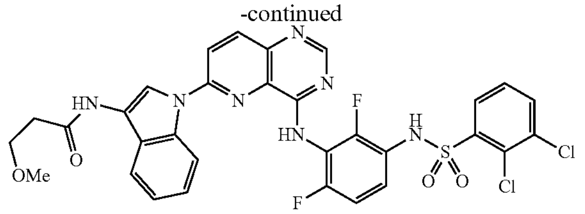

Step 1: O-(7-Azabenzotriazol-1-y)-N,N,N',N'-tetramethyluroniumhexafluorophosphate (0.173 g, 0.454 mmol) was added to a mixture of 3-methoxypropanoic acid (0.047 g, 0.454 mmol), commercially available 1H-indol-3-amine (0.030 g, 0.227 mmol) and N,N-diisopropylethylamine (2.4 mL, 1.36 mmol) in DMF (1.1 mL). The resulting mixture was stirred at rt for 1.5 h. Water was added and the aqueous mixture was extracted with EtOAc. The organics layers were combined, dried with $MgSO_4$, filtered and then concentrated under reduced pressure. The crude material was loaded onto Celite® and then purified by column chromatography (silica gel, 30-100% EtOAc in hexanes) to afford N-(1H-indol-3-yl)-3-methoxy-propanamide (0.049 g, 99% yield) as a brown oil. MS m/z 219.2 ($MH^+$). $^1H$ NMR (400 MHz, DMSO-$d_6$) δ: 10.74 (br. s., 1H), 9.81 (s, 1H), 7.76 (d, J=8.2 Hz, 1H), 7.71 (d, J=2.3 Hz, 1H), 7.32 (d, J=7.8 Hz, 1H), 7.08 (td, J=7.4, 1.2 Hz, 1H), 6.99 (td, J=7.5, 1.0 Hz, 1H), 3.64 (t, J=6.3 Hz, 2H), 3.25 (s, 3H), 2.62 (t, J=6.3 Hz, 2H).

Step 2 (Example 483, Table 4): the indole from step 2 was coupled to the chloropyridine intermediate A-13 using copper/BINOL catalysis as described for Example 1 (step 4) in general method A.

Preparation of Example 484 (Table 4)

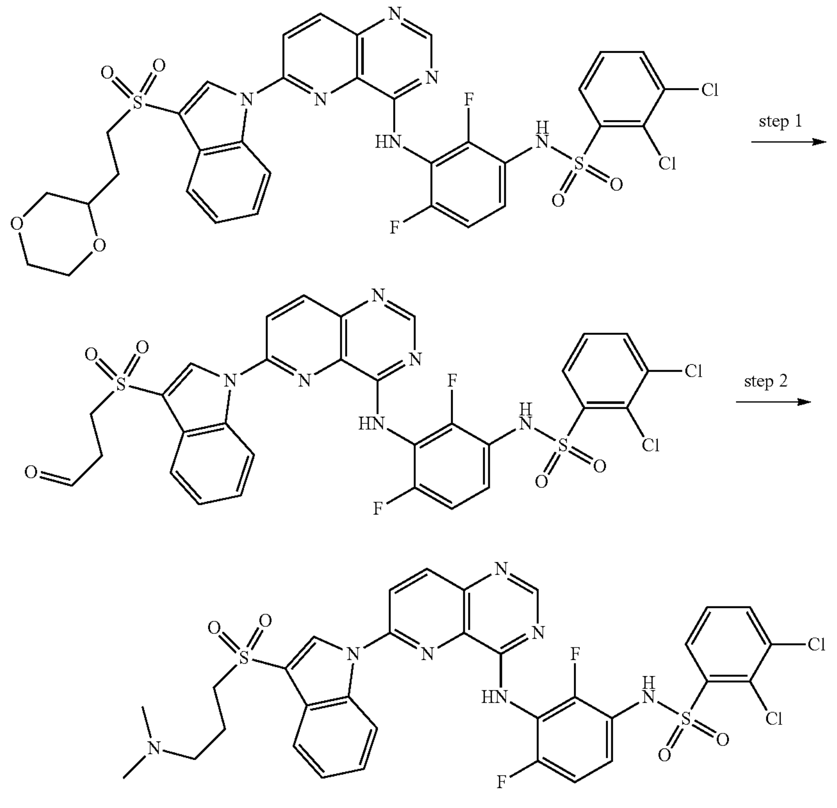

Example 484

Step 1: the sulfone acetal was prepared according to general method H using the commercially available 3-bromopropionaldehyde dioxane acetal as alkylating agent, followed by coupling with fragment A-13 (Ar=2,3-dichlorophenyl) using copper/BINOL catalysis as described for Example 1 (step 4) in general method A.

The acetal (305 mg, 0.393 mmol) in THF (4 mL) was then hydrolyzed to the corresponding aldehyde by heating under microwave irradiation for 10 min at 120° C. in the presence of 1M aq. $H_2SO_4$ (5 equivalents). The reaction was then quenched with $Na_2CO_3$ 1 M and extracted with EtOAc (10 mL) three times. The combined organic layers were washed with brine, dried over $MgSO_4$, filtered and evaporated to give 2,3-dichloro-N-(2,4-difluoro-3-((6-(3-((3-oxopropyl) sulfonyl)-1H-indol-1-yl)pyrido[3,2-d]pyrimidin-4-yl) amino)phenyl)benzenesulfonamide (188 mg, 67% yield) as a yellow foam: m/z=719.2 (M+H).

Step 2 (Example 484, Table 4): To a solution of aldehyde from step 1 (50 mg, 0.0697 mmol) in DCE (1 mL) was added dimethylamine HCl (17 mg, 0.209 mmol) and DIPEA (0.055 mL, 0.313 mmol). The reaction was stirred at rt for 15 min. Sodium triacetoxyborohydride (44 mg, 0.209 mmol) was then added portion wise at rt. The reaction was stirred at rt and was followed by LCMS. When the reaction was completed, the reaction was evaporated to dryness and the residue was dissolved in 1 mL of DMSO. The product was purified by PREP-HPLC using 20-80% MeCN in water+ 0.01% formic acid. The pure fractions were collected, evaporated and lyophilized to give the compound of Example 484 (8 mg, 15%) as a white solid: $^1H$ NMR (400 MHz, DMSO-$d_6$) δ: 9.94 (s, 1H), 9.01 (s, 1H), 8.52 (s, 1H), 8.44-8.50 (m, 2H), 8.32 (d, J=8.6 Hz, 1H), 7.89-7.98 (m, 2H), 7.81 (d, J=8.6 Hz, 1H), 7.41-7.54 (m, 3H), 7.14-7.25 (m, 1H), 6.97-7.08 (m, 1H), 3.40-3.46 (m, 3H), 2.54-2.60 (m, 1H), 2.27 (s, 6H), 1.83-1.92 (m, 2H); m/z=748.4.

Preparation of Example 486 (Table 4)

Following the procedure described for Example 357 and using A-13 (Ar=2,3-dichlorophenyl), the analog of Example 486 was obtained. Characterization of the relevant intermediates is provided below for each step: Step 1:

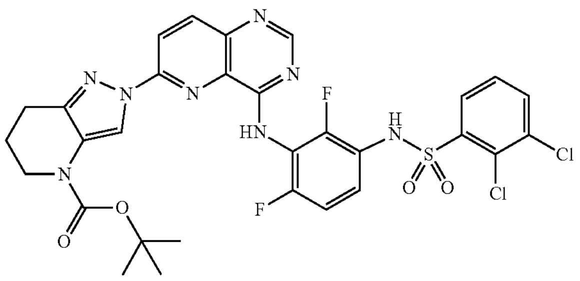 [SMILES: CC(C)(C)OC(=O)N1CCCc2nn(-c3ccc4ncnc(Nc5c(F)ccc(NS(=O)(=O)c6cccc(Cl)c6Cl)c5F)c4n3)cc21]

($ES^+$) M+H=703.4, ($ES^-$) M−H=701.4

Step 2:

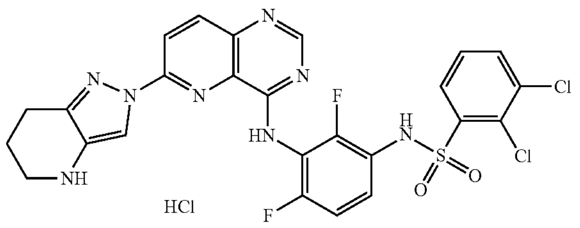 [SMILES: O=S(=O)(Nc1ccc(F)c(Nc2ncnc3ccc(-n4cc5c(n4)CCCN5)nc23)c1F)c1cccc(Cl)c1Cl ; Cl]

A solution of HCl (4 M in dioxane, 6.0 mL, 24.2 mmol) was added to a solution of compound 2a (1.70 g, 2.42 mmol) in dioxane (5 mL) at room temperature. Reaction was stirred at room temperature for 3 days. A solution of HCl (4 M in dioxane, 3.0 mL, 12.0 mmol) was added and the mixture was stirred at room temperature for additional 24 h. Reaction mixture was filtered, and filtered solid was washed with MTBE to give yellow solid (1.58 g, 102% yield, 62% purity at 254 nm). Mass for freebase ($ES^+$) M+H=603.3, ($ES^-$) M−H=601.3.

Step 3 (Example 486, Table 4):

Example 486

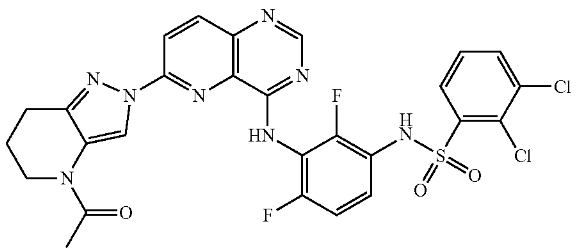

The hydrochloride salt from Step 2 (50.0 mg, 82.9 μmol) and N,N-diisopropylethylamine (22 μL, 124 μmol) were dissolved in $CH_2Cl_2$ (1.88 mL) and AcOH (470 μL). To this solution was added acetic anhydride (8.7 μL, 91.1 μmol) at room temperature. Reaction was stirred at room temperature overnight. Reaction was concentrated and purified by reverse phase column (acetonitrile/10 mM AmF in $H_2O$, from 0-25-55%). Fractions containing desired product were lyophilized to give the compound of Example 486 as a beige powder (12.4 mg, 23% yield).

Preparation of Example 488 (Table 4)

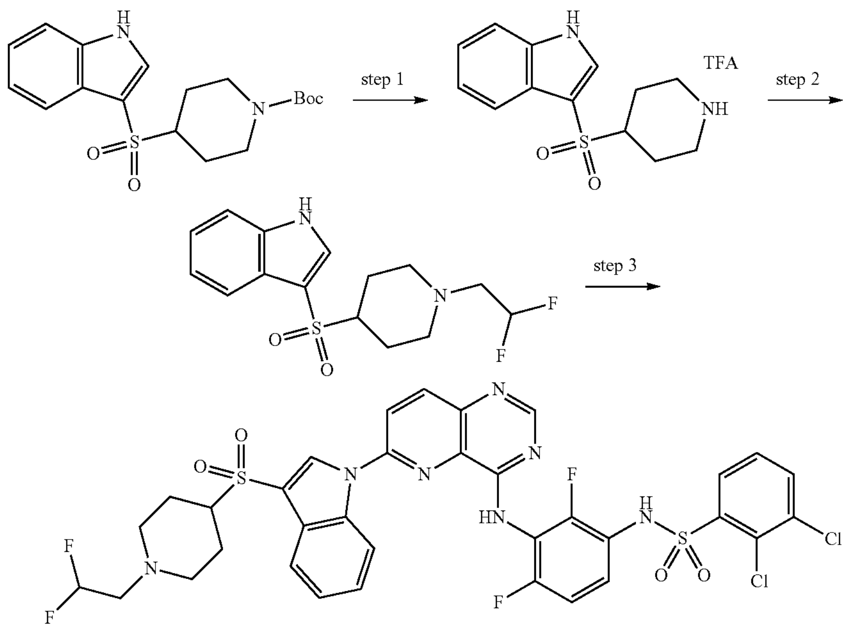

Example 488

Step 1: the N-Boc-piperidine sulfone from step 2 of the preparation of Example 465 (100 mg, 0.274 mmol) was stirred in TFA for 30 minutes at room temperature. After completion, the reaction mixture was concentrated under vacuum. The residu was coevaporated with ACN to afford the desired TFA salt (100 mg, 96%). MS m/z 265.2 ($MH^+$).

Step 2: The TFA salt from step 1 (30 mg, 0.0793 mmol), DIEA (10.0 eq, 0.14 mL, 0.793 mmol) and 2,2-Difluoroethyl trifluoromethanesulfonate (10.0 eq, 170 mg, 0.793 mmol) were mixed together in DMSO (0.8 mL) and stirred at 80° C. for 4 days. After completion, the reaction mixture was diluted in EtOAc then washed with aq. $NH_4Cl$ followed by brine. The organic layer was dried over $MgSO_4$, filtered and concentrated under vacuum to afford the desired indole derivative (20 mg, 0.061 mmol, 76% yield) which was diluted in DMSO and used as is. MS m/z 329.2 ($MH^+$).

Step 3 (Example 488, Table 4): the indole from step 2 was coupled to the chloropyridine intermediate A-13 using copper/BINOL catalysis as described for Example 1 (step 4) in general method A.

Preparation of Example 494 (Table 4)

This compound was isolated as a side product during the prep-HPLC purification of the analog of Example 495 (Table 4).

Preparation of Example 495 (Table 4)

The compound of Example 495 was prepared in a similar fashion to other indole sulfone derivatives (general method H) except that 2,2,2-trifluoroethyltrifluoromethane sulfonate was used as alkylating agent in step 1 for alkylation of the in situ-generated indole sulfide. Following coupling to the chloropyridine intermediate A-13 using copper/BINOL catalysis as described for Example 1 (step 4) in general method A, both compounds of examples 494 and 495 were isolated during the prep-HPLC purification step.

Preparation of Example 499 (Table 4)

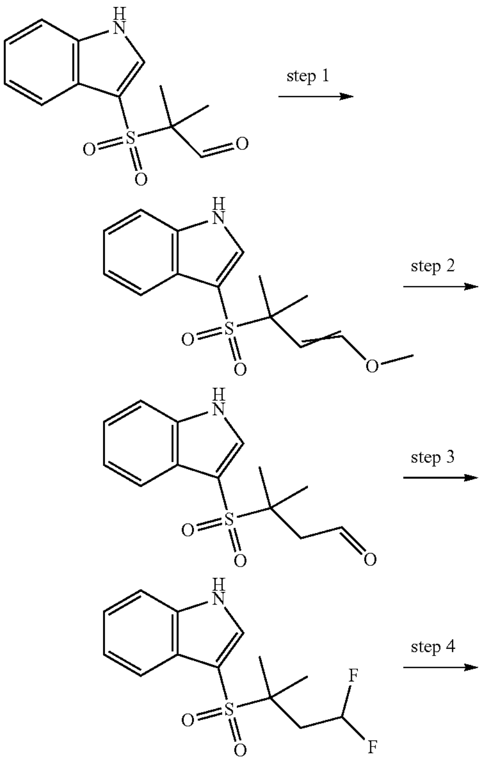

-continued

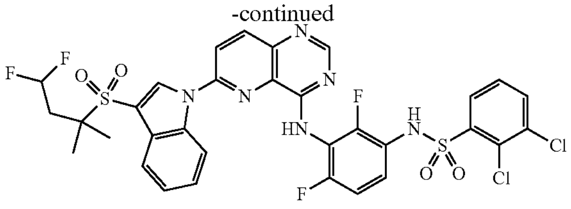

Example 499

-continued

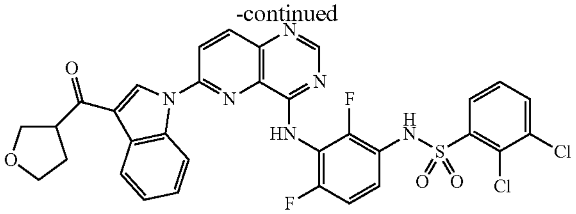

Example 500

Step 1: 1.6M nBuLi in hexanes (2.8 mL, 4.18 mmol) was added dropwise to a solution of (methoxymethyl)triphenylphosphonium chloride (477 mg, 1.39 mmol) in THF (14 mL) at 0° C. After 10 min, a solution of the aldehyde sulfone obtained as described in step 3 of the preparation of Example 457 (350 mg, 1.39 mmol) in THF (5 mL) was added dropwise, and, after 10 min at 0° C., the mixture was poured onto sat. aq. $NH_4Cl$ at 0° C. The organic phase was washed with brine, and then dried ($MgSO_4$) to afford after concentration the crude material, which was purified on $SiO_2$ with hexane/AcOEt to afford the enol ether intermediate (389 mg, 99%). $^1$H NMR (400 MHz, $CDCl_3$) δ 8.81 (br. s., 1H), 7.98-8.15 (m, 1H), 7.64-7.89 (m, 1H), 37-7.64 (m, 1H), 7.27-7.34 (m, 2H), 5.84. (d, J=7.04 Hz, 1H), 4.36 (d, J=7.04 Hz, 1H), 3.22 (s, 3H), 1.61 (s, 6H). MS m/z 278.2 (MH−).

Step 2: An aqueous solution of 6 N HCl (2.0 mL, 12.0 mmol) was added dropwise to a solution of the enol ether from step 1 (389 mg, 1.39 mmol) in THF (2 mL) and stirred at room temperature for 16 h. The reaction mixture was diluted with EtOAc then washed with sat. aq. $NaHCO_3$ and brine, and then dried ($MgSO_4$) to afford the corresponding aldehyde after concentrationa (95 mg, 0.358 mmol, 25.7% yield) which was used promptly for step 3. MS m/z 264.2 ($MH^-$).

Step 3: Under an ice bath, to the aldehyde from step 2 (68 mg, 0.271 mmol) In DCM (20 mL), diethylaminosulfur trifluoride (0.18 mL, 1.35 mmol) was slowly added dropwise and the reaction was slowly warmed to room temperature and stirred for 5 h. After completion, a saturated aqueous solution of sodium bicarbonate was slowly added dropwise to the reaction mixture. The aqueous layer was extracted with EtOAc, The separated organic layer was washed with brine, dried (MgSO4), filtered and concentrated. The crude product was purified by column chromatography on $SiO_2$ with EtOAc in hexanes to give the desired indolesulfone (22 mg, 0.0766 mmol, 21.4% yield). $^1$H NMR (400 MHz, $CDCl_3$) δ: 9.01 (br. s., 1H), 7.98 (d, J=7.83 Hz, 1H), 7.79 (d, J=3.13 Hz, 1H), 7.43-7.68 (m, 1H), 7.32-7.39 (m, 2H), 5.76-6.58 (m, 1H), 2.38 (dt, J=4.89, 17.12 Hz, 2H), 1.48 (s, 6H). MS m/z 286.2 ($MH^-$).

Step 4 (Example 499, Table 4): the indole from step 3 was coupled to the chloropyridine intermediate A-13 using copper/BINOL catalysis as described for Example 1 (step 4) in general method A.

Preparation of Examples 500 and 528 (Table 4)

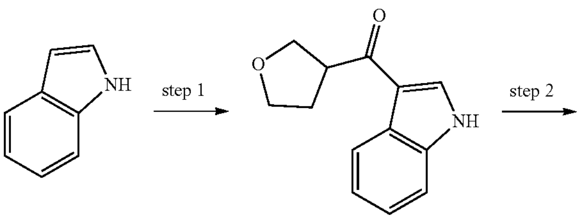

Step 1: To a 20 mL vial, was added indole (100 mg, 0.85 mmol) in 3.5 mL of DCM. The reaction was cooled to 0° C. Next, diethylaluminum chloride 25% wt (1.8M) in toluene (0.71 mL, 1.28 mmol) was added dropwise. The reaction was left to stir for 30 min at 0° C. Tetrahydrofuran-3-carbonyl chloride (172 mg, 1.28 mmol) in 3 mL of DCM was added dropwise. The reaction was warmed to room temperature and left to stir for 3 h. After completion, the reaction was quenched with 1M NaOH. The reaction was extracted with water, brine and DCM (×3). The organics were collected, dried over $MgSO_4$, filtered and then concentrated under reduced pressure. The crude material was loaded onto Celite and purified on $SiO_2$ with EtOAc in hexanes to afford the desired 3-indole ketone (12 mg, 0.055 mmol, 6.4% yield) as a white solid. MS m/z 216.3 ($MH^+$).

Step 2 (Example 500, Table 4): the indole from step 1 was coupled to the chloropyridine intermediate A-13 using copper/BINOL catalysis as described for Example 1 (step 4) in general method A.

Example 528 (Table 4) was obtained in an analogous fashion using thiophene-2-carbonyl chloride in step 1.

Preparation of Example 502 (Table 4)

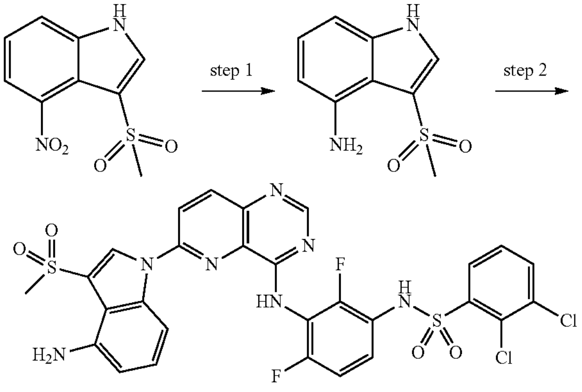

Example 502

Step 1: 4-nitro-3-methylsulfone indole, prepared in a similar fashion as described in Phosphorus, Sulfur and Silicon and the Related Elements 2014, 189, 1378 (230 mg, 0.957 mmol) was dissolved in MeOH (10 mL). To the solution 10% palladium hydroxide on carbon (75 mg, 0.0957 mmol) was added and the suspension was stirred under 1 atm of $H_2$ for 1 h. The palladium was filtered off with celite and the solvent was removed under vacuum to afford the desired 4-aminoindole derivative (110 mg, 55%). $^1$H NMR (400 MHz, DMSO-$d_6$) δ: 11.93 (br. s., 1H), 7.81 (d, J=3.13 Hz, 1H), 6.88-7.08 (m, 1H), 6.76 (d, J=7.43 Hz, 1H), 6.42 (d, J=7.04 Hz, 1H), 5.57 (s, 2H), 3.25 (s, 3H). MS m/z 211.2 ($MH^+$).

Step 2 (Example 502, Table 4): the indole from step 1 was coupled to the chloropyridine intermediate A-13 using copper/BINOL catalysis as described for Example 1 (step 4) in general method A.

Preparation of Examples 506 and 573 (Table 4)

Example 506

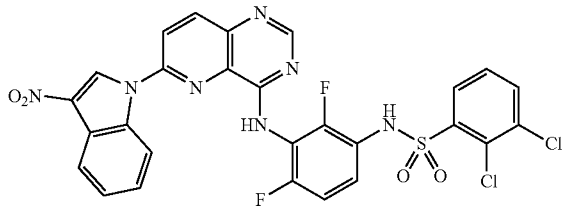

Example 573

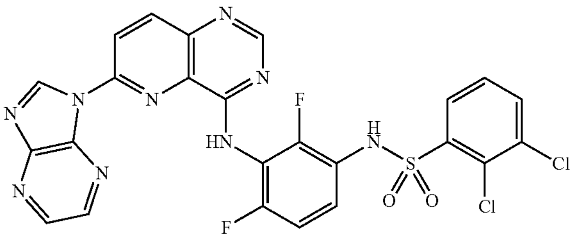

Example 506: cesium carbonate (1.50 mmol) was added to a mixture of 3-nitroindole (1.50 mmol) and A-13 (Ar=2, 3-dichlorophenyl) (1 mmol) in DMSO (8.50 mL) at room temperature. This was heated at 100° C. for 4 days until the completion of reaction. Reaction mixture was cooled to room temperature. Crude reaction mixture was purified by reverse phase chromatography (acetonitrile/water containing 0.1% AmF) to give the desired compound of Example 506.

Example 573: the same procedure described for Example 506 using 1H-imidazo[4,5-b]pyrazine provided the desired compound after heating at 80° C. for 24 h and at 100° C. for 4 days.

Preparation of Example 511 and 532 (Table 4)

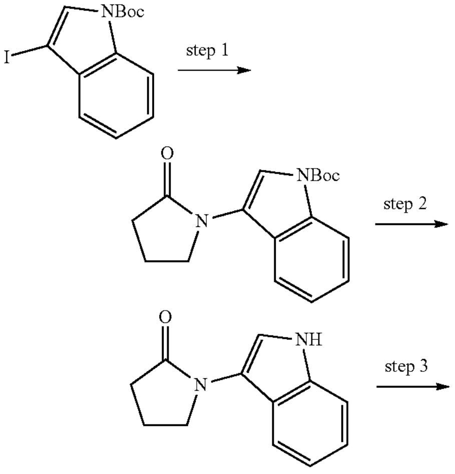

-continued

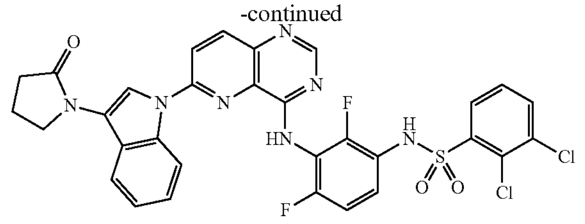

Example 511

Step 1: A flask was loaded with, tert-butyl 3-iodoindole-1-carboxylate (50 mg, 0.146 mmol), 2-pyrrolidinone (37 mg, 0.437 mmol), cesium carbonate (0.142 g, 0.437 mmol, CuI (14 mg, 0.073 mmol) and N,N"-dimethylethylenediamine (16 μL, 0.146 mmol) in dioxane (1.5 mL). The resulting mixture was heated at 80° C. and stirred for 10 h. The reaction mixture was filtered through Celite® and the crude was purified by column chromatography (silica gel, 0-100% EtOAc in hexanes) to afford tert-butyl 3-(2-oxopyrrolidin-1-yl)indole-1-carboxylate (23 mg, 53% yield) as a white film. MS m/z 301.2 ($MH^+$).

Step 2: Trifluoroacetic acid (1 mL) was added to a solution of tert-butyl 3-(2-oxopyrrolidin-1-yl)indole-1-carboxylate (23 mg, 0.077 mmol) in DCM (1.0 mL). The crude material was dissolved in MeOH and MeCN and then IRA-67 resin was added. The solution was filtered through a cotton plug and collected. The solvent was removed under reduced pressure to afford 1-(1H-indol-3-yl)pyrrolidin-2-one (7.3 mg, 47% yield). MS m/z 201.2 ($MH^+$). $^1H$ NMR (400 MHz, DMSO-d6) δ: 11.06 (br. s., 1H), 7.58 (d, J=7.8 Hz, 1H), 7.46 (d, J=2.7 Hz, 1H), 7.36 (d, J=7.4 Hz, 1H), 7.09 (t, J=7.6 Hz, 1H), 6.98 (t, J=7.8 Hz, 1H), 3.89 (t, J=7.0 Hz, 2H), 2.44 (t, J=8.2 Hz, 2H), 2.13 (quin, J=7.5 Hz, 2H).

Step 3 (Example 511, Table 4): the indole from step 2 was coupled to the chloropyridine intermediate A-13 using copper/BINOL catalysis as described for Example 1 (step 4) in general method A.

The 6-membered ring analog of example 532 (Table 4) was prepared in the same fashion as Example 511 using tert-butyl 3-(2-oxo-1-piperidyl)indole-1-carboxylate in step 1 (23 mg, 21% yield). MS m/z 315.2 ($MH^+$). The deprotected indole after treatment with TFA (step 2) gave 1-(1H-indol-3-yl)piperidin-2-one; 2,2,2-trifluoroacetic acid (25 mg, 100% yield). MS m/z 215.0 ($MH^+$) which was converted to the analog of Example 532 in the usual maner (Step 3).

Preparation of Examples 512 and 691 (Table 4)

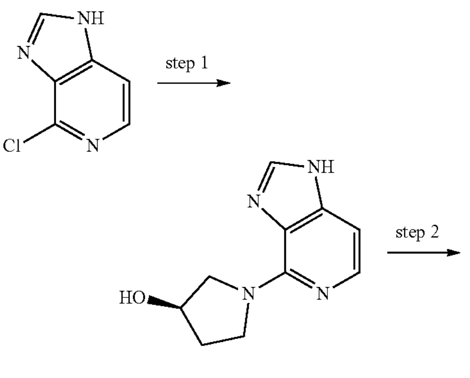

-continued

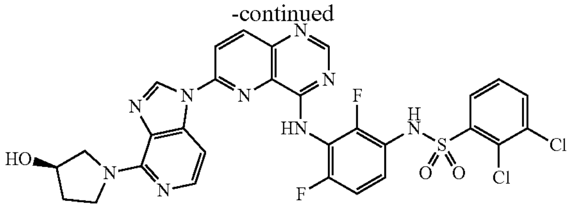

Example 512

Example 691

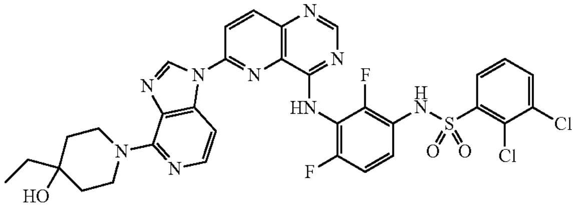

Step 1: R-(+)-3-Pyrrolidinol (0.049 mL, 0.612 mmol) was added to a solution of 4-chloro-1H-imidazo[4,5-c]pyridine (47 mg, 0.306 mmol) in isopropanol (2.0 mL). The resulting mixture was heated to 125° C. and stirred for 10 h. Upon completion, the reaction mixture was concentrated and the crude was purified by column chromatography (silica gel, 0-20% MeOH in DCM) to afford (3R)-1-(1H-imidazo[4,5-c]pyridin-4-yl)pyrrolidin-3-ol (50 mg, 80% yield) as an off-white solid. MS m/z 205.2 (MH+).

Step 2 (Example 512, Table 4): the benzimidazole from step 1 was coupled to the chloropyridine intermediate A-13 using copper/BINOL catalysis as described for Example 1 (step 4) in general method A.

Example 691 (Table 4): the compound of Example 691 was prepared in an analogous fashion replacing R-(+)-3-pyrrolidinol by 4-ethyl-4-hydroxypiperidine in step 1.

Preparation of Example 513 (Table 4)

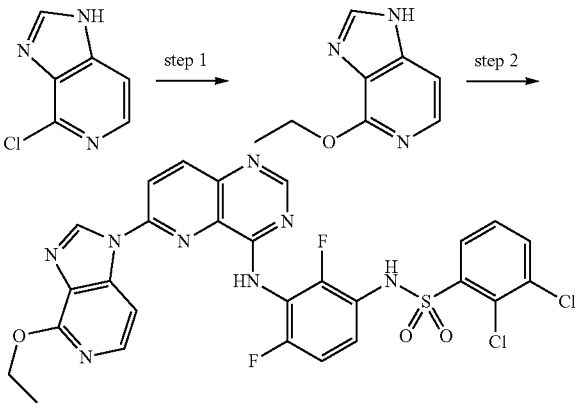

Example 513

Step 1: In a microwave vial, 4-chloro-1H-imidazo[4,5-c]pyridine (60 mg, 0.391 mmol) was dissolved in EtOH (1.3 mL) and a solution of sodium ethoxide (21% in EtOH, 0.29 mL, 0.781 mmol) was added. The result mixture was stirred in the microave at 125° C. for 2 h. Water was added and the aqueous mixture was extracted with EtOAc. The organic layers were combined, washed with brine, dried with $Na_2SO_4$, filtered and concentrated. The crude was purified by column chromatography (silica gel, 0-15% MeOH in DCM) to afford 4-ethoxy-1H-imidazo[4,5-c]pyridine (49 mg, 0.30 mmol, 76% yield) as an off-white solid. MS m/z 164.2 (MH+). $^1$H NMR (400 MHz, DMSO-$d_6$) δ: 8.21 (s, 1H), 7.81 (d, J=5.75 Hz, 1H), 7.17 (d, J=5.50 Hz, 1H), 4.48 (q, J=7.05 Hz, 2H), 1.32-1.48 (m, 3H)

Step 2 (Example 513, Table 4): the azabenzimidazole from step 1 was coupled to the chloropyridine intermediate A-13 using copper/BINOL catalysis as described for Example 1 (step 4) in general method A.

Preparation of Example 514 (Table 4)

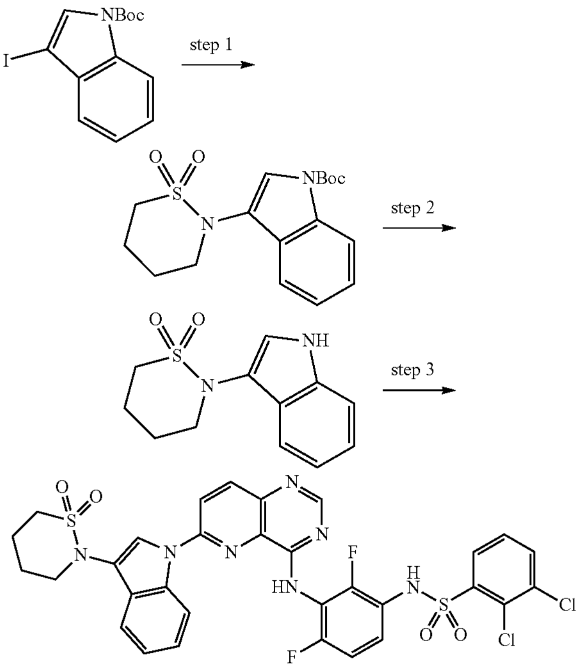

Example 514

Step 1: A flask was loaded with tert-butyl 3-iodoindole-1-carboxylate (0.10 g, 0.291 mmol), thiazinane 1,1-dioxide (0.118 g, 0.87 mmol), cesium carbonate (0.285 g, 0.874 mmol, CuI (28 mg, 0.146 mmol) and N,N"-dimethylethylenenediamine (31 μL, 0.291 mmol) in dioxane (2.0 mL). The resulting mixture was heated at 80° C. and stirred for 10 h. The reaction mixture was filtered through Celite® and the crude was purified by column chromatography (silica gel, 0-100% EtOAc in hexanes) to afford tert-butyl 3-(1,1-dioxothiazinan-2-yl)indole-1-carboxylate (30 mg, 29% yield) as a colorless oil. MS m/z 351.1 (MH+). $^1$H NMR (400 MHz, $CDCl_3$) δ: 8.09-8.18 (m, 1H), 7.63-7.71 (m, 2H), 7.32-7.38 (m, 1H), 7.25-7.31 (m, 1H), 3.76-3.81 (m, 2H), 3.24-3.32 (m, 2H), 2.34-2.44 (m, 2H), 1.94 (m, J=5.7, 5.7 Hz, 2H), 1.68 (s, 9H).

Step 2: Trifluoroacetic acid (66 μL, 0.856 mmol) was added to a solution of tert-butyl 3-(1,1-dioxothiazinan-2-yl)indole-1-carboxylate (30 mg, 0.086 mmol) in DCM (2.0 mL). The resulting mixture was stirred at rt for 2 h. Upon completion, the volatiles were removed under reduce pressure and the residue was dried under vacuum to afford 2-(1H-indol-3-yl)thiazinane 1,1-dioxide; 2,2,2-trifluoroacetic acid (30 mg, 96% yield). MS m/z 251.0 (MH+).

Step 3 (Example 514, Table 4): The indole from step 2 was coupled to the chloropyridine intermediate A-13 using copper/BINOL catalysis as described for Example 1 (step 4) in general method A.

Preparation of Example 520 (Table 4)

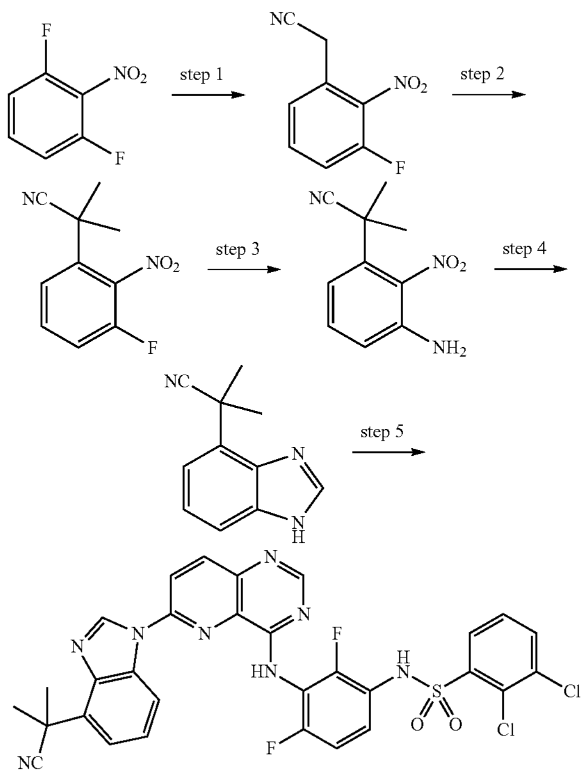

Example 520

Step 1: To a 100 mL round-bottom flask, was added 2,6-difluoronitrobenzene (1.3 mL, 12.6 mmol) and ethyl cyanoacetate (1.6 mL, 15.1 mmol) in DMF (15 mL). Next, sodium hydride (754 mg, 18.9 mmol) was added slowly at room temperature. The reaction was allowed to stir at room temperature for 15 min. The reaction was quenched with 1M HCl until the deep-red solution turned yellow and then diluted in EtOAc. The organic layer was separated then washed with aq. $NH_4Cl$, followed by brine. The organic layer was dried by MgSO4, filtered and then concentrated under reduced pressure. The crude material was dissolved in DMSO (9 mL) and water (1 mL) and transferred to a 20 mL microwave vial. The reaction was heated to 120° C. and left to stir for 16 h. The reaction mixture was cooled to room temperature and diluted in EtOAc then washed with aq. $NH_4Cl$ followed by brine. The organic layer was dried by MgSO4, filtered and then concentrated under reduced pressure. The crude material was purified by normal phase, flash column chromatography using hexanes:EtOAc to afford the desired benzylic nitrile (2.12 g, 93%) as an orange solid. $^1H$ NMR (400 MHz, DMSO-$d_6$) δ: 7.80 (td, J=7.8, 5.5 Hz, 1H), 7.65 (t, J=9.6 Hz, 1H), 7.54 (d, J=7.4 Hz, 1H), 4.28 (s, 2H). MS m/z 725.4 ($MH^+$). MS m/z 181.2 ($MH^+$).

Step 2: to a 20 mL vial, was added 2-(3-fluoro-2-nitro-phenyl)acetonitrile from step 1 (200 mg, 1.11 mmol) and sodium hydride (111 mg, 2.78 mmol) in 8 mL of DMF. Then iodomethane (346 μL, 5.55 mmol) was slowly added to the reaction. Upon addition, the reaction was stirred at room temperature for 1 h. The reaction was quenched with aq. $NH_4Cl$ and then diluted with EtOAc. The organic layer was separated then washed with brine, dried over $MgSO_4$, filtered and concentrated under vacuum to provide 2-(3-fluoro-2-nitro-phenyl)-2-methyl-propanenitrile (214 mg, 1.03 mmol, 92%). $^1H$ NMR (400 MHz, DMSO-d6) δ: 7.78 (td, J=8.4, 5.9 Hz, 1H), 7.68 (t, J=8.8 Hz, 1H), 7.63 (d, J=8.2 Hz, 1H), 1.82 (s, 6H). MS m/z 209.2 ($MH^+$).

Step 3: To a 10 mL microwave vial was added the fluoronitro derivative from step 2 (63 mg, 0.301 mmol) followed by 1.5 mL of 28%-30% ammonium hydroxide. The reaction was irradiated in the microwave at 130° C. for 1 hour. The reaction mixture was diluted with water then extracted with EtOAc (×3). The organic layer was washed with brine, dried by $MgSO_4$, filtered and then concentrated under reduced pressure to afford the desired nitroaniline (62.6 mg, 100%) as an orange solid. $^1H$ NMR (400 MHz, DMSO-$d_6$) δ: 7.27 (t, J=8.0 Hz, 1H), 6.93 (d, J=8.2 Hz, 1H), 6.80 (d, J=7.8 Hz, 1H), 6.00 (s, 2H), 1.76 (s, 6H). MS m/z 206.2 ($MH^+$).

Step 4: reduction and ring closure of the intermediate 1,2-phenylenediamine to the benzimidazole ring was performed using iron and formic acid following the procedure described in Step 2 of Method I for example 524.

Step 5 (example 520, Table 4): the benzimidazole derivative of step 4 was coupled to the chloropyridine intermediate A-13 using copper/BINOL catalysis as described for Example 1 (step 4) in general method A.

Preparation of Example 521 (Table 4)

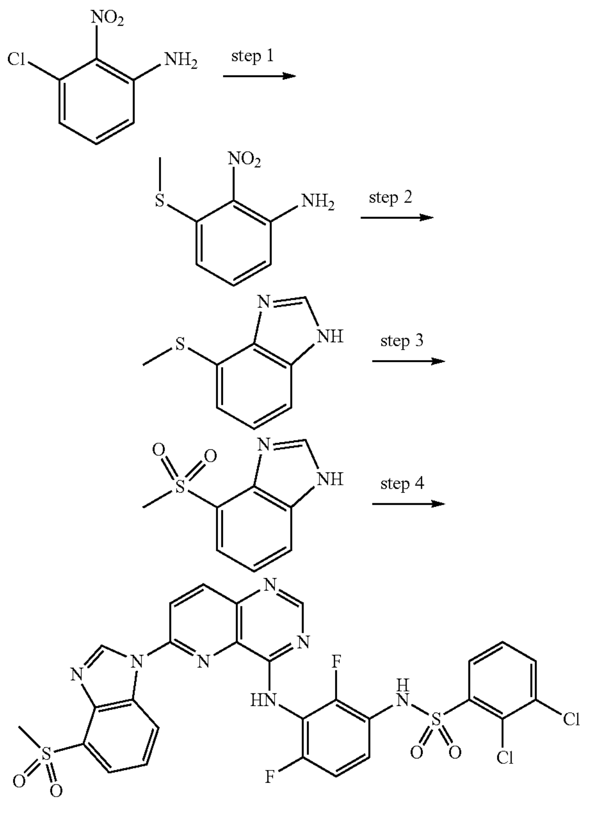

Example 521

Step 1: 3-Chloro-2-nitroaniline (2.00 g, 11.6 mmol) was charged in a 25 mL flask and dissolved in 10 mL of dry DMF affording a bright orange solution. Sodium thiomethoxide (1.06 g, 15.1 mmol) was then added as a slurry in 5 mL of DMF and 3 mL for rinse at room temperature affording a dark red solution. The resulting mixture was stirred at room temperature for 2 hours. The mixture was poured into 80 mL of water containing 3 mL of acetic acid and extracted 3× with EtOAc. The combined organic layers were washed twice with water then once with brine, dried over $MgSO_4$, filtered and concentrated. The residue was purified by flash chromatography on silica gel using DCM as eluent. The appropriate fractions were combined, concentrated and dried under reduced pressure. Affords 3-methylsulfanyl-2-nitro-aniline (2.06 g, 97% yield). MS m/z 185.2 ($MH^+$). 1H NMR (DMSO-d6) δ: 7.25 (t, J=8.2 Hz, 1H), 7.09 (br. s, 2H), 6.75 (dd, J=8.4, 1.0 Hz, 1H), 6.52 (dd, J=7.8, 0.8 Hz, 1H), 2.38 (s, 3H).

Step 2: 3-methylsulfanyl-2-nitro-aniline (1.00 g, 5.43 mmol), iron metal (3.03 g, 54.3 mmol), ammonium chloride (2.90 g, 54 mmol) and 13 mL of isopropanol were introduced in a 100 mL flask followed by formic acid (12 mL, 326 mmol). The flask was equipped with a reflux condenser then immerged in an oil bath preheated to 80° C. The yellow mixture was stirred vigorously at that temperature for 4 hours then allowed to cool to room temperature. The reaction mixture was filtered through a short pad of Celite® using isopropanol for rinse. The filtrate was concentrated to dryness then taken up as a suspension in a saturated solution of $NaHCO_3$ until no longer acidic. The mixture was then extracted 3× with EtOAc. The combined organic layers were washed once with brine then dried over $MgSO_4$, filtered and concentrated. The residue was purified by flash chromatography on silica gel using a 50% to 100% EtOAc in DCM gradient followed by 1% IPA in EtOAc. The appropriate fractions were pooled, concentrated and dried under reduced pressure. Affords 4-methylsulfanyl-1H-benzimidazole (0.83 g, 93% yield) as a salmon colored solid. MS m/z 165.0 ($MH^+$). $^1H$ NMR (DMSO-d6) δ: 12.52 (br. s., 1H), 8.18 (s, 1H), 7.31 (br. s., 1H), 7.17 (t, J=7.8 Hz, 1H), 6.99 (br. s., 1H), 2.54 (s, 3H).

Step 3: 4-methylsulfanyl-1H-benzimidazole (300 mg, 1.83 mmol) was suspended in 4 mL of MeCN to which was added diethylamine (0.038 mL, 0.37 mmol). To this mixture was added a solution of Oxone®, (1.68 g, 2.74 mmol) in 7 mL of water dropwise at room temperature. A color change was noticed. The resulting suspension was stirred at the same temperature for 15 minutes. 0.5 mL of a saturated solution of sodium thiosulfate was added. The mixture was diluted with water and the pH was adjusted to close to neutrality with the slow addition of solid $NaHCO_3$. The mixture was then extracted with EtOAc 3× and the combined organic layers were washed once with brine then dried over $MgSO_4$, filtered and concentrated. The solid residue was purified by flash chromatography on silica gel using a 70% to 100% EtOAc in DCM gradient then a 100% EtOAc to 5% IPA in EtOAc gradient was applied. The appropriate fractions were pooled, concentrated and dried under reduced pressure to afford 4-methylsulfonyl-1H-benzimidazole (264 mg, 74% yield). MS m/z 197.0 ($MH^+$). $^1H$ NMR (DMSO-d6) δ: 13.03 (br. s., 1H), 8.46 (br. s., 1H), 7.95 (d, J=7.0 Hz, 1H), 7.72 (dd, J=7.4, 0.8 Hz, 1H), 7.43 (t, J=7.8 Hz, 1H), 3.44 (br. s., 3H).

Step 4 (Example 521, Table 4): the benzimidazole derivative of step 3 was coupled to the chloropyridine intermediate A-13 using copper/BINOL catalysis as described for Example 1 (step 4) in general method A.

Preparation of Example 522 (Table 4)

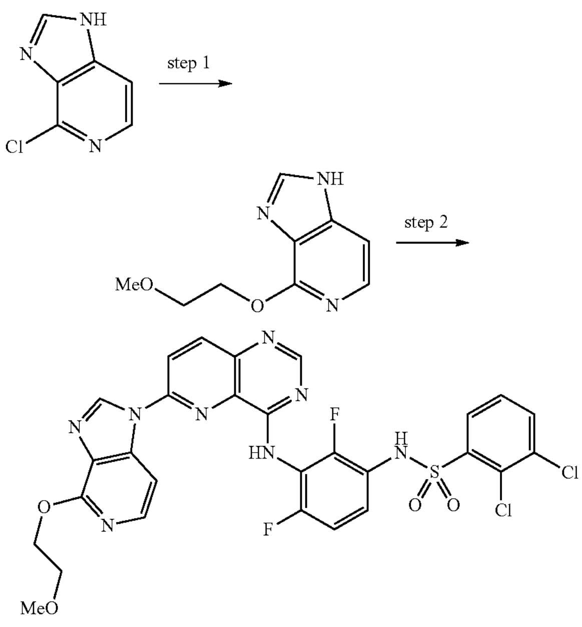

Example 522

Step 1: In a microwave vial, sodium hydride (60% in mineral oil, 49 mg, 1.23 mmol) was added to 2-methoxy-ethanol (1.1 mL, 13.3 mmol). The resulting mixture was stirred for 30 min and 4-chloro-1H-imidazo[4,5-c]pyridine (63 mg, 0.410 mmol) was added. The resulting mixture was heated in the microwave at 180° C. and stirred for 2 h. Water was added and the aqueous mixture was extracted with EtOAc. The organic layers were combined, washed with brine, dried with $Na_2SO_4$, filtered and concentrated to afford 4-(2-methoxyethoxy)-1H-imidazo[4,5-c]pyridine (59 mg, 0.305 mmol, 74% yield). MS m/z 194.0 ($MH^+$).

Step 2 (Example 522, Table 4): the azabenzimidazole from step 1 was coupled to the chloropyridine intermediate A-13 using copper/BINOL catalysis as described for Example 1 (step 4) in general method A.

Preparation of Examples 523, 538 and 598 (Table 4)

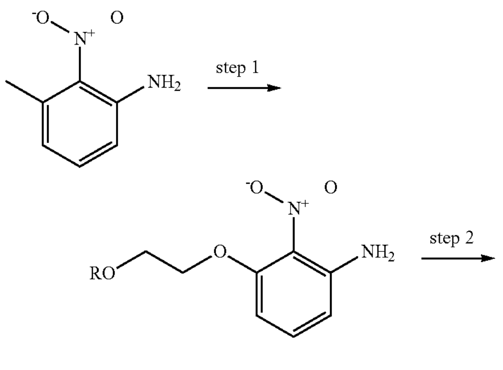

-continued

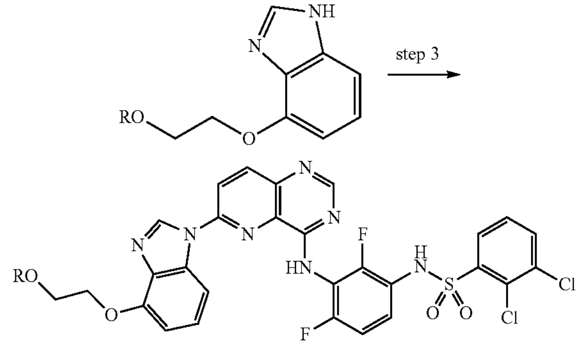

R = H (Example 523)
R = OMe (Example 538)
R = $CH_2CH_2OMe$ (Example 598)

Step 1 (R═OMe): Potassium carbonate (0.35 g, 2.56 mmol) and 2-methoxyethanol (0.40 mL, 5.12 mmol) were added to a solution of 3-fluoro-2-nitro-aniline (0.10 g, 0.641 mmol) in DMF (3.2 mL). The resulting mixture was stirred at 80° C. for 10 h. Water was added and the aqueous mixture was extracted with EtOAc. The org layers were combined, washed with brine, dried with $Na_2SO_4$, filtered and concentrated. The crude was purified by column chromatography (silica gel, 0-100% EtOAc in hexanes) to afford 3-(2-methoxyethoxy)-2-nitro-aniline (52 mg, 38% yield). MS m/z 213.1 ($MH^+$).

Step 2: reduction and ring closure of the intermediate 1,2-phenylenediamine to the benzimidazole ring was performed using iron and formic acid following the procedure described in Step 2 of Method I for example 524.

Step 3 (Example 538, Table 4): the benzimidazole derivative of step 2 was coupled to the chloropyridine intermediate A-13 using copper/BINOL catalysis as described for Example 1 (step 4) in general method A.

Analog of Example 523 was prepared in an analogous fashion using ethyleneglycol (R═H) in step 1. Analog of Example 598 (R═$CH_2CH_2OMe$) was prepared in an analogous fashion using 2-(2-methoxyethoxy)ethanol in step 1.

Preparation of Example 525 (Table 4)

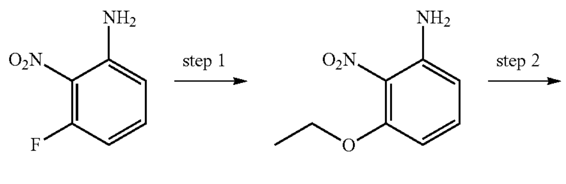

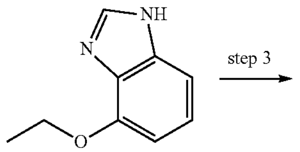

-continued

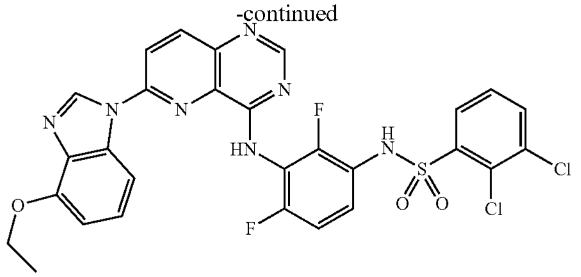

Example 525

Step 1: A solution of sodium ethoxide (21% in EtOH, 1.63 mL, 4.36 mmol) was added to a solution of 3-fluoro-2-nitro-aniline (0.23 g, 1.45 mmol) in EtOH (8 mL). The resulting mixture was stirred at 80° C. for 10 h. The reaction mixture was concentrated and water was added. The aqueous mixture was extracted with EtOAc. The organic layers were combined, washed with brine, dried with $Na_2SO_4$, filtered and concentrated. The crude was purified by colum chromatography (silica gel, 0-100% EtOAc) to afford 3-ethoxy-2-nitro-aniline (0.25 g, 94% yield). MS m/z 183.0 ($MH^+$). $^1H$ NMR (400 MHz, DMSO-$d_6$) δ: 7.10 (t, J=8.4 Hz, 1H), 6.42 (dd, J=8.4, 1.0 Hz, 1H), 6.28 (dd, J=8.2, 1.2 Hz, 1H), 5.94 (br. s, 2H), 4.03 (q, J=6.9 Hz, 2H), 1.25 (t, J=7.0 Hz, 3H).

Step 2: Iron (0.37 g, 6.70 mmol) and ammonium chloride (0.36 g, 6.70 mmol) were added to a mixture of 3-ethoxy-2-nitro-aniline (0.24 g, 1.34 mmol) in iPrOH (4.0 mL) and formic acid (1.9 mL, 49.6 mmol). The result mixture was heated at 90° C. and stirred for 10 h. The reaction mixture was cooled down to rt and filtered through Celite®. The solution was concentrated and the crude was purified by column chromatography (silica gel, 0-10% MeOH in DCM) to afford 4-ethoxy-1H-benzimidazole (133 mg, 61% yield) as an off-white solid. MS m/z 163.0 ($MH^+$). $^1H$ NMR (400 MHz, DMSO-$d_6$) δ: 7.98-8.10 (m, 1H), 7.97-8.21 (m, 2H), 7.01-7.11 (m, 1H), 6.70 (d, J=7.4 Hz, 1H), 4.23 (q, J=7.0 Hz, 2H), 1.27-1.50 (m, 3H).

Step 3 (Example 525, Table 4): the benzimidazole from step 1 was coupled to the chloropyridine intermediate A-13 using copper/BINOL catalysis as described for Example 1 (step 4) in general method A.

Preparation of Example 531 (Table 4)

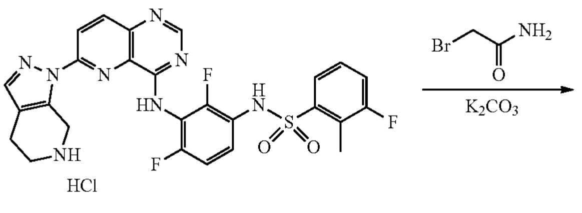

isomer a

-continued

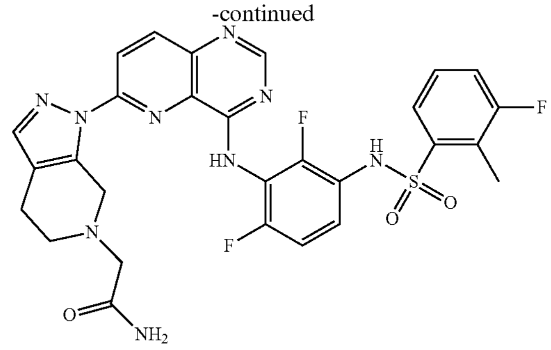

Example 531

Isomer b from step 4 of Examples 339/340 (24.1 mg, 40.0 umol) was dissolved in DMF (300 μL) and potassium carbonate (12.4 mg, 88.0 μmol) was added followed by 2-bromoacetamide (6.08 mg, 43.2 μmol) and the resulting mixture was stirred vigorously at room temperature for 18 hours. Reaction was purified by reverse phase column with 0-30-60% ACN in 10 mM ammonium formate. The compound of Example 531 (9.0 mg, 36% yield) came out at 46% ACN in 10 mM ammonium formate and was obtained as a white solid after lyophilisation.

Preparation of Examples 536 and 550 (Table 4)

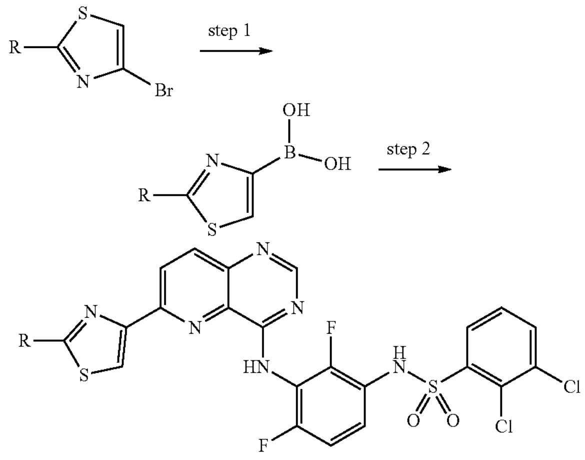

Example 536 (R = H)
Example 550 (R = Me)

Step 1: the heteroaryl bromide (1.00 mmol) was suspended in dioxane (5 mL) in a microwave vial. Bis(pinacolato)diboron (1.10 mmol), potassium acetate (1.50 mmol) and butyldi-1-adamantylphosphine; CataCXium (0.150 mmol) were added at room temperature. The resulting mixture was degassed with nitrogen for 5 min, then tris (dibenzylideneacetone)-dipalladium(0) (0.030 mmol) was added. This was heated at 150° C. in a microwave (normal absorbance) for 30 min or 90° C. in an oil bath for 20 h. The mixture was cooled to room temperature, filtered through Celite and was washed with EtOAc (3×20 mL). Filtrate was concentrated under reduced pressure and the crude boronic acid was used in the next reaction without further purification.

Step 2: potassium carbonate (3.0 mmol), the boronic acid from step 1 (4.0 mmol) and A-13 (Ar=2,3-dichlorophenyl) (1.00 mmol) were suspended in THF (10 mL) and $H_2O$ (2.5 mL) at room temperature. The resulting mixture was degassed with nitrogen for 5 min, then $Pd(PPh_3)_4$ (0.050 mmol) was added. The mixture was heated at 80° C. in an oil bath for 20 h and then cooled to room temperature, filtered through Celite using THF (3×25 mL) for rinses. The filtrate was concentrated under reduced pressure to give compounds of Examples 536 and 550 (Table 4) after purification by reverse phase chromatography (acetonitrile/water containing 0.1% AmF).

Preparation of Examples 537 and 551 (Table 4)

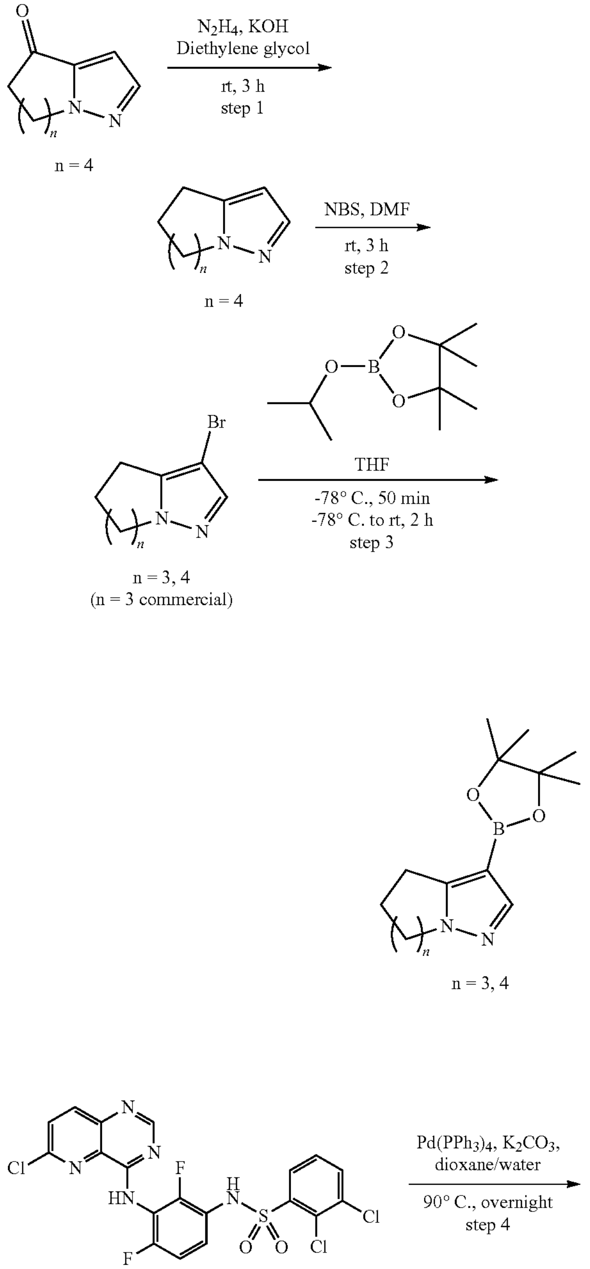

-continued

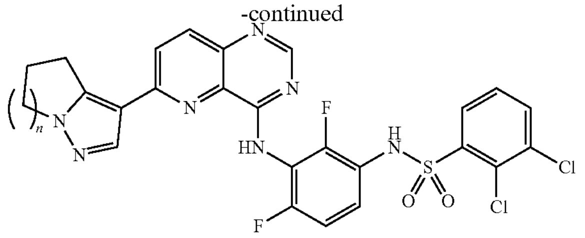

Example 551 (n = 3)
Example 537 (n = 4)

Step 1 (n=4): Hydrazine hydrate solution 50-60% (114 μL, 3.60 mmol) was added to a stirred solution of 6,7-dihydropyrazolo[1,5-a]pyridin-4(5H)-one (100 mg, 720 μmol) in diethylene glycol (1.00 mL). The resulting solution was stirred at 100° C. for 1 h to give the hydrazone intermediate (MW=150.18). The reaction was then removed from heat, and potassium hydroxide (166 mg, 2.52 mmol) was carefully added to the mixture. The resulting mixture was stirred at 100° C. for 2 h, then 120° C. for another 3 h. After cooling, the reaction mixture was diluted with water, acidified to pH=5 with aqueous hydrochloric acid (1N), and extracted with $Et_2O$ (3x30 mL). The combined organic layers were washed with water (2x20 mL) and then dried over $MgSO_4$ filtered, and concentrated under reduced pressure to give the expected pyrazolopyridine (22.0 mg, 25%) as a crude light yellow oil, used in the next step without purification: ($ES^+$) M+H=123.1. $^1$H NMR (400 MHz, CDCl3) δ 7.45 (d, J=1.8 Hz, 1H), 6.00-5.98 (m, 1H), 4.18 (t, J=6.1 Hz, 2H), 2.81 (t, J=6.4 Hz, 2H), 2.09-1.98 (m, 2H), 1.91-1.80 (m, 2H), remaining ethylene glycol.

Step 2 (n=4): To a stirred solution of the product from step 1 (800 mg, 6.55 mmol) in DMF (8 mL) was added N-bromosuccinimide (1.20 g, 6.61 mmol) in portions at room temperature and the resulting solution was stirred and monitored by LCMS. Complete conversion was observed after 3 h. The reaction mixture was concentrated under reduced pressure, and the residue was diluted with EtOAc, washed with brine, dried over Na2SO4, filtered and concentrated to afford the desired bromo derivative (1.11 g, 84% yield), which was used in the next step without purification: ($ES^+$) M+H=203.1.

Step 3 (n=3 or 4): to a stirred solution of commercially available bromide (n=3) or the product from step 2 (n=4) (1.00 mmol) in THF (4.00 mL) was added n-butyllithium (2.5 M in Hexane, 2.00 mmol) at −78° C., and the mixture was stirred at −78° C. for 50 min. 2-Isopropoxy-4,4,5,5-tetramethyl-1,3,2-dioxaborolane (2.00 mmol) was then added at −78° C. and the resulting suspension was slowly warmed to room temperature and stirred for 2 h. After completion of the reaction, the solvents were removed under reduced pressure. The mixture was diluted with EtOAc (10 mL), filtered through Celite, washed with EtOAc (10 mL) and the filtrate was evaporated to afford the boronate esters, which were used in the next step without further purification: Step 3 (n=3): 51% yield, ($ES^+$) M+H=235.5. Step 3 (n=4): quantitative yield, ($ES^+$) M+H=248.9 Step 4 (n=3 or 4): Boronate esters from Step 3 (1.00 mmol), potassium carbonate (3.00 mmol) and A-13 (Ar=2,3-dichlorophenyl) (1.20 mmol) were mixed in dioxane (10 mL) and water (3.2 mL) at room temperature. The resulting solution was degassed 10 min with nitrogen, then $Pd(PPh_3)_4$ (50.0 μmol) was added. The reaction was heated at 90° C. and stirred overnight. After completion, the mixture was cooled to room temperature and the solvent was removed under reduced pressure. The crude compound was then purified by reverse phase chromatography (gradient elution of 10-50% MeCN/H2O (0.1% of 10 mM ammonium formate buffer, product came out around 45% MeCN). Fraction of interest were collected and lyophilized to give the desired compounds.

Preparation of Examples 549 and 595 (Table 4)

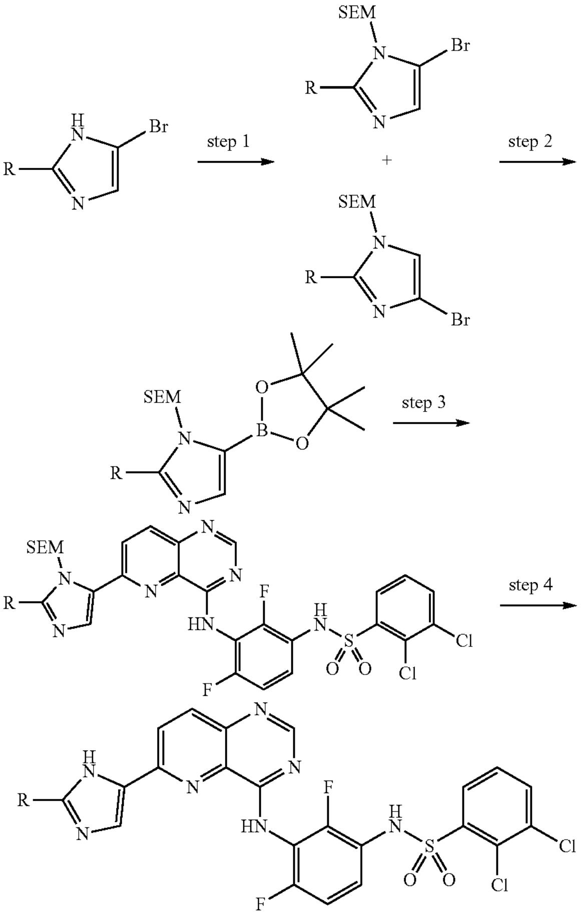

Example 549 (R = Ph)
Example 595 (R = Me)

Step 1 (R=Me): To a stirred solution of 4-bromo-2-methyl-1H-imidazole (200 mg, 1.22 mmol) in THF (3.93 mL) cooled to 0° C. was added sodium hydride 60% dispersion in mineral oil (51.1 mg, 1.28 mmol). After addition, the mixture was stirred for 30 min at 0° C. under nitrogen atmosphere. Then, a solution of (2-chloromethoxy-ethyl)trimethylsilane (251 μL, 1.28 mmol) was added drop-wise. The resulting solution was warmed up to room temperature and stirred overnight under nitrogen. The reaction was quenched by adding water (10 mL). The organic layer was separated and the aqueous layer was extracted with EtOAc (3x10 mL). The combined organics were washed with brine (40 mL), dried over $Na_2SO_4$, filtered and concentrated under reduced pressure. The crude was then purified by normal phase chromatography (40 g column, 0-60% EtOAc in hexanes, 40 mL/min) to afford the protected bromoimidazoles as a mixture of isomers (248 mg, 70% yield: ($ES^+$) M+H=293.1.

$^1$H NMR isomer 1 (400 MHz, DMSO-$d_6$) δ 7.33 (s, 1H), 5.23 (s, 2H), 3.51-3.43 (m, 2H), 2.29 (s, 3H), 0.87-0.79 (m, 2H), −0.04 (s, 9H).

$^1$H NMR isomer 2 (400 MHz, DMSO-$d_6$) δ 6.87 (s, 1H), 5.26 (s, 2H), 3.56-3.46 (m, 2H), 2.37 (s, 3H), 0.89-0.81 (m, 2H), −0.03 (s, 9H).

Step 2 (R=Me): To a stirred solution of the mixture of bromides from step 1 (130 mg, 446 μmol) in THF (1.79 mL) was added n-butyllithium (2.50 M in hexanes, 393 μL, 982 μmol) at −78° C., and the mixture was stirred at −78° C. for 50 min. 2-Isopropoxy-4,4,5,5-tetramethyl-1,3,2-dioxaborolane (204 μL, 982 μmol) was then added at −78° C. and the resulting yellow suspension was slowly warmed to room temperature and stirred for 3 h. The solvents were then removed under reduced pressure. The mixture was diluted with EtOAc (5 mL), filtered through Celite, and the filtrate was evaporated to afford the crude boronate ester (186 mg) as a yellow oil. Used directly in the next step without further purification.

Step 3 (R=Me): The boronate ester from step 2 (58.0 mg, 171 μmol), potassium carbonate (60.4 mg, 429 μmol) and compound A-13 (Ar=2,3-dichlorophenyl) (73.8 mg, 143 μmol) were mixed in dioxane (1.42 mL) and water (459 μL) at room temperature. The resulting solution was degassed 10 min with nitrogen, then $Pd(PPh_3)_4$ (8.34 mg, 7.14 μmol) was added. The reaction was heated at 90° C. and stirred overnight. After completion, the mixture was cooled to room temperature and the solvent was removed under reduced pressure. The crude compound was diluted in a $CH_2Cl_2$/hexanes mixture and sonicated, resulting in a yellow precipitate, which was filtered to give a yellow solid. This was used directly in the next step: ($ES^+$) M+H=392.3

Step 4 (R=Me): To a stirred solution of the crude compound from step 3 (90.0 mg, 130 μmol) in THF (1.30 mL) was slowly added a solution of concentrated hydrochloric acid (39.5 μL, 1.30 mmol) and the mixture was stirred at room temperature for 48 h. After concentration on the rotary evaporator, $CH_2Cl_2$ was added and the aqueous layer was neutralized with aqueous $Na_2CO_3$ until no more gas was released. The resulting solution was extracted with $CH_2Cl_2$ (4×10 mL), then the combined organic layers were washed with brine, dried over $Na_2SO_4$, filtered and concentrated under reduced pressure to afford a yellow oil. The crude was further purified by reverse phase chromatography (12 g column, gradient elution of 5-25% MeCN/H2O (0.1% of 10 mM ammonium formate buffer, 12 mL/min, product came out at 20% MeCN). Fractions of interest were collected and lyophilized to afford the compound of Example 595 (0.43 mg, 0.59% yield).

Example 549, Table 4): following the same sequence of reactions as described above for the compound of Example 595, and using the appropriate 2-phenyl-4-bromoimidazole in step 1 gave the compound of Example 549 as a pale yellow solid.

Preparation of Examples 552 (Table 4)

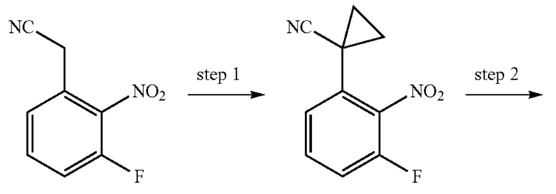

-continued

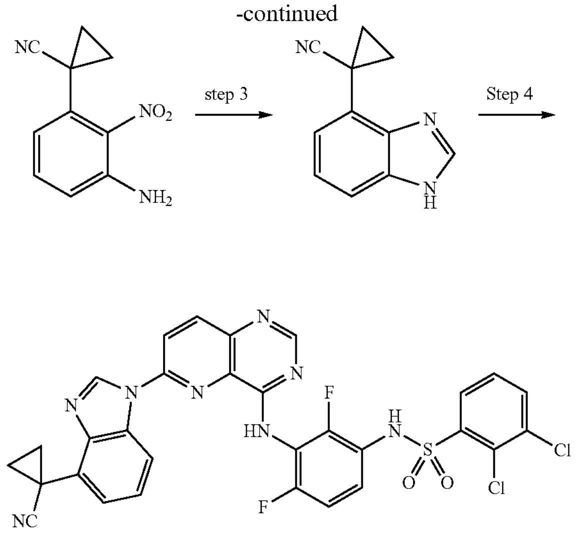

Example 552

Step 1: the phenylacetonitrile derivative obtained as described in step 1 of Example 520 (200 mg, 1.11 mmol) and DMSO (4 mL) was charged in a 25 mL flask. Then diphenyl (vinyl)sulfonium-trifluoromethanesulfonate (479 mg, 1.32 mmol) was added followed by 1,8-diazabicyclo[5.4.0]undec-7-ene (0.37 ml, 2.48 mmol) at room temperature. The mixture was stirred at that temperature for 16 hours. Upon completion, an aqueous solution of $NH_4Cl$ was added and the aqueous layer was extracted with EtOAc. The organic layer was washed with water and once with brine. The organic layer was dried over $MgSO_4$, filtered and concentrated under vacuum. The resulting residue was purified by flash chromatography through a column of silica gel using EtOAc in hexanes to yield the desired cyclopropane derivative (138 mg, 60% yield). $^1$H NMR (400 MHz, $CDCl_3$) δ: 7.47-7.59 (m, 1H), 7.29-7.41 (m, 2H), 1.69-1.85 (m, 2H), 1.29-1.39 (m, 2H). MS m/z 207.2 ($MH^+$).

Step 2: amination of the product from step 1 was performed as described in step 3 of Example 520 to afford the desired nitroaniline (62.6 mg, 100%) as an orange solid. $^1$H NMR (400 MHz, DMSO-$d_6$) δ: 7.27 (t, J=8.0 Hz, 1H), 6.93 (d, J=8.2 Hz, 1H), 6.80 (d, J=7.8 Hz, 1H), 6.00 (s, 2H), 1.76 (s, 6H). MS m/z 206.2 ($MH^+$).

Step 3: reduction and ring closure of the intermediate 1,2-phenylenediamine to the benzimidazole ring was performed using iron and formic acid following the procedure described in Step 2 of Method I for example 524.

Step 4 (example 552, Table 4): the benzimidazole derivative of step 3 was coupled to the chloropyridine intermediate A-13 using copper/BINOL catalysis as described for Example 1 (step 4) in general method A.

Preparation of Examples 553 (Table 4)

4-Methylimidazole was coupled to the chloropyridine intermediate A-13 (Ar=2,3-dichlorophenyl) using copper/BINOL catalysis as described for Example 1 (step 4) in general method A to give a mixture of regioisomers from which the major and less polar isomer (Example 553) was isolated by prep-HPLC.

Preparation of Examples 556 (Table 4)

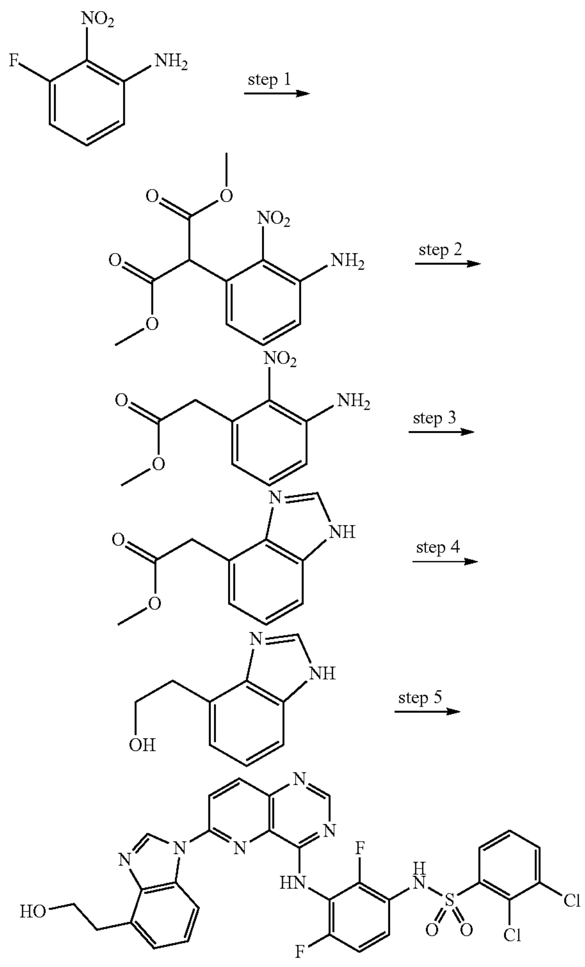

Example 556

Step 1: Cesium carbonate (8.35 g, 25.6 mmol) was charged in a 50 mL flask and suspended in 6 mL of DMSO. Dimethyl malonate (2.7 mL, 30.7 mmol) was then added at room temperature. After 10 minutes of stirring the thick slurry, 3-fluoro-2-nitro-aniline (800 mg, 5.12 mmol) was added affording a bright orange to red mixture which was stirred at 70° C. for 1 hour. The mixture was allowed to cool to room temperature then diluted with EtOAc and washed with a saturated solution of ammonium chloride. The aqueous layer was extracted 3 times with EtOAc and the combined organic layers were washed with brine then dried over $MgSO_4$, filtered and concentrated. The residue was purified by flash chromatography on silica gel using a 5% to 50% ethyl acetate in hexanes gradient. Affords dimethyl 2-(3-amino-2-nitrophenyl)malonate (1.225 g, 89% yield): MS m/z 269.1 ($MH^+$). $^1H$ NMR (DMSO-d6) δ: 7.29 (dd, J=8.2, 7.4 Hz, 1H), 7.00 (dd, J=8.6, 1.2 Hz, 1H), 6.85 (s, 2H), 6.47 (dd, J=7.4, 1.2 Hz, 1H), 5.09 (s, 1H), 3.67 (s, 6H).

Step 2: Dimethyl 2-(3-amino-2-nitrophenyl)malonate (1.37 g, 5.11 mmol) and lithium chloride (260 mg, 6.13 mmol) were charged in a 40 mL vial and dissolved in 6 mL of DMSO and 0.6 mL of water. The bright red mixture was heated at 150° C. for 2.5 hours after which time the color had become a bit darker. The mixture was allowed to cool to room temperature then diluted with water and EtOAc. The biphasic mixture was filtered through a short pad of Celite® to remove insolubles creating emulsions and the layers were separated. The aqueous layer was further extracted 3 more times with EtOAc. The combined organic layers were then washed with water twice and once with brine then dried over $MgSO_4$, filtered and concentrated. The bright red residue was purified by flash chromatography on silica gel using a 15% to 50% EtOAc in hexanes gradient. The appropriate fractions were pooled, concentrated and dried under reduced pressure. Affords methyl 2-(3-amino-2-nitro-phenyl)acetate (749 mg, 70% yield) as a bright orange solid: $^1H$ NMR (DMSO-$d_6$) δ: 7.24 (dd, J=8.4, 7.2 Hz, 1H), 6.93 (dd, J=8.4, 1.4 Hz, 1H), 6.79 (s, 2H), 6.54 (d, J=7.0 Hz, 1H), 3.85 (s, 2H), 3.59 (s, 3H).

Step 3: Methyl 2-(3-amino-2-nitro-phenyl)acetate (545 mg, 2.59 mmol) was charged in a 100 mL flask containing a magnetic stir bar. 5% Palladium on charcoal (109 mg, 0.051 mmol) was then added and the mixture was suspended in 14 mL of methanol. Triethyl orthoformate (0.91 mL, 5.45 mmol) was added followed by 2 drops of acetic acid. The reaction flask was placed under reduced pressure then hydrogen was introduced. This operation was repeated twice more then the mixture was stirred vigorously at room temperature for 24 hours under a balloon atmosphere of hydrogen. 0.2 mL of $Et_3N$ was added to the mixture to neutralize the AcOH then it was filtered through a short pad of celite, rinsing with methanol. The filtrate was concentrated to dryness then the residue was purified by flash chromatography on silica gel column using a 1:1 EtOAc/DCM to 100% EtOAc to 10% IPA in EtOAc gradient. The appropriate fractions were pooled, concentrated then dried under reduced pressure to afford methyl 2-(1H-benzimidazol-4-yl)acetate (299 mg, 61% yield). MS m/z 191.2 ($MH^+$). $^1H$ NMR shows a 0.6 to 0.4 mixture of tautomers: $^1H$ NMR (DMSO-d6) δ: 12.50 (br. s., 0.4H), 12.44 (br. s., 0.6H), 8.21 (s, 0.4H), 8.17 (s, 0.6H), 7.55 (d, J=7.4 Hz, 0.4H), 7.43 (d, J=7.8 Hz, 0.6H), 7.15 (t, J=7.4 Hz, 0.6H), 7.12 (t, J=7.8 Hz, 0.4H), 7.03-7.09 (m, 1H), 4.00 (s, 1.2H), 3.97 (s, 0.8H), 3.62 (s, 1.2H), 3.60 (s, 1.8H).

Step 4: A solution of methyl 2-(1H-benzimidazol-4-yl) acetate (40 mg, 0.21 mmol) in 2 mL of anhydrous THF was cooled in an ice/water bath and allowed to stir for 5 minutes. A 1M THF solution of lithium aluminum hydride (0.25 mL, 0.25 mmol) was then added dropwise. Some gas evolution was noticed and the clear yellow solution became a milky beige suspension. The mixture was allowed to warm to room temperature and stirred overnight. 3-4 Drops of a saturated ammonium chloride solution were added to the mixture. After 5 minutes of stirring, 100 mg of sodium sulfate decahydrate was added. After another 10 minutes of stirring, the mixture was diluted with 2-3 mL of EtOAc and filtered through a plug of Celite®, removing insoluble material. The filtrate was concentrated to a residue which was passed through a siliga gel plug using a 30% IPA in EtOAc solution as eluent. The filtrate was concentrated to dryness and the resulting tan oil crystalized upon drying under reduced pressure to afford afford 2-(1H-benzimidazol-4-yl)ethanol (34.5 mg, 100% yield) as a tan solid which was used without further purification. MS m/z 163.0 ($MH^+$).

Step 5 (example 556, Table 4): the benzimidazole derivative of step 4 was coupled to the chloropyridine intermediate A-13 using copper/BINOL catalysis as described for Example 1 (step 4) in general method A.

Preparation of Examples 534, 594 and 684 (Table 4)

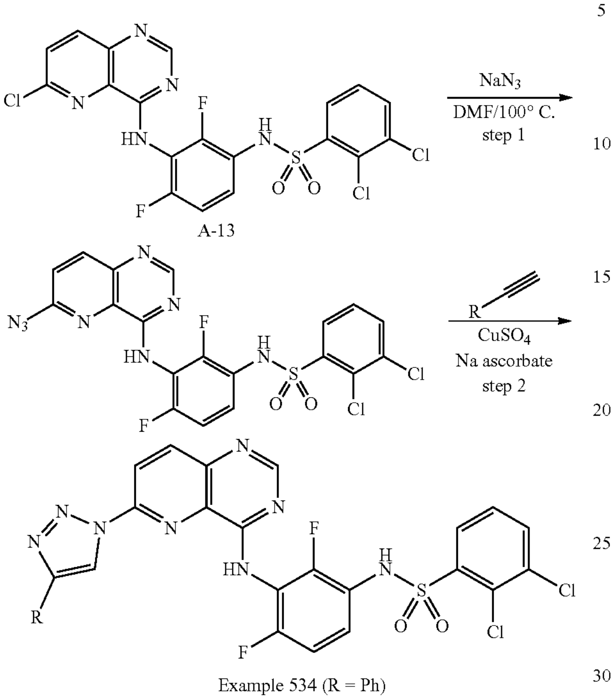

A-13

Example 534 (R = Ph)
Example 594 (R = $CH_2OH$)
Example 684 (R = $CH_3$)

Step 1: $NaN_3$ (190 mg, 2.90 mmol) and chloropyridine A-13 (1.00 g, 1.94 mmol) were mixed in DMF (5.0 mL) at room temperature. This was heated at 100° C. in an oil bath for 18 h. The reaction was cooled to room temperature and was diluted with $H_2O$ (100 mL). The solid formed was filtered and washed with $H_2O$. The solid was dried under air circulation to give the title compound as a brown solid (970 mg, 96% yield): ($ES^+$) M+H=523.2, ($ES^-$) M−H=521.2

Step 2 (Example 534, Table 4): To azide derivative from Step 1 (1.0 mmol) and phenylacetylene (2.0 mmol) in DMSO (5.0 mL) were added simultaneously (dropwise) a solution of anhydrous copper (II) sulfate (319 mg, 2.0 mmol) in water (1.5 mL) and (+)-sodium L-ascorbate (2.0 mmol) in water (1.5 mL). The resulting mixture was stirred overnight at room temperature until completion of the reaction. The mixture was diluted with MeOH (20 mL). The mixture was filtered through Celite and wash washed with MeOH. The filtrate was concentrated under reduced pressure to remove volatiles and the residue was purified by preparative HPLC to give the compound of Example 534 as a white solid (15% yield).

Step 2 (Example 594, Table 4): the same procedure as Example 534 was followed using prop-2-yne-1-ol. The compound of example 594 was obtained as a beige solid (17% yield).

Step 2 (Example 684, Table 4): the same procedure as Example 534 was followed but using a balloon filled with prop-1-yne gas which was bubbled through the mixture for 10 min and then stirred at room temperature overnight under prop-1-yne gas balloon. Purification by reverse phase chromatography (acetonitrile/water containing 0.1% AmF, 40-70%) gave the compound of Example 684 as a white solid (15% yield).

Preparation of Examples 610 (Table 4)

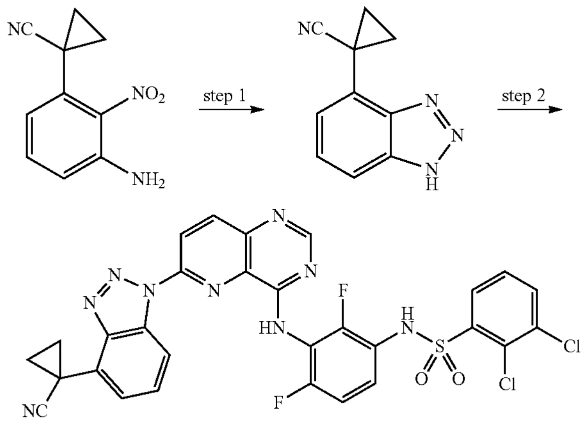

Example 610

Step 1: the nitroaniline starting material, obtained as described in steps 1 and 2 for Example 552 was converted to the desired benzotriazole as described in step 3 under general method J for Example 600.

Step 2 (Example 610, Table 4): the benzotriazole derivative of step 1 was coupled to the chloropyridine intermediate A-13 using copper/BINOL catalysis as described for Example 1 (step 4) in general method A.

Preparation of Examples 612 (Table 4)

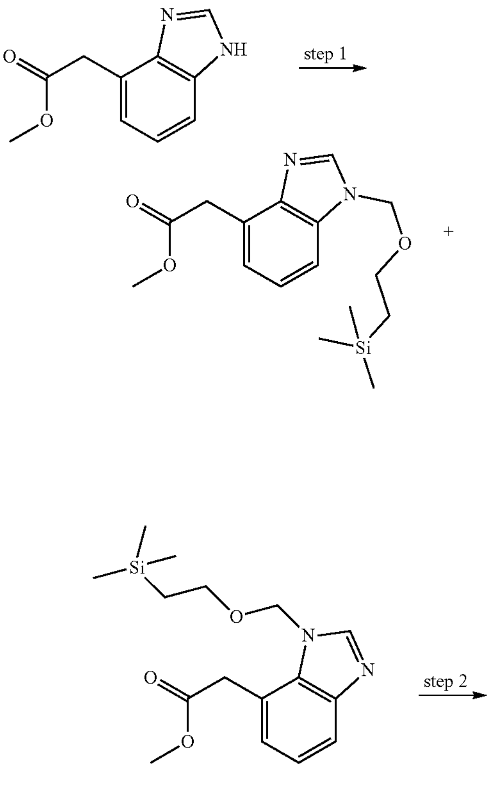

-continued

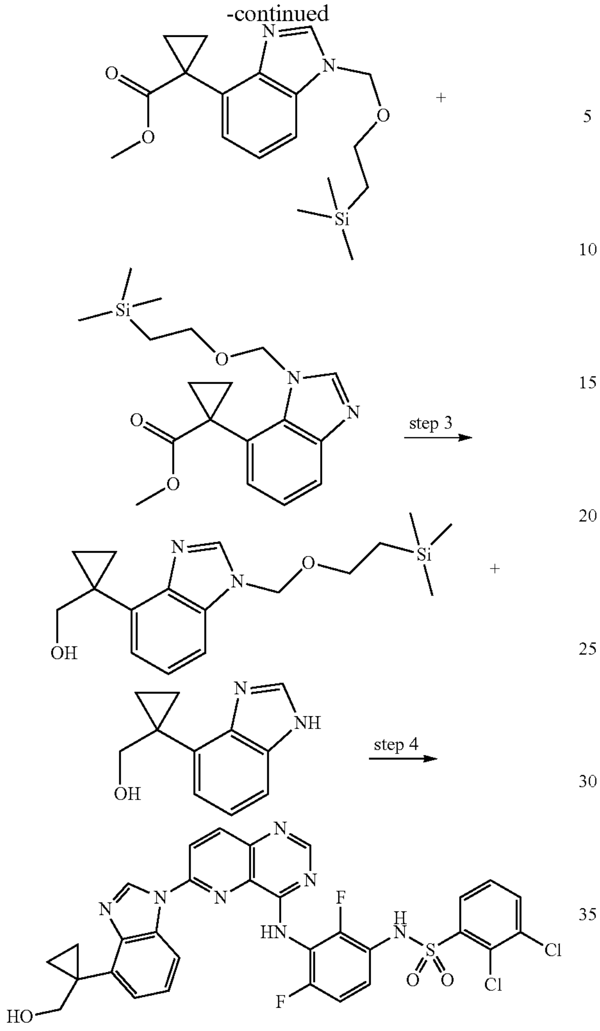

Example 612

Step 1: methyl 2-(1H-benzimidazol-4-yl)acetate prepared as described in Example 556 (303 mg, 1.59 mmol)(from step 3) was dissolved in 10 mL of DMF then potassium carbonate (661 mg, 4.78 mmol) was added followed by SEM-CI (0.42 mL, 2.39 mmol) dropwise over 10 minutes at room temperature. The mixture was allowed to stir at the same temperature for 16 hours. The mixture was poured into a saturated solution of ammonium chloride then extracted 3× with EtOAc. The combined organic layers were washed with water then brine then dried over $MgSO_4$, filtered and concentrated. The resulting residue was purified by flash chromatography on silica gel using a 20% ethyl acetate in hexanes to 100% EtOAc gradient. The appropriate fractions were pooled, concentrated and dried under reduced pressure. Affords methyl 2-[1-(2-trimethylsilylethoxymethyl)benzimidazol-4-yl]acetate (260 mg, 51% yield) as a pale yellow oil.

Step 2: A mixture of methyl 2-[1-(2-trimethylsilylethoxymethyl)benzimidazol-4-yl]acetate and methyl 2-(1-((2-(trimethylsilyl)ethoxy)methyl)-1H-benzo[d]imidazol-7-yl)acetate (265 mg, 0.83 mmol) was charged in a 25 mL flask. A solution of diphenyl(vinyl)sulfonium trifluoromethanesulfonate (479 mg, 1.32 mmol) in DMSO (4 mL) was added followed by 1,8-diazabicyclo[5.4.0]undec-7-ene (0.37 mL, 2.48 mmol) at room temperature. The mixture was stirred at that temperature for 17 hours. The reaction mixture was then diluted with water containing a bit of $NH_4Cl$ and EtOAc. The layers were separated and the aqueous layer was extracted twice more with EtOAc. The combined organic layers were washed twice with water and once with brine. The organic layer was then dried over $MgSO_4$, filtered and concentrated. The resulting residue was purified by flash chromatography on silica gel using a 20% to 100% EtOAc in hexanes gradient followed by 5% IPA in EtOAc. The appropriate fractions were pooled, concentrated and dried under reduced pressure. Affords methyl 1-(1-((2-(trimethylsilyl)ethoxy)methyl)-1H-benzo[d]imidazol-4-yl)cyclopropane-1-carboxylate and methyl 1-(1-((2-(trimethylsilyl)ethoxy)methyl)-1H-benzo[d]imidazol-7-yl)cyclopropane-1-carboxylate as an inseparable mixture of isomers (250 mg, 87% yield), pale yellow oil. MS m/z 347.2 ($MH^+$).

Step 3: A solution of the methyl esters from step 2 (275 mg, 0.79 mmol) in 4 mL of anhydrous THF was cooled in an ice/water bath and allowed to stir for 5 minutes. A 1M THF solution of lithium aluminum hydride (0.95 mL, 0.95 mmol) was then added dropwise. Some gas evolution was noticed. The mixture was allowed to warm to room temperature and stirred for 23 hours. Sodium sulfate decahydrate (0.7 g) was added to the mixture which was allowed to stir for another hour. The mixture was then diluted with EtOAc and filtered through a pad of Celite®, rinsing with EtOAc. The filtrate was then concentrated to dryness and the residue was purified by flash chromatography on silica gel using a 100% EtOAc to 30% IPA in EtOAc gradient.

The first product to elute is [1-[1-(2-trimethylsilylethoxymethyl)benzimidazol-4-yl]cyclopropyl]methanol (132 mg, 52% yield). MS m/z 319.2 ($MH^+$). 1H NMR (DMSO-d6) δ: 8.33 (s, 1H), 7.48 (d, J=8.2 Hz, 1H), 7.18 (t, J=7.8 Hz, 1H), 7.10 (d, J=7.4 Hz, 1H), 5.61 (s, 2H), 4.98 (t, J=5.7 Hz, 1H), 3.70 (d, J=5.5 Hz, 2H), 3.50 (t, J=8.0 Hz, 2H), 0.91 (d, J=2.7 Hz, 4H), 0.83 (t, J=8.0 Hz, 2H), −0.08 (s, 9H).

The second product to elute is [1-(1H-benzimidazol-4-yl)cyclopropyl]methanol (47 mg, 31% yield). MS m/z 186.9 (M−H−).

Step 4 (Example 612 (Table 4): the benzimidazole derivative of step 3 (second product) was coupled to the chloropyridine intermediate A-13 using copper/BINOL catalysis as described for Example 1 (step 4) in general method A.

Preparation of Examples 613 and 631 (Table 4)

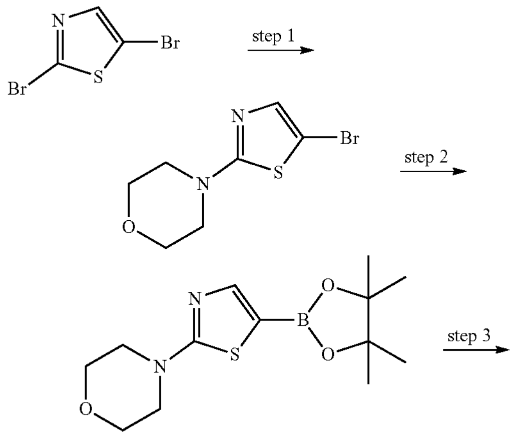

-continued

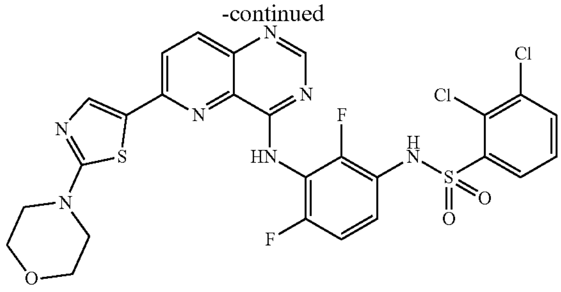

Example 631

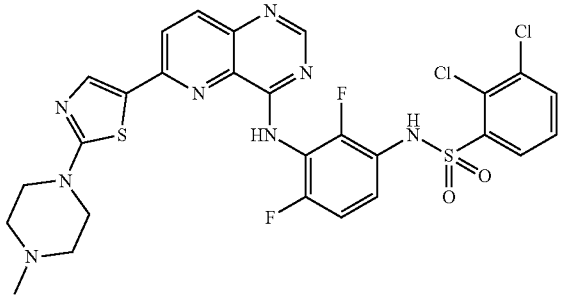

Example 613

Step 1: a mixture of 2,5-dibromothiazole (200 mg, 0.823 mmol), morpholine (0.22 mL, 2.46 mmol) and triethylamine (0.35 mL, 2.47 mmol) in anhydrous THF (4 mL) in a sealed tube was heated at 170° C. for 1 h under microwave radiation. When the reaction was completed, it was evaporated to dryness and the residue was purified on a silica column using 0-50% EtOAc in hexanes. Pure fractions were collected and evaporated to give 4-(5-bromothiazol-2-yl) morpholine (148 mg, 72% yield) as a white solid: m/z=249.0 (m+H).

Step 2: a solution of 4-(5-bromothiazol-2-yl)morpholine (148 mg, 0.594 mmol) in anhydrous THF (3 mL) was cooled to −78° C. and nBuLi in hexanes 2.5 M (0.28 mL, 0.712 mmol) was added dropwise. The light yellow solution was stirred at −78° C. for 30 min and iPrOBPin (0.18 mL, 0.891 mmol) was added dropwise. The reaction was allowed to be warmed to rt and was stirred at that temperature for 2 h. The reaction was evaporated to dryness and the residue was used as such for the next reaction.

Step 3: to a microwave vial with a stirring bar was added 2,3-dichloro-N-(3-((6-chloropyrido[3,2-d]pyrimidin-4-yl) amino)-2,4-difluorophenyl)benzenesulfonamide A-13 (61 mg, 0.118 mmol), crude 4-(5-(4,4,5,5-tetramethyl-1,3,2-dioxaborolan-2-yl)thiazol-2-yl)morpholine from step 2 (35 mg, 0.118 mmol), Pd(dppf)$Cl_2$ (19 mg, 0.0236 mmol) and $K_2CO_3$ (82 mg, 0.590 mmol) in deoxygenated dioxane: water (5:1, 1 mL). The dark red reaction mixture was deoxygenated for another 10 min. The reaction was sealed and plunged into a pre-heated oil bath of 100° C. The reaction was stirred at that temperature for 16 h. The reaction was cooled down to rt and was filtered through a pad of celite. The filter cake was washed with EtOAc. Solvent was evaporated under reduced pressure and the residue was dissolved in 1 mL of DMSO and was purified on a PREP-HPLC using 20-70% MeCN in water+0.01% formic acid. The pure fractions were collected, evaporated and lyophilized to give the analog of Example 631 of Table 4 (24 mg, 28% yield) as a light yellow solid: $^1$H NMR (400 MHz, DMSO-$d_6$) δ: 10.71 (br. s., 1H), 9.57 (s, 1H), 8.36 (br. s., 1H), 8.30 (d, J=8.9 Hz, 1H), 8.23 (s, 1H), 8.07-8.15 (m, 1H), 7.90 (d, J=8.0 Hz, 1H), 7.93 (d, J=8.1 Hz, 1H), 7.52 (dd, J=8.0 Hz, 1H), 7.23-7.30 (m, 1H), 7.14-7.22 (m, 1H), 3.75 (t, J=4.4 Hz, 4H), 3.53 (t, J=4.2 Hz, 4H); m/z=652.2

Example 613 (Table 4) was prepared in a similar fashion, replacing morpholine by N-methylpiperazine in step 1

Preparation of Example 614 (Table 4)

The nitroaniline intermediate (R═OMe$CH_2CH_2$) from step 1 in the preparation of Example 538 was converted to the benzotriazole fragment A455 following the protocol described in method J. The benzotriazole derivative was then coupled to the chloropyridine intermediate A-13 using copper/BINOL catalysis as described for Example 1 (step 4) in general method A.

Preparation of Examples 619 and 623-625 and 627 (Table 4)

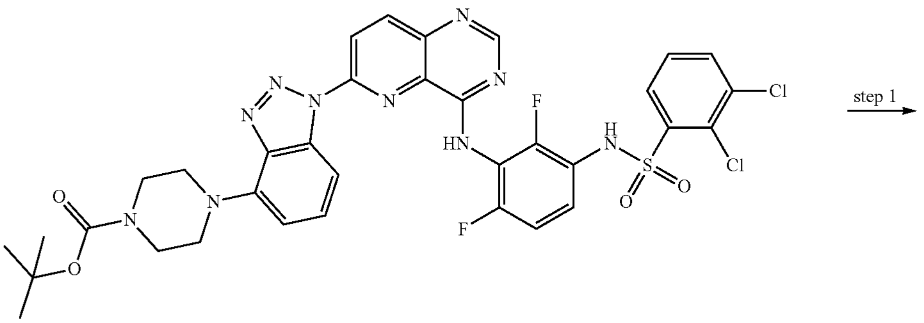

-continued

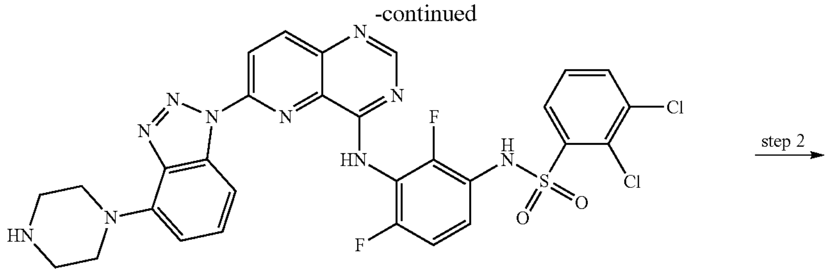

Example 619

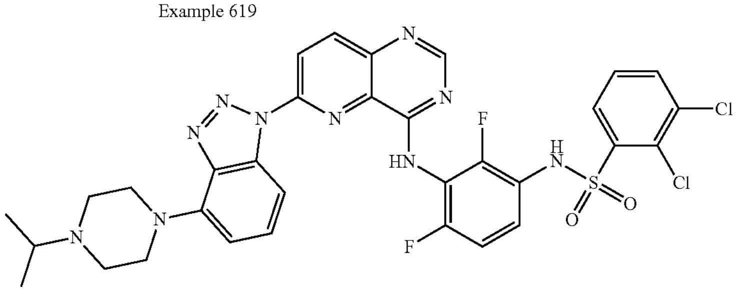

Example 623

Step 1: The N-Boc-protected piperazine prepared as described in Methode J (300 mg, 0.383 mmol) was dissolved in TFA (5.0 mL, 65.3 mmol) and stirred at RT for 30 min. After completion of the reaction, TFA was co-evaporated with ACN to afford Example 619 (298 mg, 97% yield). $^1$H NMR (400 MHz, DMSO-$d_6$) δ: 9.35 (br. s., 1H), 8.76 (d, J=9.13 Hz, 1H), 8.56 (s, 1H), 8.51 (d, J=9.13 Hz, 1H), 8.41 (d, J=8.00 Hz, 1H), 7.94 (dd, J=1.50, 7.75 Hz, 1H), 7.68 (d, J=7.88 Hz, 1H), 7.57 (t, J=8.07 Hz, 1H), 7.38 (t, J=7.88 Hz, 1H), 7.03-7.15 (m, 1H), 6.90 (d, J=7.88 Hz, 1H), 6.85 (t, J=9.26 Hz, 1H), 3.87 (m., 4H). MS m/z 683.2 ($MH^+$).

Step 2: To a suspension of the above trifluoroacetic acid salt from step 1 (60 mg, 0.0658 mmol) in DCE-ACN 1:1 (2 mL) was added triethylamine (0.046 mL, 0.329 mmol) followed by acetone (11 mg, 0.197 mmol) and sodium triacetoxyborohydride (21 mg, 0.0987 mmol). The reaction mixture was stirred at room temperature for 16 h. The reaction mixture was concentrated under vacuum and the residue was was diluted with DMSO and purified by HPLC (MeOH+0.1% formic acid in water+0.1% formic acid) to afford Example 623 (12 mg, 24% yield). $^1$H NMR (400 MHz, DMSO-$d_6$) δ: 9.43 (s, 1H), 8.77 (d, J=9.13 Hz, 1H), 8.47-8.57 (m, 2H), 8.32 (d, J=8.25 Hz, 1H), 7.92 (d, J=8.13 Hz, 1H), 7.85 (d, J=7.13 Hz, 1H), 7.54 (t, J=8.07 Hz, 1H), 7.48 (t, J=8.00 Hz, 1H), 7.24 (d, J=5.25 Hz, 1H), 7.10 (br. s., 1H), 6.84 (d, J=8.13 Hz, 1H), 3.78 (br. s., 4H), 2.87 (d, J=15.38 Hz, 5H), 1.10 (d, J=6.50 Hz, 6H). MS m/z 725.4 ($MH^+$).

Example 624, 625 and 627 were prepared following a similar procedure, using the appropriate aldehyde in the reductive amination step 2.

Preparation of Example 628 (Table 4)

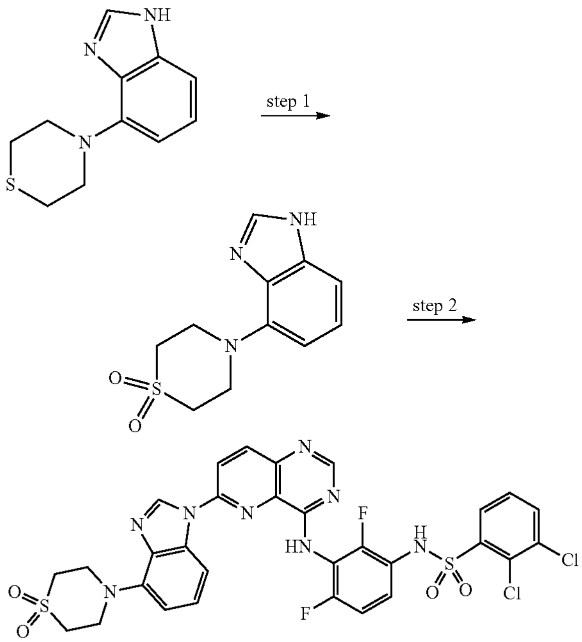

Example 628

Step 1: the starting 4-thiomorpholinebenzimidazole fragment was prepared following method I. A solution of Oxone® (1.42 g, 2.32 mmol) in water (10 mL) was added to a solution of 4-(1H-benzimidazol-4-yl)thiomorpholine (0.127 g, 0.579 mmol) in methanol (20 mL). The resulting mixture was stirred at rt for 17 h. The mixture was concentrated in vacuo and the crude was purified by column chromatography (silica gel, 0-25% MeOH in DCM) to afford 4-(1H-benzimidazol-4-yl)-1,4-thiazinane 1,1-dioxide (0.126 g, 87% yield) as a solid. MS m/z 252.2 ($MH^+$).

Step 2: (Example 628 (Table 4): the benzimidazole derivative of step 2 was coupled to the chloropyridine intermediate A-13 using copper/BINOL catalysis as described for Example 1 (step 4) in general method A.

Preparation of Example 629 (Table 4)

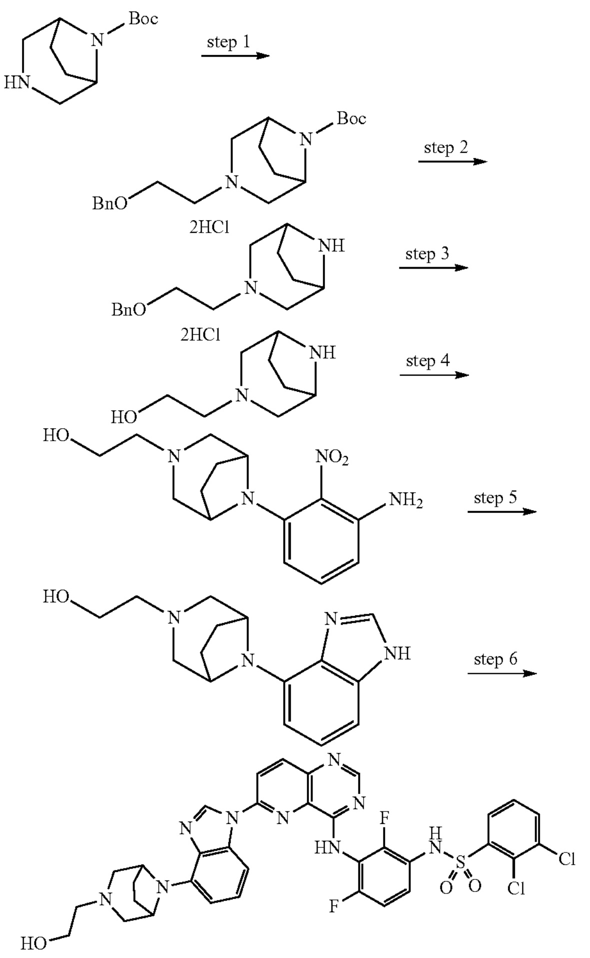

Example 629

Step 1: tert-Butyl 3,8-diazabicyclo[3.2.1]octane-8-carboxylate (0.70 g, 3.30 mmol) and potassium carbonate (1.14 g, 8.24 mmol) were charged in a 25 mL flask and suspended in 10 mL of MeCN. benzyl 2-bromoethyl ether (0.57 mL, 3.63 mmol) was then added dropwise at room temperature. The resulting mixture was allowed to stir at room temperature for 22 hours then at 40° C. for 4 hours. The reaction mixture was diluted with EtOAc. The solids were removed by filtration and the filtrate was concentrated to dryness. The resulting residue was purified by flash chromatographyl on silica gel using a 0% to 40% EtOAc in hexanes gradient. The appropriate fractions were concentrated then dried under reduced pressure to afford tert-butyl 3-(2-benzyloxyethyl)-3,8-diazabicyclo[3.2.1]octane-8-carboxylate (678 mg, 59% yield) as a colorless oil. MS m/z 347.4 ($MH^+$). $^1H$ NMR (DMSO-d6) δ: 7.24-7.39 (m, 5H), 4.47 (s, 2H), 3.99 (br. s., 2H), 3.51 (t, J=5.7 Hz, 2H), 2.64 (d, J=10.2 Hz, 2H), 2.50 (t, J=5.7 Hz, 2H), 2.19 (d, J=10.6 Hz, 2H), 1.60-1.82 (m, 4H), 1.39 (s, 9H).

Step 2: tert-butyl 3-(2-benzyloxyethyl)-3,8-diazabicyclo[3.2.1]octane-8-carboxylate (673 mg, 1.94 mmol) was charged in a 100 mL flask and dissolved in 5 mL of dioxane. A 4N solution of HCl in dioxane (1.94 mL, 7.76 mmol) was then added dropwise. After 1 hour of stirring, another portion of the HCl solution was added (2.91 mL, 11.64 mmol) and the mixture was warmed to 40° C. After another 2 hours of stirring at that temperature, a gum had separated at the bottom of the flask. The mixture was cooled to room temperature, diluted with methanol and concentrated to dryness. The residue was dissolved in methanol and concentrated to dryness once more then dried under reduced pressure. Affords 3-(2-benzyloxyethyl)-3,8-diazabicyclo[3.2.1]octane; dihydrochloride (620 mg, 100% yield) as a white gummy solid which was used as such. MS m/z 247.3 ($MH^+$). $^1H$ NMR (DMSO-d6) δ: 11.36 (br. s., 1H), 10.10 (br. s., 1H), 9.64 (br. s., 1H), 7.33-7.40 (m, 4H), 7.27-7.33 (m, 1H), 4.51 (s, 2H), 4.18 (br. s., 2H), 3.88 (br. s., 2H), 3.58-3.75 (m, 2H), 3.21 (br. s., 2H), 2.34 (br. s., 2H), 2.02 (br. s., 2H) (2H hidden underwater peak).

Step 3: To a solution of 3-(2-benzyloxyethyl)-3,8-diazabicyclo[3.2.1]octane; dihydrochloride (615 mg, 1.93 mmol) in a 100 mL flask in 15 mL of methanol was added 10% palladium on charcoal (205 mg, 0.193 mmol). The flask was placed under reduced pressure then filled with hydrogen. This operation was repeated 3 more times then the mixture was stirred vigorously under a balloon atmosphere of hydrogen over weekend. The flask was flushed with nitrogen and the reaction mixture was filtered through a short pad of Celite®. The filtrate was concentrated and dried under reduced pressure. Affords 2-(3,8-diazabicyclo[3.2.1]octan-3-yl)ethanol; dihydrochloride (406 mg, 92% yield). MS m/z 157.2 ($MH^+$). $^1H$ NMR (DMSO-d6) δ: 11.14 (br. s., 1H), 10.07 (br. s., 1H), 9.68 (br. s., 1H), 5.08 (br. s., 1H), 4.16 (br. s., 2H), 3.81 (br. s., 2H), 3.03 (br. s., 2H), 2.33 (br. s., 2H), 2.03 (br. s., 2H) (4H hidden underwater peak).

Step 4: 2-(8-(3-amino-2-nitrophenyl)-3,8-diazabicyclo[3.2.1]octan-3-yl)ethan-1-ol was prepared as described in step 1 of general method I for Example 524: MS m/z 293.2 ($MH^+$). $^1H$ NMR (DMSO-d6) δ: 7.00 (t, J=8.2 Hz, 1H), 6.32 (dd, J=8.1, 0.8 Hz, 1H), 6.18 (dd, J=8.3, 0.8 Hz, 1H), 5.83 (s, 2H), 4.30 (t, J=5.4 Hz, 1H), 3.67 (br. s., 2H), 3.45 (q, J=6.1 Hz, 2H), 2.61 (dd, J=10.7, 2.6 Hz, 2H), 2.35 (t, J=6.3 Hz, 2H), 2.25 (d, J=10.3 Hz, 2H), 1.75-1.85 (m, 2H), 1.65-1.75 (m, 2H).

Step 5: 2-[8-(3-amino-2-nitro-phenyl)-3,8-diazabicyclo[3.2.1]octan-3-yl]ethanol (228 mg, 0.78 mmol) was suspended in IPA (5 mL) and formic acid (1.8 mL, 46.8 mmol). To the bright red mixture was added ammonium chloride (417 mg, 7.80 mmol) and iron metal (436 mg, 7.80 mmol). The flask was equiped with a reflux condenser and was immersed in an oil bath pre-heated to 80° C. for 2 hours. The temperature of the oil bath was reduced to 60° C. and the reaction was allowed to go on overnight. The mixture was allowed to cool to room temperature and was then filtered through a pad of celite, rinsing with IPA. The filtrate was concentrated to dryness and the residue was taken up in 5 mL of water. 1N NaOH was added until a basic pH was obtained. The mixture was then thoroughly extracted with EtOAc. The combined organic layers were washed once with brine then dried over $MgSO_4$, filtered and concentrated. The residue was purified by flash chromatography on silica gel column starting with a 99% EtOAc/1% $Et_3N$ mixture to a 50% IPA/49% EtOAc/1% $Et_3N$ mixture as gradient. The appropriate fractions were pooled, concentrated then dried under reduced pressure. Affords 2-[8-(1H-benzimidazol-4-yl)-3,8-diazabicyclo[3.2.1]octan-3-yl]ethanol (161 mg, 76% yield) as a red foam. MS m/z 273.2 ($MH^+$). $^1H$ NMR (DMSO-d6) δ: 12.22 (br. s., 1H), 7.98 (s, 1H), 6.98 (t, J=7.9 Hz, 1H), 6.82 (d, J=7.9 Hz, 1H), 6.45 (d, J=7.8 Hz, 1H), 5.00 (br. s., 2H), 4.25 (br. s., 1H), 3.44 (dt, J=5.7, 4.1 Hz, 2H), 2.55 (dd, J=10.6, 2.3 Hz, 2H), 2.39 (d, J=10.3 Hz, 2H), 2.25 (t, J=6.3 Hz, 2H), 1.87-1.96 (m, 2H), 1.79-1.87 (m, 2H).

Step 6 (Example 629, Table 4): the benzimidazole derivative of step 5 was coupled to the chloropyridine intermediate A-13 using copper/BINOL catalysis as described for Example 1 (step 4) in general method A.

Preparation of Example 634 (Table 4)

Mono-protected N-Boc-piperazine was used to prepare the benzimidazole fragment according to method I. The benzimidazole derivative was then coupled to the chloropyridine intermediate A-13 using copper/BINOL catalysis as described for Example 1 (step 4) in general method A. The N-Boc protecting group was then removed under standard conditions using TFA and the product of Example 634 isolated by Prep-HPLC.

Preparation of examples 648 and 649 (Table 5)

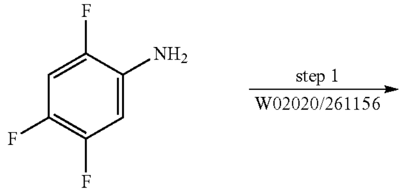

2,4,5-trifluoroaniline

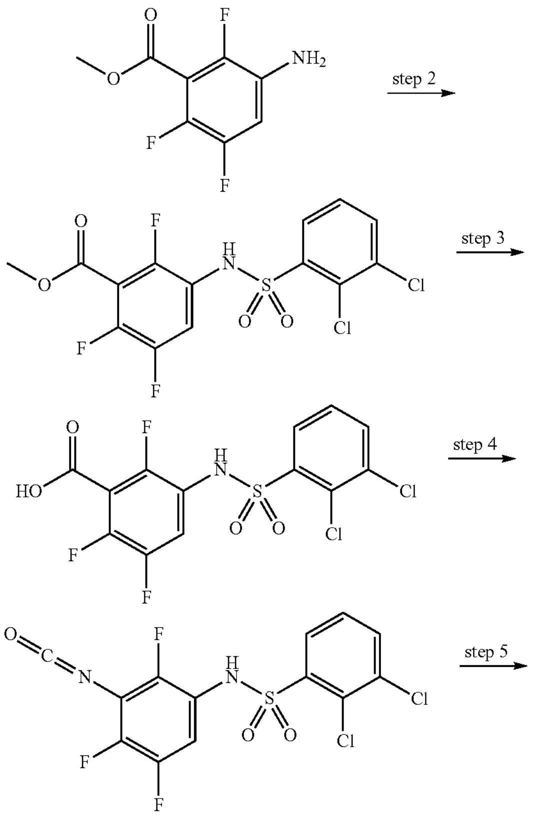

-continued

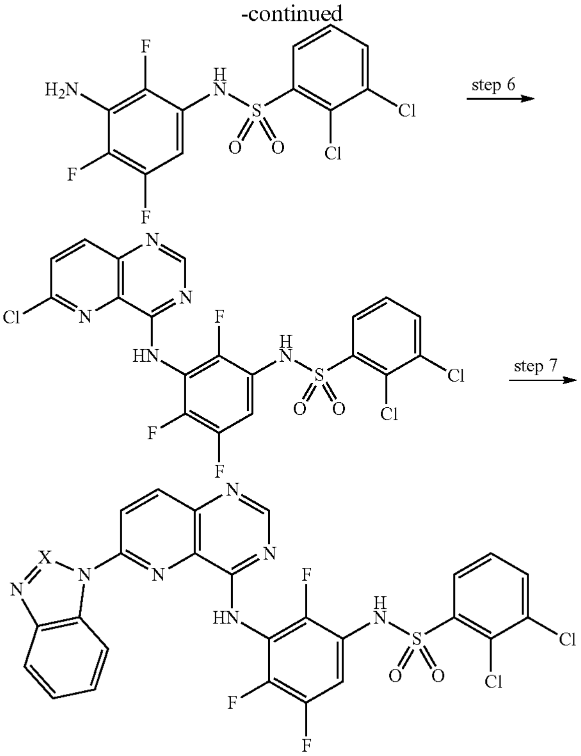

Exemple 648 (X = CH)
Exemple 649 (X = N)

Step 1: carbomethoxylation of 2,4,5-trifluoroaniline was performed as described in patent WO2020/261156.

Step 2: To a solution of methyl 3-amino-2,5,6-trifluorobenzoate (2.72 g, 13.26 mmol) in DCE/pyridine (1:1, 16 mL) was added 2,3-dichlorobenzenesulfonyl chloride (3.91 g, 15.91 mmol) portion wise at rt. The reaction was heated to 70° C. for 16 h. The reaction was monitored by LCMS. When the reaction was completed, it was quenched with HCl 1 M. The aqueous layer was extracted with EtOAc (15 mL) three times. The combined organic layers were washed with brine, dried over $MgSO_4$, filtered and evaporated to dryness. The residue was purified by chromatography on a silica gel column using 0-30% EtOAc in hexanes. The pure fractions were collected and evaporated to give methyl 3-((2,3-dichlorophenyl)sulfonamido)-2,5,6-trifluorobenzoate (5.14 g, 91% yield) as a light brown solid: m/z=412.0.

Step 3: To a solution of methyl 3-((2,3-dichlorophenyl)sulfonamido)-2,5,6-trifluorobenzoate from step 2 (5.14 g, 12.41 mmol) in 30 mL of THF:MeOH (5:1) was added 2M KOH (37 mL, 74.5 mmol) at rt. The reaction was stirred at rt overnight. When the reaction was completed, it was evaporated to dryness and residue was added water (30 mL) and diethyl ether (30 mL). The aqueous layer was washed with ether (20 mL) twice. The aqueous layer was acidified with HCl 1M to pH=2. The aqueous layer was extracted with EtOAc (30 mL) thrice. The combined organic layers were washed brine, dried over $MgSO_4$, filtered and evaporated to give 3-((2,3-dichlorophenyl)sulfonamido)-2,5,6-trifluorobenzoic acid (4.50 g, 91% yield) as a light orange oil. The compound was used as such in the next step: m/z=398.0.

Step 4: To a solution of 3-((2,3-dichlorophenyl)sulfonamido)-2,5,6-trifluorobenzoic acid from step 3 (4.50 g, 11.24 mmol) in acetonitrile (30 mL) was added triethylamine (1.71 mL, 12.37 mmol) and diphenyl phosphoryl azide (2.91 mL, 13.50 mmol) at rt. The reaction was heated to 80° C. overnight. The reaction was cooled down to rt and water (30 mL) was added. The aqueous layer was extracted with EtOAc (30 mL) three times. The combined organic layers were washed with brine, dried over $MgSO_4$, filtered and evaporated into a dark yellow residue. The crude material was purified by chromatography on a silica gel column using 0-50% EtOAc in hexanes. The pure fractions were collected and evaporated to give 2,3-dichloro-N-(2,4,5-trifluoro-3-isocyanatophenyl)benzenesulfonamide (2.29 g, 51% yield) as a brown solid: m/z=391.0.

Step 5: To a solution of 2,3-dichloro-N-(2,4,5-trifluoro-3-isocyanatophenyl)benzenesulfonamide from step 4 (1.35 g, 3.39 mmol) in THF (17 mL) was added aqueous LiOH 4M (17 mL). The pressure vessel was screwed and heated to 100° C. for 1 h in an oil bath. When the reaction was completed, it was quenched with $NH_4Cl$ sat. EtOAc was added and the layers were allowed to separate. The aqueous layer was extracted with EtOAc (20 mL) two more times. The combined organic layers were washed with brine, dried over $MgSO_4$, filtered and evaporated to give N-(3-amino-2,4,5-trifluorophenyl)-2,3-dichlorobenzenesulfonamide (1.09 g, 86% yield) as a brown solid. The compound was carried to the next step without further purification: $^1H$ NMR (400 MHz, DMSO-$d_6$) δ: 10.59 (br. s., 1H), 7.94 (dd, J=8.2, 1.6 Hz, 1H), 7.89 (dd, J=8.2, 1.6 Hz, 1H), 7.51 (dd, J=8.0 Hz, 1H), 6.34-6.43 (m, 1H), 5.72 (s, 2H). m/z=369.0.

Step 6: To a solution of N-(3-amino-2,4,5-trifluorophenyl)-2,3-dichlorobenzenesulfonamide from step 5 (300 mg, 0.808 mmol) in glacial AcOH (1 mL) was added 4,6-dichloropyrido[3,2-d]pyrimidine (162 mg, 0.808 mmol) at rt. The reaction was heated to 50° C. and was monitored by LCMS. When the reaction was completed, it was evaporated to dryness to give 2,3-dichloro-N-(3-((6-chloropyrido[3,2-d]pyrimidin-4-yl)amino)-2,4,5-trifluorophenyl)benzenesulfonamide (451 mg, 98% yield) as a light yellow foam. The compound was used as such in the next reaction. m/z=536.0

Step 7 (Examples 648 and 649 Table 5): following the general procedure described for Example 1 (step 4) in general method A using copper/BINOL catalysis, coupling of the chloropyridine from step 6 to benzimidazole gave the compound of example 648 (Table 5). Replacing benzimidazole by benzotriazole gave the compound of example 649 (Table 5)

Preparation of Example 655 (Table 4)

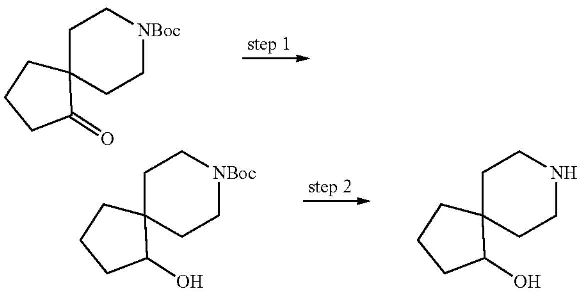

A481

Step 1 (procedure from patent CN 105503725): Sodium borohydride (0.10 g, 2.67 mmol) was added to a solution tert-butyl 4-oxo-8-azaspiro[4.5]decane-8-carboxylate (0.34 g, 1.33 mmol) in THF (6.7 mL). The resulting mixture was heated to 75° C. and stirred for 10 h. TLC show the consumption of the starting material. Water was added and the aqueous mixture was extracted with EtOAc. The organic layers were combined, washed with brine, dried with $Na_2SO_4$, filtered and concentrated to afford tert-butyl 4-hydroxy-8-azaspiro[4.5]decane-8-carboxylate (0.27 g, 79% yield) The crude was use without any purification for the next step.

Step 2: Trifluoroacetic acid (0.81 mL, 10.6 mmol) was added to a solution of tert-butyl 4-hydroxy-8-azaspiro[4.5]decane-8-carboxylate (0.27 g, 1.06 mmol) in DCM (6.7 mL) The resulting mixture was stirred at RT for 10 h. The reaction mixture was concentrated (azeotrope with toluene) and dried under vacuum to afford fragment A481 (0.28 g, 99% yield) as a colorless oil. MS m/z 156.2 ($MH^+$).

Fragment A481 was converted to the compound of Example 655 (Table 4) following general method I.

Preparation of Example 662 (Table 4)

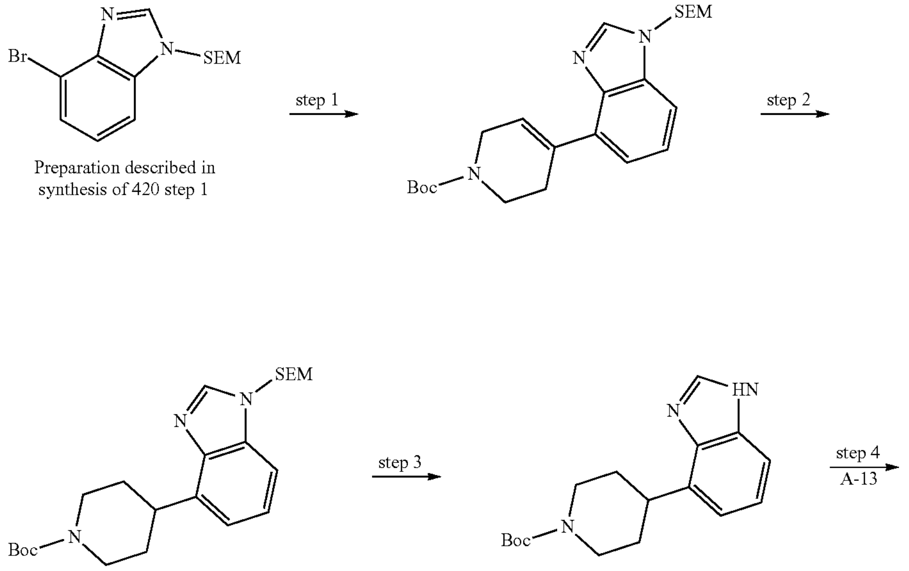

-continued

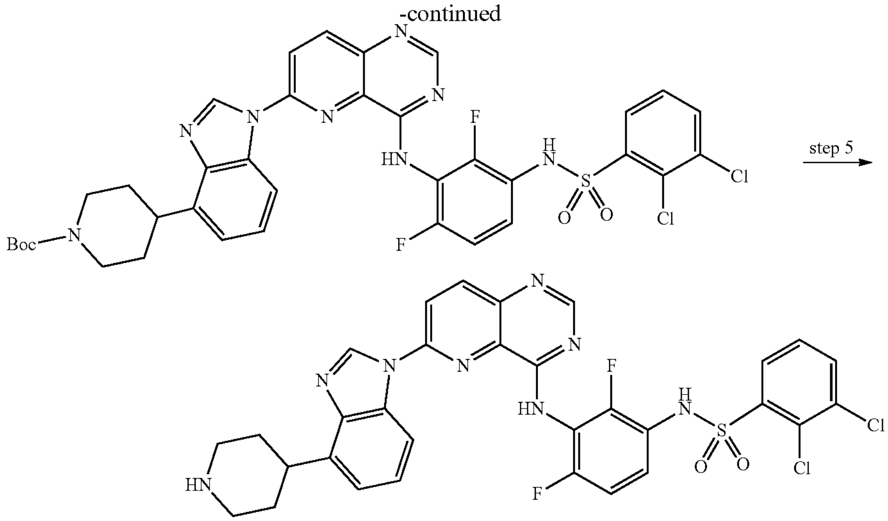

Example 662

Step 1: 2-[(4-bromobenzimidazol-1-yl)methoxy]ethyl-trimethyl-silane prepared in step 1 of Example 420 (101 mg, 0.31 mmol) was weighed in a 4 mL vial then 1-boc-4-piperidone (71 mg, 0.36 mmol) was added followed by p-toluenesulfonhydrazide (68 mg, 0.355 mmol), tris(dibemzylideneacetone)dipalladium(0)-chloroform adduct (6.4 mg, 0.006 mmol), 2-dicyclohexylphosphino-2',4',6'-tri-i-propyl-1,1'-biphenyl (12 mg, 0.025 mmol) and lithium t-butoxide (62 mg, 0.77 mmol). Dioxane (2 mL) was finally added and argon was bubbled through the mixture for 3-4 minutes. The vial was capped and heated at 110° C. The initially tan colored solution became a milky pale green suspension within 30 minutes. The reaction mixture was allowed to stir at that temperature for 24 hours then another portion of 1-boc-piperidinone (35 mg, 0.18 mmol) and p-toluenesulfonhydrazide (34 mg, 0.18 mmol) were added to the mixture at room temperature and the reaction was stirred at 110° C. overnight. The mixture was cooled to room temperature then partitioned between EtOAc and a saturated solution of ammonium chloride. The aqueous layer was extracted twice more with EtOAc and the combined organic layers were washed with brine then dried over $MgSO_4$, filtered and concentrated. The resulting residue was purified by flash chromatography on silica gel using a 10% to 50% EtOAc in hexanes gradient. Concentration and drying under reduced pressure of the appropriate fractions affords tert-butyl 4-[1-(2-trimethylsilylethoxymethyl)benzimidazol-4-yl]-3,6-dihydro-2H-pyridine-1-carboxylate (89 mg, 0.21 mmol, 67% yield) as a pale yellow film. MS m/z 430.4 ($MH^+$).

Step 2: tert-butyl 4-[1-(2-trimethylsilylethoxymethyl) benzimidazol-4-yl]-3,6-dihydro-2H-pyridine-1-carboxylate (89 mg, 0.21 mmol) was charged in a 25 mL flask along with 5% palladium on charcoal (22 mg, 0.01 mmol). The flask was flushed with nitrogen then methanol (4 mL) was then added. The flask was placed under reduced pressure the filled with hydrogen. This operation was repeated twice more then the mixture was vigorously stirred under a balloon atmosphere of hydrogen at room temperature for 6 hours at room temperature and for 16 hours at 40° C. Another portion of 5% palladium on charcoal was added (22 mg, 0.01 mmol) and the reaction was allowed to stir at 40° C. for another 24 hours under hydrogen. The flask was flushed with nitrogen and the mixture was filtered through a short pad of Celite®, rinsing with methanol. The filtrate was then concentrated to dryness then dried under reduced pressure. Affords tert-butyl 4-[1-(2-trimethylsilylethoxymethyl)benzimidazol-4-yl]piperidine-1-carboxylate (90 mg, 100% yield) which was used as such. MS m/z 432.4 ($MH^+$).

Step 3: tert-butyl 4-[1-(2-trimethylsilylethoxymethyl) benzimidazol-4-yl]piperidine-1-carboxylate (89 mg, 0.21 mmol) was dissolved in 2 mL of THF in a 20 mL vial and to the solution was added a 1M THF solution of tetra-n-butylammonium fluoride (1.0 mL, 1.03 mmol) at room temperature. The vial was capped and the mixture was heated at 65° C. for 17 hours. The mixture was allowed to cool to room temperature then diluted with EtOAc and washed once with a diluted solution of $NaHCO_3$. The aqueous layer was extracted twice then the combined organic layers were washed once with brine and dried over $MgSO_4$. The residue obtained after filtration and concentration was purified by flash chromatography on silica gel using a 100% EtOAc to 14% IPA in EtOAc gradient. The appropriate fractions were pooled, concentrated and dried under reduced pressure. Affords tert-butyl 4-(1H-benzimidazol-4-yl)piperidine-1-carboxylate (29 mg, 0.0972 mmol, 47% yield). MS m/z 302.2 ($MH^+$).

Step 4: tert-butyl 4-(1H-benzimidazol-4-yl)piperidine-1-carboxylate (27 mg, 0.09 mmol) was charged in a 4 ml vial along with 2,3-dichloro-N-[3-[(6-chloropyrido[3,2-d]pyrimidin-4-yl)amino]-2,4-difluoro-phenyl]benzenesulfonamide (40 mg, 0.08 mmol), copper (0.25 mg, 0.004 mmol), cesium carbonate (63 mg, 0.194 mmol) and (R)-(+)-1,1'-bi-2-naphthol (1.1 mg, 0.004 mmol). DMSO (0.6 mL) was then added. The vial was capped and mixture was heated at 100° C. with stirring for 2 hours. The reaction mixture was then allowed to cool to room temperature and slowly transferred into a flask containing 3 mL of water and 0.15 mL of AcOH (gas evolution). The resulting suspension was homogenized by sonication then the solids were collected by filtration on a paper filter in a Buchner funnel. The solids were then washed with a bit of water and dried under reduced pressure. Affords tert-butyl 4-[1-[4-[3-[(2,3-dichlorophenyl)sulfonylamino]-2,6-difluoro-anilino]pyrido[3,2-d]pyrimidin-6-yl]benzimidazol-4-yl]piperidine-1-carboxylate (61 mg, 100% yield). MS m/z 781.2 ($MH^+$).

Step 5: tert-butyl 4-[1-[4-[3-[(2,3-dichlorophenyl)sulfonylamino]-2,6-difluoro-anilino]pyrido[3,2-d]pyrimidin-6-yl]benzimidazol-4-yl]piperidine-1-carboxylate (61 mg, 0.08 mmol) was dissolved in 1 mL of DCM. TFA (0.50 mL, 6.53 mmol) was then added slowly at room temperature. The resulting mixture was allowed to stir for 4 hours. The mixture was diluted with 2 mL of toluene then concentrated to a residue under reduced pressure. The residue was taken into 2 mL of MeCN and basified with a few drops of conc. $NH_4OH$ affording a brown suspension. This suspension was concentrated once more and the residue was taken into 2 mL of DMSO to which was added 0.1 mL of formic acid. The resulting solution was filtered through a syringe filter and purified by prep-HPLC (3 injections, 30% to 100% MeOH in water gradient, 0.1% formic acid). The appropriate fractions were pooled and concentrated to remove MeOH. The product was lyophilized from MeCN/water. Affords 2,3-dichloro-N-[2,4-difluoro-3-[[6-[4-(4-piperidyl)benzimidazol-1-yl]pyrido[3,2-d]pyrimidin-4-yl]amino]phenyl]benzenesulfonamide (17 mg, 28% yield)

-continued

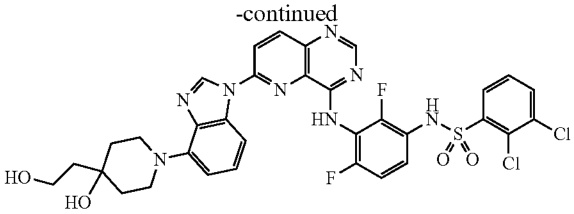

Example 671

Preparation of Examples 671 (Table 4)

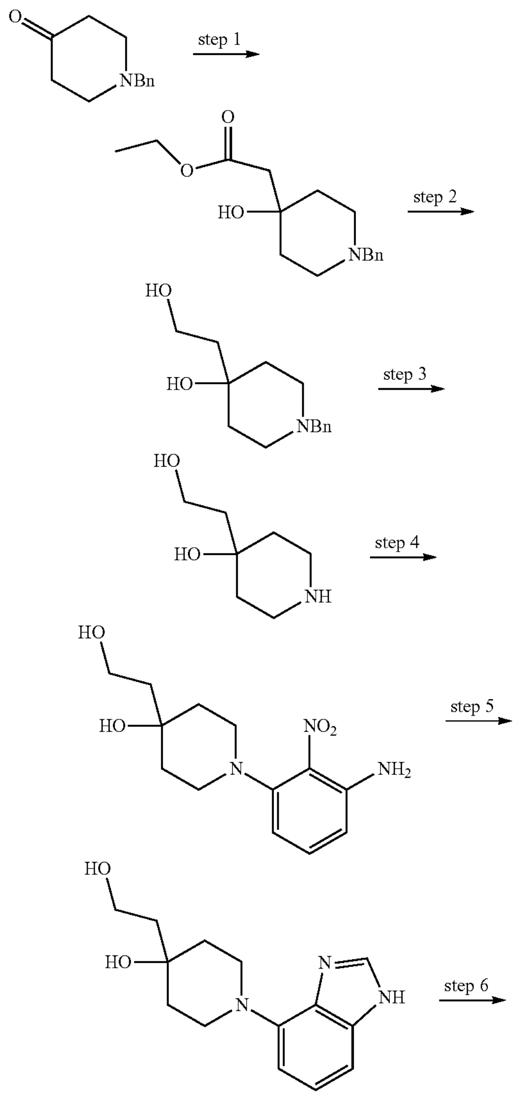

Step 1: A solution of ethyl acetate (2.4 mL, 24.1 mmol) in THF (30 mL) was added dropwise to a 2.0M solution of LDA (13 mL, 26.1 mmol) in THF at −78° C. The mixture was stirred at that temperature for 30 min. A solution of 1-benzyl-4-piperidone (3.80 g, 20.1 mmol) in THF (25 mL) was added dropwise at −78° C., then mixture was warmed to −40° C. and stirred for 3 h. The mixture was stored in a freezer at −30° C. for 14 hours. It was then quenched with saturated aqueous $NH_4Cl$ solution (30 mL) at −30° C., then warmed to room temperature and extracted with EtOAc (3×200 mL). The combined organic extract was dried ($Na_2SO_4$), concentrated and the residue was purified by silica gel chromatography using MeOH and DCM (0-30%) to obtain ethyl 2-(1-benzyl-4-hydroxy-4-piperidyl)acetate (3.99 g, 72% yield) as a yellow oil. MS m/z 278.2 ($MH^+$).

Step 2: ethyl 2-(1-benzyl-4-hydroxy-4-piperidyl)acetate (3.00 g, 10.8 mmol) was dissolved in THF (45 mL). Lithium aliminium hydride (411 mg, 10.8 mmol) was added in four portions at room temperature after which the mixture was stirred for 1 h. The reaction was quenched with water (10 mL), then a 10% aqueous NaOH solution (15 mL) was added and stirred for 30 min. The thick suspension was then filtered through pad of Celite®, and the filtrate was extracted with EtOAc (3×50 mL). The combined organic extract was dried over $Na_2SO_4$, filtered, concentrated and dried under reduced pressure to afford 1-benzyl-4-(2-hydroxyethyl)piperidin-4-ol (2.45 g, 96% yield) as a yellow oil. MS m/z 236.2 ($MH^+$).

Step 3: 20% Palladium hydroxide on carbon (0.0385 eq, 200 mg, 0.285 mmol) was weighed into a 50 mL RBF. The flask was flushed with nitrogen. A solution of 1-benzyl-4-(2-hydroxyethyl)piperidin-4-ol (1.74 g, 7.39 mmol) in methanol (20 mL) was cannulated to the flask. The reaction mixture was stirred at room temperature for 20 hours under a balloon atmosphere of hydrogen. The mixture was filtered through a pad of Celite® which was rinsed with methanol (3×20 mL). The combined filtrate was concentrated under reduced pressure to afford 4-(2-hydroxyethyl)piperidin-4-ol (1.27 g, 95% yield) as a brown oil. MS m/z 146.0 ($MH^+$).

Step 4: 4-(2-hydroxyethyl)piperidin-4-ol (384 mg, 2.11 mmol) was added to a suspension of 3-fluoro-2-nitro-aniline (300 mg, 1.92 mmol) and $K_2CO_3$ (2.00 eq, 533 mg, 3.85 mmol) in acetonitrile (5 mL). The resulting mixture was stirred at 80° C. for 20 h. The reaction mixture was cooled to rt, diluted with EtOAc (15 mL) and filtered through a pad of Celite® rinsing with EtOAc. The filtrate was purified by flash chromatography on silica gel using a 60% to 100% EtOAc in hexanes gradient. The appropriate fractions were pooled, concentrated and dried under reduced pressure. Affords 1-(3-amino-2-nitro-phenyl)-4-(2-hydroxyethyl)piperidin-4-ol (120 mg, 22% yield) as a red gum. MS m/z 282.2 ($MH^+$).

Step 5: 1-(3-amino-2-nitro-phenyl)-4-(2-hydroxyethyl)piperidin-4-ol (120 mg, 0.427 mmol) was charged in a 50 mL flask along with iron powder (238 mg, 4.27 mmol) and ammonium chloride (228 mg, 4.27 mmol). IPA (5 mL) and formic acid (0.97 mL, 25.6 mmol) were then added. The flask was equipped with a reflux condenser and was immersed in an oil bath pre-heated to 90° C.

After 2 hours of stirring, the temperature of the oil bath was reduced to 65° C. and the reaction was allowed to go overnight. The mixture was allowed to cool to room temperature and was then filtered through a pad of Celite®, rinsing with IPA. The filtrate was concentrated to dryness and the residue was taken in 5 mL of water. 1N NaOH was added until a basic pH was obtained. The mixture was then thoroughly extracted with warm EtOAc. The combined organic layers were washed once with brine then dried over $MgSO_4$, filtered and concentrated. The residue was then dried under reduced pressure. Affords 1-(1H-benzimidazol-4-yl)-4-(2-hydroxyethyl)piperidin-4-ol (91 mg, 81% yield) as a brown gum. MS m/z 262.2 ($MH^+$).

Step 6 (Example 671, Table 4): the benzimidazole derivative of step 5 was coupled to the chloropyridine intermediate A-13 using copper/BINOL catalysis as described for Example 1 (step 4) in general method A.

Preparation of Example 679 (Table 4)

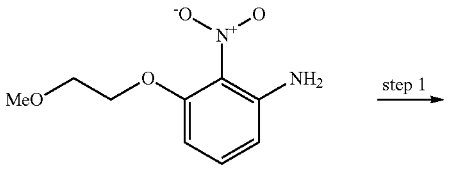

-continued

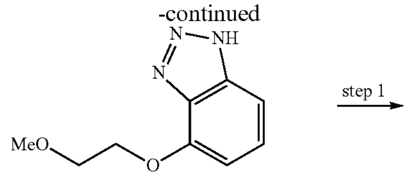

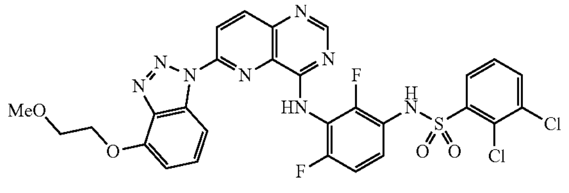

Example 679

Step 1: the product from step 1 of example 538 was converted to the benzotriazole fragment A503 using method J.

Step 2 (Example 679, Table 4): the benzotriazole derivative of step 1 was coupled to the chloropyridine intermediate A-13 using copper/BINOL catalysis as described for Example 1 (step 4) in general method A.

Preparation of Example 681 (Table 4)

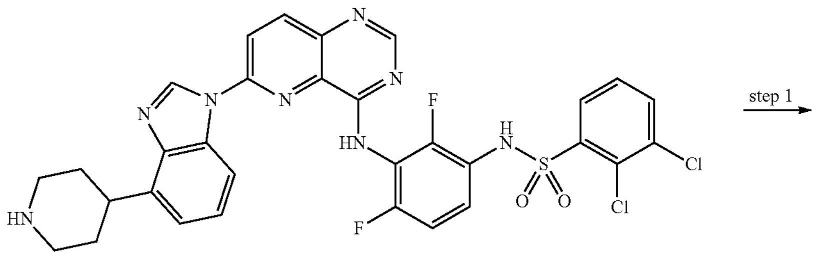

Example 662

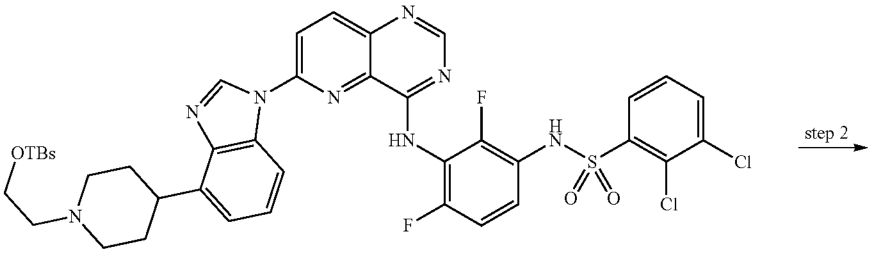

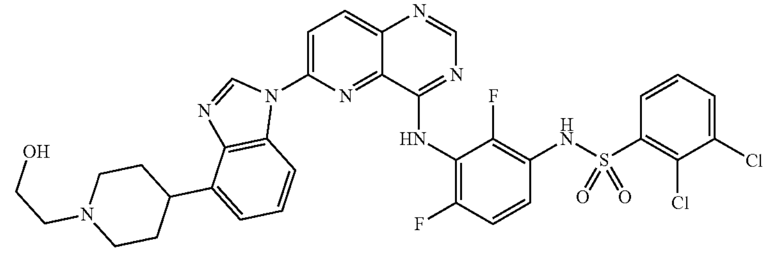

Example 681

Step 1: the compound of example 662 (17 mg, 0.022 mmol) was suspended in 2 mL of DCE and 0.5 mL of MeCN. Triethylamine (0.016 mL, 0.11 mmol) was added followed by (tert-butyldimethylsilyloxy)acetaldehyde (8 mg, 0.04 mmol) and sodium triacetoxyborohydride (9.5 mg, 0.04 mmol). The reaction mixture was allowed to stir at room temperature over weekend. It was then concentrated down to a residue which was used as such for the subsequent step. MS m/z 839.4 ($MH^+$).

Step 7 (Example 681, Table 4): the product from step 1 (18 mg, 0.021 mmol) was suspended in THF (2 mL). A 1M THF solution of tetra-N-butylammonium fluoride (0.11 mL, 0.107 mmol) was added at room temperature and the mixture was stirred for 2 days. Another portion of the TBAF solution (0.021 mL, 0.021 mmol) was added and the mixture was stirred over weekend. The yellow solution was then diluted with water and EtOAc. A milky solution of calcium sulfate (200 mg in 4 mL of water) was added. The layers were separated and the aqueous layer was extracted twice with EtOAc. The combined organic extracts were washed once with water then once with brine, dried over $MgSO_4$, filtered and concentrated. The residue was dissolved in 3 mL of DMSO, filtered through a syringe filter and purified by reverse phase chromatography using a 15% to 45% MeCN in water gradient (0.1% formic acid). The appropriate fractions were combined and lyophilized from MeCN/water to give the compound of example 681 (6.8 mg, 0.0083 mmol, 38% yield) as a white solid.

Biological Activity (a) Kinase Activity Assays for BRAF, CRAF and ARAF

Compound preparation: solid samples of each substances in 1dram vials were suspended in DMSO (Fisher Scientific) at a stock concentration of 20 mM. Stocks were kept at −20° C. and protected from light. If solubility of the compound at 20 mM appeared to be an issue, the initial concentration of the DMSO stock was changed to 10 mM or 5 mM.

In vitro enzymatic reactions were used for evaluating compounds intrinsic activity against BRAF, CRAF and ARAF. For BRAF and CRAF, 0.375 nM of purified GST-tagged kinases (cat #B4062-10UG and cat #R1656-10UG respectively from Millipore Sigma) were incubated with 75 nM of kinase-dead MEK1 substrate (cat #40075; BPS Bioscience) in the presence of 10 μM of Ultrapure ATP (cat #V9102; Promega; part V915A) with and without the test compound in a buffer containing 50 mM HEPES pH 7.5, 10 mM MgCl2, 1 mM EDTA, 0.01% Brij-35 and 2 mM DTT. Separate reactions were performed with the MEK1 substrate and ATP as a blank control. ARAF, kinase reactions were rigorously the same with the excpetion that kinase concentration was raised to 3.75 nM (cat #1768-0000-1; Reaction Biology).

For compound treatment, 5 μL/well of test substance solution are placed in a 384-well proxyplate (Perkin Elmer) and mixed with 2× concentrated kinase reactions. The dilution series is selected so that nine concentrations cover a range from 100 nM to 0.01 nM. If necessary (if the compound exhibits low intrinsic potency) the initial concentration of 100 nM is changed to 1 μM, or 0.5 μM and further dilutions are carried out accordingly. The final concentration of DMSO in the assay is set at 0.05%.

BRAF and CRAF kinase reactions were carried out for a total of 2 hours at 30° C. and then stopped by 1/2 dilution in ADP-Glo Reagent (cat #V9102; Promega; part V912C). Reactions were then incubated for 1 h at room temperature before addition of one volume of Kinase Detection Reagent (cat #V9102; Promega; part V917A). Plates were then equilibrated at room temperature for 30 minutes before detection of luminescence on a Synergy Neo2 plate reader (Biotek). The effect of each compound dilution on BRAF and CRAF kinase activity was expressed as % inhibition and calculated as follows. First, the internal 100% inhibition control (average of luminescence in kinase reactions comprising kinase dead MEK1 substrate alone) was subtracted from each data point. The average of DMSO (vehicle) controls (set as 0% inhibition) was established and used to calculate % inhibition:

$$\% \text{ inhibition}=100^*(1-((\text{Luminescence signal}_{compound})/(\text{Luminescence signal}_{DMSO})))$$

ARAF kinase reactions were carried out for a total of 2 hours at 30° C. and then stopped by addition of EDTA at a final concentration of 40 mM. Reactions were then detected using the AlphaLISA® SureFire® Ultra™ p-MEK 1/2 (Ser218/222) (PerkinElmer) kit. Reactions were performed with 5 μL of kinase reaction according to the manufacturer's specifications in 384-well proxyplates (Perkin Elmer) followed by overnight incubation of the AlphaLISA® reactions at room temperature in a humidified chamber. After completion of the detection reactions, the signals were recorded on a Synergy Neo2 plate reader (Biotek)equipped with AlphaLISA® filters. The effect of each compound dilution on the pMEK signal generated by ARAF reactions was expressed in % inhibition and calculated as follows. An internal 100% inhibition control (average of luminescence in kinase reactions comprising kinase dead MEK1 substrate alone) was included in each plate to measure of pMEK background and was subtracted from each data point. The average of DMSO (vehicle) controls (set as 0% inhibition) was also established and used to calculate % inhibition:

$$\% \text{ inhibition}=100^*(1-((\text{pMEK signal}_{compound})/(\text{pMEK signal}_{DMSO})))$$

$IC_{50}$ values were obtained by plotting the kinase inhibition values and fitting the dose-activity curves using a log (agonist) versus response—variable slope (four parameters) function using either GraphPadPrism (V7.0) or Dotmatics Screening Ultra platform. Standards included in the ARAF kinase assay were Belvarafenib (MedChem Express cat #HY-109080; CAS #1446113-23-0), LXH254 (MedChem Express cat #HY-112089; CAS #1800398-38-2) and BGB283 (cat #HY-18957; CAS #1446090-79-4).

All substances reported here are thus BRAF, CRAF and ARAF ATP-competitive kinase inhibitors as demonstrated by direct inhibition of enzymatic activity in vitro. BRAF and CRAF inhibition potencies of compounds are listed in Table 3-5 while ARAF kinase inhibition potencies of representative analogs are listed in Table A. Preferred Examples as defined in the embodiments show BRAF $IC_{50}$ values <10 nM and even more preferred Examples have BRAF $IC_{50}$ values <1 nM. Preferred Examples as defined in the embodiments show CRAF $IC_{50}$ values <50 nM and even more preferred Examples have CRAF $IC_{50}$ values <10 nM.

TABLE A

ARAF kinase inhibition results

| Example | Kinase $IC_{50}$ (nM) ARAF |
|---|---|
| 84 | ** |
| 99 | *** |
| 101 | ** |

TABLE A-continued

ARAF kinase inhibition results

| Example | Kinase $IC_{50}$ (nM) ARAF |
|---|---|
| 119 | ** |
| 248 | ** |
| 251 | ** |
| 313 | ** |
| 327 | ** |
| 342 | ** |
| 353 | ** |
| 355 | *** |
| 363 | ** |
| 385 | ** |
| 394 | ** |
| 399 | ** |
| 432 | ** |
| 509 | ** |
| 524 | ** |
| 578 | ** |
| 580 | ** |
| 582 | * |
| 583 | ** |
| 588 | ** |
| 608 | ** |
| 615 | ** |
| 621 | ** |
| 679 | ** |
| 680 | *** |
| Belvarafenib | * |
| BGB283 | * |
| LXH254 | * |

For the ARAF biochemical kinase assay, * denotes an IC50 >10 nM,  denotes a 1-10 nM IC50 range and * denotes an IC50 <1 nM.

(b) General Cell Culture Methods

All cancer cell lines (A375, A101D, A2058, RKO, HT29 SK-MEL 30, IPC298, HepG2, HCT-116, Lovo, SW620, SW480, NCI-H358, NCI-H2122, Calu-6, NCIH2087, NCIH1755, NCIH1666 and Mewo) were obtained from ATCC and cultured in RPMI-1640 medium (Gibco) supplemented with 5% heat inactivated fetal bovine serum (FBS, Wisent) at 37° C. under 5% $CO_2$. Cells were maintained in T175 flasks (Greiner). They were passaged by removing the culture medium, washing once in 10 mL of room temperature Phosphate Buffered Saline (PBS; Wisent) and incubating at 37° C. with 2 mL of 0.05% Trypsin (Thermo-Fisher). Trypsin was then inactivated by adding complete growth medium and the cells were then replated in a T175 culture dish at the appropriate dilution. All cell lines were routinely tested for *mycoplasma* contamination. Tissue type and mutational status of each cell line can be found in Table B.

TABLE B

Tumor type and RAS-ERK pathway mutational status of cancer cell lines (CCLs) used for pERK and antiproliferative profiling of substances described in this application.

| Cell line | Tissue type | Mutational status |
|---|---|---|
| A375 | Skin | BRAF V600E |
| A101D | Skin | BRAF V600E |
| A2058 | Skin | BRAF V600E |
| RKO | Colon | BRAF V600E |
| HT29 | Colon | BRAF V600E |
| NCIH2087 | Lung | BRAF L597V; KRAS Q61K |
| NCIH1755 | Lung | BRAF G469A |
| NCIH1666 | Lung | BRAF G466V |
| SK-MEL30 | Skin | NRAS-Q61K |
| IPC298 | Skin | NRAS-Q61L |
| HepG2 | Liver | NRAS-Q61L |
| HCT-116 | Colon | KRAS G13D |
| Lovo | Colon | KRAS-G13D |

TABLE B-continued

Tumor type and RAS-ERK pathway mutational status of cancer cell lines (CCLs) used for pERK and antiproliferative profiling of substances described in this application.

| Cell line | Tissue type | Mutational status |
|---|---|---|
| SW620 | Colon | KRAS-G12V |
| SW480 | Colon | KRAS G12D |
| NCI-H358 | Lung | KRAS-G12C |
| NCI-H2122 | Lung | KRAS-G12C |
| Calu-6 | Lung | KRAS Q61K |
| Mewo | Skin | NF1 LOF |

(c) Measurement of Phospho-ERK Inhibition in Cultivated Human Cancer Cell Lines by the AlphaLISA® SureFire® Ultra™ p-ERK 1/2 (Thr202/Tyr204)

AlphaLISA® SureFire® Ultra™ p-ERK 1/2 (Thr202/Tyr204) analysis was conducted on cells plated in 100 μL of complete RPMI-1640 growth medium in 96-well flat-bottomed transparent dishes (Costar) at a density indicated in Table C. Cells were maintained overnight at 37° C. under 5% $CO_2$ before treatment with compounds' dilution series for one hour. The cell density in cells/$cm^2$ corresponds to cell number divided by the area of one well of a 96-well plate (0.143 $cm^2$).

TABLE C

For each cancer cell line, number of cells plated per well.

| Cell line | Number of cells/well |
|---|---|
| A375 | 15,000 |
| NCIH2087 | 30,000 |
| NCIH1755 | 30,000 |
| NCIH1666 | 30,000 |
| SK-MEL30 | 24,000 |
| IPC298 | 20,000 |
| HepG2 | 20,000 |
| HCT-116 | 22,000 |
| Lovo | 20,000 |
| SW620 | 30,000 |
| SW480 | 15,000 |
| NCI-H358 | 20,000 |
| NCI-H2122 | 24,000 |
| Calu-6 | 15,000 |
| Mewo | 20,000 |

In a dilution series 100 μL/well of test substance dilution prepared in complete RPMI-1640 growth media was added to the cells. The dilution series is selected so that ten concentrations cover a range from 10 μM to 0.33 nM. If necessary the initial concentration of 10 μM is increased to 100 μM or lowered to 1 μM (as in the case of A375 and H1666 cells, which are generally more sensitive to the compounds) and further dilution is carried out accordingly. The final concentration of DMSO in the assay is set at 0.5%.

After treatment, media was removed and cells were lysed in 50 μL of 1× AlphaScreen Ultra Lysis Buffer (Perkin Elmer). The AlphaLISA® SureFire® Ultra™ p-ERK 1/2 (Thr202/Tyr2O4) (PerkinElmer) reactions were performed with 5 μL of cell lysate according to the manufacturer's specifications in 384-well proxyplates (Perkin Elmer) followed by overnight incubation of the reactions at room temperature in a humidified chamber. After completion of the reactions, the signals were recorded on an EnVision plate reader (Perkin Elmer) using built in AlphaLISA® settings.

The effect of each compound dilution on the pERK signal was expressed in % inhibition and calculated as follows. An internal 100% inhibition control (1 μM trametinib, cat

#HY-10999; MedChem Express; CAS #871700-17-3) was included in each plate and used as a measure of pERK background. First, the value obtained for trametinib was subtracted from each data point.

The average of DMSO (vehicle) controls (set as 0% inhibition) was established and used to calculate % inhibition:

$$\% \text{ inhibition}=100*(1-((\text{pERK signal}_{compound})/(\text{pERK signal}_{DMSO})))$$

The ability of each compound to inhibit pERK signal was expressed as an $IC_{50}$ value obtained by plotting the inhibition values for each data point of a dilution series and fitting the obtained curves using a log(agonist) versus response—variable slope (four parameters) function using GraphPad-Prism (V7.0) or Dotmatics Screening Ultra platform.

When present, paradoxical pERK induction is inferred from the negative % inhibition values observed in the pERK $IC_{50}$ curves of a compound. To classify a compound as a pERK paradoxical inducer, the % inhibition of the minimal data point of the dosage-activity curve (% $Y_{MIN}$) was set to be lower than −20% which is considered to be within expected assay variation (e.g. a compound with % $Y_{MIN}$=−30% or −50% or −150% is considered to produce a paradoxical induction of the pathway. A compound that displays an $IC_{50}$ curve with a $Y_{MIN}$=−10% is considered not to produce a paradoxical activation of the pathway). Therefore, a compound was said to inhibit the pathway without paradoxical induction in a given cell line when the following criteria were met:

1. % inhibition at the highest tested dose (30 μM, 10 μM or 1 μM) exceeded 50%.
2. % $Y_{MIN}$ of $IC_{50}$ curves was greater than −20%; where $Y_{MIN}$ corresponded to the data point having the lowest value in the $IC_{50}$ curve of the said compound.

It is well known to someone skilled in the art that some variation of inhibition values is expected in such experiments. $Y_{MIN}$ values of ±20% are considered within experimental error and are not significant. Therefore, only compounds with negative values in excess of assay variation (ca. >20%) are considered to induce a paradoxical activation of the signaling cascade and are not included within the scope of the present disclosure. FIG. 1 provides a visualization of the ICso curves for a compound that induces paradoxical pathway activation (PLX4720, commercially available from Selleck Chemicals; CAS #918505-84-7) and representative compounds as described herein exhibiting the unexpected and distinct induction-free profile.

FIG. 1 shows representative $IC_{50}$ inhibition dose response curves for compounds as described herein that do not induce paradoxical induction of pERK signaling ($Y_{MIN}$>−20%) in RAS-mutant HCT116 cells (Examples 99, 113, 128, 139, 140) and a compound (PLX4720) that causes strong induction of the pathway in the same cell line ($Y_{MIN}$~−600%).

Significantly, the present compounds do not induce paradoxical activation of the pathway according to the criteria described above. Further illustration of this highly desirable property can be illustrated using immunoblotting analysis as described below and depicted in FIG. 2 for the induction free compound (Example 99) and the inducer PLX4720.

For immunoblotting analysis, 500,000 HCT-116 cells were plated in 1 mL of complete RPMI-1640 growth medium in 24-well flat-bottomed transparent dishes (Costar). Cells were maintained overnight at 37° C. under 5% $CO_2$ before treatment with compounds' dilution series for one hour. Cells were then washed once in PBS and lized in 250 μL of Igepal Lysis Buffer (50 mM Tris-HCl pH 7.5, 150 mM NaCl, 1% Igepal-CA630, 1 mM EDTA, 10% Glycerol) supplemented with Leupeptin, Aprotinin, PMSF, phosphatase inhibitor cocktail (Sigma) and $Na_3VO_4$ at 4° C. for 15 minutes with gentle rocking. Cell extracts were then cleared by centrifugation at 20,000 g at 4° C. for 10 minutes. Cleared lysates were then transferred on ice in fresh tubes and then boiled in sample loading buffer (100 mM Tris-HCl pH 6.8, 4% SDS, 0.2% bromophenol blue, 20% glycerol, 200 mM β-mercaptoethanol) for 5 minutes prior to fractionation by SDS-PAGE and transfer to nitrocellulose membranes (PALL). Membranes were blocked for 1 hour in Tris Buffered Saline 0.2% Tween-20 (TBST; 10 mM Tris-HCl pH 8.0, 0.2% Tween-20, 150 mM NaCl) containing 2% BSA (Sigma) and then incubated at 4° C. overnight with a dilution of the following primary antibodies prepared in TBST: anti-pERK (1:2000 dilution; Sigma-Aldrich; cat. number M9692), anti-total ERK (1:1000 dilution; Cell Signaling Technology; cat. number 4695), anti-pMEK (1:1000 dilution; Cell Signaling Technology; cat. number 9121) and anti-total MEK (1:1000 dilution; Cell Signaling Technology; cat. number 9122). Secondary anti-mouse-HRP and anti-rabbit-HRP (Jackson Immunoresearch Labs; cat. number 115-035-146 and 111-035-144, respectively) were prepared in TBST at 1:5000 and 1:10000 dilutions, respectively. Immunoblots were revealed by exposition to X-ray films after one minute incubation in ECL reagent.

Figure 2:
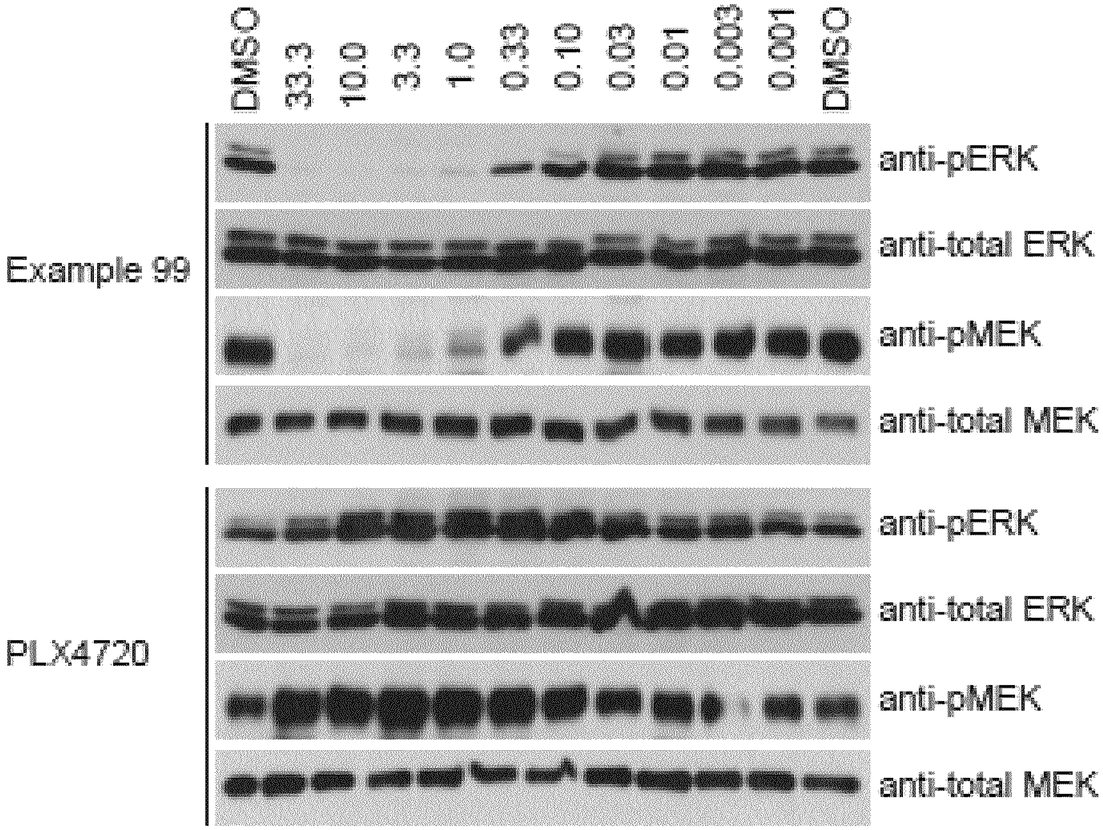
FIG. 2 shows results of immunoblot analysis of RAS-mutant HCT-116 cells treated with a representative compound (Example 99; top panels) that does not induce paradoxical induction of pERK or pMEK signaling and by comparison, a compound (PLX4720; bottom panels) that induces the pathway in the same cell line.

FIG. 2 shows results of immunoblot analysis of RAS-mutant HCT-116 cells treated with a representative compound (Example 99; top panels) that does not induce paradoxical induction of pERK or pMEK signaling and by comparison, a compound (PLX4720; bottom panels) that induces the pathway in the same cell line. Total MEK and total ERK signals were also probed by immunoblotting to ensure equal loading of protein samples across conditions. Compound concentrations in micromolar are indicated above the immunoblot panels. The concentration range used for treatment was the same for Example 99 and PLX4720.

Example compounds 1 to 691 show pERK inhibition activity in the colon G13D Ras-mutated HCT-116 cell line as shown in Tables 3-5. In addition, some Examples were also shown to display paradoxical induction-free inhibition of pERK signaling in the SW480 colon cell line harboring the G12D allele of KRAS (Tables 3-5). Furthermore, some Examples from Tables 3-5 were also tested for inhibition of pERK in A375 cells that comprise the $BRAF^{V600E}$ driver mutation and were found to be active as well (Table D-1 and D-2). All compound Examples 1-691 displayed pERK $IC_{50}$ values in the HCT116 cell line that were <30 μM. Preferred compounds had $IC_{50}$ values 1-10 μM, more preferred compounds had $IC_{50}$ values 0.5-1 μM, while even more preferred compounds had $IC_{50}$ values <0.5 μM.

Representative compounds as herein defined were also tested on additional tumor cells for their pERK inhibition activity and showed good to very good pERK inhibition activity in cancer cell lines bearing various NRAS, KRAS and NF1 alleles and representative of a large diversity of tissue types (i.e., SK-MEL 30, IPC298, HepG2, HCT-116, Lovo, SW620, SW480, NCI-H358, NCI-H2122, Calu-6 and Mewo; see Table D-1 and D-2 and refer to Table B for genotypes). The pERK inhibition activity of compounds is stronger in cancer cell lines bearing various BRAF alleles (A375, A101D, A2058, RKO, HT29, NCIH2087, NCIH1755 and NCIH1666) (Table D-1 and D-2).

TABLE D (D-1 and D-2). Induction-free pERK $IC_{50}$ values and anti-proliferative $EC_{50}$ values for select compounds in a panel of RAS-mutant cancer cell lines (see Table B for genotypes) and $BRAF^{V600E}$ mutant A375.

D-1.

| Ex. | A375 pERK Prolif. | A2058 pERK Prolif. | HT-29 pERK Prolif. | RKO pERK Prolif. | A101D pERK Prolif. | SK-MEL30 pERK Prolif. | IPC298 pERK Prolif. | HepG2 pERK Prolif. | HCT116 pERK Prolif. |
|---|---|---|---|---|---|---|---|---|---|
| 84 | *** | *** | *** | *** | *** | +++ (13) | ++ (18) | ++ (5) | ++ (4.8) |
| 84 | | | | | | *** | *** | *** | *** |
| 99 | *** | *** | *** | *** | *** | +++ (−1) | ++ (−2) | +++ (7) | ++ (−0.3) |
| 99 | | | | | | *** | *** | *** | ** |
| 101 | *** | *** | *** | *** | *** | +++ (0) | ++ (2) | +++ (11) | ++ (−11) |
| 101 | | | | | | *** | *** | *** | ** |
| 119 | *** | *** | *** | *** | *** | +++ (8) | ++ (29) | ++ (7) | ++ (−8.9) |
| 119 | | | | | | *** | *** | *** | ** |
| 251 | *** | *** | *** | *** | *** | ++ (9) | ++ (7) | ++ (7) | ++ (−6.3) |
| 251 | | | | | | *** | *** | *** | *** |
| 299 | *** | *** | *** | *** | *** | ND | ND | ND | ++ (−6.5) |
| 299 | | | | | | *** | *** | *** | *** |
| 385 | *** | *** | *** | *** | *** | +++ (3) | ++ (17) | ++ (−3) | ++ (−9) |
| 385 | | | | | | *** | *** | *** | *** |
| 432 | *** | *** | *** | *** | *** | +++ (−3) | ++ (11) | +++ (3) | ++ (−6) |
| 432 | | | | | | *** | *** | *** | *** |
| 509 | *** | *** | *** | *** | *** | +++ (−9) | +++ (13) | ++ (9) | ++ (0) |
| 509 | | | | | | *** | *** | *** | *** |
| 524 | *** | *** | *** | *** | *** | +++ (−13) | ++ (13) | ++ (2) | ++ (−3) |
| 524 | | | | | | *** | *** | *** | ** |
| 578 | *** | *** | *** | *** | *** | +++ (2) | ++ (14) | +++ (20) | ++ (−4) |
| 578 | | | | | | *** | *** | *** | *** |
| 582 | *** | *** | *** | *** | *** | +++ (6) | ++ (2) | ++ (−7) | ++ (−9) |
| 582 | | | | | | *** | *** | *** | *** |
| 588 | *** | *** | *** | *** | *** | ++ (−7) | ++ (7) | ++ (10) | ++ (−4) |
| 588 | | | | | | *** | *** | *** | ** |
| 608 | *** | *** | *** | *** | *** | +++ (11) | ++ (9) | ++ (7) | ++ (−7) |
| 608 | | | | | | *** | *** | *** | *** |
| 615 | *** | *** | *** | *** | *** | +++ (5) | ++ (8) | ++ (4) | ++ (5) |
| 615 | | | | | | *** | *** | *** | *** |
| 679 | *** | *** | *** | *** | *** | +++ (1) | ++ (13) | +++ (26) | ++ (0) |
| 679 | | | | | | *** | *** | *** | *** |
| 680 | *** | *** | *** | *** | *** | +++ (−8) | ++ (−13) | ++ (1) | ++ (8) |
| 680 | | | | | | *** | *** | *** | *** |
| Belv. | *** | ND | *** | *** | ND | +++ (−45) | ++ (−63) | ++ (−36) | ++ (−46) |
| Belv. | | | | | | *** | *** | *** | ** |

D-2.

| Ex. | Lovo pERK Prolif. | NCI-H358 pERK Prolif. | SW620 pERK Prolif. | Calu6 pERK Prolif. | NCI-H2122 pERK Prolif. | SW480 pERK Prolif. | Mewo pERK Prolif. | NCIH2087 pERK Prolif. | NCIH1755 pERK Prolif. |
|---|---|---|---|---|---|---|---|---|---|
| 84 | ++ (17) | ++ (3) | ++ (−6) | ++ (6) | ++ (9) | ++ (21) | ++ (−1) | +++ (6) | +++ (30) |
| 84 | ** | ** | ** | ** | ** | ** | ** | ** | *** |
| 99 | ++ (−15) | ++ (11) | ++ (−11) | ++ (−12) | ++ (−3) | ++ (−7) | ++ (−7) | +++ (15) | +++ (−8) |
| 99 | *** | *** | ** | ** | ** | ** | *** | ** | *** |
| 101 | ++ (10) | +++ (23) | ++ (4) | ++ (−6) | ++ (−9) | ++ (−3) | ++ (−17) | +++ (19) | +++ (−3) |
| 101 | *** | *** | ** | ** | ** | ** | *** | ND | *** |
| 119 | ++ (0) | ++ (−4) | ++ (3) | ++ (6) | ++ (5) | ++ (−1) | ++ (−6) | +++ (17) | +++ (25) |
| 119 | *** | ** | *** | ** | ** | ** | ** | ** | ** |
| 251 | ++ (15) | ++ (−15) | ++ (−12) | ++ (3) | ++ (3) | ++ (14) | ++ (3) | ++ (2) | +++ (−2) |
| 251 | ** | *** | ** | ** | * | ** | ** | ** | ** |
| 299 | ND | ND | ND | ND | ND | ND | ND | ND | ND |
| 299 | *** | *** | *** | *** | ** | *** | ** | *** | ** |
| 385 | ++ (8) | ++ (−11) | ++ (−18) | ++ (−7) | ++ (20) | ++ (−3) | ++ (−14) | +++ (−1) | +++ (2) |
| 385 | *** | *** | *** | *** | ** | ** | *** | ** | *** |
| 432 | ++ (3) | ++ (3) | ++ (−12) | +++ (10) | ++ (11) | ++ (6) | ++ (8) | +++ (12) | +++ (0) |
| 432 | *** | *** | ** | *** | ** | ** | *** | ** | ** |
| 509 | ++ (−11) | ++ (−9) | ++ (−12) | ++ (4) | ++ (−3) | ++ (4) | ++ (−13) | +++ (14) | +++ (2) |
| 509 | *** | *** | ** | ** | ** | ** | *** | ** | ** |
| 524 | ++ (−5) | ++ (−13) | ++ (−4) | ++ (−13) | ++ (13) | ++ (0) | ++ (−5) | +++ (3) | ++ (−13) |
| 524 | *** | *** | ** | ** | ** | ** | *** | *** | ** |
| 578 | ++ (−5) | ++ (25) | ++ (3) | ++ (−18) | ++ (30) | ++ (5) | ++ (3) | +++ (11) | +++ (5) |
| 578 | *** | *** | ** | ** | ** | ** | *** | *** | *** |
| 582 | +++ (25) | ++ (0) | ++ (−13) | ++ (1) | ++ (21) | ++ (6) | ++ (−4) | +++ (−8) | +++ (−7) |
| 582 | *** | *** | *** | ** | ** | ** | *** | *** | ** |
| 588 | ++ (11) | ++ (−15) | + (−13) | ++ (4) | ++ (−4) | ++ (3) | ++ (−1) | +++ (5) | +++ (−16) |
| 588 | *** | *** | ** | ** | ** | ** | *** | ** | ** |
| 608 | +++ (25) | ++ (1) | ++ (−4) | ++ (−5) | ++ (10) | ++ (7) | ++ (−12) | +++ (5) | +++ (1) |
| 608 | *** | *** | *** | *** | ** | ** | *** | *** | ** |

TABLE D-continued (D-1 and D-2). Induction-free pERK $IC_{50}$ values and anti-proliferative $EC_{50}$ values for select compounds in a panel of RAS-mutant cancer cell lines (see Table B for genotypes) and $BRAF^{V600E}$ mutant A375.

| | | | | | | | | | |
|---|---|---|---|---|---|---|---|---|---|
| 615 | +++ (25) | ++ (4) | ++ (6) | +++ (−7) | ++ (24) | ++ (2) | ++ (15) | +++ (−10) | +++ (7) |
| 615 | *** | *** | *** | ** | ** | * | ** | ** | *** |
| 679 | ++ (−12) | ++ (8) | ++ (29) | ++ (−11) | ++ (2) | ++ (−6) | ++ (−11) | +++ (−2) | +++ (−7) |
| 679 | *** | *** | * | ** | ** | ** | *** | ND | *** |
| 680 | ++ (−17) | ++ (8) | ++ (−5) | ++ (6) | + (−18) | ++ (2) | ++ (−8) | +++ (−5) | +++ (4) |
| 680 | *** | *** | ** | *** | ** | ** | *** | *** | ** |
| Belv. | +++ (−12) | ++ (−122) | ++ (−151) | ++ (−39) | ++ (−9) | ++ (−100) | ++ (−116) | +++ (6) | ++ (−79) |
| Belv. | *** | ** | ** | *** | ** | ** | ** | *** | * |

For pERK assay results, + denotes a pERK $IC_{50}$ > 0.3 μM, ++ denotes a 0.03-0.3 μM pERK $IC_{50}$ range, +++ denotes a pERK $IC_{50}$ < 0.03 μM. For proliferation assay results, * denotes a proliferation $EC_{50}$ > 3 μM,  denotes a 0.3-3 μM proliferation $EC_{50}$ range, * denotes a proliferation $EC_{50}$ < 0.03 μM.
N/A: not available.
Belv.: Belvarafenib.

For RAS-mutant cancer cell lines, the % $Y_{min}$ values for pERK $IC_{50}$ curves were all above −20% and considered to display minimal or no induction and thus compounds do not cause detectable paradoxical activation of the pathway in this panel of cancer cell lines. In contrast, the comparative results for the molecule Belvarafenib (obtained from MedChem Express cat #HY-109080; CAS #1446113-23-0) show mild to strong induction of the pathway in the same cell lines ($Y_{MIN}$<−30% in 10 of the 13 RAS-mutant cell lines tested).

(d) Measurement of Proliferation Inhibition of Cultivated Human Cancer Cell Lines (CCLs) Usinq CellTiter-Glo® Reagent CellTiter-Glo® viability analysis was conducted on cells plated in 100 μL of complete RPMI-1640 growth medium in 96-well flat-bottomed white opaque plates (Greiner or Croning) at a density indicated in Table E (for each CCL, number of cells plated per well of a 96-well plate to perform the CellTiter-Glo® cell viability assay). The cell density in cells/$cm^2$ would correspond to cell number divided by the area of one well of a 96-well plate (0.32 $cm^2$). Cells were maintained overnight at 37° C. under 5% $CO_2$ before treatment with compounds' dilution series for 3 days.

TABLE E

Number of cells plated per well of a 96-well plate to perform the CellTiter-Glo ® cell viability assay

| Cell Line | Number of cells/well |
|---|---|
| A375 | 2000 |
| A101D | 2000 |
| A2058 | 2000 |
| RKO | 2000 |
| HT29 | 2000 |
| NCIH2087 | 3600 |
| NCIH1755 | 3600 |
| NCIH1666 | 3600 |
| SK-MEL30 | 2400 |
| IPC298 | 2000 |
| HepG2 | 7200 |
| HCT-116 | 1500 |
| Lovo | 4800 |
| SW620 | 3600 |
| SW480 | 4800 |
| NCI-H358 | 2400 |
| NCI-H2122 | 4800 |
| Calu-6 | 2400 |
| Mewo | 2400 |

In a dilution series 100 μL/well of test substance dilution prepared in complete RPMI-1640 growth media was added to the cells plated initially in 100 μL of growth media. The dilution series is selected so that ten concentrations cover a range from 10 μM to 0.33 nM. If necessary (as in the case of A375 cells, which were more sensitive to the compounds) the initial concentration of 10 μM is lowered to 1 μM and further dilution is carried out accordingly. The final concentration of DMSO in the assay is set at is 0.5%.

After 3 days of incubation, the growth media were removed by aspiration and 60 μL of diluted CellTiter-Glo® reagent (10 μL CellTiter-Glo® reagent+50 μL of PBS) was added to each well. Cells were allowed to lyse and to equilibrate in CellTiter-Glo® reagent by 5 min incubation on a plate shaker followed by 10 min incubation at room temperature. Luminescence signals were then acquired on a Synergy Neo2 plate reader (Biotek).

The effect of each compound dilution on the proliferation of cancer cell lines was expressed in % inhibition and calculated as follows. An internal 100% inhibition control (1 μM of trametinib; cat #HY-10999; MedChem Express; CAS #871700-17-3) was included in each plate and used as a measure of CellTiter-Glo® signal background. The value obtained for trametinib was subtracted from each data point. The average of DMSO (vehicle) controls (set as 0% inhibition) was established and used to calculate % inhibition:

$$\% \text{ inhibition}=100*(1-((\text{CellTiter-Glo® signal}_{compound})/(\text{CellTiter-Glo® signal}_{DMSO})))$$

The ability of each compound to inhibit proliferation was expressed as a $EC_{50}$ value obtained by plotting the effect values for each data point of a dilution series and fitting the obtained curves using a log(agonist) versus response—variable slope (four parameters) function using GraphPad-Prism (V7.0) or Dotmatics Screening Ultra platform.

As shown in Table D-1 and D-2, the active substances show antiproliferative activity in various various NRAS-, KRAS- and NF1-mutant cancer cell lines that are representative of a large diversity of tissue types (i.e., SK-MEL 30, IPC298, HepG2, HCT-116, Lovo, SW620, SW480, NCI-H358, NCI-H2122, Calu-6 and Mewo; Table D-1 and D-2 and refer to Table B for genotypes). Antiproliferative activity is often even stronger in cell lines carrying BRAF driver mutations (A375, A101D, A2058, RKO, HT29, NCIH2087, NCIH1755 and NCIH1666) (Table D-1 and D-2). Of note, the $IC_{50}$ values of pERK reduction and the $EC_{50}$ values of the antiproliferative activity of the substances in KRAS- and BRAF-mutated cell lines correlate reasonably well with each other (Table D-1 and D-2). The present compounds are thus effective against several tumor types and may be used in these and other indications. This demonstrates the usefulness of the compounds as described herein for the treatment of different types of tumors.

(e) Establishment of Xenograft Tumors

NU(NCr)-Foxn1nu female mice, 6-8 weeks old, weighing approximately 18-22 g, were purchased from Charles River Laboratories. All procedures were in accordance with the regulations of the Canadian Council on Animal Care and the University of Montreal. Animals were fed a standard rodent diet and water was supplied ad libitum. A375, HCT-116, A101D, A2058, RKO, HT29 SK-MEL 30, Calu-6, HepG2, Lovo, NCI-H2122, NCIH1666 and NCIH1755 tumour cells were cultured in RPMI-1640 10% FBS at 37° C. under 5% CO2. Upon trypsinization the cells were washed once in PBS, and after the final centrifugation were re-suspended, counted, and adjusted by volume to a final concentration of $10\times10^6$ cells/mL (A375 and HCT116) or $30\times10^6$ cells/mL (A101D, A2058, RKO, HT29 SK-MEL 30, Calu-6, HepG2, Lovo, NCI-H2122, NCIH1666 and NCIH1755). The cell suspension was then mixed at a 50:50 ratio with matrigel (Corning), which brought the cell count at either $5\times10^6$ cells/mL (A375 and HCT116) or $15\times10^6$ cells/mL (A101D, A2058, RKO, HT29 SK-MEL 30, Calu-6, HepG2, Lovo, NCI-H2122, NCIH1666 and NCIH1755).

NU(NCr)-Foxn1nu mice were inoculated subcutaneously at the right flank with $1\times10^6$ (HCT-116 or A375) or $3\times10^6$ (A101D, A2058, RKO, HT29 SK-MEL 30, Calu-6, HepG2, Lovo, NCI-H2122, NCIH1666 and NCIH1755) tumour cells in 0.2 mL of the 50:50 PBS:Matrigel mixture for tumour development. Tumour measurements were taken with an electronic microcalliper three times weekly. In addition, body weights were recorded at these times. Tumor volume was calculated, taking length to be the longest diameter across the tumor and width to be the corresponding perpendicular diameter using the following formula: ((length× width×thickness)/2).

(f) Pharmacodynamic Evaluation of Example 99 Effect on the ERK Cascade.

For PK-PD experiments, the treatment was performed when mean tumour size reached approximately 200 mm3, with at least 2 mice for each time point randomized to balance the average tumour size for each group. In one experiment, mice were administered orally with a suspension of Example 99 sodium salt at the indicated concentration prepared in a formulation consisting of 1% NMP, 0.3% Tween-80, pH 9.1. Example 99: Na+ powder was directly resuspended in the complete blank formulation. Dosing volume was 10 mL/kg, yielding the indicated doses. Tumors were extracted at the indicated time points and subjected to biochemical analysis by AlphaScreen™ (see below).

Tissue extracts were obtained as follows. Tumor fragments were lized in an appropriate volume proportional to tumor size. Igepal Lysis buffer consisted of (50 mM Tris-HCl pH 7.5, 150 mM NaCl, 1% Igepal-CA630, 1 mM EDTA, 10% Glycerol) supplemented with Leupeptin, Aprotinin, PMSF, 2× phosphatase inhibitor cocktail (Sigma) and 2× $Na_3VO_4$. Tumor tissues were mechanically disrupted with a Ultra-Turrax homogenizer with a single pulse of 15 seconds and were then let to lyze for 15 minutes on ice.

Tissue extracts were cleared by centrifugation at 20,000 g at 4° C. for 10 minutes. Cleared lysates were then transferred on ice in fresh tubes. Protein quantitation of tumor extracts was then carried out using Bradford reagent and samples were diluted to 1 μg/μL in complete Igepal Lysis buffer. Samples were then further diluted 1/5 in 1.25× in Alphascreen™ compatible AlphaLisa SureFire Ultra Lysis Buffer (Perkin Elmer) to obtain a final concentration of 0.2 μg/μL. For normalization purposes, tumor extracts were analysed in parallel for pERK and total ERK signals using respectively the AlphaLISA® SureFire@ Ultra™ p-ERK 1/2 (Thr202/Tyr2O4) and the AlphaLISA® SureFire@ Ultra™ t-ERK 1/2 kits (PerkinElmer). AlphaLISA reactions were performed with 5 μL of diluted tumor lysate according to the manufacturer's specifications in 384-well proxyplates (Perkin Elmer) followed by overnight incubation of the reactions at room temperature in a humidified chamber. After completion of the reactions, the signals were recorded on an EnVision plate reader (Perkin Elmer) using built in AlphaLISA® settings.

The effect of each compound on the tumor's pERK signal was expressed as "pERK % inhibition" and calculated as follows. An internal blank control was included in each plate and used as a measure of pERK background; it consisted of buffer alone with AlphaLISA beads. First, the value obtained for the blank was subtracted from each pERK or tERK data point. Next, the blank-substracted pERK AlphaLISA counts of each tumor was devided by the blank-substratceted total ERK AlphaLISA counts, yielding a pERK/tERK ratio. The average of vehicle-treated tumors was set as 0% inhibition and was used to calculate % inhibition:

$$\%\ \text{inhibition}=100*(1-((\text{pERK/tERK ratio}_{compound})/(\text{pERK/tERK ratio}_{vehicle})))$$

Figure 3A:
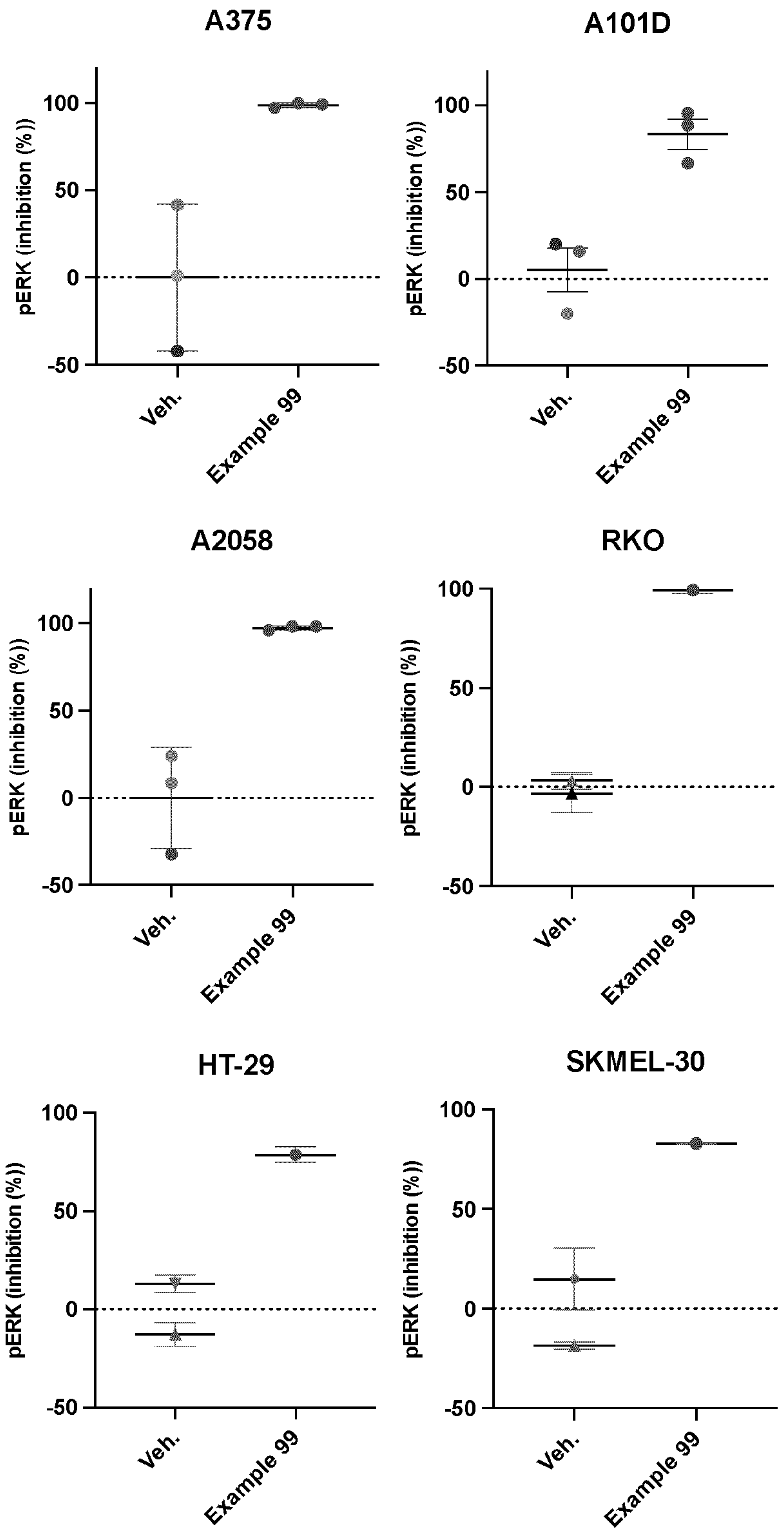
FIG. 3 (A and B) shows results of pharmacodynamic analysis of the pERK biomarker in mice bearing xenograft tumors representing a series of cancer cell lines with various mutational backgrounds (A375, A101D, A2058, RKO, HT29 SK-MEL 30, Calu-6, HepG2, Lovo, NCI-H2122, NCIH1666 and NCIH1755) compared to the vehicle (Veh.). Mice were administered orally with Example 99 at 150 mg per kg (mpk). ERK pathway suppression was determined using pERK and total ERK AlphaLISA® SureFire® Ultra™ kits following 4 h oral administration of a suspension of Example 99.
Figure 3B:
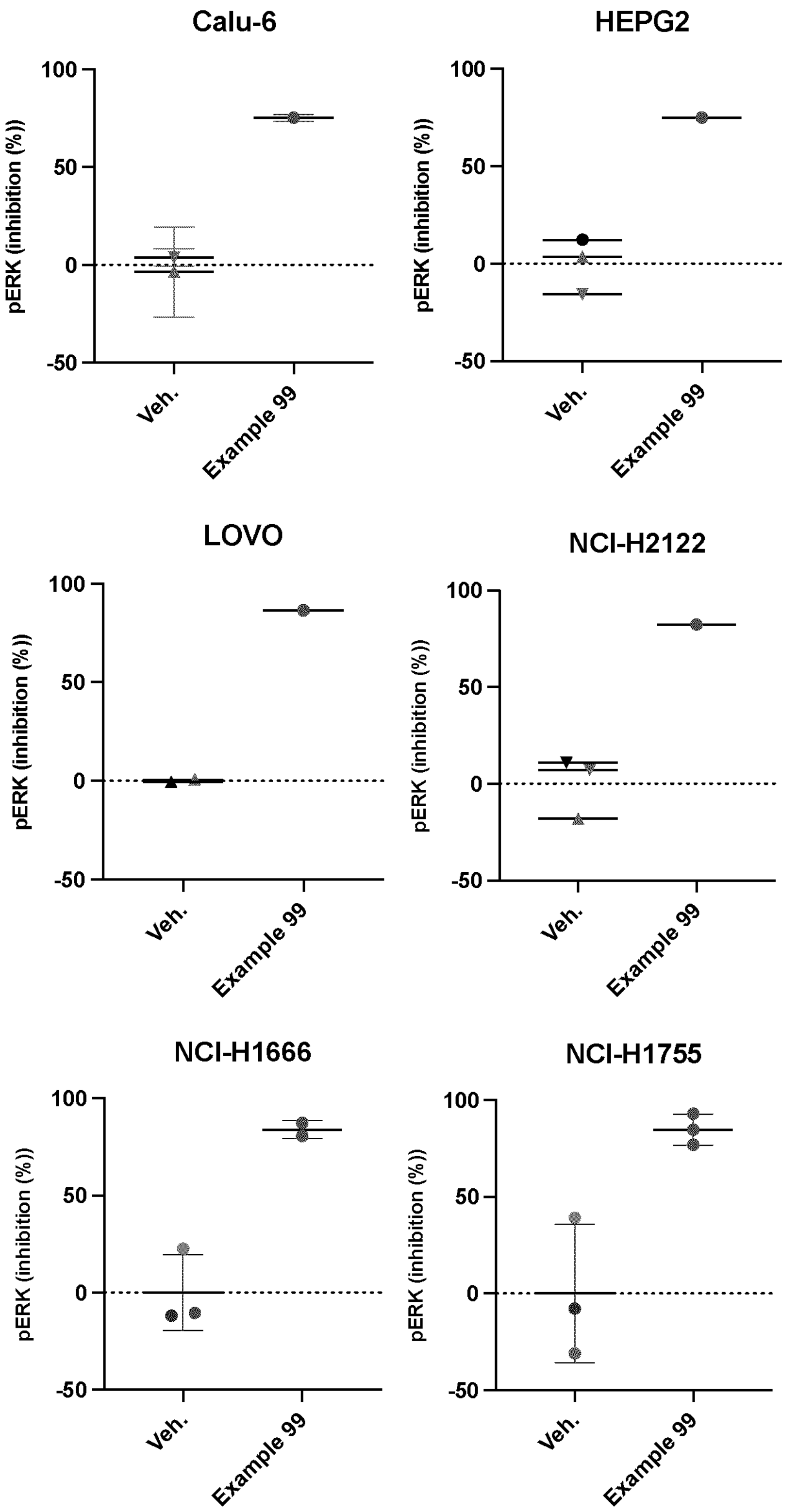

Results of PD experiments with A375, A101D, A2058, RKO, HT29 SK-MEL 30, Calu-6, HepG2, Lovo, NCI-H2122, NCIH1666 and NCIH1755 xenograft tumors are presented in FIG. 3.

(g) Tumor Growth Inhibition (TGI) Experiments.

Figure 4:
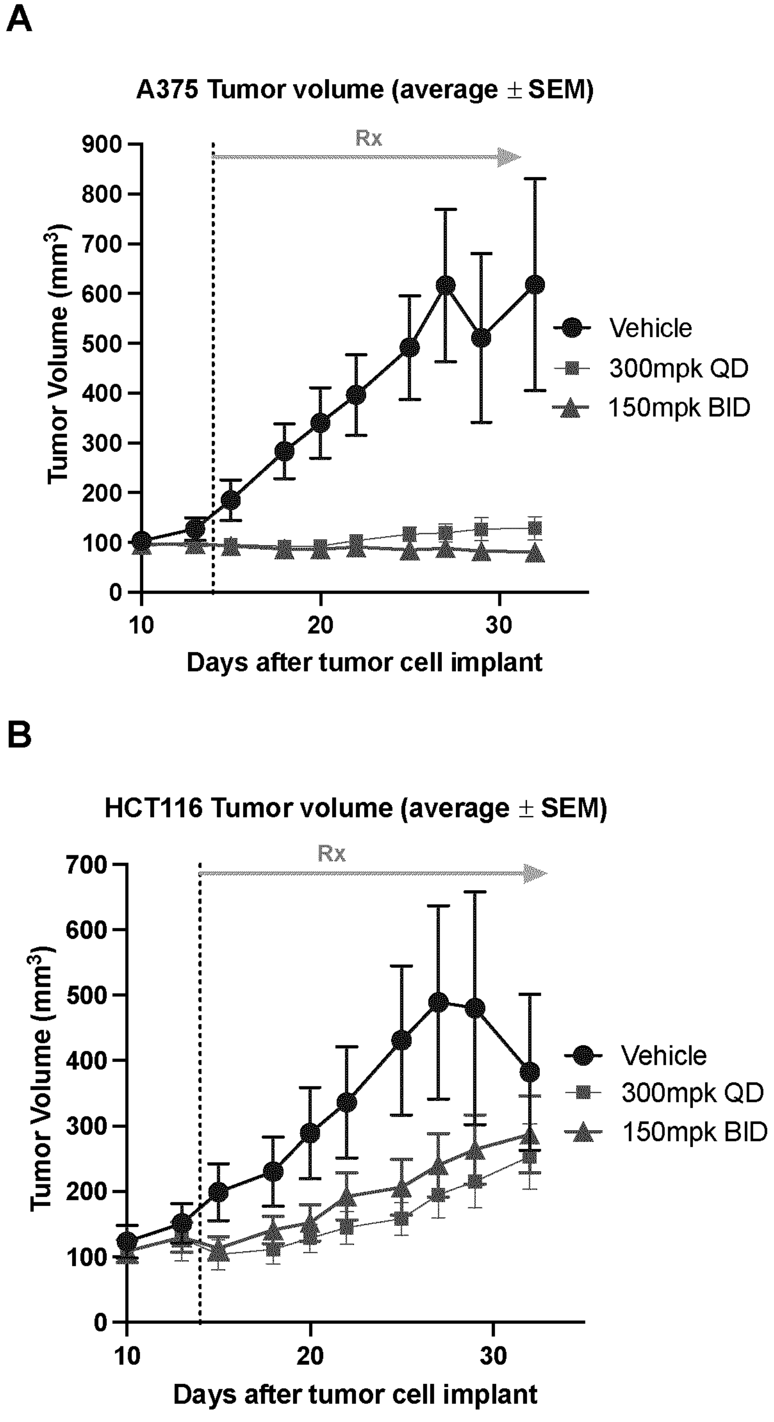
FIG. 4 shows results of tumor growth inhibition (TGI) experiments conducted in A375 (A) and HCT116 (B). Each data point represents the average±standard error of the mean (SEM) of tumor size at a given day prior and after treatment was initiated; treatment period corresponds to the arrow labeled "Rx". Mice were administered orally once or twice daily (QD or BID) with a suspension of Example 99 (doses are in mg per kg or mpk) or with blank formulation (vehicle). Tumours were measured with an electronic micro-calliper three times weekly.

For tumor growth inhibition (TGI) experiments, the treatment was performed when mean tumour size reached approximately 200 $mm^3$, with at least 7 mice for each time point randomized to balance the average tumour size for each treatment group. Mice were administered orally (QD or BID) with a suspension of Example 99 sodium salt in a formulation consisting of 1% NMP, 0.3% Tween-80, pH 9.1. Example 99: Na+ powder was directly resuspended in the complete blank formulation. Dosing volume was 10 mL/kg, yielding the indicated doses (doses are in mg per kg or mpk). Tumours were measured with an electronic microcalliper three times weekly. In addition, body weights were recorded at these times. Tumor volume was calculated as described above. Results of TGI experiments with A375 and HCT-116 xenograft tumors are presented in FIG. 4 (panels A and B respectively). Of note, body weights were recorded throughout the administration period showing that repeated treatment with Example 99 did not result in any change in body weight compared to vehicle-treated animals (not shown).

(h) Results

The following Tables 3 to 5 summarize exemplary compounds structures, methods of synthesis, and biological results. Each of these tables are followed by their respective table summarizing chemical characterization of the compounds.

TABLE 3

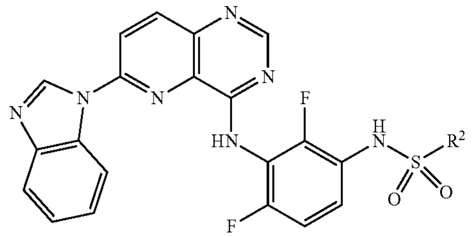

| Example | $R^2$ | Method of Synthesis | HCT116 pERK $IC_{50}$ in µM ($Y_{min}$%) | SW480 pERK $IC_{50}$ in µM ($Y_{min}$%) | Kinase $IC_{50}$ (nM) BRAF | Kinase $IC_{50}$ (nM) CRAF |
|---|---|---|---|---|---|---|
| 1 | B1 | A | ++ (8) | ++ (4) | ** | §§ |
| 2 | B2 | A | +++ (5.6) | ++ (5) | ** | §§ |
| 3 | B3 | A, B | +++ (2.3) | +++ (15) | *** | §§ |
| 4 | B4 | B | +++ (11) | ++ (−2) | * | §§ |
| 5 | B5 | B | ++ (2.7) | ++ (−7) | | |
| 6 | B6 | B | ++++ (4) | +++ (−4) | *** | §§§ |
| 7 | B7 | B | +++ (6.4) | ++ (−3.8) | ** | §§ |
| 8 | B8 | A, B | +++ (−2.5) | +++ (4.8) | ** | §§§ |
| 9 | B9 | B | ++ (−0.75) | ++ (−1.2) | ** | §§§ |
| 10 | B10 | B | + (1) | ++ (12) | * | § |
| 11 | B11 | A | ++ (−1) | ++ (7) | | |
| 12 | B12 | B | ++ (1) | ++ (16) | * | § |
| 13 | B13 | B | ++ (−1) | ++ (4) | *** | §§§ |
| 14 | B14 | B | ++ (2) | ++ (12) | | |
| 15 | B15 | B | ++ (−4) | ++ (4) | ** | §§ |
| 16 | B16 | B | ++ (2) | ++ (5) | | |
| 17 | B17 | B | ++ (−5.5) | + (−5.6) | | |
| 18 | B18 | B | ++ (−6) | ++ (3) | | |
| 19 | B19 | B | +++ (2.6) | +++ (3.3) | ** | §§§ |
| 20 | B20 | B | ++++ (4) | ++++ (5.3) | *** | §§§ |
| 21 | B21 | B | ++++ (1.9) | ++++ (0.6) | *** | §§§ |
| 22 | B22 | B | ++++ (9.9) | +++ (9.4) | ** | §§ |
| 23 | B23 | B | +++ (6.9) | +++ (14) | ** | §§ |
| 24 | B24 | B | +++ (10) | ++++ (4.4) | ** | §§§ |
| 25 | B25 | B | ++ (−10) | ++ (−2) | ** | §§ |
| 26 | B26 | B | ++ (−9) | ++ (−4) | ** | §§ |
| 27 | B27 | B | ++ (−9) | ++ (1) | ** | §§ |
| 28 | B28 | B | +++ (−2.1) | ++ (−8.5) | * | § |
| 29 | B29 | B | ++ (−2.0) | | ** | §§ |
| 30 | B30 | A | ++ (−8.6) | ++++ (−10) | *** | §§§ |
| 31 | B31 | A | +++ (6) | +++ (4.3) | ** | §§ |
| 312 | B32 | A | ++++ (−5) | | ** | §§§ |
| 313 | B33 | A | ++++ (3) | | ** | §§§ |
| 314 | B39 | A | ++++ (−12) | | *** | §§§ |
| 315 | B51 | A | ++++ (−12) | | ** | §§§ |
| 316 | B52 | A | +++ (−5) | | *** | §§§ |
| 317 | B53 | A | ++++ (−3) | | *** | §§§ |
| 318 | B43 | A | ++++ (−8) | | ** | §§§ |
| 319 | B44 | A | ++++ (−3) | | *** | §§§ |
| 320 | B54 | See text | ++ (−5) | | ** | § |
| 321 | B45 | A | +++ (−9) | | ** | §§§ |
| 322 | B46 | A | ++++ (−10) | | ** | §§ |
| 323 | B47 | A | ++ (0.4) | | ** | § |
| 324 | B55 | | | | | |
| 653 | B56 | B | ++ (−13) | | * | § |

For pERK assays, + denotes a 10-30 µM $IC_{50}$ range, ++ denotes a 1-10 µM $IC_{50}$ range, +++ denotes a 0.5-1 µM $IC_{50}$ range and ++++ denotes an $IC_{50}$ <0.5 µM. The % $Y_{min}$ value indicates the lowest value of each $IC_{50}$ curve. Compounds that exhibit $IC_{50}$ curves with $Y_{min}$ values above −20% are considered to display minimal or no induction and do not cause detectable paradoxical activation of the pathway. For the BRAF biochemical kinase assay, * denotes an $IC_{50}$ >10 nM,  denotes a 1-10 nM $IC_{50}$ range and * denotes an $IC_{50}$ <1 nM. For the CRAF biochemical kinase assay, § denotes an $IC_{50}$ >50 nM, §§ denotes a 10-50 nM $IC_{50}$ range and §§§ denotes an $IC_{50}$ <10 nM.

Characterization of compounds in Table 3

| Example | HRMS m/z ($MH^+$) | $^1H$ NMR (400 MHz) |
|---|---|---|
| 1 | 560.1 | TFA salt: $^1H$ NMR (DMSO-$d_6$) δ: 10.16 (s, 1H), 9.98 (br. s., 1H), 9.44 (br. s., 1H), 8.44-8.65 (m, 3H), 8.39 (d, J = 7.8 Hz, 1H), 7.85 (d, J = 7.0 Hz, 1H), 7.62-7.74 (m, J = 9.0 Hz, 2H), 7.36-7.52 (m, 2H), 7.17-7.32 (m, 2H), 7.03-7.15 (m, J = 9.0 Hz, 2H), 3.81 (s, 3H) |

TABLE 3-continued

| | | |
|---|---|---|
| 2 | 578.1 | $^1$H NMR (DMSO-$d_6$) δ: 10.41 (s, 1H), 9.86 (s, 1H), 9.37 (s, 1H), 8.44-8.62 (m, 3H), 8.37 (d, J = 7.8 Hz, 1H), 7.83 (d, J = 7.8 Hz, 1H), 7.62 (t, J = 8.8 Hz, 1H), 7.36-7.52 (m, 2H), 7.23 (s, 2H), 7.06 (dd, J = 12.5, 2.0 Hz, 1H), 6.90 (dd, J = 9.0, 2.3 Hz, 1H), 3.82 (s, 3H) |
| 3 | 574.1 | $^1$H NMR (DMSO-$d_6$) δ: 9.83 (s, 1H), 9.37 (s, 1H), 8.42-8.59 (m, 3H), 8.37 (d, J = 7.8 Hz, 1H), 7.83 (d, J = 7.4 Hz, 1H), 7.69 (d, J = 9.0 Hz, 1H), 7.34-7.52 (m, 2H), 7.20-7.32 (m, 1H), 7.15 (t, J = 9.0 Hz, 1H), 6.90-6.98 (m, 1H), 6.85 (dd, J = 8.8, 2.5 Hz, 1H), 3.78 (s, 3H), 2.58 (s, 3H) |
| 4 | 598.0 | $^1$H NMR (DMSO-$d_6$) δ: 10.64 (s, 1H), 9.85 (s, 1H), 9.36 (s, 1H), 8.43-8.56 (m, 3H), 8.37 (d, J = 7.4 Hz, 1H), 7.92 (d, J = 2.0 Hz, 1H), 7.88 (d, J = 8.6 Hz, 1H), 7.80-7.85 (m, 1H), 7.62 (dd, J = 8.6, 2.3 Hz, 1H), 7.36-7.50 (m, 2H), 7.18-7.36 (m, 2H) |
| 5 | 578.1 | $^1$H NMR (DMSO-$d_6$) δ: 10.44 (s, 1H), 9.84 (s, 1H), 9.36 (s, 1H), 8.43-8.62 (m, 3H), 8.37 (d, J = 7.8 Hz, 1H), 7.83 (d, J = 7.4 Hz, 1H), 7.72 (d, J = 8.6 Hz, 1H), 7.56 (d, J = 2.0 Hz, 1H), 7.35-7.52 (m, 3H), 7.24 (s, 2H), 2.62 (s, 3H) |
| 6 | 594.1 | $^1$H NMR (DMSO-$d_6$) δ: 10.36 (s, 1H), 9.87 (s, 1H), 9.37 (s, 1H), 8.43-8.58 (m, 3H), 8.37 (d, J = 7.8 Hz, 1H), 7.76-7.87 (m, 2H), 7.35-7.50 (m, 2H), 7.15-7.34 (m, 3H), 7.04 (dd, J = 8.8, 2.5 Hz, 1H), 3.84 (s, 3H) |
| 7 | 558.2 | $^1$H NMR (DMSO-$d_6$) δ: 10.26 (br. s., 1H), 9.84 (s, 1H), 9.36 (s, 1H), 8.42-8.58 (m, 3H), 8.37 (d, J = 7.8 Hz, 1H), 7.79-7.86 (m, 1H), 7.64 (d, J = 7.8 Hz, 1H), 7.33-7.51 (m, 2H), 7.11-7.33 (m, 4H), 2.58 (s, 3H), 2.30 (s, 3H) |
| 8 | 564.1 | $^1$H NMR (DMSO-$d_6$) δ: 10.53 (s, 1H), 9.85 (s, 1H), 9.36 (s, 1H), 8.46-8.54 (m, 3H), 8.37 (d, J = 7.8 Hz, 1H), 7.92 (dd, J = 8.0, 1.4 Hz, 1H), 7.83 (d, J = 7.4 Hz, 1H), 7.63-7.70 (m, 2H), 7.38-7.53 (m, 3H), 7.19-7.31 (m, 2H) |
| 9 | 544.1 | $^1$H NMR (DMSO-$d_6$) δ: 10.34 (br. s., 1H), 9.84 (s, 1H), 9.36 (s, 1H), 8.42-8.59 (m, 3H), 8.37 (d, J = 7.4 Hz, 1H), 7.79-7.88 (m, 1H), 7.76 (dd, J = 7.8, 1.2 Hz, 1H), 7.31-7.58 (m, 5H), 7.13-7.31 (m, 2H), 2.62 (s, 3H) |
| 10 | 558.2 | $^1$H NMR (DMSO-$d_6$) δ: 10.25 (s, 1H), 9.83 (s, 1H), 9.36 (s, 1H), 8.43-8.57 (m, 3H), 8.38 (d, J = 7.4 Hz, 1H), 7.78-7.88 (m, 1H), 7.68 (d, J = 8.2 Hz, 2H), 7.34-7.52 (m, 4H), 7.13-7.34 (m, 2H), 2.65 (q, J = 7.4 Hz, 2H), 1.15 (t, J = 7.6 Hz, 3H) |
| 11 | 555.1 | $^1$H NMR (DMSO-$d_6$) δ: 10.79 (br. s., 1H), 9.86 (s, 1H), 9.37 (br. s., 1H), 8.43-8.56 (m, 3H), 8.36 (d, J = 7.8 Hz, 1H), 8.11 (dd, J = 7.8, 1.2 Hz, 1H), 7.95-7.99 (m, 1H), 7.78-7.94 (m, 3H), 7.22-7.51 (m, 4H) |
| 12 | 590.1 | $^1$H NMR (DMSO-$d_6$) δ: 10.14 (s, 1H), 10.01 (br. s., 1H), 9.42 (s, 1H), 8.46-8.61 (m, 3H), 8.38 (d, J = 7.8 Hz, 1H), 7.84 (d, J = 7.4 Hz, 1H), 7.37-7.52 (m, 2H), 7.19-7.36 (m, 4H), 7.10 (d, J = 8.6 Hz, 1H), 3.81 (s, 3H), 3.74 (s, 3H) |
| 13 | 598.1 | $^1$H NMR (DMSO-$d_6$) δ: 10.52 (s, 1H), 9.92 (s, 1H), 9.38 (s, 1H), 8.43-8.59 (m, 3H), 8.36 (d, J = 7.8 Hz, 1H), 8.03-8.10 (m, 1H), 7.97-8.03 (m, 1H), 7.79-7.93 (m, 3H), 7.37-7.51 (m, 2H), 7.18-7.37 (m, 2H) |
| 14 | 550.1 | $^1$H NMR (DMSO-$d_6$) δ: 10.40 (s, 1H), 9.89 (s, 1H), 9.38 (s, 1H), 8.43-8.58 (m, 3H), 8.37 (d, J = 8.2 Hz, 1H), 7.83 (d, J = 7.4 Hz, 1H), 7.78 (d, J = 5.1 Hz, 1H), 7.37-7.51 (m, 2H), 7.21-7.37 (m, 2H), 7.03 (d, J = 5.1 Hz, 1H), 2.31 (s, 3H) |
| 15 | 574.1 | $^1$H NMR (DMSO-$d_6$) δ: 10.19 (br. s., 1H), 9.85 (s, 1H), 9.36 (s, 1H), 8.44-8.57 (m, 3H), 8.37 (d, J = 7.8 Hz, 1H), 7.83 (d, J = 7.4 Hz, 1H), 7.34-7.52 (m, 2H), 7.18-7.33 (m, 4H), 7.06 (d, J = 8.2 Hz, 1H), 6.14 (s, 2H) |
| 16 | 564.1 | $^1$H NMR (DMSO-$d_6$) δ: 10.50 (br. s., 1H), 9.84 (s, 1H), 9.36 (s, 1H), 8.44-8.55 (m, 3H), 8.37 (d, J = 7.8 Hz, 1H), 7.81-7.86 (m, 1H), 7.73-7.80 (m, 2H), 7.68-7.72 (m, 1H), 7.60-7.68 (m, 1H), 7.36-7.49 (m, 2H), 7.18-7.33 (m, 2H) |
| 17 | 544.1 | $^1$H NMR (DMSO-$d_6$) δ: 10.28 (s, 1H), 9.85 (s, 1H), 9.36 (s, 1H), 8.45-8.57 (m, 3H), 8.38 (d, J = 7.4 Hz, 1H), 7.80-7.87 (m, 1H), 7.52-7.61 (m, 2H), 7.36-7.49 (m, 4H), 7.17-7.31 (m, 2H), 2.34 (s, 3H) |
| 18 | 544.1 | $^1$H NMR (DMSO-$d_6$) δ: 9.83 (s, 1H), 9.36 (s, 1H), 8.42-8.57 (m, 3H), 8.37 (d, J = 7.8 Hz, 1H), 7.83 (d, J = 7.4 Hz, 1H), 7.65 (d, J = 8.2 Hz, 2H), 7.32-7.51 (m, 4H), 7.12-7.32 (m, 2H), 2.35 (s, 3H) |
| 19 | 570.0 | $^1$H NMR (DMSO-$d_6$) δ: 10.76 (br. s., 1H), 9.90 (s, 1H), 9.38 (s, 1H), 8.43-8.59 (m, 3H), 8.37 (d, J = 7.8 Hz, 1H), 7.99 (d, J = 4.7 Hz, 1H), 7.83 (d, J = 7.8 Hz, 1H), 7.36-7.52 (m, 2H), 7.18-7.36 (m, 3H) |
| 20 | 598.0 | $^1$H NMR (DMSO-$d_6$) δ: 10.73 (s, 1H), 9.85 (s, 1H), 9.35 (s, 1H), 8.43-8.56 (m, 3H), 8.37 (d, J = 7.4 Hz, 1H), 7.95 (dd, J = 8.2, 1.6 Hz, 1H), 7.91 (dd, J = 7.8, 1.6 Hz, 1H), 7.83 (dd, J = 7.2, 1.4 Hz, 1H), 7.54 (t, J = 8.0 Hz, 1H), 7.36-7.50 (m, 2H), 7.18-7.36 (m, 2H) |
| 21 | 578.1 | $^1$H NMR (DMSO-$d_6$) δ: 10.57 (s, 1H), 9.85 (s, 1H), 9.36 (s, 1H), 8.42-8.59 (m, 3H), 8.37 (d, J = 7.4 Hz, 1H), 7.70-7.89 (m, 3H), 7.36-7.53 (m, 3H), 7.13-7.36 (m, 2H), 2.67 (s, 3H) |
| 22 | 608.0 | $^1$H NMR (DMSO-$d_6$) δ: 10.51 (br. s., 1H), 9.86 (s, 1H), 9.36 (s, 1H), 8.43-8.57 (m, 3H), 8.37 (d, J = 7.4 Hz, 1H), 7.91-8.00 (m, 1H), 7.85-7.91 (m, 1H), 7.79-7.85 (m, 1H), 7.50-7.61 (m, 2H), 7.36-7.49 (m, 2H), 7.17-7.33 (m, 2H) |
| 23 | 582.1 | $^1$H NMR (DMSO-$d_6$) δ: 10.58 (s, 1H), 9.85 (s, 1H), 9.36 (s, 1H), 8.43-8.57 (m, 3H), 8.37 (d, J = 7.8 Hz, 1H), 7.95 (dd, J = 8.8, 6.1 Hz, 1H), 7.83 (d, J = 7.0 Hz, 1H), 7.75 (dd, J = 8.6, 2.7 Hz, 1H), 7.36-7.51 (m, 3H), 7.16-7.35 (m, 2H) |
| 24 | 582.1 | $^1$H NMR (DMSO-$d_6$) δ: 10.81 (s, 1H), 9.87 (s, 1H), 9.36 (s, 1H), 8.44-8.57 (m, 3H), 8.37 (d, J = 7.4 Hz, 1H), 7.79-7.86 (m, 1H), 7.66 (dt, J = 8.2, 5.5 Hz, 1H), 7.30-7.55 (m, 5H), 7.27 (t, J = 9.4 Hz, 1H) |
| 25 | 598.0 | $^1$H NMR (DMSO-$d_6$) δ: 10.74 (s, 1H), 9.86 (s, 1H), 9.36 (s, 1H), 8.42-8.58 (m, 3H), 8.37 (d, J = 7.8 Hz, 1H), 7.86 (d, J = 2.3 Hz, 1H), 7.83 (d, J = 7.4 Hz, 1H), 7.70-7.80 (m, 2H), 7.37-7.49 (m, 2H), 7.21-7.37 (m, 2H) |
| 26 | 558.1 | $^1$H NMR (DMSO-$d_6$) δ: 10.29 (br. s., 1H), 9.85 (s, 1H), 9.36 (s, 1H), 8.44-8.56 (m, 3H), 8.37 (d, J = 7.4 Hz, 1H), 7.76-7.86 (m, 1H), 7.55-7.61 (m, 1H), 7.37-7.51 (m, 2H), 7.15-7.37 (m, 4H), 2.53-2.58 (m, 3H), 2.28 (s, 3H) |

TABLE 3-continued

| | | |
|---|---|---|
| 27 | 578.1 | $^1$H NMR (DMSO-$d_6$) δ: 10.39 (s, 1H), 9.87 (s, 1H), 9.36 (s, 1H), 8.43-8.57 (m, 3H), 8.36 (d, J = 7.8 Hz, 1H), 7.83 (dd, J = 7.0, 1.2 Hz, 1H), 7.38-7.52 (m, 4H), 7.18-7.36 (m, 3H), 2.52-2.55 (m, 3H) |
| 28 | 558.2 | $^1$H NMR (DMSO-$d_6$) δ: 10.35 (s, 1H), 9.89 (br. s., 1H), 9.37 (s, 1H), 8.43-8.59 (m, 3H), 8.37 (d, J = 7.8 Hz, 1H), 7.83 (d, J = 7.0 Hz, 1H), 7.67 (d, J = 7.8 Hz, 1H), 7.36-7.51 (m, 3H), 7.15-7.31 (m, 3H), 2.54 (s, 3H), 2.29 (s, 3H) |
| 29 | 578.1 | $^1$H NMR (DMSO-$d_6$) δ: 10.45 (s, 1H), 9.85 (s, 1H), 9.36 (s, 1H), 8.43-8.61 (m, 3H), 8.37 (d, J = 7.4 Hz, 1H), 7.71-7.88 (m, 2H), 7.52 (s, 1H), 7.34-7.49 (m, 2H), 7.10-7.34 (m, 3H), 2.34 (s, 3H) |
| 30 | 562.1 | $^1$H NMR (DMSO-$d_6$) δ: 10.51 (br. s., 1H), 9.85 (s, 1H), 9.36 (s, 1H), 8.52 (d, J = 9.4 Hz, 1H), 8.51 (s, 1H), 8.47 (d, J = 9.0 Hz, 1H), 8.37 (d, J = 8.2 Hz, 1H), 7.83 (d, J = 7.8 Hz, 1H), 7.62 (d, J = 7.8 Hz, 1H), 7.35-7.53 (m, 4H), 7.30 (td, J = 9.0, 5.9 Hz, 1H), 7.23 (t, J = 8.6 Hz, 1H), 2.50 (s, 3H) |
| 31 | 553.2 | $^1$H NMR (DMSO-$d_6$) δ: 9.94 (s, 1H), 9.72 (s, 1H), 9.39 (s, 1H), 8.57 (s, 1H), 8.54 (d, J = 9.0 Hz, 1H), 8.50 (d, J = 9.0 Hz, 1H), 8.41 (d, J = 7.8 Hz, 1H), 7.84 (d, J = 7.4 Hz, 1H), 7.38-7.55 (m, 3H), 7.28 (td, J = 9.0, 1.2 Hz, 1H), 3.93-4.02 (m, 1H), 3.23-3.33 (m, 4H), 3.19 (s, 3H), 1.86-2.02 (m, 2H) |
| 312 | 608.2 | $^1$H NMR (400 MHz, acetic_acid) δ: 9.26 (br. s., 1H), 8.77 (d, J = 9.00 Hz, 1H), 8.70 (s, 1H), 8.43 (d, J = 9.39 Hz, 1H), 8.24 (br. s., 1H), 7.81-8.05(m, 2H), 7.56 (dt, J = 5.48, 8.80 Hz, 1H), 7.45-7.52 (m, 2H), 7.09 (t, J = 9.19 Hz, 1H), 6.94 (d, J = 9.00 Hz, 1H), 3.93 (s, 3H), 2.73 (s, 3H) |
| 313 | 592.3 | $^1$H NMR (400 MHz, acetic_acid) δ: 9.26 (br. s., 1H), 8.77 (d, J = 9.00 Hz, 1H), 8.70 (s, 1H), 8.43 (d, J = 9.00 Hz, 1H), 8.24 (br. s., 1H), 7.94 (br. s., 1H), 7.72 (d, J = 9.00 Hz, 1H), 7.52-7.63 (m, 1H), 7.50 (d, J = 5.48 Hz, 2H), 7.10 (t, J = 9.19 Hz, 1H), 6.94 (t, J = 8.41 Hz, 1H), 3.90 (s, 3H), 2.55(d, J = 2.35 Hz, 3H) |
| 314 | 595.3 | $^1$H NMR (400 MHz, DMSO-d6) δ: 10.81 (br. s., 1H), 9.62 (s, 1H), 9.13 (s, 1H), 8.62 (s, 1H), 8.41-8.52 (m, 2H), 7.94 (dd, J = 7.8, 1.6 Hz, 1H), 7.87 (d, J = 7.4 Hz, 2H), 7.45-7.54 (m, 2H), 7.04-7.20 (m, 3H), 6.59 (d, J = 7.8 Hz, 1H), 5.53 (br. s., 2 H) |
| 315 | 584.2 | $^1$H NMR (400 MHz, MeOH-$d_4$) δ: 9.19 (br. s., 1H), 8.53 (br. s., 1H), 8.38-8.47 (m, 2H), 8.24 (d, J = 8.2 Hz, 1H), 7.76-7.90 (m, 2H), 7.63 (s, 1H), 7.38-7.58 (m, 3H), 7.20-7.31 (m, 1H), 7.10-7.18 (m, 1H), 2.31 (s, 3 H) |
| 316 | 582.3 (M—H) | $^1$H NMR (400 MHz, DMSO-$d_6$) δ: 10.64 (s, 1H), 9.76 (s, 1H), 9.29 (s, 1H), 8.44-8.43 (m, 1H), 8.43-8.36 (m, 2H), 8.28 (d, J = 8.1 Hz, 1H), 7.73 (d, J = 7.7 Hz, 1H), 7 7.27 (m, 2H), 7.16 (dd, J = 14.3, 8.3 Hz, 1H), 7.02 (br m, 1H), 2.07-1.99 (m, 3H) |
| 317 | 606.2 | $^1$H NMR (400 MHz, DMSO-$d_6$) δ: 10.99 (br. s., 1 H) 9.88 (s, 1H), 9.35 (s, 1H), 18.42-8.59 (m, 3H), 8.34-8.39 (m, 1H), 8.19 (s, 1 H) 7.81 (d,, J = 7.4 Hz, 1H), 7.36-7.52 (m, 2H), 7.20-7.36 (m, 2 H) |
| 318 | 632.2 | $^1$H NMR (400 MHz, DMSO-$d_6$) δ: 10.70 (br. s., 1H), 9.79-9.92 (m, 1H), 9.35 (br. s., 1H), 8.43-8.58 (m, 2H), 8.32-8.39 (m, 1H), 8.08 (d, J = 8.2 Hz, 1H), 8.01 (d, J = 8.2 Hz, 1H), 7.75-7.90 (m, 1H), 7.50-7.64 (m, 1H), 7.16-7.48 (m, 3 H) |
| 319 | 616.3 | $^1$H NMR (400 MHz, DMSO-$d_6$) δ: 9.85 (s, 1 H) 9.34 (s, 1 H) 8.48 (m, J = 9.0, 9.0, 9.0 Hz, 3 H) 8.35 (d, J = 7.8 Hz, 1 H) 7.88-7.98 (m, 2 H) 7.81 (d, J = 7.4 Hz, 2 H) 7.35-7.48 (m, 2 H) 7.27-7.35 (m, 1 H) 7.19-7.28 (m, 1 H) |
| 320 | 564.3 | $^1$H NMR (400 MHz, DMSO-$d_6$) δ: 10.25 (br. s., 1H), 9.87 (s, 1H), 9.37 (s, 1H), 8.50-8.57 (m, 2H), 8.48 (d, J = 9.0 Hz, 1H), 8.38 (d, J = 8.2 Hz, 1H), 7.88 (s, 1 H), 7.83 (d, J = 7.4 Hz, 1H), 7.46 (t, J = 7.4 Hz, 1H), 7.40 (t, J = 7.6 Hz, 1H), 7.30 (td, J = 8.6, 5.9 Hz, 1H), 7.22 (t, J = 9.0 Hz, 1H), 2.30 (s, 3H), 2.23 (s, 3 H) |
| 321 | 580.3 | $^1$H NMR (400 MHz, DMSO-$d_6$) δ: 10.54 (br. s., 1H), 9.84 (s, 1H), 9.36 (s, 1H), 8.45-8.55 (m, 3H), 8.37 (d, J = 7.8 Hz, 1H), 7.83 (d, J = 7.4 Hz, 1H), 7.60-7.67 (m, 1H), 7.37-7.50 (m, 3H), 7.26-7.35 (m, 1H), 7.22 (dd, J = 9.0 Hz, 1H), 2.55 (d, J = 2.7 Hz, 3H) |
| 322 | 576.3 | $^1$H NMR (400 MHz, DMSO-$d_6$) δ: 10.44 (s, 1H), 9.85 (s, 1H), 9.36 (s, 1H), 8.45-8.56 (m, 3H), 8.37 (d, J = 7.9 Hz, 1H), 7.83 (d, J = 7.8 Hz, 1H), 7.52 (d, J = 8.0 Hz, 1H), 7.38-7.48 (m, 2H), 7.19-7.32 (m, 3H), 2.50 (s, 3H), 2.23-2.28 (m, 3H) |
| 323 | 596.2 | $^1$H NMR (400 MHz, DMSO-$d_6$) δ: 10.60 (br. s., 1H), 9.84 (s, 1H), 9.35 (s, 1H), 8.44-8.57 (m, 3H), 8.37 (d, J = 7.88 Hz, 1H), 7.83 (d, J = 7.63 Hz, 1H), 7.56-7.67 (m, 2H), 7.36-7.54 (m, 2H), 7.28-7.36 (m, 1H), 7.23 (t, J = 8.76 Hz, 1H), 2.55 (d, J = 2.50 Hz, 3H) |
| 324 | | Not determined |
| 653 | 632.2 | $^1$H NMR (400 MHz, DMSO-$d_6$) δ: 10.83 (br. s., 1H), 9.84 (s, 1H), 9.35 (s, 1H), 8.52 (d, J = 9.0 Hz, 1H), 8.47 (d, J = 9.0 Hz, 1H), 8.48 (s, 1H), 8.37 (d, J = 7.6 Hz, 1H), 8.16 (s, 1H), 8.11 (d, J = 8.3 Hz, 1H), 7.92 (d, J = 8.3 Hz, 1H), 7.83 (d, J = 7.3 Hz, 1H), 7.44 (td, J = 7.4, 1.1 Hz, 1H), 7.40 (td, J = 7.4, 1.0 Hz, 1H), 7.32 (td, J = 9.0, 6.1 Hz, 1H), 7.24 (t, J = 9.0 Hz, 1H) |

TABLE 4

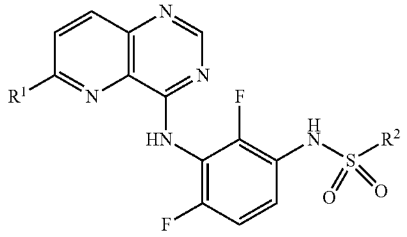

| Ex. | $R^1$ | $R^2$ | Method of Synthesis | HCT116 pERK $IC_{50}$ (μM) ($Y_{min}$%) | SW480 pERK $IC_{50}$ (μM) ($Y_{min}$%) | Kinase $IC_{50}$ (nM) BRAF | Kinase $IC_{50}$ (nM) CRAF |
|---|---|---|---|---|---|---|---|
| 32 | A1 | B1 | A | ++ (17) | ++ (2) | | |
| 33 | A2 | B1 | A | ++ (5) | ++ (0) | | |
| 34 | A3 | B1 | A | + (12) | ++ (2) | | |
| 35 | A4 | B1 | A | + (−5) | ++ (−7) | | |
| 36 | A5 | B1 | A | + (4) | ++ (9) | | |
| 37 | A1 | B2 | A | ++ (5) | ++ (1) | | |
| 38 | A3 | B3 | A | ++ (1) | ++ (2) | | |
| 39 | A1 | B3 | A | ++ (−1) | ++ (12) | | |
| 40 | A6 | B1 | A | ++ (6) | ++ (16) | * | § |
| 41 | A7 | B1 | A | ++ (4) | ++ (0) | | |
| 42 | A8 | B1 | A | ++ (4) | ++ (4) | | |
| 43 | A7 | B3 | A | +++ (4.3) | +++ (3.1) | * | §§ |
| 44 | A9 | B3 | A | +++ (10) | +++ (8.2) | | |
| 45 | A9 | B1 | A | ++ (2) | ++ (1) | | |
| 46 | A7 | B8 | A | ++++ (2.4) | ++++ (6.0) | ** | §§§ |
| 47 | A9 | B8 | A | +++ (−2.6) | +++ (-3.8) | *** | §§§ |
| 48 | A9 | B6 | A | ++ (3) | +++ (8) | | |
| 49 | A7 | B6 | A | ++ (3.1) | ++++ (9.7) | | |
| 50 | A8 | B3 | A | ++ (−11) | ++ (-5) | | |
| 51 | A10 | B3 | A | ++ (−8) | ++ (7) | | |
| 52 | A11 | B3 | A | ++ (3) | ++ (-4) | * | § |
| 53 | A12 | B1 | C | ++ (−10) | ++ (-1) | | |
| 54 | A12 | B3 | C | ++ (−7) | ++ (4) | | |
| 55 | A13 | B3 | C | ++ (−1) | ++ (11) | * | § |
| 56 | A14 | B3 | C | ++ (−9) | +++ (7) | | |
| 57 | A15 | B3 | C | ++ (−8) | ++ (-9) | | |
| 58 | A16 | B3 | C | + (−1) | ++ (2) | | |
| 59 | A17 | B3 | C | +++ (−0.7) | +++ (-4.9) | * | §§ |
| 60 | A18 | B3 | A | ++ (−10) | ++ (10) | | |
| 61 | A19 | B3 | C | ++ (−8) | ++ (3) | | |
| 62 | A20 | B3 | C | ++ (−9) | ++ (8) | * | § |
| 63 | A21 | B3 | C | ++ (−2.1) | ++++ (10) | | |
| 64 | A22 | B3 | C | ++ (4) | ++ (16) | | |
| 65 | A23 | B3 | C | + (−7) | +++ (14) | | |
| 66 | A1 | B8 | A | ++ (−2) | ++ (-5) | ** | §§ |
| 67 | A17 | B8 | C | +++ (−3.6) | +++ (-1.3) | ** | §§ |
| 68 | A7 | B19 | A | ++++ (12) | ++++ (7.1) | | |
| 69 | A24 | B3 | See text | ++ (−1) | ++ (3) | | |
| 70 | A25 | B3 | A | ++ (−3) | ++ (5) | | |
| 71 | A26 | B3 | C | ++ (−4) | ++ (8) | | |
| 72 | A27 | B3 | C | ++ (1) | ++ (-7) | | |
| 73 | A28 | B3 | C | ++ (5) | ++ (-1) | * | § |
| 74 | A29 | B3 | C | ++ (1) | ++ (3.3) | | |
| 75 | A30 | B3 | See Text | +++ (0) | +++ (1) | * | §§ |
| 76 | A31 | B3 | A | ++++ (8) | ++++ (6) | ** | §§ |
| 77 | A32 | B8 | C | ++ (−8) | ++ (2) | | |
| 78 | A33 | B8 | C | ++ (−9) | ++ (1) | | |
| 79 | A34 | B3 | See Ex 85 | +++ (1.5) | +++ (9.4) | | |
| 80 | A35 | B8 | See Text | ++ (11) | ++ (10) | | |
| 81 | A36 | B8 | See Ex 80 | ++ (−4) | ++ (15) | | |
| 82 | A37 | B8 | C | ++ (−5) | ++ (2) | | |
| 83 | A31 | B8 | See Text | ++++ (−7.3) | ++++ (2.5) | ** | §§§ |
| 84 | A31 | B21 | A | ++++ (2.9) | ++++ (4.8) | *** | §§§ |
| 85 | A34 | B8 | See text | +++ (2.9) | | ** | §§ |
| 86 | A38 | B8 | D | ++ (−10) | | ** | §§ |
| 87 | A39 | B8 | D | ++++ (−4.4) | | *** | §§ |
| 88 | A40 | B8 | A | ++ (−6) | | | |
| 89 | A41 | B8 | A | ++ (8) | ++ (−3) | ** | § |
| 90 | A42 | B8 | A | ++ (−1) | | ** | §§§ |
| 91 | A43 | B21 | See Ex 100 | ++++ (2.3) | ++++ (4.0) | | |
| 92 | A43 | B8 | See Ex 100 | ++++ (−4.6) | ++++ (18) | | |
| 93 | A43 | B3 | See Ex 100 | ++++ (6.9) | ++++ (13) | | |
| 94 | A44 | B8 | See Text | ++ (−5) | | * | § |
| 95 | A45 | B8 | See Ex 94 | ++ (−2) | | | |

TABLE 4-continued

| | | | | | | | |
|---|---|---|---|---|---|---|---|
| 96 | A46 | B8 | See Text | ++++ (12) | ++++ (12) | *** | § |
| 97 | A31 | B19 | A | ++++ (−0.6) | ++++ (18) | | |
| 98 | A43 | B19 | See Ex 100 | ++ ++ (−7.2) | ++++ (3.7) | | |
| 99 | A31 | B20 | A | ++++ (−5.4) | ++++ (−0.3) | *** | §§§ |
| 100 | A43 | B20 | See Text | ++ (−16) | ++++ (16) | *** | §§§ |
| 101 | A7 | B20 | A | ++++ (−1.9) | ++++ (−11) | ** | §§§ |
| 102 | A7 | B21 | A | ++++ (3.7) | ++++ (6.5) | ** | §§§ |
| 103 | A47 | B8 | See Ex 69 | ++ (−1) | | ** | §§ |
| 104 | A24 | B8 | See Ex 69 | ++ (−10) | | | |
| 105 | A48 | B8 | D | +++ (−10) | | *** | § |
| 106 | A49 | B8 | D | ++ (−17) | | | |
| 107 | A50 | B8 | D | ++ (−8) | | | |
| 108 | A51 | B8 | D | +++ (−9) | | | |
| 109 | A52 | B8 | D | ++++ (−1.7) | ++++ (−6.4) | | |
| 110 | A53 | B8 | D | ++ (−10) | ++++ (−4.5) | *** | § |
| 111 | A54 | B8 | D | ++ (−10) | ++++ (13) | | |
| 112 | A55 | B8 | K | ++++ (−12) | | ** | §§§ |
| 113 | A56 | B8 | D | ++++ (−10) | ++++ (5.7) | *** | §§ |
| 114 | A57 | B21 | D | ++ (7.9) | | *** | § |
| 115 | A58 | B21 | See Ex 96 | ++++ (3.3) | ++++ (−0.2) | *** | §§ |
| 116 | A59 | B21 | See Text | +++ (−18) | | *** | §§§ |
| 117 | A60 | B21 | See Text | ++ (−12) | | ** | §§§ |
| 118 | A52 | B21 | D | ++++ (−4.4) | ++++ (−12) | *** | §§ |
| 119 | A56 | B21 | D | ++++ (−7.6) | ++++ (−8.9) | *** | §§§ |
| 120 | A61 | B21 | See Text | ++ (−1) | | ** | §§ |
| 121 | A62 | B21 | See Text | ++++ (−8.7) | ++++ (3) | *** | § |
| 122 | A63 | B21 | See Text | ++ (−11) | | ** | §§ |
| 123 | A64 | B21 | K | ++++ (−5.8) | ++++ (−5.9) | ** | §§§ |
| 124 | A64 | B8 | K | ++++ (−10) | ++++ (0.75) | *** | §§ |
| 125 | A65 | B21 | D | ++++ (−11) | ++++ (−11) | | |
| 126 | A66 | B21 | D | ++++ (−3.5) | ++++ (−9) | *** | §§ |
| 127 | A67 | B21 | D | ++++ (−1.2) | ++++ (−3.8) | | |
| 128 | A68 | B21 | D | ++++ (−5.5) | ++++ (−1.2) | *** | §§§ |
| 129 | A69 | B21 | D | ++++ (−4.5) | ++++ (2.0) | | |
| 130 | A70 | B21 | D | ++++ (−14) | | ** | §§ |
| 131 | A71 | B21 | D | ++++ (−2.5) | ++++ (−4.7) | | |
| 132 | A72 | B21 | D | ++++ (−8) | | | |
| 133 | A73 | B21 | D | +++ (−6) | | *** | §§§ |
| 134 | A74 | B21 | D | ++++ (−10) | ++ (−9) | *** | § |
| 135 | A75 | B21 | D | +++ (−17) | | | |
| 136 | A76 | B21 | See Text | +++ (−10) | ++++ (1.4) | ** | §§ |
| 137 | A77 | B21 | See Text | ++ (0.9) | | *** | §§ |
| 138 | A78 | B21 | See Text | ++ (2.0) | | *** | §§§ |
| 139 | A65 | B20 | D | ++++ (5.2) | ++++ (−4.5) | *** | §§ |
| 140 | A67 | B20 | D | ++++ (1.8) | ++++ (−0.1) | | |
| 141 | A68 | B20 | D | ++++ (−1.4) | | *** | §§§ |
| 142 | A52 | B20 | D | ++++ (1.5) | +++ (5.5) | | |
| 143 | A79 | B20 | D | +++ (1.4) | | *** | §§§ |
| 144 | A80 | B20 | D | ++ (3) | | | |
| 145 | A81 | B21 | See Text | ++++ (0.0) | | | |
| 146 | A82 | B21 | See Text | +++ (−0.4) | | ** | § |
| 147 | A83 | B21 | See Text | ++ (−5) | | ** | §§ |
| 148 | A84 | B21 | See Text | ++ (−7) | | | |
| 149 | A85 | B8 | See text | +++ (8.5) | | ** | §§ |
| 150 | A86 | B8 | See Ex 149 | +++ (12) | | ** | §§ |
| 151 | A87 | B21 | See Text | ++ (11) | | ** | § |
| 152 | A88 | B21 | See Text | ++ (7) | | ** | § |
| 153 | A89 | B21 | See Text | +++ (−4.7) | | | |
| 154 | A90 | B21 | See Text | +++ (−5.6) | | ** | § |
| 155 | A91 | B21 | See Text | ++ (3) | | ** | § |
| 156 | A92 | B21 | D | +++ (3.7) | | | |
| 157 | A93 | B21 | D | +++ (3.0) | | | |
| 158 | A94 | B21 | D | ++ (5) | | | |
| 159 | A95 | B21 | D | ++ (−2) | | | |
| 160 | A96 | B21 | D | ++ (−9) | | | |
| 161 | A97 | B21 | D | +++ (1.2) | | | |
| 162 | A98 | B21 | D | ++ (3) | | *** | §§ |
| 163 | A99 | B21 | D | ++ (14) | | *** | §§ |
| 164 | A100 | B21 | D | ++ (4) | | | |
| 165 | A101 | B21 | D | ++ (−2) | | *** | §§ |
| 166 | A102 | B21 | D | +++ (−2.3) | | | |
| 167 | A103 | B21 | D | ++ (2) | | | |
| 168 | A104 | B21 | D | ++++ (2.5) | | *** | §§§ |
| 169 | A105 | B21 | D | ++++ (−3.3) | | *** | § |
| 170 | A106 | B21 | D | ++++ (−3.1) | | | |
| 171 | A107 | B21 | D | ++++ (−4.8) | | | |
| 172 | A108 | B21 | D | ++++ (0.2) | | | |
| 173 | A109 | B21 | D | +++ (−6.9) | | | |
| 174 | A110 | B21 | D | +++ (−8.3) | | | |
| 175 | A111 | B21 | D | ++++ (−1.1) | | ** | §§ |

TABLE 4-continued

| | | | | | | | |
|---|---|---|---|---|---|---|---|
| 176 | A112 | B21 | D | ++++ (−0.4) | | *** | §§ |
| 177 | A166 | B21 | D | ++++ (6.6) | | *** | §§ |
| 178 | A113 | B21 | D | ++++ (0.4) | ++ (5) | ** | § |
| 179 | A114 | B21 | D | ++ (10) | | | |
| 180 | A115 | B20 | D | ++++ (7.2) | ++++ (4.3) | *** | §§ |
| 181 | A116 | B21 | D | +++ (5.4 | | | |
| 182 | A117 | B21 | D | +++ (−11) | | *** | §§ |
| 183 | A118 | B21 | D | ++ (−4) | | | |
| 184 | A119 | B21 | D | +++ (−6) | | | |
| 185 | A120 | B21 | D | ++++ (−5.4) | | | |
| 186 | A121 | B21 | D | ++++ (−13) | | | |
| 187 | A112 | B20 | D | ++++ (−10) | | | |
| 188 | A122 | B21 | D | ++++ (−4.9) | ++++ (17) | | |
| 189 | A123 | B21 | D | ++++ (−1.1) | ++++ (−0.7) | | |
| 190 | A115 | B21 | D | ++++ (−0.2) | ++++ (4.9) | *** | § |
| 191 | A124 | B21 | D | +++ (−10) | | | |
| 192 | A125 | B21 | D | ++++ (−14) | | | |
| 193 | A126 | B21 | D | ++++ (−11) | | | |
| 194 | A127 | B21 | D | ++ (−11) | | | |
| 195 | A128 | B21 | D | ++ (−7) | | | |
| 196 | A129 | B21 | D | +++ (−5.5) | | *** | §§ |
| 197 | A130 | B21 | D | ++ (−7) | | * | § |
| 198 | A71 | B20 | D | ++++ (−13) | ++++ (1.4) | *** | §§ |
| 199 | A131 | B21 | D | ++ (−6) | | | |
| 200 | A132 | B21 | D | +++ (−7.4) | | *** | §§ |
| 201 | A133 | B21 | D | ++ (−7) | | | |
| 202 | A112 | B30 | D | ++++ (−2) | ++++ (−5) | | |
| 203 | A71 | B30 | D | ++++ (−4.8) | ++++ (−3.7) | *** | §§ |
| 204 | A65 | B30 | D | ++++ (−8.5) | ++++ (7.7) | *** | §§ |
| 205 | A31 | B30 | A | ++++ (−7.4) | ++++ (−1.2) | *** | §§§ |
| 206 | A43 | B30 | See Ex 100 | ++++ (−7.4) | ++++ (3.8) | *** | §§§ |
| 207 | A134 | B20 | See Text | ++ (−11) | | ** | §§ |
| 208 | A135 | B20 | See Text | ++ (−4) | | ** | §§§ |
| 209 | A136 | B20 | See Text | + (−6) | | ** | §§ |
| 210 | A137 | B20 | See Ex 209 | ++ (1) | | ** | §§ |
| 211 | A138 | B20 | See Ex 209 | ++ (−2) | | *** | §§§ |
| 212 | A139 | B20 | See Text | ++ (−13) | | ** | § |
| 213 | A139 | B8 | See Ex 212 | ++ (−8) | | ** | > § |
| 214 | A 140 | B8 | A | ++ (−12) | | ** | § |
| 215 | A141 | B8 | E | ++ (−9) | | ** | §§ |
| 216 | A142 | B8 | E | +++ (−8.8) | | ** | §§ |
| 217 | A143 | B8 | E | ++ (−9) | | *** | §§§ |
| 218 | A144 | B8 | E | +++ (−6) | | | |
| 219 | A145 | B8 | E | ++ (0) | | ** | §§ |
| 220 | A 146 | B8 | E | +++ (−1.7) | | | |
| 221 | A147 | B8 | E | +++ (−5) | | | |
| 222 | A148 | B8 | E | ++ (−11) | | ** | §§ |
| 223 | A149 | B8 | See Text | ++ (−9) | | ** | § |
| 224 | A150 | B8 | See Text | ++ (−5) | | ** | §§ |
| 225 | A151 | B8 | E | ++ (−8) | | ** | §§ |
| 226 | A152 | B8 | E | ++ (−9) | | ** | § |
| 227 | A153 | B8 | E | +++ (−1.9) | | | |
| 228 | A154 | B8 | E | +++ (2.0) | | | |
| 229 | A155 | B8 | E | ++ (−7) | | *** | §§ |
| 230 | A156 | B8 | E | ++ (−3) | | | |
| 231 | A157 | B8 | E | ++ (2) | | ** | §§ |
| 232 | A158 | B8 | E | ++ (−7) | | ** | §§ |
| 233 | A159 | B8 | E | ++ (0) | | ** | § |
| 234 | A160 | B8 | E | ++ (−8) | | ** | § |
| 235 | A161 | B8 | E | +++ (−4) | | | |
| 236 | A162 | B8 | E | ++ (−7) | | ** | § |
| 237 | A163 | B8 | See Text | +++ (2.8) | | | |
| 238 | A164 | B8 | See Ex 237 | ++ (−3) | | ** | §§ |
| 242 | A167 | B20 | See text | ++ (−7.4) | | | |
| 243 | A168 | B8 | F | ++++ (−3.9) | | ** | §§§ |
| 244 | A169 | B30 | D | ++++ (−14.5) | | *** | § |
| 245 | A68 | B30 | D | +++ (−17.7) | | ** | § |
| 246 | A170 | B30 | D | ++++ (−5.4) | | ** | §§ |
| 247 | A171 | B30 | D | ++++ (−4.8) | | ** | § |
| 248 | A129 | B30 | D | ++++ (−4.3) | | *** | §§ |
| 249 | A172 | B30 | D | +++ (−2.0) | | ** | §§ |
| 250 | A66 | B30 | D | ++++ (5) | | *** | § |
| 251 | A168 | B30 | F | ++++ (−6.3) | ++++ (14) | ** | §§ |
| 252 | A173 | B30 | D | ++++ (−9.4) | | *** | §§ |
| 253 | A174 | B30 | D | ++++ (−9.0) | | *** | §§ |
| 254 | A175 | B30 | D | ++ (−14.9) | | ** | §§ |
| 255 | A176 | B30 | D | ++++ (−10.9) | | *** | §§ |
| 256 | A177 | B30 | D | ++ (−7.1) | | *** | §§ |
| 257 | A178 | B30 | D | ++ (−1.2) | | *** | §§ |

TABLE 4-continued

| | | | | | | |
|---|---|---|---|---|---|---|
| 258 | A179 | B30 | D | ++ (−2.7) | ** | § |
| 259 | A180 | B30 | D | ++ (−8.3) | *** | §§ |
| 260 | A181 | B30 | D | ++++ (−8) | ** | §§ |
| 261 | A182 | B30 | D | ++++ (−1.2) | *** | §§§ |
| 262 | A183 | B30 | D | ++++ (−0.8) | ** | §§ |
| 263 | A184 | B30 | D | ++++ (−6.2) | ** | §§ |
| 264 | A185 | B30 | D | ++++ (1.1) | *** | §§§ |
| 265 | A186 | B30 | D | ++++ (−2.4) | *** | §§ |
| 266 | A187 | B30 | D | ++++ (3.2) | *** | §§ |
| 267 | A188 | B30 | D | ++++ (−3.4) | *** | §§ |
| 268 | A166 | B30 | D | ++++ (−2.2) | *** | §§ |
| 269 | A117 | B30 | D | ++++ (−6.4) | ** | §§ |
| 270 | A189 | B30 | D | ++++ (−2.9) | ** | § |
| 271 | A190 | B30 | D | ++++ (−21) | ** | § |
| 272 | A191 | B30 | F | ++++ (−0.1) | *** | §§§ |
| 273 | A192 | B30 | F | ++++ (3.3) | ** | §§ |
| 274 | A193 | B30 | D | ++++ (3.6) | *** | §§ |
| 275 | A194 | B30 | D | ++++ (−6.4) | *** | §§ |
| 276 | A195 | B30 | D | ++++ (−9.4) | ** | §§§ |
| 277 | A54 | B30 | D | ++++ (−19) | *** | §§§ |
| 278 | A196 | B30 | D | ++++ (−6.0) | *** | §§ |
| 279 | A197 | B30 | D | ++++ (−4.9) | *** | §§§ |
| 280 | A198 | B30 | D | ++++ (10) | ** | §§ |
| 281 | A199 | B30 | D | ++++ (6.6) | ** | §§ |
| 282 | A115 | B30 | D | ++++ (−13) | ** | § |
| 283 | A200 | B30 | D | ++++ (−9.6) | ** | § |
| 284 | A201 | B30 | D | ++++ (−0.4) | *** | § |
| 285 | A121 | B30 | D | ++++ (11) | *** | §§ |
| 286 | A120 | B30 | D | ++++ (4.6) | *** | §§ |
| 287 | A202 | B30 | D | +++ (−5.3) | ** | §§§ |
| 288 | A203 | B30 | D | + (−14.1) | * | § |
| 289 | A204 | B30 | D | ++ (−1.2) | ** | § |
| 290 | A205 | B30 | D | ++++ (2.0) | *** | §§ |
| 291 | A206 | B30 | D | +++ (−3.4) | *** | § |
| 292 | A207 | B30 | D | ++++ (−6.0) | *** | §§ |
| 293 | A208 | B30 | D | ++++ (−1.5) | *** | §§ |
| 294 | A209 | B30 | D | ++++ (3.4) | *** | §§ |
| 295 | A67 | B30 | D | ++++ (−12) | *** | §§ |
| 296 | A210 | B30 | D | ++++ (0.2) | *** | §§ |
| 297 | A31 | B32 | A | ++++ (−10) | ** | §§§ |
| 298 | A31 | B33 | A | ++++ (−2.1) | ** | §§§ |
| 299 | A211 | B30 | D | ++++ (−6.5) | *** | §§§ |
| 300 | A31 | B34 | A | ++++ (3.0) | ** | §§ |
| 301 | A31 | B35 | A | ++++ (2.7) | ** | §§ |
| 302 | A31 | B36 | A | +++ (4.8) | * | § |
| 303 | A31 | B37 | A | +++ (−3.3) | ** | §§ |
| 304 | A64 | B30 | K | ++++ (−6.4) | ** | §§ |
| 305 | A212 | B30 | K | ++++ (−7.5 ) | ** | §§§ |
| 306 | A213 | B30 | K | ++++ (−3.1) | ** | §§ |
| 307 | A214 | B30 | K | ++ (−4.4) | ** | §§ |
| 308 | A215 | B30 | K | ++++ (−5.9) | ** | §§ |
| 309 | A216 | B30 | K | ++++ (−4.7) | *** | §§§ |
| 310 | A217 | B30 | K | ++++ (1.3) | ** | §§ |
| 311 | A31 | B38 | A | ++ (−4.4) | ** | §§ |
| 325 | A218 | B30 | D | ++++ (0) | *** | §§ |
| 326 | A219 | B30 | D | ++++ (3) | ** | §§ |
| 327 | A31 | B1 | A | ++++ (2) | ** | §§ |
| 328 | A30 | B30 | See Ex 75 | ++++ (2) | ** | §§§ |
| 329 | A220 | B30 | See text | ++ (−3) | * | § |
| 330 | A221 | B30 | A | ++++ (5) | ** | §§§ |
| 330 | A221 | B30 | A | ++++ (5) | ** | §§§ |
| 331 | A187 | B20 | D | ++++ (0) | *** | §§ |
| 332 | A222 | B30 | A | ++ (−6) | ** | §§ |
| 333 | A1 | B30 | A | ++++ (7) | ** | §§ |
| 334 | A223 | B30 | See text | ++++ (3) | ** | §§ |
| 335 | A224 | B30 | See Ex 334 | ++++ (−7) | ** | §§ |
| 336 | A225 | B30 | See Ex 334 | ++++ (−9) | ** | §§ |
| 337 | A226 | B30 | D | ++++ (−7) | *** | §§§ |
| 338 | A227 | B30 | D | ++++ (−10) | *** | §§§ |
| 339 | A228 | B30 | See text | ++++ (−3) | ** | §§ |
| 340 | A229 | B30 | See text | ++++ (1) | ** | §§ |
| 341 | A31 | B48 | A | ++ (−17) | * | § |
| 342 | A168 | B20 | F | ++++ (4) | ** | §§§ |
| 343 | A230 | B30 | See text | ++++ (2) | ** | §§ |
| 344 | A39 | B30 | D | ++++ (5) | *** | §§ |
| 345 | A231 | B30 | See text | ++++ (−7) | ** | §§§ |
| 346 | A232 | B30 | See Ex. 334 | ++++ (−4) | *** | §§ |
| 347 | A233 | B30 | See text | ++++ (8) | ** | §§§ |
| 348 | A235 | B20 | See text | ++++ (−1) | ** | §§ |
| 349 | A235 | B30 | See text | +++ (−1) | ** | §§ |

TABLE 4-continued

| | | | | | | | |
|---|---|---|---|---|---|---|---|
| 350 | A236 | B30 | See Ex. 375 | ++++ (−6) | | ** | §§ |
| 351 | A237 | B30 | See Ex. 375 | ++++ (−2) | | ** | §§§ |
| 352 | A31 | B9 | A | ++++ (−9) | | ** | §§ |
| 353 | A31 | B49 | See text | ++ (−11) | | * | § |
| 354 | A215 | B20 | K | ++++ (−8) | | ** | §§§ |
| 355 | A216 | B20 | K | ++++ (−2) | | *** | §§§ |
| 356 | A238 | B30 | See text | ++++ (−9) | | ** | §§ |
| 357 | A239 | B30 | See text | +++ (−12) | | ** | §§§ |
| 358 | A31 | B50 | A | ++ (−17) | | ** | §§ |
| 359 | A217 | B20 | K | ++++ (−9) | | ** | §§§ |
| 345 | A240 | B30 | A | +++ (−15) | | * | §§ |
| 360 | A241 | B30 | A | ++++ (4) | | ** | §§ |
| 361 | A474 | B30 | See text | ++++ (−1) | | *** | §§§ |
| 362 | A475 | B30 | See text | ++ (−8) | | ** | §§ |
| 363 | A242 | B30 | D | ++++ (−3) | | ** | § |
| 364 | A215 | B21 | K | ++++ (−2) | | ** | §§§ |
| 365 | A216 | B21 | K | ++++ (4) | | *** | §§§ |
| 366 | A217 | B21 | K | ++++ (−16) | | *** | §§§ |
| 367 | A31 | B39 | A | ++++ (−2) | | *** | §§§ |
| 368 | A31 | B40 | A | ++ (−9) | | ** | §§ |
| 369 | A31 | B41 | See text | +++ (−16) | | * | § |
| 370 | A169 | B20 | D | ++++ (−1) | | *** | §§ |
| 371 | A169 | B33 | D | ++++ (−9) | | ** | § |
| 372 | A31 | B13 | A | ++++ (−11) | | *** | §§§ |
| 373 | A7 | B33 | A | +++ (0) | | ** | §§ |
| 374 | A7 | B32 | A | ++++ (−4) | | ** | §§ |
| 375 | A243 | B30 | See text | ++++ (−15) | | ** | §§ |
| 376 | A244 | B30 | See text | +++ (−8) | | ** | § |
| 377 | A245 | B20 | G | +++ (6) | | * | § |
| 378 | A246 | B20 | G | ++++ (−9) | | *** | §§§ |
| 379 | A247 | B30 | A | ++ (−15) | | ** | §§§ |
| 380 | A248 | B20 | G | ++ (2) | | * | § |
| 381 | A249 | B20 | H | ++++ (8) | | *** | §§§ |
| 382 | A250 | B20 | See text | +++ (−4) | | *** | §§§ |
| 383 | A251 | B30 | See text | ++ (−5) | | * | § |
| 384 | A252 | B30 | See Ex 376 | ++ (−6) | | * | § |
| 385 | A216 | B33 | K | ++++ (−9) | ++++ (−3) | *** | §§ |
| 386 | A216 | B32 | K | ++++ (−20) | | ** | §§§ |
| 387 | A253 | B20 | K | ++++ (2) | | *** | §§§ |
| 388 | A254 | B20 | K | ++++ (12) | | ** | §§ |
| 389 | A255 | B20 | K | ++++ (2) | | *** | §§§ |
| 390 | A31 | B42 | A | ++++ (−13) | | *** | §§ |
| 391 | A256 | B30 | See text | ++ (−10) | | * | § |
| 392 | A257 | B30 | See text | ++ (−11) | | ** | §§ |
| 393 | A258 | B30 | See text | +++ (−5) | | ** | §§ |
| 394 | A259 | B30 | D | +++ (−15) | | *** | § |
| 395 | A253 | B30 | K | ++++ (−7) | | *** | §§§ |
| 396 | A254 | B30 | K | ++++ (11) | | ** | §§ |
| 397 | A255 | B30 | K | ++++ (1) | | *** | §§§ |
| 398 | A260 | B30 | D | ++++ (3) | | ** | § |
| 399 | A260 | B20 | D | ++++ (−9) | | *** | § |
| 400 | A261 | B20 | G | ++++ | | *** | §§§ |
| 401 | A31 | B51 | A | ++++ (−3) | | ** | §§§ |
| 402 | A262 | B20 | G | ++++ (−2) | | ** | §§ |
| 403 | A55 | B20 | G | ++++ (−5) | | ** | §§§ |
| 404 | A263 | B20 | G | +++ (−1) | | *** | §§§ |
| 405 | A259 | B20 | K | ++ (1) | | ** | § |
| 406 | A265 | B20 | G | ++ (−7) | | ** | §§ |
| 407 | A266 | B20 | G | ++++ (2) | | ** | §§§ |
| 408 | A267 | B20 | K | ++++ (−2) | | ** | §§ |
| 409 | A268 | B20 | K | ++++ (0) | | ** | §§ |
| 410 | A269 | B20 | K | ++++ (−16) | | *** | §§§ |
| 411 | A270 | B20 | H | ++++ (−2) | | *** | §§§ |
| 412 | A271 | B20 | H | ++++ (−6) | | *** | §§§ |
| 413 | A272 | B20 | H | ++++ (−14) | | ** | §§ |
| 414 | A273 | B30 | See text | ++ (2) | | * | § |
| 415 | A274 | B30 | See text | +++ (−1) | | ** | §§ |
| 416 | A275 | B20 | G | ++++ (−5) | | *** | §§§ |
| 417 | A276 | B20 | G | ++++ (1) | | ** | §§ |
| 418 | A277 | B20 | G | ++++ (−16) | | * | § |
| 419 | A278 | B20 | G | ++++ (3) | | *** | §§§ |
| 420 | A279 | B30 | See text | ++ (−4) | | *** | §§§ |
| 421 | A31 | B53 | A | ++++ (−11) | | *** | §§§ |
| 422 | A31 | B43 | A | ++++ (−9) | | *** | §§§ |
| 423 | A31 | B44 | A | ++++ (−6) | | *** | §§§ |
| 424 | A280 | B30 | See text | ++++ (−8) | | ** | §§ |
| 425 | A281 | B30 | See text | +++ (−9) | | * | § |
| 426 | A282 | B20 | G | ++++ (−2) | | *** | §§§ |
| 427 | A283 | B20 | G | +++ (4) | | ** | §§ |
| 428 | A284 | B20 | G | ++++ (−3) | | ** | §§ |

TABLE 4-continued

| | | | | | | | |
|---|---|---|---|---|---|---|---|
| 429 | A285 | B20 | G | ++++ (5) | | ** | §§§ |
| 430 | A286 | B20 | G | ++++ (17) | | ** | §§§ |
| 431 | A287 | B20 | G | ++++ (3) | | *** | §§§ |
| 432 | A288 | B20 | G | ++++ (−6) | ++++ (6) | *** | §§§ |
| 433 | A289 | B20 | G | ++++ (−5) | | *** | §§§ |
| 434 | A290 | B20 | G | +++ (−6) | | *** | §§§ |
| 435 | A291 | B20 | G | ++++ (−4) | | ** | §§ |
| 436 | A292 | B20 | G | ++++ (−5) | | *** | §§§ |
| 437 | A293 | B20 | G | ++++(−11) | | ** | §§ |
| 438 | A294 | B20 | G | ++++ (15) | | ** | §§ |
| 439 | A295 | B20 | G | ++++ (−2) | | ** | §§§ |
| 440 | A296 | B20 | H | +++ (8) | | ** | § |
| 441 | A297 | B20 | H | +++ (−6) | | *** | §§§ |
| 442 | A298 | B20 | H | ++++ (0) | | ** | §§ |
| 443 | A299 | B20 | See text | ++++ (6) | | ** | §§§ |
| 444 | A300 | B20 | See text | ++++ (3) | | *** | §§§ |
| 445 | A301 | B20 | G | ++++ (−8) | | *** | §§§ |
| 446 | A302 | B20 | G | ++ (−16) | | *** | §§§ |
| 447 | A303 | B20 | See text | ++++ (−14) | | *** | §§§ |
| 448 | A490 | B20 | A | ++++ (11) | | ** | §§§ |
| 449 | A304 | B20 | A | ++++ (−10) | | *** | §§§ |
| 450 | A305 | B20 | G | ++++ (−2) | | ** | §§ |
| 451 | A306 | B20 | G | ++++ (−12) | | ** | §§ |
| 452 | A307 | B20 | G | ++++ (−13) | | *** | §§§ |
| 453 | A308 | B20 | G | ++++ (−14) | | *** | §§§ |
| 454 | A309 | B20 | G | ++++ (12) | | ** | §§§ |
| 455 | A310 | B20 | G | ++++ (−17) | | ** | §§§ |
| 456 | A311 | B20 | See text | ++++ (−4) | | ** | §§ |
| 457 | A312 | B20 | See text | ++++ (4) | | ** | § |
| 458 | A313 | B20 | G | ++++ (5) | | ** | §§§ |
| 459 | A314 | B20 | G | ++++ (2) | | ** | § |
| 460 | A315 | B30 | See text | ++ (−9) | | * | § |
| 461 | A316 | B20 | See text | ++++ (2) | | *** | §§§ |
| 462 | A317 | B20 | A | ++++ (9) | | ** | §§§ |
| 463 | A9 | B20 | A | +++ (4) | | ** | § |
| 464 | A140 | B20 | A | ++ (−5) | | * | § |
| 465 | A318 | B20 | See text | +++ (1) | | *** | §§§ |
| 466 | A319 | B20 | H | ++++ (3) | | ** | §§ |
| 467 | A320 | B20 | See text | ++++ (2) | | *** | §§§ |
| 468 | A321 | B20 | See text | ++++ (7) | | *** | §§§ |
| 469 | A322 | B20 | See text | ++++ (15) | | *** | §§§ |
| 470 | A323 | B20 | See text | ++++ (−4) | | ** | §§§ |
| 471 | A324 | B20 | A | ++ (−12) | | ** | § |
| 472 | A325 | B20 | See text | ++ (−11) | | *** | §§ |
| 473 | A326 | B20 | A | +++ (−14) | | ** | §§ |
| 474 | A327 | B20 | See text | ++++ (1) | | ** | §§ |
| 475 | A328 | B20 | See text | ++ (−15) | | ** | §§ |
| 476 | A329 | B20 | See text | ++ (−4) | | *** | §§ |
| 477 | A330 | B20 | See text | ++++ (−19) | | ** | §§ |
| 478 | A331 | B20 | See text | ++++ (−1) | | *** | §§ |
| 479 | A332 | B20 | See text | ++++ (−8) | | *** | §§§ |
| 480 | A333 | B20 | See Ex 69 | +++ (6) | | * | § |
| 481 | A249 | B1 | H | ++++ (−16) | | ** | § |
| 482 | A334 | B20 | A | ++ (−13) | | * | § |
| 483 | A335 | B20 | See text | ++ (−8) | | ** | § |
| 484 | A336 | B20 | See text | ++++ (−19) | | *** | §§§ |
| 485 | A337 | B30 | A | ++++ (5) | | *** | §§ |
| 486 | A239 | B20 | See text | +++ (−1) | | ** | §§§ |
| 487 | A338 | B20 | A | ++ (−6) | | * | § |
| 488 | A339 | B20 | See text | ++++ (2) | | ** | §§§ |
| 489 | A341 | B20 | A | ++ (−4) | | ** | §§ |
| 490 | A342 | B20 | H | ++++ (9) | | ** | §§§ |
| 491 | A343 | B20 | H | +++ (8) | | * | § |
| 492 | A344 | B20 | H | ++++ (−11) | | *** | §§ |
| 493 | A345 | B20 | H | ++ (−10) | | * | § |
| 494 | A346 | B20 | See text | ++++ (−9) | | ** | §§§ |
| 495 | A347 | B20 | See text | ++ (−12) | | * | §§ |
| 496 | A348 | B20 | A | +++ (−9) | | ** | §§ |
| 497 | A349 | B20 | H | ++++ (−9) | | ** | §§ |
| 498 | A350 | B20 | H | ++++ (−1) | | ** | § |
| 499 | A351 | B20 | See text | ++++ (2) | | * | § |
| 500 | A352 | B20 | See text | ++ (−12) | | * | §§ |
| 501 | A340 | B20 | A | ++ (−7) | | ** | §§ |
| 502 | A234 | B20 | See Text | ++++ (−8) | | ** | §§§ |
| 503 | A353 | B20 | A | ++ (−6) | | * | § |
| 504 | A354 | B20 | A | +++ (−2) | | ** | §§§ |
| 505 | A355 | B20 | A | ++ (−7) | | * | § |
| 506 | A356 | B20 | See text | ++ (2) | | * | §§ |
| 507 | A357 | B20 | A | ++ (−5) | | ** | §§§ |
| 508 | A358 | B20 | A | +++ (−3) | | ** | §§§ |

TABLE 4-continued

| | | | | | | | |
|---|---|---|---|---|---|---|---|
| 509 | A359 | B20 | H | ++++ (0) | ++++ (4) | *** | §§§ |
| 510 | A360 | B30 | C | ++ (−4) | | ** | §§ |
| 511 | A361 | B20 | See text | ++++ (10) | | ** | §§ |
| 512 | A362 | B20 | See text | ++ (−8) | | ** | § |
| 513 | A363 | B20 | See text | +++ (−11) | | ** | §§ |
| 514 | A364 | B20 | See text | ++++ (−4) | | ** | § |
| 515 | A365 | B20 | A | ++ (−12) | | ** | §§ |
| 516 | A1 | B20 | A | +++ (−12) | | ** | §§ |
| 517 | A11 | B20 | A | ++++ (−9) | | ** | §§§ |
| 518 | A366 | B20 | A | ++ (−8) | | ** | §§ |
| 519 | A367 | B20 | A | ++ (−6) | | * | § |
| 520 | A368 | B20 | See text | ++++ (−2) | | ** | §§ |
| 521 | A369 | B20 | See text | ++ (1) | | ** | §§§ |
| 522 | A370 | B20 | See text | +++ (−6) | | ** | §§§ |
| 523 | A371 | B20 | See Ex 538 | +++ (0) | | *** | §§§ |
| 524 | A372 | B20 | I | ++++ (−3) | ++++ (0) | ** | §§§ |
| 525 | A373 | B20 | See text | +++ (−1) | | ** | §§§ |
| 526 | A374 | B20 | I | ++++ (−2) | | ** | §§ |
| 527 | A375 | B20 | I | ++ (−5) | | ** | §§ |
| 528 | A376 | B20 | See text | ++ (10) | | ** | § |
| 529 | A7 | B30 | A | ++++ (−6) | | ** | §§§ |
| 530 | A17 | B20 | C | ++++ (3) | | *** | §§§ |
| 531 | A377 | B30 | See text | ++ (3) | | * | § |
| 532 | A378 | B20 | See Ex 511 | ++ (−3) | | ** | § |
| 533 | A379 | B20 | C | ++++ (9) | | ** | §§§ |
| 534 | A380 | B20 | See text | ++++ (−4) | | * | § |
| 535 | A381 | B20 | C | ++ (−8) | | ** | §§ |
| 536 | A382 | B20 | See text | +++ (4) | | ** | §§ |
| 537 | A383 | B20 | See text | ++ (−8) | | ** | § |
| 538 | A384 | B20 | See text | ++++ (−9) | | ** | §§§ |
| 539 | A372 | B30 | I | ++++ (0) | | ** | §§§ |
| 540 | A386 | B20 | I | ++++ (−11) | | *** | §§§ |
| 541 | A387 | B20 | I | ++++ (0) | | ** | §§§ |
| 542 | A388 | B20 | I | ++++ (3) | | ** | §§§ |
| 543 | A389 | B20 | I | ++++ (−6) | | ** | §§ |
| 544 | A390 | B20 | A | ++ (−15) | | * | § |
| 545 | A391 | B20 | I | ++++ (−3) | | * | §§ |
| 546 | A392 | B20 | I | ++++ (2) | | *** | §§§ |
| 547 | A393 | B20 | I | ++++ (−1) | | ** | § |
| 548 | A394 | B20 | I | ++++ (10) | | *** | §§ |
| 549 | A395 | B20 | See text | ++ (−10) | | * | § |
| 550 | A396 | B20 | See text | ++ (−2) | | ** | § |
| 551 | A397 | B20 | See text | ++ (−14) | | ** | § |
| 552 | A398 | B20 | See text | ++++ (−2) | | ** | §§ |
| 553 | A399 | B20 | See text | ++++ (−6) | | ** | §§§ |
| 554 | A400 | B20 | I | ++++ (−5) | | ** | §§ |
| 555 | A401 | B20 | I | ++++ (−2) | | * | § |
| 556 | A402 | B20 | See text | ++++ (−7) | | *** | §§§ |
| 557 | A403 | B20 | I | ++++ (−11) | | ** | §§ |
| 558 | A404 | B20 | I | ++++ (−9) | | * | §§ |
| 559 | A405 | B20 | I | ++++ (−10) | | * | §§ |
| 560 | A406 | B20 | I | ++++ (−10) | | *** | §§§ |
| 561 | A407 | B20 | C-Stille | ++++ (−13) | | ** | §§§ |
| 562 | A408 | B20 | C-Stille | ++++ (−15) | | *** | §§§ |
| 563 | A409 | B20 | C-Stille | ++ (−6) | | ** | §§ |
| 564 | A512 | B20 | C-Stille | ++ (−14) | | * | §§ |
| 565 | A410 | B20 | C-Stille | ++ (4) | | * | § |
| 566 | A14 | B20 | C | +++ (4) | | ** | §§ |
| 567 | A411 | B20 | C | ++ (−16) | | ** | §§ |
| 568 | A412 | B20 | I | ++++ (−8) | | ** | §§ |
| 569 | A413 | B20 | I | ++++ (−8) | | ** | §§ |
| 570 | A414 | B20 | A | ++++ (−13) | | ** | §§§ |
| 571 | A385 | B20 | J | ++++ (−7) | | ** | §§ |
| 572 | A415 | B20 | J | ++++ (6) | | ** | §§ |
| 573 | A18 | B20 | See text | ++ (−1) | | * | § |
| 574 | A416 | B20 | I | ++++ (1) | | *** | §§§ |
| 575 | A417 | B20 | J | ++++ (0) | | ** | §§ |
| 576 | A418 | B20 | I | +++ (−16) | | * | § |
| 577 | A419 | B20 | I | +++ (−10) | | ** | § |
| 578 | A420 | B20 | I | ++++ (−4) | ++++ (5) | ** | §§ |
| 579 | A421 | B20 | I | ++++ (0) | | ** | §§ |
| 580 | A422 | B20 | I | ++++ (−3) | | *** | §§§ |
| 581 | A423 | B20 | I | ++++ (−11) | | ** | §§ |
| 582 | A424 | B20 | I | ++++ (−9) | ++++ (6) | ** | §§ |
| 583 | A425 | B20 | I | ++++ (−14) | | ** | §§ |
| 584 | A426 | B20 | I | ++++ (−6) | | ** | §§ |
| 585 | A427 | B20 | I | ++++ (0) | | ** | § |
| 586 | A428 | B20 | I | ++++ (−3) | | *** | §§§ |
| 587 | A429 | B20 | I | ++++ (0) | | ** | §§ |
| 588 | A430 | B20 | I | ++++ (−4) | ++++ (4) | ** | §§ |

TABLE 4-continued

| | | | | | | | |
|---|---|---|---|---|---|---|---|
| 589 | A7 | B45 | A | +++ (−14) | | ** | §§ |
| 590 | A431 | B20 | C-Stille | ++++ (−17) | | ** | §§ |
| 591 | A432 | B20 | C-Stille | ++++ (−3) | | ** | §§ |
| 592 | A433 | B20 | I | ++++ (−14) | | * | §§ |
| 593 | A434 | B20 | I | ++++ (−3) | | * | § |
| 594 | A435 | B20 | See text | ++ (−5) | | ** | §§ |
| 595 | A436 | B20 | See text | ++ (−16) | | ** | §§ |
| 596 | A437 | B20 | I | ++++ (−10) | | ** | §§§ |
| 597 | A438 | B20 | I | ++++ (−7) | | ** | §§§ |
| 598 | A439 | B20 | See Ex 538 | ++++ (−4) | | ** | §§§ |
| 599 | A440 | B20 | I | ++++ (2) | | ** | §§ |
| 600 | A441 | B20 | J | ++++ (−2) | | ** | §§ |
| 601 | A442 | B20 | J | +++ (−14) | | * | § |
| 602 | A443 | B20 | J | ++++ (−4) | | ** | §§ |
| 603 | A444 | B20 | J | ++++ (−3) | | * | § |
| 604 | A445 | B20 | J | ++++ (−8) | | *** | §§§ |
| 605 | A446 | B20 | J | ++++ (−7) | | ** | §§ |
| 606 | A447 | B20 | J | ++++ (6) | | * | § |
| 607 | A448 | B20 | I | ++++ (−4) | | * | § |
| 608 | A449 | B20 | I | ++++ (−7) | ++++ (7) | *** | §§§ |
| 609 | A450 | B20 | I | ++++ (11) | | ** | §§ |
| 610 | A451 | B20 | See text | ++++ (−2) | | ** | §§§ |
| 611 | A452 | B20 | J | ++++ (−9) | | * | § |
| 612 | A453 | B20 | See text | ++++ (−10) | | ** | §§§ |
| 613 | A454 | B20 | See ex 631 | +++ (−3) | | ** | §§ |
| 614 | A455 | B20 | See text | ++++ (2) | | *** | §§§ |
| 615 | A456 | B20 | J | ++++ (5) | ++++ (2) | ** | §§§ |
| 616 | A457 | B20 | J | ++++ (0) | | *** | §§§ |
| 617 | A458 | B20 | J | ++++ (2) | | ** | §§ |
| 618 | A459 | B20 | I | ++ (−10) | | *** | §§§ |
| 619 | A460 | B20 | J | ++++ (7) | | *** | §§§ |
| 620 | A461 | B20 | J | ++++ (−6) | | *** | §§§ |
| 621 | A462 | B20 | I | ++++ (4) | | ** | §§ |
| 622 | A463 | B20 | I | ++++ (−10) | | * | § |
| 623 | A464 | B20 | See text | ++++ (−13) | | *** | §§§ |
| 624 | A465 | B20 | See text | +++ (−8) | | ** | §§ |
| 625 | A466 | B20 | See text | ++++ (−3) | | *** | §§§ |
| 626 | A467 | B20 | J | ++++ (4) | | *** | §§ |
| 627 | A468 | B20 | See text | ++++ (−3) | | *** | §§§ |
| 628 | A469 | B20 | See text | +++ (0) | | ++ | §§§ |
| 629 | A470 | B20 | See text | **** (−2) | | ** | §§ |
| 630 | A449 | B30 | I | ++++ (3) | | ** | §§§ |
| 631 | A471 | B20 | See text | ++++ (0) | | * | §§ |
| 632 | A449 | B21 | I | ++++ (1) | | ** | §§§ |
| 633 | A372 | B21 | I | ++++ (2) | | ** | §§ |
| 634 | A472 | B20 | See text | ++++ (−2) | | *** | §§§ |
| 635 | A473 | B20 | I | ++++ (−11) | | *** | §§§ |
| 636 | A424 | B30 | I | ++++ (−15) | | ** | §§ |
| 637 | A424 | B21 | I | ++++ (−4) | | ** | §§ |
| 638 | A425 | B30 | I | ++++ (−3.6) | | ** | §§ |
| 639 | A425 | B21 | I | ++++ (−6) | | ** | §§ |
| 640 | A422 | B30 | I | ++++ (8) | | ** | §§ |
| 641 | A422 | B21 | I | ++++ (8) | | *** | §§§ |
| 642 | A476 | B20 | I | ++++ (−19) | | ** | §§§ |
| 643 | A477 | B20 | I | ++++ (−17) | | *** | §§§ |
| 644 | A478 | B20 | I | ++++ (−10) | | ** | §§§ |
| 645 | A479 | B20 | I | ++++ (−10) | | ** | §§ |
| 654 | A480 | B20 | I | ++++ (−6) | | ** | §§ |
| 655 | A481 | B20 | See text | ++++ (−7) | | ** | §§ |
| 656 | A482 | B20 | I | ++++ (1) | | *** | §§§ |
| 657 | A483 | B20 | I | ++++ (−14) | | *** | §§§ |
| 658 | A484 | B20 | I | ++++ (−14) | | * | §§ |
| 659 | A485 | B20 | I | ++++ (−8) | | ** | §§ |
| 660 | A486 | B20 | I | ++++ (−5) | | ** | §§ |
| 661 | A487 | B20 | I | ++++(−15) | | * | § |
| 662 | A488 | B20 | See text | ++ (−6) | | *** | §§§ |
| 663 | A489 | B30 | A | ++ (−5) | | * | § |
| 664 | A491 | B30 | See text | ++ (−15) | | ** | § |
| 665 | A492 | B20 | I | ++++ (−8) | | ** | §§§ |
| 666 | A493 | B20 | I | +++ (−6) | | * | §§ |
| 667 | A494 | B20 | I | ++++ (−9) | | * | §§ |
| 668 | A495 | B20 | I | ++++ (6) | | *** | §§ |
| 669 | A496 | B20 | I | ++++ (−6) | | ** | §§ |
| 670 | A497 | B20 | I | ++++ (−6) | | ** | §§ |
| 671 | A498 | B20 | See text | ++++ (−5) | | *** | §§§ |
| 672 | A372 | B33 | I | ++++ (5) | | ** | §§ |
| 673 | A372 | B32 | I | ++++ (4) | | ** | §§ |
| 674 | A424 | B33 | I | ++++ (−8) | | * | §§ |
| 675 | A499 | B20 | I | ++++ (−5) | | *** | §§§ |
| 676 | A500 | B20 | I | ++++ (−4) | | ** | §§ |

TABLE 4-continued

| | | | | | | | |
|---|---|---|---|---|---|---|---|
| 677 | A501 | B20 | I | ++++ (10) | | ** | §§ |
| 678 | A502 | B20 | I | ++++ (−8) | | *** | §§§ |
| 679 | A503 | B20 | See text | ++++ (0) | ++++ (6) | ** | §§§ |
| 680 | A216 | B51 | K | ++++ (8) | ++++ (2) | *** | §§§ |
| 681 | A504 | B20 | See text | ++++ (−9) | | *** | §§§ |
| 682 | A424 | B32 | I | ++++ (−2) | | * | §§ |
| 683 | A505 | B20 | I | ++++ (−5) | | *** | §§§ |
| 684 | A506 | B20 | See text | ++++ (−14) | | *** | §§§ |
| 685 | A507 | B20 | I | ++++ (−2) | | ** | §§§ |
| 686 | A508 | B20 | I | ++++ (−10) | | *** | §§§ |
| 687 | A509 | B20 | I | ++++ (−6) | | *** | §§§ |
| 688 | A510 | B20 | I | ++++ (12) | | *** | §§§ |
| 689 | A511 | B20 | I | ++++ (−12) | | *** | §§§ |
| 690 | A513 | B20 | I | ++++ (0.7) | | *** | §§§ |
| 691 | A514 | B20 | See Ex 512 | ++++ (6) | | ** | §§ |

For pERK assays, + denotes a 10-30 μM $IC_{50}$ range, ++ denotes a 1-10 μM $IC_{50}$ range, +++ denotes a 0.5-1 μM $IC_{50}$ range and ++++ denotes an $IC_{50}$ <0.5 μM. The % $Y_{min}$ value indicates the lowest value of each $IC_{50}$ curve. Compounds that exhibit $IC_{50}$ curves with $Y_{min}$ values above −20% are considered to display minimal or no induction and do not cause detectable paradoxical activation of the pathway. For the BRAF biochemical kinase assay, * denotes an $IC_{50}$ >10 nM,  denotes a 1-10 nM $IC_{50}$ range and * denotes an $IC_{50}$ <1 nM. For the CRAF biochemical kinase assay, § denotes an $IC_{50}$ >50 nM, §§ denotes a 10-50 nM $IC_{50}$ range and §§§ denotes an $IC_{50}$ <10 nM.

Characterization of compounds in Table 4

| Example | MS ($MH^+$) | $^1H$ NMR (400 MHz) |
|---|---|---|
| 32 | 538.1 | $^1H$ NMR (DMSO-$d_6$) δ: 10.12 (s, 1H), 9.83 (s, 1H), 8.50 (s, 1H), 8.40 (d, J = 9.0 Hz, 1H), 8.32 (br. s., 1H), 8.12 (d, J = 9.0 Hz, 1H), 7.67 (dd, J = 8.6, 1.0 Hz, 2H), 7.14-7.33 (m, 2H), 7.07 (d, J = 9.0 Hz, 1H), 3.81 (s, 3H), 2.42 (s, 3H), 2.15 (s, 3H) |
| 33 | 510.1 | $^1H$ NMR (DMSO-$d_6$) δ: 10.16 (br. s., 1H), 10.04 (s, 1H), 9.02 (br. s., 1H), 8.32-8.56 (m, 4H), 7.67 (dd, J = 9.8, 1.0 Hz, 2H), 7.14-7.33 (m, 3H), 7.09 (d, J = 9.0 Hz, 2H), 3.81 (s, 3H) |
| 34 | 538.1 | $^1H$ NMR (DMSO-$d_6$) δ: 10.12 (s, 1H), 9.76 (s, 1H), 8.51 (br. s., 1H), 8.38 (br. s., 1H), 8.09 (d, J = 9.0 Hz, 1H), 7.67 (d, J = 8.6 Hz, 2H), 7.14-7.31 (m, 2H), 7.09 (d, J = 8.6 Hz, 2H), 3.81 (s, 3H), 2.62 (br. s., 3H), 2.14 (br. s., 3H) |
| 35 | 510.1 | $^1H$ NMR (DMSO-$d_6$) δ: 10.16 (s, 1H), 10.05 (s, 1H), 9.30 (br. s, 1H), 8.42-8.52 (m, 2H), 8.38 (d, J = 8.6 Hz, 1H), 7.93 (s, 1H), 7.68 (d, J = 8.6 Hz, 2H), 7.15-7.31 (m, 2H), 7.09 (d, J = 9.0 Hz, 2H), 6.63-6.79 (m, J = 2.0, 2.0 Hz, 1H), 3.81 (s, 3H) |
| 36 | 524.1 | $^1H$ NMR (DMSO-$d_6$) δ: 10.12 (s, 1H), 9.82 (s, 1H), 8.52 (br. s., 1H), 8.43 (d, J = 9.0 Hz, 1H), 8.14 (d, J = 8.6 Hz, 1H), 7.94 (br. s., 1H), 7.66 (dd, J = 10.2, 1.0 Hz, 2H), 7.14-7.38 (m, 2H), 7.09 (d, J = 9.0 Hz, 3H), 3.81 (s, 3H), 2.67 (br. s., 3H) |
| 37 | 556.1 | $^1H$ NMR (DMSO-$d_6$) δ: 10.38 (br. s., 1H), 9.85 (s, 1H), 8.47 (s, 1H), 8.40 (d, J = 9.0 Hz, 1H), 8.32 (br. s., 1H), 8.12 (d, J = 9.0 Hz, 1H), 7.61 (t, J = 8.8 Hz, 1H), 7.14-7.36 (m, 2H), 7.05 (dd, J = 12.5, 2.3 Hz, 1H), 6.89 (dd, J = 8.8, 2.5 Hz, 1H), 3.82 (s, 3H), 2.42 (s, 3H), 2.15 (s, 3H) |
| 38 | 552.1 | $^1H$ NMR (DMSO-$d_6$) δ: 10.14 (br. s., 1H), 9.76 (s, 1H), 8.49 (br. s., 1H), 8.38 (d, J = 9.0 Hz, 1H), 8.14 (bs, 1H), 8.09 (d, J = 9.0 Hz, 1H), 7.67 (d, J = 9.0 Hz, 1H), 7.61 (br. s., 1H), 7.10-7.38 (m, 2H), 6.94 (d, J = 2.3 Hz, 1H), 6.86 (dd, J = 8.8, 2.5 Hz, 1H), 3.80 (s, 3H), 2.57 (s, 3H), 2.14 (br. s., 3H) |
| 39 | 552.2 | $^1H$ NMR (DMSO-$d_6$) δ: 10.14 (s, 1H), 9.83 (s, 1H), 8.49 (br. s., 1H), 8.40 (d, J = 8.6 Hz, 1H), 8.34 (br. s., 1H), 8.12 (d, J = 9.0 Hz, 1H), 7.67 (d, J = 8.6 Hz, 1H), 7.09-7.32 (m, 2H), 6.94 (d, J = 2.3 Hz, 1H), 6.86 (dd, J = 9.0, 2.7 Hz, 1H), 3.81 (s, 3H), 2.57 (s, 3H), 2.42 (s, 3H), 2.15 (br. s., 3H) |
| 40 | 574.1 | $^1H$ NMR (DMSO-$d_6$) δ: 10.00 (s, 1H), 8.57 (s, 1H), 8.51 (d, J = 9.0 Hz, 1H), 8.24 (d, J = 9.0 Hz, 1H), 7.61-7.74 (m, 3H), 7.49-7.61 (m, 1H), 7.12-7.36 (m, 4H), 7.08 (d, J = 9.0 Hz, 2H), 3.80 (s, 3H), 2.75 (s, 3H) |
| 41 | 561.1 | $^1H$ NMR (DMSO-$d_6$) δ: 10.17 (br. s., 1H), 9.53 (s, 1H), 8.94 (d, J = 8.2 Hz, 1H), 8.82 (d, J = 9.0 Hz, 1H), 8.56 (s, 1H), 8.54 (d, J = 9.0 Hz, 1H), 8.26 (d, J = 8.2 Hz, 1H), 7.76 (t, J = 7.6 Hz, 1H), 7.70 (d, J = 9.8 Hz, 2H), 7.62 (t, J = 7.0 Hz, 1H), 7.17 7.34 (m, 2H), 7.10 (d, J = 9.0 Hz, 2H), 3.81 (s, 3H) |
| 42 | 560.1 | $^1H$ NMR (DMSO-$d_6$) δ: 10.16 (br. s., 1H), 9.80 (s, 1H), 9.75 (br. s., 1H), 8.61 (d, J = 3.5 Hz, 1H), 8.38-8.55 (m, 3H), 8.35 (br. s., 1H), 7.56-7.80 (m, 3H), 7.15-7.33 (m, 2H), 7.04-7.15 (m, 2H), 6.94 (d, J = 3.5 Hz, 1H), 3.81 (s, 3H) |
| 43 | 575.1 | $^1H$ NMR (DMSO-$d_6$) δ: 10.19 (s, 1H), 9.53 (s, 1H), 8.94 (d, J = 8.2 Hz, 1H), 8.82 (d, J = 9.4 Hz, 1H), 8.44-8.62 (m, 2H), 8.26 (d, J = 8.2 Hz, 1H), 7.73-7.82 (m, 1H), 7.70 (d, J = 8.6 Hz, 1H), 7.62 (t, J = 8.2 Hz, 1H), 7.16-7.35 (m, 2H), 6.95 (d, J = 2.3 Hz, 1H), 6.88 (dd, J = 8.8, 2.5 Hz, 1H), 3.79 (s, 3H), 2.59 (s, 3H) |
| 44 | 578.2 | $^1H$ NMR (DMSO-$d_6$) δ: 10.15 (s, 1H), 9.72 (s, 1H), 8.55 (s, 1H), 8.47 (s, 1H), 8.38 (d, J = 9.0 Hz, 1H), 8.10 (d, J = 9.0 Hz, 1H), 7.68 (d, J = 9.0 Hz, 1H), 7.08-7.36 (m, 2H), 6.94 (d, J = 2.3 Hz, 1H), 6.86 (dd, J = 8.8, 2.5 Hz, 1H), 3.79 (s, 3H), 2.97 (br. s., 2H), 2.52-2.61 (m, 5H), 1.67-1.86 (m, 4H) |
| 45 | 564.2 | $^1H$ NMR (DMSO-$d_6$) δ: 10.13 (s, 1H), 9.72 (s, 1H), 8.54 (s, 1H), 8.48 (s, 1H), 8.38 (d, J = 9.0 Hz, 1H), 8.11 (d, J = 9.0 Hz, 1H), 7.62-7.73 (m, 2H), 7.15-7.31 (m, 2H), 7.03-7.15 (m, 2H), 3.81 (s, 3H), 2.97 (br. s., 2H), 2.53-2.60 (m, 2H), 1.79 (br. s., 4H) |

TABLE 4-continued

| | | |
|---|---|---|
| 46 | 565.1 | $^1$H NMR (DMSO-$d_6$) δ: 10.55 (s, 1H), 9.54 (s, 1H), 8.94 (d, J = 8.6 Hz, 1H), 8.82 (d, J = 9.0 Hz, 1H), 8.42-8.60 (m, 2H), 8.26 (d, J = 8.6 Hz, 1H), 7.92 (dd, J = 7.8, 1.2 Hz, 1H), 7.72-7.80 (m, 1H), 7.58-7.72 (m, 3H), 7.47-7.57 (m, 1H), 7.12-7.38 (m, 2H) |
| 47 | 568.1 | $^1$H NMR (DMSO-$d_6$) δ: 10.52 (br. s., 1H), 9.74 (s, 1H), 8.57 (br. s., 1H), 8.47 (s, 1H), 8.38 (d, J = 8.6 Hz, 1H), 8.05-8.19 (m, 1H), 7.91 (dd, J = 7.8, 1.2 Hz, 1H), 7.61-7.74 (m, 2H), 7.45-7.56 (m, 1H), 7.11-7.33 (m, 2H), 2.97 (br. s., 2H), 2.55 (br. s, 2H), 1.79 (br. s., 4H) |
| 48 | 598.1 | $^1$H NMR (DMSO-$d_6$) δ: 9.74 (s, 1H), 8.56 (br. s., 1H), 8.46 (s, 1H), 8.38 (d, J = 9.0 Hz, 1H), 8.13 (bs, 1H), 8.11 (d, J = 9.0 Hz, 1H), 7.81 (d, J = 9.0 Hz, 1H), 7.13-7.35 (m, 3H), 7.03 (dd, J = 9.0, 2.7 Hz, 1H), 3.85 (s, 3H), 2.98 (br. s., 2H), 2.55 (br. s, 2H), 1.79 (br. s., 4H) |
| 49 | 595.1 | $^1$H NMR (DMSO-$d_6$) δ: 10.38 (s, 1H), 9.54 (s, 1H), 8.95 (d, J = 8.2 Hz, 1H), 8.83 (d, J = 9.0 Hz, 1H), 8.50-8.62 (m, 2H), 8.26 (d, J = 8.2 Hz, 1H), 7.83 (d, J = 9.0 Hz, 1H), 7.71-7.80 (m, 1H), 7.63 (t, J = 7.2 Hz, 1H), 7.15-7.39 (m, 3H), 7.04 (dd, J = 8.8, 2.5 Hz, 1H), 3.84 (s, 3H) |
| 50 | 574.1 | $^1$H NMR (DMSO-$d_6$) δ: 10.17 (br. s., 1H), 9.75 (s, 1H), 9.01 (br. s., 1H), 8.55 (d, J = 3.5 Hz, 1H), 8.48 (s, 1H), 8.44 (s, 2H), 8.36 (br. s, 1H), 7.69 (d, J = 9.0 Hz, 1H), 7.11-7.38 (m, 2H), 7.04 (d, J = 3.5 Hz, 1H), 6.95 (d, J = 2.3 Hz, 1H), 6.87 (dd, J = 8.8, 2.5 Hz, 1H), 3.79 (s, 3H), 2.58 (s, 3H) |
| 51 | 574.1 | $^1$H NMR (DMSO-$d_6$) δ: 9.68 (s, 1H), 8.81 (d, J = 8.2 Hz, 1H), 8.75 (d, J = 3.9 Hz, 1H), 8.51 (br. s., 1H), 8.38-8.49 (m, 3H), 7.69 (d, J = 9.0 Hz, 1H), 7.33 (dd, J = 8.2, 4.7 Hz, 1H), 7.22-7.30 (m, 1H), 7.19 (t, J = 8.6 Hz, 1H), 6.99 (d, J = 3.5 Hz, 1H), 6.95 (d, J = 2.3 Hz, 1H), 6.87 (dd, J = 8.8, 2.5 Hz, 1H), 3.81 (s, 3H), 2.57 (s, 3H) |
| 52 | 525.1 | $^1$H NMR (DMSO-$d_6$) δ: 10.20 (s, 1H), 10.18 (s, 1H), 9.50 (s, 1H), 8.65 (d, J = 9.0 Hz, 1H), 8.46-8.57 (m, 2H), 8.12 (d, J = 1.2 Hz, 1H), 7.67 (d, J = 8.6 Hz, 1H), 7.15-7.39 (m, 2H), 6.95 (d, J = 2.7 Hz, 1H), 6.86 (dd, J = 9.0, 2.7 Hz, 1H), 3.80 (s, 3H), 2.58 (s, 3H) |
| 53 | 521.1 | $^1$H NMR (DMSO-$d_6$) δ: 10.20 (s, 1H), 10.15 (s, 1H), 9.73 (d, J = 2.0 Hz, 1H), 8.87 (dt, J = 8.2, 1.6 Hz, 1H), 8.72 (dd, J = 4.9, 1.8 Hz, 1H), 8.65 (d, J = 9.0 Hz, 1H), 8.49 (s, 1H), 8.33 (d, J = 9.0 Hz, 1H), 7.64-7.74 (m, 2H), 7.59 (dd, J = 8.2, 4.7 Hz, 1H), 7.17-7.34 (m, 2H), 7.04-7.15 (m, 2H), 3.81 (s, 3H) |
| 54 | 535.1 | $^1$H NMR (DMSO-$d_6$) δ: 10.20 (s, 1H), 10.17 (s, 1H), 9.73 (d, J = 2.0 Hz, 1H), 8.88 (dt, J = 8.2, 1.6 Hz, 1H), 8.72 (dd, J = 4.7, 1.6 Hz, 1H), 8.65 (d, J = 9.0 Hz, 1H), 8.48 (s, 1H), 8.32 (d, J = 8.6 Hz, 1H), 7.68 (d, J = 9.0 Hz, 1H), 7.59 (dd, J = 4.7, 1.0 Hz, 1H), 7.16-7.32 (m, 2H), 6.95 (d, J = 2.3 Hz, 1H), 6.87 (dd, J = 8.8, 2.5 Hz, 1H), 3.79 (s, 3H), 2.58 (s, 3H) |
| 55 | 549.1 | $^1$H NMR (DMSO-$d_6$) δ: 10.17 (s, 1H), 10.15 (s, 1H), 9.56 (d, J = 2.3 Hz, 1H), 8.79 (dd, J = 8.0, 2.2 Hz, 1H), 8.61 (d, J = 8.6 Hz, 1H), 8.46 (s, 1H), 8.29 (d, J = 9.0 Hz, 1H), 7.68 (d, J = 8.6 Hz, 1H), 7.44 (d, J = 8.2 Hz, 1H), 7.10-7.35 (m, 2H), 6.95 (d, J = 2.7 Hz, 1H), 6.87 (dd, J = 8.6, 2.7 Hz, 1H), 3.79 (s, 3H), 2.58 (s, 3H), 2.57 (s, 3H) |
| 56 | 536.1 | $^1$H NMR (DMSO-$d_6$) δ: 10.28 (s, 1H), 10.18 (s, 1H), 9.92 (s, 2H), 9.33 (s, 1H), 8.72 (d, J = 8.6 Hz, 1H), 8.50 (s, 1H), 8.38 (d, J = 9.0 Hz, 1H), 7.68 (d, J = 8.6 Hz, 1H), 7.11-7.38 (m, 2H), 6.95 (d, J = 2.3 Hz, 1H), 6.87 (dd, J = 8.8, 2.5 Hz, 1H), 3.79 (s, 3H), 2.58 (s, 3H) |
| 57 | 566.1 | $^1$H NMR (DMSO-$d_6$) δ: 10.07-10.36 (m, 2H), 9.73 (s, 2H), 8.61 (d, J = 9.0 Hz, 1H), 8.47 (s, 1H), 8.32 (d, J = 8.6 Hz, 1H), 7.68 (d, J = 8.6 Hz, 1H), 7.11-7.34 (m, 2H), 6.94 (d, J = 2.3 Hz, 1H), 6.86 (dd, J = 8.8, 2.5 Hz, 1H), 4.03 (s, 3H), 3.79 (s, 3H), 2.58 (s, 3H) |
| 58 | 540.1 | $^1$H NMR (DMSO-$d_6$) δ: 9.99 (s, 1H), 8.67 (dd, J = 3.1, 1.2 Hz, 1H), 8.45 (d, J = 9.0 Hz, 1H), 8.43 (s, 1H), 8.25 (dd, J = 5.1, 1.0 Hz, 1H), 8.22 (d, J = 9.0 Hz, 1H), 7.73 (dd, J = 5.1, 2.7 Hz, 1H), 7.68 (d, J = 9.0 Hz, 1H), 7.15-7.31 (m, 2H), 6.95 (d, J = 2.3 Hz, 1H), 6.86 (dd, J = 8.8, 2.5 Hz, 1H), 3.79 (s, 3H), 2.58 (s, 3H) |
| 59 | 541.1 | $^1$H NMR (DMSO-$d_6$) δ: 9.87 (s, 1H), 9.29 (s, 1H), 8.91 (s, 1H), 8.48 (d, J = 8.6 Hz, 1H), 8.45 (s, 1H), 8.27 (d, J = 9.0 Hz, 1H), 7.69 (d, J = 9.0 Hz, 1H), 7.25 (td, J = 8.8, 5.9 Hz, 1H), 7.17 (t, J = 9.2 Hz, 1H), 6.94 (d, J = 2.3 Hz, 1H), 6.86 (dd, J = 8.8, 2.5 Hz, 1H), 3.79 (s, 3H), 2.57 (s, 3H) |
| 60 | 576.1 | $^1$H NMR (DMSO-$d_6$) δ: 10.34 (s, 1H), 10.20 (br. s., 2H), 9.25 (d, J = 9.0 Hz, 1H), 8.70 (d, J = 2.7 Hz, 1H), 8.64 (d, J = 2.7 Hz, 1H), 8.58 (d, J = 9.0 Hz, 1H), 8.53 (s, 1H), 7.70 (d, J = 8.6 Hz, 1H), 7.23 (br. s., 2H), 6.90 (br. s., 1H), 6.85 (br. s., 1H), 3.78 (s, 3H), 2.58 (s, 3H) |
| 61 | 585.1 | $^1$H NMR (DMSO-$d_6$) δ: 10.26 (s, 1H), 10.19 (s, 1H), 10.14 (d, J = 2.0 Hz, 1H), 9.40 (d, J = 2.3 Hz, 1H), 8.80 (d, J = 9.0 Hz, 1H), 8.50 (s, 1H), 8.38 (d, J = 9.0 Hz, 1H), 8.12 (d, J = 8.6 Hz, 2H), 7.86 (ddd, J = 8.4, 6.8, 1.2 Hz, 1H), 7.66-7.76 (m, 2H), 7.16-7.34 (m, 2H), 6.95 (d, J = 2.3 Hz, 1H), 6.87 (dd, J = 8.8, 2.5 Hz, 1H), 3.78 (s, 3H), 2.59 (s, 3H) |
| 62 | 565.1 | $^1$H NMR (DMSO-$d_6$) δ: 10.18 (br. s., 1H), 10.15 (s, 1H), 9.31 (d, J = 1.6 Hz, 1H), 8.68 (d, J = 9.0 Hz, 1H), 8.48 (s, 1H), 8.45 (d, J = 2.7 Hz, 1H), 8.38-8.43 (m, 1H), 8.32 (d, J = 9.0 Hz, 1H), 7.68 (d, J = 9.0 Hz, 1H), 7.27 (dt, J = 8.7, 5.7 Hz, 1H), 7.21 (td, J = 9.0, 1.0 Hz, 1H), 6.95 (d, J = 2.3 Hz, 1H), 6.87 (dd, J = 8.8, 2.5 Hz, 1H), 3.98 (s, 3H), 3.79 (s, 3H), 2.58 (s, 3H) |
| 63 | 535.1 | $^1$H NMR (DMSO-$d_6$) δ: 10.23 (s, 1H), 10.18 (s, 1H), 8.75-8.82 (m, 2H), 8.68 (d, J = 9.0 Hz, 1H), 8.47-8.53 (m, 3H), 8.36 (d, J = 8.6 Hz, 1H), 7.68 (d, J = 8.6 Hz, 1H), 7.27 (td, J = 9.0, 5.9 Hz, 1H), 7.21 (t, J = 8.6 Hz, 1H), 6.95 (d, J = 2.3 Hz, 1H), 6.87 (dd, J = 8.8, 2.5 Hz, 1H), 3.79 (s, 3H), 2.58 (s, 3H) |

TABLE 4-continued

| | | |
|---|---|---|
| 64 | 524.1 | $^1$H NMR (DMSO-$d_6$) δ: 13.22 (br. s., 1H), 10.18 (br. s., 1H), 9.84 (s, 1H), 8.71 (br. s., 1H), 8.44 (br. s., 1H), 8.39 (s, 1H), 8.23 (d, J = 9.0 Hz, 1H), 8.15 (d, J = 9.0 Hz, 1H), 7.68 (d, J = 9.0 Hz, 1H), 7.25 (td, J = 9.4, 6.3 Hz, 1H), 7.18 (t, J = 8.6 Hz, 1H), 6.94 (d, J = 2.3 Hz, 1H), 6.86 (dd, J = 8.8, 2.5 Hz, 1H), 3.79 (s, 3H), 2.58 (s, 3H) |
| 65 | 538.1 | $^1$H NMR (DMSO-$d_6$) δ: 10.17 (s, 1H), 9.86 (s, 1H), 8.63 (s, 1H), 8.39 (s, 2H), 8.05-8.28 (m, 2H), 7.68 (d, J = 8.6 Hz, 1H), 7.25 (td, J = 8.0, 5.7 Hz, 1H), 7.21 (t, J = 10.2 Hz, 1H), 6.95 (d, J = 2.3 Hz, 1H), 6.86 (dd, J = 8.6, 2.7 Hz, 1H), 3.93 (s, 3H), 3.79 (s, 3H), 2.58 (s, 3H) |
| 66 | 542.1 | $^1$H NMR (DMSO-$d_6$) δ: 9.84 (s, 1H), 8.50 (br. s., 1H), 8.40 (d, J = 7.8 Hz, 1H), 8.12 (d, J = 8.6 Hz, 1H), 7.91 (dd, J = 7.8, 1.6 Hz, 1H), 7.59-7.72 (m, 3H), 7.45-7.56 (m, 1H), 7.25 (td, J = 9.0, 5.5 Hz, 1H), 7.18 (t, J = 9.4 Hz, 1H), 2.44 (br. s., 3H), 2.14 (br. s., 3H) |
| 67 | 531.0 | $^1$H NMR (DMSO-$d_6$) δ: 10.53 (s, 1H), 9.89 (s, 1H), 9.29 (s, 1H), 8.91 (s, 1H), 8.49 (d, J = 8.6 Hz, 1H), 8.45 (s, 1H), 8.27 (d, J = 9.0 Hz, 1H), 7.91 (dd, J = 7.8, 1.0 Hz, 1H), 7.60-7.73 (m, 2H), 7.51 (dt, J = 7.8, 1.0 Hz, 1H), 7.26 (td, J = 7.8, 5.9 Hz, 1H), 7.20 (t, J = 9.0 Hz, 1H) |
| 68 | 571.0 | $^1$H NMR (DMSO-$d_6$) δ: 10.78 (br. s., 1H), 9.58 (s, 1H), 8.96 (d, J = 8.2 Hz, 1H), 8.83 (d, J = 9.0 Hz, 1H), 8.59 (s, 1H), 8.55 (d, J = 9.0 Hz, 1H), 8.27 (d, J = 8.2 Hz, 1H), 7.99 (br. d, J = 4.3 Hz, 1H), 7.78 (t, J = 7.4 Hz, 1H), 7.63 (t, J = 7.6 Hz, 1H), 7.12-7.41 (m, 3H) |
| 69 | 616.2 | $^1$H NMR (DMSO-$d_6$) δ: 10.17 (br. s., 1H), 9.74 (s, 1H), 8.91 (s, 1H), 8.50 (br. s, 1H), 8.48 (d, J = 9.0 Hz, 1H), 8.31-8.39 (m, 2H), 8.27 (dd, J = 7.4, 1.0 Hz, 1H), 7.68 (d, J = 8.6 Hz, 1H), 7.61 (br. s., 1H), 7.13-7.40 (m, 5H), 6.95 (d, J = 2.3 Hz, 1H), 6.87 (dd, J = 8.8, 2.5 Hz, 1H), 3.78 (s, 3H), 2.58 (s, 3H) |
| 70 | 619.1 | $^1$H NMR (DMSO-$d_6$) δ: 10.18 (s, 1H), 9.86 (s, 1H), 9.51 (s, 1H), 8.82 (d, J = 8.2 Hz, 1H), 8.43-8.66 (m, 3H), 8.20 (d, J = 7.8 Hz, 1H), 7.68 (d, J = 8.6 Hz, 1H), 7.64 (t, J = 8.2 Hz, 1H), 7.14-7.35 (m, 2H), 6.95 (d, J = 2.3 Hz, 1H), 6.87 (dd, J = 8.8, 2.5 Hz, 1H), 3.78 (s, 3H), 2.58 (s, 3H) |
| 71 | 565.1 | $^1$H NMR (DMSO-$d_6$) δ: 10.17 (br. s., 1H), 10.11 (s, 1H), 9.32 (d, J = 2.3 Hz, 1H), 8.88 (dd, J = 8.6, 2.3 Hz, 1H), 8.56 (d, J = 9.0 Hz, 1H), 8.44 (s, 1H), 8.26 (d, J = 9.0 Hz, 1H), 7.68 (d, J = 9.0 Hz, 1H), 7.26 (td, J = 9.0, 5.9 Hz, 1H), 7.19 (t, J = 9.4 Hz, 1H), 6.99 (d, J = 8.6 Hz, 1H), 6.95 (d, J = 2.3 Hz, 1H), 6.86 (dd, J = 8.6, 2.7 Hz, 1H), 3.96 (s, 3H), 3.79 (s, 3H), 2.58 (s, 3H) |
| 72 | 550.1 | $^1$H NMR (DMSO-$d_6$) δ: 10.17 (br. s., 1H), 10.07 (s, 1H), 9.63 (s, 1H), 8.44 (s, 1H), 8.44 (d, J = 9.4 Hz, 1H), 8.24 (d, J = 9.0 Hz, 1H), 7.88 (d, J = 8.2 Hz, 1H), 7.86 (s, 1H), 7.69 (d, J = 9.0 Hz, 1H), 7.35 (t, J = 8.0 Hz, 1H), 7.26 (td, J = 9.0, 5.5 Hz, 1H), 7.19 (td, J = 9.0, 1.0 Hz, 1H), 6.91-6.98 (m, 2H), 6.87 (dd, J = 8.6, 2.7 Hz, 1H), 3.79 (s, 3H), 2.58 (s, 3H) |
| 73 | 574.1 | $^1$H NMR (DMSO-$d_6$) δ: 9.38 (s, 1H), 9.02 (s, 1H), 8.85-8.88 (m, 1H), 8.84 (dt, J = 2.7, 1.6 Hz, 1H), 8.48 (d, J = 9.0 Hz, 1H), 8.40 (s, 1H), 8.19 (d, J = 9.0 Hz, 1H), 7.70 (d, J = 9.0 Hz, 1H), 7.50 (ddd, J = 9.0, 6.8, 1.0 Hz, 1H), 7.26 (td, J = 8.6, 5.9 Hz, 1H), 7.18 (t, J = 9.2 Hz, 1H), 7.12 (dt, J = 6.9, 1.2 Hz, 1H), 6.94 (d, J = 2.3 Hz, 1H), 6.87 (dd, J = 8.8, 2.5 Hz, 1H), 3.78 (s, 3H), 2.59 (s, 3H) |
| 74 | 564.2 | $^1$H NMR (DMSO-$d_6$) δ: 10.02 (s, 1H), 8.54 (d, J = 9.0 Hz, 1H), 8.45 (s, 1H), 8.35-8.43 (m, 2H), 8.27 (d, J = 9.0 Hz, 1H), 7.69 (d, J = 8.6 Hz, 1H), 7.48-7.57 (m, 2H), 7.26 (td, J = 8.7, 5.7 Hz, 1H), 7.18 (t, J = 9.2 Hz, 1H), 6.94 (d, J = 2.3 Hz, 1H), 6.86 (dd, J = 8.8, 2.5 Hz, 1H), 5.28 (br. t, J = 5.1 Hz, 1H), 4.64 (d, J = 4.3 Hz, 2H), 3.79 (s, 3H), 2.58 (s, 3H) |
| 75 | 617.2 | $^1$H NMR (DMSO-$d_6$) δ: 10.17 (s, 1H), 9.87 (s, 1H), 9.50 (s, 1H), 9.11 (br. d, J = 2.3 Hz, 1H), 8.41-8.66 (m, 3H), 8.05 (d, J = 7.4 Hz, 1H), 7.91 (d, J = 2.7 Hz, 1H), 7.69 (d, J = 9.0 Hz, 1H), 7.57 (t, J = 7.8 Hz, 1H), 7.12-7.36 (m, 2H), 6.95 (d, J = 2.3 Hz, 1H), 6.87 (dd, J = 8.8, 2.5 Hz, 1H), 3.78 (s, 3H), 2.58 (s, 3H) |
| 76 | 589.2 | $^1$H NMR (DMSO-$d_6$) δ: 10.17 (s, 1H), 9.86 (s, 1H), 9.17 (s, 1H), 8.49 (s, 1H), 8.44 (s, 2H), 7.68 (d, J = 9.0 Hz, 1H), 7.41 (d, J = 7.8 Hz, 1H), 7.15-7.35 (m, 2H), 7.11 (t, J = 8.0 Hz, 1H), 6.95 (d, J = 2.3 Hz, 1H), 6.87 (dd, J = 8.6, 2.7 Hz, 1H), 6.57 (d, J = 7.0 Hz, 1H), 5.51 (br. s, 2H), 3.79 (s, 3H), 2.58 (s, 3H) |
| 77 | 549.1 | $^1$H NMR (DMSO-$d_6$) δ: 10.56 (s, 1H), 10.20 (s, 1H), 9.12 (s, 1H), 8.80 (d, J = 7.4 Hz, 1H), 8.68 (d, J = 9.0 Hz, 1H), 8.48 (s, 1H), 8.33 (d, J = 8.6 Hz, 1H), 7.99 (d, J = 7.8 Hz, 1H), 7.92 (d, J = 8.2 Hz, 1H), 7.77 (t, J = 7.8 Hz, 1H), 7.59-7.72 (m, 2H), 7.51 (t, J = 7.4 Hz, 1H), 7.16-7.35 (m, 2H) |
| 78 | 549.0 | $^1$H NMR (DMSO-$d_6$) δ: 10.54 (s, 1H), 10.29 (s, 1H), 8.74 (br. d, J = 8.2 Hz, 2H), 8.68 (d, J = 8.6 Hz, 1H), 8.50 (s, 1H), 8.34 (d, J = 9.0 Hz, 1H), 8.01-8.09 (m, 2H), 7.92 (dd, J = 7.8, 1.6 Hz, 1H), 7.61-7.73 (m, 2H), 7.46-7.58 (m, 1H), 7.29 (td, J = 9.0, 5.9 Hz, 1H), 7.23 (dt, J = 9.0, 1.0 Hz, 1H) |
| 79 | 631.2 | Not determined |
| 80 | 567.1 | $^1$H NMR (DMSO-$d_6$) δ: 10.54 (s, 1H), 10.13 (s, 1H), 8.81 (br. s, 1H), 8.73 (br. d, J = 7.8 Hz, 1H), 8.65 (d, J = 9.0 Hz, 1H), 8.49 (s, 1H), 8.34 (d, J = 9.0 Hz, 1H), 8.14 (br. s, 1H), 8.03 (dt, J = 7.8, 1.0 Hz, 1H), 7.92 (dd, J = 7.8, 1.6 Hz, 1H), 7.60-7.73 (m, 3H), 7.45-7.60 (m, 2H), 7.29 (td, J = 9.0, 5.5 Hz, 1H), 7.23 (dt, J = 9.0, 1.0 Hz, 1H) |
| 81 | 567.1 | $^1$H NMR (DMSO-$d_6$) δ: 10.54 (s, 1H), 10.16 (s, 1H), 8.64 (d, J = 9.0 Hz, 1H), 8.62 (s, 1H), 8.60 (s, 1H), 8.47 (s, 1H), 8.30 (d, J = 8.6 Hz, 1H), 8.14 (s, 1H), 8.04 (d, J = 8.6 Hz, 2H), 7.92 (dd, J = 7.8, 1.2 Hz, 1H), 7.61-7.72 (m, 2H), 7.45-7.56 (m, 2H), 7.29 (td, J = 9.0, 5.9 Hz, 1H), 7.22 (dt, J = 9.4, 1.0 Hz, 1H) |
| 82 | 573.1 | $^1$H NMR (DMSO-$d_6$) δ: 10.51 (s, 1H), 10.08 (s, 1H), 8.56 (s, 1H), 8.54 (d, J = 9.0 Hz, 1H), 8.45 (s, 1H), 8.25 (d, J = 9.0 Hz, 1H), 7.90 (dd, J = 8.2, 1.0 Hz, 1H), 7.61-7.70 (m, 2H), 7.47-7.54 (m, 1H), 7.26 (td, J = 9.0, 5.5 Hz, 1H), 7.21 (t, J = 9.8 Hz, 1H), 2.83 (s, 3H) |

TABLE 4-continued

| | | |
|---|---|---|
| 83 | 579.1 | $^1$H NMR (DMSO-$d_6$) δ: 10.53 (br. s., 1H), 9.87 (s, 1H), 9.17 (s, 1H), 8.49 (s, 1H), 8.44 (s, 2H), 7.92 (dd, J = 8.0, 1.4 Hz, 1H), 7.61-7.72 (m, 2H), 7.48-7.55 (m, 1H), 7.41 (d, J = 7.8 Hz, 1H), 7.17-7.34 (m, 2H), 7.11 (t, J = 8.0 Hz, 1H), 6.57 (d, J = 7.4 Hz, 1H), 5.51 (br. s., 2H) |
| 84 | 593.1 | $^1$H NMR (DMSO-$d_6$) δ: 10.57 (br. s., 1H), 9.87 (s, 1H), 9.16 (s, 1H), 8.50 (s, 1H), 8.44 (s, 2H), 7.78 (d, J = 8.2 Hz, 1H), 7.75 (d, J = 8.2 Hz, 1H), 7.35-7.47 (m, 2H), 7.17-7.35 (m, 2H), 7.11 (t, J = 8.0 Hz, 1H), 6.57 (d, J = 7.8 Hz, 1H), 5.53 (br. s., 2H), 2.67 (s, 3H) |
| 85 | 621.1 | $^1$H NMR (DMSO-$d_6$) δ: 10.54 (s, 1H), 10.02 (s, 1H), 9.85 (s, 1H), 9.33 (s, 1H), 8.42-8.63 (m, 3H), 8.13 (d, J = 7.4 Hz, 1H), 8.03 (d, J = 8.2 Hz, 1H), 7.92 (dd, J = 7.8, 1.6 Hz, 1H), 7.59-7.74 (m, 2H), 7.46-7.58 (m, 1H), 7.37 (t, J = 8.2 Hz, 1H), 7.16-7.33 (m, 2H), 2.22 (s, 3H) |
| 86 | 620.1 | $^1$H NMR (DMSO-$d_6$) δ: 10.52 (s, 1H), 9.80 (s, 1H), 8.83 (s, 1H), 8.50 (s, 1H), 8.47 (d, J = 9.4 Hz, 1H), 8.30-8.37 (m, 2H), 8.24 (dd, J = 7.4, 1.0 Hz, 1H), 8.14 (br. q, J = 4.7 Hz, 1H), 7.92 (dd, J = 7.8, 1.2 Hz, 1H), 7.62-7.71 (m, 2H), 7.51 (s, 1H), 7.37 (dt, J = 7.6, 1.6 Hz, 1H), 7.32 (dt, J = 7.4, 1.2 Hz, 1H), 7.24-7.30 (m, 1H), 7.22 (dt, J = 9.0, 0.8 Hz, 1H), 2.83 (d, J = 4.7 Hz, 3H) |
| 87 | 634.1 | $^1$H NMR (DMSO-$d_6$) δ: 10.53 (s, 1H), 9.81 (s, 1H), 8.69 (s, 1H), 8.48 (s, 1H), 8.40 8.47 (m, 2H), 8.33 (d, J = 8.6 Hz, 1H), 7.91 (dd, J = 7.8, 1.2 Hz, 1H), 7.80 (d, J = 7.4 Hz, 1H), 7.61-7.71 (m, 2H), 7.48-7.54 (m, 1H), 7.38 (dt, J = 7.4, 1.0 Hz, 1H), 7.25-7.35 (m, 2H), 7.22 (br. t, J = 9.0 Hz, 1H), 3.13 (br. s., 6H) |
| 88 | 593.1 | $^1$H NMR (DMSO-$d_6$) δ: 10.53 (br. s., 1H), 9.69 (s, 1H), 8.45 (br. s., 1H), 8.25-8.41 (m, 4H), 7.92 (dd, J = 7.8, 1.2 Hz, 1H), 7.75 (d, J = 7.0 Hz, 1H), 7.60-7.72 (m, 2H), 7.47-7.55 (m, 1H), 7.31-7.38 (m, 1H), 7.15-7.31 (m, 3H), 5.10 (t, J = 5.7 Hz, 1H), 4.75 (d, J = 5.5 Hz, 2H) |
| 89 | 581.1 | $^1$H NMR (DMSO-$d_6$) δ: 10.56 (br. s., 1H), 10.16 (s, 1H), 9.64 (s, 1H), 9.34 (d, J = 9.4 Hz, 1H), 8.45-8.59 (m, 2H), 8.36 (s, 1H), 7.92 (d, J = 7.8 Hz, 1H), 7.60-7.77 (m, 2H), 7.44-7.60 (m, 3H), 7.14-7.38 (m, 2H) |
| 90 | 620.1 | $^1$H NMR (DMSO-$d_6$) δ: 10.52 (s, 1H), 9.67 (s, 1H), 8.45 (br. s., 1H), 8.34-8.40 (m, 3H), 8.29 (s, 1H), 7.92 (dd, J = 8.0, 1.4 Hz, 1H), 7.62-7.72 (m, 3H), 7.47-7.54 (m, 2H), 7.34 (dt, J = 8.2, 1.0 Hz, 1H), 7.17-7.31 (m, 3H), 6.98 (br. s., 1H), 3.59 (s, 2H) |
| 91 | 594.1 | $^1$H NMR (DMSO-$d_6$) δ: 10.57 (s, 1H), 9.39 (s, 1H), 8.78 (d, J = 9.0 Hz, 1H), 8.52 (s, 1H), 8.49 (d, J = 9.0 Hz, 1H), 7.94 (d, J = 8.2 Hz, 1H), 7.79 (d, J = 7.8 Hz, 1H), 7.75 (d, J = 7.8 Hz, 1H), 7.27-7.44 (m, 3H), 7.23 (t, J = 9.0 Hz, 1H), 6.62 (d, J = 7.4 Hz, 1H), 6.33 (s, 2H), 2.67 (s, 3H) |
| 92 | 580.1 | $^1$H NMR (DMSO-$d_6$) δ: 10.53 (s, 1H), 9.39 (s, 1H), 8.78 (d, J = 9.0 Hz, 1H), 8.52 (s, 1H), 8.48 (d, J = 9.0 Hz, 1H), 7.95 (d, J = 8.2 Hz, 1H), 7.92 (d, J = 7.8 Hz, 1H), 7.60-7.73 (m, 2H), 7.47-7.56 (m, 1H), 7.37 (t, J = 7.8 Hz, 1H), 7.16-7.33 (m, 2H), 6.62 (d, J = 7.4 Hz, 1H), 6.33 (s, 2H) |
| 93 | 590.1 | $^1$H NMR (DMSO-$d_6$) δ: 10.18 (br. s., 1H), 9.39 (s, 1H), 8.77 (d, J = 9.4 Hz, 1H), 8.52 (s, 1H), 8.49 (d, J = 9.4 Hz, 1H), 7.95 (d, J = 7.8 Hz, 1H), 7.69 (d, J = 9.0 Hz, 1H), 7.37 (t, J = 8.0 Hz, 1H), 7.13-7.33 (m, 2H), 6.95 (d, J = 2.3 Hz, 1H), 6.87 (dd, J = 8.8, 2.5 Hz, 1H), 6.62 (d, J = 7.8 Hz, 1H), 6.33 (s, 2H), 3.79 (s, 3H), 2.58 (s, 3H) |
| 94 | 546.0 | $^1$H NMR (DMSO-$d_6$) δ: 9.96 (br. s, 1H), 8.41 (s, 1H), 8.30 (d, J = 9.0 Hz, 1H), 8.21 (d, J = 9.0 Hz, 1H), 8.14 (s, 1H), 7.97 (br. s, 1H), 7.92 (dd, J = 7.6, 1.4 Hz, 1H), 7.54-7.70 (m, 2H), 7.48 (br. t, J = 7.0 Hz, 1H), 7.23 (s, 3H), 7.15 (br. s., 1H) |
| 95 | 599.0 | $^1$H NMR (DMSO-$d_6$) δ: 10.56 (br. s., 1H), 10.22 (br. s, 1H), 9.93 (s, 1H), 9.34 (br. s, 1H), 8.64 (d, J = 9.0 Hz, 1H), 8.49 (s, 1H), 8.37 (d, J = 8.6 Hz, 1H), 7.92 (dd, J = 7.8, 1.0 Hz, 1H), 7.67 (br. s., 2H), 7.50 (br. s., 1H), 7.28 (br. s, 2H) |
| 96 | 649.1 | $^1$H NMR (DMSO-$d_6$) δ: 10.54 (br. s., 1H), 9.76 (s, 1H), 8.48 (s, 1H), 8.47 (s, 1H), 8.35-8.42 (m, 2H), 7.91 (dd, J = 7.8, 1.6 Hz, 1H), 7.58-7.71 (m, 2H), 7.50 (dt, J = 7.8, 1.0 Hz, 1H), 7.46 (d, J = 8.2 Hz, 1H), 7.13-7.31 (m, 2H), 7.09 (t, J = 8.2 Hz, 1H), 6.51 (d, J = 7.8 Hz, 1H), 5.61 (br. s., 2H), 3.15 (br. s, 6H) |
| 97 | 585.0 | $^1$H NMR (DMSO-$d_6$) δ: 10.76 (br. s., 1H), 9.92 (s, 1H), 9.19 (s, 1H), 8.53 (s, 1H), 8.45 (s, 2H), 8.00 (d, J = 5.1 Hz, 1H), 7.41 (d, J = 7.8 Hz, 1H), 7.20-7.37 (m, 3H), 7.12 (t, J = 7.8 Hz, 1H), 6.57 (dt, J = 7.8, 1.0 Hz, 1H), 5.52 (br. s., 2H) |
| 98 | 586.0 | $^1$H NMR (DMSO-$d_6$) δ: 10.77 (s, 1H), 9.44 (s, 1H), 8.78 (d, J = 9.0 Hz, 1H), 8.56 (s, 1H), 8.49 (d, J = 9.0 Hz, 1H), 8.00 (d, J = 5.5 Hz, 1H), 7.97 (d, J = 7.8 Hz, 1H), 7.39 (t, J = 7.8 Hz, 1H), 7.22-7.36 (m, 3H), 6.62 (d, J = 7.4 Hz, 1H), 6.33 (s, 2H) |
| 99 | 613.1 | $^1$H NMR (DMSO-$d_6$) δ: 10.73 (br. s., 1H), 9.87 (s, 1H), 9.16 (s, 1H), 8.49 (s, 1H), 8.44 (s, 2H), 7.96 (dd, J = 7.8, 1.6 Hz, 1H), 7.90 (dd, J = 7.8, 1.6 Hz, 1H), 7.54 (t, J = 8.0 Hz, 1H), 7.41 (d, J = 8.2 Hz, 1H), 7.18-7.37 (m, 2H), 7.11 (t, J = 8.0 Hz, 1H), 6.57 (d, J = 7.4 Hz, 1H), 5.53 (br. s., 2H) |
| 100 | 614.0 | $^1$H NMR (DMSO-$d_6$) δ: 10.73 (s, 1H), 9.40 (s, 1H), 8.78 (d, J = 9.4 Hz, 1H), 8.52 (s, 1H), 8.49 (d, J = 9.0 Hz, 1H), 7.87-7.98 (m, 3H), 7.55 (t, J = 8.0 Hz, 1H), 7.37 (t, J = 8.0 Hz, 1H), 7.19-7.35 (m, 2H), 6.62 (d, J = 7.4 Hz, 1H), 6.33 (br. s., 2H) |
| 101 | 599.0 | $^1$H NMR (DMSO-$d_6$) δ: 10.74 (s, 1H), 9.54 (s, 1H), 8.93 (d, J = 8.2 Hz, 1H), 8.82 (d, J = 9.0 Hz, 1H), 8.47-8.62 (m, 2H), 8.26 (d, J = 8.6 Hz, 1H), 7.96 (dd, J = 8.0, 1.4 Hz, 1H), 7.91 (dd, J = 8.0, 1.4 Hz, 1H), 7.76 (ddd, J = 8.3, 7.1, 1.0 Hz, 1H), 7.58-7.66 (m, 1H), 7.55 (t, J = 8.0 Hz, 1H), 7.18-7.38 (m, 2H) |
| 102 | 579.1 | $^1$H NMR (DMSO-$d_6$) δ: 10.58 (s, 1H), 9.54 (s, 1H), 8.94 (d, J = 8.2 Hz, 1H), 8.82 (d, J = 9.0 Hz, 1H), 8.41-8.64 (m, 2H), 8.26 (d, J = 8.2 Hz, 1H), 7.72-7.83 (m, 3H), 7.59-7.67 (m, 1H), 7.40 (t, J = 8.0 Hz, 1H), 7.20-7.37 (m, 2H), 2.67 (s, 3H) |
| 103 | 607.1 | $^1$H NMR (DMSO-$d_6$) δ: 10.54 (s, 1H), 9.39 (s, 1H), 9.06 (d, J = 8.2 Hz, 1H), 8.90 (d, J = 9.0 Hz, 1H), 8.50 (s, 1H), 8.47 (d, J = 9.4 Hz, 1H), 8.35 (bs, 1H), 8.33 (d, J = 7.8 Hz, 1H), 7.93 (dd, J = 7.8, 1.6 Hz, 1H), 7.74 (br. s, 1H), 7.62-7.72 (m, 3H), 7.46-7.56 (m, 2H), 7.19-7.35 (m, 2H) |

TABLE 4-continued

| | | |
|---|---|---|
| 104 | 606.1 | $^1$H NMR (DMSO-$d_6$) δ: 10.52 (s, 1H), 9.75 (s, 1H), 8.91 (s, 1H), 8.50 (s, 1H), 8.48 (d, J = 9.0 Hz, 1H), 8.31-8.38 (m, 2H), 8.27 (d, J = 7.4 Hz, 1H), 7.91 (dd, J = 8.2, 1.0 Hz, 1H), 7.62-7.71 (m, 2H), 7.61 (bs, 1H), 7.51 (dt, J = 7.8, 1.0 Hz, 1H), 7.17-7.40 (m, 5H) |
| 105 | 648.1 | $^1$H NMR (DMSO-$d_6$) δ: 10.53 (br. s, 1H), 9.81 (s, 1H), 8.66 (s, 1H), 8.48 (s, 1H), 8.39-8.47 (m, 2H), 8.34 (d, J = 8.6 Hz, 1H), 7.91 (dd, J = 7.8, 1.6 Hz, 1H), 7.75 (d, J = 8.2 Hz, 1H), 7.60-7.70 (m, 2H), 7.50 (dt, J = 7.8, 1.0 Hz, 1H), 7.39 (td, J = 8.6, 1.0 Hz, 1H), 7.29-7.35 (m, 1H), 7.15-7.29 (m, 2H), 3.54 (q, J = 6.9 Hz, 2H), 3.10 (br. s., 3H), 1.17 (t, J = 7.0 Hz, 3H) |
| 106 | 648.1 | $^1$H NMR (DMSO-$d_6$) δ: 10.52 (s, 1H), 9.78 (s, 1H), 8.85 (s, 1H), 8.50 (s, 1H), 8.48 (d, J = 9.0 Hz, 1H), 8.37 (d, J = 7.8 Hz, 1H), 8.33 (d, J = 9.0 Hz, 1H), 8.26 (dd, J = 7.2, 1.8 Hz, 1H), 7.97 (d, J = 7.8 Hz, 1H), 7.92 (dd, J = 7.8, 1.6 Hz, 1H), 7.61-7.71 (m, 2H), 7.51 (dt, J = 7.4, 1.0 Hz, 1H), 7.16-7.40 (m, 4H), 4.06-4.30 (m, J = 6.7 Hz, 1H), 1.22 (d, J = 6.7 Hz, 6H) |
| 107 | 662.2 | $^1$H NMR (DMSO-$d_6$) δ: 10.53 (s, 1H), 9.82 (s, 1H), 8.61 (s, 1H), 8.48 (s, 1H), 8.43 (q, J = 9.0 Hz, 2H), 8.34 (d, J = 8.2 Hz, 1H), 7.91 (dd, J = 7.8, 1.6 Hz, 1H), 7.62-7.71 (m, 3H), 7.51 (ddd, J = 8.2, 6.8, 1.8 Hz, 1H), 7.39 (dt, J = 7.7, 1.4 Hz, 1H), 7.17-7.35 (m, 3H), 3.51 (q, J = 7.0 Hz, 4H), 1.17 (t, J = 6.8 Hz, 6H) |
| 108 | 660.1 | $^1$H NMR (DMSO-$d_6$) δ: 10.53 (br. s., 1H), 9.79 (s, 1H), 8.71 (s, 1H), 8.49 (s, 1H), 8.40-8.48 (m, 2H), 8.32 (d, J = 8.2 Hz, 1H), 8.06 (d, J = 7.4 Hz, 1H), 7.92 (dd, J = 7.8, 1.6 Hz, 1H), 7.60-7.71 (m, 2H), 7.50 (dt, J = 7.4, 1.0 Hz, 1H), 7.38 (dt, J = 7.0, 1.0 Hz, 1H), 7.31 (dt, J = 7.6, 0.8 Hz, 1H), 7.13-7.28 (m, 2H), 3.78 (br. s., 2H), 3.57 (br. s., 2H), 1.75-2.02 (m, 4H) |
| 109 | 676.1 | $^1$H NMR (DMSO-$d_6$) δ: 10.53 (br. s., 1H), 9.82 (s, 1H), 8.70 (s, 1H), 8.48 (s, 1H), 8.40-8.47 (m, 2H), 8.34 (d, J = 8.2 Hz, 1H), 7.92 (dd, J = 7.8, 1.6 Hz, 1H), 7.77 (d, J = 7.4 Hz, 1H), 7.60-7.71 (m, 2H), 7.50 (dt, J = 7.4, 1.0 Hz, 1H), 7.40 (dt, J = 7.0, 1.0 Hz, 1H), 7.33 (dt, J = 7.0, 1.0 Hz, 1H), 7.14-7.31 (m, 2H), 3.67 (br. s., 8H) |
| 110 | 691.2 | Formic acid salt: $^1$H NMR (DMSO-$d_6$) δ: 9.79 (s, 1H), 8.69 (s, 1H), 8.48 (s, 1H), 8.39-8.47 (m, 2H), 8.35 (d, J = 8.6 Hz, 1H), 7.92 (dd, J = 8.0, 1.4 Hz, 1H), 7.79 (d, J = 7.0 Hz, 1H), 7.57-7.66 (m, 2H), 7.45-7.52 (m, J = 7.4, 7.4, 1.6 Hz, 1H), 7.39 (dt, J = 7.7, 1.4 Hz, 1H), 7.32 (dt, J = 7.8, 1.0 Hz, 1H), 7.24 (td, J = 8.6, 5.5 Hz, 1H), 7.14 (dt, J = 8.6, 0.8 Hz, 1H), 3.67 (t, J = 6.5 Hz, 2H), 3.15 (br. s., 3H), 2.57-2.79 (m, 2H), 2.20-2.46 (m, 4H) |
| 111 | 635.1 | $^1$H NMR (DMSO-$d_6$) δ: 10.54 (br. s, 1H), 9.39 (s, 1H), 9.03 (d, J = 8.6 Hz, 1H), 8.60 (d, J = 9.0 Hz, 1H), 8.49 (s, 1H), 8.43 (d, J = 9.4 Hz, 1H), 8.06 (d, J = 7.8 Hz, 1H), 7.93 (dd, J = 7.8, 1.6 Hz, 1H), 7.60-7.73 (m, 3H), 7.43-7.58 (m, 2H), 7.17 7.34 (m, 2H), 3.39 (s, 3H), 3.16 (s, 3H) |
| 112 | 670.1 | $^1$H NMR (DMSO-$d_6$) δ: 10.53 (br. s., 1H), 9.94 (s, 1H), 8.89 (s, 1H), 8.39-8.64 (m, 3H), 8.32 (d, J = 8.2 Hz, 1H), 7.98 (d, J = 7.0 Hz, 1H), 7.91 (dd, J = 7.8, 1.6 Hz, 1H), 7.58-7.71 (m, 2H), 7.37-7.56 (m, 3H), 7.11-7.33 (m, 2H), 2.73 (s, 6H) |
| 113 | 689.2 | $^1$H NMR (DMSO-$d_6$) δ: 9.83 (s, 1H), 8.69 (s, 1H), 8.48 (s, 1H), 8.39-8.47 (m, 2H), 8.34 (d, J = 8.6 Hz, 1H), 7.92 (dd, J = 7.8, 1.6 Hz, 1H), 7.74 (d, J = 7.4 Hz, 1H), 7.61-7.70 (m, 2H), 7.48-7.54 (m, J = 7.5, 7.5, 1.8 Hz, 1H), 7.40 (td, J = 9.0, 1.0 Hz, 1H), 7.34 (dt, J = 7.8, 1.0 Hz, 1H), 7.23-7.31 (m, 1H), 7.20 (dt, J = 8.6, 1.0 Hz, 1H), 3.68 (br. s., 4H), 2.44 (br. s., 4H), 2.27 (s, 3H) |
| 114 | 720.2 | Formic acid salt: $^1$H NMR (DMSO-$d_6$) δ: 9.75 (br. s., 1H), 8.47 (s, 1H), 8.45 (br. s., 1H), 8.33-8.42 (m, 2H), 7.79 (d, J = 8.2 Hz, 1H), 7.69 (d, J = 7.8 Hz, 1H), 7.46 (d, J = 8.2 Hz, 1H), 7.36 (t, J = 8.0 Hz, 1H), 7.26 (td, J = 8.8, 5.9 Hz, 1H), 7.02-7.18 (m, 2H), 6.50 (d, J = 7.8 Hz, 1H), 3.70 (t, J = 6.7 Hz, 2H), 3.16 (br. s., 2H), 2.67 (br. s, 6H), 2.33 (br. s., 3H) |
| 115 | 705.2 | $^1$H NMR (DMSO-$d_6$) δ: 10.56 (br. s., 1H), 9.76 (s, 1H), 8.48 (s, 1H), 8.32-8.43 (m, 3H), 7.78 (dd, J = 7.8, 0.8 Hz, 1H), 7.74 (d, J = 8.2 Hz, 1H), 7.47 (d, J = 7.8 Hz, 1H), 7.39 (t, J = 8.0 Hz, 1H), 7.26-7.34 (m, 1H), 7.22 (t, J = 8.6 Hz, 1H), 7.10 (t, J = 8.0 Hz, 1H), 6.52 (d, J = 7.4 Hz, 1H), 5.53 (br. s., 2H), 3.72-3.83 (m, J = 4.7 Hz, 4H), 3.67 (s, 4H), 2.67 (s, 3H) |
| 116 | 594.1 | $^1$H NMR (DMSO-$d_6$) δ: 10.56 (br. s., 1H), 10.06 (s, 1H), 9.87 (s, 1H), 9.21 (s, 1H), 8.50 (s, 1H), 8.46 (s, 2H), 7.78 (d, J = 7.8 Hz, 1H), 7.73 (t, J = 8.8 Hz, 2H), 7.39 (t, J = 8.0 Hz, 1H), 7.17-7.35 (m, 3H), 6.77 (d, J = 7.8 Hz, 1H), 2.65 (s, 3H) |
| 117 | 595.1 | $^1$H NMR (DMSO-$d_6$) δ: 11.03 (s, 1H), 9.42 (s, 1H), 8.79 (d, J = 9.4 Hz, 1H), 8.54 (s, 1H), 8.51 (d, J = 9.4 Hz, 1H), 8.31 (d, J = 8.2 Hz, 1H), 7.80 (d, J = 7.8 Hz, 1H), 7.61-7.76 (m, 1H), 7.52 (t, J = 8.0 Hz, 1H), 7.36 (t, J = 7.8 Hz, 1H), 7.27 (s, 1H), 7.15 (br. s., 1H), 6.89 (d, J = 7.8 Hz, 1H), 2.66 (s, 3H) |
| 118 | 690.2 | $^1$H NMR (DMSO-$d_6$) δ: 10.57 (s, 1H), 9.83 (s, 1H), 8.69 (s, 1H), 8.49 (s, 1H), 8.39-8.47 (m, 2H), 8.34 (d, J = 8.2 Hz, 1H), 7.67-7.92 (m, 3H), 7.17-7.47 (m, 5H), 3.67 (br. s., 8H), 2.67 (s, 3H) |
| 119 | 703.2 | $^1$H NMR (DMSO-$d_6$) δ: 9.82 (s, 1H), 8.68 (s, 1H), 8.49 (s, 1H), 8.39-8.48 (m, 2H), 8.34 (d, J = 8.2 Hz, 1H), 7.76-7.81 (m, 1H), 7.71-7.76 (m, 2H), 7.25-7.44 (m, 4H), 7.17-7.25 (m, 1H), 3.70 (br. s., 4H), 2.60-2.71 (m, 3H), 2.57 (br. s., 4H), 2.32 (s, 3H) |
| 120 | 655.1 | $^1$H NMR (DMSO-$d_6$) δ: 10.54 (br. s., 1H), 9.49 (s, 1H), 8.51 (s, 1H), 8.36-8.46 (m, 1H), 8.32 (dd, J = 9.0, 1.0 Hz, 1H), 7.78 (d, J = 7.8 Hz, 1H), 7.74 (d, J = 8.2 Hz, 1H), 7.38 (t, J = 8.0 Hz, 1H), 7.13-7.34 (m, 2H), 6.68 (s, 1H), 3.86-4.04 (m, 2H), 3.55-3.78 (m, 6H), 2.77 (s, 3H), 2.67 (s, 3H) |
| 121 | 668.2 | $^1$H NMR (DMSO-$d_6$) δ: 9.48 (s, 1H), 8.51 (s, 1H), 8.42 (d, J = 9.4 Hz, 1H), 8.31 (d, J = 9.0 Hz, 1H), 7.78 (dd, J = 8.0, 1.0 Hz, 1H), 7.70-7.75 (m, 1H), 7.38 (t, J = 8.0 Hz, 1H), 7.23-7.32 (m, 1H), 7.13-7.23 (m, 1H), 6.66 (d, J = 0.8 Hz, 1H), 3.84-4.00 (m, 2H), 3.58-3.75 (m, 2H), 2.77 (s, 3H), 2.66 (s, 3H), 2.45 (br. s., 4H), 2.26 (s, 3H) |

TABLE 4-continued

| | | |
|---|---|---|
| 122 | 585.1 | $^1$H NMR (DMSO-$d_6$) δ: 10.54 (br. s., 1H), 9.46 (s, 1H), 8.51 (s, 1H), 8.42-8.49 (m, 2H), 7.82 (br. s, 1H), 7.78 (d, J = 7.8 Hz, 1H), 7.73 (d, J = 7.8 Hz, 1H), 7.43 (br. s, 1H), 7.38 (t, J = 8.0 Hz, 1H), 7.23-7.33 (m, 1H), 7.18 (br. t, J = 9.0 Hz, 1H), 6.72 (s, 1H), 2.78 (s, 3H), 2.66 (s, 3H) |
| 123 | 739.1 | $^1$H NMR (DMSO-$d_6$) δ: 9.96 (s, 1H), 8.86 (s, 1H), 8.39-8.61 (m, 3H), 8.30 (d, J = 8.6 Hz, 1H), 7.95 (d, J = 8.2 Hz, 1H), 7.78 (d, J = 7.8 Hz, 1H), 7.73 (d, J = 8.2 Hz, 1H), 7.34-7.52 (m, 3H), 7.25-7.34 (m, 1H), 7.21 (t, J = 9.0 Hz, 1H), 3.06 (br. s., 4H), 2.67 (s, 3H), 2.42 (br. s., 4H), 2.15 (s, 3H) |
| 124 | 725.1 | $^1$H NMR (DMSO-$d_6$) δ: 9.97 (s, 1H), 8.87 (s, 1H), 8.53 (br. s., 1H), 8.42-8.51 (m, 2H), 8.30 (d, J = 8.2 Hz, 1H), 7.95 (d, J = 7.4 Hz, 1H), 7.91 (dd, J = 7.8, 1.6 Hz, 1H), 7.60-7.71 (m, 2H), 7.45-7.54 (m, 2H), 7.42 (t, J = 7.0 Hz, 1H), 7.27 (td, J = 8.6, 5.9 Hz, 1H), 7.20 (t, J = 9.2 Hz, 1H), 3.05 (br. s., 4H), 2.41 (br. s., 4H), 2.14 (s, 3H) |
| 125 | 691.1 | $^1$H NMR (DMSO-$d_6$) δ: 10.58 (br. s., 1H), 9.38 (s, 1H), 9.02 (d, J = 8.6 Hz, 1H), 8.59 (d, J = 9.4 Hz, 1H), 8.50 (s, 1H), 8.43 (d, J = 9.4 Hz, 1H), 8.07 (d, J = 7.8 Hz, 1H), 7.80 (d, J = 7.8 Hz, 1H), 7.74 (d, J = 7.8 Hz, 1H), 7.67 (t, J = 7.8 Hz, 1H), 7.49 (t, J = 7.4 Hz, 1H), 7.39 (t, J = 8.0 Hz, 1H), 7.31 (td, J = 9.0, 2.7 Hz, 1H), 7.22 (t, J = 9.0 Hz, 1H), 3.94-4.09 (m, 2H), 3.78 (s, 4H), 3.63-3.73 (m, 2H), 2.68 (s, 3H) |
| 126 | 704.2 | Formic acid salt: $^1$H NMR (DMSO-$d_6$) δ: 9.38 (s, 1H), 9.02 (d, J = 8.6 Hz, 1H), 8.58 (d, J = 9.0 Hz, 1H), 8.50 (s, 1H), 8.44 (d, J = 9.4 Hz, 1H), 8.03 (d, J = 8.2 Hz, 1H), 7.80 (d, J = 7.8 Hz, 1H), 7.74 (d, J = 7.8 Hz, 1H), 7.67 (t, J = 7.6 Hz, 1H), 7.49 (t, J = 7.6 Hz, 1H), 7.39 (t, J = 8.0 Hz, 1H), 7.30 (td, J = 9.0, 5.9 Hz, 1H), 7.22 (t, J = 8.6 Hz, 1H), 3.95 (br. m., 2H), 3.81 (br. m., 2H), 2.68 (s, 3H), 2.55 (s, 4H), 2.32 (s, 3H) |
| 127 | 690.2 | $^1$H NMR (DMSO-$d_6$) δ: 9.31 (br. s., 1H), 9.05 (d, J = 8.6 Hz, 1H), 8.58 (d, J = 9.0 Hz, 1H), 8.50 (s, 1H), 8.42 (d, J = 9.0 Hz, 1H), 8.06 (d, J = 8.2 Hz, 1H), 7.83 (d, J = 7.8 Hz, 1H), 7.68 (t, J = 7.8 Hz, 1H), 7.60 (d, J = 8.2 Hz, 1H), 7.49 (t, J = 7.6 Hz, 1H), 7.31 (t, J = 8.0 Hz, 1H), 7.22 (td, J = 9.0, 5.9 Hz, 1H), 7.01 (t, J = 9.2 Hz, 1H), 4.06 (br. m., 2H), 3.85 (br. m., 2H), 2.92-3.11 (m, 4H), 2.68 (s, 3H) |
| 128 | 734.2 | $^1$H NMR (DMSO-$d_6$) δ: 9.38 (s, 1H), 9.02 (d, J = 8.6 Hz, 1H), 8.58 (d, J = 9.4 Hz, 1H), 8.50 (s, 1H), 8.44 (d, J = 9.4 Hz, 1H), 8.03 (d, J = 8.2 Hz, 1H), 7.80 (d, J = 8.2 Hz, 1H), 7.74 (d, J = 7.0 Hz, 1H), 7.63-7.71 (m, 1H), 7.49 (t, J = 7.6 Hz, 1H), 7.39 (t, J = 7.8 Hz, 1H), 7.31 (td, J = 8.7, 5.7 Hz, 1H), 7.23 (t, J = 9.2 Hz, 1H), 4.57 (br. s., 1H), 3.96 (br. s., 2H), 3.81 (br. s., 2H), 3.57 (br. t, J = 5.5 Hz, 2H), 2.68 (s, 3H), 2.65 (br. m., 4H), 2.56 (br. t, J = 5.5 Hz, 2H) |
| 129 | 691.1 | $^1$H NMR (DMSO-$d_6$) δ: 10.58 (br. s., 1H), 9.40 (s, 1H), 9.03 (d, J = 8.6 Hz, 1H), 8.63 (dd, J = 9.0, 1.0 Hz, 1H), 8.51 (s, 1H), 8.45 (dd, J = 7.8, 1.0 Hz, 1H), 8.26-8.33 (m, 1H), 7.80 (dd, J = 8.0, 1.0 Hz, 1H), 7.74 (d, J = 7.8 Hz, 1H), 7.66 (br. t, J = 7.6 Hz, 1H), 7.50 (t, J = 7.6 Hz, 1H), 7.40 (t, J = 8.0 Hz, 1H), 7.32 (td, J = 8.7, 5.7 Hz, 1H), 7.24 (t, J = 9.0 Hz, 1H), 5.06 (dd, J = 4.3, 3.5 Hz, 1H), 4.42 (br. d, J = 19.6 Hz, 1H), 4.08-4.29 (m, 2H), 4.00-4.08 (m, 1H), 3.57-3.81 (m, 2H), 2.68 (s, 3H), 1.80-2.15 (m, 2H) |
| 130 | 677.1 | $^1$H NMR (DMSO-$d_6$) δ: 10.58 (br. s., 1H), 9.40 (s, 1H), 9.03 (d, J = 8.6 Hz, 1H), 8.63 (d, J = 9.0 Hz, 1H), 8.50 (s, 1H), 8.45 (d, J = 9.0 Hz, 1H), 8.33 (d, J = 8.2 Hz, 1H), 7.80 (d, J = 7.8 Hz, 1H), 7.74 (d, J = 7.8 Hz, 1H), 7.62-7.70 (m, 1H), 7.50 (t, J = 7.4 Hz, 1H), 7.39 (t, J = 8.0 Hz, 1H), 7.31 (td, J = 8.6, 5.9 Hz, 1H), 7.23 (t, J = 9.0 Hz, 1H), 5.85 (d, J = 6.3 Hz, 1H), 4.99 (s, 1H), 4.58-4.69 (m, 1H), 4.51 (dd, J = 10.6, 4.3 Hz, 1H), 4.39 (dd, J = 10.2, 7.4 Hz, 1H), 3.91 (dd, J = 10.4, 3.7 Hz, 1H), 2.67 (s, 3H) |
| 131 | 705.2 | $^1$H NMR (DMSO-$d_6$) δ: 10.58 (br. s, 1H), 9.38 (s, 1H), 9.02 (d, J = 8.6 Hz, 1H), 8.57 (d, J = 9.4 Hz, 1H), 8.50 (s, 1H), 8.44 (d, J = 9.0 Hz, 1H), 7.99 (d, J = 8.2 Hz, 1H), 7.80 (dd, J = 8.0, 1.0 Hz, 1H), 7.75 (d, J = 8.2 Hz, 1H), 7.67 (ddd, J = 8.3, 7.1, 1.0 Hz, 1H), 7.48 (t, J = 7.6 Hz, 1H), 7.40 (t, J = 8.0 Hz, 1H), 7.32 (td, J = 8.6, 5.9 Hz, 1H), 7.24 (t, J = 8.8 Hz, 1H), 4.85 (d, J = 3.9 Hz, 1H), 4.09-4.23 (m, 2H), 3.84 (td, J = 8.1, 4.1 Hz, 1H), 3.48-3.60 (m, J = 10.0, 10.0 Hz, 1H), 3.36-3.46 (m, 1H), 2.68 (s, 3H), 1.81-1.99 (m, J = 12.1, 12.1 Hz, 2H), 1.43-1.58 (m, 2H) |
| 132 | 719.2 | $^1$H NMR (DMSO-$d_6$) δ: 10.58 (br. s., 1H), 9.36 (s, 1H), 9.03 (d, J = 8.6 Hz, 1H), 8.56 (d, J = 9.4 Hz, 1H), 8.50 (s, 1H), 8.44 (d, J = 9.4 Hz, 1H), 7.98 (d, J = 7.8 Hz, 1H), 7.80 (dd, J = 7.8, 1.0 Hz, 1H), 7.72 (d, J = 7.8 Hz, 1H), 7.63-7.70 (m, 1H), 7.48 (t, J = 7.4 Hz, 1H), 7.38 (t, J = 8.0 Hz, 1H), 7.30 (td, J = 8.8, 5.9 Hz, 1H), 7.20 (br. t, J = 8.8 Hz, 1H), 4.65 (br. d, J = 12.9 Hz, 1H), 4.55 (t, J = 5.3 Hz, 1H), 4.41 (br. d, J = 12.9 Hz, 1H), 3.22 (br. t, J = 12.1 Hz, 1H), 2.91 (dt, J = 12.9, 2.0 Hz, 1H), 2.68 (s, 3H), 1.85 (br. d, J = 12.9 Hz, 1H), 1.69-1.81 (m, 2H), 1.15-1.35 (m, 2H) |
| 133 | 704.1 | $^1$H NMR (DMSO-$d_6$) δ: 10.58 (br. s., 1H), 9.39 (s, 1H), 9.03 (d, J = 8.6 Hz, 1H), 8.60 (dd, J = 9.0, 3.5 Hz, 1H), 8.51 (s, 1H), 8.46 (dd, J = 9.0, 5.9 Hz, 1H), 8.17-8.28 (m, 1H), 8.07-8.17 (m, 1H), 7.80 (d, J = 7.8 Hz, 1H), 7.72 (d, J = 7.8 Hz, 1H), 7.68 (t, J = 7.8 Hz, 1H), 7.50 (t, J = 7.6 Hz, 1H), 7.38 (t, J = 8.0 Hz, 1H), 7.25-7.34 (m, 1H), 7.21 (br. t, J = 9.0 Hz, 1H), 4.67 (s, 1H), 4.28 (s, 1H), 4.22 (br. t, J = 5.1 Hz, 1H), 3.88-4.06 (m, 1H), 3.39-3.44 (m, 2H), 2.68 (s, 3H) |
| 134 | 702.2 | Formic acid salt: $^1$H NMR (DMSO-$d_6$) δ: 9.28 (br. s., 1H), 9.02 (dd, J = 21.1, 8.6 Hz, 1H), 8.57 (dd, J = 9.2, 1.0 Hz, 1H), 8.50 (d, J = 5.1 Hz, 1H), 8.29-8.44 (m, 1H), 8.21 (s, 1H), 7.84 (dt, J = 7.8, 1.0 Hz, 1H), 7.64 (dt, J = 9.9, 8.2 Hz, 1H), 7.56 (d, J = 7.8 Hz, 1H), 7.47 (dt, J = 14.0, 7.3 Hz, 1H), 7.29 (t, J = 7.8 Hz, 1H), 7.19 (tdd, J = 8.9, 6.3, 2.5 Hz, 1H), 6.95 (t, J = 9.2 Hz, 1H), 5.70 (s, 1H), 5.06 (s, 1H), 4.41 (br. s., 2H), 4.34 (d, J = 11.7 Hz, 1H), 4.19-4.29 (m, J = 9.8 Hz, 1H), 3.69-3.83 (m, 2H), 3.48-3.62 (m, 2H), 3.34 (dd, J = 16.0, 9.8 Hz, 1H), 2.67 (d, J = 3.1 Hz, 3H), 2.16 (t, J = 10.6 Hz, 1H), 1.95 (t, J = 11.9 Hz, 1H) |

TABLE 4-continued

| | | |
|---|---|---|
| 135 | 730.2 | $^1H$ NMR (DMSO-$d_6$) δ: 9.37 (s, 1H), 9.03 (d, J = 8.6 Hz, 1H), 8.58 (d, J = 9.0 Hz, 1H), 8.50 (s, 1H), 8.44 (d, J = 9.0 Hz, 1H), 8.02 (d, J = 8.2 Hz, 1H), 7.80 (dd, J = 8.0, 1.0 Hz, 1H), 7.72 (d, J = 7.8 Hz, 1H), 7.67 (ddd, J = 8.3, 7.1, 1.0 Hz, 1H), 7.44-7.53 (m, 1H), 7.38 (t, J = 8.0 Hz, 1H), 7.30 (td, J = 9.0, 5.9 Hz, 1H), 7.20 (br. t, J = 7.8 Hz, 1H), 3.87 (br. t, J = 4.3 Hz, 2H), 3.75 (br. t, J = 4.7 Hz, 2H), 2.59-2.79 (m, 4H), 2.68 (s, 3H), 1.72 (tt, J = 6.6, 3.4 Hz, 1H), 0.41-0.55 (m, 2H), 0.26-0.41 (m, 2H) |
| 136 | 655.1 | $^1H$ NMR (DMSO-$d_6$) δ: 10.54 (s, 1H), 9.97 (s, 1H), 8.51 (s, 1H), 8.43 (d, J = 9.0 Hz, 1H), 8.36 (s, 1H), 8.21 (d, J = 9.0 Hz, 1H), 7.76 (t, J = 8.0 Hz, 2H), 7.38 (t, J = 8.0 Hz, 1H), 7.29 (td, J = 8.7, 5.7 Hz, 1H), 7.21 (t, J = 9.0 Hz, 1H), 3.63 (br. s., 6H), 2.58-2.74 (m, 6H) |
| 137 | 668.2 | $^1H$ NMR (DMSO-$d_6$) δ: 9.96 (s, 1H), 8.51 (s, 1H), 8.43 (d, J = 9.0 Hz, 1H), 8.34 (s, 1H), 8.21 (d, J = 9.0 Hz, 1H), 7.75-7.80 (m, 1H), 7.73 (d, J = 7.8 Hz, 1H), 7.37 (t, J = 8.0 Hz, 1H), 7.28 (td, J = 8.7, 5.7 Hz, 1H), 7.18 (t, J = 9.6 Hz, 1H), 4.19 (br. s., 2H), 3.64 (br. s., 2H), 2.66 (s, 3H), 2.65 (s, 3H), 2.45 (br. s., 4H), 2.28 (s, 3H) |
| 138 | 585.1 | $^1H$ NMR (DMSO-$d_6$) δ: 10.54 (br. s, 1H), 9.98 (s, 1H), 8.51 (s, 1H), 8.43 (d, J = 9.0 Hz, 1H), 8.37 (s, 1H), 8.22 (d, J = 8.6 Hz, 1H), 7.76 (t, J = 8.2 Hz, 2H), 7.43 (br. s., 1H), 7.38 (t, J = 8.0 Hz, 1H), 7.30 (td, J = 8.7, 5.7 Hz, 1H), 7.14-7.25 (m, 2H), 2.67 (s, 3H), 2.65 (s, 3H) |
| 139 | 711.1 | $^1H$ NMR (DMSO-$d_6$) δ: 10.73 (br. s., 1H), 9.39 (s, 1H), 9.03 (d, J = 8.6 Hz, 1H), 8.59 (d, J = 9.4 Hz, 1H), 8.49 (s, 1H), 8.44 (d, J = 9.4 Hz, 1H), 8.07 (br. d, J = 7.8 Hz, 1H), 7.94 (d, J = 7.8 Hz, 1H), 7.89-7.93 (m, J = 7.8, 1.0 Hz, 1H), 7.67 (ddd, J = 8.5, 7.1, 1.2 Hz, 1H), 7.45-7.59 (m, 2H), 7.26-7.37 (m, 1H), 7.23 (br. t, J = 9.4 Hz, 1H), 4.00 (br. t, J = 4.3 Hz, 2H), 3.74-3.87 (m, 4H), 3.71 (br. t, J = 4.3 Hz, 2H) |
| 140 | 710.1 | Formic acid salt: $^1H$ NMR (DMSO-$d_6$) δ: 9.31 (s, 1H), 9.06 (d, J = 8.6 Hz, 1H), 8.58 (d, J = 9.4 Hz, 1H), 8.50 (s, 1H), 8.42 (d, J = 9.0 Hz, 1H), 8.08 (d, J = 7.8 Hz, 1H), 7.94 (dd, J = 7.8, 1.6 Hz, 1H), 7.77 (dd, J = 8.2, 1.6 Hz, 1H), 7.68 (ddd, J = 8.3, 7.1, 1.0 Hz, 1H), 7.49 (t, J = 7.4 Hz, 1H), 7.44 (t, J = 8.0 Hz, 1H), 7.17 (td, J = 9.1, 6.1 Hz, 1H), 6.97 (t, J = 9.2 Hz, 1H), 4.13 (br. s., 2H), 3.89 (br. s., 2H), 3.13 (br. s., 4H) |
| 141 | 754.1 | Formic acid salt: $^1H$ NMR (DMSO-$d_6$) δ: 9.38 (s, 1H), 9.03 (d, J = 8.6 Hz, 1H), 8.58 (d, J = 9.4 Hz, 1H), 8.49 (s, 1H), 8.44 (d, J = 9.4 Hz, 1H), 8.03 (d, J = 8.2 Hz, 1H), 7.92 (ddd, J = 7.9, 6.6, 1.6 Hz, 2H), 7.63-7.76 (m, 1H), 7.54 (t, J = 8.2 Hz, 1H), 7.49 (t, J = 7.4 Hz, 1H), 7.30 (td, J = 9.0, 5.9 Hz, 1H), 7.21 (t, J = 9.0 Hz, 1H), 4.60 (br. s, 1H), 3.97 (br. s., 2H), 3.82 (br. s., 2H), 3.58 (t, J = 6.1 Hz, 2H), 2.61-2.77 (m, 4H), 2.57 (t, J = 5.9 Hz, 2H) |
| 142 | 710.1 | $^1H$ NMR (DMSO-$d_6$) δ: 10.72 (s, 1H), 9.83 (s, 1H), 8.69 (s, 1H), 8.48 (s, 1H), 8.40-8.47 (m, 2H), 8.34 (d, J = 8.6 Hz, 1H), 7.95 (dd, J = 8.2, 1.2 Hz, 1H), 7.90 (dd, J = 8.0, 1.4 Hz, 1H), 7.77 (br. d, J = 7.8 Hz, 1H), 7.54 (t, J = 8.0 Hz, 1H), 7.37-7.44 (m, 1H), 7.27-7.37 (m, 2H), 7.23 (t, J = 9.0 Hz, 1H), 3.67 (br. s., 8H) |
| 143 | 709.1 | Formic acid salt: $^1H$ NMR (DMSO-$d_6$) δ: 9.72 (br. s., 1H), 8.74 (s, 1H), 8.49 (s, 1H), 8.40-8.47 (m, 2H), 8.35 (d, J = 8.2 Hz, 1H), 8.16 (s, 1H), 7.93 (dd, J = 8.0, 1.4 Hz, 1H), 7.80 (d, J = 7.8 Hz, 1H), 7.75 (dd, J = 7.8, 1.6 Hz, 1H), 7.37-7.45 (m, 2H), 7.33 (t, J = 7.4 Hz, 1H), 7.14 (td, J = 9.0, 5.9 Hz, 1H), 6.93 (td, J = 8.6, 1.0 Hz, 1H), 3.72-3.90 (m, 4H), 3.08 (br. s., 4H) |
| 144 | 753.1 | Formic acid salt: $^1H$ NMR (DMSO-$d_6$) δ: 10.72 (s, 1H), 9.84 (s, 1H), 9.79 (br. s, 1H), 8.70 (s, 1H), 8.51 (s, 1H), 8.42-8.49 (m, 2H), 8.39 (d, J = 8.6 Hz, 1H), 7.96 (dd, J = 8.2, 1.6 Hz, 1H), 7.91 (dd, J = 7.8, 1.0 Hz, 1H), 7.84 (d, J = 7.8 Hz, 1H), 7.54 (t, J = 8.0 Hz, 1H), 7.39-7.45 (m, 1H), 7.35 (dt, J = 7.8, 1.0 Hz, 1H), 7.30 (td, J = 9.4, 5.9 Hz, 1H), 7.24 (dt, J = 9.0, 1.0 Hz, 1H), 4.33-4.57 (m, 2H), 3.76 (t, J = 5.5 Hz, 3H), 3.52-3.63 (m, 2H), 3.49 (br. s., 2H), 3.26 (br. m, 2H), 3.17 (br. s., 2H) |
| 145 | 641.1 | $^1H$ NMR (DMSO-$d_6$) δ: 10.58 (br. s, 1H), 10.13 (s, 1H), 9.36 (d, J = 2.3 Hz, 1H), 8.49 (s, 1H), 8.37-8.47 (m, 2H), 7.71-7.82 (m, 2H), 7.38 (t, J = 8.0 Hz, 1H), 7.28-7.36 (m, 1H), 7.25 (t, J = 8.2 Hz, 1H), 7.00 (d, J = 2.7 Hz, 1H), 4.01 (br. t, J = 1.0 Hz, 2H), 3.69 (br. s, 6H), 2.66 (s, 3H) |
| 146 | 654.2 | $^1H$ NMR (DMSO-$d_6$) δ: 10.12 (s, 1H), 9.36 (d, J = 2.0 Hz, 1H), 8.49 (s, 1H), 8.40-8.47 (m, 2H), 7.77 (d, J = 8.2 Hz, 1H), 7.75 (d, J = 8.2 Hz, 1H), 7.38 (t, J = 8.0 Hz, 1H), 7.31 (td, J = 8.7, 5.7 Hz, 1H), 7.19-7.28 (m, 1H), 6.99 (d, J = 2.7 Hz, 1H), 4.00 (br. s., 2H), 3.74 (br. s., 2H), 2.68 (s, 3H), 2.62 (br. s., 2H), 2.36 (br. s, 3H) |
| 147 | 655.2 | $^1H$ NMR (DMSO-$d_6$) δ: 10.58 (br. s., 1H), 10.02 (s, 1H), 9.38 (s, 1H), 8.47 (s, 1H), 8.35-8.43 (m, 2H), 7.77 (d, J = 7.8 Hz, 1H), 7.74 (d, J = 7.8 Hz, 1H), 7.38 (t, J = 7.8 Hz, 1H), 7.27-7.35 (m, 1H), 7.19-7.27 (m, 1H), 3.60 (br. s., 8H), 2.66 (s, 3H), 2.34 (s, 3H) |
| 148 | 668.2 | $^1H$ NMR (DMSO-$d_6$) δ: 10.02 (s, 1H), 8.46 (s, 1H), 8.35-8.42 (m, 2H), 7.78 (d, J = 8.2 Hz, 1H), 7.72 (d, J = 7.8 Hz, 1H), 7.37 (t, J = 8.0 Hz, 1H), 7.25-7.34 (m, 1H), 7.13-7.25 (m, 1H), 3.58 (br. s., 4H), 2.66 (s, 3H), 2.30-2.44 (m, 7H), 2.23 (br. s, 3H) |
| 149 | 692.1 | $^1H$ NMR (DMSO-$d_6$) δ: 10.54 (br. s, 1H), 9.84 (s, 1H), 9.28 (s, 1H), 8.43-8.54 (m, 4H), 7.98 (d, J = 8.2 Hz, 1H), 7.92 (dd, J = 7.8, 1.6 Hz, 1H), 7.81 (d, J = 7.8 Hz, 1H), 7.60-7.72 (m, 2H), 7.47-7.56 (m, 1H), 7.35 (t, J = 8.2 Hz, 1H), 7.15-7.32 (m, 2H), 3.59-3.79 (m, 4H), 3.45-3.57 (m, 4H) |
| 150 | 650.1 | $^1H$ NMR (DMSO-$d_6$) δ: 10.54 (br. s., 1H), 9.84 (s, 1H), 9.29 (s, 1H), 8.35-8.60 (m, 3H), 8.09 (s, 1H), 7.86-7.98 (m, 3H), 7.60-7.73 (m, 2H), 7.51 (t, J = 6.8 Hz, 1H), 7.16-7.42 (m, 3H), 3.04 (s, 6H) |
| 151 | 642.1 | $^1H$ NMR (DMSO-$d_6$) δ: 10.60 (br. s., 1H), 10.18 (s, 1H), 10.04 (s, 1H), 8.54 (s, 1H), 8.49 (d, J = 9.0 Hz, 1H), 8.36 (d, J = 9.0 Hz, 1H), 7.76 (t, J = 8.0 Hz, 2H), 7.38 (t, J = 8.2 Hz, 1H), 7.22-7.35 (m, 2H), 3.66-3.74 (m, 6H), 3.59-3.65 (m, 2H), 2.67 (s, 3H) |

TABLE 4-continued

| | | |
|---|---|---|
| 152 | 655.2 | $^1$H NMR (DMSO-$d_6$) δ: 10.18 (s, 1H), 10.03 (s, 1H), 8.54 (s, 1H), 8.49 (d, J = 9.0 Hz, 1H), 8.35 (d, J = 9.0 Hz, 1H), 7.77 (dd, J = 7.8, 1.2 Hz, 1H), 7.74 (dt, J = 7.8, 1.0 Hz, 1H), 7.38 (t, J = 8.0 Hz, 1H), 7.32 (td, J = 8.7, 5.7 Hz, 1H), 7.24 (dt, J = 9.0, 1.0 Hz, 1H), 3.71 (br. t, J = 4.3 Hz, 2H), 3.65 (br. t, J = 4.7 Hz, 2H), 2.67 (s, 3H), 2.43 (dt, J = 4.3, 1.0 Hz, 2H), 2.28 (s, 3H) |
| 153 | 655.1 | $^1$H NMR (DMSO-$d_6$) δ: 10.59 (br. s., 1H), 10.07 (s, 1H), 9.15 (br. s, 1H), 8.48 (s, 1H), 8.38 (s, 2H), 7.77 (d, J = 8.2 Hz, 1H), 7.74 (d, J = 8.2 Hz, 1H), 7.38 (t, J = 8.0 Hz, 1H), 7.32 (td, J = 8.7, 5.7 Hz, 1H), 7.24 (t, J = 9.0 Hz, 1H), 3.56-3.84 (m, 8H), 2.67 (s, 3H), 2.19 (s, 3H) |
| 154 | 668.2 | $^1$H NMR (DMSO-$d_6$) δ: 10.06 (s, 1H), 9.15 (s, 1H), 8.47 (s, 1H), 8.36-8.39 (m, 2H), 7.78 (d, J = 7.8 Hz, 1H), 7.73 (d, J = 7.4 Hz, 1H), 7.34-7.40 (m, 2H), 7.25-7.34 (m, 1H), 7.17-7.25 (m, 1H), 3.69 (br. s., 4H), 2.67 (s, 3H), 2.45 (br. s., 4H), 2.27 (s, 3H) |
| 155 | 698.2 | $^1$H NMR (DMSO-$d_6$) δ: 10.07 (s, 1H), 9.15 (s, 1H), 8.47 (s, 1H), 8.34-8.41 (m, 2H), 7.77 (d, J = 7.8 Hz, 1H), 7.73 (d, J = 8.6 Hz, 1H), 7.38 (t, J = 7.8 Hz, 1H), 7.26-7.35 (m, 1H), 7.18-7.26 (m, 1H), 4.53 (br. s., 1H), 3.69 (br. s., 4H), 3.55 (br. q, J = 5.5 Hz, 4H), 2.67 (s, 3H), 2.16 (s, 3H) |
| 156 | 704.2 | $^1$H NMR (DMSO-$d_6$) δ: 10.56 (br. s., 1H), 9.79 (br. s., 1H), 8.69 (s, 1H), 8.49 (s, 1H), 8.40-8.48 (m, 2H), 8.33 (d, J = 8.2 Hz, 1H), 8.04 (br. s., 1H), 7.78 (d, J = 7.8 Hz, 1H), 7.74 (d, J = 7.8 Hz, 1H), 7.38 (s, 2H), 7.26-7.35 (m, 2H), 7.22 (t, J = 8.6 Hz, 1H), 4.77 (br. s, 1H), 4.64 (br. s, 1H), 3.76-3.98 (m, 1H), 3.67 (br. s., 1H), 3.50-3.60 (m, 1H), 3.40-3.50 (m, 2H), 2.67 (s, 3H), 2.37 (dt, J = 14.2, 7.2 Hz, 1H), 1.83-2.09 (m, 1H), 1.71 (br. s., 1H) |
| 157 | 704.2 | $^1$H NMR (DMSO-$d_6$) δ: 10.56 (br. s., 1H), 9.79 (br. s., 1H), 8.69 (s, 1H), 8.49 (s, 1H), 8.40-8.48 (m, 2H), 8.33 (d, J = 8.2 Hz, 1H), 7.98-8.11 (m, 1H), 7.78 (dd, J = 8.2, 1.0 Hz, 1H), 7.74 (d, J = 7.8 Hz, 1H), 7.34-7.43 (m, 2H), 7.26-7.34 (m, 2H), 7.22 (t, J = 9.4 Hz, 1H), 4.71 (m, 1H), 3.73-3.98 (m, 2H), 3.67 (br. s., 1H), 3.50-3.60 (m, 1H), 3.37-3.50 (m, 2H), 2.68 (s, 3H), 2.26-2.45 (m, 1H), 1.90-2.06 (m, 1H), 1.71 (br. s., 1H) |
| 158 | 703.2 | Formic acid salt: $^1$H NMR (DMSO-$d_6$) δ: 8.73 (s, 1H), 8.49 (s, 1H), 8.37-8.47 (m, 2H), 8.32 (d, J = 8.6 Hz, 1H), 7.84 (d, J = 7.8 Hz, 1H), 7.72 (d, J = 7.8 Hz, 1H), 7.49 (d, J = 7.8 Hz, 1H), 7.41 (t, J = 7.8 Hz, 1H), 7.33 (t, J = 7.4 Hz, 1H), 7.25 (t, J = 8.0 Hz, 1H), 7.11 (dt, J = 9.1, 6.1 Hz, 1H), 6.82 (t, J = 9.4 Hz, 1H), 4.32 (br. s., 2H), 3.26-3.41 (m, 2H), 2.99-3.20 (m, 2H), 2.67 (s, 3H), 1.96 (d, J = 11.3 Hz, 2H), 1.35-1.55 (m, 2H) |
| 159 | 717.2 | Formic acid salt: $^1$H NMR (DMSO-$d_6$) δ: 9.73 (br. s., 1H), 8.75 (s, 1H), 8.49 (s, 1H), 8.37-8.48 (m, 2H), 8.32 (d, J = 8.2 Hz, 1H), 7.85 (d, J = 7.4 Hz, 1H), 7.74 (d, J = 7.8 Hz, 1H), 7.48 (d, J = 7.8 Hz, 1H), 7.37-7.44 (m, 1H), 7.29-7.37 (m, 1H), 7.25 (t, J = 8.0 Hz, 1H), 7.08 (dt, J = 9.3, 6.1 Hz, 1H), 6.81 (t, J = 9.4 Hz, 1H), 3.01 (br. s., 2H), 2.78 (d, J = 6.7 Hz, 3H), 2.67 (s, 3H), 1.74-1.95 (m, 3H), 1.19-1.35 (m, 2H) |
| 160 | 704.2 | $^1$H NMR (DMSO-$d_6$) δ: 10.56 (br. s., 1H), 9.83 (s, 1H), 8.67 (s, 1H), 8.48 (s, 1H), 8.38-8.47 (m, 2H), 8.33 (d, J = 8.2 Hz, 1H), 7.76-7.81 (m, 1H), 7.74 (d, J = 8.2 Hz, 1H), 7.71 (d, J = 7.8 Hz, 1H), 7.35-7.43 (m, 2H), 7.26-7.35 (m, 2H), 7.21 (t, J = 9.0 Hz, 1H), 4.91 (br. s., 1H), 3.87 (br. s., 1H), 3.53 (br. s., 1H), 3.13-3.26 (m, 2H), 2.68 (s, 3H), 1.82-2.02 (m, 1H), 1.75 (br. s., 1H), 1.44 (t, J = 8.6 Hz, 2H) |
| 161 | 704.2 | $^1$H NMR (DMSO-$d_6$) δ: 10.56 (br. s., 1H), 9.83 (s, 1H), 8.67 (s, 1H), 8.48 (s, 1H), 8.38-8.47 (m, 2H), 8.33 (d, J = 8.2 Hz, 1H), 7.78 (d, J = 7.8 Hz, 1H), 7.74 (d, J = 7.8 Hz, 1H), 7.71 (d, J = 7.8 Hz, 1H), 7.35-7.43 (m, 2H), 7.26-7.35 (m, 2H), 7.22 (t, J = 9.0 Hz, 1H), 4.90 (br. s., 1H), 3.53 (br. s., 1H), 3.06-3.28 (m, 2H), 2.69 (s, 3H), 1.84-1.98 (m, 1H), 1.75 (br. s., 1H), 1.35-1.53 (m, J = 8.4, 8.4 Hz, 2H) |
| 162 | 689.2 | Formic acid salt: $^1$H NMR (DMSO-$d_6$) δ: 9.72 (br. s., 1H), 8.73 (br. s., 1H), 8.50 (s, 1H), 8.40-8.46 (m, 2H), 8.32 (d, J = 8.2 Hz, 1H), 8.08 (d, J = 7.8 Hz, 1H), 7.83 (d, J = 7.8 Hz, 1H), 7.52 (d, J = 8.2 Hz, 1H), 7.40 (t, J = 7.6 Hz, 1H), 7.32 (t, J = 7.4 Hz, 1H), 7.26 (t, J = 7.8 Hz, 1H), 7.13 (td, J = 9.1, 6.1 Hz, 1H), 6.87 (t, J = 9.2 Hz, 1H), 3.79-3.89 (m, 2H), 3.68 (br. s., 2H), 2.66 (s, 3H), 2.13-2.31 (m, 2H), 1.83-2.11 (m, 2H) |
| 163 | 689.2 | Formic acid salt: $^1$H NMR (DMSO-$d_6$) δ: 9.75 (br. s., 1H), 8.73 (br. s., 1H), 8.50 (s, 1H), 8.39-8.46 (m, 2H), 8.32 (d, J = 8.6 Hz, 1H), 8.08 (d, J = 7.8 Hz, 1H), 7.83 (d, J = 7.4 Hz, 1H), 7.52 (d, J = 7.8 Hz, 1H), 7.40 (t, J = 7.8 Hz, 1H), 7.32 (t, J = 7.6 Hz, 1H), 7.27 (t, J = 8.0 Hz, 1H), 7.14 (td, J = 9.0, 5.9 Hz, 1H), 6.88 (t, J = 9.2 Hz, 1H), 3.78-3.91 (m, 2H), 3.70 (br. s., 2H), 2.66 (s, 3H), 2.16-2.29 (m, 2H), 1.94-2.03 (m, 2H) |
| 164 | 718.2 | $^1$H NMR (DMSO-$d_6$) δ: 10.57 (br. s., 1H), 9.82 (s, 1H), 8.69 (s, 1H), 8.49 (s, 1H), 8.40-8.47 (m, 2H), 8.34 (d, J = 8.6 Hz, 1H), 7.78 (dd, J = 7.8, 1.0 Hz, 1H), 7.70 7.77 (m, 2H), 7.26-7.43 (m, 5H), 7.22 (t, J = 9.4 Hz, 1H), 3.49-3.70 (m, 2H), 2.67 (s, 3H), 1.10 (br. s., 6H) |
| 165 | 703.2 | Formic acid salt: $^1$H NMR (DMSO-$d_6$) δ: 9.71 (br. s., 1H), 8.67 (s, 1H), 8.49 (s, 1H), 8.38-8.45 (m, 2H), 8.34 (d, J = 8.6 Hz, 1H), 7.78-7.88 (m, J = 7.8, 1.2 Hz, 2H), 7.50-7.57 (m, 1H), 7.36-7.45 (m, 1H), 7.32 (t, J = 7.4 Hz, 1H), 7.27 (t, J = 7.8 Hz, 1H), 7.15 (td, J = 9.2, 5.9 Hz, 1H), 6.90 (t, J = 9.2 Hz, 1H), 3.82-3.90 (m, 2H), 3.79 (t, J = 5.9 Hz, 2H), 3.22 (br. s, 1H), 3.04-3.15 (m, 2H), 2.67 (s, 3H), 1.84-2.05 (m, 2H) |
| 166 | 720.2 | $^1$H NMR (DMSO-$d_6$) δ: 10.56 (br. s., 1H), 9.78 (s, 1H), 8.66 (s, 1H), 8.49 (s, 1H), 8.42 (s, 2H), 8.36 (d, J = 8.2 Hz, 1H), 7.70-7.81 (m, 3H), 7.36-7.43 (m, 2H), 7.26-7.36 (m, 2H), 7.22 (t, J = 9.0 Hz, 1H), 4.93 (t, J = 5.1 Hz, 1H), 3.93 (br. d, J = 10.6 Hz, 1H), 3.85 (br. d, J = 9.0 Hz, 1H), 3.71 (br. s., 1H), 3.53-3.66 (m, 2H), 3.46 (t, J = 11.3 Hz, 1H), 2.67 (s, 3H) |

TABLE 4-continued

| | | |
|---|---|---|
| 167 | 703.2 | Formic acid salt: $^1$H NMR (DMSO-$d_6$) δ: 9.69 (br. s., 1H), 8.72 (s, 1H), 8.50 (s, 1H), 8.38-8.46 (m, 2H), 8.34 (d, J = 8.2 Hz, 1H), 7.84 (d, J = 7.8 Hz, 1H), 7.77 (d, J = 7.8 Hz, 1H), 7.50 (d, J = 7.8 Hz, 1H), 7.41 (t, J = 7.8 Hz, 1H), 7.33 (t, J = 7.4 Hz, 1H), 7.25 (t, J = 7.8 Hz, 1H), 7.12 (td, J = 9.2, 5.9 Hz, 1H), 6.84 (t, J = 9.0 Hz, 1H), 4.36 (br. s., 1H), 4.11 (br. s., 1H), 3.12 (s, 2H), 2.67 (s, 3H), 2.03 (br. s., 1H), 1.79 (br. s., 1H), 1.43-1.63 (m, 2H) |
| 168 | 703.2 | Formic acid salt: $^1$H NMR (DMSO-$d_6$) δ: 9.75 (s, 1H), 8.66 (s, 1H), 8.49 (s, 1H), 8.39-8.47 (m, 2H), 8.35 (d, J = 8.2 Hz, 1H), 7.81 (d, J = 7.8 Hz, 1H), 7.72 (d, J = 7.8 Hz, 1H), 7.63 (d, J = 7.8 Hz, 1H), 7.37-7.45 (m, 1H), 7.28-7.37 (m, 2H), 7.22 (td, J = 9.0, 5.9 Hz, 1H), 7.04 (t, J = 9.2 Hz, 1H), 4.58 (br. s., 1H), 4.04 (d, J = 13.7 Hz, 1H), 3.26 (t, J = 11.9 Hz, 1H), 2.88-3.10 (m, 3H), 2.72-2.85 (m, 1H), 2.67 (s, 3H), 1.32 (d, J = 6.7 Hz, 3H) |
| 169 | 703.2 | Formic acid salt: $^1$H NMR (DMSO-$d_6$) δ: 9.74 (s, 1H), 8.66 (s, 1H), 8.49 (s, 1H), 8.39-8.47 (m, 2H), 8.35 (d, J = 8.2 Hz, 1H), 7.81 (d, J = 7.8 Hz, 1H), 7.72 (d, J = 7.8 Hz, 1H), 7.62 (d, J = 7.8 Hz, 1H), 7.37-7.45 (m, 1H), 7.28-7.37 (m, 2H), 7.22 (td, J = 9.0, 5.9 Hz, 1H), 7.04 (t, J = 9.2 Hz, 1H), 4.57 (br. s., 1H), 4.04 (br. d, J = 12.9 Hz, 1H), 3.26 (t, J = 12.9 Hz, 1H), 2.88-3.11 (m, 3H), 2.78 (td, J = 12.5, 2.7 Hz, 1H), 2.67 (s, 3H), 1.32 (d, J = 7.0 Hz, 3H) |
| 170 | 703.2 | Formic acid salt: $^1$H NMR (DMSO-$d_6$) δ: 9.74 (s, 1H), 8.71 (s, 1H), 8.49 (s, 1H), 8.39-8.47 (m, 2H), 8.35 (d, J = 8.6 Hz, 1H), 7.81 (d, J = 7.8 Hz, 1H), 7.77 (d, J = 7.8 Hz, 1H), 7.61 (d, J = 8.2 Hz, 1H), 7.37-7.44 (m, 1H), 7.27-7.37 (m, 2H), 7.20 (td, J = 9.0, 5.9 Hz, 1H), 7.01 (t, J = 9.2 Hz, 1H), 4.25 (br. s., 1H), 3.19 (br. s., 2H), 3.12 (d, J = 12.5 Hz, 2H), 2.96-3.06 (m, J = 6.3 Hz, 1H), 2.80-2.95 (m, 2H), 2.67 (s, 3H), 1.09 (d, J = 5.1 Hz, 3H) |
| 171 | 703.2 | Formic acid salt: $^1$H NMR (DMSO-$d_6$) δ: 9.74 (br. s., 1H), 8.71 (s, 1H), 8.49 (s, 1H), 8.38-8.47 (m, 2H), 8.35 (d, J = 8.6 Hz, 1H), 7.81 (d, J = 7.8 Hz, 1H), 7.77 (d, J = 7.8 Hz, 1H), 7.61 (d, J = 7.8 Hz, 1H), 7.37-7.44 (m, 1H), 7.26-7.37 (m, 2H), 7.20 (td, J = 9.0, 5.9 Hz, 1H), 7.01 (t, J = 9.0 Hz, 1H), 4.25 (br. s., 1H), 3.19 (br. s., 2H), 3.12 (d, J = 12.1 Hz, 2H), 2.95-3.06 (m, 1H), 2.77-2.95 (m, 2H), 2.67 (s, 3H), 1.09 (d, J = 5.5 Hz, 3H) |
| 172 | 720.2 | $^1$H NMR (DMSO-$d_6$) δ: 10.56 (br. s, 1H), 9.83 (s, 1H), 8.70 (s, 1H), 8.49 (s, 1H), 8.39-8.47 (m, 2H), 8.34 (d, J = 8.2 Hz, 1H), 7.71-7.83 (m, 3H), 7.26-7.44 (m, 4H), 7.23 (t, J = 9.0 Hz, 1H), 4.78 (br. s., 1H), 3.89 (br. d, J = 9.4 Hz, 1H), 3.48-3.57 (m, 1H), 3.46 (s, 2H), 3.35-3.41 (m, 1H), 2.67 (s, 3H) |
| 173 | 720.2 | $^1$H NMR (DMSO-$d_6$) δ: 10.56 (br. s, 1H), 9.82 (s, 1H), 8.70 (s, 1H), 8.49 (s, 1H), 8.39-8.48 (m, 2H), 8.34 (d, J = 8.2 Hz, 1H), 7.70-7.82 (m, 3H), 7.26-7.45 (m, 4H), 7.22 (t, J = 9.0 Hz, 1H), 4.78 (br. s., 1H), 3.89 (br. d, J = 9.4 Hz, 1H), 3.51 (dt, J = 11.3, 2.3 Hz, 1H), 3.41-3.48 (m, J = 7.0 Hz, 2H), 3.35-3.41 (m, 1H), 2.67 (s, 3H) |
| 174 | 720.2 | $^1$H NMR (DMSO-$d_6$) δ: 10.56 (br. s., 1H), 9.79 (s, 1H), 8.66 (s, 1H), 8.49 (s, 1H), 8.39-8.46 (m, 2H), 8.36 (d, J = 8.2 Hz, 1H), 7.72-7.81 (m, 3H), 7.26-7.43 (m, 4H), 7.22 (d, J = 9.0 Hz, 1H), 4.93 (t, J = 5.1 Hz, 1H), 3.89-4.07 (m, 2H), 3.78-3.89 (m, J = 8.2 Hz, 1H), 3.71 (br. s., 1H), 3.54-3.66 (m, 2H), 3.46 (t, J = 10.8 Hz, 1H), 2.67 (s, 3H) |
| 175 | 705.2 | $^1$H NMR (DMSO-$d_6$) δ: 10.58 (br. s., 1H), 9.39 (s, 1H), 9.03 (d, J = 8.6 Hz, 1H), 8.63 (dd, J = 9.2, 6.5 Hz, 1H), 8.50 (s, 1H), 8.45 (dd, J = 9.2, 6.5 Hz, 1H), 8.27 (t, J = 8.0 Hz, 1H), 7.80 (d, J = 7.8 Hz, 1H), 7.73 (d, J = 8.2 Hz, 1H), 7.66 (t, J = 7.8 Hz, 1H), 7.49 (t, J = 7.4 Hz, 1H), 7.39 (t, J = 8.0 Hz, 1H), 7.26-7.35 (m, 1H), 7.23 (t, J = 9.4 Hz, 1H), 4.76 (dt, J = 11.3, 5.5 Hz, 1H), 4.13-4.27 (m, 1H), 4.08 (dt, J = 11.7, 7.4 Hz, 1H), 3.78-3.89 (m, 1H), 3.70-3.78 (m, 1H), 3.57-3.68 (m, 1H), 3.38-3.57 (m, 3H), 2.68 (s, 3H), 2.35-2.48 (m, 1H), 1.94-2.14 (m, 1H), 1.68-1.88 (m, 1H) |
| 176 | 705.2 | $^1$H NMR (DMSO-$d_6$) δ: 10.58 (br. s., 1H), 9.39 (s, 1H), 9.03 (d, J = 8.6 Hz, 1H), 8.62 (dd, J = 9.4, 6.3 Hz, 1H), 8.51 (s, 1H), 8.44 (ddt, J = 6.7, 2.3, 1.0 Hz, 1H), 8.27 (t, J = 8.0 Hz, 1H), 7.80 (d, J = 7.8 Hz, 1H), 7.73 (d, J = 7.8 Hz, 1H), 7.66 (t, J = 7.8 Hz, 1H), 7.49 (t, J = 7.6 Hz, 1H), 7.39 (t, J = 8.0 Hz, 1H), 7.26-7.35 (m, 1H), 7.21 (t, J = 9.0 Hz, 1H), 4.76 (dt, J = 11.0, 5.5 Hz, 1H), 4.15-4.28 (m, 1H), 4.07 (dt, J = 11.5, 7.5 Hz, 1H), 3.78-3.89 (m, 1H), 3.70-3.78 (m, 1H), 3.62 (dt, 12.1, 7.8 Hz, 1H), 3.37-3.57 (m, 3H), 2.69 (s, 3H), 2.35-2.48 (m, 1H), 1.95-2.15 (m, 1H), 1.68-1.88 (m, 1H) |
| 177 | 705.2 | $^1$H NMR (DMSO-$d_6$) δ: 10.58 (br. s., 1H), 9.38 (s, 1H), 9.02 (d, J = 8.6 Hz, 1H), 8.53-8.64 (m, 1H), 8.50 (s, 1H), 8.44 (d, J = 9.4 Hz, 1H), 7.99 (d, J = 8.2 Hz, 1H), 7.80 (d, J = 7.8 Hz, 1H), 7.74 (d, J = 8.2 Hz, 1H), 7.67 (t, J = 7.6 Hz, 1H), 7.48 (t, J = 7.6 Hz, 1H), 7.40 (t, J = 7.8 Hz, 1H), 7.31 (td, J = 8.2, 5.9 Hz, 1H), 7.23 (t, J = 9.0 Hz, 1H), 5.09 (d, J = 3.9 Hz, 0.5H), 4.85 (d, J = 3.9 Hz, 0.5H), 4.31 (br. dd., J = 12.9, 3.5 Hz, 0.5H), 4.09 (br. t, J = 10.2 Hz, 1H), 4.00 (br. d, J = 12.5 Hz, 0.5H), 3.63 (s, 1H), 3.36-3.46 (m, 2H), 2.69 (s, 3H), 1.75-2.02 (m, 2H), 1.43-1.63 (m, (2H) |
| 178 | 732.2 | $^1$H NMR (DMSO-$d_6$) δ: 10.56 (br. s., 1H), 9.80 (s, 1H), 8.62 (s, 1H), 8.48 (s, 1H), 8.38-8.46 (m, 2H), 8.36 (d, J = 8.2 Hz, 1H), 7.78 (d, J = 8.2 Hz, 1H), 7.74 (d, J = 8.2 Hz, 1H), 7.68 (br. d, J = 7.4 Hz, 1H), 7.39 (t, J = 7.8 Hz, 2H), 7.26-7.35 (m, 2H), 7.22 (t, J = 8.6 Hz, 1H), 4.51 (br. t, J = 4.9 Hz, 1H), 3.44 (br. s., 2H), 2.67 (s, 3H), 1.86-2.05 (m, 1H), 1.78 (dq, J = 13.7, 6.8 Hz, 1H), 1.65 (br. s., 6H), 1.33-1.52 (m, 1H) |
| 179 | 711.2 | $^1$H NMR (DMSO-$d_6$) δ: 10.56 (s, 1H), 9.34 (s, 1H), 8.90 (d, J = 8.6 Hz, 1H), 8.46 (s, 1H), 8.29 (d, J = 9.0 Hz, 1H), 8.11 (d, J = 7.8 Hz, 1H), 7.78 (d, J = 7.8 Hz, 1H), 7.74 (d, J = 7.8 Hz, 1H), 7.60 (t, J = 7.4 Hz, 1H), 7.45 (t, J = 7.4 Hz, 1H), 7.32-7.41 (m, 5H), 7.26-7.32 (m, 2H), 7.23 (t, J = 9.0 Hz, 1H), 3.55 (s, 3H), 2.66 (s, 3H) |

TABLE 4-continued

| | | |
|---|---|---|
| 180 | 724.1 | Formic acid salt: $^1$H NMR (DMSO-$d_6$) δ: 9.31 (br. s., 1H), 9.05 (d, J = 8.6 Hz, 1H), 8.57 (d, J = 9.0 Hz, 1H), 8.50 (s, 1H), 8.43 (d, J = 9.4 Hz, 1H), 8.03 (d, J = 7.8 Hz, 1H), 7.94 (dd, J = 7.8, 1.6 Hz, 1H), 7.79 (dd, J = 8.0, 1.4 Hz, 1H), 7.63-7.73 (m, 1H), 7.39-7.54 (m, 3H), 7.19 (td, J = 9.0, 5.9 Hz, 1H), 7.01 (t, J = 8.8 Hz, 1H), 4.87 (br. s., 1H), 4.50 (br. d, J = 13.3 Hz, 1H), 3.05 (br. s., 1H), 2.80-2.94 (m, 1H), 1.45 (br. s., 3H) |
| 181 | 675.1 | $^1$H NMR (DMSO-$d_6$) δ: 10.58 (br. s, 1H), 9.40 (s, 1H), 9.03 (d, J = 8.6 Hz, 1H), 8.63 (d, J = 9.4 Hz, 1H), 8.50 (s, 1H), 8.44 (d, J = 9.0 Hz, 1H), 8.28 (d, J = 7.8 Hz, 1H), 7.80 (d, J = 8.2 Hz, 1H), 7.75 (d, J = 8.2 Hz, 1H), 7.62-7.70 (m, J = 7.8, 7.8, 1.2 Hz, 1H), 7.49 (t, J = 7.6 Hz, 1H), 7.40 (t, J = 8.0 Hz, 1H), 7.31 (td, J = 8.2, 5.9 Hz, 1H), 7.26 (t, J = 9.0 Hz, 1H), 4.10 (t, J = 6.7 Hz, 2H), 3.65 (t, J = 6.8 Hz, 2H), 2.68 (s, 3H), 2.00 (q, J = 6.1 Hz, 2H), 1.94 (q, J = 6.4 Hz, 2H) |
| 182 | 705.2 | $^1$H NMR (DMSO-$d_6$) δ: 10.58 (s, 1H), 9.38 (s, 1H), 9.02 (d, J = 8.6 Hz, 1H), 8.53-8.65 (m, 1H), 8.50 (s, 1H), 8.44 (d, J = 9.0 Hz, 1H), 7.99 (d, J = 8.2 Hz, 1H), 7.80 (d, J = 8.2 Hz, 1H), 7.75 (d, J = 7.8 Hz, 1H), 7.67 (t, J = 7.6 Hz, 1H), 7.48 (t, J = 7.4 Hz, 1H), 7.40 (t, J = 8.0 Hz, 1H), 7.31 (td, J = 9.0, 5.5 Hz, 1H), 7.24 (t, J = 9.0 Hz, 1H), 5.09 (d, J = 3.9 Hz, 0.5H), 4.85 (d, J = 3.9 Hz, 0.5H), 4.09 (t, J = 10.2 Hz, 1H), 4.00 (br. d, J = 11.7 Hz, 0.5H), 3.55-3.71 (m, 1H), 3.36-3.47 (m, 2H), 3.05 (dd, J = 12.5, 9.0, 0.5H), 3.05 (dd, J = 12.5, 9.0, 0.5H), 2.68 (s, 3H), 2.00-1.76 (m, 2H), 1.41-1.63 (m, J = 7.8 Hz, 2H). |
| 183 | 705.2 | $^1$H NMR (DMSO-$d_6$) δ: 10.58 (br. s, 1H), 9.40 (s, 0.6H), 9.39 (s, 0.4H), 9.03 (d, J = 8.6 Hz, 1H), 8.67 (d, J = 9.0 Hz, 0.4H), 8.63 (d, J = 9.0 Hz, 0.6H), 8.51 (s, 1H), 8.44 (d, J = 9.4 Hz, 0.6H), 8.42 (d, J = 9.4 Hz, 0.4H), 8.27 (d, J = 7.8 Hz, 0.6H), 8.23 (d, J = 7.8 Hz, 0.4H), 7.80 (d, J = 7.8 Hz, 1H), 7.75 (d, J = 7.8 Hz, 1H), 7.66 (t, J = 7.8 Hz, 1H), 7.45-7.54 (m, 1H), 7.40 (t, J = 8.0 Hz, 1H), 7.32 (td, J = 8.6, 5.9 Hz, 1H), 7.17-7.28 (m, 1H), 4.87-4.95 (m, 1.3H), 4.34 (m, 0.6H), 4.00-4.18 (m, 1.3H), 3.59-3.77 (m, 1.8H), 3.55 (dt, J = 10.6, 6.5 Hz, 0.6H), 3.36-3.46 (m, 0.6H), 2.68 (s, 3H), 1.87-2.16 (m, 4H) |
| 184 | 705.2 | $^1$H NMR (DMSO-$d_6$) δ: 10.58 (br. s, 1H), 9.40 (s, 0.6H), 9.39 (s, 0.4H), 9.03 (d, J = 8.6 Hz, 1H), 8.67 (d, J = 9.0 Hz, 0.4H), 8.63 (d, J = 9.0 Hz, 0.6H), 8.51 (s, 1H), 8.44 (d, J = 9.4 Hz, 0.6H), 8.42 (d, J = 9.4 Hz, 0.4H), 8.27 (d, J = 7.8 Hz, 0.6H), 8.23 (d, J = 7.8 Hz, 0.4H), 7.80 (d, J = 7.8 Hz, 1H), 7.75 (d, J = 7.8 Hz, 1H), 7.66 (t, J = 7.8 Hz, 1H), 7.45-7.54 (m, 1H), 7.40 (t, J = 8.0 Hz, 1H), 7.32 (td, J = 8.6, 5.9 Hz, 1H), 7.17-7.28 (m, 1H), 4.87-4.95 (m, 1.3H), 4.34 (m, 0.6H), 4.00-4.18 (m, 1.3H), 3.59-3.77 (m, 1.8H), 3.55 (dt, J = 10.6, 6.5 Hz, 0.6H), 3.36-3.46 (m, 0.6H), 2.68 (s, 3H), 1.87-2.16 (m, 4H) |
| 185 | 721.2 | $^1$H NMR (DMSO-$d_6$) δ: 10.58 (br. s., 1H), 9.39 (s, 1H), 9.03 (d, J = 8.6 Hz, 1H), 8.60 (t, J = 9.4 Hz, 1H), 8.50 (s, 1H), 8.42 (t, J = 9.6 Hz, 1H), 8.08 (d, J = 8.2 Hz, 1H), 7.79 (dd, J = 7.8, 1.0 Hz, 1H), 7.74 (d, J = 8.2 Hz, 1H), 7.68 (t, J = 7.4 Hz, 1H), 7.50 (t, J = 7.6 Hz, 1H), 7.40 (t, J = 8.0 Hz, 1H), 7.31 (td, J = 9.0, 6.3 Hz, 1H), 7.23 (t, J = 9.0 Hz, 1H), 4.90 (t, J = 5.5 Hz, 0.5H), 4.90 (t, J = 5.5 Hz, 0.5H), 4.69 (d, J = 12.9 Hz, 0.5H), 4.63 (d, J = 12.9 Hz, 0.5H), 4.52 (d, J = 13.3 Hz, 0.5H), 4.47 (d, J = 13.3 Hz, 0.5H), 4.02 (d, J = 12.5 Hz, 0.5H), 3.92 (d, J = 12.5 Hz, 0.5H), 3.35-3.65 (m, 7H), 3.18 (dd, J = 13.1, 10.4 Hz, 0.5H), 3.10 (dt, J = 10.8, 3.1 Hz, 0.5H), 2.84 (dd, J = 12.9, 9.8 Hz, 0.5H), 2.68 (s, 3H) |
| 186 | 721.2 | $^1$H NMR (DMSO-$d_6$) δ: 10.58 (br. s., 1H), 9.39 (s, 1H), 9.03 (d, J = 8.6 Hz, 1H), 8.60 (t, J = 9.4 Hz, 1H), 8.50 (s, 1H), 8.42 (t, J = 9.6 Hz, 1H), 8.08 (d, J = 8.2 Hz, 1H), 7.79 (dd, J = 7.8, 1.0 Hz, 1H), 7.74 (d, J = 8.2 Hz, 1H), 7.68 (t, J = 7.4 Hz, 1H), 7.50 (t, J = 7.6 Hz, 1H), 7.40 (t, J = 8.0 Hz, 1H), 7.31 (td, J = 9.0, 6.3 Hz, 1H), 7.23 (t, J = 9.0 Hz, 1H), 4.90 (t, J = 5.5 Hz, 0.5H), 4.90 (t, J = 5.5 Hz, 0.5H), 4.69 (d, J = 12.9 Hz, 0.5H), 4.63 (d, J = 12.9 Hz, 0.5H), 4.52 (d, J = 13.3 Hz, 0.5H), 4.47 (d, J = 13.3 Hz, 0.5H), 4.02 (d, J = 12.5 Hz, 0.5H), 3.92 (d, J = 12.5 Hz, 0.5H), 3.35-3.65 (m, 7H), 3.18 (dd, J = 13.1, 10.4 Hz, 0.5H), 3.10 (dt, J = 10.8, 3.1 Hz, 0.5H), 2.84 (dd, J = 12.9, 9.8 Hz, 0.5H), 2.68 (s, 3H) |
| 187 | 725.1 | $^1$H NMR (DMSO-$d_6$) δ: 10.74 (br. s, 1H), 9.40 (s, 1H), 9.03 (d, J = 8.6 Hz, 1H), 8.64 (d, J = 6.7 Hz, 1H), 8.62 (d, J = 6.7 Hz, 1H), 8.49 (s, 1H), 8.46 (d, J = 6.7 Hz, 1H), 8.44 (d, J = 6.7 Hz, 1H), 8.27 (t, J = 8.2 Hz, 1H), 7.95 (d, J = 8.2 Hz, 1H), 7.91 (dd, J = 7.8, 1.6 Hz, 1H), 7.66 (t, J = 7.8 Hz, 1H), 7.54 (t, J = 8.0 Hz, 1H), 7.49 (t, J = 7.6 Hz, 1H), 7.32 (td, J = 8.6, 5.9 Hz, 1H), 7.24 (t, J = 8.8 Hz, 1H), 4.78 (t, J = 5.5 Hz, 0.5H), 4.75 (t, J = 5.5 Hz, 0.5H), 4.16-4.26 (m, 1H), 4.09 (t, J = 7.5 Hz, 0.5H), 4.06 (t, J = 7.5 Hz, 0.5H), 3.70-3.88 (m, 1.5H), 3.64 (t, J = 7.5 Hz, 0.5H), 3.61 (t, J = 7.5 Hz, 0.5H), 3.38-3.55 (m, 3H), 2.36-2.51 (m, 1H), 1.95-2.14 (m, 1H), 1.68-1.88 (m, 1H) |
| 188 | 704.2 | Formic acid salt: $^1$H NMR (DMSO-$d_6$) δ: 9.32 (br. s., 1H), 9.04 (d, J = 8.6 Hz, 1H), 8.57 (t, J = 9.0 Hz, 0.5H), 8.52 (t, J = 9.0 Hz, 0.5H), 8.50 (s, 1H), 8.44 (t, J = 8.8 Hz, 1H), 8.05 (t, J = 7.0 Hz, 1H), 7.82 (dd, J = 7.8, 1.0 Hz, 1H), 7.65-7.71 (m, 1H), 7.63 (d, J = 7.4 Hz, 1H), 7.49 (t, J = 7.4 Hz, 1H), 7.33 (t, J = 7.8 Hz, 1H), 7.24 (td, J = 9.0, 5.9 Hz, 1H), 7.06 (t, J = 9.0 Hz, 1H), 4.43-4.66 (m, 2H), 3.46 (t, J = 11.0 Hz, 0.5H), 3.02-3.29 (m, 2H), 2.95 (dt, J = 12.5, 3.1 Hz, 1H), 2.82 (t, J = 11.3 Hz, 0.5H), 2.68 (s, 3H), 1.21 (d, J = 6.3 Hz, 1H), 1.09 (d, J = 5.9 Hz, 2H) |
| 189 | 704.2 | Formic acid salt: $^1$H NMR (DMSO-$d_6$) δ: 9.32 (br. s., 1H), 9.04 (d, J = 8.6 Hz, 1H), 8.57 (t, J = 9.0 Hz, 0.5H), 8.52 (t, J = 9.0 Hz, 0.5H), 8.50 (s, 1H), 8.44 (t, J = 8.8 Hz, 1H), 8.05 (t, J = 7.0 Hz, 1H), 7.82 (dd, J = 7.8, 1.0 Hz, 1H), 7.65-7.71 (m, 1H), 7.63 (d, J = 7.4 Hz, 1H), 7.49 (t, J = 7.4 Hz, 1H), 7.33 (t, J = 7.8 Hz, 1H), 7.24 (td, J = 9.0, 5.9 Hz, 1H), 7.06 (t, J = 9.0 Hz, 1H), 4.43-4.66 (m, 2H), 3.46 (t, J = 11.0 Hz, 0.5H), 3.02-3.29 (m, 2H), 2.95 (dt, J = 12.5, 3.1 Hz, 1H), 2.82 (t, J = 11.3 Hz, 0.5H), 2.68 (s, 3H), 1.21 (d, J = 6.3 Hz, 1H), 1.09 (d, J = 5.9 Hz, 2H) |

TABLE 4-continued

| | | |
|---|---|---|
| 190 | 704.2 | Formic acid salt: $^1$H NMR (DMSO-$d_6$) δ: 9.32 (s, 1H), 9.04 (d, J = 8.6 Hz, 1H), 8.57 (d, J = 9.4 Hz, 1H), 8.50 (s, 1H), 8.44 (d, J = 9.0 Hz, 1H), 8.02 (d, J = 7.8 Hz, 1H), 7.82 (d, J = 7.8 Hz, 1H), 7.65-7.71 (m, 1H), 7.63 (d, J = 7.8 Hz, 1H), 7.49 (t, J = 7.4 Hz, 1H), 7.33 (t, J = 8.0 Hz, 1H), 7.24 (td, J = 8.9, 5.7 Hz, 1H), 7.06 (t, J = 8.8 Hz, 1H), 4.67-4.98 (br. m., 1H), 4.26-4.55 (br. m., 1H), 2.99 (br. s., 1H), 2.80 (dt, J = 12.5, 3.1 Hz, 2H), 2.68 (s, 3H), 1.45 (br. s., 3H) |
| 191 | 707.2 | $^1$H NMR (DMSO-$d_6$) δ: 10.58 (br. s., 1H), 9.38 (s, 1H), 9.03 (dd, J = 8.4, 3.3 Hz, 1H), 8.57 (d, J = 9.4 Hz, 1H), 8.51 (s, 1H), 8.45 (d, J = 9.0 Hz, 1H), 8.00 (t, J = 7.6 Hz, 1H), 7.80 (d, J = 8.2 Hz, 1H), 7.73 (d, J = 7.8 Hz, 1H), 7.67 (t, J = 7.8 Hz, 1H), 7.49 (t, J = 6.7 Hz, 1H), 7.39 (t, J = 8.0 Hz, 1H), 7.26-7.35 (m, 1H), 7.22 (br. t, J = 8.6 Hz, 1H), 4.87 (t, J = 51.6 Hz, 1H), 4.75 (br. s., 1H), 4.30-4.47 (m, 1H), 4.27 (dt, J = 12.5, 4.3 Hz, 0.5H), 4.13 (dt, J = 14.5, 4.3 Hz, 0.5H), 3.87 (dd, J = 26.2, 12.9 Hz, 0.5H), 3.53-3.72 (m, 1H), 2.68 (s, 3H), 1.79-2.05 (m, 3H), 1.65 (s, 1H) |
| 192 | 693.1 | $^1$H NMR (DMSO-$d_6$) δ: 10.59 (br. s., 1H), 9.38 (s, 1H), 9.05 (dd, J = 8.6, 3.5 Hz, 1H), 8.67 (dd, J = 9.0, 3.9 Hz, 1H), 8.51 (s, 1H), 8.44 (dd, J = 9.4, 3.9 Hz, 1H), 8.30 (t, J = 7.4 Hz, 1H), 7.81 (d, J = 7.8 Hz, 1H), 7.69 (br. s., 1H), 7.68 (dt, J = 8.6, 1.0 Hz, 1H), 7.51 (t, J = 7.4 Hz, 1H), 7.37 (t, J = 7.6 Hz, 1H), 7.24-7.33 (m, 1H), 7.16 (br. s., 1H), 5.55 (dt, J = 23.9, 3.1 Hz, 0.5H), 5.42 (dt, J = 23.9, 3.1 Hz, 0.5H), 4.39-4.57 (m, 1H), 4.30 (ddd, J = 39.5, 14.0, 3.5 Hz, 0.5H), 4.15 (dt, J = 11.2, 6.8 Hz, 0.5H), 3.75-4.04 (m, 1.5H), 3.68 (dt, J = 11.5, 7.0 Hz, 0.4H), 2.68 (s, 3H), 2.29-2.40 (m, 1H), 2.19-2.29 (m, 1H), 2.10-2.39 (m, 1H) |
| 193 | 693.1 | $^1$H NMR (DMSO-$d_6$) δ: 10.59 (br. s., 1H), 9.38 (s, 1H), 9.05 (dd, J = 8.6, 3.5 Hz, 1H), 8.67 (dd, J = 9.0, 3.9 Hz, 1H), 8.51 (s, 1H), 8.44 (dd, J = 9.4, 3.9 Hz, 1H), 8.30 (t, J = 7.4 Hz, 1H), 7.81 (d, J = 7.8 Hz, 1H), 7.69 (br. s., 1H), 7.68 (dt, J = 8.6, 1.0 Hz, 1H), 7.51 (t, J = 7.4 Hz, 1H), 7.37 (t, J = 7.6 Hz, 1H), 7.24-7.33 (m, 1H), 7.16 (br. s., 1H), 5.55 (dt, J = 23.9, 3.1 Hz, 0.5H), 5.42 (dt, J = 23.9, 3.1 Hz, 0.5H), 4.39-4.57 (m, 1H), 4.30 (ddd, J = 39.5, 14.0, 3.5 Hz, 0.5H), 4.15 (dt, J = 11.2, 6.8 Hz, 0.5H), 3.75-4.04 (m, 1.5H), 3.68 (dt, J = 11.5, 7.0 Hz, 0.4H), 2.68 (s, 3H), 2.29-2.40 (m, 1H), 2.19-2.29 (m, 1H), 2.10-2.39 (m, 1H) |
| 194 | 689.2 | $^1$H NMR (DMSO-$d_6$) δ: 10.58 (br. s, 1H), 9.40 (s, 1H), 9.03 (d, J = 8.2 Hz, 1H), 8.64 (d, J = 9.0 Hz, 0.6H), 8.59 (d, J = 9.0 Hz, 0.6H), 8.51 (s, 1H), 8.47 (d, J = 9.0 Hz, 0.4H), 8.44 (d, J = 9.0 Hz, 0.6H), 8.27 (d, J = 7.8 Hz, 0.6H), 8.24 (d, J = 7.8 Hz, 0.4H), 7.80 (d, J = 7.8 Hz, 1H), 7.75 (d, J = 8.2 Hz, 1H), 7.66 (t, J = 7.6 Hz, 1H), 7.49 (t, J = 7.4 Hz, 1H), 7.40 (t, J = 8.0 Hz, 1H), 7.32 (td, J = 8.7, 5.7 Hz, 1H), 7.25 (t, J = 9.0 Hz, 1H), 5.01 (quin, J = 6.3 Hz, 0.4H), 4.34-4.45 (m, 0.6H), 4.12-4.22 (m, 0.7H), 4.04 (dt, J = 11.4, 7.2 Hz, 0.7H), 3.65-3.74 (m, 0.7H), 2.68 (s, 3H), 2.00-2.17 (m, 2H), 1.88-2.00 (m, 1H), 1.77 (m, 0.4H), 1.65 (m, 0.6H), 1.33 (d, J = 6.3 Hz, 2H), 1.29 (d, J = 6.3 Hz, 1H) |
| 195 | 689.2 | $^1$H NMR (DMSO-$d_6$) δ: 10.58 (br. s, 1H), 9.40 (s, 1H), 9.03 (d, J = 8.2 Hz, 1H), 8.64 (d, J = 9.0 Hz, 0.6H), 8.59 (d, J = 9.0 Hz, 0.6H), 8.51 (s, 1H), 8.47 (d, J = 9.0 Hz, 0.4H), 8.44 (d, J = 9.0 Hz, 0.6H), 8.27 (d, J = 7.8 Hz, 0.6H), 8.24 (d, J = 7.8 Hz, 0.4H), 7.80 (d, J = 7.8 Hz, 1H), 7.75 (d, J = 8.2 Hz, 1H), 7.66 (t, J = 7.6 Hz, 1H), 7.49 (t, J = 7.4 Hz, 1H), 7.40 (t, J = 8.0 Hz, 1H), 7.32 (td, J = 8.7, 5.7 Hz, 1H), 7.25 (t, J = 9.0 Hz, 1H), 5.01 (quin, J = 6.3 Hz, 0.4H), 4.34-4.45 (m, 0.6H), 4.12-4.22 (m, 0.7H), 4.04 (td, J = 11.4, 7.2 Hz, 0.7H), 3.65-3.74 (m, 0.7H), 2.68 (s, 3H), 2.00-2.17 (m, 2H), 1.88-2.00 (m, 1H), 1.77 (m, 0.4H), 1.65 (m, 0.6H), 1.33 (d, J = 6.3 Hz, 2H), 1.29 (d, J = 6.3 Hz, 1H) |
| 196 | 719.2 | $^1$H NMR (DMSO-$d_6$) δ: 10.58 (s, 1H), 9.38 (s, 1H), 9.02 (d, J = 8.6 Hz, 1H), 8.56 (d, J = 9.4 Hz, 1H), 8.50 (s, 1H), 8.44 (d, J = 9.0 Hz, 1H), 8.00 (d, J = 7.8 Hz, 1H), 7.79 (d, J = 7.8 Hz, 1H), 7.75 (d, J = 7.8 Hz, 1H), 7.62-7.70 (m, 1H), 7.48 (t, J = 7.6 Hz, 1H), 7.40 (t, J = 8.0 Hz, 1H), 7.32 (td, J = 8.6, 5.5 Hz, 1H), 7.25 (t, J = 9.0 Hz, 1H), 4.51 (s, 1H), 4.24 (dt, J = 12.5, 3.1 Hz, 1H), 4.08 (dt, J = 13.3, 3.1 Hz, 1H), 3.56-3.67 (m, 1H), 3.35-3.43 (m, 1H), 2.68 (s, 3H), 1.53-1.69 (m, 4H), 1.21 (s, 3H) |
| 197 | 773.2 | $^1$H NMR (DMSO-$d_6$) δ: 10.58 (br. s., 1H), 9.38 (s, 1H), 9.03 (d, J = 8.6 Hz, 1H), 8.58 (d, J = 9.0 Hz, 1H), 8.50 (s, 1H), 8.45 (d, J = 9.0 Hz, 1H), 8.04 (br. d, J = 8.2 Hz, 1H), 7.80 (dd, J = 7.4, 1.0 Hz, 1H), 7.74 (d, J = 7.8 Hz, 1H), 7.67 (ddd, J = 9.4, 7.8, 1.2 Hz, 1H), 7.49 (t, J = 7.4 Hz, 1H), 7.39 (t, J = 8.0 Hz, 1H), 7.31 (td, J = 8.6, 5.9 Hz, 1H), 7.22 (t, J = 9.0 Hz, 1H), 6.24 (s, 1H), 4.65 (d, J = 12.9 Hz, 1H), 4.56 (d, J = 13.7 Hz, 1H), 3.43-3.56 (m, 1H), 3.16 (td, J = 12.5, 2.7 Hz, 1H), 2.68 (s, 3H), 1.72-1.95 (m, 4H) |
| 198 | 725.1 | $^1$H NMR (DMSO-$d_6$) δ: 10.74 (br. s, 1H), 9.38 (s, 1H), 9.02 (d, J = 8.6 Hz, 1H), 8.57 (d, J = 9.0 Hz, 1H), 8.49 (s, 1H), 8.44 (d, J = 9.0 Hz, 1H), 7.99 (d, J = 8.2 Hz, 1H), 7.96 (dd, J = 8.0, 1.4 Hz, 1H), 7.91 (dd, J = 8.0, 1.4 Hz, 1H), 7.67 (ddd, J = 9.0, 7.8, 0.8 Hz, 1H), 7.55 (t, J = 8.0 Hz, 1H), 7.48 (t, J = 7.4 Hz, 1H), 7.32 (td, J = 9.0, 5.9 Hz, 1H), 7.25 (t, J = 9.4 Hz, 1H), 4.85 (d, J = 4.3 Hz, 1H), 4.05-4.25 (m, 2H), 3.78-3.90 (m, 1H), 3.53 (ddd, J = 14.1, 11.0, 2.7 Hz, 1H), 3.40 (ddd, J = 13.3, 10.6, 2.7 Hz, 1H), 1.89 (br. t, J = 11.9 Hz, 2H), 1.43-1.58 (m, 2H) |
| 199 | 725.1 | $^1$H NMR (DMSO-$d_6$) δ: 10.58 (br. s, 1H), 9.39 (s, 1H), 9.03 (d, J = 8.6 Hz, 1H), 8.60 (d, J = 9.4 Hz, 1H), 8.50 (s, 1H), 8.45 (d, J = 9.0 Hz, 1H), 8.08 (d, J = 8.2 Hz, 1H), 7.79 (dd, J = 7.4, 1.0 Hz, 1H), 7.75 (d, J = 7.8 Hz, 1H), 7.68 (ddd, J = 9.0, 6.7, 1.2 Hz, 1H), 7.50 (t, J = 7.2 Hz, 1H), 7.40 (t, J = 8.0 Hz, 1H), 7.32 (td, J = 8.6, 5.5 Hz, 1H), 7.24 (t, J = 9.0 Hz, 1H), 4.07 (br. t, J = 4.7 Hz, 2H), 3.91 (br. t, J = 4.7 Hz, 2H), 2.68 (s, 3H), 2.16-2.27 (m, 3H), 2.12-2.26 (m, J = 14.1 Hz, 4H) |

TABLE 4-continued

| | | |
|---|---|---|
| 200 | 718.2 | Formic acid salt: $^1$H NMR (DMSO-$d_6$) δ: 9.30 (s, 1H), 9.05 (d, J = 8.6 Hz, 1H), 8.55 (d, J = 9.4 Hz, 1H), 8.50 (s, 1H), 8.45 (d, J = 9.0 Hz, 1H), 8.02 (d, J = 8.2 Hz, 1H), 7.83 (dd, J = 7.8, 0.8 Hz, 1H), 7.68 (ddd, J = 8.2, 6.7, 1.0 Hz, 1H), 7.59 (d, J = 7.8 Hz, 1H), 7.49 (t, J = 7.6 Hz, 1H), 7.31 (t, J = 8.0 Hz, 1H), 7.21 (td, J = 9.0, 5.9 Hz, 1H), 7.00 (t, J = 9.0 Hz, 1H), 4.78 (t, J = 6.3 Hz, 1H), 4.28 (d, J = 13.7 Hz, 1H), 3.30 (dd, J = 13.1, 4.5 Hz, 1H), 2.77 (d, J = 13.3 Hz, 1H), 2.68 (s, 3H), 1.45 (br. d, J = 6.3 Hz, 3H), 1.24 (d, J = 6.7 Hz, 3H) |
| 201 | 689.2 | $^1$H NMR (DMSO-$d_6$) δ: 10.58 (br. s, 1H), 9.40 (s, 1H), 9.02 (dd, J = 8.6, 2.0 Hz, 1H), 8.62 (dd, J = 9.2, 7.6 Hz, 1H), 8.51 (s, 1H), 8.45 (dd, J = 9.0, 7.0 Hz, 1H), 8.27 (t, J = 8.0 Hz, 1H), 7.80 (dd, J = 8.2, 1.0 Hz, 1H), 7.75 (d, J = 7.4 Hz, 1H), 7.66 (ddd, J = 9.0, 7.8, 1.0 Hz, 1H), 7.49 (t, J = 7.4 Hz, 1H), 7.40 (t, J = 8.0 Hz, 1H), 7.32 (td, J = 8.6, 5.9 Hz, 1H), 7.24 (t, J = 9.0 Hz, 1H), 4.19-4.33 (m, 1H), 4.05 (dt, J = 11.5, 7.7 Hz, 0.5H), 3.86 (dd, J = 11.9, 7.2 Hz, 0.5H), 3.78 (ddd, J = 12.1, 8.2, 3.9 Hz, 0.5H), 3.53-3.65 (m, 1H), 3.16 (dd, J = 11.9, 8.0 Hz, 0.5H), 2.68 (s, 3H), 2.26-2.45 (m, 1H), 2.02-2.20 (m, 1H), 1.49-1.72 (m, 1H), 1.12 (d, J = 6.7 Hz, 1.5H), 1.11 (d, J = 6.7 Hz, 1.5H) |
| 202 | 689.2 | $^1$H NMR (DMSO-$d_6$) δ: 10.52 (br. s, 1H), 9.42 (s, 1H), 9.02 (d, J = 8.6 Hz, 1H), 8.62 (dd, J = 9.0, 6.3 Hz, 1H), 8.50 (s, 1H), 8.45 (dd, J = 9.0, 6.7 Hz, 1H), 8.27 (t, J = 8.0 Hz, 1H), 7.61-7.70 (m, 2H), 7.49 (t, J = 8.0 Hz, 2H), 7.41 (dt, J = 7.8, 5.5 Hz, 1H), 7.31 (td, J = 8.6, 5.9 Hz, 1H), 7.24 (t, J = 9.0 Hz, 1H), 4.78 (t, J = 5.5 Hz, 0.5H), 4.74 (t, J = 5.5 Hz, 0.5H), 4.15-4.26 (m, 1H), 4.07 (dt, J = 11.6, 7.5 Hz, 0.5H), 3.84 (dd, J = 11.3, 6.7 Hz, 0.5H), 3.78-3.87 (m, 1H), 3.62 (dt, J = 11.7, 7.8 Hz, 0.5H), 3.38-3.55 (m, 3H), 2.34-2.48 (m, 1H), 1.95-2.13 (m, 1H), 1.67-1.88 (m, 1H) |
| 203 | 689.2 | $^1$H NMR (DMSO-$d_6$) δ: 10.52 (br. s, 1H), 9.37 (s, 1H), 9.02 (d, J = 8.2 Hz, 1H), 8.56 (d, J = 9.4 Hz, 1H), 8.49 (s, 1H), 8.44 (d, J = 9.4 Hz, 1H), 7.99 (d, J = 8.2 Hz, 1H), 7.67 (m, 1H), 7.63 (d, J = 7.8 Hz, 1H), 7.44-7.53 (m, 2H), 7.41 (td, J = 8.2, 5.5 Hz, 1H), 7.31 (td, J = 9.0, 5.9 Hz, 1H), 7.24 (t, J = 9.4 Hz, 1H), 4.85 (d, J = 3.9 Hz, 1H), 4.01-4.26 (m, 2H), 3.83 (td, J = 8.1, 4.1 Hz, 1H), 3.53 (ddd, J = 13.0, 9.8, 2.7 Hz, 1H), 3.39 (ddd, J = 12.0, 8.8, 2.7 Hz, 1H), 2.50 (s, 3H), 1.88 (br. t, J = 12.7 Hz, 2H), 1.38-1.59 (m, 2H) |
| 204 | 675.2 | $^1$H NMR (DMSO-$d_6$) δ: 10.51 (br. s, 1H), 9.39 (s, 1H), 9.02 (d, J = 8.6 Hz, 1H), 8.58 (d, J = 9.0 Hz, 1H), 8.49 (s, 1H), 8.43 (d, J = 9.0 Hz, 1H), 8.07 (d, J = 7.8 Hz, 1H), 7.65-7.71 (m, 1H), 7.63 (d, J = 7.8 Hz, 1H), 7.45-7.53 (m, 2H), 7.37-7.45 (m, 1H), 7.31 (dt, J = 9.0, 5.9 Hz, 1H), 7.23 (t, J = 9.0 Hz, 1H), 3.99 (br. t, J = 1.0 Hz, 2H), 3.73-3.85 (m, J = 7.0 Hz, 4H), 3.71 (br. t, J = 4.3 Hz, 2H), 2.50 (s, 3H) |
| 205 | 577.1 | Hydrochloride salt: $^1$H NMR (DMSO-$d_6$) δ: 10.58 (s, 1H), 10.42 (br. s., 1H), 9.65 (s, 1H), 8.70 (s, 1H), 8.54-8.66 (m, 2H), 8.06 (br. d, J = 7.8 Hz, 1H), 7.62 (d, J = 7.8 Hz, 1H), 7.37-7.54 (m, 3H), 7.13-7.37 (m, 3H), 2.50 (s, 3H) |
| 206 | 576.0 | Hydrochloride salt: $^1$H NMR (DMSO-$d_6$) δ: 10.54 (s, 1H), 9.68 (br. s., 1H), 8.82 (d, J = 9.0 Hz, 1H), 8.62 (s, 1H), 8.52 (d, J = 9.4 Hz, 1H), 7.95 (d, J = 8.2 Hz, 1H), 7.63 (d, J = 7.4 Hz, 1H), 7.49 (t, J = 8.2 Hz, 1H), 7.36-7.46 (m, 3H), 7.32 (td, J = 8.6, 5.9 Hz, 1H), 7.25 (t, J = 9.4 Hz, 2H), 6.64 (d, J = 7.8 Hz, 1H), 2.50 (s, 3H) |
| 207 | 663.1 | TFA salt: $^1$H NMR (DMSO-$d_6$) δ: 10.73 (br. s., 1H), 9.89 (s, 1H), 9.16 (s, 1H), 8.54 (d, J = 8.6 Hz, 1H), 8.53 (s, 1H), 8.46 (d, J = 8.2 Hz, 1H), 8.43 (d, J = 9.0 Hz, 1H), 8.10 (d, J = 7.8 Hz, 1H), 7.96 (d, J = 8.2 Hz, 1H), 7.90 (d, J = 8.2 Hz, 1H), 7.87 (s, 2H), 7.44-7.59 (m, 3H), 7.27-7.35 (m, 1H), 7.24 (t, J = 9.0 Hz, 1H) |
| 208 | 682.0 | $^1$H NMR (DMSO-$d_6$) δ: 13.03 (br. s., 1H), 10.74 (br. s., 1H), 9.44 (s, 1H), 9.07 (d, J = 8.6 Hz, 1H), 8.64 (d, J = 9.4 Hz, 1H), 8.50 (s, 1H), 8.46 (d, J = 9.4 Hz, 1H), 8.20 (d, J = 8.2 Hz, 1H), 7.95 (dd, J = 8.2, 1.2 Hz, 1H), 7.91 (dd, J = 7.8, 1.0 Hz, 1H), 7.74 (t, J = 7.6 Hz, 1H), 7.58 (t, J = 7.8 Hz, 1H), 7.54 (t, J = 7.8 Hz, 1H), 7.32 (td, J = 9.0, 6.0 Hz, 1H), 7.25 (t, J = 9.0 Hz, 1H) |
| 209 | 709.1 | $^1$H NMR (DMSO-$d_6$) δ: 10.74 (br. s., 1H), 9.41 (s, 1H), 9.06 (d, J = 8.6 Hz, 1H), 8.64 (d, J = 9.0 Hz, 1H), 8.40-8.58 (m, 2H), 8.32 (d, J = 7.8 Hz, 1H), 7.96 (br. d, J = 8.2 Hz, 1H), 7.91 (dd, J = 7.8, 1.0 Hz, 1H), 7.72 (t, J = 7.8 Hz, 1H), 7.57 (t, J = 8.6 Hz, 1H), 7.55 (t, J = 8.2 Hz, 1H), 7.33 (td, J = 8.6, 5.9 Hz, 1H), 7.25 (t, J = 9.4 Hz, 1H), 3.17 (s, 6H) |
| 210 | 695.1 | $^1$H NMR (DMSO-$d_6$) δ: 10.74 (s, 1H), 9.43 (s, 1H), 9.07 (d, J = 8.6 Hz, 1H), 8.60 (d, J = 9.4 Hz, 1H), 8.50 (s, 1H), 8.46 (d, J = 9.4 Hz, 1H), 8.34 (d, J = 8.2 Hz, 1H), 8.02 (q, J = 4.7 Hz, 1H), 7.96 (d, J = 7.8 Hz, 1H), 7.91 (d, J = 8.2 Hz, 1H), 7.73 (t, J = 7.8 Hz, 1H), 7.58 (t, J = 7.4 Hz, 1H), 7.55 (t, J = 8.2 Hz, 1H), 7.33 (td, J = 8.6, 5.9 Hz, 1H), 7.26 (t, J = 9.0 Hz, 1H), 2.96 (d, J = 4.7 Hz, 3H) |
| 211 | 681.1 | $^1$H NMR (DMSO-$d_6$) δ: 10.74 (s, 1H), 9.43 (s, 1H), 9.07 (d, J = 8.6 Hz, 1H), 8.59 (d, J = 9.4 Hz, 1H), 8.50 (s, 1H), 8.47 (d, J = 9.4 Hz, 1H), 8.35 (d, J = 8.2 Hz, 1H), 7.96 (dd, J = 8.2, 1.0 Hz, 1H), 7.91 (dd, J = 7.8, 1.2 Hz, 1H), 7.73 (t, J = 7.8 Hz, 1H), 7.63 (br. s, 2H), 7.58 (t, J = 7.8 Hz, 1H), 7.55 (t, J = 7.8 Hz, 1H), 7.33 (td, J = 9.0, 6.3 Hz, 1H), 7.25 (t, J = 9.0 Hz, 1H) |
| 212 | 664.1 | $^1$H NMR (DMSO-$d_6$) δ: 10.74 (s, 1H), 9.49 (br. s., 1H), 9.11 (d, J = 8.6 Hz, 1H), 8.81 (d, J = 9.4 Hz, 1H), 8.56 (d, J = 9.4 Hz, 1H), 8.53 (s, 1H), 8.48 (d, J = 7.8 Hz, 1H), 7.96 (dd, J = 8.2, 1.2 Hz, 1H), 7.92 (dd, J = 8.2, 1.0 Hz, 1H), 7.70-7.79 (m, 3H), 7.59 (t, J = 7.8 Hz, 1H), 7.55 (t, J = 7.8 Hz, 1H), 7.33 (td, J = 8.6, 5.9 Hz, 1H), 7.26 (t, J = 9.0 Hz, 1H) |
| 213 | 630.1 | $^1$H NMR (DMSO-$d_6$) δ: 10.54 (s, 1H), 9.48 (br. s., 1H), 9.11 (d, J = 8.6 Hz, 1H), 8.81 (d, J = 9.4 Hz, 1H), 8.55 (d, J = 7.8 Hz, 1H), 8.53 (s, 1H), 8.49 (d, J = 1.0 Hz, 1H), 7.93 (dd, J = 7.8, 1.2 Hz, 1H), 7.49-7.77 (m, 9H), 7.30 (td, J = 9.0, 6.3 Hz, 1H), 7.24 (t, J = 9.4 Hz, 1H) |
| 214 | 605.1 | $^1$H NMR (DMSO-$d_6$) δ: 10.53 (br. s., 1H), 9.83 (s, 1H), 9.15 (s, 1H), 8.48-8.54 (m, 3H), 8.35 (br. s, 1H), 8.33 (br. s, 1H), 7.91 (d, J = 7.4 Hz, 1H), 7.62-7.70 (m, 2H), 7.51 (t, J = 7.4 Hz, 1H), 7.35-7.46 (m, 2H), 7.28 (td, J = 9.0, 6.3 Hz, 1H), 7.22 (t, J = 9.0 Hz, 1H), 2.62 (s, 3H) |

TABLE 4-continued

| | | |
|---|---|---|
| 215 | 607.1 | TFA salt: $^{1}$H NMR (DMSO-$d_6$) δ: 10.54 (s, 1H), 9.85 (br. s, 1H), 9.45 (s, 1H), 8.85-9.04 (m, 2H), 8.44-8.60 (m, 4H), 7.92 (dd, J = 8.0, 1.4 Hz, 1H), 7.62-7.72 (m, 2H), 7.49-7.55 (m, 3H), 7.28 (td, J = 9.0, 5.5 Hz, 1H), 7.23 (t, J = 9.0 Hz, 1H), 4.61 (t, J = 5.7 Hz, 2H), 2.67 (t, J = 5.3 Hz, 3H) |
| 216 | 621.1 | TFA salt: $^{1}$H NMR (DMSO-$d_6$) δ: 10.54 (s, 1H), 9.85 (s, 1H), 9.75 (br. s., 1H), 9.45 (s, 1H), 8.49-8.58 (m, 4H), 7.92 (dd, J = 7.8, 1.6 Hz, 1H), 7.62-7.71 (m, 2H), 7.49-7.59 (m, 3H), 7.28 (td, J = 9.4, 6.3 Hz, 1H), 7.23 (t, J = 9.0 Hz, 1H), 4.74 (br. d, J = 2.3 Hz, 2H), 2.84 (d, J = 2.0 Hz, 6H) |
| 217 | 593.1 | TFA salt: $^{1}$H NMR (DMSO-$d_6$) δ: 10.54 (s, 1H), 9.85 (s, 1H), 9.46 (s, 1H), 8.49-8.59 (m, 3H), 8.44 (dd, J = 6.7, 2.7 Hz, 1H), 8.33 (br. s., 2H), 7.92 (dd, J = 7.8, 1.6 Hz, 1H), 7.62-7.72 (m, 2H), 7.48-7.55 (m, 3H), 7.28 (td, J = 9.0, 6.3 Hz, 1H), 7.23 (t, J = 9.4 Hz, 1H), 4.51 (q, J = 5.7 Hz, 2H) |
| 218 | 633.1 | TFA salt: $^{1}$H NMR (DMSO-$d_6$) δ: 10.54 (s, 1H), 10.08 (br. s., 1H), 9.83 (s, 1H), 9.45 (s, 1H), 8.56 (d, J = 9.0 Hz, 1H), 8.54 (s, 1H), 8.52 (d, J = 9.0 Hz, 1H), 8.50 (d, J = 7.4 Hz, 1H), 8.48 (dd, J = 8.0, 1.0 Hz, 1H), 7.92 (dd, J = 8.0, 1.4 Hz, 1H), 7.63-7.72 (m, 2H), 7.47-7.56 (m, 3H), 7.28 (td, J = 9.0, 5.9 Hz, 1H), 7.23 (t, J = 9.0 Hz, 1H), 4.81 (d, J = 5.9 Hz, 2H), 4.21-4.34 (m, 2H), 4.01-4.15 (m, 2H), 2.27 2.45 (m, 2H) |
| 219 | 647.2 | TFA salt: $^{1}$H NMR (DMSO-$d_6$) δ: 10.54 (s, 1H), 9.94 (br. s., 1H), 9.84 (s, 1H), 9.45 (s, 1H), 8.56 (d, J = 9.0 Hz, 1H), 8.54 (s, 1H), 8.52 (d, J = 9.0 Hz, 1H), 8.50 (d, J = 7.4 Hz, 1H), 7.92 (dd, J = 7.8, 1.6 Hz, 1H), 7.62-7.72 (m, 2H), 7.49-7.61 (m, 3H), 7.28 (td, J = 9.4, 5.9 Hz, 1H), 7.23 (t, J = 9.0 Hz, 1H), 4.81 (d, J = 5.1 Hz, 2H), 3.43 (br. s., 2H), 3.31 (br. s., 2H), 2.07 (br. s., 2H), 1.89 (br. s., 2H) |
| 220 | 663.2 | TFA salt: $^{1}$H NMR (DMSO-$d_6$) δ: 10.54 (s, 1H), 9.84 (s, 1H), 9.47 (s, 1H), 8.47-8.59 (m, 4H), 7.92 (dd, J = 8.0, 1.4 Hz, 1H), 7.48-7.73 (m, 5H), 7.28 (td, J = 9.0, 6.3 Hz, 1H), 7.23 (t, J = 9.0 Hz, 1H), 4.81 (s, 2H), 3.33 (br. s., 4H) |
| 221 | 635.2 | TFA salt: $^{1}$H NMR (DMSO-$d_6$) δ: 10.54 (s, 1H), 9.85 (s, 1H), 9.54 (br. s., 1H), 9.46 (s, 1H), 8.45-8.61 (m, 4H), 7.92 (dd, J = 7.8, 1.6 Hz, 1H), 7.62-7.72 (m, 2H), 7.48-7.62 (m, 3H), 7.28 (td, J = 9.4, 6.3 Hz, 1H), 7.23 (t, J = 9.0 Hz, 1H), 4.80 (br. d, J = 10.6 Hz, 1H), 4.70 (br. d, J = 9.8 Hz, 1H), 3.29 (br. s., 1H), 3.16 (br. s., 1H), 2.78 (d, J = 4.3 Hz, 3H), 1.32 (t, J = 7.2 Hz, 3H) |
| 222 | 635.2 | TFA salt: $^{1}$H NMR (DMSO-$d_6$) δ: 10.54 (s, 1H), 9.85 (s, 1H), 9.48 (s, 1H), 8.81-8.95 (m, 2H), 8.56 (d, J = 9.0 Hz, 1H), 8.54 (s, 1H), 8.51 (d, J = 9.4 Hz, 1H), 8.48 (d, J = 7.4 Hz, 1H), 7.92 (dd, J = 7.8, 1.2 Hz, 1H), 7.62-7.72 (m, 2H), 7.48-7.60 (m, 3H), 7.28 (td, J = 9.4, 6.7 Hz, 1H), 7.23 (t, J = 9.0 Hz, 1H), 4.62 (t, J = 5.9 Hz, 2H), 3.40 (spt, J = 6.3 Hz, 1H), 1.34 (d, J = 6.7 Hz, 6H) |
| 223 | 620.1 | TFA salt: $^{1}$H NMR (DMSO-$d_6$) δ: 10.53 (s, 1H), 9.81 (s, 1H), 9.30 (s, 1H), 8.57 (d, J = 8.2 Hz, 1H), 8.55 (s, 1H), 8.50 (d, J = 9.0 Hz, 1H), 8.41-8.47 (m, 1H), 8.30-8.36 (m, 1H), 8.26 (br. t, J = 4.7 Hz, 3H), 7.92 (dd, J = 7.8, 1.2 Hz, 1H), 7.62-7.72 (m, 2H), 7.43-7.56 (m, 3H), 7.28 (td, J = 8.6, 6.7 Hz, 1H), 7.23 (t, J = 9.4 Hz, 1H), 4.53 (q, J = 5.9 Hz, 2H) |
| 224 | 648.1 | $^{1}$H NMR (DMSO-$d_6$) δ: 9.82 (s, 1H), 9.20 (s, 1H), 8.53 (s, 1H), 8.51 (d, J = 7.4 Hz, 1H), 8.46 (d, J = 9.0 Hz, 1H), 8.36-8.41 (m, 1H), 8.29-8.36 (m, 1H), 7.92 (dd, J = 7.8, 1.6 Hz, 1H), 7.59-7.72 (m, 2H), 7.38-7.55 (m, 3H), 7.27 (td, J = 9.0, 5.9 Hz, 1H), 7.20 (t, J = 9.0 Hz, 1H), 4.21 (br. s., 2H), 2.56 (br. s, 6H) |
| 225 | 649.1 | $^{1}$H NMR (DMSO-$d_6$) δ: 9.81 (s, 1H), 9.33 (s, 1H), 8.52 (d, J = 9.0 Hz, 1H), 8.51 (s, 1H), 8.47 (d, J = 9.0 Hz, 1H), 8.28 (d, J = 7.8 Hz, 1H), 8.14 (s, 1H), 7.93 (dd, J = 7.8, 1.6 Hz, 1H), 7.55-7.68 (m, 2H), 7.45-7.50 (m, 1H), 7.32-7.45 (m, 2H), 7.23 (td, J = 8.8, 5.9 Hz, 1H), 7.12 (t, J = 9.0 Hz, 1H), 4.26 (quin, J = 5.9 Hz, 1H), 4.21 (s, 2H), 3.72 (t, J = 7.2 Hz, 2H), 3.15 (t, J = 7.4 Hz, 3H) |
| 226 | 663.2 | $^{1}$H NMR (DMSO-$d_6$) δ: 9.83 (s, 1H), 9.32 (s, 1H), 8.51 (s, 1H), 8.50 (d, J = 8.2 Hz, 1H), 8.47 (d, J = 9.0 Hz, 1H), 8.26 (br. d, J = 7.8 Hz, 1H), 7.92 (dd, J = 7.8, 1.2 Hz, 1H), 7.57-7.70 (m, 2H), 7.45-7.53 (m, 1H), 7.41 (t, J = 7.6 Hz, 1H), 7.34 (d, J = 7.0 Hz, 1H), 7.25 (td, J = 9.0, 5.9 Hz, 1H), 7.16 (t, J = 8.6 Hz, 1H), 4.15 (br. s., 2H), 4.02 (quin, J = 5.5 Hz, 1H), 3.16 (s, 3H), 3.11 (br. t, J = 4.7 Hz, 2H) |
| 227 | 651.1 | $^{1}$H NMR (DMSO-$d_6$) δ: 9.84 (s, 1H), 9.31 (s, 1H), 8.51 (d, J = 9.0 Hz, 1H), 8,51 (s, 1H), 8.47 (d, J = 9.0 Hz, 1H), 8.25 (d, J = 8.2 Hz, 1H), 7.92 (dd, J = 7.8, 1.2 Hz, 1H), 7.60-7.70 (m, 3H), 7.47-7.53 (m, 1H), 7.41 (t, J = 7.8 Hz, 1H), 7.33 (d, J = 7.4 Hz, 1H), 7.27 (td, J = 8.7, 5.7 Hz, 1H), 7.19 (t, J = 9.0 Hz, 1H), 5.20-5.34 (m, 1H), 5.12 (quin, J = 5.3 Hz, 1H), 4.12 (s, 2H), 3.55-3.74 (m, 2H) |
| 228 | 661.2 | $^{1}$H NMR (DMSO-$d_6$) δ: 9.80 (s, 1H), 9.31 (s, 1H), 8,51 (s, 1H), 8.51 (d, J = 9.0 Hz, 1H), 8.47 (d, J = 9.4 Hz, 1H), 8.29 (dd, J = 6.3, 2.7 Hz, 1H), 7.93 (dd, J = 7.8, 1.6 Hz, 1H), 7.56-7.68 (m, 2H), 7.45-7.51 (m, 1H), 7.39-7.45 (m, 2H), 7.24 (td, J = 8.8, 5.9 Hz, 1H), 7.13 (t, J = 9.2 Hz, 1H), 4.10 (s, 2H), 2.60 (br. s., 4H), 1.49-1.65 (m, 4H), 1.35-1.49 (m, 2H) |
| 229 | 677.2 | $^{1}$H NMR (DMSO-$d_6$) δ: 9.81 (br. s, 1H), 9.31 (s, 1H), 8.51 (s, 1H), 8.51 (d, J = 9.0 Hz, 1H), 8.47 (d, J = 9.4 Hz, 1H), 8.28 (dd, J = 7.4, 1.6 Hz, 1H), 8.15 (s, 1H), 7.92 (dd, J = 8.0, 1.4 Hz, 1H), 7.63-7.68 (m, 1H), 7.57-7.63 (m, 1H), 7.46-7.52 (m, 1H), 7.39-7.46 (m, 2H), 7.24 (td, J = 8.6, 5.9 Hz, 1H), 7.15 (t, J = 9.0 Hz, 1H), 4.61 (br. s., 1H), 4.10 (br. s., 2H), 3.51 (br. s., 1H), 2.79-3.00 (m, 2H), 2.33 (br. s., 2H), 1.75 (d, J = 9.8 Hz, 2H), 1.31-1.54 (m, 2H) |
| 230 | 662.2 | Bis-TFA salt: $^{1}$H NMR (DMSO-$d_6$) δ: 10.54 (s, 1H), 9.83 (s, 1H), 9.40 (s, 1H), 8.72 (br. s., 1H), 8.48-8.57 (m, 3H), 8.39-8.47 (m, 1H), 7.92 (dd, J = 7.8, 1.6 Hz, 1H), 7.68-7.72 (m, 1H), 7.66 (td, J = 8.2, 1.6 Hz, 1H), 7.47-7.55 (m, 3H), 7.17-7.33 (m, 2H), 4.44 (br. s., 2H), 3.25 (br. s., 4H), 3.06 (br. s., 4H) |

TABLE 4-continued

| | | |
|---|---|---|
| 231 | 693.2 | $^1$H NMR (DMSO-$d_6$) δ: 10.53 (br. s., 1H), 9.86 (s, 1H), 9.35 (s, 1H), 8.51 (s, 1H), 8.51 (d, J = 9.0 Hz, 1H), 8.47 (d, J = 9.0 Hz, 1H), 8.24 (br. d, J = 7.4 Hz, 1H), 7.92 (dd, J = 7.8, 1.2 Hz, 1H), 7.60-7.72 (m, 2H), 7.51 (ddd, J = 8.2, 7.0, 1.2 Hz, 1H), 7.35-7.44 (m, 2H), 7.28 (td, J = 9.0, 5.9 Hz, 1H), 7.21 (t, J = 9.4 Hz, 1H), 5.11 (br. s., 1H), 4.57 (d, J = 13.3 Hz, 1H), 3.79-3.86 (m, 1H), 3.78 (dd, J = 11.2, 2.9 Hz, 1H), 3.57-3.68 (m, 3H), 3.43 (t, J = 10.2 Hz, 1H), 2.63 (d, J = 12.1 Hz, 1H), 2.29 (br. t, J = 10.2 Hz, 1H) |
| 232 | 693.2 | $^1$H NMR (DMSO-$d_6$) δ: 10.53 (br. s., 1H), 9.86 (s, 1H), 9.35 (s, 1H), 8.51 (s, 1H), 8.51 (d, J = 9.0 Hz, 1H), 8.47 (d, J = 9.0 Hz, 1H), 8.24 (br. d, J = 7.4 Hz, 1H), 7.92 (dd, J = 7.8, 1.2 Hz, 1H), 7.60-7.72 (m, 2H), 7.51 (ddd, J = 8.2, 7.0, 1.2 Hz, 1H), 7.35-7.44 (m, 2H), 7.28 (td, J = 9.0, 5.9 Hz, 1H), 7.21 (t, J = 9.4 Hz, 1H), 5.11 (br. s., 1H), 4.57 (d, J = 13.3 Hz, 1H), 3.79-3.86 (m, 1H), 3.78 (dd, J = 11.2, 2.9 Hz, 1H), 3.57-3.68 (m, 3H), 3.43 (t, J = 10.2 Hz, 1H), 2.63 (d, J = 12.1 Hz, 1H), 2.29 (br. t, J = 10.2 Hz, 1H) |
| 233 | 691.2 | $^1$H NMR (DMSO-$d_6$) δ: 9.82 (s, 1H), 9.31 (s, 1H), 8.51 (s, 1H), 8.51 (d, J = 9.0 Hz, 1H), 8.47 (d, J = 9.4 Hz, 1H), 8.28 (dd, J = 6.1, 2.9 Hz, 1H), 8.14 (br. s, 1H), 7.92 (dd, J = 7.8, 1.2 Hz, 1H), 7.57-7.68 (m, 2H), 7.45-7.52 (m, 1H), 7.40-7.45 (m, 2H), 7.24 (td, J = 9.0, 5.5 Hz, 1H), 7.15 (t, J = 9.4 Hz, 1H), 4.11 (br. s., 2H), 3.29 (dd, J = 10.6, 5.5 Hz, 1H), 3.18 (dd, J = 10.6, 7.4 Hz, 1H), 3.05 (br. d, J = 10.2 Hz, 1H), 2.95 (br. d, J = 11.0 Hz, 1H), 2.21 (br. t, J = 10.6 Hz, 1H), 1.96 (br. t, J = 9.8 Hz, 1H), 1.45-1.75 (m, 4H), 0.86-1.02 (m, 1H) |
| 234 | 691.2 | $^1$H NMR (DMSO-$d_6$) δ: 9.82 (s, 1H), 9.31 (s, 1H), 8.51 (s, 1H), 8.51 (d, J = 9.0 Hz, 1H), 8.47 (d, J = 9.4 Hz, 1H), 8.28 (dd, J = 6.1, 2.9 Hz, 1H), 8.14 (br. s, 1H), 7.92 (dd, J = 7.8, 1.2 Hz, 1H), 7.57-7.68 (m, 2H), 7.45-7.52 (m, 1H), 7.40-7.45 (m, 2H), 7.24 (td, J = 9.0, 5.5 Hz, 1H), 7.15 (t, J = 9.4 Hz, 1H), 4.11 (br. s., 2H), 3.29 (dd, J = 10.6, 5.5 Hz, 1H), 3.18 (dd, J = 10.6, 7.4 Hz, 1H), 3.05 (br. d, J = 10.2 Hz, 1H), 2.95 (br. d, J = 11.0 Hz, 1H), 2.21 (br. t, J = 10.6 Hz, 1H), 1.96 (br. t, J = 9.8 Hz, 1H), 1.45-1.75 (m, 4H), 0.86-1.02 (m, 1H) |
| 235 | 677.2 | $^1$H NMR (DMSO-$d_6$) δ: 9.84 (s, 1H), 9.37 (s, 1H), 8.51 (s, 1H), 8.51 (d, J = 9.0 Hz, 1H), 8.48 (d, J = 9.0 Hz, 1H), 8.28 (dd, J = 7.0, 2.0 Hz, 1H), 8.14 (br. s., 1H), 7.92 (dd, J = 7.8, 1.2 Hz, 1H), 7.57-7.68 (m, 2H), 7.45-7.53 (m, 1H), 7.36-7.45 (m, 2H), 7.24 (td, J = 9.0, 5.9 Hz, 1H), 7.14 (t, J = 9.0 Hz, 1H), 4.58 (d, J = 13.3 Hz, 1H), 3.97 (br. d, J = 12.1 Hz, 1H), 3.53 (qd, J = 11.2, 4.9 Hz, 2H), 2.90 (br. s., 2H), 1.82-1.97 (m, 1H), 1.53-1.75 (m, 3H) |
| 236 | 677.2 | $^1$H NMR (DMSO-$d_6$) δ: 9.84 (s, 1H), 9.37 (s, 1H), 8.51 (s, 1H), 8.51 (d, J = 9.0 Hz, 1H), 8.48 (d, J = 9.0 Hz, 1H), 8.28 (dd, J = 7.0, 2.0 Hz, 1H), 8.14 (br. s., 1H), 7.92 (dd, J = 7.8, 1.2 Hz, 1H), 7.57-7.68 (m, 2H), 7.45-7.53 (m, 1H), 7.36-7.45 (m, 2H), 7.24 (td, J = 9.0, 5.9 Hz, 1H), 7.14 (t, J = 9.0 Hz, 1H), 4.58 (d, J = 13.3 Hz, 1H), 3.97 (br. d, J = 12.1 Hz, 1H), 3.53 (qd, J = 11.2, 4.9 Hz, 2H), 2.90 (br. s., 2H), 1.82-1.97 (m, 1H), 1.53-1.75 (m, 3H) |
| 237 | 677.2 | $^1$H NMR (DMSO-$d_6$) δ: 9.83 (s, 1H), 9.26 (s, 1H), 8.51 (s, 1H), 8.50 (d, J = 8.6 Hz, 1H), 8.47 (d, J = 9.0 Hz, 1H), 8.22 (dd, J = 7.4, 2.0 Hz, 1H), 7.92 (dd, J = 8.0, 1.4 Hz, 1H), 7.60-7.71 (m, 2H), 7.51 (ddd, J = 7.8, 6.7, 1.6 Hz, 1H), 7.37-7.46 (m, 2H), 7.28 (td, J = 9.0, 5.9 Hz, 1H), 7.21 (t, J = 9.0 Hz, 1H), 4.39 (q, J = 6.7 Hz, 1H), 3.58 (t, J = 4.5 Hz, 4H), 2.25-2.44 (m, 2H), 1.44 (d, J = 7.0 Hz, 3H) |
| 238 | 635.2 | TFA salt: $^1$H NMR (DMSO-$d_6$) δ: 10.54 (s, 1H), 9.93 (br. s., 1H), 9.88 (br. s., 1H), 9.43 (s, 1H), 8.56 (d, J = 8.6 Hz, 1H), 8.55 (s, 1H), 8.52 (d, J = 9.0 Hz, 1H), 8.49 (d, J = 7.8 Hz, 1H), 7.92 (dd, J = 7.8, 1.2 Hz, 1H), 7.63-7.72 (m, 2H), 7.54-7.63 (m, 2H), 7.48-7.54 (m, 1H), 7.28 (td, J = 9.0, 5.9 Hz, 1H), 7.23 (t, J = 9.0 Hz, 1H), 5.21 (quin, J = 5.9 Hz, 1H), 2.88 (br. s., 3H), 2.67 (br. s., 3H), 1.81 (d, J = 6.7 Hz, 3H) |
| 242 | 655.1 | $^1$H NMR (DMSO-$d_6$) δ: 10.74 (s, 1H), 9.98 (br. s., 1H), 9.20 (s, 1H), 8.53 (s, 1H), 8.46 (s, 2H), 7.96 (dd, J = 8.0, 1.4 Hz, 1H), 7.91 (dd, J = 7.8, 1.2 Hz, 1H), 7.54 (t, J = 8.0 Hz, 1H), 7.47 (d, J = 8.2 Hz, 1H), 7.24-7.37 (m, 2H), 7.22 (t, J = 8.2 Hz, 1H), 6.53 (d, J = 8.2 Hz, 1H), 3.25 (t, J = 7.0 Hz, 2H), 1.67 (sxt, J = 7.3 Hz, 2H), 0.97 (t, J = 7.4 Hz, 3H) |
| 243 | 641.1 | $^1$H NMR (DMSO-$d_6$) δ: 10.54 (s, 1H), 9.87 (s, 1H), 9.38 (s, 1H), 9.27 (br. s., 1H), 8.63 (br. s., 1H), 8.48-8.58 (m, 3H), 8.38-8.48 (m, 2H), 7.92 (dd, J = 7.8, 1.6 Hz, 1H), 7.68-7.74 (m, 2H), 7.65 (td, J = 7.4, 1.0 Hz, 1H), 7.57 (t, J = 7.8 Hz, 1H), 7.54-7.62 (m, 1H), 7.51 (td, J = 7.8, 1.6 Hz, 1H), 7.26-7.36 (m, 1H), 7.23 (t, J = 9.2 Hz, 1H) |
| 244 | 724.2 | $^1$H NMR (DMSO-$d_6$) δ: 10.52 (s, 1H), 9.40 (s, 1H), 9.00 (t, J = 8.4 Hz, 1H), 8.72 (d, J = 9.4 Hz, 0.65H), 8.58 (d, J = 9.4 Hz, 0.35H), 8.55 (d, J = 5.1 Hz, 0.35H), 8.50 (s, 1H), 8.42 (t, J = 9.8 Hz, 1H), 8.33 (d, J = 4.7 Hz, 0.65H), 7.98 (d, J = 7.8 Hz, 0.35H), 7.94 (d, J = 8.2 Hz, 0.65H), 7.76 (t, J = 7.6 Hz, 0.35H), 7.62-7.70 (m, 2H), 7.60 (t, J = 7.4 Hz, 0.65H), 7.38-7.54 (m, 3.35H), 7.19-7.36 (m, 3H), 7.07 (dd, J = 6.8, 5.3 Hz, 0.65H), 4.23 (t, J = 7.2 Hz, 1.3H), 3.96 (t, J = 7.6 Hz, 0.7H), 3.23 (t, J = 7.4 Hz, 1.3H), 3.17 (s, 2H), 3.16 (t, J = 7.4 Hz, 0.7H), 2.52 (s, 1H), 2.51 (s, 3H) |
| 245 | 718.2 | $^1$H NMR (DMSO-$d_6$) δ: 10.48 (br. s., 1H), 9.39 (s, 1H), 9.02 (d, J = 8.6 Hz, 1H), 8.58 (d, J = 9.0 Hz, 1H), 8.50 (s, 1H), 8.44 (d, J = 9.4 Hz, 1H), 8.04 (d, J = 8.2 Hz, 1H), 7.61-7.71 (m, 2H), 7.45-7.53 (m, 2H), 7.37-7.45 (m, 1H), 7.27-7.35 (m, 1H), 7.20-7.27 (m, 1H), 4.50 (br. s., 1H), 3.92 (br. s., 2H), 3.79 (br. s., 1H), 3.57 (br. s., 2H), 3.30 (s, 3H), 2.59 (br. s., 7H) |
| 246 | 710.2 | $^1$H NMR (DMSO-$d_6$) δ: 10.52 (s, 1H), 9.39 (br. s., 1H), 9.09 (t, J = 6.1 Hz, 1H), 9.05 (d, J = 8.6 Hz, 1H), 8.86 (d, J = 9.0 Hz, 1H), 8.53-8.58 (m, 1H), 8.51 (t, J = 4.7 Hz, 2H), 8.33 (d, J = 8.2 Hz, 1H), 7.71-7.77 (m, 1H), 7.61-7.69 (m, 2H), 7.51 (t, J = 7.4 Hz, 1H), 7.49 (br. s., 1H), 7.41 (br. s, 1H), 7.36 (d, J = 7.8 Hz, 1H), 7.30 (br. s., 1H), 7.17-7.28 (m, 2H), 3.75 (q, J = 6.9 Hz, 2H), 3.29 (s, 3H), 3.11 (t, J = 7.4 Hz, 2H) |

TABLE 4-continued

| | | |
|---|---|---|
| 247 | 696.2 | $^1$H NMR (DMSO-$d_6$) δ: 10.52 (br. s., 1H), 9.62 (t, J = 6.3 Hz, 1H), 9.41 (s, 1H), 9.07 (d, J = 8.6 Hz, 1H), 8.91 (d, J = 9.4 Hz, 1H), 8.54 (br. s., 2H), 8.48-8.52 (m, 2H), 8.33 (d, J = 7.8 Hz, 1H), 7.61-7.71 (m, 2H), 7.45-7.55 (m, 2H), 7.37-7.45 (m, 3H), 7.28-7.36 (m, 1H), 7.24 (t, J = 9.0 Hz, 1H), 4.63 (d, J = 6.3 Hz, 2H), 2.52 (s, 3H) |
| 248 | 703.2 | $^1$H NMR (DMSO-$d_6$) δ: 10.52 (s, 1H), 9.37 (s, 1H), 9.02 (d, J = 8.6 Hz, 1H), 8.56 (d, J = 9.0 Hz, 1H), 8.49 (s, 1H), 8.44 (d, J = 9.4 Hz, 1H), 7.99 (d, J = 8.2 Hz, 1H), 7.67 (t, J = 7.4 Hz, 1H), 7.64 (d, J = 7.4 Hz, 1H), 7.45-7.53 (m, 2H), 7.37-7.45 (m, 1H), 7.27-7.35 (m, 1H), 7.24 (t, J = 9.0 Hz, 1H), 4.51 (s, 1H), 4.24 (br. d, J = 13.3 Hz, 1H), 4.08 (br. d, J = 12.9 Hz, 1H), 3.55-3.68 (m, 1H), 3.35-3.41 (m, 1H), 2.51 (br. s., 3H), 1.55-1.68 (m, 4H), 1.21 (s, 3H) |
| 249 | 675.2 | $^1$H NMR (DMSO-$d_6$) δ: 10.52 (br. s., 1H), 9.41 (s, 1H), 9.05 (d, J = 8.6 Hz, 1H), 8.91 (d, J = 9.4 Hz, 1H), 8.78 (t, J = 6.1 Hz, 1H), 8.51 (s, 1H), 8.47-8.51 (m, 1H), 8.34 (d, J = 7.8 Hz, 1H), 7.66 (t, J = 7.1 Hz, 1H), 7.64 (d, J = 7.0 Hz, 1H), 7.45-7.55 (m, 2H), 7.43 (dd, J = 7.8, 5.9 Hz, 1H), 7.32 (dt, J = 8.2, 6.3 Hz, 1H), 7.25 (t, J = 9.0 Hz, 1H), 5.56 (s, 1H), 3.55 (d, J = 5.9 Hz, 2H), 2.51 (br. s., 3H), 0.58-0.70 (m, 4H) |
| 250 | 688.2 | $^1$H NMR (DMSO-$d_6$) δ: 10.46 (br. s., 1H), 9.39 (s, 1H), 9.02 (d, J = 8.6 Hz, 1H), 8.58 (d, J = 9.4 Hz, 1H), 8.50 (s, 1H), 8.44 (d, J = 9.0 Hz, 1H), 8.03 (d, J = 8.2 Hz, 1H), 7.67 (dd, J = 7.4 Hz, 1H), 7.64 (d, J = 7.8 Hz, 1H), 7.50 (d, J = 7.8 Hz, 1H), 7.48 (dd, J = 7.1, 3.5 Hz, 1H), 7.41 (td, J = 7.8, 5.5 Hz, 1H), 7.31 (td, J = 8.4, 5.9 Hz, 1H), 7.23 (t, J = 9.2 Hz, 1H), 3.96 (br. s., 2H), 3.82 (br. s., 2H), 3.30 (br. s., 3H), 2.57 (br. s., 4H), 2.33 (br. s., 3H) |
| 251 | 639.2 | $^1$H NMR (DMSO-$d_6$) δ: 10.52 (br. s., 1H), 9.86 (s, 1H), 9.36 (s, 1H), 9.26 (br. s., 1H), 8.62 (br. s., 1H), 8.47-8.54 (m, 3H), 8.44 (d, J = 8.2 Hz, 1H), 8.40 (d, J = 8.6 Hz, 1H), 7.67 (d, J = 7.8 Hz, 1H), 7.62 (d, J = 7.8 Hz, 1H), 7.56 (br. s, 1H), 7.55 (t, J = 7.8 Hz, 1H), 7.47 (t, J = 9.0 Hz, 1H), 7.39 (q, J = 7.5 Hz, 1H), 7.26-7.35 (m, 1H), 7.23 (t, J = 9.4 Hz, 1H), 2.51 (br. s., 3H) |
| 252 | 700.2 | $^1$H NMR (DMSO-$d_6$) δ: 9.32 (s, 1H), 9.04 (d, J = 8.6 Hz, 1H), 8.56 (d, J = 9.4 Hz, 1H), 8.50 (s, 1H), 8.44 (d, J = 9.4 Hz, 1H), 8.02 (d, J = 7.8 Hz, 1H), 7.61-7.75 (m, 2H), 7.49 (t, J = 7.4 Hz, 1H), 7.28-7.40 (m, 2H), 7.23 (td, J = 8.8, 6.3 Hz, 1H), 7.04 (t, J = 9.0 Hz, 1H), 4.46 (d, J = 13.7 Hz, 1H), 4.40 (d, J = 12.9 Hz, 1H), 3.88 (br. s., 1H), 3.74 (br. s., 1H), 3.57 (d, J = 13.3 Hz, 1H), 3.18 (d, J = 12.9 Hz, 1H), 2.52 (br. s., 3H), 1.73-1.93 (m, 4H) |
| 253 | 693.2 | $^1$H NMR (DMSO-$d_6$) δ: 10.52 (br. s., 1H), 9.39 (br. s, 1H), 9.01 (dd, J = 13.9, 8.4 Hz, 1H), 8.57-8.67 (m, 1H), 8.49 (br. s, 1H), 8.42 (t, J = 9.4 Hz, 1H), 8.05 (dd, J = 11.7, 7.8 Hz, 1H), 7.67 (t, J = 7.0 Hz, 1H), 7.64 (d, J = 8.2 Hz, 1H), 7.37-7.53 (m, 3H), 7.31 (td, J = 8.6, 5.9 Hz, 1H), 7.24 (t, J = 9.0 Hz, 1H), 4.93 (d, J = 5.5 Hz, 0.5H), 4.85 (d, J = 5.1 Hz, 0.5H), 4.68 (t, J = 5.9 Hz, 0.5H), 4.59 (t, J = 5.5 Hz, 0.5H), 3.87-3.99 (m, 1H), 3.71-3.87 (m, 1.5H), 3.42-3.50 (m, 1H), 3.43 (s, 1.5H), 3.21-3.30 (m, 1.5H), 3.19 (s, 1.5H), 2.52 (br. s., 3H) |
| 254 | 679.2 | $^1$H NMR (DMSO-$d_6$) δ: 10.52 (s, 1H), 9.40 (s, 1H), 9.05 (d, J = 8.6 Hz, 1H), 8.88 (d, J = 9.0 Hz, 1H), 8.75 (t, J = 5.9 Hz, 1H), 8.51 (s, 1H), 8.49 (d, J = 9.8 Hz, 1H), 8.34 (d, J = 8.2 Hz, 1H), 7.66 (ddd, J = 8.2, 7.1, 1.2 Hz, 1H), 7.64 (d, J = 7.0 Hz, 1H), 7.52 (d, J = 7.4 Hz, 1H), 7.48 (d, J = 8.6 Hz, 1H), 7.42 (td, J = 7.8, 5.5 Hz, 1H), 7.32 (td, J = 9.0, 5.9 Hz, 1H), 7.25 (t, J = 9.0 Hz, 1H), 4.94 (d, J = 4.7 Hz, 1H), 4.67 (t, J = 5.7 Hz, 1H), 3.74 (sxt, J = 5.6 Hz, 1H), 3.55 (dt, J = 13.1, 5.8 Hz, 1H), 3.43 (t, J = 5.5 Hz, 2H), 3.34-3.38 (m, 1H), 2.51 (br. s., 3H) |
| 255 | 691.2 | $^1$H NMR (DMSO-$d_6$) δ: 10.52 (s, 1H), 9.41 (s, 1H), 9.06 (d, J = 8.6 Hz, 1H), 8.95 (t, J = 6.5 Hz, 1H), 8.89 (d, J = 9.0 Hz, 1H), 8.51 (s, 1H), 8.50 (d, J = 9.4 Hz, 1H), 8.35 (d, J = 8.2 Hz, 1H), 7.67 (ddd, J = 8.2, 7.0, 1.2 Hz, 1H), 7.64 (d, J = 8.6 Hz, 1H), 7.53 (d, J = 7.8 Hz, 1H), 7.45-7.51 (m, 1H), 7.42 (dd, J = 8.0, 5.7 Hz, 1H), 7.32 (td, J = 8.7, 5.7 Hz, 1H), 7.24 (t, J = 9.2 Hz, 1H), 5.98 (s, 1H), 4.59 (d, J = 6.7 Hz, 2H), 4.46 (d, J = 6.7 Hz, 2H), 3.71 (d, J = 6.3 Hz, 2H), 2.51 (br. s. 3H) |
| 256 | 728.2 | Formic acid salt: $^1$H NMR (DMSO-$d_6$) δ: 9.30 (br. s., 0.5H), 9.27 (br. s., 0.5H), 9.06 (d, J = 8.6 Hz, 0.5H), 9.02 (d, J = 8.6 Hz, 0.5H), 8.63 (d, J = 6.7 Hz, 0.5H), 8.60 (d, J = 6.7 Hz, 0.5H), 8.51 (s, 0.5H), 8.50 (s, 0.5H), 8.43 (d, J = 9.4 Hz, 0.5H), 8.40 (d, J = 9.4 Hz, 0.5H), 8.29 (d, J = 8.2 Hz, 0.5H), 8.22 (d, J = 8.2 Hz, 0.5H), 7.61-7.72 (m, 2H), 7.48 (q, J = 7.0 Hz, 1H), 7.26-7.35 (m, 2H), 7.14-7.25 (m, 1H), 6.88-7.04 (m, 1H), 4.23 (t, J = 7.0 Hz, 1H), 4.00 (s, 1H), 3.74 (t, J = 7.0 Hz, 1H), 3.62 (s, 1H), 3.15 (t, J = 5.9 Hz, 2H), 3.05-3.13 (m, 2H), 2.51 (br. s., 3H), 2.00 (t, J = 6.8 Hz, 1H), 1.93 (t, J = 7.2 Hz, 1H), 1.69-1.86 (m, 4H) |
| 257 | 714.2 | $^1$H NMR (DMSO-$d_6$) δ: 9.30 (br. s., 1H), 9.03 (d, J = 8.6 Hz, 1H), 8.65 (d, J = 9.0 Hz, 1H), 8.50 (s, 1H), 8.38 (d, J = 9.0 Hz, 1H), 8.31 (d, J = 8.2 Hz, 1H), 7.62-7.71 (m, 2H), 7.49 (t, J = 7.4 Hz, 1H), 7.28-7.38 (m, 2H), 7.22 (td, J = 8.9, 6.1 Hz, 1H), 7.00 (t, J = 8.2 Hz, 1H), 4.60 (s, 2H), 3.98 (s, 2H), 3.14 (dtd, J = 18.6, 12.6, 5.9 Hz, 5H), 2.52 (d, J = 2.3 Hz, 3H), 2.00 (t, J = 5.1 Hz, 4H) |
| 258 | 700.2 | $^1$H NMR (DMSO-$d_6$) δ: 9.33 (br. s., 1H), 9.05 (d, J = 8.2 Hz, 1H), 8.70 (d, J = 9.0 Hz, 0.5H), 8.62 (d, J = 9.4 Hz, 0.5H), 8.52 (s, 0.5H), 8.51 (s, 0.5H), 8.44 (d, J = 9.0 Hz, 1H), 8.29 (d, J = 8.2 Hz, 0.5H), 8.28 (d, J = 8.2 Hz, 0.5H), 7.61-7.73 (m, 2H), 7.50 (t, J = 7.6 Hz, 1H), 7.28-7.41 (m, 2H), 7.17-7.28 (m, 1H), 7.05 (br. s., 1H), 4.36 (s, 1H), 4.20 (t, J = 6.8 Hz, 1H), 4.14 (d, J = 3.1 Hz, 1H), 4.11 (d, J = 3.1 Hz, 1H), 3.96 (t, J = 10.6 Hz, 2H), 3.90 (s, 1H), 3.69 (t, J = 6.8 Hz, 1H), 2.51 (br. s., 3H), 2.32 (t, J = 6.8 Hz, 1H), 2.24 (t, J = 6.8 Hz, 1H) |

TABLE 4-continued

| | | |
|---|---|---|
| 259 | 729.2 | Formic acid salt: $^1$H NMR (DMSO-$d_6$) δ: 9.29 (br. s., 1H), 9.06 (d, J = 8.6 Hz, 1H), 8.66 (d, J = 9.0 Hz, 1H), 8.51 (s, 1H), 8.41 (d, J = 9.0 Hz, 1H), 8.33 (d, J = 8.2 Hz, 1H), 7.65-7.69 (m, 2H), 7.50 (t, J = 7.6 Hz, 1H), 7.24-7.33 (m, 2H), 7.18 (td, J = 9.1, 6.1 Hz, 1H), 6.92 (t, J = 9.4 Hz, 1H), 4.85 (dd, J = 10.4, 7.2 Hz, 1H), 4.59 (dd, J = 10.4, 4.9 Hz, 1H), 4.22 (dd, J = 10.2, 7.0 Hz, 1H), 4.00 (dd, J = 10.0, 4.9 Hz, 1H), 3.53 (br. s., 1H), 3.08 (br. s., 4H), 2.58 (br. s., 4H), 2.51 (br. s., 3H) |
| 260 | 663.2 | $^1$H NMR (DMSO-$d_6$) δ: 10.52 (s, 1H), 9.40 (s, 1H), 9.05 (d, J = 8.6 Hz, 1H), 8.93 (br. t, J = 5.5 Hz, 1H), 8.90 (d, J = 9.4 Hz, 1H), 8.51 (s, 1H), 8.49 (d, J = 9.0 Hz, 1H), 8.33 (d, J = 7.8 Hz, 1H), 7.66 (ddd, J = 8.2, 7.0, 1.2 Hz, 1H), 7.64 (d, J = 6.7 Hz, 1H), 7.52 (d, J = 7.4 Hz, 1H), 7.48 (d, J = 7.8 Hz, 1H), 7.41 (td, J = 8.1, 5.7 Hz, 1H), 7.32 (td, J = 9.0, 5.7 Hz, 1H), 7.25 (br. t, J = 9.0 Hz, 1H), 3.56 (br. d, J = 2.0 Hz, 4H), 3.32 (s, 3H), 2.51 (br. s., 3H) |
| 261 | 677.2 | $^1$H NMR (DMSO-$d_6$) δ: 10.52 (br. s., 1H), 9.39 (br. s., 1H), 9.03 (d, J = 7.4 Hz, 0.5H), 9.01 (d, J = 7.4 Hz, 0.5H), 8.61 (d, J = 9.4 Hz, 0.5H), 8.55 (d, J = 9.0 Hz, 0.5H), 8.49 (s, 1H), 8.45 (d, J = 7.0 Hz, 0.5H), 8.43 (d, J = 7.1 Hz, 0.5H), 8.04 (t, J = 8.2 Hz, 1H), 7.60-7.71 (m, 2H), 7.45-7.54 (m, 2H), 7.36-7.45 (m, 1H), 7.28 7.36 (m, 1H), 7.24 (t, J = 9.0 Hz, 1H), 3.96 (t, J = 4.9 Hz, 1H), 3.79 (t, J = 5.5 Hz, 1H), 3.58-3.72 (m, 2H), 3.41 (s, 1.5H), 3.34 (s, 1.5H), 3.18 (s, 1.5H), 3.16 (s, 1.5H), 2.51 (br. s., 3H) |
| 262 | 677.2 | $^1$H NMR (DMSO-$d_6$) δ: 10.52 (s, 1H), 9.39 (s, 1H), 9.05 (d, J = 8.6 Hz, 1H), 8.94 (t, J = 5.9 Hz, 1H), 8.88 (d, J = 9.4 Hz, 1H), 8.51 (s, 1H), 8.49 (d, J = 8.2 Hz, 1H), 8.33 (d, J = 8.2 Hz, 1H), 7.60-7.70 (m, 2H), 7.46-7.53 (m, 2H), 7.42 (td, J = 8.0, 5.5 Hz, 1H), 7.32 (td, J = 8.6, 6.0 Hz, 1H), 7.25 (br. t, J = 9.0 Hz, 1H), 3.45 (t, J = 6.3 Hz, 4H), 3.28 (s, 3H), 2.51 (br. s., 3H), 1.86 (q. J = 6.7 Hz, 2H) |
| 263 | 696.2 | $^1$H NMR (DMSO-$d_6$) δ: 10.53 (s, 1H), 9.58 (t, J = 6.1 Hz, 1H), 9.41 (s, 1H), 9.07 (d, J = 8.6 Hz, 1H), 8.92 (d, J = 9.4 Hz, 1H), 8.56 (d, J = 3.9 Hz, 1H), 8.51 (s, 1H), 8.50 (d, J = 9.0 Hz, 1H), 8.34 (d, J = 8.2 Hz, 1H), 7.81 (td, J = 7.7, 1.8 Hz, 1H), 7.67 (ddd, J = 8.2, 7.0, 1.2 Hz, 1H), 7.64 (d, J = 9.0 Hz, 1H), 7.53 (d, J = 7.4 Hz, 1H), 7.45-7.50 (m, J = 12.1 Hz, 2H), 7.42 (td, J = 8.2, 5.9 Hz, 1H), 7.28-7.36 (m, 2H), 7.25 (t, J = 9.0 Hz, 1H), 4.71 (d, J = 6.3 Hz, 2H), 2.51-2.53 (m, 3H) |
| 264 | 710.2 | $^1$H NMR (DMSO-$d_6$) δ: 10.52 (br. s., 1H), 9.41 (s, 0.5H), 9.35 (s, 0.5H), 9.04 (d, J = 8.6 Hz, 0.5H), 8.97 (d, J = 8.2 Hz, 0.5H), 8.63 (d, J = 9.4 Hz, 0.5H), 8.60 (d, J = 5.1 Hz, 0.5H), 8.56 (d, J = 4.3 Hz, 0.5H), 8.50 (s, 0.5H), 8.47 (s, 0.5H), 8.43 (d, J = 9.4 Hz, 0.5H), 8.28 (d, J = 9.0 Hz, 0.5H), 8.14 (d, J = 7.4 Hz, 0.5H), 8.12 (d, J = 7.1 Hz, 0.5H), 8.02 (d, J = 9.4 Hz, 0.5H), 7.85 (td, J = 7.4, 1.6 Hz, 0.5H), 7.81 (td, J = 7.4, 1.6 Hz, 0.5H), 7.59-7.73 (m, 2H), 7.37-7.55 (m, 4H), 7.18-7.36 (m, 3H), 5.18 (s, 1H), 4.93 (s, 1H), 3.47 (s, 1.5H), 3.20 (s, 1.5H), 2.51 (br. s, 3H) |
| 265 | 724.2 | $^1$H NMR (DMSO-$d_6$) δ: 10.52 (br. s., 1H), 9.41 (s, 0.5H), 9.35 (s, 0.5H), 9.05 (d, J = 8.6 Hz, 0.5H), 8.98 (d, J = 8.6 Hz, 0.5H), 8.54-8.62 (m, 2.5H), 8.45-8.51 (m, 1.5H), 8.22 (d, J = 9.0 Hz, 0.5H), 8.15 (d, J = 7.8 Hz, 0.5H), 8.10 (d, J = 8.2 Hz, 0.5H), 7.93 (d, J = 9.4 Hz, 0.5H), 7.60-7.72 (m, 2H), 7.45-7.54 (m, 2H), 7.36-7.45 (m, 3H), 7.19-7.36 (m, 2H), 5.13 (s, 1H), 4.86 (s, 1H), 3.80 (q, J = 7.2 Hz, 1H), 3.61 (q, J = 7.0 Hz, 1H), 2.52 (br. s., 3H), 1.34 (t, J = 7.0 Hz, 1.5H), 1.25 (t, J = 7.0 Hz, 1.5H) |
| 266 | 710.2 | $^1$H NMR (DMSO-$d_6$) δ: 10.52 (br. s., 1H), 9.42 (s, 0.5H), 9.36 (s, 0.5H), 9.04 (d, J = 8.6 Hz, 0.5H), 8.98 (d, J = 8.6 Hz, 0.5H), 8.64 (d, J = 9.0 Hz, 0.5H), 8.59 (br. s., 2H), 8.50 (s, 0.5H), 8.47 (s, 0.5H), 8.43 (d, J = 9.0 Hz, 0.5H), 8.23 (d, J = 9.0 Hz, 0.5H), 8.14 (t, J = 7.8 Hz, 1H), 7.96 (d, J = 9.0 Hz, 0.5H), 7.58-7.73 (m, 2H), 7.45 7.55 (m, 2H), 7.36-7.45 (m, 3H), 7.19-7.36 (m, 2H), 5.13 (s, 1H), 4.88 (s, 1H), 3.45 (s, 1.5H), 3.15 (s, 1.5H), 2.52 (br. s, 3H) |
| 267 | 744.2 | Formic acid salt: $^1$H NMR (DMSO-$d_6$) δ: 9.25 (br. s, 1H), 9.05 (d, J = 8.6 Hz, 1H), 8.54 (d, J = 9.4 Hz, 1H), 8.50 (s, 1H), 8.41 (d, J = 9.4 Hz, 1H), 8.01 (d, J = 7.8 Hz, 1H), 7.63-7.72 (m, 2H), 7.47 (t, J = 7.6 Hz, 1H), 7.22-7.32 (m, 2H), 7.17 (td, J = 8.8, 6.3 Hz, 1H), 6.90 (t, J = 9.0 Hz, 1H), 4.03-4.21 (m, 2H), 3.79-4.03 (m, 3H), 3.61-3.79 (m, 4H), 2.51 (br. s., 3H), 2.24 (dd, J = 13.5, 8.0 Hz, 1H), 1.82-1.97 (m, 2H), 1.62-1.82 (m, 3H) |
| 268 | 689.2 | $^1$H NMR (DMSO-$d_6$) δ: 10.52 (s, 1H), 9.38 (s, 1H), 9.02 (d, J = 8.6 Hz, 1H), 8.59 (d, J = 9.4 Hz, 0.5H), 8.56 (d, J = 9.4 Hz, 0.5H), 8.49 (s, 1H), 8.44 (d, J = 9.4 Hz, 1H), 7.99 (d, J = 7.8 Hz, 1H), 7.67 (ddd, J = 8.2, 7.0, 1.2 Hz, 1H), 7.64 (d, J = 7.8 Hz, 1H), 7.45-7.53 (m, 2H), 7.41 (td, J = 8.1, 5.7 Hz, 1H), 7.31 (td, J = 8.8, 5.6 Hz, 1H), 7.24 (br. t, J = 9.0 Hz, 1H), 5.09 (d, J = 4.3 Hz, 0.5H), 4.85 (d, J = 3.9 Hz, 0.5H), 4.31 (dd, J = 12.7, 3.3 Hz, 0.5H), 4.07-4.15 (m, 1H), 3.95-4.04 (m, 0.5H), 3.57-3.70 (m, 1H), 3.36-3.44 (m, 1.5H), 3.05 (dd, J = 12.1, 8.6 Hz, 0.5H), 2.51 (br. s., 3H), 1.76-2.01 (m, 2H), 1.42-1.61 (m, 2H) |
| 269 | 689.2 | $^1$H NMR (DMSO-$d_6$) δ: 10.52 (s, 1H), 9.38 (s, 1H), 9.02 (d, J = 8.6 Hz, 1H), 8.59 (d, J = 9.0 Hz, 0.5H), 8.56 (d, J = 9.4 Hz, 0.5H), 8.49 (s, 1H), 8.44 (d, J = 9.0 Hz, 1H), 7.99 (d, J = 8.2 Hz, 1H), 7.67 (ddd, J = 8.2, 7.4, 0.8 Hz, 1H), 7.64 (d, J = 7.4 Hz, 1H), 7.45-7.53 (m, 2H), 7.41 (td, J = 7.8, 5.5 Hz, 1H), 7.31 (td, J = 8.6, 5.6 Hz, 1H), 7.24 (br. t, J = 9.0 Hz, 1H), 5.09 (d, J = 4.3 Hz, 0.5H), 4.85 (d, J = 3.9 Hz, 0.5H), 4.31 (dd, J = 12.1, 3.1 Hz, 0.5H), 4.04-4.15 (m, 1H), 3.95-4.04 (m, 0.5H), 3.57-3.70 (m, 1H), 3.36-3.45 (m, 1.5H), 3.05 (dd, J = 12.3, 8.8 Hz, 0.5H), 2.51 (br. s., 3H), 1.77-2.01 (m, 2H), 1.42-1.62 (m, 2H) |
| 270 | 724.2 | $^1$H NMR (DMSO-$d_6$) δ: 10.52 (br. s., 1H), 9.39 (s, 0.5H), 9.36 (s, 0.5H), 9.04 (d, J = 8.2 Hz, 0.5H), 9.02 (d, J = 8.2 Hz, 0.5H), 8.55-8.68 (m, 1.5H), 8.49 (s, 0.5H), 8.49 (s, 0.5H), 8.41 (d, J = 9.0 Hz, 0.5H), 8.38 (d, J = 9.4 Hz, 0.5H), 8.31 (d, J = 9.4 Hz, 0.5H), 8.08 (dd, J = 7.8, 4.7 Hz, 1H), 7.78-7.91 (m, 1H), 7.67 (t, J = 8.4 Hz, 1H), 7.64 (d, J = 7.8 Hz, 1H), 7.43-7.54 (m, 3H), 7.38-7.43 (m, 1H), 7.26-7.38 (m, 2H), 7.21 (br. t, J = 9.0 Hz, 1H), 6.06 (q, J = 7.0 Hz, 0.5H), 5.93 (q, J = 7.0 Hz, 0.5H), 3.18 (s, 1.5H), 2.93 (s, 1.5H), 2.51 (br. s., 3H), 1.74 (d, J = 7.0 Hz, 1.5H), 1.69 (d, J = 7.0 Hz, 1.5H) |

TABLE 4-continued

| | | |
|---|---|---|
| 271 | 696.2 | $^1$H NMR (DMSO-$d_6$) δ: 10.52 (s, 1H), 9.59 (t, J = 6.3 Hz, 1H), 9.41 (s, 1H), 9.06 (d, J = 8.6 Hz, 1H), 8.89 (d, J = 9.4 Hz, 1H), 8.66 (d, J = 2.0 Hz, 1H), 8.51 (s, 1H), 18.49 (dd, J = 5.1, 1.6 Hz, 1H), 8.49 (d, J = 9.3 Hz, 1H), 8.34 (d, J = 8.2 Hz, 1H), 7.84 (dt, J = 8.0, 1.7 Hz, 1H), 7.67 (ddd, J = 8.4, 7.0, 1.0 Hz, 1H), 7.64 (d, J = 7.8 Hz, 1H), 7.52 (d, J = 7.4 Hz, 1H), 7.48 (d, J = 9.0 Hz, 1H), 7.41 (td, J = 8.8, 5.3 Hz, 2H), 7.32 (td, J = 9.0, 5.7 Hz, 1H), 7.25 (br. t, J = 9.0 Hz, 1H), 4.63 (d, J = 6.3 Hz, 2H), 2.52 (br. s., 3H) |
| 272 | 640.1 | $^1$H NMR (DMSO-$d_6$) δ: 10.52 (s, 1H), 9.87 (s, 1H), 9.52 (br. s., 2H), 9.43 (s, 1H), 9.25 (br. s., 1H), 8.56 (d, J = 9.0 Hz, 1H), 8.47-8.55 (m, 3H), 7.81 (d, J = 7.4 Hz, 1H), 7.63 (d, J = 7.8 Hz, 1H), 7.61 (t, J = 7.8 Hz, 1H), 7.49 (t, J = 8.8 Hz, 1H), 7.41 (td, J = 8.0, 5.9 Hz, 1H), 7.31 (td, J = 8.6, 5.9 Hz, 1H), 7.24 (t, J = 9.2 Hz, 1H), 2.51 (br. s., 3H) |
| 273 | 639.1 | $^1$H NMR (DMSO-$d_6$) δ: 10.50 (br. s., 1H), 9.84 (s, 1H), 9.37 (s, 1H), 8.55 (s, 1H), 8.53 (br. s., 2H), 8.47 (d, J = 8.2 Hz, 1H), 7.77 (d, J = 7.8 Hz, 1H), 7.61 (d, J = 7.4 Hz, 1H), 7.56 (t, J = 7.8 Hz, 1H), 7.47 (t, J = 8.4 Hz, 1H), 7.39 (td, J = 7.9, 5.7 Hz, 1H), 7.29 (td, J = 8.6, 5.9 Hz, 1H), 7.22 (t, J = 9.0 Hz, 1H). |
| 274 | 649.1 | $^1$H NMR (DMSO-$d_6$) δ: 10.52 (s, 1H), 9.40 (s, 1H), 9.05 (d, J = 8.6 Hz, 1H), 8.89 (d, J = 9.0 Hz, 1H), 8.84 (t, J = 5.9 Hz, 1H), 8.51 (s, 1H), 8.49 (d, J = 9.0 Hz, 1H), 8.34 (d, J = 7.8 Hz, 1H), 7.66 (ddd, J = 8.2, 7.1, 1.2 Hz, 1H), 7.64 (br. d, J = 6.7 Hz, 1H), 7.50 (q, J = 7.4 Hz, 2H), 7.42 (td, J = 8.2, 5.5 Hz, 1H), 7.32 (td, J = 8.6, 5.7 Hz, 1H), 7.25 (br. t, J = 9.0 Hz, 1H), 4.84 (t, J = 5.5 Hz, 1H), 3.61 (q, J = 6.0 Hz, 2H), 3.47 (q, J = 6.1 Hz, 2H), 2.52 (br. s., 3H) |
| 275 | 663.1 | $^1$H NMR (DMSO-$d_6$) δ: 10.52 (br. s., 1H), 9.39 (s, 0.5H), 9.38 (s, 0.5H), 9.03 (d, J = 6.7 Hz, 0.5H), 9.01 (d, J = 6.7 Hz, 0.5H), 8.61 (d, J = 9.0 Hz, 0.5H), 8.56 (d, J = 9.0 Hz, 0.5H), 8.49 (s, 1H), 8.43 (d, J = 9.4 Hz, 1H), 8.06 (d, J = 8.2 Hz, 0.5H), 8.02 (d, J = 7.8 Hz, 0.5H), 7.61-7.71 (m, 2H), 7.44-7.52 (m, 2H), 7.41 (td, J = 7.8, 5.8 Hz, 1H), 7.31 (td, J = 8.6, 5.9 Hz, 1H), 7.24 (t, J = 9.0 Hz, 1H), 4.88 (t, J = 5.3 Hz, 0.5H), 4.76 (t, J = 5.5 Hz, 0.5H), 3.84 (t, J = 5.7 Hz, 1H), 3.64-3.76 (m, 3H), 3.42 (s, 1.5H), 3.17 (s, 1.5H), 2.52 (br. s., 3H) |
| 276 | 663.1 | $^1$H NMR (DMSO-$d_6$) δ: 10.52 (s, 1H), 9.39 (s, 1H), 9.05 (d, J = 8.6 Hz, 1H), 8.93 (t, J = 5.9 Hz, 1H), 8.88 (d, J = 9.0 Hz, 1H), 8.50 (s, 1H), 8.49 (d, J = 9.0 Hz, 1H), 18.33 (d, J = 8.2 Hz, 1H), 7.66 (ddd, J = 8.3, 7.1, 1.2 Hz, 1H), 7.64 (br. d, J = 7.5 Hz, 1H), 7.46-7.53 (m, 2H), 7.42 (td, J = 7.8, 5.5 Hz, 1H), 7.32 (td, J = 9.0, 5.5 Hz, 1H), 7.25 (br. t, J = 9.0 Hz, 1H), 4.57 (t, J = 5.1 Hz, 1H), 3.54 (q, J = 5.9 Hz, 2H), 3.45 (q, J = 6.7 Hz, 2H), 2.52 (br. s., 3H), 1.78 (quin, J = 6.7 Hz, 2H) |
| 277 | 633.1 | $^1$H NMR (DMSO-$d_6$) δ: 10.52 (br. s., 1H), 9.45 (s, 0.3H), 9.39 (s, 0.7H), 9.02 (d, J = 8.2 Hz, 0.3H), 9.01 (d, J = 8.6 Hz, 0.7H), 8.64 (d, J = 9.4 Hz, 0.3H), 8.60 (d, J = 9.4 Hz, 0.7H), 8.51 (s, 0.3H), 8.49 (s, 0.7H), 8.46 (d, J = 9.4 Hz, 0.3H), 8.43 (d, J = 9.4 Hz, 0.7H), 8.25 (d, J = 8.2 Hz, 0.3H), 8.06 (d, J = 7.8 Hz, 0.7H), 7.59-7.72 (m, 2H), 7.45-7.57 (m, 2H), 7.41 (td, J = 7.8, 5.5 Hz, 1H), 7.32 (td, J = 8.9, 6.1 Hz, 1H), 7.25 (br. t, J = 9.0 Hz, 1H), 3.39 (s, 3H), 3.15 (s, 3H), 2.51 (br. s., 3H) |
| 278 | 677.2 | $^1$H NMR (DMSO-$d_6$) δ: 10.52 (br. s., 1H), 9.40 (s, 1H), 9.02 (d, J = 8.6 Hz, 0.5H), 9.01 (d, J = 8.2 Hz, 0.5H), 8.64 (d, J = 9.4 Hz, 0.5H), 8.61 (d, J = 9.4 Hz, 0.5H), 8.49 (s, 1H), 8.43 (d, J = 4.7 Hz, 0.5H), 8.41 (d, J = 5.1 Hz, 0.5H), 8.05 (d, J = 8.2 Hz, 1H), 7.60-7.72 (m, 2H), 7.45-7.54 (m, 2H), 7.41 (td, J = 8.2, 5.5 Hz, 1H), 7.32 (td, J = 8.6, 5.9 Hz, 1H), 7.24 (br. t, J = 9.0 Hz, 1H), 4.58 (t, J = 5.3 Hz, 0.5H), 4.52 (t, J = 4.7 Hz, 0.5H), 3.82 (t, J = 7.4 Hz, 1H), 3.65 (t, J = 7.2 Hz, 1H), 3.55 (q, J = 5.9 Hz, 1H), 3.44 (q, J = 5.5 Hz, 1H), 3.37 (s, 1.5H), 3.14 (s, 1.5H), 2.52 (br. s., 1.5H), 2.51 (br. s., 1.5H), 1.89 (quin, J = 7.2 Hz, 1H), 1.84 (quin, J = 7.2 Hz, 1H) |
| 279 | 691.2 | $^1$H NMR (DMSO-$d_6$) δ: 10.52 (br. s., 1H), 9.40 (s, 1H), 9.02 (d, J = 8.6 Hz, 1H), 8.62 (d, J = 9.0 Hz, 0.5H), 8.61 (d, J = 9.4 Hz, 0.5H), 8.50 (br. s., 1H), 8.39-8.47 (m, 1H), 8.06 (d, J = 8.2 Hz, 1H), 7.66 (t, J = 7.8 Hz, 1H), 7.64 (d, J = 7.0 Hz, 1H), 7.45-7.55 (m, 2H), 7.41 (td, J = 7.8, 5.9 Hz, 1H), 7.32 (td, J = 8.6, 5.9 Hz, 1H), 7.24 (br. t, J = 9.0 Hz, 1H), 3.84 (t, J = 7.2 Hz, 1H), 3.64 (t, J = 7.2 Hz, 1H), 3.46 (t, J = 6.1 Hz, 1H), 3.39 (t, J = 6.2 Hz, 1H), 3.37 (s, 1.5H), 3.29 (s, 1.5H), 3.13 (s, 1.5H), 3.07 (s, 1.5H), 2.51 (br. s., 3H), 1.97 (quin, J = 6.7 Hz, 1H), 1.92 (quin, J = (6.7 Hz, 1H) |
| 280 | 675.2 | $^1$H NMR (DMSO-$d_6$) δ: 10.52 (br. s., 1H), 9.39 (s, 1H), 9.05 (d, J = 8.6 Hz, 1H), 9.03 (d, J = 7.8 Hz, 1H), 8.98 (d, J = 9.4 Hz, 1H), 8.51 (s, 1H), 8.48 (d, J = 9.4 Hz, 1H), 8.30 (br. d, J = 8.2 Hz, 1H), 7.65 (ddd, J = 8.6, 7.4, 1.6 Hz, 1H), 7.64 (br. d, J = 8.2 Hz, 1H), 7.46-7.53 (m, 2H), 7.41 (td, J = 7.8, 5.6 Hz, 1H), 7.32 (td, J = 8.2, 5.9 Hz, 1H), 7.24 (br. t, J = 9.0 Hz, 1H), 5.18 (d, J = 5.5 Hz, 1H), 3.99-4.12 (m, 1H), 3.93 (sxt, J = 6.9 Hz, 1H), 2.57-2.69 (m, 2H), 2.52 (br. s., 3H), 2.04-2.14 (m, 2H) |
| 281 | 675.2 | $^1$H NMR (DMSO-$d_6$) δ: 10.52 (br. s., 1H), 9.39 (s, 1H), 9.05 (d, J = 7.0 Hz, 1H), 9.03 (d, J = 5.9 Hz, 1H), 8.95 (d, J = 9.4 Hz, 1H), 8.51 (s, 1H), 8.49 (d, J = 9.4 Hz, 1H), 8.31 (br. d, J = 8.2 Hz, 1H), 7.66 (ddd, J = 8.2, 7.1, 1.2 Hz, 1H), 7.64 (br. d, J = 8.4 Hz, 1H), 7.45-7.53 (m, 2H), 7.42 (td, J = 7.8, 5.5 Hz, 1H), 7.32 (td, J = 9.0, 5.9 Hz, 1H), 7.25 (br. t, J = 9.0 Hz, 1H), 5.09 (d, J = 5.5 Hz, 1H), 4.56-4.68 (m, 1H), 4.35-4.45 (m, 1H), 2.52 (br. s., 3H), 2.39-2.48 (m, 2H), 2.19-2.29 (m, 2H) |
| 282 | 688.2 | Formic acid salt: $^1$H NMR (DMSO-$d_6$) δ: 9.33 (br. s., 1H), 9.04 (d, J = 8.6 Hz, 1H), 8.57 (d, J = 9.0 Hz, 1H), 8.50 (s, 1H), 8.44 (d, J = 9.0 Hz, 1H), 8.02 (d, J = 8.2 Hz, 1H), 7.63-7.71 (m, 2H), 7.48 (t, J = 7.2 Hz, 1H), 7.32-7.43 (m, 2H), 7.25 (td, J = 8.9, 5.7 Hz, 1H), 7.10 (td, J = 9.0, 1.2 Hz, 1H), 4.65-4.98 (m, 1H), 4.27-4.59 (m, 1H), 3.15 (br. s., 2H), 2.98 (br. s., 3H), 2.79 (td, J = 12.5, 3.1 Hz, 1H), 2.52 (br. s., 3H), 1.44 (br. s., 3H) |

TABLE 4-continued

| | | |
|---|---|---|
| 283 | 701.2 | $^1$H NMR (DMSO-$d_6$) δ: 10.52 (br. s., 1H), 9.40 (s, 1H), 9.03 (d, J = 8.2 Hz, 1H), 8.58 (d, J = 9.0 Hz, 1H), 8.50 (s, 1H), 8.44 (d, J = 9.0 Hz, 1H), 8.22 (d, J = 8.2 Hz, 1H), 7.61-7.73 (m, 2H), 7.45-7.55 (m, 2H), 7.37-7.45 (m, 1H), 7.17-7.36 (m, 2H), 5.24 (br. s, 1H), 4.75 (d, J = 5.9 Hz, 1H), 3.89 (d, J = 11.4 Hz, 1H), 3.80 (d, J = 10.8 Hz, 1H), 3.74 (s, 2H), 2.51 (br. s., 3H), 1.96-2.10 (m, 4H) |
| 284 | 686.2 | Formic acid salt: $^1$H NMR (DMSO-$d_6$) δ: 9.33 (s, 1H), 9.07 (d, J = 8.6 Hz, 1H), 8.64 (d, J = 9.0 Hz, 1H), 8.51 (s, 1H), 8.44 (d, J = 9.0 Hz, 1H), 8.24 (d, J = 8.2 Hz, 1H), 7.65-7.73 (m, 2H), 7.52 (ddd, J = 7.8, 7.4, 0.8 Hz, 1H), 7.28-7.38 (m, 2H), 7.22 (td, J = 9.0, 5.9 Hz, 1H), 7.01 (t, J = 9.4 Hz, 1H), 4.58 (d, J = 11.7 Hz, 1H), 4.49 (d, J = 12.5 Hz, 1H), 4.21 (br. s., 1H), 4.16 (br. s., 1H), 4.11 (d, J = 12.9 Hz, 1H), 3.98 (d, J = 12.9 Hz, 1H), 2.73-2.79 (m, 1H), 2.52 (br. s., 3H), 1.80 (d, J = 9.8 Hz, 1H) |
| 285 | 705.2 | $^1$H NMR (DMSO-$d_6$) δ: 10.53 (s, 1H), 9.53 (br. s., 1H), 9.02 (d, J = 8.6 Hz, 1H), 8.62 (t, J = 9.4 Hz, 1H), 8.54 (s, 1H), 8.43 (t, J = 9.2 Hz, 1H), 8.08 (d, J = 8.2 Hz, 1H), 7.68 (t, J = 7.8 Hz, 1H), 7.64 (d, J = 7.8 Hz, 1H), 7.51 (d, J = 8.2 Hz, 1H), 7.49 (dd, J = 8.2, 3.1 Hz, 1H), 7.42 (td, J = 7.8, 5.9 Hz, 1H), 7.32 (td, J = 8.2, 5.9 Hz, 1H), 7.25 (br. t, J = 9.0 Hz, 1H), 4.68 (d, J = 12.9 Hz, 0.5H), 4.62 (d, J = 13.3 Hz, 0.5H), 4.49 (t, J = 14.9 Hz, 1H), 4.02 (d, J = 9.0 Hz, 0.5H), 3.92 (d, J = 11.3 Hz, 0.5H), 3.52-3.69 (m, 5H), 3.04-3.22 (m, 1.5H), 2.84 (dd, J = 12.7, 10.8 Hz, 0.5H), 2.51 (br. s., 3H) |
| 286 | 705.2 | $^1$H NMR (DMSO-$d_6$) δ: 10.52 (s, 1H), 9.43 (br. s., 1H), 9.02 (d, J = 8.6 Hz, 1H), 8.61 (t, J = 9.4 Hz, 1H), 8.50 (s, 1H), 8.42 (t, J = 9.4 Hz, 1H), 8.07 (d, J = 7.8 Hz, 1H), 7.68 (t, J = 8.0 Hz, 1H), 7.64 (d, J = 7.8 Hz, 1H), 7.50 (d, J = 7.8 Hz, 1H), 7.48 (dd, J = 8.4, 2.0 Hz, 1H), 7.41 (td, J = 7.8, 5.5 Hz, 1H), 7.32 (td, J = 8.6, 5.9 Hz, 1H), 7.25 (t, J = 9.0 Hz, 1H), 4.69 (d, J = 13.3 Hz, 0.5H), 4.62 (d, J = 12.9 Hz, 0.5H), 4.52 (d, J = 14.0 Hz, 0.5H), 4.47 (d, J = 14.0 Hz, 0.5H), 4.02 (d, J = 9.0 Hz, 0.5H), 3.92 (d, J = 11.7 Hz, 0.5H), 3.43-3.67 (m, 5H), 3.03-3.22 (m, 1.5H), 2.80-2.91 (m, 0.5H), 2.51 (br. s., 3H) |
| 287 | 677.2 | $^1$H NMR (DMSO-$d_6$) δ: 10.52 (s, 1H), 9.41 (s, 1H), 9.05 (d, J = 8.6 Hz, 1H), 8.88 (d, J = 9.0 Hz, 1H), 8.55 (t, J = 6.1 Hz, 1H), 8.51 (s, 1H), 8.49 (d, J = 8.6 Hz, 1H), 8.34 (d, J = 8.2 Hz, 1H), 7.67 (ddd, J = 7.4, 6.4, 1.6 Hz, 1H), 7.64 (d, J = 7.8 Hz, 1H), 7.50 (q, J = 8.0 Hz, 2H), 7.41 (td, J = 7.8, 5.5 Hz, 1H), 7.32 (td, J = 9.0, 5.9 Hz, 1H), 7.25 (br. t, J = 9.0 Hz, 1H), 4.70 (s, 1H), 3.39 (s, 1H), 3.37 (s, 1H), 2.52 (br. s., 3H), 1.19 (s, 6H) |
| 288 | 724.2 | $^1$H NMR (DMSO-$d_6$) δ: 10.53 (s, 1H), 9.42 (s, 1H), 9.23 (s, 1H), 9.06 (d, J = 8.6 Hz, 1H), 8.94 (d, J = 9.0 Hz, 1H), 8.59-8.64 (m, 1H), 8.50-8.54 (m, 2H), 8.27 (d, J = 8.2 Hz, 1H), 7.82 (td, J = 7.7, 1.8 Hz, 1H), 7.66 (ddd, J = 8.2, 7.0, 1.2 Hz, 1H), 7.63 (t, J = 8.2 Hz, 2H), 7.45-7.53 (m, 2H), 7.42 (td, J = 8.2, 5.9 Hz, 1H), 7.28-7.36 (m, 2H), 7.25 (t, J = 9.0 Hz, 1H), 2.52 (br. s., 3H), 1.83 (s, 6H) |
| 289 | 710.2 | $^1$H NMR (DMSO-$d_6$) δ: 10.52 (br. s., 1H), 9.41 (s, 1H), 9.25 (d, J = 8.2 Hz, 1H), 9.07 (d, J = 8.6 Hz, 1H), 8.99 (d, J = 9.0 Hz, 1H), 8.59 (d, J = 5.1 Hz, 1H), 8.51 (s, 1H), 8.50 (d, J = 8.6 Hz, 1H), 8.31 (d, J = 7.8 Hz, 1H), 7.81 (td, J = 7.7, 1.8 Hz, 1H), 7.66 (ddd, J = 8.6, 7.4, 1.2 Hz, 1H), 7.64 (d, J = 7.0 Hz, 1H), 7.54 (d, J = 8.2 Hz, 1H), 7.45-7.52 (m, 2H), 7.41 (td, J = 7.8, 5.5 Hz, 1H), 7.28-7.35 (m, 2H), 7.24 (t, J = 9.0 Hz, 1H), 5.36 (quin, J = 7.2 Hz, 1H), 2.52 (br. s., 3H), 1.63 (d, J = 7.0 Hz, 3H) |
| 290 | 691.2 | $^1$H NMR (DMSO-$d_6$) δ: 10.52 (s, 1H), 9.39 (s, 0.5H), 9.38 (s, 0.5H), 9.03 (d, J = 8.6 Hz, 0.5H), 9.00 (d, J = 8.6 Hz, 0.5H), 8.62 (d, J = 9.0 Hz, 0.5H), 8.51 (d, J = 9.0 Hz, 0.5H), 8.49 (s, 1H), 8.40-8.47 (m, 1H), 8.00 (d, J = 7.8 Hz, 0.5H), 7.99 (d, J = 7.8 Hz, 0.5H), 7.67 (t, J = 7.8 Hz, 1H), 7.64 (d, J = 7.8 Hz, 1H), 7.49 (t, J = 8.2 Hz, 2H), 7.37-7.45 (m, 1H), 7.28-7.36 (m, 1H), 7.24 (t, J = 9.0 Hz, 1H), 4.68 (s, 0.5H), 4.54 (s, 0.5H), 3.90 (s, 1H), 3.62 (s, 1H), 3.44 (s, 1.5H), 3.25 (s, 1.5H), 2.51 (br. s., 3H), 1.23 (s, 3H), 0.99 (s, 3H) |
| 291 | 686.2 | $^1$H NMR (DMSO-$d_6$) δ: 10.54 (s, 1H), 9.62 (br. s., 1H), 9.58 (br. s., 0.5H), 9.50 (br. s, 0.5H), 9.10 (br. s., 0.5H), 9.05 (t, J = 7.6 Hz, 1H), 8.93 (br. s., 0.5H), 8.69 (d, J = 9.0 Hz, 0.5H), 8.64 (d, J = 9.4 Hz, 0.5H), 8.58 (s, 0.5H), 8.57 (s, 0.5H), 8.50 (d, J = 9.0 Hz, 0.5H), 8.47 (d, J = 9.4 Hz, 0.5H), 8.36 (d, J = 7.8 Hz, 0.5H), 8.26 (d, J = 7.8 Hz, 0.5H), 7.70 (t, J = 7.6 Hz, 1H), 7.64 (d, J = 7.8 Hz, 1H), 7.51-7.58 (m, 1H), 7.48 (d, J = 8.6 Hz, 1H), 7.42 (td, J = 7.8, 5.9 Hz, 1H), 7.32 (td, J = 9.4, 6.3 Hz, 1H), 7.26 (t, J = 9.0 Hz, 1H), 5.78 (s, 0.5H), 5.09 (s, 0.5H), 4.55 (br. s., 1H), 4.39-4.47 (m, 0.5H), 4.23-4.33 (m, 0.5H), 3.84 (br. d, J = 12.1 Hz, 0.5H), 3.76 (br. d, J = 12.1 Hz, 0.5H), 3.64-3.73 (m, 1H), 3.56-3.63 (m, 1H), 2.51-2.56 (m, 3H), 2.17-2.29 (m, 1H), 1.94-2.05 (m, 1H) |
| 292 | 732.2 | $^1$H NMR (DMSO-$d_6$) δ: 10.50 (br. s., 1H), 9.39 (s, 1H), 9.02 (d, J = 8.6 Hz, 1H), 8.60 (d, J = 9.4 Hz, 1H), 8.49 (s, 1H), 8.44 (d, J = 9.4 Hz, 1H), 8.06 (d, J = 8.2 Hz, 1H), 7.67 (ddd, J = 8.2, 7.0, 0.8 Hz, 1H), 7.64 (d, J = 7.8 Hz, 1H), 7.45-7.52 (m, 2H), 7.39-7.45 (m, 1H), 7.28-7.35 (m, 1H), 7.24 (t, J = 9.0 Hz, 1H), 3.94 (t, J = 6.3 Hz, 1H), 3.75 (t, J = 6.1 Hz, 1H), 3.62 (br. s., 1.5H), 3.37 (br. s., 2H), 3.24 (br. s., 1.5H), 3.16 (s, 2H), 2.63-2.71 (m, 1H), 2.60 (t, J = 5.5 Hz, 1H), 2.53-2.57 (m, 2H), 2.52 (br. s., 3H), 2.22 (br. s., 2H) |
| 293 | 700.2 | Formic acid salt: $^1$H NMR (DMSO-$d_6$) δ: 9.32 (br. s., 0.5H), 9.30 (br. s., 0.5H), 9.07 (d, J = 9.0 Hz, 0.5H), 9.04 (d, J = 8.6 Hz, 0.5H), 8.62 (d, J = 9.4 Hz, 0.5H), 8.55 (d, J = 9.0 Hz, 0.5H), 8.51 (s, 0.5H), 8.50 (s, 0.5H), 8.45 (d, J = 8.2 Hz, 0.5H), 8.43 (d, J = 8.2 Hz, 0.5H), 8.29 (d, J = 7.8 Hz, 0.5H), 8.13 (d, J = 8.6 Hz, 0.5H), 7.63-7.71 (m, 2H), 7.50 (q, J = 8.1 Hz, 1H), 7.27-7.36 (m, 2H), 7.20 (td, J = 8.9, 5.7 Hz, 1H), 6.98 (t, J = 8.8 Hz, 1H), 5.08 (br. s., 0.5H), 4.79 (br. s., 0.5H), 4.45 (d, J = 12.1 Hz, 0.5H), 4.32 (d, J = 12.5 Hz, 0.5H), 3.89 (d, J = 13.3 Hz, 0.5H), 3.78 (d, J = 7.0 Hz, 1H), 3.72 (d, J = 11.0 Hz, 0.5H), 3.48-3.55 (m, 2H), 2.51 (br. s., 3H), 2.23 (br. s., 0.5H), 2.04 (br. s., 1.5H), 1.87-2.01 (m, 2H) |

TABLE 4-continued

| | | |
|---|---|---|
| 294 | 711.2 | $^1$H NMR (DMSO-$d_6$) δ: 10.52 (br. s., 1H), 9.41 (s, 0.5H), 9.36 (s, 0.5H), 9.04 (d, J = 8.2 Hz, 0.5H), 8.96 (d, J = 8.6 Hz, 0.5H), 8.76 (s, 0.5H), 8.68 (s, 0.5H), 8.55-8.66 (m, 2H), 8.40-8.53 (m, 2H), 8.30 (d, J = 9.4 Hz, 0.5H), 8.11 (t, J = 8.2 Hz, 1H), 8.00 (d, J = 9.4 Hz, 0.5H), 7.59-7.71 (m, 2H), 7.45-7.54 (m, 2H), 7.41 (td, J = 8.0, 5.1 Hz, 1H), 7.32 (td, J = 8.6, 5.9 Hz, 1H), 7.25 (t, J = 9.0 Hz, 1H), 5.28 (s, 1H), 4.99 (s, 1H), 3.54 (s, 1.5H), 3.23 (s, 1.5H), 2.51 (br. s., 3H) |
| 295 | 674.2 | $^1$H NMR (DMSO-$d_6$) δ: 9.34 (s, 1H), 9.04 (d, J = 8.6 Hz, 1H), 8.59 (d, J = 9.0 Hz, 1H), 8.50 (s, 1H), 8.43 (d, J = 9.4 Hz, 1H), 8.06 (d, J = 8.2 Hz, 1H), 7.63-7.71 (m, 2H), 7.49 (t, J = 7.4 Hz, 1H), 7.31-7.42 (m, 2H), 7.24 (td, J = 8.9, 5.7 Hz, 1H), 7.08 (t, J = 9.0 Hz, 1H), 4.05 (br. s., 2H), 3.85 (br. s., 2H), 3.06 (br. s., 4H), 2.51 (br. s., 3H) |
| 296 | 711.2 | $^1$H NMR (DMSO-$d_6$) δ: 10.51 (br. s., 1H), 9.42 (s, 0.5H), 9.35 (s, 0.5H), 9.19 (d, J = 4.3 Hz, 0.5H), 9.19 (d, J = 4.3 Hz, 0.5H), 9.05 (d, J = 8.6 Hz, 0.5H), 8.96 (d, J = 8.2 Hz, 0.5H), 8.82 (d, J = 5.1 Hz, 0.5H), 8.79 (d, J = 5.5 Hz, 0.5H), 8.66 (d, J = 9.0 Hz, 0.5H), 8.50 (s, 0.5H), 8.47 (s, 0.5H), 8.45 (d, J = 9.4 Hz, 0.5H), 8.28 (d, J = 9.4 Hz, 0.5H), 8.17 (d, J = 8.2 Hz, 0.5H), 8.12 (d, J = 8.2 Hz, 0.5H), 7.91 (d, J = 9.4 Hz, 0.5H), 7.60-7.72 (m, 2H), 7.56 (d, J = 5.1 Hz, 1H), 7.45-7.54 (m, 2H), 7.36-7.45 (m, 1H), 7.18-7.36 (m, 2H), 5.24 (s, 1H), 4.94 (s, 1H), 3.56 (s, 1.5H), 3.25 (s, 1.5H), 2.52 (br. s., 3H) |
| 297 | 607.2 | $^1$H NMR (DMSO-$d_6$) δ: 10.34 (br. s., 1H), 9.87 (s, 1H), 9.17 (s, 1H), 8.49 (s, 1H), 8.45 (s, 2H), 7.59 (d, J = 9.0 Hz, 1H), 7.42 (d, J = 8.2 Hz, 1H), 7.27-7.33 (m, 1H), 7.22 (t, J = 9.0 Hz, 1H), 7.14 (t, J = 8.6 Hz, 1H), 7.12 (t, J = 7.8 Hz, 1H), 6.57 (d, J = 7.8 Hz, 1H), 5.52 (br. s., 2H), 3.88 (s, 3H), 2.51 (br. s., 3H) |
| 298 | 623.2 | $^1$H NMR (DMSO-$d_6$) δ: 10.40 (br. s., 1H), 9.86 (s, 1H), 9.16 (s, 1H), 8.47 (s, 1H), 8.44 (s, 2H), 7.77 (d, J = 9.0 Hz, 2H), 7.41 (dd, J = 8.2 Hz, 2H), 7.30 (td, J = 8.7, 5.7 Hz, 2H), 7.21 (t, J = 9.0 Hz, 2H), 7.13 (d, J = 9.0 Hz, 1H), 7.11 (t, J = 8.0 Hz, 1H), 6.57 (dd, J = 7.8, 0.8 Hz, 2H), 5.51 (br. s., 2H), 3.91 (s, 3H), 2.66 (s, 3H) |
| 299 | 710.1 | $^1$H NMR (DMSO-$d_6$) δ: 10.52 (br. s., 1H), 9.39 (d, J = 12.1 Hz, 1H), 9.02 (dd, J = 13.9, 8.4 Hz, 1H), 8.68 br. s., 1H), 8.62 (d, J = 9.0 Hz. 1H), 8.56 (d, J = 12.9 Hz, 1H), 8.48 (d, J = 8.6 Hz, 1H), 8.28-8.43 (m, 1H), 8.12 (d, J = 8.2 Hz, 1H), 7.84 (dd, J = 12.7, 8.0 Hz, 1H), 7.60-7.72 (m, 2H), 7.36-7.53 (m, 4H), 7.19-7.36 (m, 2H), 5.12 (s, 1H), 4.87 (s, 1H), 3.41 (s, 2H), 3.11 (s, 1H) |
| 300 | 573.4 | $^1$H NMR (MeOH-$d_4$) δ: 9.03 (s, 1H), 8.33-8.51 (m, 3H), 7.85 (dd, J = 7.8, 1.2 Hz, 1H), 7.49-7.55 (m, 1H), 7.39-7.45 (m, 3H), 7.25-7.32 (m, 1H), 7.21 (t, J = 8.0 Hz, 1H), 7.05 (td, J = 9.2, 2.0 Hz, 1H), 6.69 (d, J = 7.8 Hz, 1H), 3.08 (q, J = 7.4 Hz, 2H), 1.27 (t, J = 1.0 Hz, 3 H). |
| 301 | 591.4 | $^1$H NMR (DMSO-$d_6$) δ: 9.83 (s, 1H), 9.16 (s, 1H), 8.48 (s, 1H), 8.42 (s, 2H), 7.63 (d, J = 7.8 Hz, 1H), 7.39 (m, J = 7.8 Hz, 2H), 7.17-7.27 (m, 1H), 7.10 (t, J = 8.0 Hz, 1H), 6.46-6.59 (m, 1H), 5.49 (br. s., 1H), 3.00 (m, J = 7.4 Hz, 2H), 1.15 (t, J = 7.4 Hz, 3 H). |
| 302 | 627.2 | $^1$H NMR (DMSO-$d_6$) δ: 9.80 (s, 1H), 9.15 (s, 1H), 8.42 (s, 3H), 8.09 (d, J = 7.8 Hz, 1H), 7.85-7.96 (m, 1H), 7.48-7.57 (m, 1H), 7.38 (s, 1 H) 7.18-7.29 (m, 1 H), 7.09 (s, 1H), 6.54 (m, J = 7.8 Hz, 1H), 2.75 (s, 3 H). |
| 303 | 607.3 | $^1$H NMR (DMSO-$d_6$) δ: 10.62 (br. s., 1H), 9.87 (s, 1H), 9.17 (s, 1H), 8.50 (s, 1H), 8.44 (s, 2H), 7.78 (d, J = 7.43 Hz, 1H), 7.72 (br. d, J = 1.00 Hz, 1H), 7.40 (d, J = 7.83 Hz, 1H), 7.38 (t, J = 16.40 Hz, 1H), 7.15-7.31 (m, 2H), 7.11 (t, J = 8.02 Hz, 1H), 6.57 (d, J = 7.83 Hz, 1H), 5.51 (br. s., 2H), 3.15 (q, J = 7.30 Hz, 2H), 1.20 (t, J = 7.43 Hz, 3H) |
| 304 | 723-3 | $^1$H NMR (DMSO-$d_6$) δ: 9.96 (s, 1H), 8.86 (s, 1H), 8.52 (s, 1H), 8.48 (dd, J = 14.5, 9.0 Hz, 2H), 8.30 (d, J = 8.2 Hz, 1H), 7.95 (d, J = 7.4 Hz, 1H), 7.62 (d, J = 7.8 Hz, 1H), 7.36-7.50 (m, 4H), 7.29 (td, J = 8.7, 5.7 Hz, 1H), 7.21 (t, J = 9.4 Hz, 1H), 3.05 (br. s., 4H), 2.50 (s, 3H), 2.40 (m, 4H), 2.14 (s, 3H). |
| 305 | 745.4 | $^1$H NMR (DMSO-$d_6$) δ: 10.50 (s, 1H), 9.94 (s, 1H), 8.98 (s, 1H), 8.58 (br. s., 1H), 8.47-8.52 (m, 3H), 8.35 (d, J = 8.2 Hz, 1H), 8.02 (d, J = 7.8 Hz, 1H), 7.61 (d, J = 8.2 Hz, 1H), 7.21-7.52 (m, 9H), 4.34 (s, 2H), 2.74 (s, 3H), 2.50 (s, 3H). |
| 306 | 710.3 | $^1$H NMR (DMSO-$d_6$) δ: 10.51 (br. s., 1H), 9.96 (s, 1H), 8.89 (s, 1H), 8.42-8.55 (m, 3H), 8.31 (d, J = 8.2 Hz, 1H), 7.95 (d, J = 7.4 Hz, 1H), 7.62 (d, J = 7.8 Hz, 1H), 7.34-7.53 (m, 4H), 7.23-7.33 (m, 1H), 7.19 (dd, J = 11.0, 9.0 Hz, 1H), 3.65 (t, J = 4.3 Hz, 4H), 3.03 (t, J = 4.3 Hz, 4H |
| 307 | 738.2 | $^1$H NMR (DMSO-$d_6$) δ: 10.50 (s, 1H), 9.93 (s, 1H), 8.86 (s, 1H), 8.43-8.54 (m, 3H), 8.32 (d, J = 8.2 Hz, 1H), 7.95 (d, J = 7.8 Hz, 1H), 7.62 (d, J = 7.8 Hz, 1H), 7.37-7.52 (m, 4H), 7.27-7.34 (m, 1H), 7.23 (dd, J = 9.8 Hz, 1H), 4.45 (t, J = 5.3 Hz, 1H), 3.79 (d, J = 12.1 Hz, 2H), 3.20 (t, J = 5.7 Hz, 2H), 2.37 (t, J = 11.0 Hz, 2H), 1.72 (d, J = 12.1 Hz, 2H), 1.29 (br. s., 1H), 1.13-1.25 (m, 2H) |
| 308 | 712.2 | $^1$H NMR (DMSO-$d_6$) δ: 10.50 (s, 1H), 9.93 (s, 1H), 8.90 (s, 1H), 8.43-8.54 (m, 3H), 8.32 (d, J = 8.2 Hz, 1H), 7.96 (d, J = 7.4 Hz, 1H), 7.62 (d, J = 7.8 Hz, 1H), 7.36-7.52 (m, 4H), 7.26-7.34 (m, 1H), 7.22 (dd, J = 9.0 Hz, 1H), 3.50 (t, J = 5.7 Hz, 2H), 3.22-3.27 (m, 5H), 2.82 (s, 3H) |
| 309 | 725.2 | $^1$H NMR (DMSO-$d_6$) δ: 10.49 (br. s., 1H), 9.90 (s, 1H), 8.93 (s, 1H), 8.43-8.54 (m, 3H), 8.33 (d, J = 8.2 Hz, 1H), 7.98 (d, J = 8.6 Hz, 1H), 7.63 (d, J = 7.4 Hz, 1H), 7.33-7.51 (m, 4H), 7.23-7.31 (m, 1H), 7.16 (dd, J = 10.6 Hz, 1H), 3.21 (t, J = 6.5 Hz, 2H), 2.81 (s, 3H), 2.63 (t, J = 5.3 Hz, 2H), 2.31 (s, 6H) |
| 310 | 724.3 | $^1$H NMR (DMSO-$d_6$) δ: 10.52 (br. s., 1H), 9.93 (s, 1H), 8.87 (s, 1H), 8.42-8.55 (m, 3H), 8.32 (d, J = 8.2 Hz, 1H), 7.95 (d, J = 7.8 Hz, 1H), 7.63 (d, J = 7.4 Hz, 1H), 7.34-7.50 (m, 4H), 7.23-7.31 (m, 1H), 7.10-7.19 (m, 1H), 4.63 (d, J = 3.9 Hz, 1H), 3.48-3.58 (m, 1H), 3.25-3.30 (m, 2H), 2.85-2.94 (m, 2H), 1.71-1.81 (m, 2H), 1.40-1.52 (m, 2H) |
| 311 | 625.3 | $^1$H NMR (DMSO-$d_6$) δ 9.85 (s, 1H), 9.15 (s, 1H), 8.42 (s, 2H), 7.73 (dd, J = 1.17, 7.83 Hz, 1H), 7.21-7.45 (m, 5H), 7.10 (t, J = 8.02 Hz, 1H), 6.55 (d, J = 7.43 Hz, 1H) |

TABLE 4-continued

| | | |
|---|---|---|
| 325 | 711.2 | $^1$H NMR (400 MHz, DMSO-$d_6$) δ:10.51 (br. s., 1H), 9.41 (s, 0.33H), 9.34 (s, 0.66H), 9.05 (d, J = 8.61 Hz, 0.33H), 8.95 (d, J = 8.22 Hz, 0.66H), 8.72-8.90 (m, 2H), 8.64 (d, J = 9.39 Hz, 0.33H), 8.41-8.60 (m, 1H), 8.34 (d, J = 9.00 Hz, 0.66H), 8.17 (d, J = 8.22 Hz, 0.66H), 8.11 (d, J = 8.22 Hz, 0.33H), 7.96 (d, J = 9.00 Hz, 1H), 7.57-7.72 (m, 2H), 7.36-7.57 (m, 5H), 7.10-7.36 (m, 3H), 5.34 (s, 2H), 5.03 (s, 1H), 3.55 (s, 2H) , 3.31 (s, 1H) |
| 326 | 619.1 | $^1$H NMR (DMSO-$d_6$) δ: 10.52 (s, 1H), 9.39 (s, 1H), 9.04 (d, J = 8.6 Hz, 1H), 8.89 (d, J = 4.7 Hz, 1H), 8.86 (d, J = 9.0 Hz, 1H), 8.47-8.53 (m, 2H),8.33 (d, J = 7.8 Hz, 1H), 7.61-7.69 (m, 2H), 7.45-7.53 (m, 2H), 7.38-7.45 (m, 1H), 7.28-7.35 (m, 1H), 7.24 (t, J = 9.4 Hz, 1H), 2.91 (d, J = 4.7Hz, 3H) |
| 327 | 575.2 | $^1$H NMR (DMSO-$d_6$) δ: 10.15 (s, 1H), 9.86 (s, 1H), 9.16 (s, 1H), 8.37-8.55 (m, 3H), 7.69 (d, J = 8.6 Hz, 2H), 7.41 (d, J = 7.8 Hz, 1H), 7.17-7.32(m, 3H), 7.04-7.17 (m, 3H), 6.57 (d, J = 7.8 Hz, 1H), 5.51 (br. s., 1H), 3.81 (s, 3H) |
| 328 | 605.4 | $^1$H NMR (400 MHz, DMSO-$d_6$) δ: 10.51 (s, 1H), 9.88 (s, 1H), 9.49 (s, 1H), 9.03-9.22 (m, 1H), 8.44-8.62 (m, 4H), 8.05 (d, J = 7.43 Hz, 1H), 7.86-7.96 (m, 1H), 7.62 (d, J = 7.83 Hz, 1H), 7.57 (t, J = 7.83 Hz, 1H), 7.45-7.54 (m, 1H), 7.41 (dd, J = 5.67, 8.02 Hz, 1H), 7.30 (dd, J = 5.48, 8.22 Hz, 1H), 7.25 (d, J = 9.39 Hz, 1H), 2.54 (s, 3H) |
| 329 | 587.2 | $^1$H NMR (400 MHz, ACETONITRILE-$d_3$) δ: 9.00 (s, 1H), 8.51-8.61 (m, 3H), 8.48 (d, J = 9.00 Hz, 1H), 8.27 (d, J = 9.00 Hz, 1H), 7.83 (d, J = 7.43 Hz, 1H), 7.63-7.73 (m, 1H), 7.59 (t, J = 8.02 Hz, 1H), 7.30-7.46 (m, 3H), 7.06-7.15 (m, 1H), 2.55 (d, J = 2.35 Hz, 3H) |
| 330 | 551.1 | $^1$H NMR (400 MHz, DMSO-$d_6$) δ: 10.52 (br. s., 1H), 10.08 (s, 1H), 9.01 (s, 1H), 8.47 (s, 1H), 8.37-8.45 (m, 3H), 7.61 (d, J = 8.22 Hz, 1H), 7.44-7.51 (m, 1H), 7.36-7.44 (m, 1H), 7.13-7.36 (m, 2H), 4.00 (s, 2H), 2.55 (d, J = 2.35 Hz, 3H) |
| 331 | 748.0 | $^1$H NMR (400 MHz, DMSO-$d_6$) δ: 10.72 (br. s., 1H), 9.32-9.54 (m, 1H), 8.87-9.10 (m, 1H), 8.65 (d, J = 9.00 Hz, 1H), 8.37-8.55 (m, 1H), 8.24 (d, J = 8.61 Hz, 2H), 7.85-8.05 (m, 2H), 7.67 (td, J = 7.97, 11.84 Hz, 1H), 7.42-7.60 (m, 4H), 7.19-7.37 (m, 2H), 5.15 (s., 1.5H), 4.90 (s, 1.5H), 3.47 (s, 1.5H), 3.17 (s, 1.5H) |
| 332 | 554.1 | $^1$H NMR (400 MHz, DMSO-$d_6$) δ: 10.52 (br. s., 1H), 10.00 (s, 1H), 8.90 (br. s., 1H), 8.45 (br. s., 1H), 8.36 (q, J = 9.26 Hz, 2H), 8.18 (br. s., 1H), 7.62 (d, J = 7.43 Hz, 1H), 7.43-7.52 (m, 1H), 7.35-7.43 (m, 1H), 7.26-7.35 (m, 1H), 7.18-7.26 (m, 1H), 4.66 (br. s., 1H), 3.71 (br. s., 2H), 2.71 (br. s., 2H), 2.55 (d, J = 2.35 Hz, 3H) |
| 333 | 540.1 | $^1$H NMR (400 MHz, DMSO-$d_6$) δ: 10.48 (br. s., 1H), 9.87 (s, 1H), 8.50 (s, 2H), 8.43 (d, J = 9.00 Hz, 1H), 8.15 (d, J = 9.00 Hz, 1H), 7.61 (d, J = 7.83 Hz, 1H), 7.49 (t, J = 8.41 Hz, 1H), 7.40 (dt, J = 5.48, 8.02 Hz, 1H), 7.17-7.32 (m, 2H), 2.51 (s, 3H), 2.42 (s, 3H), 2.18 (s, 3H) |
| 334 | 660.2 | $^1$H NMR (400 MHz, DMSO-$d_6$) δ: 10.52 (br. s., 1H), 10.13 (s, 0.5H), 10.09 (s, 0.5H), 9.39 (br. s., 0.5H), 9.33 (br. s., 0.5H), 8.58 (br. s., 2H), 8.38-8.53 (m, 2H), 8.32 (d, J = 9.00 Hz, 0.5H), 8.02 (d, J = 9.00 Hz, 0.5H), 7.61 (dd, J = 4.30, 7.43 Hz, 1H), 7.47 (d, J = 8.22 Hz, 1H), 7.14-7.43 (m, 5H), 7.08 (d, J = 2.74 Hz, 0.5H), 7.01 (d, J = 2.74 Hz, 0.5H),5.11 (s, 1), 4.77 (s, 1H), 3.39 (s, 1.5H), 3.03 (s, 1.5H), 2.51 (s, 3H) |
| 335 | 674.2 | $^1$H NMR (400 MHz, DMSO-$d_6$) δ: 10.52 (d, J = 6.26 Hz, 1H), 10.13 (s, 0.5H), 10.08 (s, 0.5H), 9.19 (s, 0.5H), 9.11 (s, 0.5H), 8.78 (br. s., 2H), 8.32-8.60 (m, 2H), 8.25 (d, J = 9.00 Hz, 0.5H), 7.81 (d, J = 9.00 Hz, 10.5H), 7.70 (d, J = 5.09 Hz, 2H), 7.55-7.65 (m, 1H), 7.45-7.55 (m, 1H), 7.36-7.45 (m, 1H), 7.20-7.36 (m, 2H), 5.06 (s, 1H), 4.91 (s, 1H), 3.30 (s, 1.5H), 3.07 (s, 1.5H), 2.51 (s, 3H), 2.23 (s, 1.5H), 2.22 (s, 1.5H) |
| 336 | 674.2 | $^1$H NMR (400 MHz, DMSO-$d_6$) δ: 10.48 (br. s., 1H), 9.51 (s, 0.5H), 9.45 (s, 0.5H), 8.56 (br. s., 3H), 8.49 (d, J = 11.35 Hz, 1H), 8.42 (d, J = 9.00 Hz, 0.5H), 8.36 (d, J = 9.00 Hz, 0.5H), 8.31 (d, J = 9.00 Hz, 0.5H), 7.97 (d, J = 9.00 Hz, 0.5H), 7.61 (dd, J = 4.30, 7.43 Hz, 1H), 7.44-7.53 (m, 1H), 7.34-7.44 (m, 1H), 7.24-7.34 (m, 3H), 7.09-7.24 (m, 1H), 5.09 (s, 1H), 4.74 (s, 1H), 3.34 (s, 1.5H), 3.00 (s, 1.5H), 2.76-2.82 (m, 1.5H), 2.75 (s, 1.5H), 2.51 (s, 3H) |
| 337 | 709.4 | $^1$H NMR (400 MHz, DMSO-$d_6$) δ: 10.50 (br. s., 1H), 9.79 (br. s., 1H), 8.74 (br. s., 3H), 8.49 (s, 1H), 8.44 (s, 2H), 8.37 (d, J = 8.22 Hz, 1H), 7.86 (d, J = 7.43 Hz, 1H), 7.62 (d, J = 7.83 Hz, 1H), 7.49 (t, J = 8.80 Hz, 3H), 7.37-7.45 (m, 3H), 7.13-7.37 (m, 4H), 4.88 (s, 3H), 3.20 (br. s., 3H) |
| 338 | 690.4 | $^1$H NMR (400 MHz, DMSO-$d_6$) δ: 10.49 (br. s., 1H), 9.75 (s, 1H), 8.66 (s, 1H), 8.32-8.49 (m, 4H), 7.76 (br. s., 1H), 7.61 (d, J = 7.83 Hz, 1H), 7.43 (d, J = 8.22 Hz, 1H), 7.22-7.40 (m, 5H), 7.17 (br. s., 1H), 4.64 (br. s., 1H), 3.55 (s, 3H), 3.26 (br. s., 3H), 1.19 (br. s., 6H) |
| 339 | 611.6 | $^1$H NMR (400 MHz, DMSO-$d_6$) δ: 10.49 (br. s., 1H), 10.01 (s, 1H), 9.06 (s, 1H), 8.43 (s, 1H), 8.29-8.36 (m, 2H), 7.61 (d, J = 7.55 Hz, 1H), 7.48 (t, J = 8.58 Hz, 1H), 7.39 (dt, J = 5.72, 8.00 Hz, 1H), 7.26-7.34 (m, 1H), 7.20-7.26 (m, 1H), 4.62 (br. s., 1H), 3.76 (br. s., 2H), 3.63 (q, J = 5.64 Hz, 2H), 2.78-2.90 (m, 2H), 2.73 (br. s., 4H), 2.51 (s, 3H) |
| 340 | 611.6 | $^1$H NMR (400 MHz, DMSO-$d_6$) δ: 9.78 (s, 1H), 8.35-8.40 (m, 2H), 8.25-8.28 (m, 1H), 8.16-8.20 (m, 1H), 7.61 (d, J = 7.78 Hz, 1H), 7.42-7.52 (m, 1H), 7.34-7.42 (m, 1H), 7.25-7.34 (m, 1H), 7.21 (br. s., 1H), 4.71 (t, J = 5.15 Hz, 1H), 3.62-3.70 (m, 2H), 3.15 (t, J = 6.06 Hz, 2H), 3.06-3.12 (m, 2H), 2.73 (t, J = 6.52 Hz, 2H), 1.92-2.01 (m, 2H), 2.51 (s, 3H) |
| 341 | 590.4 | $^1$H NMR (400 MHz, DMSO-$d_6$) δ: 10.41 (br. s., 1H), 9.86 (s, 1H), 9.16 (s, 1H), 8.38-8.50 (m, 3H), 7.31-7.49 (m, 2H), 7.18-7.31 (m, 2H), 7.11 (t, J = 8.02 Hz, 1H), 6.88 (s, 1H), 6.56 (d, J = 7.43 Hz, 1H), 5.51 (br. s., 2H), 3.89 (s, 3H), 2.57 (s, 3H) |

TABLE 4-continued

| | | |
|---|---|---|
| 342 | 676.2 | $^1$H NMR (400 MHz, DMSO-$d_6$) δ: 10.73 (br. s., 1H), 9.85 (s, 1H), 9.38 (s, 1H), 9.26 (br. s., 1H), 8.63 (br. s., 1H), 8.39-8.57 (m, 5H), 7.91 (dd, J = 1.57, 7.83 Hz, 2H), 7.69 (d, J = 7.04 Hz, 1H), 7.44-7.62 (m, 3H), 7.28 (br. s., 2H) |
| 343 | 563.2 | $^1$H NMR (400 MHz, DMSO-$d_6$) δ: 10.53 (s, 1H), 10.16 (s, 1H), 9.13 (s, 1H), 8.74 (s, 1H), 8.50 (s, 1H), 8.38-8.48 (m, 2H), 7.61 (d, J = 7.83 Hz, 1H), 7.57 (d, J = 16.04 Hz, 1H), 7.49 (t, J = 8.41 Hz, 1H), 7.40 (dt, J = 5.48, 8.02 Hz, 1H), 7.28-7.36 (m, 1H), 7.22-7.28 (m, 1H), 6.24 (d, J = 16.04 Hz, 1H), 2.51 (s, 3H) |
| 344 | 632.4 | $^1$H NMR (400 MHz, DMSO-$d_6$) δ: 10.50 (br. s., 1H), 9.80 (s, 1H), 8.68 (s, 1H), 8.37-8.50 (m, 3H), 8.33 (d, J = 8.22 Hz, 1H), 7.80 (d, J = 7.83 Hz, 1H), 7.62 (d, J = 7.83 Hz, 1H), 7.44-7.55 (m, 1H), 7.35-7.44 (m, 2H), 7.25-7.35 (m, 2H), 7.12-7.25 (m, 1H), 3.13 (br. s., 6H), 2.51 (s, 3H) |
| 345 | 592.4 | $^1$H NMR (400 MHz, DMSO-$d_6$) δ: 10.51 (s, 1H), 9.83 (s, 1H), 9.31 (s, 1H), 8.49 (q, J = 9.26 Hz, 3H), 8.23 (dd, J = 1.57, 7.43 Hz, 1H), 7.63 (d, J = 7.83 Hz, 1H), 7.36-7.51 (m, 4H), 7.25-7.34 (m, 1H), 7.21 (br. s., 1H), 5.26 (t, J = 5.67 Hz, 1H), 5.00 (d, J = 5.48 Hz, 2H), 2.50 (s, 3H) |
| 346 | 688.4 | $^1$H NMR (400 MHz, DMSO-$d_6$) δ: 10.48 (d, J = 4.70 Hz, 1H), 9.47 (d, J = 25.04 Hz, 1H), 8.58 (br. s., 2H), 8.48 (d, J = 10.56 Hz, 1H), 8.35 (dd, J = 23.87, 9.39 Hz, 1 H), 8.12 (dd, J = 118.17, 8.61 Hz, 1H), 7.61 (dd, J = 7.63, 4.50 Hz, 1H), 7.44-7.53 (m, 1H), 7.41 (dt, J = 8.22, 4.50 Hz, 1H), 7.33 (d, J = 5.09 Hz, 1H), 7.25-7.31 (m, 2H), 7.16- 7.25 (m, 1H), 4.81 (d, J = 48.52 Hz, 2H), 3.07 (d, J = 63.00 Hz, 3H), 2.67 (d, J = 19.17 Hz, 3H), 2.11 (d, J = 6.26 Hz, 3 H) |
| 347 | 565.4 | $^1$H NMR (400 MHz, DMSO-$d_6$) δ: 10.51 (br. s., 1H), 10.00 (s, 1H), 8.96 (s, 1H), 8.43-8.49 (m, 1H), 8.32-8.43 (m, 2H), 8.30 (s, 1H), 7.62 (d, J = 7.83 Hz, 1H), 7.41-7.49 (m, 1H), 7.33-7.41 (m, 1H), 7.23-7.33 (m, 1H), 7.18 (br. s., 1H), 2.87 (s, 4H), 2.50 (s, 3H) |
| 348 | 615.2 | $^1$H NMR (400 MHz, DMSO-$d_6$) δ: 9.88 (s, 1H), 9.24 (s, 1H), 8.51 (s, 1H), 8.41-8.50 (m, 3H), 7.81-7.98 (m, 4H), 7.53 (t, J = 8.02Hz, 1H), 7.48 (d, J = 5.48 Hz, 1 H), 7.24-7.34 (m, 1H), 7.15-7.24 (m, 1H), 6.57 (s, 1 H) |
| 349 | 579.4 | $^1$H NMR (400 MHz, DMSO-$d_6$) δ: 9.88 (s, 1H), 9.23 (s, 1H), 8.51 (s, 1 H) , 8.41-8.49 (m, 3H), 7.87 (br. s., 1H), 7.62 (d, J = 7.83 Hz, 1H), 7.43-7.50 (m, 2H), 7.36-7.43 (m, 1H), 7.25-7.33 (m, 1H), 7.21 (t, J = 9.19 Hz, 1H), 6.48 (br. s., 2 H), 2.54 (s, 3H) |
| 350 | 621.4 | $^1$H NMR (400 MHz, DMSO-$d_6$) δ: 10.51 (br. s., 1H), 9.86 (s, 1H), 9.19 (s, 1H), 8.49 (s, 1H), 8.45 (s, 2H), 7.63 (d, J = 8.22 Hz, 1H), 7.34-7.49 (m, 3H), 7.11-7.32 (m, 3H), 6.51 (d, J = 7.83 Hz, 1H), 5.71 (t, J = 5.87 Hz, 1H), 4.85 (t, J = 5.28 Hz, 1H), 3.68 (q, J = 5.87 Hz, 2H), 3.33-3.36 (m, 1H), 2.50 (s, 3H) |
| 351 | 665.4 | $^1$H NMR (400 MHz, DMSO-$d_6$) δ: 9.83 (s, 1H), 9.10 (s, 1H), 8.50 (s, 1H), 8.38-8.49 (m, 2H), 7.63 (d, J = 7.43 Hz, 1H), 7.52 (d, J = 8.22 Hz, 1H), 7.32-7.49 (m, 2H), 7.08-7.32 (m, 3H), 6.63 (d, J = 8.22 Hz, 1H), 4.80 (t, J = 5.09 Hz, 2H), 3.79-3.90 (m, 4H), 3.67 (q, J = 5.74 Hz, 4H), 2.50 (s, 3H) |
| 352 | 559.4 | $^1$H NMR (400 MHz, AcOH-$d_4$) δ: 9.19 (s, 1H), 8.70-8.79 (m, 2H), 8.42 (d, J = 9.00 Hz, 1H), 7.91 (d, J = 7.83 Hz, 1H), 7.47-7.60 (m, 3H), 7.16-7.43 (m, 3H), 7.10 (t, J = 9.19 Hz, 1H), 6.86 (d, J = 7.83 Hz, 1H), 2.68 (s, 3H) |
| 353 | 575.4 | $^1$H NMR (400 MHz, AcOH-$d_4$) δ: 9.15 (s, 1H), 8.56-8.84 (m, 2H), 8.42 (d, J = 9.00 Hz, 1H), 8.08 (s, 1H), 7.98 (d, J = 9.39 Hz, 1H), 7.54 (s, 1H), 7.29 (s, 1H), 7.18 (s, 1H), 6.85 (d, J = 7.83 Hz, 1H), 6.75 (d, J = 9.39 Hz, 1H), 2.65 (s, 3H) |
| 354 | 750.3 | $^1$H NMR (400 MHz, DMSO-$d_6$) δ: 10.72 (br. s., 1H), 9.93 (s, 1H), 8.90 (s, 1H), 8.41-8.54 (m, 3H), 8.32 (d, J = 8.2 Hz, 1H), 7.87-7.99 (m, 3H), 7.39-7.56 (m, 3H), 7.26-7.34 (m, 1H), 7.16-7.24 (m, 1H), 3.50 (t, J = 5.7 Hz, 2H), 3.21-3.27 (m, 5H), 2.82 (s, 3H) |
| 355 | 763.4 | $^1$H NMR (400 MHz, DMSO-$d_6$) δ: 9.87 (s, 1H), 8.95 (s, 1H), 8.43-8.54 (m, 3H), 8.34 (d, J = 8.2 Hz, 1H), 7.98 (d, J = 7.4 Hz, 1H), 7.91 (dd, J = 8.2, 1.6 Hz, 1H), 7.82 (dd, J = 8.0, 1.4 Hz, 1H), 7.39-7.51 (m, 4H), 7.17-7.24 (m, J = 9.0, 9.0, 5.9 Hz, 1H), 7.04 (dd, J = 11.0, 8.6 Hz, 1H), 3.22 (t, J = 6.5 Hz, 2H), 2.81 (s, 3H), 2.67 (t, J = 6.5 Hz, 2H), 2.34 (s, 6H) |
| 356 | 581.2 | $^1$H NMR (400 MHz, DMSO-$d_6$) δ: 10.54 (s, 1H), 9.77 (s, 1H), 8.46 (s, 1H), 8.38 (s, 1H), 8.27 (d, J = 9.1 Hz, 1H), 8.20 (d, J = 9.1 Hz, 1H), 7.61 (d, J = 7.7 Hz, 1H), 7.47 (t, J = 8.7 Hz, 1H), 7.38 (dd, J = 13.5, 7.8 Hz, 1H), 7.30 (dd, J = 14.4, 8.6 Hz, 1H), 7.22 , 2H), 2.78-2.69 (m, 5H), 2.49-2.48 (m, 3H), 2.04-1.96 (m, 2H) |
| 357 | 609.2 | $^1$H NMR (400 MHz, DMSO-$d_6$) δ: 10.52 (s, 1H), 10.16 (s, 1H), 9.41 (s, 1H), 8.46-8.24 (m, 3H), 7.62 (d, J = 7.7 Hz, 1H), 7.47 (t, J = 8.7 Hz, 1H), 7.39 (dd, J = 13.5, 7.1 Hz, 1H), 7.30 (dd, J = 13.5, 6.6 Hz, 1H), 7.20 ( 2H), 2.49-2.48 (m, 3H), 2.25 (s, 3H) , 2.03 (s, 2H). |
| 358 | 574.4 | $^1$H NMR (400 MHz, acetic_acid) δ: 9.13 (s, 1H), 8.74 (d, J = 9.39 Hz, 1H), 8.69 (s, 1H), 8.57 (d, J = 5.87 Hz, 1H), 8.40 (d, J = 9.00 Hz, 1H), 7.80(d, J = 5.48 Hz, 1H), 7.44-7.63 (m, 2H), 7.19-7.36 (m, 1H), 7.14 (t, J = 9.00 Hz, 1H), 6.83 (d, J = 7.83 Hz, 1H), 2.63 (d, J = 7.83 Hz, 6H) |
| 359 | 762.2 | $^1$H NMR (400 MHz, DMSO-$d_6$) δ: 10.72 (br. s., 1H), 9.95 (s, 1H), 8.86 (s, 1H), 8.41-8.54 (m, 3H), 8.32 (d, J = 8.2 Hz, 1H), 7.87-7.98 (m, 3H), 7.53 (dd, J = 8.6 Hz, 1H), 7.39-7.50 (m, 2H), 7.27-7.34 (m, 1H), 7.22 (dd, J = 10.6, 9.4 Hz, 1H), 4.63 (d, J = 3.5 Hz, 1H), 3.49-3.57 (m, 1H), 3.25-3.29 (m, 2H), 2.85-2.94 (m, 2H), 1.71-1.82 (m, 2H), 1.40-1.52 (m, 2H) |
| 345 | 360.4 | $^1$H NMR (400 MHz, DMSO-$d_6$) δ: 10.51 (br. s., 1H), 9.84 (s, 1H), 9.42 (s, 1H), 8.69 (d, J = 8.2 Hz, 1H), 8.48-8.58 (m, 3H), 7.75 (d, J = 7.8 Hz, 1H), 7.56-7.65 (m, 2H), 7.48 (t, J = 9.0 Hz, 1H), 7.40 (td, J = 7.8, 5.5 Hz, 1H), 7.30 (td, J = 8.6, 5.9 Hz, 1H), 7.22 (t, J = 9.0 Hz, 1H), 2.50 (br. s., 3 H) |

TABLE 4-continued

| | | |
|---|---|---|
| 360 | 598.2 | $^1$H NMR (400 MHz, DMSO-$d_6$) δ: 10.51 (br. s., 1H), 9.88 (s, 1H), 9.37 (s, 1H), 8.41-8.54 (m, 3H), 7.93 (dd, J = 10.8, 7.6 Hz, 1H), 7.62 (d, J = 7.4 Hz, 1H), 7.46 (t, J = 8.8 Hz, 1H), 7.39 (td, J = 7.8, 5.9 Hz, 1H), 7.29 (td, J = 8.6, 5.9 Hz, 1H), 7.20 (t, J = 9.0 Hz, 1H), 2.50 (br. s., 3 H) |
| 361 | 601.3 | $^1$H NMR (400 MHz, DMSO-$d_6$) δ: 10.51 (br. s., 1H), 9.82 (s, 1H), 9.38 (s, 1H), 8.46-8.55 (m, 3H), 8.36 (d, J = 7.8 Hz, 1H), 7.63 (d, J = 7.8 Hz, 1H), 7.41-7.50 (m, 3H), 7.35-7.41 (m, 1H), 7.29 (td, J = 9.0, 6.3 Hz, 1H), 7.19 (t, J = 9.4 Hz, 1 H), 4.38 (s, 2H), 2.50 (br. s., 3 H) |
| 362 | 610.3 | $^1$H NMR (400 MHz, DMSO-$d_6$) δ: 9.81 (s, 1H), 8.59 (s, 1H), 8.39 (s, 1H), 8.27-8.18 (m, 3H), 7.67 (dd, J(t, J = 9.2 Hz, 1H), 3.25 (t, J = 6.0 Hz, 2H), 3.09 (t, J = 5.4Hz, 2H), 3.05-3.00 (m, 2H), 2.75 (t, J = 6.4 Hz, 2H), 2.49 (s, 3H), 2.06-1.99 (m, 2H). |
| 363 | 723.4 | $^1$H NMR (400 MHz, DMSO-$d_6$) δ: 10.50 (br. s., 1H), 9.78 (s, 1H), 8.58 (br. s., 1 H), 8.48 (s, 1H), 8.40-8.47 (m, 3H), 8.35 (d, J = 8.61 Hz, 1H), 7.72-7.73 (m, 1 H), 7.65 (d, J = 8.22 Hz, 3H), 7.63 (d, J = 7.83 Hz, 1H), 7.45 (d, J = 8.22 Hz, 1H), 7.33-7.42 (m, 2H), 7.24-7.33 (m, 3H), 7.19 (br. s., 2H), 3.90 (t, J = 7.43 Hz, 2 H), 3.06-3.13 (m, 5 H) |
| 364 | 728.4 | $^1$H NMR (400 MHz, DMSO-$d_6$) δ: 10.56 (br. s., 1H), 9.92 (s, 1H), 8.91 (s, 1H), 8.42-8.55 (m, 3H), 8.32 (d, J = 8.2 Hz, 1H), 7.96 (d, J = 7.4 Hz, 1H), 7.78 (d, J = 7.8 Hz, 1H), 7.72 (d, J = 7.8 Hz, 1H), 7.34-7.51 (m, 3H), 7.25-7.33 (m, 1H), 7.15-7.24 (m, 1H), 3.50 (t, J = 5.5 Hz, 2H), 3.21-3.27 (m, 5H), 2.82 (s, 3H), 2.67 (s, 3H) |
| 365 | 743.4 | $^1$H NMR (400 MHz, DMSO-$d_6$) δ: 9.88 (s, 1H), 8.93 (s, 1H), 8.43-8.56 (m, 3H), 8.33 (d, J = 8.2 Hz, 1H), 7.98 (d, J = 7.8 Hz, 1H), 7.80 (d, J = 7.8 Hz, 1H), 7.66 (d, J = 7.8 Hz, 1H), 7.39-7.52 (m, 2H), 7.34 (dd, J = 9.8, 7.8 Hz, 1H), 7.20-7.29 (m, 1H), 7.04-7.14 (m, 1H), 3.20 (t, J = 6.5 Hz, 2H), 2.81 (s, 3H), 2.67 (s, 3H), 2.58 (t, J = 6.3 Hz, 2H), 2.27 (s, 6H) |
| 366 | 742.4 | $^1$H NMR (400 MHz, DMSO-$d_6$) δ: 10.56 (br. s., 1H), 9.95 (s, 1H), 8.86 (s, 1H), 8.43-8.54 (m, 3H), 8.32 (d, J = 8.2 Hz, 1H), 7.95 (d, J = 8.2 Hz, 1H), 7.78 (d, J = 7.8 Hz, 1H), 7.73 (d, J = 8.2 Hz, 1H), 7.35-7.50 (m, 3H), 7.27-7.34 (m, 1H), 7.17-7.25 (m, 1H), 4.63 (d, J = 3.9 Hz, 1H), 3.49-3.58 (m, 1H), 3.24-3.28 (m, 2H), 2.85-2.94 (m, 2H), 2.67 (s, 3H), 1.71-1.81 (m, 2H), 1.40-1.51 (m, 2H) |
| 367 | 593.3 | $^1$H NMR (400 MHz, AcOH-$d_4$) δ: 9.24 (br. s., 1H), 8.78 (d, J = 8.61 Hz, 1H), 8.72 (s, 1H), 8.43 (d, J = 9.00 Hz, 1H), 8.08 (s, 1H), 7.91 (d, J = 7.43 Hz, 1H), 7.47-7.68 (m, 2H), 7.24-7.40 (m, 2H), 7.09 (t, J = 9.20 Hz, 1H), 6.89 (d, J = 7.43 Hz, 1H), 2.42 (s, 3H) |
| 368 | 604.4 | $^1$H NMR (400 MHz, AcOH-$d_4$) δ: 9.14 (br. s., 1H), 8.66-8.77 (m, 2H), 8.41 (d, J = 9.00 Hz, 1H), 8.19 (s, 1H), 8.10 (s, 2H), 7.50-7.61 (m, 1H), 7.20-7.38 (m, 2H), 6.93-7.20 (m, 1H), 6.84 (d, J = 7.43 Hz, 1H), 2.73-2.89 (m, 3H) |
| 369 | 574.4 | $^1$H NMR (400 MHz, AcOH-$d_4$) δ: 9.18 (br. s., 1H), 8.57-8.84 (m, 2H), 8.42 (d, J = 9.00 Hz, 1H), 8.08 (s, 1H), 7.51-7.69 (m, 2H), 7.29 (td, J = 3.96, 8.12 Hz, 1H), 6.98-7.18 (m, 1H), 6.84 (d, J = 7.83 Hz, 1H), 6.57 (s, 1H), 6.52 (d, J = 8.61 Hz, 1H), 2.53 (s, 3H) |
| 370 | 760.4 | $^1$H NMR (400 MHz, DMSO-$d_6$) δ: 10.74 (br. s., 1H), 9.40 (s, 1H), 8.96-9.04 (m, 1H), 8.73 (d, J = 9.00 Hz, 1H), 8.49 (s, 1H), 8.38-8.46 (m, 1H), 8.33 (d, J = 4.30 Hz, 1H), 7.88-8.00 (m, 3H), 7.58-7.69 (m, 2H), 7.55 (t, J = 8.02 Hz, 1 H), 7.39-7.50 (m, 1H), 7.28-7.36 (m, 1H), 7.21-7.28 (m, 2H), 7.07 (dd, J = 7.04, 5.48 Hz, 1H), 4.23 (t, J = 7.24 Hz, 1H), 3.96 (t, J = 7.43 Hz, 1H), 3.23 (t, J = 7.24 Hz, 2H), 3.17 (s, 3 H) rotamers ratio 1:2 |
| 371 | 754.4 | $^1$H NMR (400 MHz, DMSO-$d_6$) δ: 10.35 (br. s., 1H), 9.39 (s, 1H), 8.95-9.05 (m, 1H), 8.73 (d, J = 9.00 Hz, 1H), 8.49 (s, 1H), 8.38-8.46 (m, 1H), 8.33 (d, J = 3.91 Hz, 1H), 7.92-8.00 (m, 1H), 7.58-7.69 (m, 3H), 7.39-7.50 (m, 1H), 7.24-7.33 (m, 2H), 7.17-7.24 (m, 1H), 7.13 (t, J = 8.61 Hz, 1H), 7.07 (dd, J = 7.04, 5.48 Hz, 1H), 4.23 (t, J = 7.43 Hz, 1H), 3.96 (t, J = 7.43 Hz, 1H), 3.88 (s, 3H), 3.23 (t, J = 7.43 Hz, 2H), 3.12-3.20 (m, 3H), rotamers ratio 1:2 |
| 372 | 613.2 | $^1$H NMR (400 MHz, MeOH-$d_4$) δ: 8.95-9.15 (m, 1H), 8.24-8.56 (m, 3H), 8.03 (d, J = 7.4 Hz, 1H), 7.93 (d, J = 7.0 Hz, 1H), 7.68-7.82 (m, 2H), 7.36-7.52 (m, 2H), 7.21 (t, J = 7.6 Hz, 1H), 7.06-7.17 (m, 1H), 6.68 (d, J = 7.0 Hz, 1 H) |
| 373 | 593.3 | $^1$H NMR (400 MHz, DMSO-$d_6$) δ: 9.49 (s, 1H), 8.96 (d, J = 8.6 Hz, 1H), 8.82 (d, J = 9.0 Hz, 1H), 8.50-8.56 (m, 2H), 8.26 (d, J = 8.2 Hz, 1H), 7.76 (t, J = 7.8 Hz, 1 H), 7.57-7.66 (m, 2H), 7.25 (m, J = 5.5 Hz, 1H), 7.08 (t, J = 8.2 Hz, 2H), 6.53 (br. s., 1H), 3.86 (s, 3H), 2.49 (br. s., 3 H) |
| 374 | 609.3 | $^1$H NMR (400 MHz, DMSO-$d_6$) δ: 10.41 (br. s., 1H), 9.53 (s, 1H), 8.94 (d, J = 8.2 Hz, 1H), 8.82 (d, J = 9.4 Hz, 1H), 8.50-8.58 (m, 2H), 8.26 (d, J = 8.2 Hz, 1H), 7.73-7.82 (m, 2H), 7.62 (t, J = 7.6 Hz, 1H), 7.31 (td, J = 8.6, 5.5 Hz, 1H), 7.22 (t, J = 9.4 Hz, 1H), 7.13 (d, J = 9.4 Hz, 1H), 3.91 (s, 3H), 2.67 (s, 3 H) |
| 375 | 691.4 | $^1$H NMR (400 MHz, DMSO-$d_6$) δ: 9.85 (br. s., 1H), 9.17 (s, 1H), 8.50 (s, 1H), 8.39-8.48 (m, 2H), 7.64 (d, J = 8.2 Hz, 1H), 7.55 (d, J = 7.8 Hz, 1H), 7.36 (dd, J = 13.9, 7.6 Hz, 2H), 7.23 (t, J = 8.0 Hz, 2H), 7.08 (br. s., 2H), 6.66 (d, J = 8.2 Hz, 1H), 4.73 (t, J = 4.7 Hz, 2H), 3.69 (t, J = 7.0 Hz, 4H), 3.52 (dd, J = 10.6, 5.5 Hz, 4 H), 2.50 (br. s, 3H), 1.76 (dt, J = 13.5, 6.6 Hz, 4 H) |
| 376 | 693.4 | $^1$H NMR (400 MHz, DMSO-$d_6$) δ: 10.50 (br. s., 1H), 9.85 (s, 1H), 9.10 (s, 1H), 8.50 (s, 1H), 8.46 (d, J = 9.4 Hz, 1H), 8.42 (d, J = 9.0 Hz, 1H), 7.63 (d, J = 7.8 Hz, 1H), 7.54 (d, J = 7.8 Hz, 1H), 7.45 (t, J = 8.6 Hz, 1H), 7.34-7.42 (m, 1H), 7.23-7.31 (m, 1H), 7.21 (t, J = 8.0 Hz, 2H), 6.61 (d, J = 7.8 Hz, 1H), 3.95 (t, J = 5.9 Hz, 4H), 3.59 (t, J = 6.1 Hz, 4H), 3.27 (s, 6H), 2.50 (s, 3 H) |

TABLE 4-continued

| | | |
|---|---|---|
| 377 | 822.4 | $^1$H NMR (400 MHz, DMSO-$d_6$) δ: 10.72 (br. s., 1H), 9.94 (s, 1H), 8.90 (s, 1H), 8.39-8.57 (m, 3H), 8.29 (d, J = 7.83 Hz, 1H), 8.04 (dd, J = 1.76,4.89 Hz, 1H), 7.98 (d, J = 7.04 Hz, 1H), 7.85-7.94 (m, 1H), 7.37-7.59 (m, 4H), 7.27 (br. s., 2H), 6.78 (d, J = 8.61 Hz, 1H), 6.60 (dd, J = 5.09,7.04 Hz, 1H), 3.57-3.67 (m, 4H), 3.07-3.16 (m, 4H) |
| 378 | 833.4 | $^1$H NMR (400 MHz, DMSO-$d_6$) δ: 9.96 (s, 1H), 8.86 (s, 1H), 8.39-8.58 (m, 4H), 8.30 (d, J = 8.22 Hz, 1H), 7.82-8.02 (m, 4H), 7.40-7.54 (m, 4H),7.28 (br. s., 1H), 7.21 (s, 1H), 3.37-3.50 (m, 6H), 3.03 (br. s., 4H), 2.45 (br. s., 4H) |
| 379 | 542.3 | $^1$H NMR (400 MHz, DMSO-$d_6$) δ: 10.51 (br. s., 1H), 10.06 (s, 1H), 8.93 (br. s., 1H), 8.45 (s, 1H), 8.38 (s, 2H), 8.21-8.35 (m, 1H), 7.62 (d, J = 7.43 Hz, 1H), 7.45-7.55 (m, 1H), 7.35-7.44 (m, 1H), 7.30 (dt, J = 5.87, 8.61 Hz, 1H), 7.23 (t, J = 8.80 Hz, 1H), 5.11 (br. s., 1H), 4.46 (d, J = 4.70 Hz, 2H), 2.50 (s, 3H) |
| 380 | 829.4 | $^1$H NMR (400 MHz, DMSO-$d_6$) δ: 9.95 (s, 1H), 8.86 (s, 1H), 8.49-8.55 (m, 1H), 8.43-8.49 (m, 1H), 8.30 (d, J = 8.22 Hz, 1H), 8.13 (s, 1H), 7.95 (d, J = 7.43 Hz, 1H), 7.84-7.93 (m, 3H), 7.34-7.56 (m, 4H), 7.23-7.34 (m, 1H), 7.09-7.23 (m, 2H), 3.01 (br. s., 4H), 2.60 (br. s., 4H), 2.23 (br. s., 1H), 1.66 (d, J = 6.65 Hz, 4H), 0.95-1.19 (m, 4H) |
| 381 | 677.2 | $^1$H NMR (400 MHz, DMSO-$d_6$) δ: 10.73 (s, 1H), 10.02 (s, 1H), 8.97 (s, 1H), 8.51 (s, 1H), 8.45-8.50 (m, 2H), 8.30 (d, J = 7.83 Hz, 1H), 7.96-8.00 (m, 1H), 7.94 (s, 1H), 7.90 (dd, J = 1.57, 8.22 Hz, 1H), 7.41-7.56 (m, 3H), 7.28-7.37 (m, 1H), 7.24 (d, J = 9.39 Hz, 1H), 3.34 (s, 3H) |
| 382 | 713.3 | $^1$H NMR (400 MHz, DMSO-$d_6$) δ: 665.410.08 (s, 1H), 8.80 (s, 1H), 8.43-8.51 (m, 2H), 8.38 (d, J = 9.39 Hz, 1H), 8.32 (t, J = 2.54 Hz, 1H), 8.14 (s, 1H), 7.91 (dd, J = 1.57, 7.83 Hz, 1H), 7.81 (d, J = 7.04 Hz, 1H), 7.45 (t, J = 7.83 Hz, 1H), 7.21 (d, J = 5.87 Hz, 1H), 7.04 (s, 1H), 6.71 (dd, J = 1.76, 3.33 Hz, 1H), 3.12 (t, J = 6.46 Hz, 2H), 2.73 (s, 3H), 2.60-2.72 (m, 2H), 2.32-2.39 (m, 6H) |
| 383 | 652.3 | $^1$H NMR (400 MHz, DMSO-$d_6$) δ: 10.54 (br, 1H), 9.77 (br, 1H), 8.45 (br, 1H), 8.38 (s, 1H), 8.23 (dd, J = 27.2, 9.2 Hz, 2H), 7.95 (t, J = 5.7 Hz, 1H), 7.61 (d, J = 7.8 Hz, 1H), 7.47 (t, J = 8.8 Hz, 1H), 7.39 (dd, J = 13.5, 7.9 Hz, 1H), 7.34-7.26 (m, 1H), 7.22 (t, J = 9.5 Hz, 1H), 3.36-3.30 (m, 2H, overlapped with water peak), 3.11 .74 (t, J = 6.6 Hz, 2H), 2.50 (s, 3H, overlapped with DMSO), 2.02-1.93 (m,2H), 1.78 (s, 3H) |
| 384 | 721.4 | $^1$H NMR (400 MHz, DMSO-$d_6$) δ: 10.50 (s, 1H), 9.88 (s, 1H), 9.11 (s, 1H), 8.50 (s, 1H), 8.46 (d, J = 9.0 Hz, 1H), 8.42 (d, J = 9.0 Hz, 1H), 7.62 (d, J = 7.8 Hz, 1H), 7.52 (d, J = 8.2 Hz, 1H), 7.48 (t, J = 8.6 Hz, 1H), 7.40 (td, J = 8.2, 5.5 Hz, 1H), 7.30 (td, J = 8.7, 5.7 Hz, 1H), 7.22 (q, J = 8.2 Hz, 2H), 6.59 (d, J = 8.2 Hz, 1H), 3.70-3.78 (m, 4H), 3.39 (t, J = 6.1 Hz, 4H), 3.24 (s, 6H), 2.50 (s, 3H), 1.78-1.88 (m, 4 H) |
| 385 | 755.4 | $^1$H NMR (400 MHz, DMSO-$d_6$) δ: 9.90 (s, 1H), 8.92 (s, 1H), 8.43-8.52 (m, 3 H), 8.33 (d, J = 8.2 Hz, 1H), 7.97 (d, J = 7.4 Hz, 1H), 7.58 (d, J = 9.0 Hz, 1H), 7.45-7.50 (m, 1H), 7.42 (t, J = 7.4 Hz, 1H), 7.27 (td, J = 8.8, 5.9 Hz, 1H), 7.07-7.19 (m, 2H), 3.86 (s, 3H), 3.18 (t, J = 6.7 Hz, 2H), 2.80 (s, 3H), 2.49 (br. s., 3H), 2.47-2.49 (m, 2H), 2.19 (s, 6 H) |
| 386 | 771.4 | $^1$H NMR (400 MHz, DMSO-$d_6$) δ: 9.90 (br. s., 1H), 8.91 (s, 1H), 8.43-8.51 (m, 2H), 8.32 (d, J = 8.2 Hz, 1H), 7.97 (d, J = 7.8 Hz, 1H), 7.77 (d, J = 8.6 Hz, 1H), 7.45-7.50 (m, 1H), 7.42 (t, J = 7.4 Hz, 1H), 7.28 (td, J = 8.8, 5.9 Hz, 1H), 7.15 (t, J = 9.4 Hz, 1H), 7.10 (d, J = 9.0 Hz, 1H), 3.89 (s, 3H), 3.16-3.22 (m, 2H), 2.80 (s, 3H), 2.65 (s, 3H), 2.51-2.56 (m, 2H), 2.23 (s, 6 H) |
| 387 | 789.4 | $^1$H NMR (400 MHz, DMSO-$d_6$) δ: 9.84 (s, 1H), 8.93 (s, 1H), 8.43-8.55 (m, 3H), 8.34 (d, J = 8.6 Hz, 1H), 7.89-7.99 (m, 2H), 7.73-7.80 (m, 1H), 7.38-7.52 (m, 3H), 7.11-7.21 (m, 2H), 6.96 (dd, J = 11.3, 9.4 Hz, 1H), 3.81 (d, J = 11.7 Hz, 2H), 2.41-2.48 (m, 3H), 2.30 (s, 6H), 1.87 (d, J = 11.7 Hz, 2H), 1.47-1.60 (m, 2H) |
| 388 | 775.3 | $^1$H NMR (400 MHz, DMSO-$d_6$) δ: 9.95 (s, 1H), 8.87 (s, 1H), 8.43-8.54 (m, 3H), 8.31 (d, J = 8.6 Hz, 1H), 7.87-7.98 (m, 3H), 7.39-7.55 (m, 4H), 7.23-7.31 (m, 1H), 7.17 (dd, J = 8.6 Hz, 1H), 3.05 (br. s., 4H), 2.47 (br. s., 4H), 2.32 (q, J = 7.0 Hz, 2H), 0.90 (t, J = 7.2 Hz, 3H) |
| 389 | 791.4 | $^1$H NMR (400 MHz, DMSO-$d_6$) δ: 9.95 (s, 1H), 8.87 (s, 1H), 8.43-8.55 (m, 4H), 8.30 (d, J = 8.2 Hz, 1H), 7.86-8.00 (m, 3H), 7.38-7.55 (m, 3H), 7.23-7.33 (m, 1H), 7.11-7.22 (m, 1H), 3.04 (br. s., 4H), 2.52 (br. s., 2H), 2.36 (br. s., 2H) |
| 390 | 595.4 | $^1$H NMR (400 MHz, MeOH-$d_4$) δ: 9.04 (s, 1H), 8.32-8.52 (m, 3H), 7.84-7.93 (m, 2H), 7.72-7.79 (m, 1H), 7.60-7.67 (m, 1H), 7.37-7.58 (m, 3H), 7.18-7.26 (m, 1H), 7.11 (td, J = 9.1, 1.8 Hz, 1H), 6.69 (d, J = 7.8 Hz, 1 H) |
| 391 | 625.2 | $^1$H NMR (400 MHz, DMSO-$d_6$) δ: 10.45 (br. s., 1H), 9.17 (br. s., 1H), 9.12 (s, 1H), 9.00 (d, J = 9.15 Hz, 1H), 8.92 (d, J = 9.15 Hz, 1H), 8.40 (br. s., 1H), 8.03 (br. s., 2H), 7.94 (br. s., 1H), 7.70 (br. s., 1H), 5.26 (br. s., 1H), 4.24 (t, J = 6.17 Hz, 2H), 4.08 (br. s., 2H), 3.86 (t, J = 7.20 Hz, 2H), 3.69-3.77 (m, 2H), 3.48 (t, J = 6.40 Hz, 2H), 2.68-2.77 (m, 2H), 1.98 (br. s., 1H), 1.92 (br. s., 1H) |
| 392 | 624.3 | $^1$H NMR (400 MHz, DMSO-$d_6$) δ: 10.14 (br. s., 1H), 9.50 (s, 1H), 8.39-8.43 (m, 2H), 8.28 (d, J = 9.15 Hz, 1H), 8.16 (s, 1H), 7.65-7.69 (m, 1H), 7.25-7.30 (m, 2H), 7.16 (dt, J = 5.95, 9.15 Hz, 1H), 6.90 (t, J = 9.26 Hz, 1H), 4.02 (s, 2H), 3.72-3.80 (m, 2H), 2.85 (t, J = 6.17 Hz, 2H), 2.50 (br. s., 3H), 2.04 (br. s., 2H) |
| 393 | 609.2 | $^1$H NMR (400 MHz, DMSO-$d_6$) δ: 10.53 (br. s., 1H), 10.02 (br. s., 1H), 9.13 (s, 1H), 8.44 (s, 1H), 8.31-8.39 (m, 2H), 7.62 (d, J = 7.78 Hz, 1H), 7.41-7.49 (m, 1H), 7.33-7.41 (m, 1H), 7.23-7.32 (m, 1H), 7.18 (br. s., 1H), 4.69-4.76 (m, 2H), 3.69-3.78 (m, 2H), 2.79 (t, J = 5.49 Hz, 1H), 2.67 (t, J = 5.49 Hz, 1H), 2.50 (s, 3H), 2.12-2.15 (m, 3H) |

TABLE 4-continued

| | | |
|---|---|---|
| 394 | 700.2 | $^1$H NMR (400 MHz, DMSO-$d_6$) δ: 10.50 (s, 1H), 9.83 (s, 1H), 8.68 (s, 1H), 8.49 (s, 1H), 8.40-8.48 (m, 2H), 8.33 (d, J = 8.22 Hz, 1H), 7.84 (d, J = 7.04 Hz, 1H), 7.62 (d, J = 8.22 Hz, 1H), 7.44-7.51 (m, 1H), 7.28-7.44 (m, 4H), 7.14-7.25 (m, 1H), 4.48 (br. s., 2H), 3.73 (d, J = 10.17 Hz, 2H), 3.62 (d, J = 10.17 Hz, 2H), 1.95 (s, 4H) |
| 395 | 751.4 | $^1$H NMR (400 MHz, DMSO-$d_6$) δ: 9.85 (s, 1H), 8.90 (s, 1H), 8.42-8.54 (m, 3H), 8.33 (d, J = 8.2 Hz, 1H), 7.95 (d, J = 7.8 Hz, 1H), 7.62-7.67 (m, 1H), 7.39-7.50 (m, 2H), 7.27-7.37 (m, 2H), 7.17-7.25 (m, 1H), 6.96-7.04 (m, 1H), 3.76 (d, J = 11.7 Hz, 2H), 2.43-2.48 (m, 2H), 2.17 (s, 7H), 1.82 (d, J = 12.9 Hz, 2H), 1.41 1.54 (m, 2H) |
| 396 | 737.4 | $^1$H NMR (400 MHz, DMSO-$d_6$) δ: 10.47 (br. s., 1H), 9.96 (s, 1H), 8.86 (s, 1H), 8.43-8.55 (m, 3H), 8.30 (d, J = 8.2 Hz, 1H), 7.95 (d, J = 7.8 Hz, 1H), 7.62 (d, J = 7.4 Hz, 1H), 7.36-7.51 (m, 4H), 7.25-7.33 (m, 1H), 7.20 (dd, J = 9.0 Hz, 1H), 3.04 (br. s., 4H), 2.45 (br. s., 4H), 2.30 (q, J = 7.0 Hz, 2H), 0.90 (t, J = 7.0 Hz, 3H) |
| 397 | 753.4 | $^1$H NMR (400 MHz, DMSO-$d_6$) δ: 10.51 (br. s., 1H), 9.96 (s, 1H), 8.86 (s, 1H), 8.43-8.56 (m, 3H), 8.30 (d, J = 8.2 Hz, 1H), 7.95 (d, J = 8.2 Hz, 1H), 7.62 (d, J = 8.2 Hz, 1H), 7.35-7.51 (m, 4H), 7.25-7.33 (m, 1H), 7.20 (dd, J = 10.2, 9.2 Hz, 1H), 4.33 (br. s., 1H), 3.39 (br. s., 2H), 3.33 (br. s., 3H), 3.03 (br. s., 3H), 2.50 (m, 5H), 2.35 (t, J = 5.3 Hz, 2H) |
| 398 | 714.4 | $^1$H NMR (400 MHz, DMSO-$d_6$) δ: 10.51 (br. s., 1H), 9.39 (s, 1H), 9.03 (d, J = 9.00 Hz, 1H), 8.57 (d, J = 9.00 Hz, 1H), 8.50 (s, 1H), 8.46 (d, J = 9.78 Hz, 1H), 8.20 (d, J = 8.22 Hz, 1H), 7.61-7.70 (m, 2H), 7.49 (t, J = 7.43 Hz, 2H), 7.36-7.44 (m, 1H), 7.25-7.35 (m, 1H), 7.20-7.25 (m, 1H), 5.17-5.25 (m, 1H), 4.75-4.83 (m, 1H), 2.89 (d, J = 10.17 Hz, 1H), 2.81 (d, J = 12.13 Hz, 1H), 2.50 (s, 3H) 2.40-2.46 (m, 2H), 2.24 (s, 3H), 1.84-2.00 (m, 4H) |
| 399 | 750.2 | $^1$H NMR (400 MHz, DMSO-$d_6$) δ: 10.70 (br. s., 1H), 9.43 (s, 1H), 9.05 (d, J = 8.22 Hz, 1H), 8.63 (d, J = 9.39 Hz, 1H), 8.51 (s, 1H), 8.45 (d, J = 9.39 Hz, 1H), 8.28 (d, J = 7.83 Hz, 1H), 7.96 (dd, J = 1.37, 8.02 Hz, 1H), 7.92 (dd, J = 1.37, 8.02 Hz, 1H), 7.69 (t, J = 8.02 Hz, 1H), 7.48-7.59 (m, 2H), 7.30-7.37 (m, 1H), 7.21-7.30 (m, 1H), 5.61 (br. s., 1H), 4.99 (br. s., 1H), 3.56 (br. s., 2H), 2.82 (d, J = 8.22 Hz, 3H), 2.20 (br. s., 2H), 1.96-2.14 (m, 4H) |
| 400 | 736.3 | $^1$H NMR (400 MHz, DMSO-$d_6$) δ: 10.73 (br. s., 1H), 9.97 (s, 1H), 8.84 (s, 1H), 8.37-8.56 (m, 3H), 8.29 (d, J = 8.22 Hz, 1H), 8.01 (d, J = 7.04 Hz,1H), 7.95 (dd, J = 1.37, 8.02 Hz, 1H), 7.90 (dd, J = 1.57, 8.22 Hz, 1H), 7.82 (t, J = 5.87 Hz, 1H), 7.53 (t, J = 8.02 Hz, 1H), 7.37-7.50 (m, 2H),7.31 (dt, J = 5.67, 8.71 Hz, 1H), 7.23 (t, J = 9.00 Hz, 1H), 3.31 (br. s., 2H), 3.13 (s, 3H), 2.99 (q, J = 5.87 Hz, 2H) |
| 401 | 599.2 | $^1$H NMR (400 MHz, MeOH-$d_4$) δ: 8.32-8.64 (m, 3H), 8.08-8.21 (m, 1H), 7.39-7.61 (m, 4H), 7.19-7.30 (m, 1H), 7.02-7.16 (m, 1H), 6.62-6.76 (m, 1 H) |
| 402 | 767.2 | $^1$H NMR (400 MHz, DMSO-$d_6$) δ: 10.73 (br. s., 1H), 9.95 (s, 1H), 8.92 (s, 1H), 8.51 (s, 1H), 8.41-8.50 (m, 4H), 8.28 (d, J = 8.22 Hz, 1H), 7.94 (d, J = 7.83 Hz, 1H), 7.90 (dd, J = 1.37, 8.02 Hz, 1H), 7.59-7.66 (m, 1H), 7.53 (t, J = 8.02 Hz, 1H), 7.38 (dt, J = 1.17, 7.83 Hz, 1H), 7.25-7.35 (m,2H), 7.23 (d, J = 9.00 Hz, 1H), 7.13-7.19 (m, 1H), 7.05 (d, J = 8.22 Hz, 1H), 3.28 (s, 3H) |
| 403 | 704.2 | $^1$H NMR (400 MHz, DMSO-$d_6$) δ: 10.72 (br. s., 1H), 9.91 (br. s., 1H), 8.89 (s, 1H), 8.34-8.62 (m, 3H), 8.32 (d, J = 8.22 Hz, 1H), 7.98 (d, J = 7.43Hz, 1H), 7.68-7.94 (m, 2H), 7.34-7.62 (m, 3H), 7.30 (s, 2H), 2.73 (s, 6H) |
| 404 | 676.2 | $^1$H NMR (400 MHz, DMSO-$d_6$) δ: 10.69 (br. s., 1H), 9.96 (s, 1H), 8.78 (s, 1H), 8.48 (s, 1H), 8.42 (s, 2H), 8.28 (d, J = 8.22 Hz, 1H), 8.02 (d, J = 7.04 Hz, 1H), 7.83-7.99 (m, 2H), 7.51 (t, J = 8.02 Hz, 1H), 7.35-7.49 (m, 3H), 7.22-7.35 (m, 1H), 7.19 (br. s., 1H) |
| 405 | 774.2 | $^1$H NMR (400 MHz, DMSO-$d_6$) δ: 9.91 (br. s., 1H), 8.95 (s, 1H), 8.41-8.54 (m, 3H), 8.33 (d, J = 7.8 Hz, 1H), 7.94-7.98 (m, 1H), 7.91 (dd, J = 7.8, 1.6 Hz, 1H), 7.81-7.87 (m, 1H), 7.40-7.52 (m, 3H), 7.08-7.28 (m, 2H), 4.21 (br. s., 2H), 3.58 (s, 3H), 1.69 (d, J = 7.0 Hz, 2H), 1.37-1.46 (m, 2H) |
| 406 | 784.3 | $^1$H NMR (400 MHz, DMSO-$d_6$) δ: 10.74 (br. s., 1H), 9.97 (s, 1H), 8.93 (s, 1H), 8.52 (s, 1H), 8.44-8.51 (m, 2H), 8.32 (d, J = 8.50 Hz, 1H), 7.95 (d, J = 7.75 Hz, 1H), 7.91 (dd, J = 1.31, 7.94 Hz, 1H), 7.54 (t, J = 7.94 Hz, 1H), 7.36-7.49 (m, 2H), 7.33-7.36 (m, 1H), 7.31 (d, J = 7.38 Hz, 1H),7.19-7.28 (m, 4H), 7.11-7.19 (m, 1H), 3.24 (s, 3H) |
| 407 | 767.3 | $^1$H NMR (400 MHz, DMSO-$d_6$) δ: 9.95 (s, 1H), 9.03 (s, 1H), 8.44-8.65 (m, 3H), 8.26 (d, J = 8.61 Hz, 1H), 7.81-8.04 (m, 2H), 7.44-7.62 (m, 3H), 7.40 (t, J = 7.83 Hz, 1H), 7.10-7.35 (m, 5H), 3.37 (s, 3H) |
| 408 | 787.3 | $^1$H NMR (400 MHz, DMSO-$d_6$) δ: 10.68 (br. s., 1H), 9.96 (s, 1H), 8.92 (s, 1H), 8.42-8.53 (m, 3H), 8.32 (d, J = 7.8 Hz, 1H), 7.87-7.97 (m, 3H), 7.53 (dd, J = 8.0 Hz, 1H), 7.40-7.50 (m, 2H), 7.27-7.34 (m, 1H), 7.22 (dd, J = 10.2, 9.0 Hz, 1H), 4.26 (br. s., 2H), 2.69 (d, J = 11.0 Hz, 2H), 2.12-2.25 (m, 5H), 1.56-1.65 (m, 2H), 1.26-1.35 (m, 2H) |
| 409 | 797.3 | $^1$H NMR (400 MHz, DMSO-$d_6$) δ: 10.72 (br. s., 1H), 9.94 (s, 1H), 8.89 (s, 1H), 8.41-8.53 (m, 4H), 8.31 (d, J = 8.6 Hz, 1H), 7.87-7.98 (m, 3H), 7.63-7.70 (m, J = 7.6, 7.6 Hz, 1H), 7.53 (dd, J = 8.0 Hz, 1H), 7.46 (dd, J = 7.2 Hz, 1H), 7.40 (dd, J = 8.6, 7.6 Hz, 1H), 7.15-7.35 (m, 4H), 3.48 (t, J = 7.2 Hz, 2H), 2.99 (t, J = 7.2 Hz, 2H), 2.82 (s, 3H) |
| 410 | 791.4 | $^1$H NMR (400 MHz, DMSO-$d_6$) δ: 9.88 (s, 1H), 8.95 (s, 1H), 8.43-8.55 (m, 3H), 8.34 (d, J = 8.2 Hz, 1H), 7.95-8.00 (m, 1H), 7.91 (dd, J = 7.8, 1.6 Hz, 1H), 7.83 (dd, J = 8.2, 1.2 Hz, 1H), 7.40-7.51 (m, 3H), 7.18-7.25 (m, 1H), 7.07 (dd, J = 9.0 Hz, 1H), 3.22 (t, J = 6.8 Hz, 2H), 2.77-2.86 (m, 5H), 2.65-2.75 (m, 4H), 1.01 (t, J = 7.0 Hz, 6H) |

TABLE 4-continued

| | | |
|---|---|---|
| 411 | 703.3 | $^1$H NMR (400 MHz, DMSO-$d_6$) δ: 10.73 (br. s., 1H), 9.99 (s, 1H), 8.94 (s, 1H), 8.39-8.59 (m, 3H), 8.30 (d, J = 8.22 Hz, 1H), 7.77-8.01 (m, 3H),7.36-7.64 (m, 3H), 7.30 (br. s., 2H), 3.41-3.48 (m, 1H), 1.29 (d, J = 7.04 Hz, 6H) |
| 412 | 689.2 | $^1$H NMR (400 MHz, DMSO-$d_6$) δ: 10.73 (br. s., 1H), 10.01 (s, 1H), 8.96 (s, 1H), 8.35-8.60 (m, 3H), 8.30 (d, J = 8.22 Hz, 1H), 7.83-8.00 (m, 3H),7.39-7.66 (m, 3H), 7.15-7.36 (m, 2H), 3.38 (d, J = 7.04 Hz, 2H), 1.22 (t, J = 7.24 Hz, 3H) |
| 413 | 729.2 | $^1$H NMR (400 MHz, DMSO-$d_6$) δ: 10.73 (br. s., 1H), 9.97 (s, 1H), 8.99 (s, 1H), 8.50-8.57 (m, 1H), 8.41-8.50 (m, 2H), 8.31 (d, J = 8.22 Hz, 1H), 7.94-8.02 (m, 1H), 7.90 (dd, J = 1.37, 8.02 Hz, 2H), 7.35-7.56 (m, 3H), 7.27 (d, J = 5.87 Hz, 1H), 7.16 (br. s., 1H), 3.66-3.88 (m, 1H), 1.97-2.09 (m, 2H), 1.77-1.93 (m, 2H), 1.44-1.72 (m, 4H) |
| 414 | 624.3 | $^1$H NMR (400 MHz, DMSO-$d_6$) δ: 8.92 (br. s., 1H), 8.48-8.52 (m, 1H), 8.39-8.45 (m, 1H), 8.33-8.39 (m, 1H), 8.19 (s, 1H), 7.80 (d, J = 3.66 Hz, 1H), 7.68 (d, J = 7.55 Hz, 1H), 7.21-7.27 (m, 1H), 7.15-7.21 (m, 1H), 6.99-7.10 (m, 1H), 6.76 (dt, J = 4.00, 8.86 Hz, 1H), 5.42 (s, 1H), 5.29 (s, 1H), 3.95 (d, J = 11.66 Hz, 2H), 3.84 (t, J = 5.37 Hz, 1H), 3.64-3.70 (m, 1H), 2.76 (br. s., 1H), 2.61-2.69 (m, 1H), 2.50 (br. s., 4H) |
| 415 | 610.3 | $^1$H NMR (400 MHz, DMSO-$d_6$) δ: 8.51 (s, 1H), 8.37 (s, 2H), 8.16 (s, 1H), 7.73 (s, 1H), 7.67-7.71 (m, 1H), 7.16-7.29 (m, 2H), 7.04 (dt, J = 5.95, 9.38 Hz, 1H), 6.76 (t, J = 9.03 Hz, 1H), 4.33 (s, 2H), 3.00 (t, J = 5.95 Hz, 2H), 2.76-2.86 (m, 4H), 2.62-2.69 (m, 2H), 2.51 (s, 3H) |
| 416 | 749.2 | $^1$H NMR (400 MHz, DMSO-$d_6$) δ: 9.89 (s, 1H), 8.89 (s, 1H), 8.39-8.55 (m, 3H), 8.31 (d, J = 8.2 Hz, 1H), 8.00 (d, J = 8.2 Hz, 1H), 7.92 (dd, J = 7.8, 1.2 Hz, 1H), 7.79 (d, J = 8.2 Hz, 1H), 7.66 (br. s., 1H), 7.38-7.51 (m, 3H), 7.13-7.23 (m, 1H), 7.00 (dd, J = 11.0, 9.2 Hz, 1H), 2.97 (t, J = 6.5 Hz, 2H), 2.43-2.48 (m, 2H), 2.19 (s, 6H) |
| 417 | 754.3 | $^1$H NMR (400 MHz, DMSO-$d_6$) δ: 10.73 (br. s., 1H), 9.92 (s, 1H), 8.97-9.00 (m, 1H), 8.42-8.66 (m, 3H), 8.34 (d, J = 8.22 Hz, 1H), 7.75-8.04 (m,3H), 7.37-7.57 (m, 3H), 7.31 (d, J = 5.48 Hz, 1H), 7.22 (br. s., 1H), 5.98-6.47 (m, 1H), 3.57 (dt, J = 3.72, 14.77 Hz, 2H), 2.80-3.03 (m, 3H) |
| 418 | 766.2 | $^1$H NMR (400 MHz, DMSO-$d_6$) δ: 9.96 (s, 1H), 9.04 (s, 1H), 8.42-8.70 (m, 3H), 8.36 (s, 1H), 7.77-8.05 (m, 3H), 7.76 (d, J = 1.56 Hz, 1H), 7.33-7.55 (m, 3H), 7.11-7.32 (m, 2H), 5.89-6.30 (m, 1H), 3.92 (t, J = 8.61 Hz, 2H), 3.78 (dd, J = 5.87, 8.61 Hz, 2H), 2.96 (tdd, J = 6.02, 9.19, 12.42Hz, 1H) |
| 419 | 773.2 | $^1$H NMR (400 MHz, DMSO-$d_6$) δ: 9.93 (s, 1H), 8.96 (s, 1H), 8.43-8.54 (m, 3H), 8.33 (d, J = 8.22 Hz, 1H), 7.96-8.07 (m, 1H), 7.91 (td, J = 1.71,7.92 Hz, 2H), 7.38-7.66 (m, 3H), 7.21-7.33 (m, 1H), 7.16 (s, 1H), 3.41-3.57 (m, 4H), 3.10-3.27 (m, 3H), 3.04 (dd, J = 7.63, 9.98 Hz, 1H), 2.08(s, 6H) |
| 420 | 654.4 | $^1$H NMR (400 MHz, DMSO-$d_6$) δ: 9.76 (br. s., 1H), 9.36 (s, 1H), 8.45-8.60 (m, 4H), 8.42 (d, J = 8.2 Hz, 1H), 8.16 (br. s., 1H), 7.59-7.75 (m, 2H), 7.55 (t, J = 7.2 Hz, 1H), 7.25-7.45 (m, 4H), 7.15-7.25 (m, 1H), 7.02 (t, J = 9.0 Hz, 1H), 6.12 (br. s., 2H), 2.51 (s, 3 H) |
| 421 | 621.2 | $^1$H NMR (400 MHz, DMSO-$d_6$) δ: 11.04 (br. s, 2H), 9.90 (s, 1H), 9.16 (s, 1H), 8.50 (s, 1H), 8.43 (s, 1H), 8.19 (s, 1H), 7.40 (d, J = 8.2 Hz, 1H), 7.21-7.36 (m, 2H), 7.10 (t, J = 8.0 Hz, 1H), 6.55 (d, J = 7.8 Hz, 1H), 5.49 (s, 2 H) |
| 422 | 647.2 | $^1$H NMR (400 MHz, DMSO-$d_6$) δ: 9.87 (s, 1H), 9.14 (s, 1H), 8.48 (s, 1H), 8.42 (s, 2H), 8.07 (d, J = 8.2 Hz, 1H), 7.99 (d, J = 8.2 Hz, 1H), 7.76-7.88 (m, 1H), 7.40 (d, J = 7.8 Hz, 1H), 7.18-7.33 (m, 2H), 7.10 (t, J = 8.0 Hz, 1H), 6.55 (d, J = 7.4 Hz, 1H), 5.49 (br. s., 1 H) |
| 423 | 631.3 | $^1$H NMR (400 MHz, DMSO-$d_6$) δ: 10.67 (br. s., 1H), 9.87 (s, 1H), 9.14 (s, 1H), 8.30-8.56 (m, 2H), 7.89-8.01 (m, 1H), 7.73-7.88 (m, 1H), 7.40 (d, J = 7.83 Hz, 1H), 7.28-7.36 (m, J = 5.50, 8.60, 8.60 Hz, 1H), 7.19-7.28 (m, 1H), 7.10 (t, J = 8.02 Hz, 1H), 6.44-6.61 (m, 1H), 5.49 (br. s., 1H) |
| 424 | 654.4 | $^1$H NMR (400 MHz, DMSO-$d_6$) δ: 9.76 (br. s., 1H), 9.37 (s, 1H), 8.44-8.59 (m, 3H), 8.40 (d, J = 8.2 Hz, 1H), 8.16 (s, 1H), 8.06 (d, J = 4.3 Hz, 1H), 7.61-7.74 (m, 1H), 7.46-7.59 (m, 2H), 7.38 (d, J = 7.0 Hz, 1H), 7.30 (br. s., 2H), 7.19 (br. s., 1H), 6.98 (br. s., 1H), 6.70-6.80 (m, 1H), 5.63 (br. s., 2H), 2.51 (s, 3 H) |
| 425 | 611.3 | $^1$H NMR (400 MHz, DMSO-$d_6$) δ: 10.50 (br. s., 1H), 8.93 (s, 1H), 8.43 (s, 1H), 8.36 (d, J = 9.15 Hz, 1H), 8.28 (d, J = 9.15 Hz, 1H), 7.63 (d, J = 7.78 Hz, 1H), 7.60 (s, 1H), 7.44 (d, J = 8.69 Hz, 1H), 7.34-7.41 (m, 1H), 7.21-7.30 (m, 1H), 7.15 (br. s., 1H), 4.61 (t, J = 5.26 Hz, 1H), 3.60 (q, J = 6.02 Hz, 2H), 3.28-3.32 (m, 2H), 3.11 (t, J = 6.06 Hz, 2H), 3.00-3.07 (m, 2H), 2.51 (s, 3H), 1.85-1.93 (m, 2H) |
| 426 | 773.3 | $^1$H NMR (400 MHz, DMSO-$d_6$) δ: 9.88 (s, 1H), 8.91 (s, 1H), 8.39-8.50 (m, 2H), 8.33 (d, J = 8.22 Hz, 1H), 8.14 (s, 1H), 7.82-8.04 (m, 3H), 7.81(d, J = 7.43 Hz, 1H), 7.34-7.59 (m, 3H), 7.20 (d, J = 5.48 Hz, 1H), 7.02 (br. s., 1H), 3.72 (d, J = 9.39 Hz, 2H), 2.97 (br. s., 2H), 1.93-2.10 (m,2H), 0.99 (d, J = 6.26 Hz, 6H) |
| 427 | 760.3 | $^1$H NMR (400 MHz, DMSO-$d_6$) δ: 9.93 (s, 1H), 8.91 (s, 1H), 8.42-8.68 (m, 3H), 8.33 (d, J = 8.22 Hz, 1H), 7.90 (d, J = 8.22 Hz, 1H), 7.94 (d, J = 7.04 Hz, 2H), 7.40-7.56 (m, 3H), 7.29 (d, J = 6.65 Hz, 1H), 4.74 (br. s., 1H), 3.71-3.93 (m, 1H), 3.39-3.57 (m, 4H), 2.75 (s, 3H), 1.84-1.96 (m,1H), 1.58 (dd, J = 4.89, 13.11 Hz, 1H) |
| 428 | 760.3 | $^1$H NMR (400 MHz, DMSO-$d_6$) δ: 9.95 (s, 1H), 8.92 (s, 1H), 8.39-8.59 (m, 3H), 8.33 (d, J = 7.83 Hz, 1H), 7.85-7.97 (m, 3H), 7.40-7.69 (m, 3H), 7.28 (d, J = 7.04 Hz, 1H), 7.19 (br. s., 1H), 3.92-4.12 (m, 1H), 3.75 (d, J = 7.83 Hz, 1H), 3.45-3.66 (m, 2H), 3.38 (dd, J = 2.74, 11.74 Hz, 2H),3.16-3.28 (m, 2H), 1.12-1.19 (m, 3H) |
| 429 | 760.2 | $^1$H NMR (400 MHz, DMSO-$d_6$) δ: 9.95 (s, 1H), 8.81 (s, 1H), 8.34-8.56 (m, 3H), 8.30 (d, J = 8.22 Hz, 1H), 8.03 (d, J = 7.43 Hz, 1H), 7.91 (d, J = 1.17 Hz, 1H), 7.64 (t, J = 6.26 Hz, 1H), 7.34-7.54 (m, 3H), 7.27 (br. s., 2H), 4.40 (t, J = 5.67 Hz, 1H), 3.24 (d, J = 5.48 Hz, 2H), 2.87 (d, J = 5.87Hz, 2H), 0.26-0.38 (m, 4H) |

TABLE 4-continued

| | | |
|---|---|---|
| 430 | 746.2 | $^1$H NMR (400 MHz, DMSO-$d_6$) δ: 9.96 (s, 1H), 8.99 (s, 1H), 8.42-8.58 (m, 3H), 8.35 (d, J = 8.22 Hz, 1H), 7.83-8.03 (m, 3H), 7.39-7.60 (m, 3H), 7.25 (br. s., 1H), 4.61 (t, J = 5.28 Hz, 1H), 3.81 (t, J = 8.41 Hz, 2H), 3.58 (dd, J = 5.87, 8.22 Hz, 2H), 3.25 (t, J = 5.87 Hz, 4H) |
| 431 | 746.3 | $^1$H NMR (400 MHz, DMSO-$d_6$) δ: 9.95 (s, 1H), 8.86 (s, 1H), 8.39-8.58 (m, 4H), 8.32 (d, J = 7.83 Hz, 1H), 7.98-8.06 (m, 1H), 7.78-7.98 (m, 2H), 7.40-7.59 (m, 3H), 7.27 (br. s., 1H), 7.17 (br. s., 1H), 4.61 (d, J = 6.26 Hz, 2H), 4.12 (d, J = 6.26 Hz, 2H), 1.52 (s, 3H) |
| 432 | 803.2 | $^1$H NMR (400 MHz, DMSO-$d_6$) δ: 9.92 (s, 1H), 8.92 (s, 1H), 8.43-8.54 (m, 3H), 8.32 (d, J = 8.22 Hz, 1H), 7.87-7.99 (m, 3H), 7.39-7.56 (m, 3H),7.17-7.34 (m, 2H), 3.52 (t, J = 4.70 Hz, 4H), 3.17-3.25 (m, 4H), 2.83 (s, 3H), 2.38 (br. s., 4H) |
| 433 | 732.2 | $^1$H NMR (400 MHz, DMSO-$d_6$) δ: 9.95 (s, 1H), 8.83 (s, 1H), 8.64 (d, J = 7.43 Hz, 1H), 8.35-8.56 (m, 3H), 8.30 (d, J = 7.83 Hz, 1H), 7.94-8.05(m, 1H), 7.90 (dd, J = 1.37, 8.02 Hz, 2H), 7.37-7.60 (m, 3H), 7.28 (d, J = 5.48 Hz, 1H), 7.18 (br. s., 1H), 4.39-4.60 (m, 3H), 4.14-4.39 (m, 2H) |
| 434 | 746.2 | $^1$H NMR (400 MHz, DMSO-$d_6$) δ: 9.96 (s, 1H), 8.99 (s, 1H), 8.42-8.58 (m, 3H), 8.35 (d, J = 8.22 Hz, 1H), 7.83-8.03 (m, 3H), 7.39-7.60 (m, 3H), 7.25 (br. s., 1H), 4.61 (t, J = 5.28 Hz, 1H), 3.81 (t, J = 8.41 Hz, 2H), 3.58 (dd, J = 5.87, 8.22 Hz, 2H), 3.25 (t, J = 5.87 Hz, 4H) |
| 435 | 776.3 | $^1$H NMR (400 MHz, DMSO-$d_6$) δ: 10.72 (br. s., 1H), 9.95 (s, 1H), 8.95 (s, 1H), 8.41-8.56 (m, 3H), 8.33 (d, J = 7.8 Hz, 1H), 7.98-8.03 (m, 1H), 7.90 (dd, J = 7.8, 1.6 Hz, 1H), 7.94 (dd, J = 7.8, 1.2 Hz, 1H), 7.53 (dd, J = 8.2 Hz, 1H), 7.40-7.50 (m, 2H), 7.27-7.34 (m, 1H), 7.22 (dd, J = 10.6, 9.0 Hz, 1H), 3.83-3.92 (m, 1H), 3.56 (dd, J = 9.4, 3.5 Hz, 1H), 3.23-3.40 (m, 6H), 1.65-1.82 (m, 2H), 1.41-1.52 (m, 2H) |
| 436 | 775.4 | $^1$H NMR (400 MHz, DMSO-$d_6$) δ: 9.88 (s, 1H), 8.92 (s, 1H), 8.42-8.55 (m, 3H), 8.33 (d, J = 8.2 Hz, 1H), 7.88-7.97 (m, 2H), 7.84 (dd, J = 8.2, 1.2 Hz, 1H), 7.39 7.51 (m, 3H), 7.18-7.26 (m, 1H), 7.07 (dd, J = 10.2, 9.0 Hz, 1H), 3.40-3.50 (m, 4H), 2.72-2.78 (m, 2H), 2.64-2.70 (m, 2H), 2.34 (s, 3H), 1.76-1.84 (m, 2H) |
| 437 | 764.3 | $^1$H NMR (400 MHz, DMSO-$d_6$) δ: 10.72 (br. s., 1H), 9.93 (s, 1H), 8.91 (s, 1H), 8.40-8.56 (m, 3H), 8.32 (d, J = 7.8 Hz, 1H), 7.85-7.99 (m, 3H), 7.53 (dd, J = 12.5, 8.0 Hz, 1H), 7.40-7.49 (m, 2H), 7.27-7.34 (m, 1H), 7.19-7.25 (m, 1H), 3.45-3.52 (m, 2H), 3.25-3.40 (m, 4H), 3.22 (s, 3H), 1.07 (t, J = 7.0 Hz, 3H) |
| 438 | 760.3 | $^1$H NMR (400 MHz, DMSO-$d_6$) δ: 10.72 (br. s., 1H), 9.93 (s, 1H), 8.91 (s, 1H), 8.38-8.62 (m, 3H), 8.33 (d, J = 7.83 Hz, 1H), 7.81-8.02 (m, 3H),7.38-7.67 (m, 3H), 7.30 (d, J = 5.87 Hz, 2H), 4.71-4.81 (m, 1H), 3.65-3.85 (m, 1H), 3.38-3.65 (m, 3H), 2.75 (s, 3H), 1.76-2.02 (m, 1H), 1.53-1.63 (m, 1H) |
| 439 | 760.3 | $^1$H NMR (400 MHz, DMSO-$d_6$) δ: 9.94 (s, 1H), 8.88 (s, 1H), 8.41-8.62 (m, 3H), 8.32 (d, J = 8.22 Hz, 1H), 7.87-7.97 (m, 3H), 7.37-7.65 (m, 3H), 7.28 (br. s., 1H), 7.20 (br. s., 1H), 4.96 (d, J = 4.70 Hz, 1H), 3.50-3.67 (m, 2H), 3.45 (d, J = 10.96 Hz, 2H), 2.16-2.39 (m, 1H), 1.64-1.88 (m,2H), 1.47 (d, J = 5.48 Hz, 1H), 1.08 (d, J = 10.96 Hz, 1H) |
| 440 | 803.2 | $^1$H NMR (400 MHz, DMSO-$d_6$) δ: 10.01 (s, 1H), 9.00 (s, 1H), 8.41-8.68 (m, 3H), 8.31 (d, J = 7.83 Hz, 1H), 7.80-8.04 (m, 3H), 7.39-7.57 (m,3H), 7.29 (d, J = 7.43 Hz, 1H), 7.19 (br. s., 1H), 1.57 (s, 6H), 1.24 (s, 9H) |
| 441 | 745.2 | $^1$H NMR (400 MHz, DMSO-$d_6$) δ: 10.73 (br. s., 1H), 10.00 (s, 1H), 8.97 (s, 1H), 8.41-8.68 (m, 3H), 8.31 (d, J = 8.22 Hz, 1H), 7.74-8.04 (m, 3H),7.39-7.67 (m, 3H), 7.28 (br. s., 1H), 7.20 (br. s., 1H), 4.22 (t, J = 6.46 Hz, 1H), 3.58-3.68 (m, 3H), 3.53 (dt, J = 6.06, 7.92 Hz, 1H), 1.95-2.09(m, 1H), 1.70-1.85 (m, 2H), 1.52 1.70 (m, 1H) |
| 442 | 759.3 | $^1$H NMR (400 MHz, DMSO-$d_6$) δ: 9.97 (s, 1H), 8.99 (s, 1H), 8.42-8.62 (m, 3H), 8.32 (d, J = 8.22 Hz, 1H), 7.82-8.05 (m, 3H), 7.38-7.62 (m, 3H), 7.26 (d, J = 5.48 Hz, 1H), 7.14 (br. s., 1H), 3.70-3.86 (m, 2H), 3.38 (br. s., 2H), 3.25 (d, J = 1.96 Hz, 2H), 2.12-2.30 (m, 1H), 1.52-1.81 (m, 2H), 1.24-1.52 (m, 2H) |
| 443 | 767.3 | $^1$H NMR (400 MHz, DMSO-$d_6$) δ: 9.84 (s, 1H), 8.83-8.97 (m, 1H), 8.42-8.55 (m, 2H), 8.37 (dd, J = 9.0, 4.3 Hz, 1H), 7.89 (dd, J = 7.8, 1.6 Hz, 1H), 7.66-7.85 (m, 3H), 7.45 (t, J = 8.0 Hz, 1H), 7.30 (td, J = 9.2, 2.7 Hz, 1H), 7.20 (m, J = 8.9, 8.9, 6.1 Hz, 1H), 7.06 (t, J = 8.8 Hz, 1H), 2.96 (t, J = 6.5 Hz, 2H), 2.50-2.56 (m, 2H), 2.15-2.29 (m, 6 H) |
| 444 | 781.3 | $^1$H NMR (400 MHz, DMSO-$d_6$) δ: 9.81 (s, 1H), 8.99 (s, 1H), 8.49-8.55 (m, 1H), 8.46 (s, 1H), 8.40 (dd, J = 9.2, 4.5 Hz, 1H), 7.89 (dd, J = 7.8, 1.6 Hz, 1H), 7.83 (dd, J = 8.2, 1.6 Hz, 1H), 7.65 (dd, J = 9.0, 2.7 Hz, 1H), 7.46 (t, J = 8.0 Hz, 1H), 7.31 (td, J = 9.2, 2.7 Hz, 1H), 7.21 (td, J = 8.9, 5.7 Hz, 1H), 7.06 (t, J = 9.2 Hz, 1H), 3.23 (t, J = 6.5 Hz, 2H), 2.79 (s, 3H), 2.68-2.76 (m, 2H), 2.38 (s, 6 H) |
| 445 | 762.2 | $^1$H NMR (400 MHz, DMSO-$d_6$) δ: 10.72 (br. s., 1H), 9.94 (s, 1H), 8.91 (s, 1H), 8.43-8.54 (m, 3H), 8.33 (d, J = 7.8 Hz, 1H), 7.87-7.97 (m, 3H), 7.40-7.57 (m, 3H), 7.26-7.35 (m, 1H), 7.22 (dd, J = 9.0 Hz, 1H), 4.70-4.79 (m, 1H), 3.71-3.80 (m, 1H), 3.38-3.56 (m, 3H), 2.75 (s, 3H), 1.86-1.95 (m, 1H), 1.53-1.63 (m, 1H) |
| 446 | 764.3 | $^1$H NMR (400 MHz, DMSO-$d_6$) δ: 10.72 (br. s., 1H), 9.95 (s, 1H), 8.90 (s, 1H), 8.42-8.53 (m, 3H), 8.32 (d, J = 8.2 Hz, 1H), 7.99 (d, J = 7.4 Hz, 1H), 7.88-7.95 (m, 2H), 7.37-7.56 (m, 3H), 7.25-7.33 (m, 1H), 7.15-7.24 (m, 1H), 5.04 (d, J = 3.1 Hz, 1H), 3.82 (br. s., 2H), 3.46 (dd, J = 10.6, 3.5 Hz, 2H), 3.21 (d, J = 11.0 Hz, 2H) |
| 447 | 733.3 | $^1$H NMR (400 MHz, DMSO-$d_6$) δ: 9.95 (s, 1H), 8.88 (s, 1H), 8.41-8.61 (m, 3H), 8.16-8.41 (m, 1H), 7.87-7.98 (m, 3H), 7.37-7.61 (m, 3H), 7.13- 7.35 (m, 2H), 5.01 (t, J = 6.06 Hz, 1H), 3.50-3.71 (m, 2H), 1.31 (s, 6H) |
| 448 | 633.2. | $^1$H NMR (400 MHz, DMSO-$d_6$) δ: 10.72 (br. s., 1H), 9.86 (s, 1H), 9.52 (s, 1H), 8.49-8.59 (m, 2H), 8.41 (d, J = 5.5 Hz, 1H), 8.34 (d, J = 5.9 Hz, 1H), 7.92-7.96 (m, 1H), 7.86-7.91 (m, 1H), 7.48-7.59 (m, 1H), 7.13-7.36 (m, 2 H) |

TABLE 4-continued

| | | |
|---|---|---|
| 449 | 630.2 | $^1$H NMR (400 MHz, DMSO-$d_6$) δ: 10.71 (s, 1H), 9.86 (s, 1H), 9.22 (s, 1H), 8.41-8.55 (m, 2H), 7.84-8.02 (m, 2H), 7.48-7.57 (m, 1H), 7.11-7.38 (m, 3H), 6.92 (d, J = 8.2 Hz, 1H), 3.97 (s, 3 H) |
| 450 | 789.4 | $^1$H NMR (400 MHz, DMSO-$d_6$) δ: 10.72 (br. s., 1H), 9.93 (s, 1H), 8.93 (s, 1H), 8.42-8.54 (m, 3H), 8.32-8.38 (m, 1H), 7.98-8.03 (m, 1H), 7.87-7.96 (m, 2H), 7.40-7.57 (m, 3H), 7.24-7.33 (m, 1H), 7.14-7.23 (m, 1H), 4.36 (s, 1H), 3.90 (dd, J = 8.6, 3.5 Hz, 1H), 3.63-3.72 (m, 1H), 3.22-3.30 (m, 1H), 1.76-1.87 (m, 1H), 1.57-1.69 (m, 1H), 1.18-1.29 (m, 4H), 1.16 (s, 3H), 0.98-1.09 (m, 1H) |
| 451 | 774.2 | $^1$H NMR (400 MHz, DMSO-$d_6$) δ: 10.72 (s, 1H), 9.97 (s, 1H), 8.90 (s, 1H), 8.42-8.57 (m, 3H), 8.31 (d, J = 8.2 Hz, 1H), 7.86-8.02 (m, 3H), 7.38-7.57 (m, 3H), 7.26-7.35 (m, 1H), 7.16-7.25 (m, 1H), 3.61-3.68 (m, 2H), 3.42 (dd, J = 9.0, 3.1 Hz, 2H), 3.24-3.35 (m, 2H), 3.03 (dd, J = 10.2, 3.1 Hz, 2H), 2.74-2.82 (m, 2H) |
| 452 | 762.3 | $^1$H NMR (400 MHz, DMSO-$d_6$) δ: 10.72 (br. s., 1H), 9.98 (s, 1H), 8.87 (s, 1H), 8.41-8.56 (m, 3H), 8.32 (d, J = 8.2 Hz, 1H), 8.12 (d, J = 7.0 Hz, 1H), 7.99-8.06 (m, 1H), 7.87-7.97 (m, 2H), 7.39-7.57 (m, 3H), 7.26-7.36 (m, 1H), 7.21 (dd, J = 14.5, 9.2 Hz, 1H), 3.82 (dd, J = 8.2, 7.4 Hz, 1H), 3.66 (dd, J = 8.2, 6.7 Hz, 1H), 3.34-3.39 (m, 2H), 3.09-3.16 (m, 1H), 1.99-2.08 (m, 1H), 0.74 (d, J = 6.7 Hz, 3H) |
| 453 | 764.4 | $^1$H NMR (400 MHz, DMSO-$d_6$) δ: 10.72 (br. s., 1H), 9.98 (s, 1H), 8.85 (s, 1H), 8.39-8.55 (m, 3H), 8.30 (d, J = 8.2 Hz, 1H), 8.00 (d, J = 7.4 Hz, 1H), 7.86-7.97 (m, 2H), 7.37-7.57 (m, 4H), 7.26-7.35 (m, 1H), 7.22 (dd, J = 11.0, 9.0 Hz, 1H), 4.24 (s, 1H), 2.87-2.97 (m, 2H), 1.47-1.56 (m, 2H), 0.98 (s, 6H) |
| 454 | 776.4 | $^1$H NMR (400 MHz, DMSO-$d_6$) δ: 10.72 (s, 1H), 9.92 (s, 1H), 8.84 (s, 1H), 8.50 (s, 1H), 8.45 (s, 2H), 8.31 (d, J = 7.4 Hz, 1H), 7.87-8.03 (m, 3H), 7.53 (dd, J = 12.1, 8.0 Hz, 1H), 7.37-7.49 (m, 2H), 7.17-7.34 (m, 2H), 4.85 (t, J = 5.7 Hz, 1H), 3.64 (dd, J = 10.6, 5.5 Hz, 1H), 3.54 (dd, J = 10.6, 5.5 Hz, 1H), 3.44 (t, J = 6.7 Hz, 2H), 2.09-2.17 (m, 1H), 1.65-1.82 (m, 2H), 1.47-1.59 (m, 1H), 1.36 (s, 3H) |
| 455 | 734.2 | $^1$H NMR (400 MHz, DMSO-$d_6$) δ: 10.73 (br. s., 1H), 9.97 (s, 1H), 8.99 (s, 1H), 8.44-8.56 (m, 3H), 8.35 (d, J = 8.2 Hz, 1H), 7.86-7.98 (m, 3H), 7.40-7.55 (m, 3H), 7.26 (br. s., 2H), 7.16 (br. s., 1H), 5.66 (d, J = 6.3 Hz, 1H), 4.23-4.34 (m, 1H), 3.91-4.01 (m, 2H), 3.48 (dd, J = 8.4, 6.1 Hz, 2H) |
| 456 | 760.4 | $^1$H NMR (400 MHz, DMSO-$d_6$) δ: 9.90 (s, 1H), 8.87 (s, 1H), 8.39-8.61 (m, 3H), 8.29 (d, J = 7.43 Hz, 1H), 7.78-7.95 (m, 3H), 7.31-7.59 (m, 3H), 7.21 (d, J = 4.70 Hz, 1H), 7.07 (br. s., 1H), 2.66 (s, 2H), 2.22 (s, 6H), 1.33 (s, 6H) |
| 457 | 802.2 | $^1$H NMR (400 MHz, DMSO-$d_6$) δ: 9.75-9.78 (m, 1H), 8.37-8.49 (m, 1H), 8.17 (s, 1H), 7.88-8.00 (m, 2H), 7.77 (d, J = 7.43 Hz,1H), 7.52 (d, J = 7.43 Hz, 1H), 7.39-7.50 (m, 1H), 7.17-7.30 (m, 2H), 6.54 (br. s., 1H), 4.92 (t, J = 5.87 Hz, 1H), 3.53 (d, J = 5.48 Hz, 3H), 3.16(d, J = 3.91 Hz, 2H), 2.46 (d, J = 4.70 Hz, 3H), 1.34 (s, 4H), 1.20 (s, 6H) |
| 458 | 774.3 | $^1$H NMR (400 MHz, DMSO-$d_6$) δ: 9.96 (s, 1H), 8.86 (s, 1H), 8.36-8.58 (m, 3H), 8.31 (d, J = 8.61 Hz, 1H), 7.82-7.98 (m, 3H), 7.38-7.55 (m, 3H), 7.26 (br. s., 1H), 7.16 (br. s., 1H), 3.49 (br. s., 2H), 2.57-2.80 (m, 2H), 1.45-1.70 (m, 4H), 1.07 (s, 3H) |
| 459 | 787.3 | $^1$H NMR (400 MHz, DMSO-$d_6$) δ: 9.90 (br. s., 1H), 8.92 (s, 1H), 8.39-8.59 (m, 3H), 8.35 (d, J = 8.22 Hz, 1H), 7.79-7.95 (m, 3H), 7.40-7.52 (m,3H), 7.22 (br. s., 2H), 4.13-4.20 (m, 2H), 2.47 (s, 2H), 1.92-2.13 (m, 3H), 1.57 (dd, J = 4.30, 11.35 Hz, 2H), 1.39 (d, J = 7.04 Hz, 6H) |
| 460 | 581.3 | $^1$H NMR (400 MHz, DMSO-$d_6$) δ: 10.49 (s, 1H), 8.97 (s, 1H), 8.43 (s, 1H), 8.36 (d, J = 9.1 Hz, 1H), 8.29(d, J = 9.1 Hz, 1H), 7.65 (s, 1H), 7.62 (d, J = 7.6 Hz, 1H), 7.47 (t, J = 8.7 Hz, 1H), 7.39 (td, J = 7.9, 5.7Hz, 1H), 7.30-7.23 (m, 1H), 7.18 (t, J = 8.8 Hz, 1 , 2.87-2.81 (m, 2H), 2.69(s, 3H), 2.50 (s, 3H), 1.97-1.89 (m, 2H) |
| 461 | 746.3 | $^1$H NMR (400 MHz, DMSO-$d_6$) δ: 9.87 (s, 1H), 8.96 (s, 1H), 8.53 (s, 1H), 8.47 (s, 2H), 8.33 (d, J = 8.22 Hz, 1H), 8.14 (s, 1H), 7.84-8.02 (m, 2H), 7.78 (d, J = 7.83 Hz, 1H), 7.31-7.58 (m, 3H), 7.17 (d, J = 5.87 Hz, 1H), 6.98 (br. s., 1H), 2.92 (br. s., 2H), 2.38 (s, 3H), 1.36 (s, 6H) |
| 462 | 632.2 | $^1$H NMR (400 MHz, DMSO-$d_6$) δ: 10.71 (s, 1H), 9.84 (s, 1H), 9.38 (s, 1 H,) 8.44-8.55 (m, 2H), 8.34 (dd, J = 8.0, 1.0 Hz, 1H), 7.94 (dd, J = 8.2, 1.6 Hz, 1H), 7.88 (dd, J = 8.2, 1.6 Hz, 1H), 7.46-7.56 (m, 2H), 7.41 (t, J = 7.8 Hz, 1H), 7.29 (td, J = 8.7, 5.7 Hz, 1H), 7.18-7.25 (m, 1 H) |
| 463 | 604.2 | $^1$H NMR (400 MHz, DMSO-$d_6$) δ: 10.43-10.94 (m, 2H), 9.71 (s, 1H), 8.41-8.53 (m, 1H), 8.36 (d, J = 8.6 Hz, 1H), 8.09 (d, J = 9.0 Hz, 1H), 7.93 (dd, J = 8.0, 1.4 Hz, 1H), 7.88 (dd, J = 7.8, 1.6 Hz, 1H), 7.51 (t, J = 8.0 Hz, 1H), 7.27 (td, J = 8.8, 5.9 Hz, 1H), 7.13-7.23 (m, 1H), 2.87-3.03 (m, 4H), 1.73-1.82 (m, 4 H) |
| 464 | 639.3 | $^1$H NMR (400 MHz, DMSO-$d_6$) δ: 10.73 (br. s., 1H), 9.84 (s, 1H), 9.15 (s, 1H), 8.46-8.54 (m, 3H), 8.33 (d, J = 7.4 Hz, 2H), 7.95 (d, J = 7.8 Hz, 1H), 7.90 (d, J = 7.8 Hz, 1H), 7.54 (t, J = 8.0 Hz, 1H), 7.40 (quin, J = 7.0 Hz, 2H), 7.31 (td, J = 8.6, 5.9 Hz, 1H), 7.23 (t, J = 9.0 Hz, 1H), 2.62 (s, 3 H) |
| 465 | 744.3 | $^1$H NMR (400 MHz, DMSO-$d_6$) δ: 9.84 (s, 1H), 9.05 (s, 1H), 8.54 (s, 1H), 8.43-8.52 (m, 2H), 8.34 (d, J = 8.61 Hz, 1H), 8.16 (s, 1H), 7.88-7.99(m, 2H), 7.65 (dd, J = 1.17, 7.83 Hz, 1H), 7.43-7.59 (m, 2H), 7.36 (t, J = 8.02 Hz, 1H), 6.96-7.13 (m, 1H), 6.72-6.89 (m, 1H), 3.47-3.60 (m,1H), 3.24 (br. s., 2H), 2.78 (t, J = 11.93 Hz, 2H), 2.14 (d, J = 12.13 Hz, 2H), 1.72 (d, J = 9.39 Hz, 2H) |
| 466 | 745.3 | $^1$H NMR (400 MHz, DMSO-$d_6$) δ: 9.93(s, 1H), 8.90-9.07 (m, 1H), 8.43-8.56 (m, 3H), 8.30 (d, J = 8.61 Hz, 1H), 7.84-8.05 (m, 3H), 7.72-7.72 (m, 1H), 7.37-7.57 (m, 3H), 7.26 (d, J = 5.48 Hz, 1H), 7.16 (br. s., 1H), 3.91 (dd, J = 3.52, 11.35 Hz, 2H), 3.54 (tt, J = 3.62, 12.03 Hz, 1H), 3.28 (br. s., 2H), 1.83-1.98 (m, 2H), 1.67 (dq, J = 4.70, 12.39 Hz, 2H) |

TABLE 4-continued

| | | |
|---|---|---|
| 467 | 758.3 | $^1$H NMR (400 MHz, DMSO-$d_6$) δ: 9.92 (s, 1H), 8.82-9.10 (m, 1H), 8.35-8.63 (m, 3H), 8.31 (d, J = 8.22 Hz, 1H), 7.85-8.00 (m, 3H), 7.39- 7.60 (m, 3H), 7.23 (d, J = 5.09 Hz, 1H), 7.09 (br. s., 1H), 3.18-3.23 (m, 1H), 2.95 (br. s., 2H), 2.24 (br. s., 3H), 2.03 (d, J = 12.91 Hz, 4H), 1.54-1.77 (m, 2H) |
| 468 | 786.3 | $^1$H NMR (400 MHz, DMSO-$d_6$) δ: 9.89 (s, 1H), 8.97 (s, 1H), 8.38-8.63 (m, 3H), 8.31 (d, J = 8.22 Hz, 1H), 8.14 (s, 2H), 7.78-8.07 (m, 2H), 7.73(br. s., 1H), 7.37-7.52 (m, 3H), 7.14 (br. s., 1H), 6.92 (br. s., 1H), 2.92 (d, J = 10.96 Hz, 2H), 2.77 (br. s., 1H), 2.28-2.35 (m, 1H), 2.24 (br. s.,1H), 1.94-2.09 (m, 2H), 1.56-1.69 (m, 2H), 0.80-1.09 (m, 6H) |
| 469 | 798.3 | $^1$H NMR (400 MHz, DMSO-$d_6$) δ: 9.94 (s, 1H), 8.97 (s, 1H), 8.44-8.54 (m, 3H), 8.31 (d, J = 8.22 Hz, 1H), 8.14 (s, 1H), 7.86-8.06 (m, 2H), 7.82 (br. s., 1H), 7.42-7.53 (m, 3H), 7.20 (br. s., 1H), 7.05 (br. s., 1H), 3.04 (br. s., 2H), 2.44 (br. s., 2H), 1.98 (d, J = 12.13 Hz, 5H), 1.67 (d, J = 9.00 Hz, 2H), 0.97 (t, J = 7.04 Hz, 4H) |
| 470 | 798.3 | $^1$H NMR (400 MHz, DMSO-$d_6$) δ: 9.93 (s, 1H), 8.78-8.97 (m, 1H), 8.35-8.60 (m, 3H), 8.29 (d, J = 8.61 Hz, 1H), 8.12 (s, 1H), 7.77-7.95 (m, 3H), 7.40-7.50 (m, 3H), 7.21 (br. s., 1H), 7.08 (br. s., 1H), 3.14-3.26 (m, 2H), 2.86 (br. s., 2H), 1.96-2.16 (m, 2H), 1.85-1.96 (m, 2H), 1.71 (d, J = 10.56 Hz, 4H), 1.46-1.64 (m, 4H)) |
| 471 | 653.3 | $^1$H NMR (400 MHz, DMSO-$d_6$) δ: 10.73 (s, 1H), 9.82 (s, 1H), 9.16 (s, 1H), 8.45-8.56 (m, 3H), 8.30-8.39 (m, 2H), 7.94 (d, J = 8.2 Hz, 1H), 7.90 (dd, J = 8.0, 1.4 Hz, 1H), 7.53 (t, J = 8.0 Hz, 1H), 7.35-7.45 (m, 2H), 7.26-7.35 (m, 1H), 7.23 (t, J = 8.6 Hz, 1H), 3.08 (q, J = 7.4 Hz, 2H), 1.17 (t, J = 7.2 Hz, 3 H) |
| 472 | 673.2 | $^1$H NMR (400 MHz, DMSO-$d_6$) δ: 10.72 (br. s., 1H), 9.79 (s, 1H), 8.58 (d, J = 4.70 Hz, 1H), 8.49 (s,1H), 8.44 (s, 2H), 8.35 (d, J = 8.22 Hz, 1H), 7.98 (d, J = 7.83 Hz, 1H), 7.93 (d, J = 7.83 Hz, 1H), 7.90 (dd, J = 7.83, 1.57 Hz, 1H), 7.52(t, J = 8.02 Hz, 1H), 7.38-7.48 (m, 1H), 7.31-7.38 (m, 1H), 7.28 (br. s., 1H), 7.20 (br. s., 1 H), 1.83 (s, 3 H) 1.80 (s, 3 H) |
| 473 | 770.2 | $^1$H NMR (400 MHz, DMSO-$d_6$) δ: 10.73 (s, 1H), 9.82 (s, 1H), 8.67 (s, 1H), 8.51 (s, 1H), 8.41-8.49 (m, 2H), 8.38 (d, J = 9.0 Hz, 1H), 7.95 (dd, J = 7.8, 1.2 Hz, 1H), 7.86-7.92 (m, 2H), 7.54 (t, J = 8.0 Hz, 1H), 7.39 (dd, J = 9.0, 2.3 Hz, 1H), 7.27-7.36 (m, 1H), 7.20-7.27 (m, 1H), 4.53 (br. s., 2H), 3.74 (d, J = 10.6 Hz, 2H), 3.63 (d, J = 10.2 Hz, 2H), 1.94 (br. s., 4H) |
| 474 | 801.2 | $^1$H NMR (400 MHz, DMSO-$d_6$) δ: 9.97 (s, 1H), 8.92 (s, 1H), 8.36-8.64 (m, 4H), 8.28 (d, J = 8.61 Hz, 1H), 7.83-8.03 (m, 3H), 7.44-7.50 (m, 3H), 7.42 (s, 1H), 4.38-4.51 (m, 2H), 4.31 (t, J = 6.06 Hz, 3H), 2.72 (br. s., 2H), 2.31 (s, 1H), 1.99 (br. s., 2H), 1.75 (m, 2H), 1.63 (m, 2H) |
| 475 | 814.4 | $^1$H NMR (400 MHz, DMSO-$d_6$) δ: 9.95 (s, 1H), 8.91 (s, 1H), 8.50 (s, 1H), 8.46 (d, J = 6.26 Hz, 2H), 8.29 (d, J = 8.61 Hz, 1H), 7.85-8.07 (m, 3H), 7.43 (d, J = 8.22 Hz, 1H), 7.48 (d, J = 7.43 Hz, 2H), 7.25 (s, 1H), 2.80 (br. s., 2H), 2.52 (s, 1H), 2.19 (s, 2H), 2.00 (s, 2H), 1.87 (s, 2H), 1.68 (s, 2H), 0.77 (s, 9H) |
| 476 | 824.2 | $^1$H NMR (400 MHz, DMSO-$d_6$) δ: 9.94 (s, 1H), 8.92 (s, 1H), 8.41-8.57 (m, 3H), 8.30 (d, J = 8.22 Hz, 1H), 7.81-8.01 (m, 3H), 7.38-7.61 (m, 3H),7.17-7.33 (m, 1H), 7.10 (t, J = 8.22 Hz, 1H), 6.89 (br. s., 2H), 6.52 (s, 1H), 3.46 (br. s., 2H), 2.85 (d, J = 9.78 Hz, 2H), 2.01 (br. s., 4H), 1.64 (d, J = 9.39 Hz, 2H) |
| 477 | 828.4 | $^1$H NMR (400 MHz, DMSO-$d_6$) δ: 10.72 (br. s., 1H), 10.01 (s, 1H), 8.85 (s, 1H), 8.42-8.63 (m, 3H), 8.20-8.42 (m, 2H), 7.86-8.00 (m, 1H), 7.75-7.81 (m, 1H), 7.40-7.56 (m, 3H), 7.11-7.40 (m, 4H), 4.86 (s, 2H) |
| 478 | 824.4 | $^1$H NMR (400 MHz, DMSO-$d_6$) δ: 9.87 (s, 1H), 8.87-9.11 (m, 1H), 8.53 (s, 1H), 8.41-8.51 (m, 2H), 8.31 (d, J = 8.22 Hz, 1H), 8.17 (s, 1H), 7.88-7.99 (m, 2H), 7.68 (br. s., 1H), 7.30-7.56 (m, 5H), 7.09 (br. s., 1H), 6.86 (br. s., 1H), 3.15-3.24 (m, 2H), 2.89 (d, J = 10.96 Hz, 2H), 1.99 (d, J = 10.56 Hz, 2H), 1.85-1.94 (m, 2H), 1.54-1.72 (m, 2H) |
| 479 | 838.4 | $^1$H NMR (400 MHz, DMSO-$d_6$) δ: 9.96 (s, 1H), 8.92 (s, 1H), 8.37-8.59 (m, 3H), 8.30 (d, J = 8.22 Hz, 1H), 7.80-8.05 (m, 3H), 7.35-7.60 (m, 3H), 7.27 (d, J = 5.48 Hz, 1H), 7.16 (s, 1H), 7.06 (s, 1H), 6.75 (s, 1H), 3.58 (s, 3H), 3.49 (br. s., 2H), 3.10-3.26 (m, 2H), 2.86 (br. s., 2H), 1.99 (br. s., 4H), 1.64 (br. s., 2H) |
| 480 | 622.2 | $^1$H NMR (400 MHz, DMSO-$d_6$) δ: 10.73 (s, 1H), 9.94 (s, 1H), 9.29 (s, 1H), 8.42-8.61 (m, 3H), 8.37 (d, J = 8.22 Hz, 1H), 7.86-8.05 (m, 2H), 7.81(d, J = 7.04 Hz, 1H), 7.35-7.63 (m, 3H), 7.10-7.35 (m, 2H) |
| 481 | 637.3 | $^1$H NMR (400 MHz, DMSO-$d_6$) δ: 10.15 (br. s., 1H), 10.01 (s, 1H), 8.98 (s, 1H), 8.40-8.57 (m, 3H), 8.30 (d, J = 8.22 Hz, 1H), 7.98 (dd, J = 1.37,7.24 Hz, 1H), 7.64-7.73 (m, 2H), 7.40-7.61 (m, 2H), 7.15-7.35 (m, 2H), 6.96-7.15 (m, 2H), 3.81 (s, 3H), 3.34 (s, 3H) |
| 482 | 667.4 | $^1$H NMR (400 MHz, DMSO-$d_6$) δ: 10.73 (s, 1H), 9.81 (s, 1H), 9.18 (s, 1H), 8.48-8.54 (m, 3H), 8.34 (d, J = 7.4 Hz, 1H), 8.37 (d, J = 6.7 Hz, 1H), 7.95 (d, J = 8.6 Hz, 1H), 7.90 (d, J = 8.2 Hz, 1H), 7.54 (t, J = 8.2 Hz, 1H), 7.40 (t, J = 6.5 Hz, 2H), 7.31 (m, J = 6.3 Hz, 1H), 7.24 (t, J = 8.6 Hz, 1H), 3.66 (m, J = 6.7, 6.7, 6.7 Hz, 1H), 1.21 (d, J = 3.1 Hz, 3H), 1.20 (d, J = 2.7 Hz, 3 H) |
| 483 | 698.3 | $^1$H NMR (400 MHz, DMSO-$d_6$) δ: 10.71 (br. s., 1H), 10.14 (s, 1H), 9.63 (s, 1H), 8.60 (s, 1H), 8.41-8.47 (m, 2H), 8.33 (d, J = 8.6 Hz, 1H), 8.25 (d, J = 9.0 Hz, 1 H), 7.98 (d, J = 7.4 Hz, 1H), 7.94 (d, J = 8.2 Hz, 1H), 7.91 (d, J = 7.8 Hz, 1H), 7.53 (t, J = 7.8 Hz, 1H), 7.37 (t, J = 7.8 Hz, 1H), 7.25-7.31 (m, 2H), 7.20 (t, J = 7.0 Hz, 1H), 3.69 (t, J = 6.1 Hz, 2H), 3.27 (s, 3H), 2.72 (t, J = 6.1 Hz, 2 H) |
| 484 | 748.4 | $^1$H NMR (400 MHz, DMSO-$d_6$) δ: 9.94 (s, 1H), 9.01 (s, 1H), 8.52 (s, 1H), 8.44-8.50 (m, 2H), 8.32 (d, J = 8.6 Hz, 1H), 7.89-7.98 (m, 2H), 7.81 (d, J = 8.6 Hz, 1H), 7.41-7.54 (m, 3H), 7.14-7.25 (m, 1H), 6.97-7.08 (m, 1H), 3.40-3.46 (m, 3H), 2.54-2.60 (m, 1H), 2.27 (s, 6H), 1.83-1.92 (m, 2H) |

TABLE 4-continued

| | | |
|---|---|---|
| 485 | 702.4 | $^1$H NMR (400 MHz, DMSO-$d_6$) δ: 10.51 (br. s., 1H), 9.82 (s, 1H), 8.66 (s, 1H), 8.48 (s, 1H), 8.43 (q, J = 9.3 Hz, 2H), 8.33 (d, J = 8.2 Hz, 1H), 7.71 (d, J = 7.4 Hz, 1H), 7.62 (d, J = 7.8 Hz, 1H), 7.45-7.52 (m, 1H), 7.36-7.43 (m, 2H), 7.26-7.36 (m, 2H), 7.17-7.26 (m, 1H), 4.45 (s, 1H), 3.62-4.22 (m, 2H), 3.37-3.50 (m, 2H), 1.41-1.60 (m, 4H), 1.17 (s, 3H) |
| 486 | 645.3 | $^1$H NMR (400 MHz, DMSO-$d_6$) δ: 10.74(s, 1H), 10.16 (s, 1H), 9.41 (s, 1H), 8.44-8.38 (m, 2H), 8.28 (d, J = 9.1 Hz, 1H), 7.96-7.87 (m, 2H), 7.52 (t, J = 7.9 Hz, 1H), 7.33-7.25 (1H), 3.84- 3.75 (m, 2H), 2.83 (t, J = 6.3 Hz, 2H), 2.25 (s, 3H), 2.06-1.99 (m, 2H). |
| 487 | 665.3 | $^1$H NMR (400 MHz, DMSO-$d_6$) δ: 10.73 (br. s., 1H), 9.86 (s, 1H), 9.36 (s, 1H), 8.46-8.57 (m, 3H), 8.35 (t, J = 7.8 Hz, 2H), 7.94 (d, J = 8.2 Hz, 1H), 7.90 (dd, J = 7.8, 1.2 Hz, 1H), 7.53 (t, J = 8.0 Hz, 1H), 7.35-7.45 (m, 2H), 7.30 (td, J = 9.0, 5.9 Hz, 1H), 7.22 (t, J = 9.0 Hz, 1H), 2.89-2.99 (m, 1H), 1.05-1.12 (m, 2H), 0.96-1.05 (m, 2 H) |
| 488 | 808.4 | $^1$H NMR (400 MHz, DMSO-$d_6$) δ: 10.72 (br. s., 1H), 10.00 (s, 1H), 8.92 (s, 1H), 8.44-8.61 (m, 3H), 8.29 (d, J = 8.22 Hz, 1H), 7.86-8.04 (m, 3H),7.39-7.59 (m, 3H), 7.17-7.39 (m, 2H), 3.11-3.29 (m, 1H), 2.95 (d, J = 11.35 Hz, 2H), 2.68 (dt, J = 4.30, 15.65 Hz, 2H), 2.18 (t, J = 10.76 Hz,2H), 1.99 (d, J = 10.96 Hz, 2H), 1.61 (dd, J = 3.72, 11.93 Hz, 2H) |
| 489 | 626.2 | $^1$H NMR (400 MHz, DMSO-$d_6$) δ: 10.74 (br. s, 1H), 10.01 (s, 1H), 9.06 (s, 1H), 8.88 (s, 1H), 8.40-8.50 (m, 3H), 7.94 (dd, J = 8.0, 1.4 Hz, 1H), 7.85-7.91 (m, 3 H), 7.52 (t, J = 8.0 Hz, 1H), 7.43 (t, J = 7.6 Hz, 2H), 7.21-7.37 (m, 3 H) |
| 490 | 752.4 | $^1$H NMR (400 MHz, DMSO-$d_6$) δ: 10.73 (br. s., 1H), 10.00 (s, 1H), 8.88 (s, 1H), 8.36-8.59 (m, 5H), 8.29 (d, J = 8.61 Hz, 1H), 7.85-7.99 (m, 2H), 7.65 (d, J = 7.83 Hz, 1H), 7.38-7.60 (m, 2H), 7.13-7.38 (m, 5H), 4.82 (s, 2H) |
| 491 | 770.2 | $^1$H NMR (400 MHz, DMSO-$d_6$) δ: 9.97 (br. s., 1H), 8.87 (s, 1H), 8.38-8.62 (m, 2H), 8.33 (s, 1H), 8.29 (d, J = 8.61 Hz, 1H), 7.92 (t, J = 8.02 Hz,2H), 7.82 (d, J = 7.43 Hz, 1H), 7.60 (d, J = 7.04 Hz, 1H), 7.37-7.54 (m, 2H), 7.20-7.37 (m, 4H), 6.98-7.20 (m, 2H), 4.73 (s, 2H) |
| 492 | 752.2 | $^1$H NMR (400 MHz, DMSO-$d_6$) δ: 10.72 (br. s., 1H), 10.01 (s, 1H), 8.85 (s, 1H), 8.42-8.63 (m, 3H), 8.20-8.42 (m, 2H), 7.86-8.00 (m, 1H), 7.75-7.81 (m, 1H), 7.40-7.56 (m, 3H), 7.11-7.40 (m, 4H), 4.86 (s, 2H) |
| 493 | 769.3 | $^1$H NMR (400 MHz, DMSO-$d_6$) δ: 9.97 (br. s., 1H), 8.88 (s, 1H), 8.35-8.57 (m, 3H), 8.29 (d, J = 8.22 Hz, 1H), 7.78-8.03 (m, 1H), 7.60 (d, J = 7.83 Hz, 1H), 7.41-7.51 (m, 2H), 7.19-7.38 (m, 4H), 7.06-7.19 (m, 3H), 5.74 (s, 2H) |
| 494 | 676.2 | $^1$H NMR (400 MHz, DMSO-$d_6$) δ: 10.73 (br. s., 1H), 10.02 (s, 1H), 8.98 (s, 1H), 8.38-8.67 (m, 3H), 8.30 (d, J = 7.83 Hz, 1H), 7.84-8.04 (m, 3H), 7.44-7.56 (m, 3H), 7.31 (d, J = 6.26 Hz, 1H), 7.23 (br. s., 1H) |
| 495 | 743.2 | Not determined |
| 496 | 613.2 | $^1$H NMR (400 MHz, DMSO-$d_6$) δ: 10.48 (br. s., 1H), 9.82 (m, J = 4.3 Hz, 1H), 9.28 (s, 1H), 8.42-8.55 (m, 2H), 8.10-8.19 (m, 1H), 7.81-7.96 (m, 1H), 7.67-7.78 (m, 2H), 7.48-7.65 (m, 1H), 7.17-7.36 (m, 3H), 2.61 (s, 3 H) |
| 497 | 757.2 | $^1$H NMR (400 MHz, DMSO-$d_6$) δ: 10.73 (br. s., 1H), 9.88-10.07 (m, 1H), 8.95 (s, 1H), 8.52 (s, 1H), 8.47 (s, 2H), 8.29 (d, J = 7.83 Hz, 1H), 7.79-8.03 (m, 3H), 7.37-7.58 (m, 3H), 7.28 (br. s., 1H), 7.22 (br. s., 1H), 4.42 (t, J = 6.85 Hz, 1H), 2.42-2.49 (m, 2H), 2.13-2.33 (m, 2H), 1.92-2.06(m, 1H), 1.84 (d, J = 5.48 Hz, 2H), 1.70 (br. s., 1H) |
| 498 | 728.2 | $^1$H NMR (400 MHz, DMSO-$d_6$) δ: 10.72 (br. s., 1H), 10.00 (s, 1H), 9.09 (s, 1H), 8.42-8.59 (m, 3H), 8.30 (d, J = 7.83 Hz, 1H), 7.97-8.06 (m, 1H),7.78-7.97 (m, 2H), 7.39-7.68 (m, 3H), 7.27 (br. s., 2H), 1.76 (s, 6H) |
| 499 | 767.3 | $^1$H NMR (400 MHz, DMSO-$d_6$) δ: 10.72 (s, 1H), 9.96 (s, 1H), 8.96 (s, 1H), 8.41-8.59 (m, 3H), 8.32 (d, J = 7.43 Hz, 1H), 7.77-8.04 (m, 3H), 7.40- 7.63 (m, 3H), 7.29 (d, J = 9.00 Hz, 1H), 7.22 (br. s., 1H), 6.14-6.61 (m, 1H), 2.34 (dt, J = 4.70, 17.61 Hz, 2H), 1.42 (s, 6H) |
| 500 | 695.2 | $^1$H NMR (400 MHz, DMSO-$d_6$) δ: 10.73 (br. s., 1H), 9.77 (s, 1H), 9.21 (s, 1H), 8.42-8.62 (m, 3H), 8.37 (m, J = 8.6 Hz, 2H), 7.91 (m, J = 7.8 Hz, 2H), 7.51 (t, J = 8.0 Hz, 1H), 7.35-7.47 (m, 2H), 7.27 (br. s., 1H), 7.18 (br. s., 1H), 4.15-4.26 (m, 1H), 4.11 (t, J = 8.2 Hz, 1H), 3.76-3.89 (m, 3H), 2.21 (q, J = 7.2 Hz, 2 H) |
| 501 | 616.1 | $^1$H NMR (400 MHz, DMSO-$d_6$) δ: 10.69 (br. s, 1H), 9.69-9.81 (m, 1H), 8.45-8.51 (m, 1H), 8.40 (d, J = 9.0 Hz, 1H), 8.13 (d, J = 9.0 Hz, 1H), 7.94 (dd, J = 8.2, 1.6 Hz, 1H), 7.84-7.91 (m, 1H), 7.68 (d, J = 3.5 Hz, 1H), 7.52 (t, J = 8.0 Hz, 1H), 7.14-7.34 (m, 2H), 6.58 (d, J = 3.5 Hz, 1H), 3.20-3.26 (m, 2H), 2.41 (t, J = 6.3 Hz, 2H), 2.00-2.12 (m, 2 H) |
| 502 | 690.2 | $^1$H NMR (400 MHz, DMSO-$d_6$) δ: 10.72 (br. s., 1H), 10.04 (s, 1H), 8.70 (s, 1H), 8.50 (s, 1H), 8.30-8.47 (m, 2H), 7.83-8.02 (m, 2H), 7.52 (t, J = 8.02 Hz, 1H), 7.39 (d, J = 8.22 Hz, 1H), 7.30 (d, J = 3.91 Hz, 1H), 7.19 (t, J = 8.22 Hz, 2H), 6.67 (d, J = 7.83 Hz, 1H), 5.82 (s, 2H), 3.40 (s, 3H) |
| 503 | 670.2 | $^1$H NMR (400 MHz, DMSO-$d_6$) δ: 10.73 (br. s, 1H), 10.08 (s, 1H), 9.40 (s, 1H), 8.52 (br. s, 1H), 8.50 (s, 2H), 8.32 (d, J = 2.0 Hz, 1H), 7.95 (dd, J = 8.2, 1.6 Hz, 1 H), 7.90 (dd, J = 7.8, 1.6 Hz, 1H), 7.63 (d, J = 1.6 Hz, 1H), 7.53 (t, J = 8.0 Hz, 1H), 7.28-7.38 (m, 1H), 7.20-7.28 (m, 1 H) |
| 504 | 629.2 | $^1$H NMR (400 MHz, DMSO-$d_6$) δ: 9.85 (br. s, 1H), 9.34 (s, 1H), 8.43-8.59 (m, 5 H), 8.07 (d, J = 5.9 Hz, 1H), 7.95 (d, J = 6.3 Hz, 1H), 7.89 (d, J = 7.8 Hz, 2H), 4.05 (s, 3 H) |
| 505 | 633.2 | $^1$H NMR (400 MHz, DMSO-$d_6$) δ: 10.21 (s, 1H), 10.03 (s, 1H), 9.38 (d, J = 9.0 Hz, 1H), 8.44-8.63 (m, 3H), 7.94 (d, J = 8.2 Hz, 1H), 7.89 (dd, J = 8.0, 1.4 Hz, 1H), 7.65 (d, J = 5.5 Hz, 1H), 7.52 (t, J = 8.0 Hz, 1H), 7.19-7.35 (m, 2 H) |
| 506 | 642.4 | $^1$H NMR (400 MHz, DMSO-$d_6$) δ: 10.73 (s, 1H), 10.10 (s, 1H), 9.54 (s, 1H), 8.55-8.49 (m,3H), 8.32-8.26 (m, 2H), 7.93 (d, J = 7.5 H 1.5 Hz, 1H), 7.59-7.50(m, 3H), 7.34-7.27 (m, 1H), 7.21 (s, 1H). |

TABLE 4-continued

| | | |
|---|---|---|
| 507 | 599.3 | $^1$H NMR (400 MHz, DMSO-$d_6$) δ: 10.70 (s, 1H), 10.13 (s, 1H), 8.83 (dd, J = 9.1, 0.9 Hz, 1H), 8.59-8.50(m, 2H), 8.11 (ddd, J = 6.7, 3.1, 1.0 Hz, 2H), 7.95 (dd, J = 8.1, 1.3 Hz, 1H), 7.91 (dd, J = 8.0, 1.5 Hz,1H), 7.64-7.58 (m, 2H), 7.54 (t, J = 8.0 Hz, 1H), 7.30 (td, J = 8.7, 5.8 Hz, 1H), 7.20 (t, J = 9.1 Hz, 1H) |
| 508 | 616.0 | $^1$H NMR (400 MHz, DMSO-$d_6$) δ: 10.76 (br. s., 1H), 10.14 (s, 1H), 9.19 (s, 1H), 9.13 (s, 2H), 8.47-8.53 (m, 2H), 7.84-7.99 (m, 2H), 7.53 (t, J = 8.02 Hz, 1H), 7.16-7.36 (m, 2H) |
| 509 | 790.2 | $^1$H NMR (400 MHz, DMSO-$d_6$) δ: 10.71 (br. s., 1H), 9.99 (s, 1H), 8.98 (s, 1H), 8.44-8.54 (m, 3H), 8.31 (d, J = 7.8 Hz, 1H), 7.88-7.97 (m, 3H), 7.43-7.56 (m, 3H), 7.24-7.33 (m, 1H), 7.15-7.23 (m, 1H), 3.39-3.47 (m, 5H), 2.50 (br. s., 2H), 2.32 (t, J = 6.7 Hz, 2H), 2.18-2.25 (m, 3H), 1.78-1.88 (m, 2H) |
| 510 | 652.3 | $^1$H NMR (400 MHz, DMSO-$d_6$) δ: 9.34 (s, 1H), 9.02 (s, 1H), 8.85 (d, J = 7.83 Hz, 2H), 8.47 (d, J = 9.00 Hz, 1H), 8.40 (s, 1H), 8.18 (d, J = 9.00 Hz,1H), 7.65 (d, J = 7.43 Hz, 1H), 7.50 (t, J = 8.02 Hz, 1H), 7.36 (br. s., 2H), 7.24 (br. s., 1H), 6.94-7.19 (m, 2H), 6.53 (br. s., 1H), 2.54 (s, 3H) |
| 511 | 680.2 | $^1$H NMR (400 MHz, DMSO-$d_6$) δ: 10.73 (br. s., 1H), 9.69 (s, 1H), 8.49 (s, 1H), 8.45 (s, 1H), 8.34-8.42 (m, 3H), 7.94 (d, J = 7.8 Hz, 1H), 7.90 (dd, J = 7.8, 1.2 Hz, 1H), 7.75 (d, J = 7.8 Hz, 1H), 7.53 (t, J = 8.0 Hz, 1H), 7.37 (t, J = 7.4 Hz, 1H), 7.17-7.33 (m, 3H), 3.98 (t, J = 7.0 Hz, 2H), 2.52-2.56 (m, 2H), 2.21 (quin, J = 7.5 Hz, 2 H) |
| 512 | 684.2 | $^1$H NMR (400 MHz, DMSO-$d_6$) δ: 9.84 (m, J = 3.1 Hz, 1 H) 9.11 (s, 1 H) 8.38-8.54 (m, 3 H) 7.95 (m, J = 5.9 Hz, 1 H) 7.90 (td, J = 8.3, 1.4 Hz, 1 H) 7.72-7.77 (m, 1 H) 7.58-7.70 (m, 1 H) 7.52 (t, J = 8.0 Hz, 1 H) 7.45 (m, J = 5.7, 2.2 Hz, 1 H) 7.13-7.33 (m, 2 H) 4.94 (d, J = 3.1 Hz, 1 H) 4.41 (br. s., 1 H) 3.82-4.04 (m, 4 H) 1.83-2.09 (m, 2 H) |
| 513 | 643.2 | $^1$H NMR (400 MHz, DMSO-$d_6$) δ: 9.87 (s, 1H), 9.33 (s, 1H), 8.50 (s, 1H), 8.46-8.49 (m, 2H), 8.05 (d, J = 5.9 Hz, 1H), 7.84-7.95 (m, 3H), 7.47-7.56 (m, 1H), 7.12-7.34 (m, 2H), 4.52 (q, J = 7.0 Hz, 2H), 1.41 (t, J = 7.0 Hz, 3 H) |
| 514 | 730.2 | $^1$H NMR (400 MHz, DMSO-$d_6$) δ: 9.65 (br. s, 1 H) 8.49 (s, 1 H) 8.44 (m, J = 7.8 Hz, 1 H) 8.34-8.42 (m, 3 H) 7.89 (d, J = 7.8 Hz, 2 H) 7.69 (d, J = 7.4 Hz, 1 H) 7.50 (t, J = 8.0 Hz, 1 H) 7.32-7.39 (m, 1 H) 7.22-7.31 (m, 2 H) 7.16 (br. s., 1 H) 3.72-3.81 (m, 2 H) 3.38-3.43 (m, 2 H) 2.16-2.30 (m, 2 H) 1.84-1.96 (m, 2 H) |
| 515 | 633.2 | $^1$H NMR (400 MHz, MeOH-$d_4$) δ: 9.55 (s, 1 H) 9.43 (s, 1 H) 8.55 (s, 1 H) 8.46-8.52 (m, 3 H) 7.94 (dd, J = 8.0, 1.4 Hz, 1 H) 7.78 (dd, J = 8.0, 1.4 Hz, 1 H) 7.37-7.51 (m, 2 H) 7.08 (td, J = 9.1, 1.8 Hz, 1 H) |
| 516 | 576.2 | $^1$H NMR (400 MHz, DMSO-$d_6$) δ: 10.75 (br. s., 1H), 9.85 (s, 1H), 8.48 (s, 1H), 8.40 (d, J = 9.0 Hz, 1H), 8.34 (br. s., 1H), 8.12 (d, J = 9.0 Hz, 1H), 7.95 (dd, J = 8.2, 1.2 Hz, 1H), 7.89 (dd, J = 8.2, 1.2 Hz, 1H), 7.53 (t, J = 8.0 Hz, 1H), 7.29 (td, J = 9.0, 5.9 Hz, 1H), 7.21 (t, J = 9.0 Hz, 1H), 2.41 (s, 3H), 2.15 (s, 3 H) |
| 517 | 549.2 | $^1$H NMR (400 MHz, DMSO-$d_6$) δ: 10.76 (br. s., 1H), 10.19 (s, 1H), 9.49 (s, 1H), 8.64 (d, J = 9.0 Hz, 1H), 8.47-8.56 (m, 2H), 8.12 (s, 1H), 7.95 (d, J = 8.2 Hz, 1 H), 7.90 (d, J = 7.8 Hz, 1H), 7.53 (t, J = 8.0 Hz, 1H), 7.29-7.38 (m, 1H), 7.26 (t, J = 9.0 Hz, 1 H) |
| 518 | 549.2 | $^1$H NMR (400 MHz, DMSO-$d_6$) δ: 10.68 (s, 1H), 9.96 (s, 1H), 8.56 (d, J = 9.0 Hz, 1H), 8.49 (s, 1H), 8.47 (d, J = 9.0 Hz, 1H), 8.33 (s, 2H), 7.95 (dd, J = 7.8, 1.2 Hz, 1H), 7.90 (dd, J = 8.0, 1.4 Hz, 1H), 7.54 (t, J = 8.0 Hz, 1H), 7.28 (td, J = 8.7, 6.1 Hz, 1H), 7.19 (t, J = 9.0 Hz, 1 H) |
| 519 | 577.2 | $^1$H NMR (400 MHz, DMSO-$d_6$) δ: 10.71 (br. s., 1H), 9.51 (s, 1H), 8.50 (br. s., 1 H), 8.41 (d, J = 9.4 Hz, 1H), 8.26 (d, J = 9.0 Hz, 1H), 7.95 (d, J = 8.2 Hz, 1H), 7.89 (d, J = 6.7 Hz, 1H), 7.54 (t, J = 8.0 Hz, 1H), 7.30 (td, J = 8.6, 5.9 Hz, 1H), 7.22 (t, J = 9.4 Hz, 1H), 2.86 (s, 3H), 2.34 (s, 3 H) |
| 520 | 665.2 | $^1$H NMR (400 MHz, DMSO-$d_6$) δ: 10.73 (s, 1H), 9.83 (s, 1H), 9.31 (s, 1H), 8.46 8.57 (m, 3H), 8.36 (quin, J = 3.9 Hz, 1H), 7.95 (dd, J = 7.8, 1.2 Hz, 1H), 7.90 (dd, J = 8.0, 1.4 Hz, 1H), 7.54 (t, J = 8.0 Hz, 1H), 7.43-7.50 (m, 2H), 7.31 (td, J = 9.0, 5.9 Hz, 1H), 7.23 (t, J = 9.0 Hz, 1H), 2.00 (s, 6 H) |
| 521 | 676.2 | $^1$H NMR (400 MHz, DMSO-$d_6$) δ: 10.73 (s, 1H), 9.85 (s, 1H), 9.49 (s, 1H), 8.74 (d, J = 7.8 Hz, 1H), 8.51-8.59 (m, 3H), 7.96 (dd, J = 8.0, 1.4 Hz, 1H), 7.91 (d, J = 7.0 Hz, 1H), 7.90 (dd, J = 8.2, 1.6 Hz, 1H), 7.65 (t, J = 8.0 Hz, 1H), 7.54 (t, J = 8.0 Hz, 1H), 7.32 (td, J = 8.8, 5.9 Hz, 1H), 7.24 (t, J = 9.0 Hz, 1H), 3.55 (s, 3H) |
| 522 | 673.2 | $^1$H NMR (400 MHz, MeOH-$d_4$) δ: 9.10-9.27 (m, 1H), 8.34-8.63 (m, 3H), 8.05-8.12 (m, 1H), 7.93-7.99 (m, 1H), 7.73-7.84 (m, 2H), 7.36-7.53 (m, 2H), 7.00-7.23 (m, 2H), 4.65-4.73 (m, 2H), 3.83-3.92 (m, 2H), 2.65 (s, 3 H) |
| 523 | 660.2 | $^1$H NMR (400 MHz, DMSO-$d_6$) δ: 9.86 (s, 1H), 9.22 (s, 1H), 8.47-8.52 (m, 1H), 8.45 (d, J = 2.3 Hz, 2H), 7.83-7.92 (m, 3H), 7.43-7.54 (m, 1H), 7.32 (t, J = 8.2 Hz, 1H), 6.93 (d, J = 8.2 Hz, 1H), 6.51 (s, 1H), 4.97 (t, J = 5.5 Hz, 1H), 4.26 (t, J = 5.1 Hz, 2H), 3.81 (q, J = 5.2 Hz, 2 H) |
| 524 | 711.2 | $^1$H NMR (400 MHz, DMSO-$d_6$) δ: 10.73 (br s, 1H), 9.85 (s, 1H), 9.10 (s, 1H), 8.34-8.61 (m, 3H), 7.94 (d, J = 8.2 Hz, 1H), 7.90 (dd, J = 7.8, 1.6 Hz, 1H), 7.73 (d, J = 8.2 Hz, 1H), 7.53 (t, J = 8.0 Hz, 1H), 7.17-7.36 (m, 3H), 6.77 (d, J = 7.8 Hz, 1H), 4.33 (s, 1H), 3.73-3.89 (m, 2H), 3.38-3.42 (m, 2H), 1.59-1.79 (m, 4 H), 1.20 (s, 3 H) |
| 525 | 644.2 | $^1$H NMR (400 MHz, DMSO-$d_6$) δ: 9.89 (s, 1H), 9.21 (s, 1H), 8.46-8.50 (m, 3H), 7.95 (dd, J = 8.0, 1.4 Hz, 1H), 7.90 (dd, J = 7.8, 1.6 Hz, 1H), 7.87 (d, J = 8.2 Hz, 1 H), 7.54 (t, J = 8.0 Hz, 1H), 7.18-7.38 (m, 3H), 6.92 (d, J = 7.8 Hz, 1H), 4.30 (q, J = 7.0 Hz, 2H), 1.44 (t, J = 7.0 Hz, 3 H) |
| 526 | 711.3 | $^1$H NMR (400 MHz, DMSO-$d_6$) δ: 10.70 (b. s, 1H), 9.79 (s, 1H), 9.06 (s, 1H), 8.36-8.55 (m, 2H), 7.77-7.95 (m, 2H), 7.47-7.59 (m, 1H), 7.06-7.35 (m, 3H), 6.24 (d, J = 7.83 Hz, 1H), 4.40 (s, 1H), 4.09-4.19 (m, 2H), 3.97-4.08 (m, 2H), 2.76 (t, J = 7.43 Hz, 1H), 1.04-1.12 (m, 6H) |

TABLE 4-continued

| | | |
|---|---|---|
| 527 | 697.2 | $^1$H NMR (400 MHz, DMSO-$d_6$) δ: 10.71 (br s, 1H), 9.85 (s, 1H), 9.10-9.21 (m, 1H), 8.35-8.53 (m, 2H), 7.75-7.99 (m, 2H), 7.51 (t, J = 8.02 Hz, 1H), 7.43 (d, J = 8.22 Hz, 1H), 7.09-7.34 (m, 4H), 6.57 (d, J = 7.83 Hz, 1H), 5.52 (d, J = 9.00 Hz, 1H), 3.86-3.96 (m, 2H), 3.68-3.85 (m, 1H), 3.39-3.50 (m, 2H), 1.87-2.00 (m, 2H), 1.47-1.68 (m, 2H) |
| 528 | 707.2 | $^1$H NMR (400 MHz, DMSO-$d_6$) δ: 10.71 (br s, 1H), 9.91 (s, 1H), 9.03 (s, 1H), 8.42-8.58 (m, 3H), 8.30 (dt, J = 7.1, 1.7 Hz, 2H), 8.19 (d, J = 3.5 Hz, 1H), 8.06 (d, J = 5.1 Hz, 1H), 7.93 (d, J = 7.8 Hz, 1H), 7.89 (dd, J = 8.0, 1.4 Hz, 1H), 7.52 (t, J = 8.0 Hz, 1H), 7.39-7.49 (m, 2H), 7.32 (dd, J = 4.7, 3.9 Hz, 1H), 7.24-7.30 (m, 1H), 7.19 (t, J = 8.6 Hz, 1 H) |
| 529 | 563.3 | $^1$H NMR (400 MHz, DMSO-$d_6$) δ: 9.52 (b. s, 1H), 8.91 (d, J = 8.2 Hz, 1H), 8.80 (d, J = 9.0 Hz, 1H), 8.49-8.56 (m, 2H), 8.24 (d, J = 8.2 Hz, 1H), 7.71-7.78 (m, 1H), 7.58-7.64 (m, 2H), 7.44-7.51 (m, 1H), 7.36-7.43 (m, 1H), 7.27-7.35 (m, 1 H), 7.19-7.27 (m, 1H), 2.47 (s, 3 H) |
| 530 | 565.2 | $^1$H NMR (400 MHz, DMSO-$d_6$) δ: 10.72 (s, 1H), 9.88 (s, 1H), 9.29 (s, 1H), 8.91 (s, 1H), 8.49 (d, J = 9.0 Hz, 1H), 8.44 (s, 1H), 8.27 (d, J = 8.6 Hz, 1H), 7.94 (d, J = 8.2 Hz, 1H), 7.90 (d, J = 7.4 Hz, 1H), 7.53 (t, J = 8.0 Hz, 1H), 7.25-7.34 (m, 1 H), 7.20 (t, J = 8.6 Hz, 1 H) |
| 531 | 624.4 | $^1$H NMR (400 MHz, DMSO-$d_6$) δ: 10.51 (br, 1H), 8.97 (s, 1H), 8.47 (s, 1H), 8.38 (q, J = 9.1 Hz, 2H), 7.74(s, 1H), 7.62 (d, J = 7.7 Hz, 1H), 7.51-7.44 (m, 1H), 7.43-7.36 m, 1H), 7.33 ), 4.37 (s,2H), 3.14 (s, 2H), 2.79-2.72 (m, 2H), 2.69-2.62 (m, 2H), 2.49 (s, 3H) |
| 532 | 694.3 | $^1$H NMR (400 MHz, DMSO-$d_6$) δ: 10.73 (br. s., 1H), 9.72 (s, 1H), 8.51 (s, 1H), 8.45 (s, 1H), 8.32-8.43 (m, 3H), 7.94 (d, J = 7.8 Hz, 1H), 7.90 (dd, J = 8.0, 1.4 Hz, 1H), 7.53 (t, J = 8.0 Hz, 1H), 7.46 (d, J = 7.8 Hz, 1H), 7.33-7.39 (m, 1H), 7.18-7.33 (m, 3H), 3.73 (t, J = 5.5 Hz, 2H), 2.47 (br. s., 2H), 1.87-2.02 (m, 4 H) |
| 533 | 579.2 | $^1$H NMR (400 MHz, DMSO-$d_6$) δ: 10.72 (br. s., 1H), 9.82 (s, 1H), 8.63 (s, 1H), 8.43 (s, 1H), 8.40 (d, J = 9.0 Hz, 1H), 8.24 (d, J = 8.6 Hz, 1H), 7.94 (d, J = 8.2 Hz, 1H), 7.90 (dd, J = 8.2, 1.6 Hz, 1H), 7.53 (t, J = 8.0 Hz, 1H), 7.29 (td, J = 8.5, 6.1 Hz, 1H), 7.20 (t, J = 9.0 Hz, 1H), 2.73 (s, 3 H) |
| 534 | 625.2 | $^1$H NMR (400 MHz, DMSO-$d_6$) δ: 10.80 (s, 1H), 10.11 (s, 1H), 9.82 (s, 1H), 8.68 (d, J = 9.1 Hz, 1H), 8.55 (s, 1H), 8.53 (7.49 (m, 3H), 7.45 (t, J = 7.4 Hz, 1H), 7.37-718 (m, 2H) |
| 535 | 548.2 | $^1$H NMR (400 MHz, DMSO-$d_6$) δ: 13.70 (br. s., 0.4H), 13.24 (br. s., 0.6H), 10.74 (br. s., 1H), 10.08 (s, 0.4H), 9.92 (s, 0.6H), 8.44-8.52 (m, 1H), 8.42 (s, 0.6H), 8.34 (d, J = 8.6 Hz, 0.4H), 8.29 (d, J = 8.2 Hz, 0.4H), 8.21 (d, J = 9.0 Hz, 0.6H), 7.86-7.98 (m, 2.6H), 7.68 (s, 0.4H), 7.53 (t, J = 8.0 Hz, 1H), 7.38 (br. s., 0.6H), 7.25 7.34 (m, 1H), 7.15-7.25 (m, 1.4 H) |
| 536 | 565.2 | $^1$H NMR (400 MHz, DMSO-$d_6$) δ: 10.76 (br s, 1H), 10.12 (s, 1H), 9.33 (d, J = 2.1 Hz, 1H), 9.04 (s, 1H), 8.60 (d, J = 8.8 Hz, 1H), 8.46 (s, 1H), 8.31 (d, J = 8.8 Hz, 1H), 7.92 (s, 1H), 7.90 (s, 1H), 7.51 (t, J = 8.0 Hz, 1H), 7.36-7.23 (m, 1H), 7.19 (br m, 1H). |
| 537 | 602.3 | $^1$H NMR (400 MHz, DMSO-$d_6$) δ: 10.72 (s, 1H), 9.33 (s, 1H), 8.38 (s, 1H), 8.33 (s, 1H), 8.13 (q,J = 8.9 Hz, 2H), 7.95 (d, J = 7.9 Hz, 1H), 7.90 (dd, J = 8.0, 1.5 Hz, 1H), 7.54 (t, J = 8.1 Hz, 1H), 7.33-7.25 (m, 1H), 7.25-7.16 (m, 1H), 4.15 (t, J = 5.8 Hz, 2H), 3.25 (t, J = 6.3 Hz, 2H), 2.05-1.96 (m, 2H), 1.92-1.82 (m, 2H). |
| 538 | 672.2 | $^1$H NMR (400 MHz, DMSO-$d_6$) δ: 10.71 (br. s., 1H), 9.85 (s, 1H), 9.21 (s, 1H), 8.43-8.57 (m, 3H), 7.84-7.96 (m, 3H), 7.50 (t, J = 7.8 Hz, 1H), 7.10-7.37 (m, 3H), 6.93 (d, J = 8.2 Hz, 1H), 4.37 (dd, J = 5.3, 3.7 Hz, 2H), 3.67-3.85 (m, 2H), 2.52 (s, 3 H) |
| 539 | 675.4 | $^1$H NMR (400 MHz, DMSO-$d_6$) δ: 9.82 (s, 1H), 9.08 (s, 1H), 8.36-8.54 (m, 3H), 7.71 (d, J = 8.2 Hz, 1H), 7.60 (d, J = 7.8 Hz, 1H), 7.43-7.51 (m, 1H), 7.34-7.42 (m, 1H), 7.16-7.31 (m, 3H), 6.75 (d, J = 7.8 Hz, 1H), 4.30 (s, 1H), 3.72-3.86 (m, 2H), 3.50-3.44 (m, 2H), 1.51-1.74 (m, 4H), 2.47 (s, 3H), 1.18 (s, 3 H) |
| 540 | 696.2 | $^1$H NMR (400 MHz, DMSO-$d_6$) δ: 9.78 (s, 1H), 9.14 (s, 1H), 8.33-8.59 (m, 3H), 7.89 (dd, J = 8.0, 1.4 Hz, 1H), 7.78-7.87 (m, 2H), 7.47 (t, J = 8.0 Hz, 1H), 7.18-7.32 (m, 2H), 7.02-7.13 (m, 1H), 6.76 (d, J = 8.2 Hz, 1H), 3.57-3.69 (m, 4H), 2.73-2.85 (m, 4H), 2.42 (s, 3 H) |
| 541 | 683.2 | $^1$H NMR (400 MHz, DMSO-$d_6$) δ: 10.70 (br s, 1H), 9.75-9.91 (m, 1H), 9.03 (s, 1H), 8.34-8.56 (m, 3H), 7.94 (dd, J = 8.0, 1.4 Hz, 1H), 7.89 (dd, J = 7.8, 1.6 Hz, 1H), 7.52 (t, J = 8.0 Hz, 1H), 7.47 (d, J = 8.2 Hz, 1H), 7.11-7.33 (m, 3H), 6.36 (d, J = 8.2 Hz, 1H), 4.92 (d, J = 3.5 Hz, 1H), 4.41 (d, J = 2.7 Hz, 1H), 3.88 (dd, J = 11.0, 4.7 Hz, 1H), 3.73 (dd, J = 8.2, 5.5 Hz, 2H), 3.65 (d, J = 11.0 Hz, 1H), 1.98-2.11 (m, 1H), 1.85-1.95 (m, 1 H) |
| 542 | 683.2 | $^1$H NMR (400 MHz, MeOH-$d_4$) δ: 8.50-8.53 (m, 1H), 7.87 (d, J = 8.61 Hz, 1H), 7.83 (d, J = 7.83 Hz, 1H), 7.75-7.80 (m, 1H), 7.28 (d, J = 9.00 Hz, 1H), 7.21-7.26 (m, 2H), 7.14-7.18 (m, 2H), 6.97-7.03 (m, J = 8.60 Hz, 2H), 6.88 (d, J = 6.65 Hz, 1H), 3.43-3.51 (m, 4H), 3.06-3.16 (m, 4H) |
| 543 | 697.2 | $^1$H NMR (400 MHz, DMSO-$d_6$) δ: 10.70 (s, 1H), 9.82 (s, 1H), 9.01 (s, 1H), 8.33-8.55 (m, 3H), 7.71-7.99 (m, 2H), 7.41-7.59 (m, 2H), 7.09-7.36 (m, 4H), 6.37 (d, J = 8.2 Hz, 1H), 4.70 (s, 1H), 3.60-3.90 (m, 3H), 3.42-3.55 (m, 3H), 2.37-2.46 (m, 1H), 1.95-2.12 (m, 1H), 1.66-1.87 (m, 1 H) |
| 544 | 617.2 | $^1$H NMR (400 MHz, DMSO-$d_6$) δ: 10.77 (br s, 1H), 10.22 (s, 1H), 10.12 (s, 1H), 8.68 (d, J = 9.06 Hz, 1H), 8.44-8.60 (m, 2H), 7.80-8.00 (m,2H), 7.52 (t, J = 8.04 Hz, 1H), 7.28-7.44 (m, 1H), 7.10-7.28 (m, 1H) |
| 545 | 749.2 | $^1$H NMR (400 MHz, DMSO-$d_6$) δ: 10.73 (s, 1H), 9.85 (s, 1 H,) 9.15 (s, 1H), 8.35-8.53 (m, 2H), 7.96 (d, J = 7.6 Hz, 1H), 7.88-7.94 (m, 1H), 7.81 (d, J = 8.2 Hz, 1 H), 7.55 (t, J = 7.9 Hz, 1H), 7.14-7.39 (m, 3H), 6.80 (d, J = 7.6 Hz, 1H), 4.42 (d, J = 12.3 Hz, 2H), 2.86 (t, J = 11.7 Hz, 2H), 2.55-2.67 (m, 1H), 1.96 (d, J = 11.7 Hz, 2H), 1.71 (qd, J = 12.5, 3.5 Hz, 2 H) |

TABLE 4-continued

| | | |
|---|---|---|
| 546 | 697.2 | $^1$H NMR (400 MHz, DMSO-$d_6$) δ: 10.73 (br s, 1H), 9.84 (s, 1H), 9.12 (s, 1H), 8.43-8.53 (m, 3H), 7.95 (d, J = 8.2 Hz, 1H), 7.90-7.93 (m, 1H), 7.76 (d, J = 8.2 Hz, 1H), 7.54 (t, J = 7.9 Hz, 1H), 7.21-7.34 (m, 3H), 6.77 (d, J = 7.6 Hz, 1H), 4.71 (d, J = 4.1 Hz, 1H), 4.03-4.09 (m, 2H), 3.65-3.75 (m, 1H), 3.05-3.11 (m, 2H), 1.88-1.95 (m, 2H), 1.56-1.65 (m, 2 H) |
| 547 | 681.2 | $^1$H NMR (400 MHz, DMSO-$d_6$) δ: 10.73 (br s, 1H), 9.84 (s, 1H), 9.12 (s, 1H), 8.37 8.55 (m, 3H), 7.94-7.98 (m, 1H), 7.91 (dd, J = 1.46, 7.89 Hz, 1H), 7.77 (d, J = 8.19 Hz, 1H), 7.54 (s, 1H), 7.27 (t, J = 8.04 Hz, 3H), 6.76 (d, J = 7.89 Hz, 1H), 3.49-3.57 (m, 4H), 1.68-1.80 (m, 4H), 1.58-1.66 (m, 2 H) |
| 548 | 710.2 | $^1$H NMR (400 MHz, DMSO-$d_6$) δ: 9.75 (s, 1H), 9.15 (s, 1H), 8.51 (s, 1H), 8.31-8.49 (m, 2H), 7.93 (dd, J = 7.9, 1.2 Hz, 1H), 7.75 (d, J = 7.3 Hz, 1H), 7.62 (d, J = 8.2 Hz, 1H), 7.42 (t, J = 7.9 Hz, 1H), 7.25 (t, J = 8.2 Hz, 1H), 7.14 (m, J = 5.8 Hz, 1H), 6.84-7.02 (m, 1H), 6.61 (d, J = 8.2 Hz, 1H), 3.99-4.26 (m, 2H), 3.71 (t, J = 6.1 Hz, 3H), 2.94-3.09 (m, 2H), 2.60-2.72 (m, 3H), 2.16 (d, J = 4.4 Hz, 2H) |
| 549 | 624.3 | $^1$H NMR (400 MHz, MeOH-$d_4$) δ: 8.39 (s, 1H), 8.33 (d, J = 8.9 Hz, 1H), 8.14 (d, J = 8.9 Hz, 1H), 8.08 (s, 1H), 8.02-7.98 (m, 2H), 7.96 (dd, J = 8.0, 1.5 Hz, 1H), 7.81 (dd, J = 8.1, 1.5 Hz, 1H), 7.55-7.43 (m, 4H), 7.43 (dd, J = 10.3, 5.7 Hz, 1H), 7.11 (td, J = 9.1, 1.9 Hz, 1H) |
| 550 | 579.2 | $^1$H NMR (400 MHz, MeOH-$d_4$) δ: 8.51 (s, 1H), 8.46 (s, 1H), 8.41 (s, 1H), 8.20 (d, J = 8.9 Hz, 1H), 7.96 (dd, J = 8.0, 1.4 Hz, 1H), 7.80 (dd, J = 8.1, 1.4 Hz, 1H), 7.51-7.43 (m, 1H), 7.42 (t, J = 8.1 Hz, 1H), 7.09 (td, J = 9.2, 1.8 Hz, 1H), 2.84 (s, 3H) |
| 551 | 588.2 | $^1$H NMR (400 MHz, DMSO-$d_6$) δ: 10.72 (s, 1H), 9.56 (s, 1H), 8.44 (s, 1H), 8.38 (s, 1H), 8.15 (d, J = 8.8 Hz, 1H), 8.01 (d, J = 8.8 Hz, 1H), 7.95 (d, J = 8.0 Hz, 1H), 7.90 (dd, J = 8.0, 1.4 Hz, 1H), 7.53 (t, J = 8.0 Hz, 1H), 7.32-7.24 (m, 1H), 7.21 (t, J = 8.9 Hz, 1H), 4.15 (t, J = 7.3 Hz, 2H), 3.28 (t, J = 7.4 Hz, 2H), 2.70-2.61 (m, 2H) |
| 552 | 663.2 | $^1$H NMR (400 MHz, DMSO-$d_6$) δ: 10.73 (br s, 1H), 9.81 (s, 1H), 9.30 (s, 1H), 8.47-8.53 (m, 3H), 8.35 (d, J = 7.9 Hz, 1H), 7.93 (br s, 1H), 7.90 (dd, J = 7.9, 1.2 Hz, 1H), 7.53 (t, J = 7.9 Hz, 1H), 7.39-7.49 (m, 2H), 7.29 (br s, 1H), 7.21 (br s, 1H), 1.89-1.93 (m, 2H), 1.80-1.83 (m, 2H) |
| 553 | 562.2 | $^1$H NMR (400 MHz, DMSO-$d_6$) δ: 10.74 (br s, 1H), 10.01 (s, 1H), 8.89 (br s, 1H), 8.44 (s, 1H), 8.38 (d, J = 9.1 Hz, 1H), 8.32 (d, J = 9.1 Hz, 1H), 8.13 (br s, 1H), 7.95 (d, J = 7.9 Hz, 1H), 7.90 (dd, J = 8.0, 1.3 Hz, 1H), 7.53 (t, J = 8.0 Hz, 1H), 7.27-7.34 (m, 1H), 7.23 (t, J = 8.8 Hz, 1H), 2.21 (s, 3H) |
| 554 | 725.2 | $^1$H NMR (400 MHz, DMSO-$d_6$) δ: 10.73 (br s, 1H), 9.85 (s, 1H), 9.12 (s, 1H), 8.33-8.57 (m, 3H), 7.96 (d, J = 8.2 Hz, 1H), 7.91 (dd, J = 7.9, 1.5 Hz, 1H), 7.75 (d, J = 8.2 Hz, 1H), 7.54 (t, J = 7.9 Hz, 1H), 7.15-7.41 (m, 3H), 6.77 (d, J = 8.2 Hz, 1H), 4.56 (t, J = 5.0 Hz, 1H), 3.72-3.90 (m, 2H), 3.10-3.27 (m, 4H), 1.61-1.78 (m, 2H), 1.40 (d, J = 13.4 Hz, 2H), 0.97 (s, 3H) |
| 555 | 718.2 | $^1$H NMR (400 MHz, DMSO-$d_6$) δ: 10.73 (s, 1H), 9.85 (s, 1H), 9.16 (s, 1H), 8.33-8.61 (m, 3H), 7.96 (d, J = 7.6 Hz, 1H), 7.91 (dd, J7.9, 1.5 Hz, 1H), 7.84 (d, J = 8.2 Hz, 1H), 7.54 (t, J = 7.9 Hz, 1H), 7.28-7.37 (m, 2H), 7.24 (m, J = 8.2 Hz, 1H), 6.85 (d, J = 8.2 Hz, 1H), 3.73 (t, J = 5.3 Hz, 4H), 2.12-2.24 (m, 4 H) |
| 556 | 642.2 | $^1$H NMR (400 MHz, DMSO-$d_6$) δ: 10.73 (s, 1H), 9.85 (s, 1H), 9.29 (s, 1H), 8.36-8.58 (m, 3H), 8.18 (d, J = 8.2 Hz, 1H), 7.94-8.00 (m, 1H), 7.88-7.94 (m, 1H), 7.55 (t, J = 7.9 Hz, 1H), 7.29-7.41 (m, 2H), 7.19-7.28 (m, 2H), 4.78 (t, J = 5.0 Hz, 1H), 3.67-3.85 (m, 2H), 3.14-3.21 (m, 2 H) |
| 557 | 729.2 | $^1$H NMR (400 MHz, DMSO-$d_6$) δ: 10.73 (s, 1H), 9.85 (s, 1H), 9.14 (s, 1H), 8.39-8.54 (m, 3H), 7.96 (d, J = 7.88 Hz, 1H), 7.91 (d, J = 8.00 Hz, 1H), 7.79 (d, J = 8.25 Hz, 1H), 7.55 (t, J = 8.00 Hz, 1H), 7.16-7.36 (m, 3H), 6.82 (d, J = 8.00 Hz, 1H), 5.01 (t, J = 5.94 Hz, 1H), 4.10 (d, J = 12.13 Hz, 2H), 3.43-3.59 (m, 2H), 3.09-3.24 (m, 2H), 1.81-2.04 (m, 4H) |
| 558 | 723.2 | $^1$H NMR (400 MHz, DMSO-$d_6$) δ: 10.73 (s, 1H), 9.85 (s, 1H), 9.29 (s, 1H), 8.36 8.58 (m, 3H), 8.18 (d, J = 8.2 Hz, 1H), 7.94-8.00 (m, 1H), 7.88-7.94 (m, 1H), 7.55 (t, J = 7.9 Hz, 1H), 7.29-7.41 (m, 2H), 7.19-7.28 (m, 2H), 4.78 (t, J = 5.0 Hz, 1H), 3.67-3.85 (m, 2H), 3.14-3.21 (m, 2 H) |
| 559 | 697.2 | $^1$H NMR (400 MHz, DMSO-$d_6$) δ: 10.70 (br s, 1H), 9.83 (s, 1H), 9.04 (s, 1H), 8.36-8.51 (m, 3H), 7.93 (d, J = 7.8 Hz, 1H), 7.89 (dd, J = 8.0, 1.4 Hz, 1H), 7.46-7.56 (m, 2H), 7.15-7.33 (m, 3H), 6.39 (d, J = 7.8 Hz, 1H), 4.04-4.14 (m, 1H), 3.79-3.92 (m, 2H), 3.62-3.77 (m, 2H), 3.27 (s, 3H), 2.02-2.12 (m, 2 H) |
| 560 | 724.2 | $^1$H NMR (400 MHz, DMSO-$d_6$) δ: 10.72 (br s, 1H), 9.83 (s, 1H), 9.16 (s, 1H), 8.51 (s, 1H), 8.46 (d, J = 1.6 Hz, 2H), 7.87-7.95 (m, 2H), 7.84 (d, J = 7.8 Hz, 1H), 7.52 (t, J = 8.0 Hz, 1H), 7.24-7.33 (m, 2H), 7.19 (br. s., 1H), 6.78 (d, J = 7.8 Hz, 1H), 3.65-3.74 (m, 4H), 3.54-3.59 (m, 2H), 3.45-3.51 (m, 2H), 2.07 (s, 3H) |
| 561 | 602.2 | $^1$H NMR (400 MHz, DMSO-$d_6$) δ: 10.75 (br s, 1H), 9.20 (s, 1H), 8.40 (s, 1H), 8.10 8.25 (m, 3H), 7.90 (d, J = 7.83 Hz, 2H), 7.76 (br. s., 1H), 7.51 (t, J = 8.02 Hz, 1H), 7.19-7.33 (m, 1H), 7.16 (d, J = 8.22 Hz, 1H), 4.55 (t, J = 5.67 Hz, 2H), 2.86 (br. s., 1H), 1.95 (d, J = 4.70 Hz, 2H), 1.86 (br.s., 2H) |
| 562 | 565.1 | $^1$H NMR (400 MHz, DMSO-$d_6$) δ: 10.70 (br s, 1H), 9.92 (br. s., 1H), 8.59 (d, J = 8.61 Hz, 1H), 8.47 (s, 1H), 8.31 (d, J = 8.61 Hz, 1H), 8.08 (d, J = 3.52 Hz, 1H), 8.03 (d, J = 3.13 Hz, 1H), 7.74-7.93 (m, 2H), 7.46 (br s, 1H), 7.19 (br s, 2H) |
| 563 | 549.0 | $^1$H NMR (400 MHz, DMSO-$d_6$) δ: 10.68 (br s, 1H), 9.99 (br s, 1H), 8.39-8.59 (m, 3H), 8.35 (d, J = 9.00 Hz, 1H), 7.91 (dd, J = 1.57, 7.83 Hz,1H), 7.69-7.87 (m, 1H), 7.59 (s, 1H), 7.48 (br s, 1H), 7.19 (br s, 1H), 7.08 (br s, 1H) |
| 564 | 562.2 | $^1$H NMR (400 MHz, DMSO-$d_6$) δ: 10.69 (br s, 1H), 9.81 (s, 1H), 8.38 (s, 1H), 7.97-8.26 (m, 2H), 7.73-7.97 (m, 2H), 7.37-7.65 (m, 2H), 7.19-7.37 (m, 1H), 7.15 (br s, 1H), 6.38 (dd, J = 0.98, 3.33 Hz, 1H), 2.05 (s, 3H) |
| 565 | 562.2 | $^1$H NMR (400 MHz, DMSO-$d_6$) δ: 10.71 (br s, 1H), 9.83 (s, 1H), 8.24-8.45 (m, 2H), 8.03-8.24 (m, 2H), 7.79-8.03 (m, 2H), 7.75 (d, J = 1.17 Hz,1H), 7.50 (t, J = 8.02 Hz, 1H), 7.11-7.31 (m, 2H), 3.75 (s, 3H) |

TABLE 4-continued

| | | |
|---|---|---|
| 566 | 560.2 | $^1$H NMR (400 MHz, DMSO-$d_6$) δ: 10.72 (br s, 1H), 10.26 (s, 1H), 9.90 (s, 2H), 9.31 (s, 1H), 8.70 (d, J = 9.00 Hz, 1H), 8.48 (s, 1H), 8.36 (d, J = 9.00 Hz, 1H), 7.86-7.96 (m, 2H), 7.51 (t, J = 8.02 Hz, 1H), 7.11-7.40 (m, 2H) |
| 567 | 565.1 | $^1$H NMR (400 MHz, DMSO-$d_6$) δ: 10.73 (s, 1H), 10.10 (s, 1H), 10.00 (s, 1H), 9.69 (s, 1H), 8.37-8.61 (m, 2H), 8.30 (d, J = 8.61 Hz, 1H), 7.87-7.98 (m, 2H), 7.53 (t, J = 8.02 Hz, 1H), 7.17-7.35 (m, 2H) |
| 568 | 725.3 | $^1$H NMR (400 MHz, DMSO-$d_6$) δ: 10.70 (s, 1H), 9.83 (s, 1H), 9.09 (s, 1H), 8.34-8.57 (m, 3H), 7.93 (dd, J = 8.0, 1.4 Hz, 1H), 7.89 (dd, J = 8.2, 1.6 Hz, 1H), 7.74 (d, J = 8.2 Hz, 1H), 7.52 (t, J = 8.0 Hz, 1H), 7.16-7.37 (m, 3H), 6.75 (d, J = 8.2 Hz, 1H), 3.81 (m, J = 12.0, 4.0, 4.0 Hz, 2H), 3.19-3.27 (m, 2H), 3.14 (s, 3H), 1.76-1.91 (m, 2H), 1.63-1.74 (m, 2H), 1.16 (s, 3 H) |
| 569 | 711.3 | $^1$H NMR (400 MHz, DMSO-$d_6$) δ: 10.70 (br s, 1H), 9.84, (s, 1H) 9.13 (s, 1H), 8.38-8.52 (m, 3H), 7.93 (dd, J = 8.2, 1.2 Hz, 1H), 7.89 (dd, J = 8.0, 1.4 Hz, 1H), 7.74 (d, J = 8.2 Hz, 1H), 7.52 (t, J = 8.0 Hz, 1H), 7.11-7.35 (m, 3H), 6.74 (d, J = 7.8 Hz, 1H), 4.69 (t, J = 5.5 Hz, 1H), 4.11 (d, J = 11.7 Hz, 1H), 3.99 (d, J = 9.0 Hz, 1H), 3.40-3.49 (m, 1H), 2.72-2.94 (m, 2H), 1.59-1.92 (m, 4H), 1.04-1.34 (m, 1H) |
| 570 | 617.2 | $^1$H NMR (400 MHz, DMSO-$d_6$) δ: 10.73 (br s, 1H), 9.54 (s, 1H), 8.74-8.83 (m, 2H), 8.39-8.64 (m, 2H), 7.83-8.01 (m, 2H), 7.75 (dt, J = 4.89,8.12 Hz, 1H), 7.35-7.63 (m, 2H), 7.28 (b. s, 2H) |
| 571 | 726.2 | $^1$H NMR (400 MHz, DMSO-$d_6$) δ: 10.73 (s, 1H), 9.45 (s, 1H), 8.76 (d, J = 9.00 Hz, 1H), 8.49-8.55 (m, 2H), 8.22 (d, J = 8.22 Hz, 1H), 7.91 (dd, J = 1.57, 7.83 Hz, 2H), 7.50 (t, J = 8.02 Hz, 2H), 7.29 (br. s., 2H), 6.82 (d, J = 8.22 Hz, 1H), 4.58 (t, J = 5.48 Hz, 1H), 4.01-4.09 (m, 2H), 3.37-3.65(m, 2H), 3.25 (d, J = 5.48 Hz, 3H), 1.56-1.86 (m, 2H), 1.42 (d, J = 14.09 Hz, 2H), 0.89-1.10 (m, 3H) |
| 572 | 712.3 | $^1$H NMR (400 MHz, DMSO-$d_6$) δ: 10.73 (br s, 1H), 9.44 (s, 1H), 8.76 (d, J = 9.00 Hz, 1H), 8.39-8.62 (m, 2H), 8.23 (d, J = 8.22 Hz, 1H), 7.91 (dd, J = 1.17, 7.83 Hz, 2H), 7.51 (t, J = 8.02 Hz, 2H), 7.27 (br. s., 1H), 7.17 (br. s., 1H), 6.83 (d, J = 8.22 Hz, 1H), 4.41 (s, 1H), 3.98-4.15 (m, 2H),3.51-3.60 (m, 2H), 1.54-1.79 (m, 4H), 1.17-1.38 (m, 3H) |
| 573 | 600.2 | $^1$H NMR (400 MHz, DMSO-$d_6$) δ: 10.77 (s, 1H), 10.32 (s, 1H), 10.25 (s, 1H), 9.26 (d, J = 9.1 Hz, 1H), 8.71 (d, J = 2.7 Hz, 1H), 8.65 (d, J = 2.7 Hz, 1H), 8.59 (d, J = 9.1 Hz, 1H), 8.52 (s, 1H), 8.01-7.88 (m, 2H), 7.53 (t, J = 7.9 Hz, 1H), 7.38-7.15 (m, 2H). |
| 574 | 713.2 | $^1$H NMR (400 MHz, DMSO-$d_6$) δ: 10.71 (s, 1H), 9.74-9.89 (m, 1H), 9.13 (s, 1H), 8.43-8.54 (m, 2H), 7.93 (dd, J = 1.37, 8.02 Hz, 1H), 7.88 (dd, J = 1.56, 7.83 Hz, 1H), 7.81 (d, J = 8.22 Hz, 1H), 7.52 (t, J = 8.02 Hz, 1H), 7.17-7.33 (m, 2H), 6.74 (d, J = 7.83 Hz, 1H), 4.78 (t, J = 5.67 Hz, 1H), 4.06-4.32 (m, 2H), 3.90-4.03 (m, 1H), 3.65-3.86 (m, 2H), 3.40-3.63 (m, 2H), 2.85 (dt, J = 3.33, 11.64 Hz, 1H), 2.56-2.72 (m, 1H) |
| 575 | 695.2 | $^1$H NMR (400 MHz, DMSO-$d_6$) δ: 10.72 (br s, 1H), 9.84 (s, 1H), 9.08 (s, 1H), 8.50 (s, 1H), 8.44 (d, J = 4.3 Hz, 2H), 7.85-7.97 (m, 2H), 7.47-7.58 (m, 2H), 7.14-7.31 (m, 3H), 6.47 (d, J = 8.2 Hz, 1H), 5.62 (s, 1H), 4.66 (s, 1H), 3.73-3.86 (m, 3H), 3.35 (br s, 1H), 1.97-2.03 (m, 1H), 1.89 (d, J = 9.4 Hz, 1H) |
| 576 | 699.2 | $^1$H NMR (400 MHz, DMSO-$d_6$) δ: 10.72 (s, 1H), 9.87 (s, 1H), 9.11 (s, 1H), 8.50 (s, 1H), 8.42-8.48 (m, 2H), 7.95 (d, J = 7.8 Hz, 1H), 7.90 (dd, J = 7.8, 1.6 Hz, 1H), 7.59 (d, J = 7.8 Hz, 1H), 7.54 (t, J = 8.0 Hz, 1H), 7.26-7.33 (m, 1H), 7.23 (t, J = 8.0 Hz, 2H), 6.57 (d, J = 7.8 Hz, 1H), 3.91-3.98 (m, 2H), 3.37 (t, J = 6.3 Hz, 2H), 3.21 (s, 3H), 3.09 (s, 3H), 1.79-1.87 (m, 2H) |
| 577 | 723.2 | $^1$H NMR (400 MHz, DMSO-$d_6$) δ: 10.72 (s, 1H), 9.85 (s, 1H), 9.07 (s, 1H), 8.50 (s, 1H), 8.43-8.48 (m, 2H), 7.94 (d, J = 7.0 Hz, 1H), 7.91 (dd, J = 7.8, 1.6 Hz, 1H), 7.50-7.58 (m, 2H), 7.14-7.36 (m, 3H), 6.71 (d, J = 8.2 Hz, 1H), 5.12 (br. s., 2H), 4.33 (d, J = 5.9 Hz, 1H), 3.93-4.04 (m, 1H), 1.95-2.04 (m, 2H), 1.70-1.79 (m, 4H), 1.51-1.60 (m, 2H) |
| 578 | 737.2 | $^1$H NMR (400 MHz, DMSO-$d_6$) δ: 9.83 (s, 1H), 9.09 (s, 1H), 8.34-8.53 (m, 3H), 7.93 (dd, J = 8.0, 1.4 Hz, 1H), 7.89 (dd, J = 8.2, 1.6 Hz, 1H), 7.74 (d, J = 8.2 Hz, 1 H), 7.52 (t, J = 8.0 Hz, 1H), 7.17-7.34 (m, 3H), 6.75 (d, J = 7.8 Hz, 1H), 3.75 (t, J = 6.8 Hz, 2H), 3.58-3.69 (m, 2H), 3.51 (ddd, J = 12.0, 7.7, 4.5 Hz, 2H), 1.84-1.96 (m, 2H), 1.67-1.79 (m, 6 H) |
| 579 | 709.2 | $^1$H NMR (400 MHz, DMSO-$d_6$) δ: 10.70 (br s, 1H), 9.83 (s, 1H), 9.06 (s, 1H), 8.36-8.58 (m, 3H), 7.84-7.97 (m, 2H), 7.62 (d, J = 7.8 Hz, 1H), 7.51 (t, J = 8.0 Hz, 1H), 7.13-7.35 (m, 3H), 6.74 (d, J = 8.2 Hz, 1H), 3.80 (d, J = 11.0 Hz, 2H), 3.49 (d, J = 10.2 Hz, 2H), 1.92-2.03 (m, 4 H) |
| 580 | 699.2 | $^1$H NMR (400 MHz, DMSO-$d_6$) δ: 10.71 (s, 1H), 9.82 (s, 1H), 9.09 (s, 1H), 8.36-8.53 (m, 3H), 7.93 (d, J = 7.83 Hz, 1H), 7.88 (dd, J = 1.56, 7.83 Hz, 1H), 7.74 (d, J = 8.22 Hz, 1H), 7.52 (t, J = 8.02 Hz, 1H), 7.14-7.37 (m, 3H), 6.73 (d, J = 8.22 Hz, 1H), 4.84 (d, J = 4.70 Hz, 1H), 4.22 (dd, J = 3.91, 11.35 Hz, 1H), 4.04-4.12 (m, J = 11.30 Hz, 1H), 3.71 (dt, J = 4.70, 9.39 Hz, 1H), 2.77 (dt, J = 2.54, 11.64 Hz, 1H), 2.58 (dd, J = 9.78, 11.35 Hz, 1H), 1.92-2.03 (m, 1H), 1.76-1.84 (m, 1H), 1.55-1.74 (m, 1H), 1.24-1.38 (m, 1H) |
| 581 | 699.2 | $^1$H NMR (400 MHz, DMSO-$d_6$) δ: 10.71 (s, 1H), 9.82 (s, 1H), 9.09 (s, 1H), 8.34-8.56 (m, 3H), 7.94 (dd, J = 1.57, 8.22 Hz, 1H), 7.88-7.91 (m, 1H), 7.74 (d, J = 8.22 Hz, 1H), 7.52 (t, J = 8.02 Hz, 1H), 7.16-7.34 (m, 3H), 6.73 (d, J = 7.83 Hz, 1H), 4.84 (d, J = 4.70 Hz, 1H), 4.22 (dd, J = 3.91, 11.35 Hz, 1H), 4.07 (d, J = 12.13 Hz, 1H), 3.71 (dt, J = 4.70, 9.59 Hz, 1H), 2.77 (dt, J = 2.74, 11.54 Hz, 1H), 2.58 (dd, J = 9.59, 11.15 Hz, 1H), 1.90-2.03 (m, 1H), 1.74-1.88 (m, 1H), 1.56-1.72 (m, 1H), 1.22-1.42 (m, 1H) |

TABLE 4-continued

| | | |
|---|---|---|
| 582 | 765.2 | $^1$H NMR (400 MHz, DMSO-$d_6$) δ: 10.66 (s, 1H), 9.78 (s, 1H), 9.07 (s, 1H), 8.26-8.48 (m, 3H), 7.89 (dd, J = 1.50, 8.13 Hz, 1H), 7.84 (dd, J = 1.50, 8.00 Hz, 1H), 7.73 (d, J = 8.13 Hz, 1H), 7.47 (t, J = 8.00 Hz, 1H), 7.09-7.35 (m, 3H), 6.76 (d, J = 8.00 Hz, 1H), 5.94 (s, 1H), 4.20 (d, J = 11.88 Hz, 2H), 2.96-3.09 (m, 2H), 1.87 (dt, J = 4.31, 12.73 Hz, 2H), 1.73 (d, J = 12.26 Hz, 2H) |
| 583 | 711.2 | $^1$H NMR (400 MHz, DMSO-$d_6$) δ: 10.71 (br s, 1H), 9.83 (s, 1H), 9.10 (s, 1H), 8.36-8.54 (m, 3H), 7.93 (dd, J = 8.0, 1.4 Hz, 1H), 7.89 (dd, J = 7.8, 1.6 Hz, 1H),, 7.75 (d, J = 8.2 Hz, 1H), 7.52 (t, J = 8.0 Hz, 1H), 7.16-7.34 (m, 4H), 6.74 (d, J = 7.8 Hz, 1H), 3.88-4.07 (m, 2H), 3.27 (s, 1H), 3.06-3.18 (m, 3H), 1.94-2.10 (m, 2H), 1.61 (dt, J = 9.0, 3.3 Hz, 2 H) |
| 584 | 727.3 | $^1$H NMR (400 MHz, DMSO-$d_6$) δ: 10.70 (br s, 1H), 9.85 (s, 1H), 9.08 (s, 1H), 8.25-8.55 (m, 2H), 7.76-8.00 (m, 2H), 7.52 (t, J = 8.0 Hz, 1H), 7.45 (d, J = 8.2 Hz, 1H), 7.05-7.35 (m, 2H), 6.62 (d, J = 8.2 Hz, 1H), 5.08 (d, J = 7.0 Hz, 1H), 4.35 (s, 1H), 3.88-4.02 (m, 1H), 3.45-3.55 (m, 1H), 2.00-2.17 (m, 2H), 1.75 1.93 (m, 2H), 1.08-1.12 (m, 3H), 1.00-1.07 (m, 3 H) |
| 585 | 711.2 | $^1$H NMR (400 MHz, DMSO-$d_6$) δ: 10.70 (br s, 1H), 9.82 (s, 1H), 9.11 (s, 1H), 8.37 8.58 (m, 3H), 7.93 (dd, J = 8.0, 1.4 Hz, 1H), 7.89 (dd, J = 8.0, 1.4 Hz, 1H), 7.79 (d, J = 8.2 Hz, 1H), 7.52 (t, J = 8.0 Hz, 1H), 7.14-7.35 (m, 3H), 6.68-6.84 (m, 1H), 4.22 (d, J = 11.3 Hz, 2H), 3.66-3.91 (m, 2H), 2.42 (t, J = 11.0 Hz, 2H), 1.09-1.20 (m, 6H) |
| 586 | 726.2 | $^1$H NMR (400 MHz, DMSO-$d_6$) δ: 9.81 (s, 1H), 9.15 (s, 1H), 8.37-8.56 (m, 3H), 7.89-7.93 (m, 1H), 7.87 (dd, J = 8.2, 1.6 Hz, 1H), 7.82 (d, J = 8.2 Hz, 1H), 7.49 (t, J = 8.0 Hz, 1H), 7.21-7.32 (m, 2H), 7.09-7.16 (m, 1H), 6.77 (d, J = 7.8 Hz, 1 H), 3.16-3.55 (m, 8H), 2.85-2.94 (m, 4H), 2.66-2.74 (m, 2 H) |
| 587 | 711.2 | $^1$H NMR (400 MHz, DMSO-$d_6$) δ: 10.71 (br s, 1H), 9.84 (s, 1H), 9.14 (s, 1H), 8.34-8.54 (m, 2H), 7.93 (dd, J = 1.37, 8.02 Hz, 1H), 7.89 (dd, J = 1.37, 8.02 Hz, 1H), 7.74 (d, J = 8.22 Hz, 1H), 7.52 (t, J = 8.02 Hz, 1H), 7.09-7.33 (m, 2H), 6.75 (d, J = 8.22 Hz, 1H), 4.25 (dd, J = 3.13, 11.35 Hz, 1H), 3.80-3.91 (m, 1H), 3.42-3.51 (m, 1H), 3.36 (s, 3H), 2.83-3.02 (m, 2H), 2.04 (td, J = 4.16, 12.42 Hz, 1H), 1.84 (dd, J = 4.11, 9.19 Hz, 1H), 1.64 (dd, J = 3.13, 10.17 Hz, 1H), 1.17-1.46 (m, 1H) |
| 588 | 706.3 | $^1$H NMR (400 MHz, DMSO-$d_6$) δ: 10.71 (br s, 1H), 9.82 (s, 1H), 9.12 (s, 1H), 8.34-8.57 (m, 3H), 7.93 (dd, J = 8.0, 1.4 Hz, 1H), 7.89 (dd, J = 8.0, 1.4 Hz, 1H), 7.76-7.83 (m, 1H), 7.52 (t, J = 8.0 Hz, 1H), 7.16-7.35 (m, 3H), 6.78 (d, J = 7.8 Hz, 1H), 3.72-3.85 (m, 2H), 3.37-3.45 (m, 2H), 3.00-3.17 (m, 1H), 1.99-2.15 (m, 2H), 1.83-1.99 (m, 2H) |
| 589 | 581.2 | $^1$H NMR (400 MHz, DMSO-$d_6$) δ: 10.56 (br s, 1H), 9.54 (s, 1H), 8.93 (d, J = 8.2 Hz, 1H), 8.82 (d, J = 9.0 Hz, 1H), 8.56 (br s, 2H), 8.26 (d, J = 8.2 Hz, 1H), 7.77 (dd, J = 7.4 Hz, 1H), 7.59-7.68 (m, 2H), 7.42-7.53 (m, 1H), 7.20-7.38 (m, 2H), 2.56 (d, J = 2.3 Hz, 3H) |
| 590 | 664.2 | $^1$H NMR (400 MHz, DMSO-$d_6$) δ: 10.66 (br s, 1H), 9.99 (s, 1H), 8.59 (d, J = 8.76 Hz, 1H), 8.48 (s, 1H), 8.34 (d, J = 8.76 Hz, 1H), 7.82-8.02 (m,3H), 7.42-7.61 (m, 2H), 7.16-7.42 (m, 3H), 3.67 (br. s., 4H), 3.38-3.45 (m, 2H), 2.99-3.23 (m, 2H) |
| 591 | 595.2 | $^1$H NMR (400 MHz, DMSO-$d_6$) δ: 10.72 (br s, 1H), 9.99 (s, 1H), 8.57 (d, J = 8.88 Hz, 1H), 8.47 (s, 1H), 8.31 (d, J = 8.75 Hz, 1H), 7.80-7.98 (m,3H), 7.53 (t, J = 8.00 Hz, 1H), 7.29 (d, J = 5.88 Hz, 1H), 7.22 (d, J = 8.88 Hz, 1H), 5.77 (t, J = 5.57 Hz, 1H), 4.79 (d, J = 5.50 Hz, 2H) |
| 592 | 720.3 | $^1$H NMR (400 MHz, DMSO-$d_6$) δ: 10.66 (br s, 1H), 9.78 (s, 1H), 9.08 (s, 1H), 8.31-8.49 (m, 3H), 7.88 (d, J = 8.1 Hz, 1H), 7.84 (dd, J = 8.0, 1.4 Hz, 1H), 7.76 (d, J = 8.3 Hz, 1H), 7.47 (t, J = 8.0 Hz, 1H), 7.10-7.30 (m, 3H), 6.77 (d, J = 8.0 Hz, 1H), 4.21 (d, J = 12.8 Hz, 2H), 2.93 (t, J = 11.5 Hz, 2H), 1.94-2.01 (m, 2H), 1.70-1.81 (m, 2H), 1.37 (s, 3H) |
| 593 | 711.3 | $^1$H NMR (400 MHz, DMSO-$d_6$) δ: 10.72 (br s, 1H), 9.87 (s, 1H), 9.11 (s, 1H), 8.49 (s, 1H), 8.44 (d, J = 3.3 Hz, 2H), 7.93 (d, J = 8.1 Hz, 1H), 7.88-7.92 (m, 1H), 7.53 (t, J = 8.0 Hz, 1H), 7.49 (d, J = 8.1 Hz, 1H), 7.25-7.33 (m, 1H), 7.21 (t, J = 8.1 Hz, 2H), 6.45 (d, J = 8.1 Hz, 1H), 4.90-5.01 (m, 1H), 3.74 (t, J = 8.4 Hz, 1H), 3.60 (dd, J = 9.2, 3.3 Hz, 1H), 3.35-3.43 (m, 1H), 3.28 (s, 4H), 1.91-2.09 (m, 4H) |
| 594 | 579.2 | $^1$H NMR (400 MHz, DMSO-$d_6$) δ: 10.25 (s, 1H), 9.43 (s, 1H), 8.62 (d, J = 9.0 Hz, 1H), 8.56-8.45 (m,, 2H), 7.90 (d, J = 7.8 Hz, 2H), 7.50 (t, J = 8.0 Hz, 1H), 7.33-7.24 (m, 1H), 7.22-7.00 (m, 2H), 5.50 (t, J = 5.5 Hz, 1H, OH), 4.70 (d, J = 5.4 Hz, 2H) |
| 595 | 562.2 | $^1$H NMR (400 MHz, MeOH-$d_4$) δ: 8.38 (s, 1H), 8.33 (s, 1H), 8.21 (d, J = 8.9 Hz, 1H), 8.10 (d, J = 8.9 Hz, 1H), 7.96 (dd, J = 8.0, 1.5 Hz, 1H), 7.83 (s, 1H), 7.81 (dd, J = 8.1, 1.5 Hz, 1H), 7.49-7.44 (m, 1H), 7.43 (t, J = 8.1 Hz, 1H), 7.09 (td, J = 9.2, 1.9 Hz, 1H), 2.49 (s, 3H) |
| 596 | 751.2 | $^1$H NMR (400 MHz, DMSO-$d_6$) δ: 9.78 (s, 1H), 9.07 (s, 1H), 8.29-8.44 (m, 1H), 7.86 (dd, J = 7.88, 16.13 Hz, 2H), 7.73 (d, J = 8.13 Hz, 1H), 7.47 (t, J = 8.00 Hz, 1H), 7.08-7.31 (m, 4H), 6.74 (d, J = 7.88 Hz, 1H), 3.63-3.84 (m, 2H), 3.42-3.52 (m, 2H), 2.58 (t, J = 8.3 Hz, 2H), 2.05 (t, J = 8.2 Hz, 2H), 1.79-1.98 (m, 4 H) |
| 597 | 713.3 | $^1$H NMR (400 MHz, DMSO-$d_6$) δ: 9.77 (s, 1H), 9.05 (s, 1H), 8.31-8.51 (m, 3H), 7.86 (m, J = 16.2, 7.9 Hz, 2H), 7.69 (d, J = 8.3 Hz, 1H), 7.47 (t, J = 7.8 Hz, 1H), 7.08-7.31 (m, 3H), 6.69 (d, J = 7.8 Hz, 1H), 4.44 (br s, 1H), 4.23 (d, J = 11.5 Hz, 2H), 2.71 (t, J = 11.7 Hz, 2H), 1.73 (d, J = 12.0 Hz, 2H), 1.32 (q, J = 11.3 Hz, 2H) |
| 598 | 716.2 | $^1$H NMR (400 MHz, DMSO-$d_6$) δ: 10.72 (s, 1H), 9.86 (s, 1H), 9.23 (s, 1H), 8.50 (s, 1H), 8.47 (d, J = 2.6 Hz, 2H), 7.88-7.93 (m, 3H), 7.52 (t, J = 8.0 Hz, 1H), 7.34 (t, J = 8.2 Hz, 1H), 7.23-7.30 (m, 1H), 7.18 (br. s., 1H), 6.95 (d, J = 8.0 Hz, 1H), 4.37-4.41 (m, 2H), 3.84-3.87 (m, 2H), 3.64-3.67 (m, 2H), 3.48-3.51 (m, 2H), 3.26 (s, 3H) |

TABLE 4-continued

| | | |
|---|---|---|
| 599 | 751.2 | $^1$H NMR (400 MHz, DMSO-$d_6$) δ: 10.66 (br s, 1H), 9.78 (s, 1H), 9.05 (s, 1H), 8.33-8.49 (m, 3H), 7.88 (d, J = 8.1 Hz, 1H), 7.79-7.86 (m, 1H), 7.70 (d, J = 8.3 Hz, 1H), 7.47 (t, J = 7.9 Hz, 1H), 7.10-7.30 (m, 3H), 6.71 (d, J = 8.0 Hz, 1H), 4.04 (d, J = 12.3 Hz, 2H), 3.02 (t, J = 11.5 Hz, 2H), 2.22 (t, J = 7.3 Hz, 2H), 1.78-1.97 (m, 4H), 1.71 (t, J = 11.0 Hz, 2H), 1.44 (d, J = 13.0 Hz, 2H) |
| 600 | 707.2 | $^1$H NMR (400 MHz, DMSO-$d_6$) δ: 9.45 (br s, 1H), 8.76 (d, J = 9.01 Hz, 1H), 8.45-8.63 (m, 2H), 8.31 (d, J = 8.00 Hz, 1H), 7.73-8.02 (m, 2H),7.41-7.70 (m, 2H), 7.25 (br. s., 1H), 7.13 (br. s., 1H), 6.87 (d, J = 8.00 Hz, 1H), 4.01 (d, J = 12.38 Hz, 2H), 3.60 (t, J = 10.38 Hz, 2H), 3.20 (br. s.,2H), 2.11 (br. s., 2H), 1.96 (d, J = 10.01 Hz, 2H) |
| 601 | 712.3 | $^1$H NMR (400 MHz, DMSO-$d_6$) δ: 10.74 (br s, 1H), 9.47 (br s, 1H), 8.76 (d, J = 8.75 Hz, 1H), 8.46-8.62 (m, 2H), 8.30 (d, J = 8.13 Hz, 1H), 7.91(d, J = 7.88 Hz, 2H), 7.53 (q, J = 7.75 Hz, 2H), 7.27 (br s, 1H), 7.18 (br. s., 1H), 6.85 (d, J = 7.75 Hz, 1H), 4.43 (d, J = 11.88 Hz, 2H), 3.88 (br s,2H), 2.56-2.75 (m, 2H), 1.22 (d, J = 5.88 Hz, 6H) |
| 602 | 712.3 | $^1$H NMR (400 MHz, DMSO-$d_6$) δ: 10.73 (br s, 1H), 9.45 (br. s., 1H), 8.77 (d, J = 9.13 Hz, 1H), 8.34-8.63 (m, 2H), 8.26 (d, J = 8.13 Hz, 1H), 7.91(d, J = 7.88 Hz, 2H), 7.51 (t, J = 7.63 Hz, 2H), 7.27 (br s, 1H), 7.17 (br. s., 1H), 6.84 (d, J = 7.75 Hz, 1H), 4.18 (d, J = 12.51 Hz, 3H), 3.38-3.62(m, 5H), 2.06 (d, J = 10.88 Hz, 2H), 1.65 (d, J = 10.38 Hz, 2H) |
| 603 | 712.2 | $^1$H NMR (400 MHz, DMSO-$d_6$) δ: 10.73 (br. s., 1H), 9.44 (br s, 1H), 8.78 (d, J = 8.88 Hz, 1H), 8.43-8.62 (m, 2H), 8.25 (d, J = 8.25 Hz, 1H), 7.91 (d, J = 8.00 Hz, 2H), 7.51 (t, J = 7.57 Hz, 3H), 7.27 (br s, 1H), 7.20 (br. s., 1H), 6.83 (s, 1H), 4.37 (d, J = 11.76 Hz, 1H), 4.04 (d, J = 12.38 Hz,1H), 3.48 (br s, 1H), 2.07 (s, 2H), 1.89 (br s, 1H), 1.67 (m, 1H), 1.51 (m, 1H) |
| 604 | 727.3 | $^1$H NMR (400 MHz, DMSO-$d_6$) δ: 9.26-9.43 (m, 1H), 8.63-8.86 (m, 1H), 8.41-8.63 (m, 2H), 8.25-8.41 (m, 1H), 7.93 (dd, J = 1.50, 7.88 Hz, 1H), 7.62-7.84 (m, 1H), 7.54 (t, J = 8.00 Hz, 1H), 7.42 (d, J = 7.25 Hz, 1H), 7.13 (br. s., 1H), 6.92 (br. s., 1H), 6.83 (d, J = 8.00 Hz, 1H), 4.49 (br.s., 1H), 3.75 (br s, 4H), 3.58 (d, J = 4.13 Hz, 2H), 2.72 (br s, 4H) |
| 605 | 726.4 | $^1$H NMR (400 MHz, DMSO-$d_6$) δ: 10.73 (br s, 1H), 9.46 (s, 1H), 8.76 (d, J = 9.13 Hz, 1H), 8.41-8.59 (m, 2H), 8.22 (d, J = 8.25 Hz, 1H), 7.84-7.98 (m, 2H), 7.50 (t, J = 8.13 Hz, 1H), 7.53 (t, J = 8.07 Hz, 1H), 7.25-7.44 (m, 1H), 7.22 (br s, 1H), 6.83 (d, J = 8.00 Hz, 1H), 4.09-4.27 (m,3H), 3.41-3.54 (m, 2H), 1.54-1.78 (m, 4H), 1.46 (q, J = 7.42 Hz, 2H), 0.89 (t, J = 7.44 Hz, 3H) |
| 606 | 726.2 | $^1$H NMR (400 MHz, DMSO-$d_6$) δ: 10.73 (br s, 1H), 9.41 (s, 1H), 8.76 (d, J = 9.13 Hz, 1H), 8.39-8.66 (m, 2H), 8.03 (d, J = 8.00 Hz, 1H), 7.82-7.99 (m, 2H), 7.31-7.60 (m, 2H), 7.30 (d, J = 6.00 Hz, 1H), 7.09-7.25 (m, 1H), 6.57 (d, J = 8.13 Hz, 1H), 4.34 (s, 1H), 4.05-4.25 (m, 1H), 3.72-3.94 (m, 3H), 2.16 (br s, 1H), 1.74-1.95 (m, 3H), 1.54-1.74 (m, 1H), 1.49 (d, J = 10.88 Hz, 1H), 1.11-1.22 (s, 3H) |
| 607 | 727.3 | $^1$H NMR (400 MHz, DMSO-$d_6$) δ: 10.64 (br s, 1H), 9.79 (s, 1H), 8.99 (s, 1H), 8.31-8.54 (m, 2H), 7.78-7.99 (m, 2H), 7.33-7.54 (m, 2H), 6.99-7.30 (m, 3H), 6.45 (d, J = 8.13 Hz, 1H), 4.17 (s, 1H), 3.97-4.11 (m, 1H), 3.51-3.80 (m, 3H), 1.94-2.14 (m, 1H), 1.79-1.92 (m, 1H), 1.65-1.79 (m, 2H), 1.51-1.64 (m, 1H), 1.34-1.50 (m, 1H), 1.09 (s, 3H) |
| 608 | 725.2 | $^1$H NMR (400 MHz, DMSO-$d_6$) δ: 9.84 (s, 1H), 9.11 (s, 1H), 8.39-8.49 (m, 2H), 7.88-8.02 (m, 2H), 7.75 (d, J = 8.0 Hz, 1H), 7.54 (t, J = 7.9 Hz, 1H), 7.12-7.36 (m, 3H), 6.78 (d, J = 7.9 Hz, 1H), 4.09 (br. s., 1H), 3.93 (d, J = 11.4 Hz, 2H), 3.18-3.27 (m, 2H), 1.57-1.78 (m, 4H), 1.47 (q, J = 7.3 Hz, 2H), 0.90 (t, J = 7.2 Hz, 3H) |
| 609 | 739.3 | $^1$H NMR (400 MHz, DMSO-$d_6$) δ: 10.73 (br s, 1H), 9.85 (s, 1H), 9.13 (s, 1H), 8.34-8.62 (m, 3H), 7.93 (dd, J = 17.9, 7.9 Hz, 2H), 7.78 (d, J = 8.1 Hz, 1H), 7.54 (t, J = 8.0 Hz, 1H), 7.19-7.41 (m, 3H), 6.78 (d, J = 8.0 Hz, 1H), 3.79 (t, J = 6.9 Hz, 2H), 3.43-3.66 (m, 6H), 1.66-1.89 (m, 6H) |
| 610 | 664.2 | $^1$H NMR (400 MHz, DMSO-$d_6$) δ: 10.74 (br s, 1H), 9.55 (s, 1H), 8.89 (d, J = 8.25 Hz, 1H), 8.80 (d, J = 9.13 Hz, 1H), 8.50-8.59 (m, 2H), 7.81-8.06 (m, 2H), 7.63-7.81 (m, 2H), 7.54 (t, J = 8.00 Hz, 1H), 7.14-7.38 (m, 2H), 2.03-2.16 (m, 2H), 1.92-2.03 (m, 2H) |
| 611 | 738.3 | $^1$H NMR (400 MHz, DMSO-$d_6$) δ: 10.73 (br s, 1H), 9.47 (s, 1H), 8.77 (d, J = 9.13 Hz, 1H), 8.48-8.57 (m, 2H), 8.24 (d, J = 8.26 Hz, 1H), 7.84-7.99 (m, 2H), 7.52 (q, J = 8.17 Hz, 2H), 7.31 (d, J = 5.75 Hz, 1H), 7.22 (br s, 1H), 6.84 (d, J = 8.00 Hz, 1H), 3.85-4.07 (m, 2H), 3.79 (t, J = 6.75 Hz, 2H), 3.70 (ddd, J = 4.00, 8.47, 12.54 Hz, 2H), 1.86-1.97 (m, 2H), 1.67-1.84 (m, 6H) |
| 612 | 670.2 | $^1$H NMR (400 MHz, DMSO-$d_6$) δ: 10.66 (br s, 1H), 9.76 (s, 1H), 9.17 (s, 1H), 8.27-8.48 (m, 3H), 8.11 (d, J = 8.00 Hz, 1H), 7.89 (d, J = 8.00 Hz, 1H), 7.84 (d, J = 8.00 Hz, 1H), 7.47 (t, J = 7.75 Hz, 1H), 7.03-7.31 (m, 4H), 4.72 (br s, 1H), 3.70 (br s, 2H), 0.88 (d, J = 4.63 Hz, 4H) |
| 613 | 665.2 | $^1$H NMR (400 MHz, DMSO-$d_6$) δ: 10.69 (br s, 1H), 9.52 (s, 1H), 8.36 (s, 1H), 8.29 (d, J = 8.9 Hz, 1H), 8.20 (s, 1H), 8.09 (d, J = 9.0 Hz, 1H), 7.86-7.94 (m, 2H), 7.50 (dd, J = 8.0 Hz, 1H), 7.19-7.27 (m, 1H), 7.07-7.15 (m, 1H), 3.52-3.59 (m, 4H), 2.47-2.50 (m, 4H), 2.26 (s, 3H) |
| 614 | 717.3 | $^1$H NMR (400 MHz, DMSO-$d_6$) δ: 9.50 (s, 1H), 8.80 (d, J = 9.13 Hz, 1H), 8.48-8.59 (m, 2H), 8.45 (d, J = 8.38 Hz, 1H), 7.81-8.04 (m, 2H), 7.57-7.65 (m, 1H), 7.53 (t, J = 8.00 Hz, 1H), 7.31 (d, J = 5.75 Hz, 1H), 7.22 (br. s., 1H), 7.08 (d, J = 7.88 Hz, 1H), 4.38-4.54 (m, 2H), 3.80-3.96 (m,2H), 3.67 (dd, J = 3.88, 5.63 Hz, 2H), 3.50 (dd, J = 3.88, 5.63 Hz, 2H), 3.26 (s, 3H), 2.67 (dd, J = 1.56, 3.44 Hz, 2H) |

TABLE 4-continued

| | | |
|---|---|---|
| 615 | 761.2 | $^{1}$H NMR (400 MHz, DMSO-$d_6$) δ: 10.73 (br s, 1H), 9.47 (s, 1H), 8.77 (d, J = 9.13 Hz, 1H), 8.48-8.58 (m, 2H), 8.29 (d, J = 8.13 Hz, 1H), 7.82-8.00 (m, 2H), 7.38-7.61 (m, 2H), 7.30 (d, J = 6.38 Hz, 1H), 7.20 (br s, 1H), 6.89 (d, J = 7.88 Hz, 1H), 4.71 (d, J = 12.88 Hz, 2H), 3.06-3.20 (m,3H), 2.99 (s, 3H), 2.19 (d, J = 10.88 Hz, 2H), 1.85 (dq, J = 4.13, 12.42 Hz, 2H) |
| 616 | 713.3 | $^{1}$H NMR (400 MHz, DMSO-$d_6$) δ: 9.40 (br s, 1H), 8.65-8.93 (m, 1H), 8.41-8.65 (m, 2H), 8.25-8.41 (m, 1H), 7.78-8.10 (m, 5H), 7.42-7.63(m, 2H), 7.22 (d, J = 5.50 Hz, 1H), 7.07 (br. s., 1H), 6.89 (d, J = 7.88 Hz, 1H), 4.21-4.31 (m, 2H), 3.49 (t, J = 10.26 Hz, 2H), 1.92-2.04 (m, 2H), 1.82-1.92 (m, 2H), 1.42 (s, 3H) |
| 617 | 726.3 | $^{1}$H NMR (400 MHz, DMSO-$d_6$) δ: 10.72 (br s, 1H), 9.45 (s, 1H), 8.77 (d, J = 9.1 Hz, 1H), 8.38-8.63 (m, 2H), 8.24 (d, J = 8.25 Hz, 1H), 7.84-8.04 (m, 2H), 7.52 (q, J = 7.8 Hz, 2H), 7.14-7.32 (m, 2H), 6.82 (d, J = 7.9 Hz, 1H), 4.51 (d, J = 12.63 Hz, 2H), 4.40 (br s, 1H), 3.44-3.62 (m,2H), 3.00 (t, J = 11.3 Hz, 2H), 1.84 (d, J = 11.4 Hz, 2H), 1.58-1.77 (m, 1H), 1.32-1.50 (m, 4H) |
| 618 | 712.4 | $^{1}$H NMR (400 MHz, DMSO-$d_6$) δ: 9.61 (br s, 1H), 9.12 (s, 1H), 8.46 (s, 1H), 8.30 8.42 (m, 2H), 7.87 (dd, J = 1.5, 7.9 Hz, 1H), 7.75 (d, J = 8.1 Hz, 1H), 7.58 (dd, J = 1.3, 7.94 Hz, 1H), 7.30 (t, J = 7.9 Hz, 1H), 7.23 (t, J = 8.1 Hz, 1H), 6.99 (dt, J = 5.9, 9.22 Hz, 1H), 6.63-6.79 (m, 2H), 3.96 (d, J = 10.4 Hz, 2H), 3.14-3.29 (m, 2H), 1.83-1.95 (m, 2H), 1.67-1.83 (m, 2H), 1.32 (s., 3H) |
| 619 | 683.2 | $^{1}$H NMR (400 MHz, DMSO-$d_6$) δ: 9.35 (br s, 1H), 8.76 (d, J = 9.1 Hz, 1H), 8.56 (s, 1H), 8.51 (d, J = 9.1 Hz, 1H), 8.41 (d, J = 8.0 Hz, 1H), 7.94 (dd, J = 1.5, 7.75 Hz, 1H), 7.68 (d, J = 7.9 Hz, 1H), 7.57 (t, J = 8.1 Hz, 1H), 7.38 (t, J = 7.9 Hz, 1H), 7.03 7.15 (m, 1H), 6.90 (d, J = 7.9 Hz, 1H), 6.85 (t, J = 9.3 Hz, 1H), 3.87 (m., 4H) |
| 620 | 739.2 | $^{1}$H NMR (400 MHz, DMSO-$d_6$) δ: 9.47 (s, 1H), 8.77 (d, J = 9.1 Hz, 1H), 8.48-8.57 (m, 2H), 8.31 (d, J = 8.3 Hz, 1H), 7.86-7.98 (m, 2H), 7.42-7.62 (m, 2H), 7.29 (d, J = 5.6 Hz, 1H), 7.20 (br s, 1H), 6.84 (d, J = 8.0 Hz, 1H), 4.61 (t, J = 6.5 Hz, 2H), 4.52 (t, J = 6.1 Hz, 2H), 3.78 (br s, 4H), 3.45-3.59 (m, 1H), 2.52-2.60 (m, 4H) |
| 621 | 727.2 | $^{1}$H NMR (400 MHz, DMSO-$d_6$) δ: 9.83 (s, 1H), 9.10 (s, 1H), 8.34-8.48 (m, 2H), 7.94 (dd, J = 1.31, 8.07 Hz, 1H), 7.89 (dd, J = 1.44, 7.94 Hz, 1H), 7.75 (d, J = 8.13 Hz, 1H), 7.53 (t, J = 8.00 Hz, 1H), 7.12-7.37 (m, 3H), 6.74 (d, J = 8.00 Hz, 1H), 4.32-4.43 (m, 1H), 4.26 (d, J = 11.63 Hz, 2H), 3.47-3.56 (m, 2H), 2.76 (t, J = 11.07 Hz, 2H), 1.78 (d, J = 11.63 Hz, 2H), 1.32-1.49 (m, 4H) |
| 622 | 783.3 | $^{1}$H NMR (400 MHz, DMSO-$d_6$) δ: 10.73 (s, 1H), 9.85 (s, 1H), 9.16 (s, 1H), 8.42-8.55 (m, 3H), 7.89-8.00 (m, 2H), 7.85 (d, J = 8.13 Hz, 1H), 7.54 (t, J = 8.07 Hz, 1H), 7.30 (t, J = 8.13 Hz, 2H), 6.79 (d, J = 7.88 Hz, 1H), 3.47-3.68 (m, 8H), 1.45 (s, 9H) |
| 623 | 725.4 | $^{1}$H NMR (400 MHz, DMSO-$d_6$) δ: 9.43 (s, 1H), 8.77 (d, J = 9.13 Hz, 1H), 8.47-8.57 (m, 2H), 8.32 (d, J = 8.25 Hz, 1H), 7.92 (d, J = 8.13 Hz, 1H), 7.85 (d, J = 7.13 Hz, 1H), 7.54 (t, J = 8.07 Hz, 1H), 7.48 (t, J = 8.00 Hz, 1H), 7.24 (d, J = 5.25 Hz, 1H), 7.10 (br. s., 1H), 6.84 (d, J = 8.13 Hz, 1H), 3.78 (br. s., 4H), 2.87 (d, J = 15.38 Hz, 5H), 1.10 (d, J = 6.50 Hz, 6H) |
| 624 | 753.2 | $^{1}$H NMR (400 MHz, DMSO-$d_6$) δ: 10.70 (br s, 1H), 9.47 (s, 1H), 8.77 (d, J = 9.13 Hz, 1H), 8.45-8.55 (m, 2H), 8.28 (d, J = 8.00 Hz, 1H), 7.88-7.97 (m, 2H), 7.53 (t, J = 7.94 Hz, 2H), 7.25-7.36 (m, 1H), 7.21 (b. s, 1H), 6.82 (d, J = 7.88 Hz, 1H), 3.74 (br. s., 4H), 2.77 (br s, 4H), 2.18 (br s, 2H), 0.92 (s, 9H) |
| 625 | 725.4 | $^{1}$H NMR (400 MHz, DMSO-$d_6$) δ: 9.45 (s, 1H), 8.77 (d, J = 9.13 Hz, 1H), 8.45-8.58 (m, 2H), 8.31 (d, J = 8.13 Hz, 1H), 7.83-8.00 (m, 2H), 7.45-7.62 (m, 2H), 7.18-7.37 (m, 1H), 7.14 (br. s., 1H), 6.84 (d, J = 7.63 Hz, 1H), 3.77 (br. s., 4H), 2.74 (br. s., 4H), 2.44 (br. s., 2H), 1.54 (sxt, J = 7.43 Hz, 2H), 0.84-0.98 (m, 3H) |
| 626 | 753.4 | $^{1}$H NMR (400 MHz, DMSO-$d_6$) δ: 10.69 (br s, 1H), 9.45 (s, 1H), 8.75 (d, J = 9.1 Hz, 1H), 8.44-8.56 (m, 2H), 8.09 (d, J = 8.0 Hz, 1H), 7.83-8.00 (m, 2H), 7.39-7.64 (m, 2H), 7.29 (d, J = 6.1 Hz, 1H), 7.21 (d, J = 7.6 Hz, 1H), 6.81 (d, J = 8.1 Hz, 1H), 5.13 (br s, 2H), 4.34 (br s, 1H), 3.47 (d, J = 4.25 Hz, 2H), 2.61-2.76 (m, 2H), 2.46 (br s, 2H), 2.32 (br s, 2H), 2.05 (d, J = 7.25 Hz, 2H), 1.98 (d, J = 9.0 Hz, 2H) |
| 627 | 711.3 | $^{1}$H NMR (400 MHz, DMSO-$d_6$) δ: 9.44 (s, 1H), 8.77 (d, J = 9.13 Hz, 1H), 8.39-8.59 (m, 2H), 8.32 (d, J = 8.38 Hz, 1H), 7.79-7.98 (m, 3H), 7.54 (t, J = 8.13 Hz, 1H), 7.50 (t, J = 7.94 Hz, 1H), 7.19-7.31 (m, 1H), 7.14 (d, J = 8.63 Hz, 1H), 6.85 (d, J = 8.00 Hz, 1H), 3.79 (br. s., 4H), 2.80 (br. s., 4H), 2.58 (d, J = 5.75 Hz, 2H), 1.11 (t, J = 7.19 Hz, 3H) |
| 628 | 731.2 | $^{1}$H NMR (400 MHz, DMSO-$d_6$) δ: 10.72 (s, 1H), 9.84 (s, 1H), 9.18 (s, 1H), 8.40-8.56 (m, 3H), 7.94 (d, J = 8.0 Hz, 1H), 7.90 (d, J = 7.9 Hz, 1H), 7.85 (d, J = 8.3 Hz, 1H), 7.53 (t, J = 8.1 Hz, 1H), 7.27-7.36 (m, 2H), 7.18-7.26 (m, 1H), 6.90 (d, J = 8.0 Hz, 1H), 4.18 (s, 4H), 3.27 (s, 4H) |
| 629 | 752.3 | $^{1}$H NMR (400 MHz, DMSO-$d_6$) δ: 10.62 (br s, 1H), 9.84 (s, 1H), 9.06 (s, 1H), 8.50 (s, 1H), 8.47 (d, J = 9.3 Hz, 1H), 8.43 (d, J = 9.1 Hz, 1H), 7.92 (t, J = 8.4 Hz, 2H), 7.59 (d, J = 8.1 Hz, 1H), 7.52 (t, J = 8.0 Hz, 1H), 7.25-7.33 (m, 1H), 7.13-7.24 (m, 2H), 6.74 (d, J = 8.1 Hz, 1H), 5.08 (br. s., 2H), 4.36 (br. s., 1H), 3.48 (t, J = 5.1 Hz, 2H), 2.62-2.78 (m, 2H), 2.52-2.59 (m, 2H), 2.29-2.41 (m, 2H), 1.86-2.04 (m, 4H) |
| 630 | 783.3 | $^{1}$H NMR (400 MHz, DMSO-$d_6$) δ: 10.73 (s, 1H), 9.85 (s, 1H), 9.16 (s, 1H), 8.42-8.55 (m, 3H), 7.89-8.00 (m, 2H), 7.85 (d, J = 8.13 Hz, 1H), 7.54 (t, J = 8.07 Hz, 1H), 7.30 (t, J = 8.13 Hz, 2H), 6.79 (d, J = 7.88 Hz, 1H), 3.47-3.68 (m, 8H), 1.45 (s, 9H) |
| 631 | 652.2 | $^{1}$H NMR (400 MHz, DMSO-$d_6$) δ: 10.71 (br s, 1H), 9.57 (s, 1H), 8.36 (br. s., 1H), 8.30 (d, J = 8.9 Hz, 1H), 8.23 (s, 1H), 8.07-8.15 (m, 1H), 7.90 (d, J = 8.0 Hz, 1H), 7.93 (d, J = 8.1 Hz, 1H), 7.52 (dd, J = 8.0 Hz, 1H), 7.23-7.30 (m, 1H), 7.14-7.22 (m, 1H), 3.75 (t, J = 4.4 Hz, 4H), 3.53 (t, J = 4.2 Hz, 4H) |

TABLE 4-continued

| | | |
|---|---|---|
| 632 | 783.3 | $^1$H NMR (400 MHz, DMSO-$d_6$) δ: 10.73 (s, 1H), 9.85 (s, 1H), 9.16 (s, 1H), 8.42-8.55 (m, 3H), 7.89-8.00 (m, 2H), 7.85 (d, J = 8.13 Hz, 1H), 7.54 (t, J = 8.07 Hz, 1H), 7.30 (t, J = 8.13 Hz, 2H), 6.79 (d, J = 7.88 Hz, 1H), 3.47-3.68 (m, 8H), 1.45 (s, 9H) |
| 633 | 691.4 | $^1$H NMR (400 MHz, DMSO-$d_6$) δ: 10.49 (br s, 1H), 9.77 (s, 1H), 9.04 (s, 1H), 8.23 8.52 (m, 3H), 7.59-7.84 (m, 3H), 7.04-7.39 (m, 4H), 6.70 (d, J = 8.0 Hz, 1H), 4.23 (s, 1H), 3.73 (d, J = 11.9 Hz, 2H), 3.14-3.25 (m, 2H), 2.60 (s, 3H), 1.48-1.75 (m, 4H), 0.99-1.19 (m, 3H) |
| 634 | 684.3 | $^1$H NMR (400 MHz, DMSO-$d_6$) δ: 9.67 (s, 1H), 9.14 (s, 1H), 8.36-8.49 (m, 4H), 7.81-7.91 (m, 2H), 7.61-7.74 (m, 1H), 7.33-7.43 (m, 1H), 7.26 (t, J = 8.07 Hz, 1H), 7.02-7.16 (m, 1H), 6.77 (d, J = 7.88 Hz, 1H), 3.57-3.81 (m, 4H), 3.25-3.32 (m, 4H) |
| 635 | 713.3 | $^1$H NMR (400 MHz, DMSO-$d_6$) δ: 10.72 (s, 1H), 9.84 (s, 1H), 9.15 (s, 1H), 8.50 (s, 1H), 8.48 (d, J = 9.1 Hz, 1H), 8.45 (d, J = 9.1 Hz, 1H), 7.95 (d, J = 8.1 Hz, 1H), 7.90 (dd, J = 8.0, 1.5 Hz, 1H), 7.83 (d, J = 8.1 Hz, 1H), 7.53 (t, J = 8.1 Hz, 1H), 7.26-7.36 (m, 2H), 7.22 (t, J = 9.0 Hz, 1H), 6.76 (d, J = 7.9 Hz, 1H), 4.79 (t, J = 5.8 Hz, 1H), 4.12-4.30 (m, 2H), 3.98 (d, J = 10.0 Hz, 1H), 3.80 (td, J = 11.3, 2.2 Hz, 1H), 3.72 (dtd, J = 10.0, 5.6, 2.3 Hz, 1H), 3.54 (dt, J = 11.1, 5.4 Hz, 1H), 3.45 (dt, J = 11.5, 5.8 Hz, 1H), 2.87 (td, J = 11.7, 3.2 Hz, 1H), 2.62 (t, J = 11.0 Hz, 1H) |
| 636 | 729.4 | $^1$H NMR (400 MHz, DMSO-$d_6$) δ: 10.51 (br s, 1H), 9.82 (s, 1H), 9.14 (s, 1H), 8.42-8.53 (m, 3H), 7.80 (d, J = 8.3 Hz, 1H), 7.63 (d, J = 7.8 Hz, 1H), 7.35-7.49 (m, 2H), 7.24-7.32 (m, 2H), 7.11-7.22 (m, 1H), 6.82 (d, J = 8.0 Hz, 1H), 6.00 (s, 1H), 4.27 (d, J = 11.4 Hz, 2H), 3.10 (t, J = 11.8 Hz, 2H), 1.88-1.99 (m, 2H), 1.79 (d, J = 12.9 Hz, 2H) |
| 637 | 745.3 | $^1$H NMR (400 MHz, DMSO-$d_6$) δ: 10.56 (br s, 1H), 9.83 (s, 1H), 9.13 (s, 1H), 8.36-8.58 (m, 3H), 7.67-7.84 (m, 3H), 7.15-7.42 (m, 4H), 6.82 (d, J = 7.9 Hz, 1H), 6.00 (s, 1H), 4.26 (d, J = 12.0 Hz, 2H), 3.10 (t, J = 11.7 Hz, 2H), 2.67 (s, 3H), 1.87 1.99 (m, 2H), 1.79 (d, J = 12.9 Hz, 2H) |
| 638 | 675.4 | $^1$H NMR (400 MHz, DMSO-$d_6$) δ: 10.52 (br s, 1H), 9.82 (s, 1H), 9.12 (s, 1H), 8.39-8.56 (m, 3H), 7.77 (d, J = 8.1 Hz, 1H), 7.63 (d, J = 7.8 Hz, 1H), 7.35-7.50 (m, 2H), 7.22-7.32 (m, 2H), 7.13-7.21 (m, 1H), 6.76 (d, J = 8.0 Hz, 1H), 3.94-4.04 (m, 2H), 3.36-3.44 (m, 1H), 3.10-3.19 (m, 2H), 2.50 (s, 3H), 1.98-2.07 (m, 2H), 1.57-1.69 (m, 2H) |
| 639 | 691.4 | $^1$H NMR (400 MHz, DMSO-$d_6$) δ: 10.57 (br s, 1H), 9.84 (s, 1H), 9.12 (s, 1H), 8.51 (br. s., 1H), 8.38-8.48 (m, 2H), 7.69-7.81 (m, 3H), 7.14-7.42 (m, 4H), 6.76 (d, J = 7.9 Hz, 1H), 3.92-4.04 (m, 2H), 3.34-3.44 (m, 1H), 3.14 (t, J = 9.9 Hz, 2H), 2.67 (s, 3H), 1.97-2.06 (m, 2H), 1.56-1.69 (m, 2H) |
| 640 | 661.4 | $^1$H NMR (400 MHz, DMSO-$d_6$) δ: 10.51 (br s, 1H), 9.83 (s, 1H), 9.11 (s, 1H), 8.35-8.58 (m, 3H), 7.75 (d, J = 8.1 Hz, 1H), 7.62 (d, J = 7.8 Hz, 1H), 7.35-7.52 (m, 2H), 7.17-7.33 (m, 3H), 6.74 (d, J = 8.0 Hz, 1H), 4.85 (br s, 1H), 4.24 (d, J = 8.3 Hz, 1H), 4.08 (d, J = 11.8 Hz, 1H), 3.72 (br. s., 1H), 2.74-2.85 (m, 1H), 2.59 (t, J = 10.3 Hz, 1H), 2.50 (s, 3H), 1.93-2.02 (m, 1H), 1.76-1.84 (m, 1H), 1.59-1.73 (m, 1H), 1.25-1.37 (m, 1H) |
| 641 | 677.3 | $^1$H NMR (400 MHz, DMSO-$d_6$) δ: 10.57 (br s, 1H), 9.83 (s, 1H), 9.11 (s, 1H), 8.35-8.60 (m, 3H), 7.68-7.83 (m, 3H), 7.15-7.43 (m, 4H), 6.74 (d, J = 7.9 Hz, 1H), 4.78-4.91 (m, 1H), 4.24 (d, J = 8.5 Hz, 1H), 4.08 (d, J = 11.6 Hz, 1H), 3.73 (br. s., 1H), 2.79 (t, J = 10.8 Hz, 1H), 2.67 (s, 3H), 2.60 (t, J = 10.3 Hz, 1H), 1.98 (d, J = 9.4 Hz, 1H), 1.75-1.86 (m, 1H), 1.66 (q, J = 12.2 Hz, 1H), 1.25-1.39 (m, 1H) |
| 642 | 685.2 | $^1$H NMR (400 MHz, DMSO-$d_6$) δ: 10.71 (s, 1H), 9.83 (s, 1H), 9.03 (s, 1H), 8.31-8.53 (m, 3H), 7.94 (dd, J = 8.2, 1.6 Hz, 1H), 7.89 (dd, J = 8.0, , 1.4 Hz, 1H), 7.52 (t, J = 8.0 Hz, 1H), 7.46 (d, J = 8.2 Hz, 1H), 7.06-7.36 (m, 3H), 6.36 (d, J = 8.2 Hz, 1H), 4.92 (d, J = 3.5 Hz, 1H), 4.41 (d, J = 2.7 Hz, 1H), 3.88 (dd, J = 11.0, 5.1 Hz, 1 H), 3.73 (dd, J = 8.6, 5.5 Hz, 2H), 3.58-3.69 (m, 1H), 2.01-2.14 (m, 1H), 1.76-1.95 (m, 1 H) |
| 643 | 759.2 | $^1$H NMR (400 MHz, DMSO-$d_6$) δ: 10.72 (s, 1H), 9.84 (s, 1H), 9.15 (s, 1H), 8.48-8.53 (m, 1H), 8.42-8.48 (m, 2H), 7.95 (d, J = 8.0 Hz, 1H), 7.90 (dd, J = 8.0, 1.4 Hz, 1H), 7.80 (d, J = 8.1 Hz, 1H), 7.53 (t, J = 8.0 Hz, 1H), 7.26-7.34 (m, 2H), 7.17-7.26 (m, 1H), 6.80 (d, J = 8.0 Hz, 1H), 4.49 (d, J = 12.3 Hz, 2H), 2.99 (s, 3H), 2.89 (t, J = 11.5 Hz, 2H), 2.15 (d, J = 10.9 Hz, 2H), 1.78-1.93 (m, 2H) |
| 644 | 760.2 | $^1$H NMR (400 MHz, DMSO-$d_6$) δ: 9.77 (s, 1H), 9.19 (s, 1H), 8.51 (s, 1H), 8.45 (s, 2H), 7.92 (d, J = 7.6 Hz, 1H), 7.86 (d, J = 8.3 Hz, 1H), 7.78 (s, 1H), 7.38-7.52 (m, 1H), 7.31 (t, J = 8.1 Hz, 1H), 7.17 (br. s., 1H), 7.00 (br. s., 1H), 6.81 (d, J = 7.9 Hz, 1H), 6.52 (s, 1H), 3.65 (s, 4H), 3.36-3.40 (m, 4H), 2.96 (s, 3H) |
| 645 | 752.2 | $^1$H NMR (400 MHz, DMSO-$d_6$) δ: 10.72 (s, 1H), 9.84 (s, 1H), 9.16 (s, 1H), 8.50 (s, 1H), 8.41-8.48 (m, 2H), 7.94 (d, J = 7.9 Hz, 1H), 7.90 (dd, J = 8.0, 1.3 Hz, 1H), 7.84 (d, J = 8.1 Hz, 1H), 7.53 (t, J = 8.0 Hz, 1H), 7.26-7.34 (m, 2H), 7.18-7.26 (m, 1H), 6.78 (d, J = 8.0 Hz, 1H), 3.66-3.81 (m, 4H), 3.56 (s, 2H), 3.47 (s, 2H), 2.88-3.01 (m, 1H), 1.05 (s, 3H), 1.03 (s, 3H) |
| 654 | 752.2 | $^1$H NMR (400 MHz, DMSO-$d_6$) δ: 9.83 (s, 1H), 9.06-9.17 (m, 1H), 8.50 (s, 1H), 8.39-8.47 (m, 2H), 7.95 (d, J = 7.88 Hz, 1H), 7.91 (dd, J = 1.38, 7.88 Hz, 1H), 7.59 (d, J = 8.13 Hz, 1H), 7.54 (t, J = 8.00 Hz, 1H), 7.26-7.35 (m, 1H), 7.18-7.26 (m, 2H), 6.30 (d, J = 7.75 Hz, 1H), 5.52 (s, 1H), 4.12 (d, J = 8.13 Hz, 2H), 3.96 (d, J = 8.00 Hz, 2H), 1.52 (s, 3H) |
| 655 | 685.2 | $^1$H NMR (400 MHz, DMSO-$d_6$) δ: 9.85 (s, 1H), 9.12 (s, 1H), 8.31-8.55 (m, 1H), 7.96 (d, J = 8.00 Hz, OH), 7.91 (dd, J = 1.25, 8.00 Hz, OH), 7.75 (d, J = 8.13 Hz, 1H), 7.54 (t, J = 8.07 Hz, 1H), 7.18-7.36 (m, 4H), 6.76 (d, J = 7.88 Hz, 1H), 4.41-4.61 (m, 1H), 3.94 (d, J = 5.13 Hz, 2H), 3.03-3.18 (m, 2H), 1.88 (d, J = 10.01 Hz, 2H), 1.62-1.82 (m, 4H), 1.41-1.62 (m, 4H), 1.34 (d, J = 12.88 Hz, 1H) |

TABLE 4-continued

| | | |
|---|---|---|
| 656 | 760.2 | $^1$H NMR (400 MHz, DMSO-$d_6$) δ: 9.64 (br s 1H), 9.14 (s, 1H), 8.46 (s, 1H), 8.31-8.41 (m, 2H), 7.87 (dd, J = 1.38, 7.88 Hz, 1H), 7.81 (d, J = 8.25 Hz, 1H), 7.63 (d, J = 7.63 Hz, 1H), 7.32 (t, J = 7.88 Hz, 1H), 7.21-7.29 (m, 1H), 7.03 (dt, J = 6.00, 9.07 Hz, 1H), 6.71-6.87 (m, 2H), 4.38 (d, J = 11.51 Hz, 2H), 3.07-3.28 (m, 2H), 2.59-2.74 (m, 2H), 1.19 (d, J = 6.25 Hz, 6H) |
| 657 | 712.4 | $^1$H NMR (400 MHz, DMSO-$d_6$) δ: 9.67 (br s, 1H), 9.11 (s, 1H), 8.45 (s, 1H), 8.31-8.42 (m, 2H), 7.86 (dd, J = 1.44, 7.82 Hz, 1H), 7.75 (d, J = 8.25 Hz, 1H), 7.67 (d, J = 7.13 Hz, 1H), 7.35 (t, J = 7.94 Hz, 1H), 7.22 (t, J = 8.07 Hz, 1H), 7.00-7.13 (m, J = 6.00, 9.10, 9.10 Hz, 1H), 6.86 (t, J = 9.07 Hz, 1H), 6.72 (d, J = 8.00 Hz, 1H), 4.36 (d, J = 12.01 Hz, 2H), 2.84-2.97 (m, 1H), 2.75 (t, J = 11.76 Hz, 2H), 2.49-2.58 (m, 6H), 1.87-2.05 (m, 2H), 1.57-1.79 (m, 2H) |
| 658 | 726.3 | $^1$H NMR (400 MHz, DMSO-$d_6$) δ: 10.65 (s, 1H), 9.76 (s, 1H), 9.08 (s, 1H), 8.33-8.47 (m, 3H), 7.88 (d, J = 7.88 Hz, 1H), 7.84 (dd, J = 1.31, 7.94 Hz, 1H), 7.60 (d, J = 8.13 Hz, 1H), 7.47 (t, J = 8.00 Hz, 1H), 7.10-7.29 (m, 4H), 6.33 (d, J = 7.88 Hz, 1H), 4.42 (d, J = 9.63 Hz, 2H), 4.11 (d, J = 9.51 Hz, 2H) |
| 659 | 739.2 | $^1$H NMR (400 MHz, DMSO-$d_6$) δ: 10.71 (br s, 1H), 9.83 (br s, 1H), 9.10 (s, 1H), 8.50 (s, 1H), 8.37-8.48 (m, 2H), 7.91 (d, J = 7.88 Hz, 2H), 7.44-7.59 (m, 2H), 7.12-7.35 (m, 3H), 6.60 (d, J = 8.13 Hz, 1H), 4.77 (t, J = 5.19 Hz, 1H), 3.72-3.86 (m, 4H), 3.61-3.72 (m, 2H), 1.17 (t, J = 6.94 Hz, 3H) |
| 660 | 685.3 | $^1$H NMR (400 MHz, DMSO-$d_6$) δ: 10.72 (br s, 1H), 9.88 (s, 1H), 9.17 (s, 1H), 8.50 (s, 1H), 8.40-8.49 (m, 2H), 7.91 (d, J = 8.00 Hz, 2H), 7.62 (d, J = 8.13 Hz, 1H), 7.52 (t, J = 7.94 Hz, 1H), 7.25 (m, 3H), 6.63 (d, J = 8.13 Hz, 1H), 4.92 (t, J = 5.50 Hz, 1H), 3.86 (t, J = 6.94 Hz, 2H), 3.52 (q, J = 5.96 Hz, 2H), 3.04 (s, 3H), 1.76 (quin, J = 6.50 Hz, 2H) |
| 661 | 685.3 | $^1$H NMR (400 MHz, DMSO-$d_6$) δ: 10.72 (br s, 1H), 9.82 (s, 1H), 9.14 (s, 1H), 8.50 (s, 1H), 8.38-8.48 (m, 2H), 7.87-7.99 (m, 2H), 7.65 (d, J = 8.3 Hz, 1H), 7.52 (t, J = 7.9 Hz, 1H), 7.08-7.38 (m, 3H), 6.36 (d, J = 7.9 Hz, 1H), 4.17-4.39 (m, 4H), 1.69 (d, J = 22.0 Hz, 3H) |
| 662 | 681.3 | $^1$H NMR (400 MHz, DMSO-$d_6$) δ: 9.68 (br s, 1H), 9.33 (s, 1H), 8.53 (s, 1H), 8.49 (d, J = 9.1 Hz, 1H), 8.46 (d, J = 9.1 Hz, 1H), 8.24 (d, J = 8.3 Hz, 1H), 8.18 (br. s., 1H), 7.94 (dd, J = 7.8, 1.4 Hz, 1H), 7.65 (dd, J = 7.9, 1.2 Hz, 1H), 7.42 (t, J = 7.9 Hz, 1H), 7.37 (t, J = 7.9 Hz, 1H), 7.22 (d, J = 7.5 Hz, 1H), 7.07 (td, J = 9.2, 6.1 Hz, 1H), 6.80 (t, J = 9.1 Hz, 1H), 3.56-3.65 (m, 1H), 3.40-3.46 (m, 2H), 3.08-3.20 (m, 2H), 2.52-2.55 (m, 1H), 2.00-2.25 (m, 4H) |
| 663 | 589.2 | $^1$H NMR (400 MHz, DMSO-$d_6$) δ: 10.51 (s, 1H), 10.14 (s, 1H), 9.38 (d, J = 2.35 Hz, 1H), 8.53-8.73 (m, 2H), 8.48 (s, 1H), 8.42 (d, J = 9.00 Hz, 1H), 8.18 (d, J = 8.22 Hz, 1H), 7.95 (dt, J = 1.57, 7.83 Hz, 1H), 7.60 (d, J = 7.43 Hz, 1H), 7.45-7.53 (m, 1H), 7.35-7.45 (m, 2H), 7.18-7.35 (m, 3H), 2.50 (s, 3H) |
| 664 | 581.2 | $^1$H NMR (400 MHz, DMSO-$d_6$) δ: 9.97 (s, 1H), 9.07 (s, 1H), 8.43 (s, 1H), 8.32 (q, J = 9.1 Hz, 2H), 8.14 (s, (m, 2H), 7.23 (dd, J = 14.8, 8.9 Hz, 1H), 7.08 (t, J = 9.2Hz, 1H), 3.55 (s, 2H), 2.72 (t, J = 5.4 Hz, 2H), 2.68-2.61 (m, 2H), 2.49 (s, 3H), 2.42 (s, 3H) |
| 665 | 739.2 | $^1$H NMR (400 MHz, DMSO-$d_6$) δ: 10.66 (br s, 1H), 9.77 (s, 1H), 9.03 (s, 1H), 8.43 (s, 1H), 8.32-8.42 (m, 2H), 7.79-7.87 (m, 2H), 7.68 (d, J = 8.1 Hz, 1H), 7.46 (t, J = 8.0 Hz, 1H), 7.08-7.29 (m, 3H), 6.70 (d, J = 7.9 Hz, 1H), 4.00 (d, J = 11.5 Hz, 2H), 3.89 (s, 1H), 2.99-3.12 (m, 2H), 1.65 (dt, J = 4.0, 12.6 Hz, 2H), 1.43-1.56 (m, 3H), 0.78-0.89 (m, 6H) |
| 666 | 689.2 | $^1$H NMR (400 MHz, DMSO-$d_6$) δ: 10.73 (s, 1H), 9.84 (s, 1H), 9.18 (s, 1H), 8.51 (s, 1H), 8.40-8.49 (m, 2H), 7.96 (d, J = 8.0 Hz, 1H), 7.91 (dd, J = 1.5, 8.0 Hz, 1H), 7.75 (d, J = 8.0 Hz, 1H), 7.54 (t, J = 8.1 Hz, 1H), 7.17-7.36 (m, 3H), 6.47 (d, J = 7.6 Hz, 1H), 4.60 (t, J = 12.4 Hz, 4H) |
| 667 | 685.2 | $^1$H NMR (400 MHz, DMSO-$d_6$) δ: 10.72 (br s, 1H), 9.81 (s, 1H), 9.12 (s, 1H), 8.48-8.57 (m, 1H), 8.35-8.48 (m, 2H), 7.91 (dd, J = 1.3, 7.9 Hz, 2H), 7.59 (d, J = 8.0 Hz, 1H), 7.51 (t, J = 8.0 Hz, 1H), 7.12-7.35 (m, 3H), 6.30 (d, J = 7.6 Hz, 1H), 4.74 (d, J = 6.0 Hz, 1H), 4.63 (d, J = 6.0 Hz, 1H), 4.18-4.36 (m, 2H), 3.99 (dd, J = 5.6, 8.1 Hz, 2H), 2.96-3.22 (m, 1H) |
| 668 | 752.3 | $^1$H NMR (400 MHz, DMSO-$d_6$) δ: 9.65 (br s, 1H), 9.07-9.17 (m, 1H), 8.45 (s, 1H), 8.38 (d, J = 3.3 Hz, 2H), 7.86 (dd, J = 1.5, 7.9 Hz, 1H), 7.75 (d, J = 8.1 Hz, 1H), 7.61-7.70 (m, 1H), 7.29-7.38 (m, 1H), 7.22 (s, 1H), 6.99-7.12 (m, 1H), 6.79-6.91 (m, 1H), 6.72 (d, J = 8.0 Hz, 1H), 4.25-4.39 (m, 2H), 3.22-3.33 (m, 1H), 2.94-3.13 (m, 4H), 2.72-2.86 (m, 2H), 2.04-2.10 (m, 2H), 1.76-1.86 (m, 4H), 1.60-1.76 (m, 2H) |
| 669 | 699.2 | $^1$H NMR (400 MHz, DMSO-$d_6$) δ: 10.73 (s, 1H), 9.83 (s, 1H), 9.10 (s, 1H), 8.41-8.62 (m, 2H), 7.81-8.05 (m, 2H), 7.49-7.66 (m, 2H), 7.10-7.38 (m, 3H), 6.30 (d, J = 7.75 Hz, 1H), 5.43 (s, 1H), 4.14 (d, J = 8.4 Hz, 2H), 3.92 (d, J = 8.3 Hz, 2H), 1.79 (q, J = 7.3 Hz, 2H), 0.98 (t, J = 7.3 Hz, 3H) |
| 670 | 671.2 | $^1$H NMR (400 MHz, DMSO-$d_6$) δ: 9.66 (s, 1H), 9.09 (s, 1H), 8.44 (s, 1H), 8.29-8.41 (m, 2H), 8.08 (br. s., 1H), 7.86 (dd, J = 1.44, 7.82 Hz, 1H), 7.66 (d, J = 7.63 Hz, 1H), 7.59 (d, J = 8.13 Hz, 1H), 7.34 (t, J = 7.94 Hz, 1H), 7.18 (t, J = 8.00 Hz, 1H), 7.05 (d, J = 6.00 Hz, 1H), 6.84 (br. s., 1H), 6.29 (d, J = 7.88 Hz, 1H), 5.30-5.65 (m, 1H), 4.39-4.54 (m, 2H), 4.02-4.24 (m, 2H) |
| 671 | 741.2 | $^1$H NMR (400 MHz, DMSO-$d_6$) δ: 10.72 (br s, 1H), 9.84 (s, 1H), 9.10 (s, 1H), 8.50 (s, 1H), 8.47 (d, J = 9.0 Hz, 1H), 8.43 (d, J = 9.0 Hz, 1H), 7.94 (d, J = 7.9 Hz, 1H), 7.90 (dd, J = 8.0, 1.4 Hz, 1H), 7.74 (d, J = 8.1 Hz, 1H), 7.53 (t, J = 8.0 Hz, 1H), 7.30 (td, J = 8.9, 5.8 Hz, 1H), 7.26 (t, J = 8.1 Hz, 1H), 7.22 (t, J = 9.0 Hz, 1H), 6.76 (d, J = 8.0 Hz, 1H), 4.40 (t, J = 4.9 Hz, 1H), 4.30 (s, 1H), 3.88 (dt, J = 12.0, 3.6 Hz, 2H), 3.63 (q, J = 6.0 Hz, 2H), 3.24-3.29 (m, 2H), 1.70-1.80 (m, 2H), 1.58-1.70 (m, 4H) |

TABLE 4-continued

| | | |
|---|---|---|
| 672 | 719.4 | $^1$H NMR (400 MHz, DMSO-$d_6$) δ: 10.33 (br s, 1H), 9.83 (s, 1H), 9.11 (s, 1H), 8.37-8.57 (m, 3H), 7.74 (d, J = 8.1 Hz, 1H), 7.58 (d, J = 8.9 Hz, 1H), 7.17-7.32 (m, 3H), 7.12 (dd, J = 8.5 Hz, 1H), 6.77 (d, J = 8.0 Hz, 1H), 4.08 (s, 1H), 3.89-3.96 (m, 2H), 3.87 (s, 3H), 3.19-3.29 (m, 2H), 2.50 (s, 3H), 1.54-1.72 (m, 4H), 1.46 (q, J = 7.2 Hz, 2H), 0.89 (t, J = 7.4 Hz, 3H) |
| 673 | 735.4 | $^1$H NMR (400 MHz, DMSO-$d_6$) δ: 10.40 (br s, 1H), 9.83 (s, 1H), 9.10 (s, 1H), 8.39-8.53 (m, 3H), 7.74 (d, J = 8.1 Hz, 1H), 7.77 (d, J = 9.0 Hz, 1H), 7.07-7.34 (m, 4H), 6.77 (d, J = 7.9 Hz, 1H), 4.08 (s, 1H), 3.85-3.98 (m, 5H), 3.21-3.28 (m, 2H), 2.66 (s, 3H), 1.55-1.73 (m, 4H), 1.46 (q, J = 7.1 Hz, 2H), 0.89 (t, J = 7.4 Hz, 3H) |
| 674 | 759.3 | $^1$H NMR (400 MHz, DMSO-$d_6$) δ: 10.33 (br s, 1H), 9.84 (s, 1H), 9.14 (s, 1H), 8.41-8.54 (m, 3H), 7.79 (d, J = 8.1 Hz, 1H), 7.58 (d, J = 8.9 Hz, 1H), 7.17-7.34 (m, 3H), 7.13 (dd, J = 8.6 Hz, 1H), 6.82 (d, J = 8.0 Hz, 1H), 6.00 (s, 1H), 4.27 (d, J = 11.9 Hz, 2H), 3.87 (s, 3H), 3.10 (t, J = 11.5 Hz, 2H), 2.50 (s, 3H), 1.87-2.00 (m, 2H), 1.79 (d, J = 12.5 Hz, 2H) |
| 675 | 729.2 | $^1$H NMR (400 MHz DMSO-$d_6$) δ: 10.72 (s, 1H), 9.85 (s, 1H), 9.12 (s, 1H), 8.50 (s, 1H), 8.39-8.48 (m, 2H), 7.95 (d, J = 7.9 Hz, 1H), 7.90 (d, J = 7.8 Hz, 1H), 7.75 (d, J = 8.1 Hz, 1H), 7.54 (t, J = 8.0 Hz, 1H), 7.18-7.34 (m, 3H), 6.79 (d, J = 8.0 Hz, 1H), 4.79 (s, 1H), 4.23 (d, J = 47.9 Hz, 2H), 4.03 (d, J = 11.9 Hz, 2H), 3.24 (t, J = 11.1 Hz, 2H), 1.76-1.86 (m, 2H), 1.61 (d, J = 13.0 Hz, 2H) |
| 676 | 711.2 | $^1$H NMR (400 MHz, DMSO-$d_6$) δ: 10.72 (br s, 1H), 9.85 (s, 1H), 9.16 (s, 1H), 8.50 (s, 1H), 8.39-8.48 (m, 2H), 7.94 (d, J = 8.0 Hz, 1H), 7.90 (dd, J = 1.3, 7.94 Hz, 1H), 7.76 (d, J = 8.3 Hz, 1H), 7.53 (t, J = 8.1 Hz, 1H), 7.10-7.36 (m, 3H), 6.77 (d, J = 8.0 Hz, 1H), 4.27 (dd, J = 2.8, 11.2 Hz, 1H), 3.79-3.95 (m, 1H), 3.43-3.53 (m, 1H), 3.36 (s, 3H), 2.91-3.04 (m, 2H), 1.99-2.13 (m, 1H), 1.86 (dd, J = 4.4, 9.0 Hz, 1H), 1.55-1.77 (m, 1H), 1.31-1.51 (m, 1H) |
| 677 | 697.2 | $^1$H NMR (400 MHz, DMSO-$d_6$) δ: 10.72 (br s, 1H), 9.86 (s, 1H), 9.16 (s, 1H), 8.46-8.51 (m, 1H), 8.44 (s, 2H), 7.94 (br. s., 1H), 7.87-7.93 (m, 1H), 7.52 (t, J = 8.0 Hz, 1H), 7.44 (d, J = 8.3 Hz, 1H), 7.24-7.39 (m, 1H), 7.19 (t, J = 8.0 Hz, 2H), 6.51 (d, J = 7.4 Hz, 1H), 6.00 (t, J = 5.9 Hz, 1H), 3.69-3.90 (m, 2H), 3.64 (q, J = 7.8 Hz, 1H), 3.54 (dd, J = 5.4, 8.50 Hz, 1H), 3.27 (t, J = 6.7 Hz, 2H), 2.60-2.74 (m, 1H), 1.94-2.09 (m, 1H), 1.54-1.83 (m, 1H) |
| 678 | 673.2 | $^1$H NMR (400 MHz, DMSO-$d_6$) δ: 10.72 (br s, 1H), 9.85 (s, 1H), 9.10 (s, 1H), 8.50 (s, 1H), 8.36-8.48 (m, 2H), 7.91 (d, J = 7.9 Hz, 2H), 7.58 (d, J = 8.1 Hz, 1H), 7.52 (t, J = 7.5 Hz, 1H), 7.23 (t, J = 8.1 Hz, 3H), 6.59 (d, J = 8.1 Hz, 1H), 4.81 (t, J = 5.1 Hz, 1H), 3.95 (t, J = 6.1 Hz, 2H), 3.69 (q, J = 6.1 Hz, 2H), 3.12 (s, 3H) |
| 679 | 671.4 | $^1$H NMR (400 MHz, DMSO-$d_6$) δ: 10.74 (br s, 1H), 9.49 (s, 1H), 8.80 (d, J = 9.1 Hz, 1H), 8.53 (s, 1H), 8.45 (d, J = 8.3 Hz, 1H), 7.95 (br s, 1H), 7.91 (dd, J = 1.4, 8.0 Hz, 1H), 7.63 (t, J = 8.1 Hz, 1H), 7.53 (t, J = 7.94Hz, 1H), 7.27-7.37 (m, 1H), 7.23 (d, J = 8.9 Hz, 1H), 7.08 (d, J = 7.9 Hz, 1H), 4.48 (dd, J = 3.6, 5.3 Hz, 2H), 3.79-3.89 (m, 2H), 3.38 (s, 4H) |
| 680 | 747.2 | $^1$H NMR (400 MHz, MeOH-$d_4$) δ: 8.78 (s, 1H), 8.52 (s, 1H), 8.40 (q, J = 9.0 Hz, 2H), 8.24 (d, J = 8.6 Hz, 1H), 8.05 (d, J = 7.8 Hz, 1H), 7.59 (s, 1H), 7.46-7.53 (m, 2H), 7.38-7.44 (m, 1H), 7.10 (dt, J = 1.8, 9.1 Hz, 1H), 3.26-3.33 (m, 2H), 2.88 (s, 3H), 2.74 (t, J = 6.9 Hz, 2H), 2.43 (s, 6H), 2.31 (s, 3H) |
| 681 | 725.4 | $^1$H NMR (DMSO-$d_6$) δ: 9.72 (s, 1H), 9.30 (s, 1H), 8.52 (s, 1H), 8.49 (d, J = 9.1 Hz, 1H), 8.46 (d, J = 9.1 Hz, 1H), 8.21 (d, J = 8.1 Hz, 1H), 8.14 (s, 1H), 7.93 (dd, J = 7.8, 1.4 Hz, 1H), 7.74 (d, J = 7.8 Hz, 1H), 7.41 (td, J = 7.8, 3.2 Hz, 2H), 7.24 (d, J = 7.5 Hz, 1H), 7.13 (td, J = 8.8, 6.4 Hz, 1H), 6.93 (t, J = 8.4 Hz, 1H), 4.93 (br. s., 1H), 3.68 (t, J = 5.7 Hz, 2H), 2.88 (br. s., 2H), 2.69-2.83 (m, 2H), 2.06-2.20 (m, 2H), 1.95-2.05 (m, 2H) |
| 682 | 775.3 | $^1$H NMR (400 MHz, DMSO-$d_6$) δ: 10.39 (br s, 1H), 9.83 (s, 1H), 9.13 (s, 1H), 8.41-8.54 (m, 3H), 7.73-7.82 (m, 2H), 7.18-7.34 (m, 3H), 7.13 (d, J = 9.1 Hz, 1H), 6.82 (d, J = 8.0 Hz, 1H), 6.00 (s, 1H), 4.27 (d, J = 11.9 Hz, 2H), 3.90 (s, 3H), 3.10 (t, J = 11.5 Hz, 2H), 2.66 (s, 3H), 1.93 (td, J = 12.7, 4.1 Hz, 2H), 1.79 (d, J = 12.5 Hz, 2H) |
| 683 | 669.2 | $^1$H NMR (400 MHz, DMSO-$d_6$) δ: 10.72 (s, 1H), 9.83 (s, 1H), 9.10 (s, 1H), 8.39-8.53 (m, 3H), 7.87-7.98 (m, 2H), 7.50-7.60 (m, 2H), 7.18-7.34 (m, 3H), 6.29 (d, J = 7.9 Hz, 1H), 5.61 (d, J = 6.5 Hz, 1H), 4.62 (sxt, J = 5.9 Hz, 1H), 4.43 (t, J = 7.4 Hz, 2H), 3.84 (dd, J = 8.4, 5.1 Hz, 2H) |
| 684 | 563.1 | $^1$H NMR (400 MHz, DMSO-$d_6$) δ: 10.77 (s, 1H), 10.18 (s, 1H), 9.23 (s, 1H), 8.60 (d, J = 9.0 Hz, 1H), 8.52 (s, 1H), 8.47 (d, J = 9.0 Hz, 1H), 7.95 (d, J = 8.0 Hz, 1H), 7.90 (d, J = 7.9 Hz, 1H), 7.53 (t, J = 8.0 Hz, 1H), 7.32 (dd, J = 14.4, 8.4 Hz, 1H), 7.24 (t, J = 9.1 Hz, 1H), 2.41 (s, 3H) |
| 685 | 683.3 | $^1$H NMR (400 MHz, DMSO-$d_6$) δ: 10.72 (s, 1H), 9.83 (s, 1H), 9.10 (s, 1H), 8.49 (s, 1H), 8.38-8.47 (m, 2H), 7.95 (d, J = 7.88 Hz, 1H), 7.90 (dd, J = 1.25, 8.00 Hz, 1H), 7.50-7.59 (m, 2H), 7.25-7.36 (m, 1H), 7.15-7.25 (m, 2H), 6.26 (d, J = 7.88 Hz, 1H), 4.77 (t, J = 5.25 Hz, 1H), 4.19 (t, J = 7.88 Hz, 2H), 3.92 (dd, J = 5.57, 7.82 Hz, 2H), 3.64 (t, J = 5.82 Hz, 2H), 2.75-2.92 (m, 1H) |
| 686 | 713.2 | $^1$H NMR (400 MHz, DMSO-$d_6$) δ: 10.72 (br s, 1H), 9.85 (s, 1H), 9.10 (s, 1H), 8.50 (s, 1H), 8.47 (d, J = 9.3 Hz, 1H), 8.44 (d, J = 9.0 Hz, 1H), 7.95 (d, J = 8.1 Hz, 1H), 7.90 (dd, J = 7.9, 1.1 Hz, 1H), 7.76 (d, J = 8.3 Hz, 1H), 7.54 (t, J = 8.1 Hz, 1H), 7.17-7.36 (m, 3H), 6.73 (d, J = 8.0 Hz, 1H), 4.77 (d, J = 8.8 Hz, 1H), 4.64 (t, J = 5.1 Hz, 1H), 4.05 (d, J = 11.0 Hz, 1H), 3.95 (d, J = 10.4 Hz, 1H), 3.75-3.85 (m, 2H), 3.70 (td, J = 11.2, 2.6 Hz, 1H), 3.47 (d, J = 12.0 Hz, 1H), 3.23-3.28 (m, 2H) |

TABLE 4-continued

| | | |
|---|---|---|
| 687 | 713.2 | $^1$H NMR (400 MHz, DMSO-$d_6$) δ: 10.72 (br s, 1H), 9.85 (s, 1H), 9.10 (s, 1H), 8.50 (s, 1H), 8.47 (d, J = 9.1 Hz, 1H), 8.44 (d, J = 9.1 Hz, 1H), 7.95 (d, J = 7.9 Hz, 1H), 7.90 (d, J = 8.0 Hz, 1H), 7.76 (d, J = 8.1 Hz, 1H), 7.54 (t, J = 8.0 Hz, 1H), 7.16-7.36 (m, 3H), 6.73 (d, J = 8.0 Hz, 1H), 4.77 (d, J = 9.0 Hz, 1H), 4.64 (t, J = 5.2 Hz, 1H), 4.05 (d, J = 10.9 Hz, 1H), 3.95 (d, J = 11.0 Hz, 1H), 3.74-3.86 (m, 2H), 3.70 (td, J = 11.2, 2.6 Hz, 1H), 3.47 (d, J = 11.9 Hz, 1H), 3.23-3.29 (m, 2H) |
| 688 | 710.2 | $^1$H NMR (400 MHz, DMSO-$d_6$) δ: 10.72 (s, 1H), 9.84 (s, 1H), 9.19 (s, 1H), 8.48-8.54 (m, 1H), 8.42-8.48 (m, 2H), 7.91 (d, J = 7.9 Hz, 2H), 7.84 (d, J = 8.1 Hz, 1H), 7.51 (t, J = 7.8 Hz, 1H), 7.23-7.35 (m, 2H), 7.10-7.23 (m, 1H), 6.78 (d, J = 8.0 Hz, 1H), 4.15 (s, 2H), 3.93 (t, J = 5.0 Hz, 2H), 3.51 (t, J = 5.1 Hz, 2H), 2.93 (s, 3H) |
| 689 | 724.2 | $^1$H NMR (400 MHz, DMSO-$d_6$) δ: 9.78 (s, 1H), 9.16 (s, 1H), 8.51 (s, 1H), 8.40-8.49 (m, 2H), 7.92 (d, J = 7.8 Hz, 1H), 7.83 (d, J = 8.0 Hz, 2H), 7.47 (t, J = 7.9 Hz, 1H), 7.29 (t, J = 8.1 Hz, 1H), 7.15-7.25 (m, 1H), 7.05 (t, J = 8.6 Hz, 1H), 6.77 (d, J = 7.9 Hz, 1H), 3.62 (s, 4H), 2.90 (s, 5H), 1.13 (s, 3H), 1.12 (s, 3H) |
| 690 | 727.2 | $^1$H NMR (400 MHz DMSO-$d_6$) δ: 10.72 (s, 1H), 9.85 (s, 1H), 9.10 (s, 1H), 8.50 (s, 1H), 8.41-8.48 (m, 2H), 7.95 (d, J = 8.1 Hz, 1H), 7.90 (d, J = 7.9 Hz, 1H), 7.73 (d, J = 8.1 Hz, 1H), 7.54 (t, J = 8.0 Hz, 1H), 7.19-7.34 (m, 3H), 6.77 (d, J = 7.9 Hz, 1H), 4.58 (t, J = 5.6 Hz, 1H), 4.16 (s, 1H), 4.01 (d, J = 11.5 Hz, 2H), 3.26 (d, J = 5.5 Hz, 2H), 3.15-3.24 (m, 2H), 1.77-1.88 (m, 2H), 1.49 (d, J = 12.9 Hz, 2H) |
| 691 | 726.2 | $^1$H NMR (400 MHz, DMSO-$d_6$) δ: 9.86 (s, 1H), 9.11 (s, 1H), 8.38-8.61 (m, 3H), 7.99 (d, J = 5.63 Hz, 1H), 7.95 (d, J = 8.13 Hz, 1H), 7.90 (d, J = 7.88 Hz, 1H), 7.46-7.59 (m, 2H), 7.27-7.35 (m, 1H), 7.19-7.27 (m, 1H), 4.82 (d, J = 12.88 Hz, 2H), 4.16 (s, 1H), 3.48-3.68 (m, 2H), 1.46-1.61 (m, 3H), 1.26-1.45 (m, J = 7.30, 7.30, 7.30 Hz, 2H), 0.85 (t, J = 7.38 Hz, 3H) |

TABLE 5

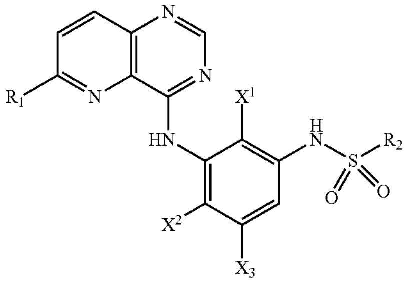

| Example | $R_1$ | $R_2$ | $X^1/X^2/X^3$ | HCT116 PERK $IC_{50}$ (μM) ($Y_{min}$%) | SW480 PERK $IC_{50}$ (μM) ($Y_{min}$%) | Kinase $IC_{50}$ (nM) BRAF | Kinase $IC_{50}$ (nM) CRAF |
|---|---|---|---|---|---|---|---|
| 239 | A165 | B1 | Cl/F/H (L3) | ++ (6.7) | | * | § |
| 240 | A165 | B21 | F/H/H (L2) | ++++ (7) | ++++ (−8) | ** | §§ |
| 241 | A65 | B21 | F/H/H (L2) | ++ (−0.9) | | | |
| 646 | A165 | B20 | F/H/H (L2) | ++++ (−3) | | ** | §§ |
| 647 | A31 | B20 | F/H/H (L2) | ++++ (−2) | | ** | §§ |
| 648 | A165 | B20 | F/F/F (L4) | ++++ (−1) | | ** | §§§ |
| 649 | A7 | B20 | F/F/F (L4) | ++++ (3) | | ** | §§§ |
| 650 | A216 | B20 | Cl/F/H (L3) | ++++ (−15) | | *** | §§§ |
| 651 | A64 | B20 | Cl/F/H (L3) | ++++ (−3) | | ** | §§ |
| 652 | A31 | B20 | Cl/F/H (L3) | ++++ (−10) | | * | §§ |

For pERK assays, + denotes a 10-30 μM $IC_{50}$ range, ++ denotes a 1-10 μM $IC_{50}$ range, +++ denotes a 0.5-1 μM $IC_{50}$ range and ++++ denotes an $IC_{50}$ < 0.5 μM. The % $Y_{min}$ value indicates the lowest value of each $IC_{50}$ curve. Compounds that exhibit $IC_{50}$ curves with $Y_{min}$ values above −20% are considered to display minimal or no induction and do not cause detectable paradoxical activation of the pathway. For the BRAF biochemical kinase assay, * denotes an $IC_{50}$ >10 nM,  denotes a 1-10 nM $IC_{50}$ range and * denotes an $IC_{50}$ < 1 nM. For the CRAF biochemical kinase assay, § denotes an $IC_{50}$ >50 nM, §§ denotes a 10-50 nM $IC_{50}$ range and §§§ denotes an $IC_{50}$ < 10 nM.

Characterization of Compounds in Table 5

| Example | HRMS m/z ($MH^+$) | Method of preparation | $^1$H NMR (400 MHz) |
|---|---|---|---|
| 239 | 576.1 | See text | $^1$H NMR (DMSO-$d_6$) δ: 10.00 (s, 1H), 9.91 (s, 1H), 9.36 (s, 1H), 8.52 (s, 1H), 8.52 (d, J = 9.4 Hz, 1H), 8.47 (d, J = 9.4 Hz, 1H), 8.40 (br. d, J = 7.4 Hz, 1H), 7.83 (br. dd, J = 7.4, 1.2 Hz, 1H), 7.67 − 7.73 (m, 2H), 7.34 − 7.47 (m, 3H), 7.28 (dd, J = 9.0, 5.5 Hz, 1H), 7.07 − 7.13 (m, 2H), 3.82 (s, 3H) |

TABLE 5-continued

| | | | |
|---|---|---|---|
| 240 | 560.1 | See text | ${}^{1}$H NMR (DMSO-$d_6$) δ: 10.66 (br s, 1H), 9.70 (s, 1H), 9.34 (s, 1H), 8.62 (s, 1H), 8.52 (d, J = 9.0 Hz, 1H), 8.48 (d, J = 9.0 Hz, 1H), 8.37 – 8.43 (m, 1H), 7.80 – 7.91 (m, 3H), 7.73 (d, J = 7.8 Hz, 1H), 7.40 – 7.47 (m, 2H), 7.37 (t, J = 8.0 Hz, 1H), 7.20 (q, J = 7.4 Hz, 1H), 7.16 (t, J = 7.4 Hz, 1H), 2.68 (s, 3H) |
| 241 | 673.2 | See text | ${}^{1}$H NMR (DMSO-$d_6$) δ: 10.69 (br s, 1H), 9.38 (s, 1H), 8.90 (d, J = 8.6 Hz, 1H), 8.65 (s, 1H), 8.55 (d, J = 9.4 Hz, 1H), 8.44 (d, J = 9.0 Hz, 1H), 8.11 (d, J = 8.2 Hz, 1H), 8.03 (t, J = 7.0 Hz, 1H), 7.85 (d, J = 7.8 Hz, 1H), 7.72 (d, J = 7.8 Hz, 1H), 7.66 (t, J = 7.8 Hz, 1H), 7.53 (t, J = 7.4 Hz, 1H), 7.37 (t, J = 8.0 Hz, 1H), 7.20 (t, J = 7.8 Hz, 1H), 7.10 – 7.17 (m, 1H), 4.00 (br. t, J = 3.9 Hz, 2H), 3.73 – 3.85 (m, J = 6.3 Hz, 4H), 3.70 (br. t, J = 4.3 Hz, 2H), 2.72 (s, 3H) |
| 646 | 580.2 | See Ex. 240 | ${}^{1}$H NMR (400 MHz, DMSO-$d_6$) δ: 10.81 (br s, 1 H), 9.68 (s, 1 H), 9.37 (br. s., 1 H), 8.64 (br. s., 1 H), 8.45 – 8.58 (m, 2 H), 8.42 (br. s., 1 H), 7.78 – 7.97 (m, 4 H), 7.51 (t, J=7.8 Hz, 1 H), 7.44 (d, J=4.7 Hz, 2 H), 7.10 – 7.25 (m, 2 H) |
| 647 | 595.3 | See Ex. 240 | ${}^{1}$H NMR (400 MHz, DMSO-$d_6$) δ: 10.81 (br s, 1 H), 9.62 (s, 1 H), 9.13 (s, 1 H), 8.62 (s, 1 H), 8.41 – 8.52 (m, 2 H), 7.94 (dd, J=7.8, 1.6 Hz, 1 H), 7.87 (d, J=7.4 Hz, 2 H), 7.45 – 7.54 (m, 2 H), 7.04 – 7.20 (m, 3 H), 6.59 (d, J=7.8 Hz, 1 H), 5.53 (br. s., 2 H) |
| 648 | 618.2 | See text | ${}^{1}$H NMR (400 MHz, DMSO-$d_6$) δ: 11.03 (br s, 1H), 9.96 (s, 1H), 9.35 (br. s., 1H), 8.45 – 8.60 (m, 3H), 8.36 (d, J = 8.2 Hz, 1H), 7.91 – 8.00 (m, 2H), 7.83 (d, J = 7.4 Hz, 1H), 7.35 – 7.59 (m, 4H) |
| 649 | 619.2 | See text | ${}^{1}$H NMR (400 MHz, DMSO-$d_6$) δ: 11.04 (br s, 1H), 9.64 (s, 1H), 8.91 (d, J = 8.2 Hz, 1H), 8.83 (d, J = 9.0 Hz, 1H), 8.56 (d, J = 9.4 Hz, 2H), 8.27 (d, J = 8.2 Hz, 1H), 7.96 (dd, J = 8.0, 2.2 Hz, 2H), 7.77 (dd, J = 7.4 Hz, 1H), 7.45 – 7.67 (m, 3H) |
| 650 | 777.3 | K | ${}^{1}$H NMR (400 MHz, DMSO-$d_6$) δ: 9.87 (s, 1H), 8.98 (s, 1H), 8.42 – 8.56 (m, 3H), 8.39 (d, J = 8.2 Hz, 1H), 7.99 (d, J = 7.8 Hz, 1H), 7.90 (d, J = 7.8 Hz, 1H), 7.75 (d, J = 7.8 Hz, 1H), 7.38 – 7.52 (m, 3H), 7.20 (dd, J = 9.0, 5.5 Hz, 1H), 7.09 (dd, J = 10.2 Hz, 1H), 3.32 (br. s., 2H), 3.26 (t, J = 6.5 Hz, 2H), 2.81 (s, 3H), 2.45 (br. s., 6H) |
| 651 | 777.2 | K | ${}^{1}$H NMR (400 MHz, DMSO-$d_6$) δ: 9.99 (s, 1H), 8.90 (s, 1H), 8.42 – 8.52 (m, 3H), 8.35 (d, J = 8.6 Hz, 1H), 7.95 (d, J = 7.4 Hz, 1H), 7.82 7.90 (m, 2H), 7.39 – 7.51 (m, 3H), 7.20 – 7.28 (m, 2H), 3.07 (br. s., 4H), 2.43 (br. s., 4H), 2.16 (s, 3H) |
| 652 | 629.2 | See Ex. 239 | ${}^{1}$H NMR (400 MHz, DMSO-$d_6$) δ: 10.64 (br s, 1H), 9.94 (s, 1H), 9.16 (s, 1H), 8.49 (s, 1H), 8.44 (s, 2H), 7.94 (d, J = 7.8 Hz, 1H), 7.87 (dd, J = 7.8, 1.6 Hz, 1H), 7.53 (dd, J = 8.0 Hz, 1H), 7.44 (d, J = 8.2 Hz, 1H), 7.33 – 7.40 (m, 1H), 7.27 – 7.32 (m, 1H), 7.11 (dd, J = 8.0 Hz, 1H), 6.57 (d, J = 7.4 Hz, 1H), 5.52 (br. s., 2H) |

Numerous modifications could be made to any of the embodiments described above without departing from the scope of the present invention. Any references, patents or scientific literature documents referred to in the present document are incorporated herein by reference in their entirety for all purposes.

The invention claimed is:

1. A compound of formula:

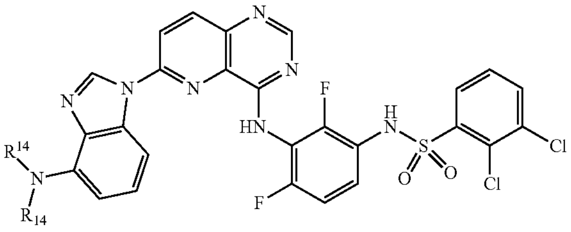

or a pharmaceutically acceptable salt thereof, wherein each $R^{14}$ is, independently, selected from H, optionally substituted $C_{1-6}$ alkyl, optionally substituted $C_{2-6}$ alkenyl, optionally substituted $C_{2-6}$ alkynyl, optionally substituted $C_{3-10}$ cycloalkyl, optionally substituted $C_{4-10}$ heterocycloalkyl, optionally substituted $C_6$ aryl, and optionally substituted $C_{5-10}$ heteroaryl, or each $R^{14}$ and their adjacent nitrogen atom together form an optionally substituted $C_{4-10}$ heterocycloalkyl group.

2. The compound of claim 1, wherein each $R^{14}$ and their adjacent nitrogen atom together form an optionally substituted $C_{4-10}$ heterocycloalkyl group.

3. The compound of claim 2, wherein the optionally substituted $C_{4-10}$ heterocycloalkyl group is monocyclic or bicyclic and comprises from 1 to 3 heteroatoms.

4. The compound of claim 2, wherein the optionally substituted $C_{4-10}$ heterocycle is substituted with at least one group selected from F, OH, oxo, CN, $NH_2$, $SO_2CH_3$, $COCH_3$, $COOC(CH_3)_3$, $COCH(CH_3)_2$, pyrrolidine, optionally substituted $C_{1-4}$ alkyl, and optionally substituted $OC_{1-4}$ alkyl.

5. The compound of claim 4, wherein the optionally substituted $C_{1-4}$ alkyl is substituted with at least one group selected from F, OH, and $OC_{1-3}$ alkyl.

6. The compound of claim 1, wherein each $R^{14}$, their adjacent nitrogen atom, and the benzimidazolyl ring to which the adjacent nitrogen is bound together form a moiety: selected from the group consisting of:

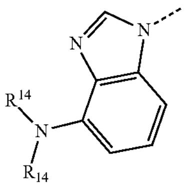
,
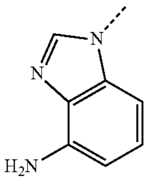
,

-continued
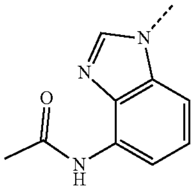,
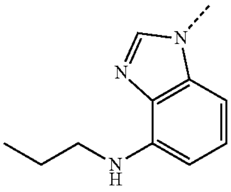,
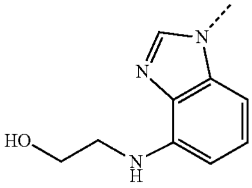,
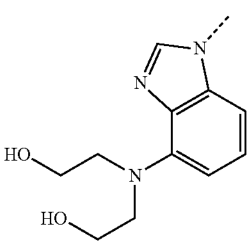,
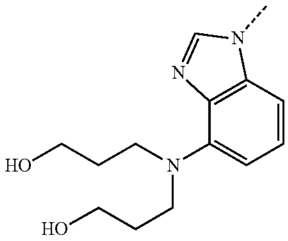,
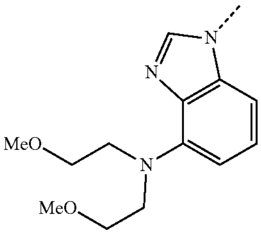,
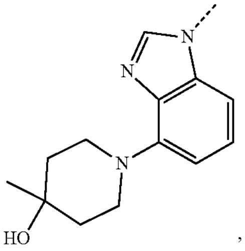,
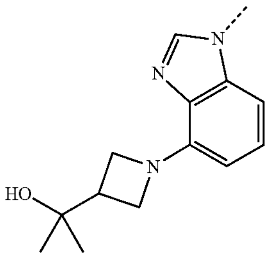,
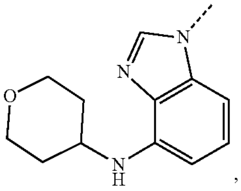,
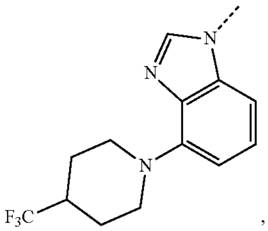,
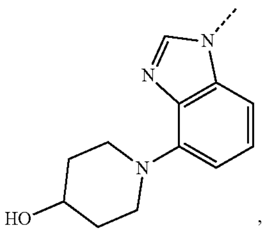,
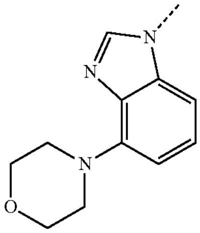,
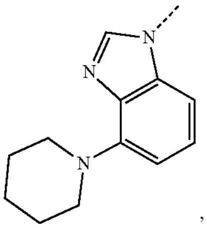,
-continued
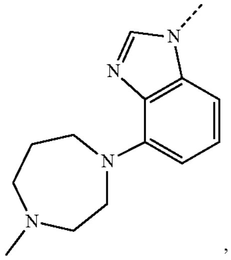,
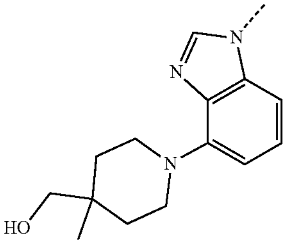,
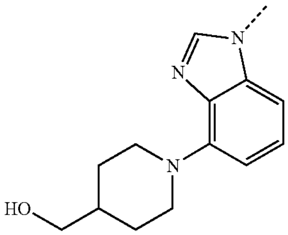,
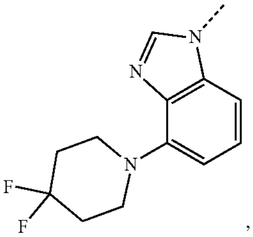,
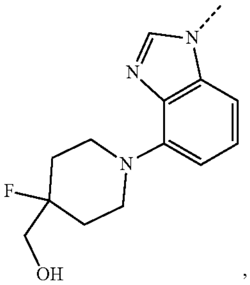,
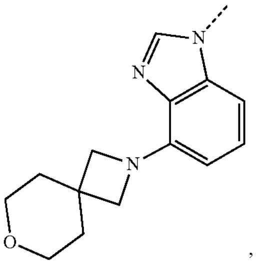,
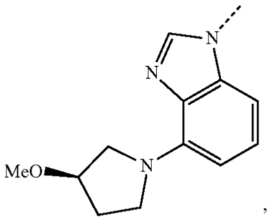,
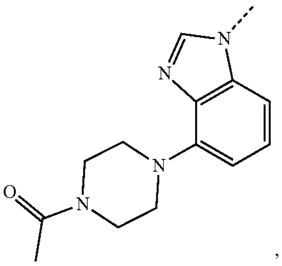,
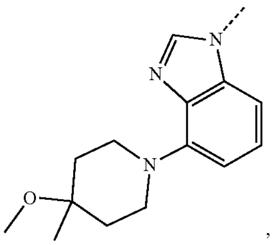,
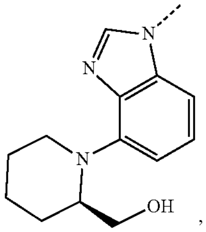,
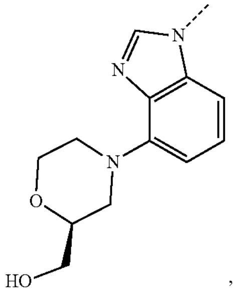,
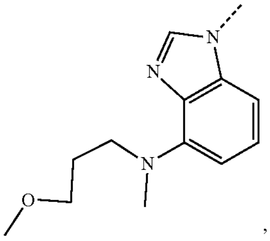, -continued
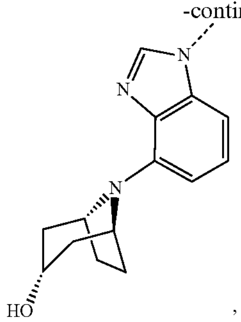
,
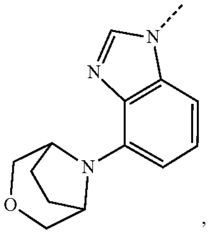
,
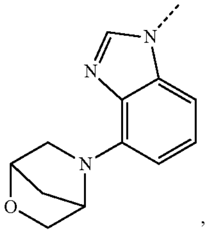
,
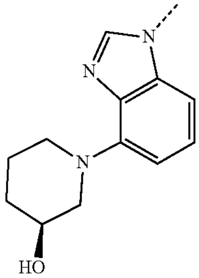
,
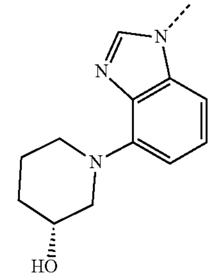
,
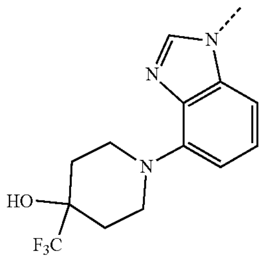
,
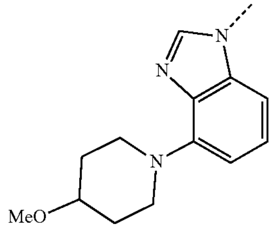
,
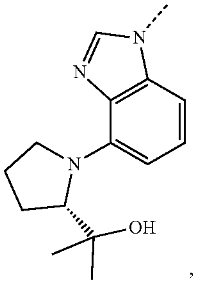
,
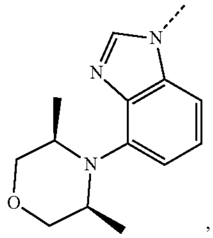
,
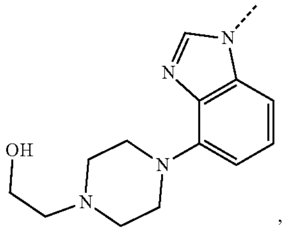
,
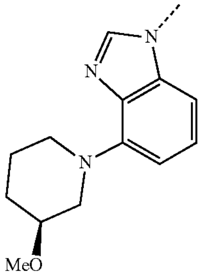
,
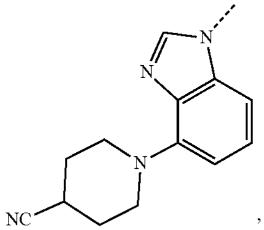
,
-continued
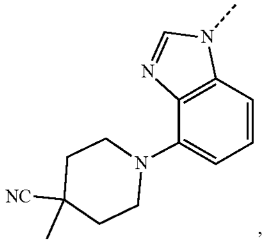
,
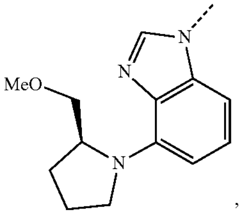
,
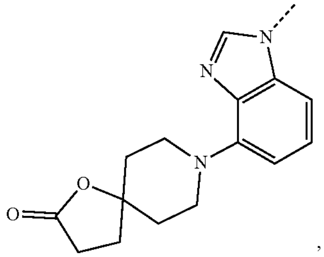
,
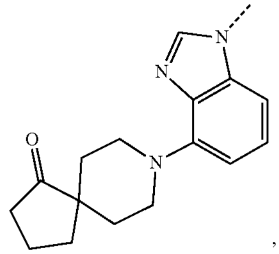
,
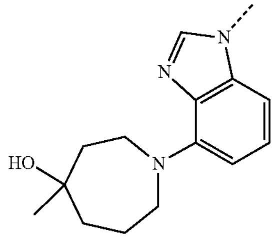
,
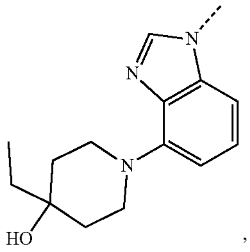
,
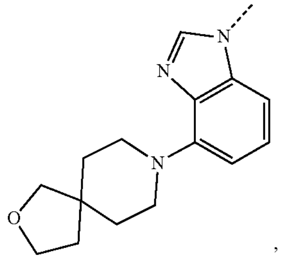
,
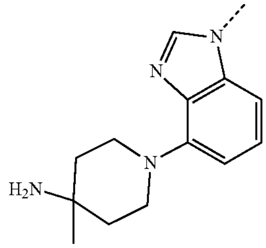
,
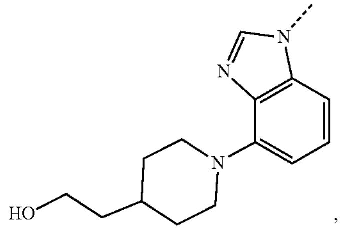
, -continued
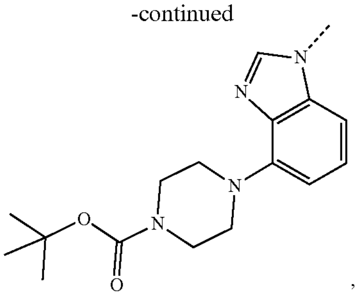
,
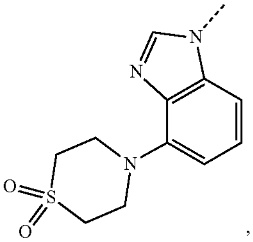
,
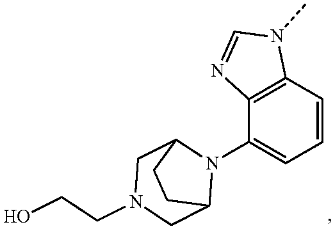
,
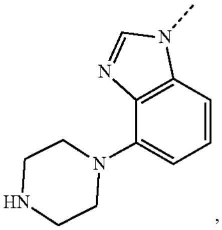
,
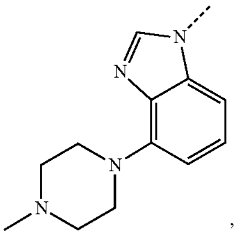
,
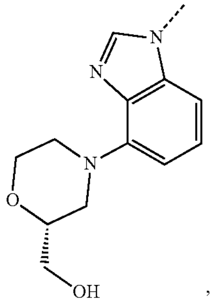
,
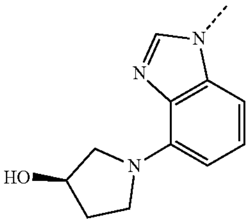
,
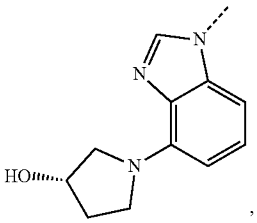
,
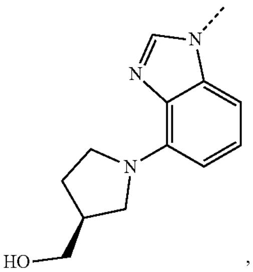
,
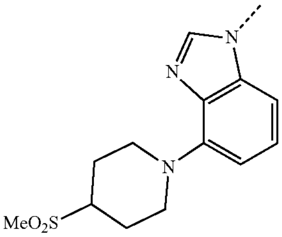
,
-continued
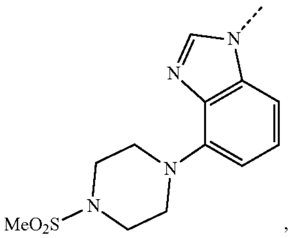
,
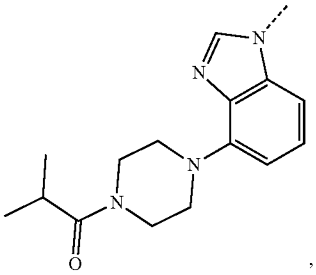
,
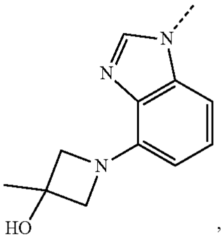
,
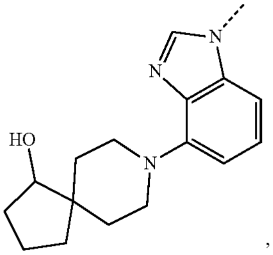
,
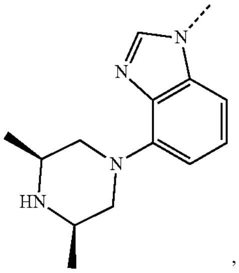
,
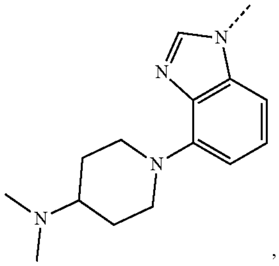
,
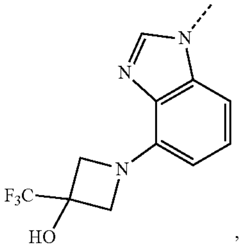
,
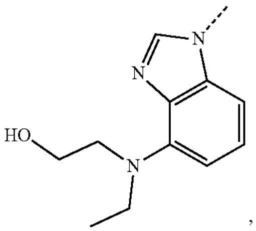
,
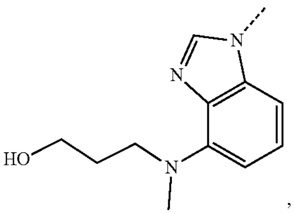
,
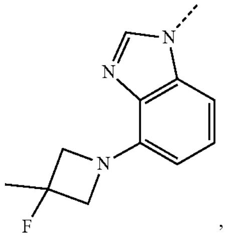
,
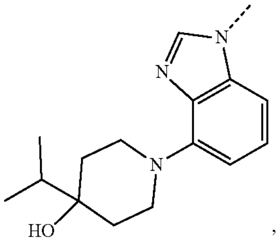
, -continued

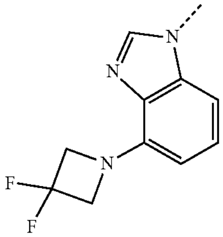
,
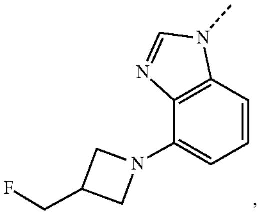
,
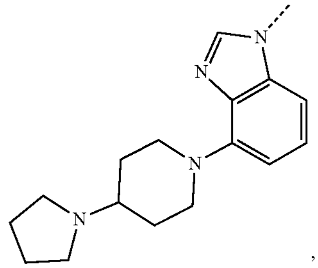
,
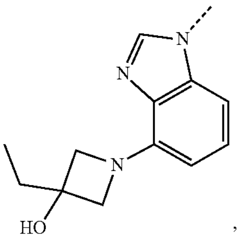
,
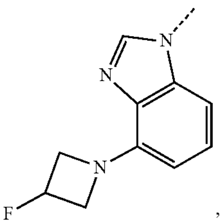
,
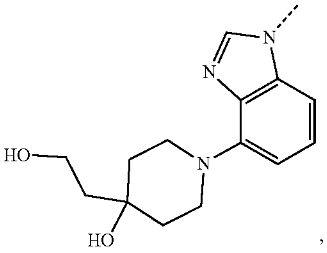
,
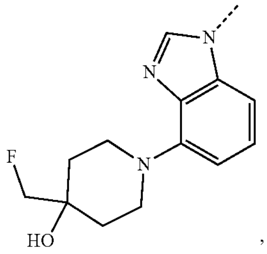
,
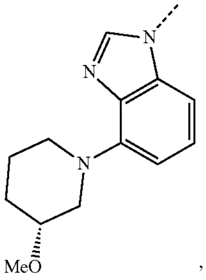
,
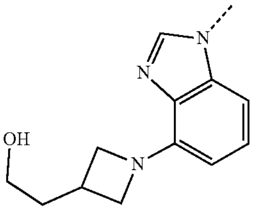
,
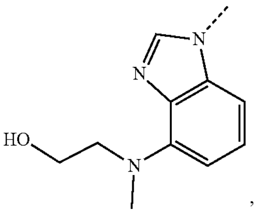
,
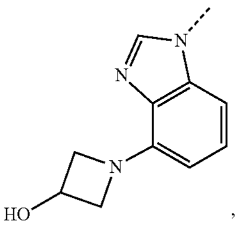
,
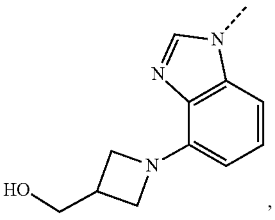
,
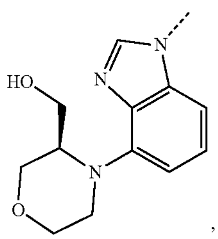
,
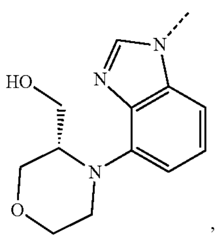
, -continued

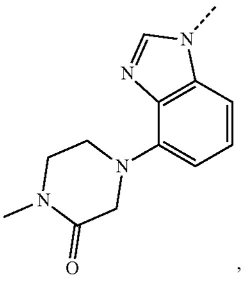
,
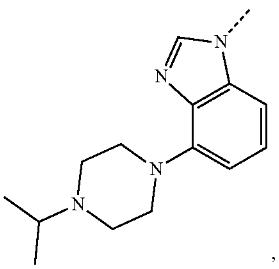
, and
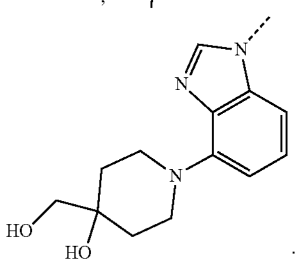
.

7. A pharmaceutical composition comprising the compound of claim 1 and a pharmaceutically acceptable carrier, diluent, or excipient.

8. A method of inhibiting RAS-ERK in a subject in need thereof, comprising administering to the subject a compound of formula:

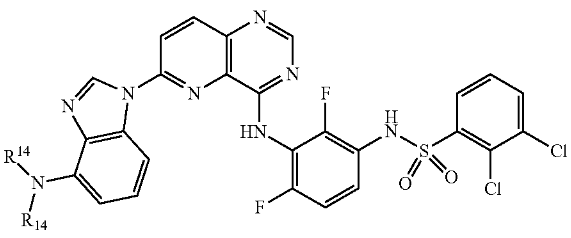

or a pharmaceutically acceptable salt thereof, wherein each $R^{14}$ is, independently, selected from H, optionally substituted $C_{1-6}$ alkyl, optionally substituted $C_{2-6}$ alkenyl, optionally substituted $C_{2-6}$ alkynyl, optionally substituted $C_{3-10}$ cycloalkyl, optionally substituted $C_{4-10}$ heterocycloalkyl, optionally substituted $C_6$ aryl, and optionally substituted $C_{5-10}$ heteroaryl, or each $R^{14}$ and their adjacent nitrogen atom together an optionally substituted $C_{4-10}$ heterocycloalkyl group.

9. The method of claim 8, wherein each $R^{14}$ and their adjacent nitrogen atom together form an optionally substituted $C_{4-10}$ heterocycloalkyl group.

10. The method of claim 9, wherein the optionally substituted $C_{4-10}$ heterocycloalkyl group is monocyclic or bicyclic and comprises from 1 to 3 heteroatoms.

11. The method of claim 9, wherein the optionally substituted $C_{4-10}$ heterocycle is substituted with at least one group selected from F, OH, oxo, CN, $NH_2$, $SO_2CH_3$, $COCH_3$, $COOC(CH_3)_3$, $COCH(CH_3)_2$, pyrrolidine, optionally substituted $C_{1-4}$ alkyl, and optionally substituted $OC_{1-4}$ alkyl.

12. The method of claim 11, wherein the optionally substituted $C_{1-4}$ alkyl is substituted with at least one group selected from F, OH, and $OC_{1-3}$ alkyl.

13. The method of claim 8, wherein each $R^{14}$, their adjacent nitrogen atom, and the benzimidazolyl ring to which the adjacent nitrogen is bound together form a moiety: selected from the group consisting of:
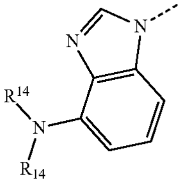, 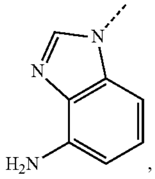,
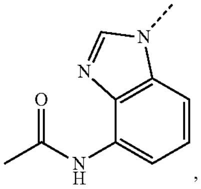, 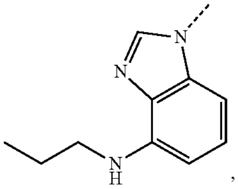,
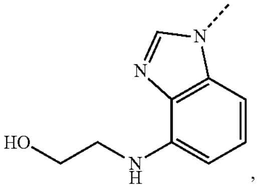, 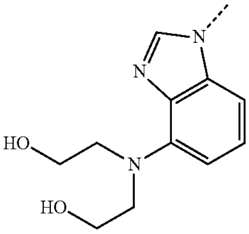,
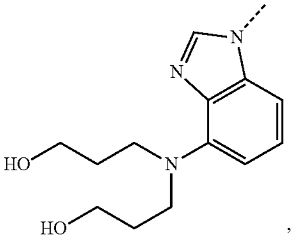,
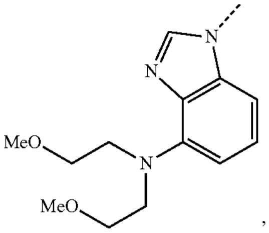, 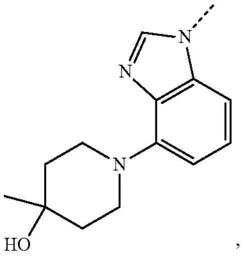,
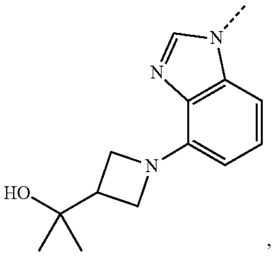, 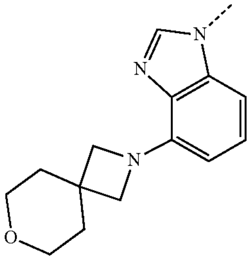,
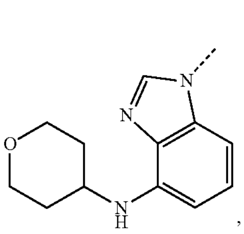, 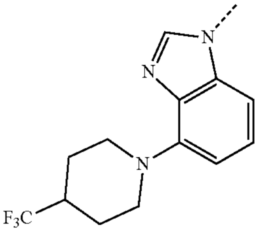,
-continued
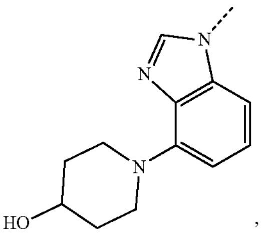, 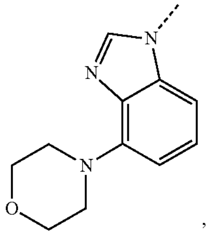,
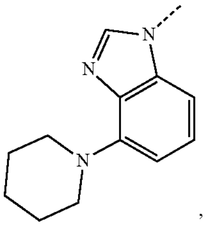, 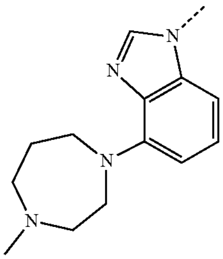,
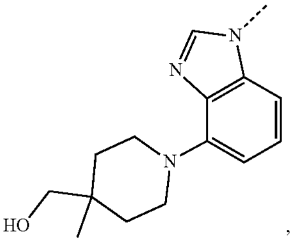,
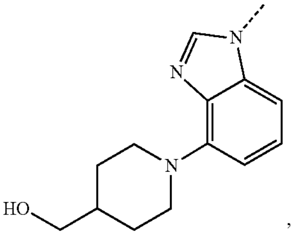, 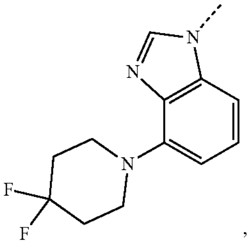,
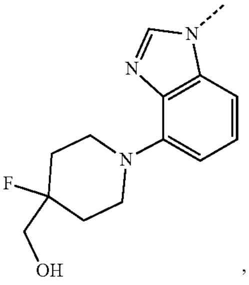, 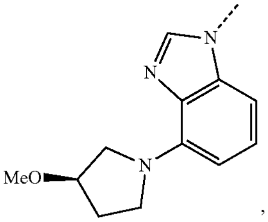,
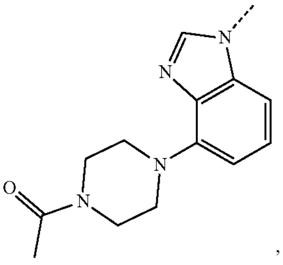, 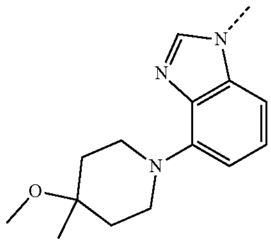, -continued
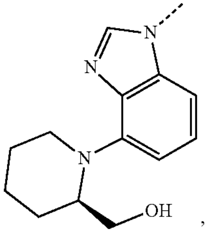
,
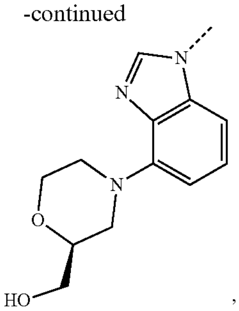
,
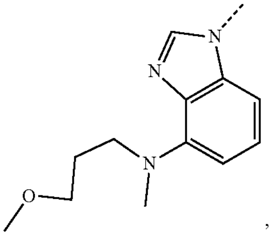
,
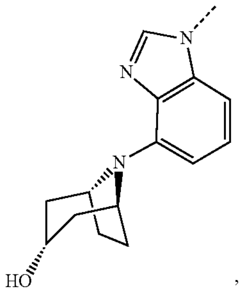
,
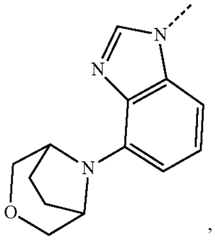
,
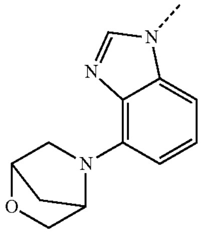
,
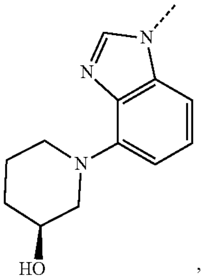
,
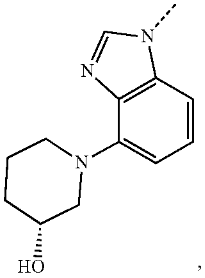
,
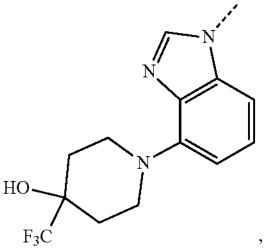
,
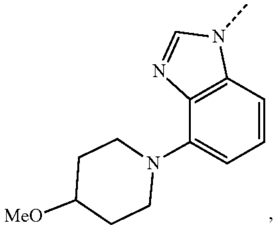
,
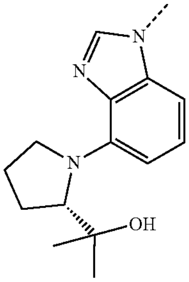
,
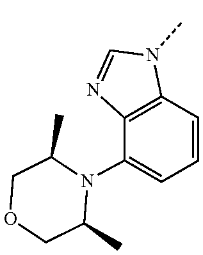
,
-continued
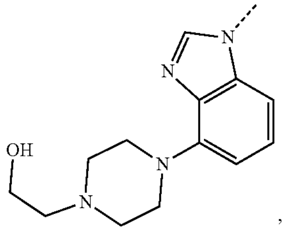
,
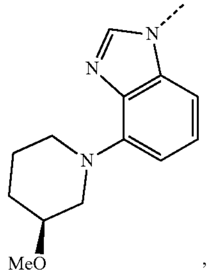
,
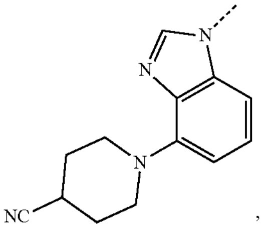
,
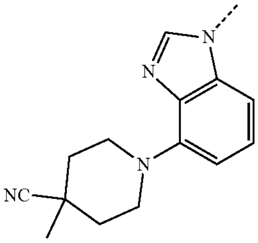
,
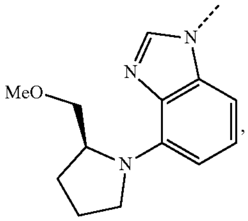
,
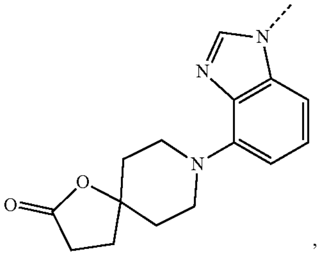
,
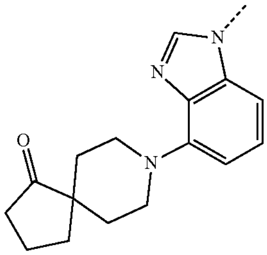
,
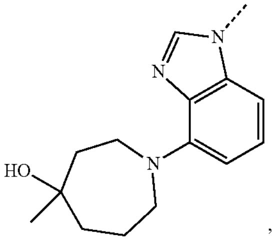
,
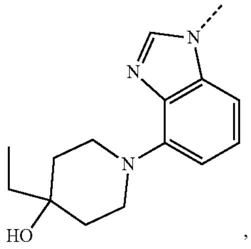
,
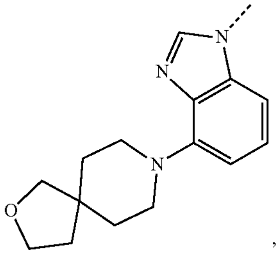
, -continued
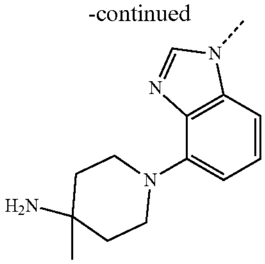
,
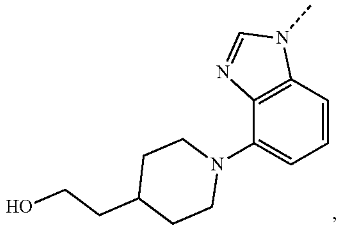
,
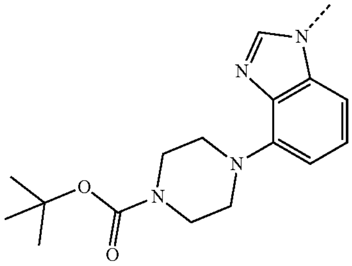
,
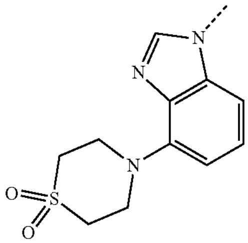
,
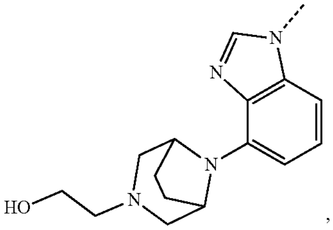
,
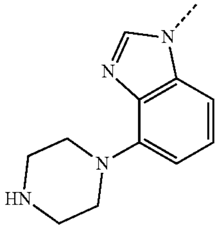
,
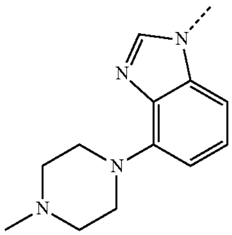
,
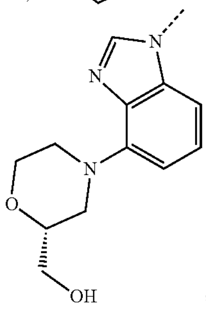
,
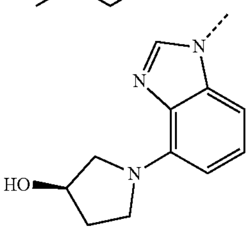
,
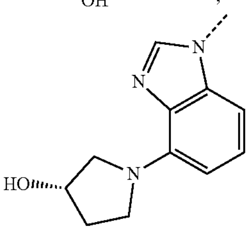
,
-continued
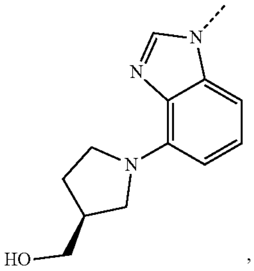
,
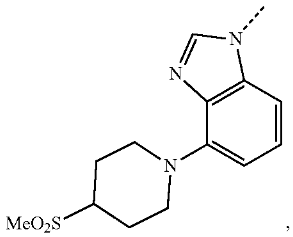
,
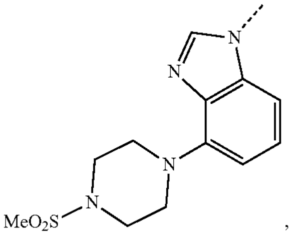
,
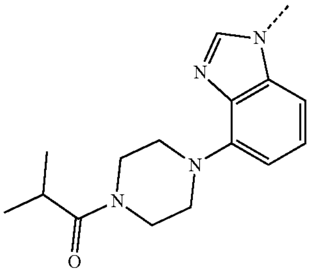
,
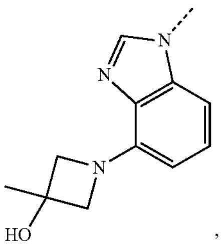
,
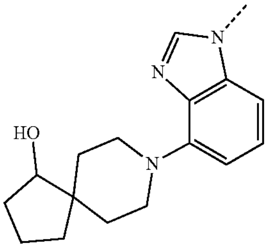
,
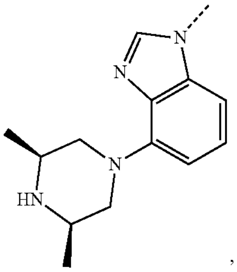
,
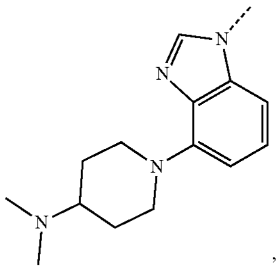
,
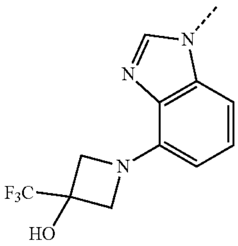
,
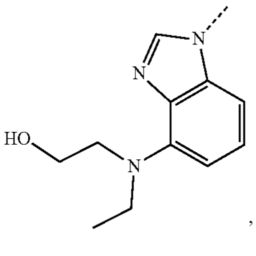
,
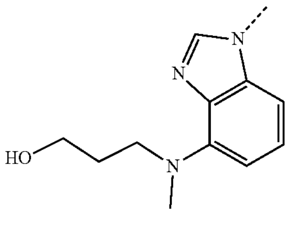
, -continued

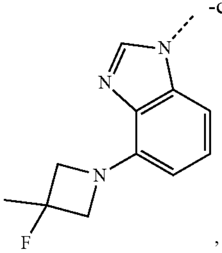,
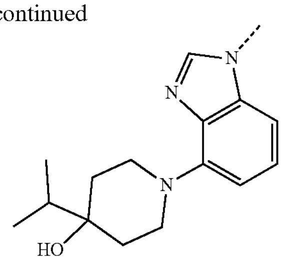,
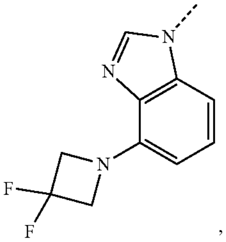,
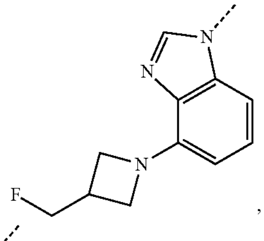,
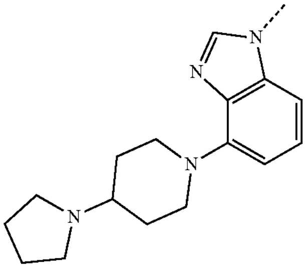,
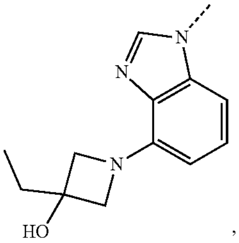,
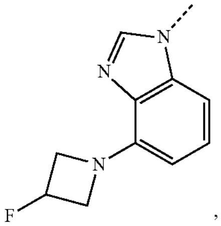,
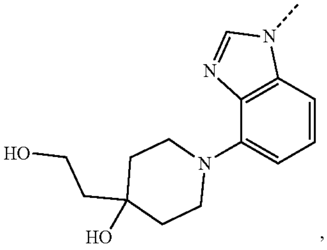,
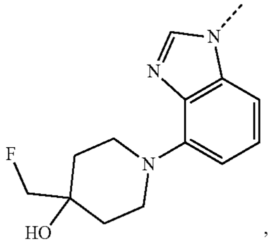,
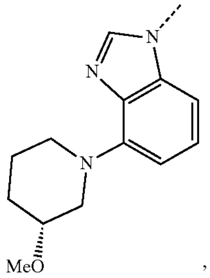,
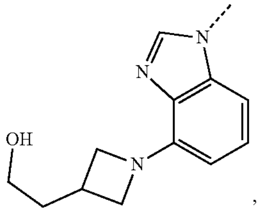,
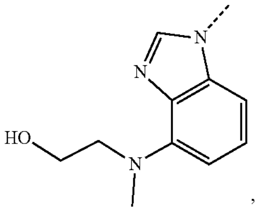,
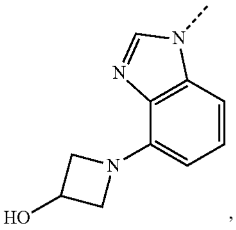,
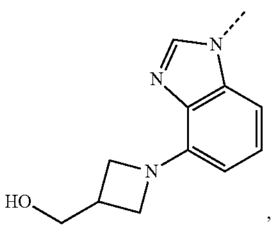, -continued

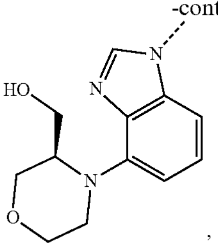,
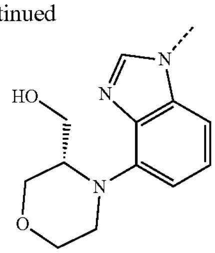,
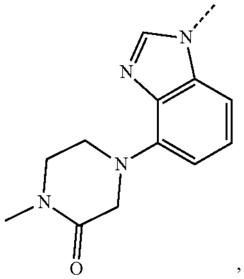,
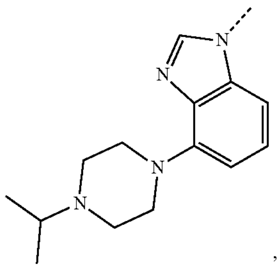, and
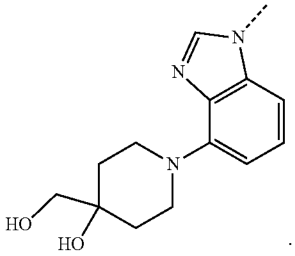.

14. A method of inhibiting RAS-ERK in a subject suffering from a melanoma, comprising administering to the subject a compound of formula:

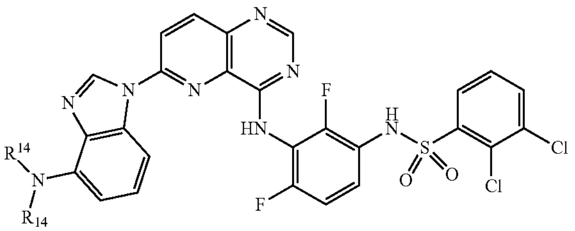

or a pharmaceutically acceptable salt thereof, wherein each $R^{14}$ is, independently, selected from H, optionally substituted $C_{1-6}$ alkyl, optionally substituted $C_{2-6}$ alkenyl, optionally substituted $C_{2-6}$ alkynyl, optionally substituted $C_{3-10}$ cycloalkyl, optionally substituted $C_{4-10}$ heterocycloalkyl, optionally substituted $C_6$ aryl, and optionally substituted $C_{5-10}$ heteroaryl, or each $R^{14}$ and their adjacent nitrogen atom together form an optionally substituted $C_{4-10}$ heterocycloalkyl group.

15. The method of claim 14, wherein each $R^{14}$ and their adjacent nitrogen atom together form an optionally substituted $C_{4-10}$ heterocycloalkyl group.

16. The method of claim 15, wherein the optionally substituted $C_{4-10}$ heterocycloalkyl group is monocyclic or bicyclic and comprises from 1 to 3 heteroatoms.

17. The method of claim 15, wherein the optionally substituted $C_{4-10}$ heterocycle is substituted with at least one group selected from F, OH, oxo, CN, $NH_2$, $SO_2CH_3$, $COCH_3$, $COOC(CH_3)_3$, $COCH(CH_3)_2$, pyrrolidine, optionally substituted $C_{1-4}$ alkyl, and optionally substituted $OC_{1-4}$ alkyl.

18. The method of claim 17, wherein the optionally substituted $C_{1-4}$ alkyl is substituted with at least one group selected from F, OH, and $OC_{1-3}$ alkyl.
19. The method of claim 14, wherein each $R^{14}$, their adjacent nitrogen atom, and the benzimidazolyl ring to which the adjacent nitrogen is bound together form a moiety: selected from the group consisting of:
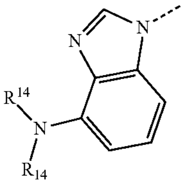
,
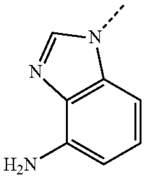
,
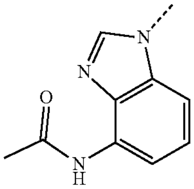
,
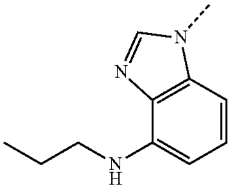
,
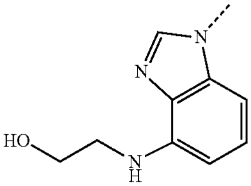
,
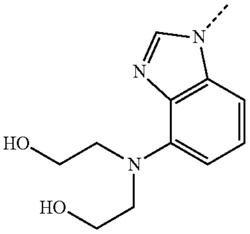
,
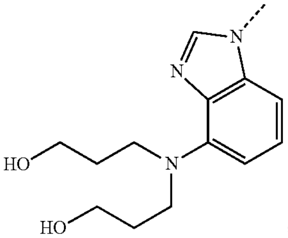
,
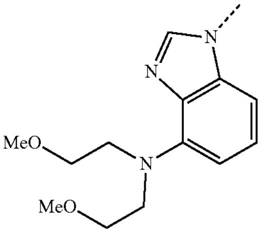
,
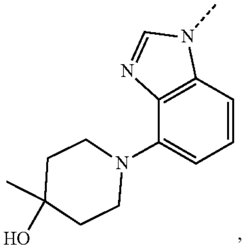
,
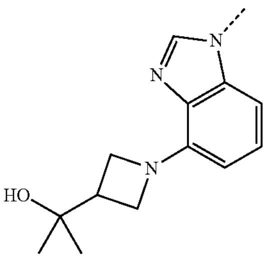
,
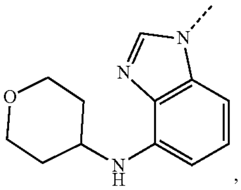
,
-continued
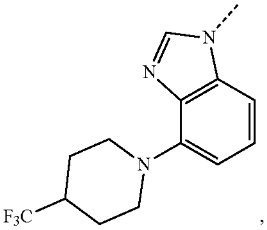
,
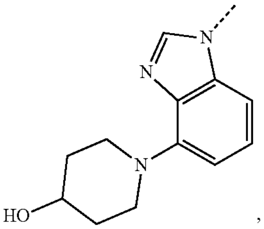
,
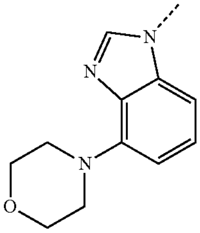
,
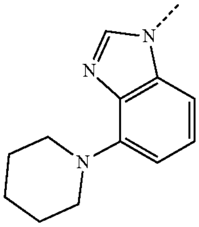
,
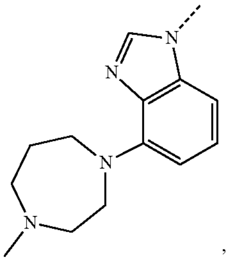
,
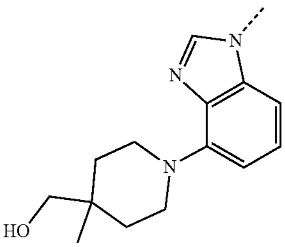
,
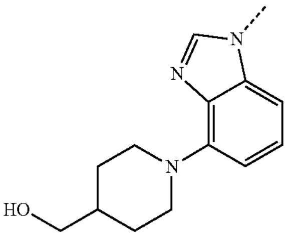
,
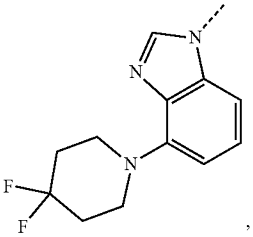
,
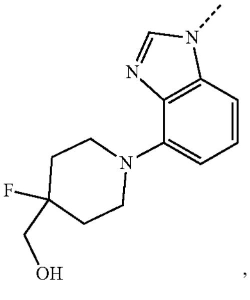
,
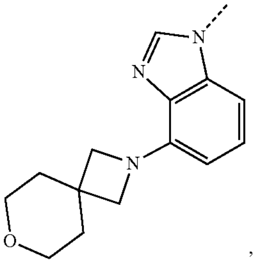
,
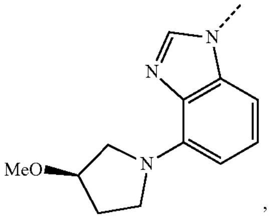
,
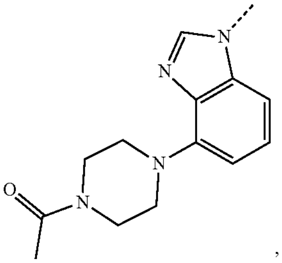
, -continued
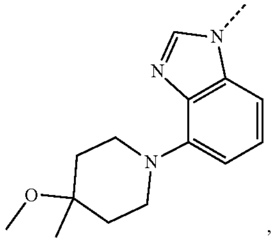,
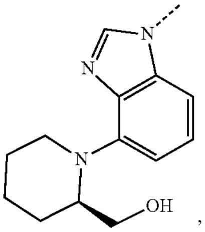,
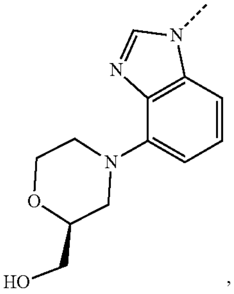,
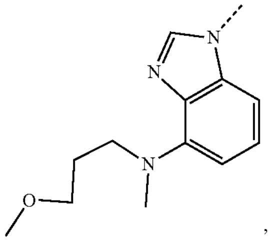,
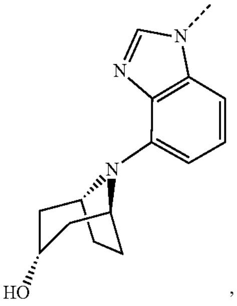,
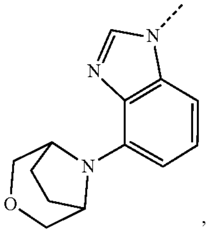,
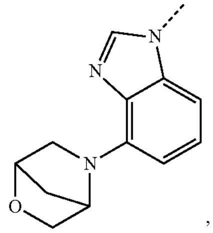,
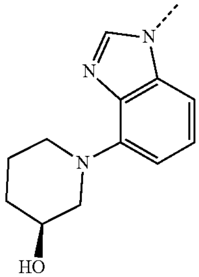,
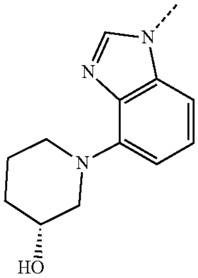,
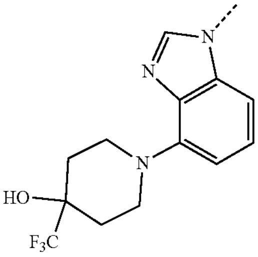,
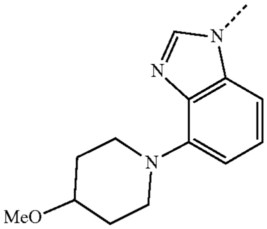,
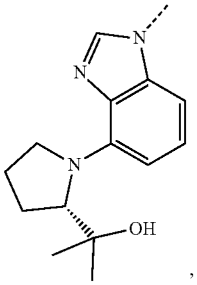,
-continued
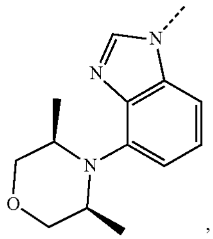,
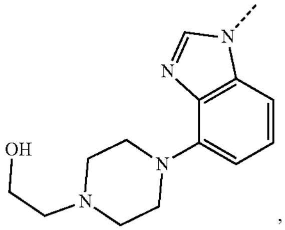,
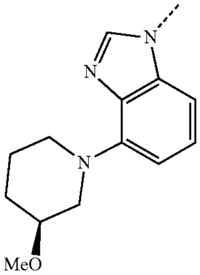,
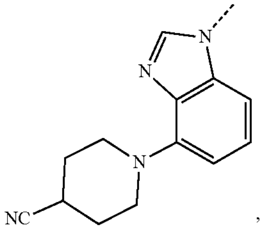,
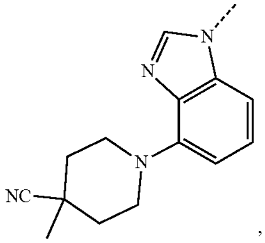,
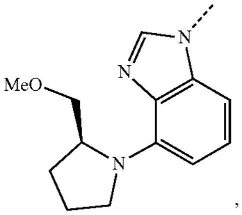,
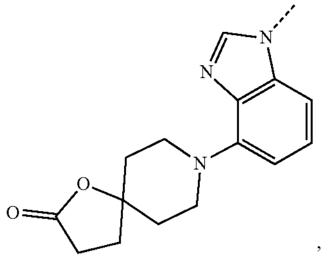,
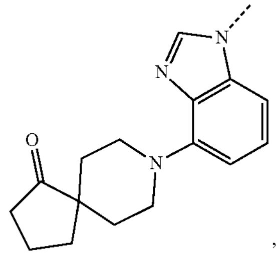,
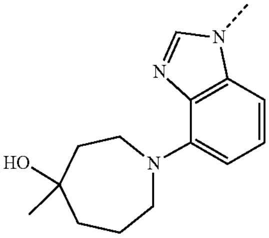,
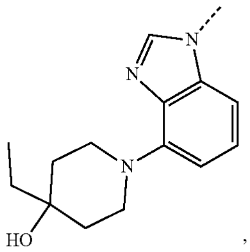,
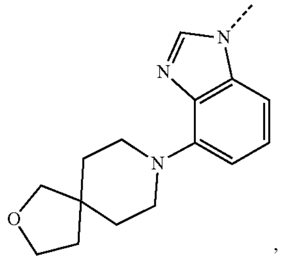, -continued
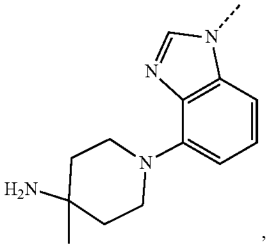
,
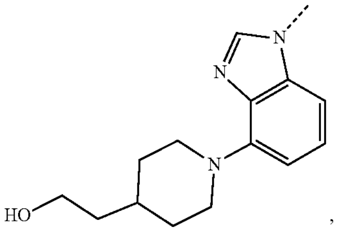
,
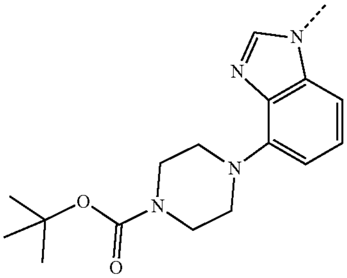
,
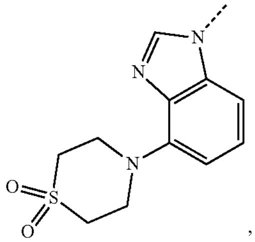
,
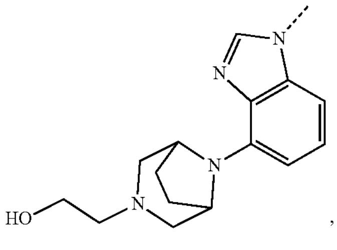
,
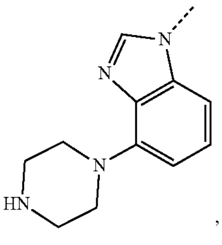
,
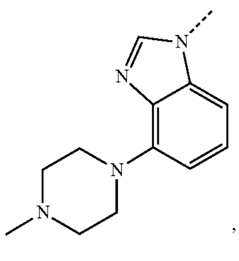
,
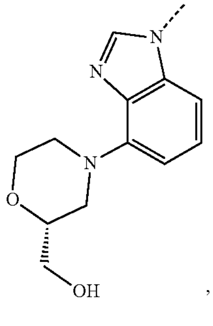
,
-continued
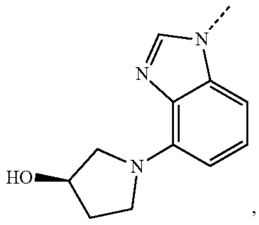
,
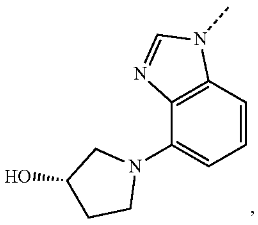
,
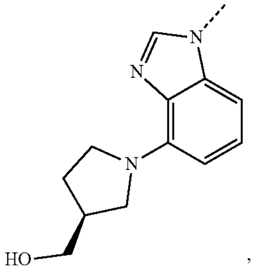
,
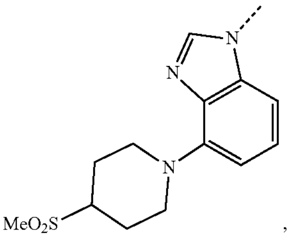
,
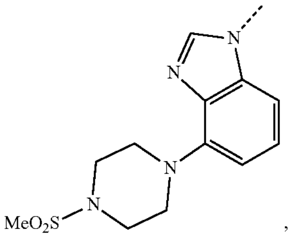
,
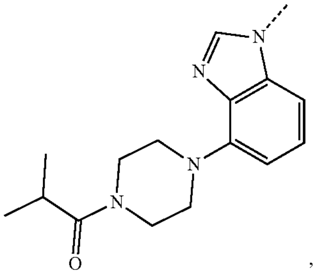
,
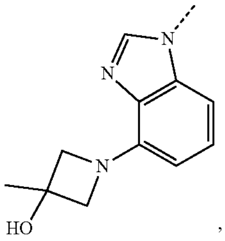
,
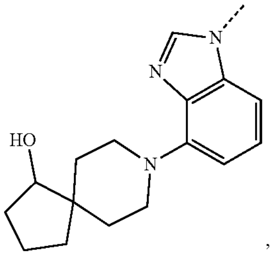
,
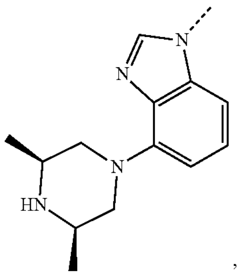
,
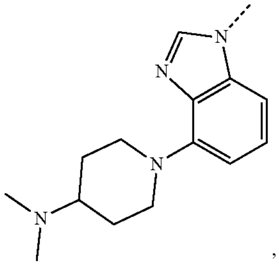
,
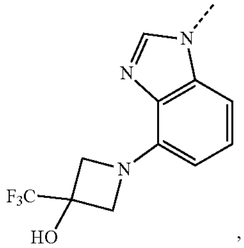
, -continued
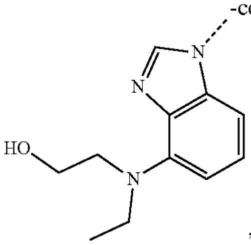,
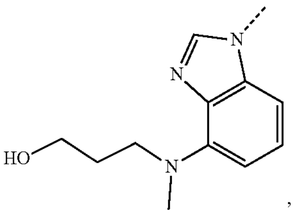,
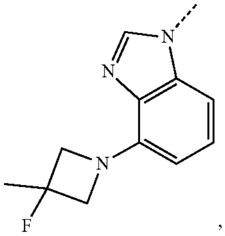,
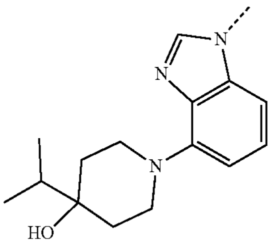,
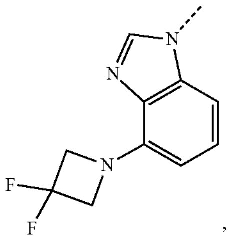,
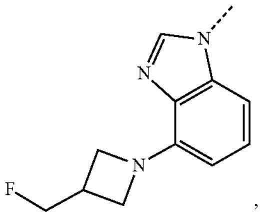,
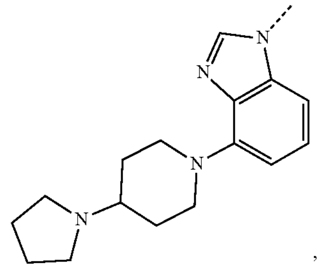,
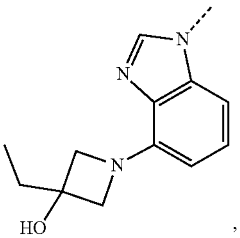,
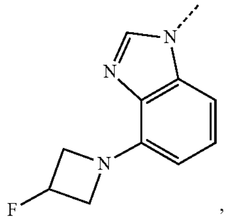,
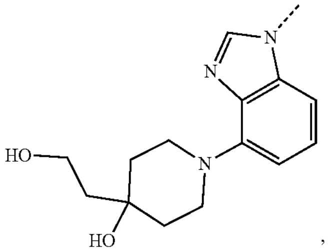,
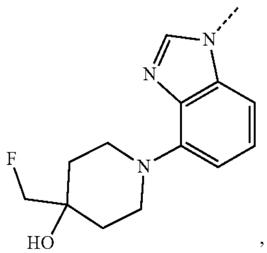,
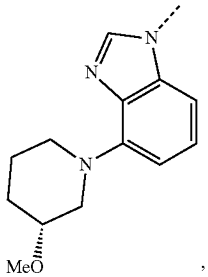,
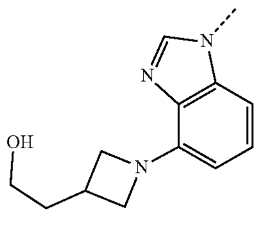,
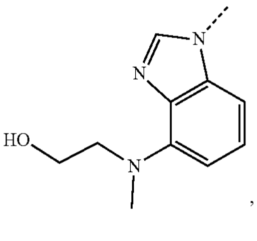,
-continued
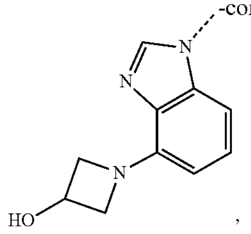,
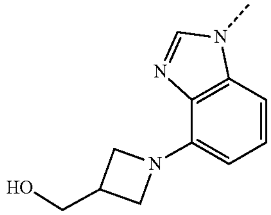,
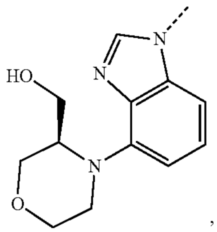,
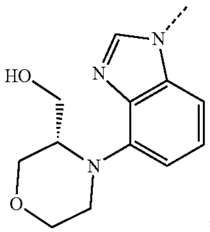,
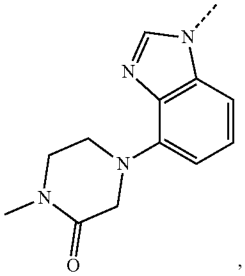,
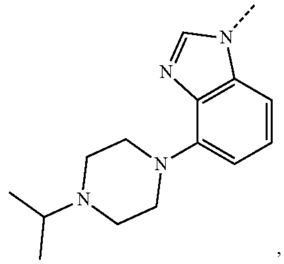, and
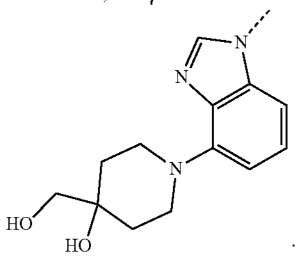.
20. The compound of claim 1, wherein each $R^{14}$, their adjacent nitrogen atom, and the benzimidazolyl ring to which the adjacent nitrogen is bound together form a moiety: selected from the group consisting of:
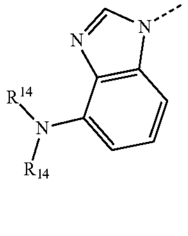,
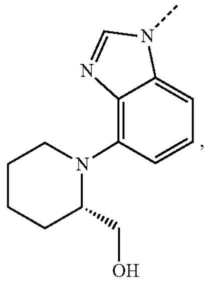,
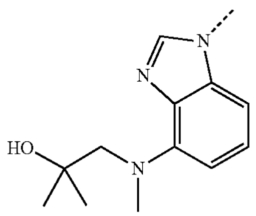,
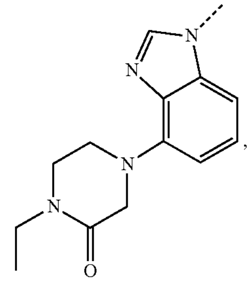, and -continued

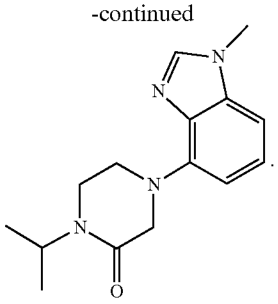

21. The method of claim 8, wherein each $R^{14}$, their adjacent nitrogen atom, and the benzimidazolyl ring to which the adjacent nitrogen is bound together form a moiety: selected from the group consisting of:

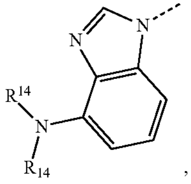
,
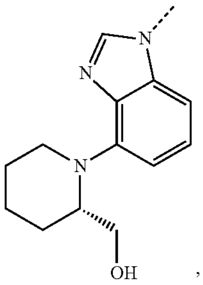
,
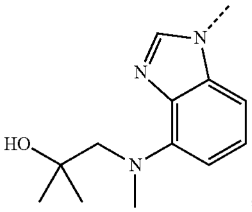
,
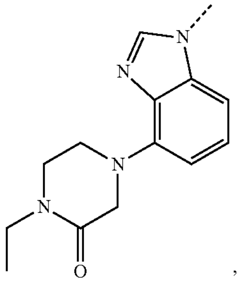
, and
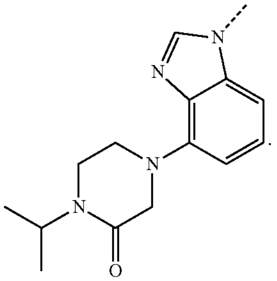

22. The method of claim 14, wherein each $R^{14}$, their adjacent nitrogen atom, and the benzimidazolyl ring to which the adjacent nitrogen is bound together form a moiety: selected from the group consisting of:

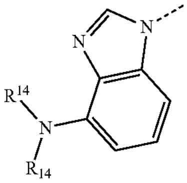
,
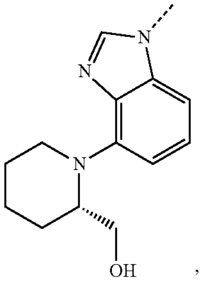
,
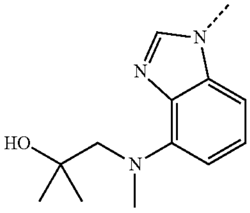
,
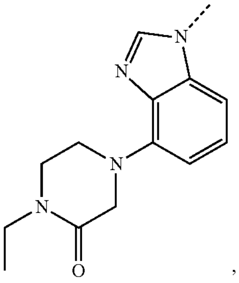
, and
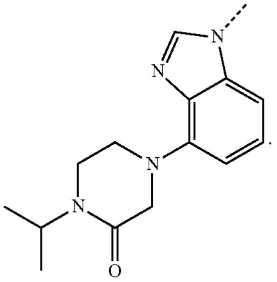

* * * * *